(12) United States Patent
Herbert et al.

(10) Patent No.: US 11,693,006 B2
(45) Date of Patent: Jul. 4, 2023

(54) BLOOD PROFILING WITH PROTEASE INHIBITORS

(71) Applicant: Sangui Bio Pty. Ltd, Manly (AU)

(72) Inventors: Benjamin Ross Herbert, North Epping (AU); Elisabeth Karsten, Northmead (AU)

(73) Assignee: Sangui Bio Pty. Ltd, Manly (AU)

( * ) Notice: Subject to any disclaimer, the term of this patent is extended or adjusted under 35 U.S.C. 154(b) by 793 days.

(21) Appl. No.: 16/471,479

(22) PCT Filed: Dec. 18, 2017

(86) PCT No.: PCT/AU2017/000282
§ 371 (c)(1),
(2) Date: Jun. 19, 2019

(87) PCT Pub. No.: WO2018/112500
PCT Pub. Date: Jun. 28, 2018

(65) Prior Publication Data
US 2020/0096512 A1    Mar. 26, 2020

Related U.S. Application Data

(60) Provisional application No. 62/436,875, filed on Dec. 20, 2016, provisional application No. 62/482,582, filed on Apr. 6, 2017, provisional application No. 62/523,489, filed on Jun. 22, 2017.

(51) Int. Cl.
*G01N 33/49* (2006.01)
*G01N 33/574* (2006.01)
*C12Q 1/37* (2006.01)

(52) U.S. Cl.
CPC ......... *G01N 33/57419* (2013.01); *C12Q 1/37* (2013.01); *G01N 33/57484* (2013.01); *G01N 2333/95* (2013.01)

(58) Field of Classification Search
CPC ..................................................... G01N 33/49
See application file for complete search history.

(56) References Cited

U.S. PATENT DOCUMENTS

| | | | |
|---|---|---|---|
| 4,931,276 | A | 6/1990 | Franco et al. |
| 5,858,358 | A | 1/1999 | June et al. |
| 10,273,455 | B2 | 4/2019 | Baek et al. |
| 2008/0095749 | A1 | 4/2008 | Aggarwal et al. |
| 2009/0054741 | A1 | 2/2009 | Mcaleer |
| 2012/0195869 | A1 | 8/2012 | Terman et al. |
| 2014/0154221 | A1 | 6/2014 | Castro et al. |
| 2018/0306817 | A1 | 10/2018 | Karsten et al. |
| 2019/0000884 | A1 | 1/2019 | Karsten et al. |
| 2020/0096512 | A1 | 3/2020 | Herbert et al. |

FOREIGN PATENT DOCUMENTS

| | | |
|---|---|---|
| CN | 1662817 A | 8/2005 |
| CN | 1795387 A | 6/2006 |
| CN | 1922304 A | 2/2007 |
| CN | 1969184 A | 5/2007 |
| CN | 101248187 A | 8/2008 |
| FR | 2778851 B1 | 7/2002 |
| JP | 2007510149 A | 4/2007 |
| JP | 2012530133 A | 11/2012 |
| JP | 2013501926 A | 1/2013 |
| JP | 2015055620 A | 3/2015 |
| JP | 2015523384 A | 8/2015 |
| WO | WO 1992/005801 A1 | 4/1992 |
| WO | WO 2002/007752 A3 | 1/2002 |
| WO | WO 2003/087833 A3 | 10/2003 |
| WO | WO 2004/088324 | 10/2004 |
| WO | WO 2005/043121 | 5/2005 |
| WO | WO 2005/045441 A1 | 5/2005 |
| WO | WO 2005/103678 A3 | 11/2005 |
| WO | WO 2006/081324 A3 | 8/2006 |
| WO | WO 2008/134526 | 11/2008 |
| WO | WO 2009/019317 A1 | 2/2009 |
| WO | WO 2009/111595 | 9/2009 |
| WO | WO 2009/137629 A3 | 11/2009 |
| WO | WO 2010/147621 A1 | 12/2010 |
| WO | WO 2011/018288 A1 | 2/2011 |
| WO | WO 2011/091154 A3 | 7/2011 |
| WO | WO 2011/127056 | 10/2011 |
| WO | WO 2012/166055 | 12/2012 |
| WO | WO 2013/045885 A1 | 4/2013 |
| WO | WO 2013/139906 A1 | 9/2013 |
| WO | WO 2013/156806 A3 | 10/2013 |
| WO | WO 2014/011901 A3 | 1/2014 |
| WO | WO 2014/181309 A1 | 11/2014 |
| WO | WO 2015/156586 A1 | 10/2015 |
| WO | WO 2016/187353 | 11/2016 |
| WO | WO 2017/059477 | 4/2017 |
| WO | WO 2017/106899 | 6/2017 |

OTHER PUBLICATIONS

Ayache S et al., "Effects of storage time and exogenous protease inhibitors on plasma protein levels", American Journal of Clinical Pathology, 2006, 126(2): 174-184.*
D'Amici etal, Proteomic Analysis of RBC Membrane Protein Degradation during Blood Storage. Journal of Proteome Research 2007, 6, 3242-3255. Published on Web Jun. 22, 2007.*
Anniss et al., 2005, "Proteomic analysis of supernatants of stored red blood cell products", Transfusion, 45(9):1426-1433.
Autunes et al., 2011, "Red blood cells release factors with growth and survival bioactivities for normal and leukemic T cells," Immunol Cell Biol., 89(1):111-121.
Baruchel et al., 2015, "Updated Clinical Activity of Graspa Versus Native l-Asparaginase in Combination with Cooprall Regimen in Phase 3 Randomized Trial in Patients with Relapsed Acute Lymphoblastic Leukemia (NCT01518517)", Blood, 126(23):3723.

(Continued)

*Primary Examiner* — Tekchand Saidha
(74) *Attorney, Agent, or Firm* — Jones Day

(57) ABSTRACT

The present disclosure relates to methods for generating blood protein profiles from whole blood, red blood cell enriched blood samples, or red blood cell components. The methods involve the comparison of protein levels before and after incubation with protease inhibitors, or the comparison of protein levels after incubation in the presence and absence of protease inhibitors. The protein profiles are used for monitoring and diagnosing diseases and disorders in subjects including colorectal cancer and preeclampsia.

21 Claims, 235 Drawing Sheets

(56) References Cited

OTHER PUBLICATIONS

Bjork et al., 1996, "A new enzyme activity in human blood cells and isolation of the responsible protein (D-dopachrome tautomerase) from erythrocytes", Eur J Haematol, 57(3):254-256.
Bruil et al., 1995, "The mechanisms of leukocyte removal by filtration", Transfus Med Rev., 9(2):145-166.
Cassell et al., 1962, "Transfusion of buffy coat-poor red cell suspensions prepared by dextran sedimentation: description of newly designed equipment and evaluation of its use", Transfusion, 2:216-220.
Dalton, 2017, "Blood tests at your fingertips", Chemical & Engineering News, 95(1):16-19.
Danesh et al., 2014, "Exosomes from red blood cell units bind to monocytes and induce proinflammatory cytokines, boosting T-cell responses in vitro", Blood, 123(5):687-696 (Epub 2013).
Darbonne et al., 1991, "Red blood cells are a sink for interleukin 8, a leukocyte chemotaxin", J Clin Invest., 88(4):1362-1369.
Day et al., 1989, "Expression and regulation of erythrocyte autoantibodies in mice following immunization with rat erythrocytes", Eur J Immunol., 19(5):795-801.
Dzieciatkowska et al., 2013, "Proteomic analysis of the supernatant of red blood cell units: the effects of storage and leucoreduction", Vox Sang, 105(3):210-218.
Ferru et al., 2012, "A new method for the capture of surface proteins in Plasmodium falciparum parasitized erythrocyte", J Infect Dev Ctries, 6(6):536-541.
Fonseca et al., 2001, "Red blood cells inhibit activation-induced cell death and oxidative stress in human peripheral blood T lymphocytes," Blood, 97(10):3152-3160.
Fredriksson et al., 2003, "Red blood cells stimulate human lung fibroblasts to secrete interleukin-8," Inflammation, 27(2):71-78.
Hanahan et al., 1974, "The preparation of red cell ghosts (membranes)", Methods Enzymol., 31:168-172.
Hansell et al., 2011, "DARC and D6: silent partners in chemokine regulation?", Immunol Cell Biol., 89(2):197-206 (Epub 2010).
Haudek et al., 2009, "Proteome maps of the main human peripheral blood constituents", J Proteome Res., 8(8):3834-3843.
International Search Report and Written Opinion for International Patent Application No. PCT/AU2016/000341 (published as WO 2017059477) dated Dec. 20, 2016 (13 pages).
International Search Report and Written Opinion for International Patent Application No. PCT/AU2016/000404 (published as WO 2017106899) dated Aug. 17, 2017 (17 pages).
Karsten et al., 2018, "Red blood cells are dynamic reservoirs of cytokines", Sci Rep., 8(1):3101 (12 pages).
Kumar et al., 2015, "Enrichment of reticulocytes from whole blood using aqueous multiphase systems of polymers," Am. J. Hematol., 90(1):31-36 (Epub 2014).
Makinen et al., 1977, "Migration inhibition factor and the blood clotting system: effects of defibrination, heparin and thrombin", Clin Exp Immunol., 29(1):181-186.
Mayeux, 2004, "Biomarkers: potential uses and limitations", NeuroRx, 1(2):182-188.
Mayr et al., 2008, "Duffy antigen modifies the chemokine response in human endotoxemia", Crit Care Med., 36(1):159-165.
McDade et al., 2007, "What a drop can do: dried blood spots as a minimally invasive method for integrating biomarkers into population-based research", Demography, 44(4):899-925.
Pasini et al., 2006, "In-depth analysis of the membrane and cytosolic proteome of red blood cells", Blood, 108(3):791-801.
Pasini et al., 2010, "Red blood cell (RBC) membrane proteomics—Part I: Proteomics and RBC physiology", J Proteomics, 73(3):403-420 (Epub 2009).
Rubin et al., 2012, "Red blood cell microparticles: clinical relevance", Transfus Med Hemother, 39(5):342-347.
Schnabel et al., 2010, "Duffy antigen receptor for chemokines (Darc) polymorphism regulates circulating concentrations of monocyte chemoattractant protein-1 and other inflammatory mediators", Blood, 115(26):5289-5299 (Epub 2009).
Sirchia et al., 1980, "Evaluation of three procedures for the preparation of leukocyte-poor and leukocyte-free red blood cells for transfusion", Vox Sang, 38(4):197-204.
Sparrow et al., 2004, "Supernatant from stored red blood cell primes inflammatory cells: influence of prestorage white cell reduction", Transfusion, 44(5):722-730.
Tenczar, 1973, "Comparison of inverted centrifugation, saline washing, and dextran sedimentation in the preparation of leukocyte-poor red cells", Transfusion, 13(4):183-188.
Villanueva et al., 1988, "Chromatography, flow injection analysis and electrophoresis in computer-assisted comparative biochemistry: its application and possibilities in clinical research. Preliminary studies on Crohn's disease", J Chromatogr, 440:261-273.
Waikar et al., 2012, "Imperfect gold standards for kidney injury biomarker evaluation", J Am Soc Nephrol., 23(1):13-21 (Epub 2011).
Zaccaria et al., 2015, "Accessing to the minor proteome of red blood cells through the influence of the nanoparticle surface properties on the corona composition", Int J Nanomedicine, 10:1869-1883.
Zecher et al., 2014, "Erythrocyte-derived microvesicles amplify systemic inflammation by thrombin-dependent activation of complement", Arterioscler Thromb Vasc Biol., 34(2):313-320 (Epub 2013).
Zeng et al., 2014, "Mechanical response of red blood cells entering a constriction", Biomicrofluidics, 8(6):064123.
Zhou et al., 2012, "Opsonization of malaria-infected erythrocytes activates the inflammasome and enhances inflammatory cytokine secretion by human macrophages", Malar J., 11:343 (13 pages).
International Search Report dated Feb. 28, 2018 for PCT/AU2017/000282.
Ayache S et al., "Effects of storage time and exogenous protease in inhibitors on plasma protein levels", American Journal of Clinical Pathology, 206, 126(2): 174-184 abstract pp. 175-176, whole document.
Li L et al.; "Development and characterization of dried blood spot materials for the measurement of immunoreactive trypsinogen" Journal of Medical Screening, 2006, 13(2):79-84 abstract, p. 80, whole document.
Oliveri E et al., "The effect of protease inhibitors on the two-dimensional electrophoresis pattern of red blood cell membranes", Electrophoresis, 2001, 22(3):560-565 abstract, p. 560-563, whole document.
D'Amici GM et al., "Proteomic analysis of RBC membrane protein degradation during blood storage", Journal of Proteome Research, 2007, 6(8):3242-3255, abstract, p. 3252, whole document.
Bowyer PW et al., "Global profiling of proteolysis during rupture of Plasmodium falciparum from the host erythrocyte", Molecular and Cellular Proteomics, 2011, 10(5):M110.001636 [retrieved from internet Feb. 22, 2018] <URL:http//www.mcponline.org/content/10/5/M110.001636.short> abstract, pp. 2, 3, 9, 11, figure 5, Supplement figures, whole document.
Official Action dated Oct. 26, 2022 in corresponding Chinese Application No. 201780087011.X (with English translation).
Official Action dated Jan. 24, 2023 in corresponding European Application No. 17882505.5.
Bütikofer, P. et al., "Modulation of red cell vesiculation by protease inhibitors", Biochimica et Biophysica Acta, 904:2 (Nov. 13, 1987) 259-267.
De Franceschi, Lucia et al., "Pharmacological inhibition of calpain-1 prevents red cell dehydration and reduces Gardos channel activity in a mouse model of sickle cell disease", The FASEB Journal, 27:2 (Oct. 19, 2012) 750-759.
Gov, N. et al., "Chapter 4: Cytoskeletal Control of Red Blood Cell Shape", Advances in Planar Lipid Bilayers and Liposomes, vol. 10 (Jan. 1, 2009) Elsevier Science & Technology, 95-119.
Anderson, H. Luke et al., "The Evolving Erythrocyte: Red Blood Cells as Modulators of Innate Immunity," J Immunol, (2018) 201(5):1343-1351.
Sut, Caroline et al., "Duration of Red Blood Cell Storage and Inflammatory Marker Generation," Blood Transfusion (2017) 15:145-152.

(56) References Cited

OTHER PUBLICATIONS

Watkins, Thomas et al., "Transfusion Indications for Patients with Cancer," *Cancer Control*, Jan. 2015, 22(1):38-46.

\* cited by examiner

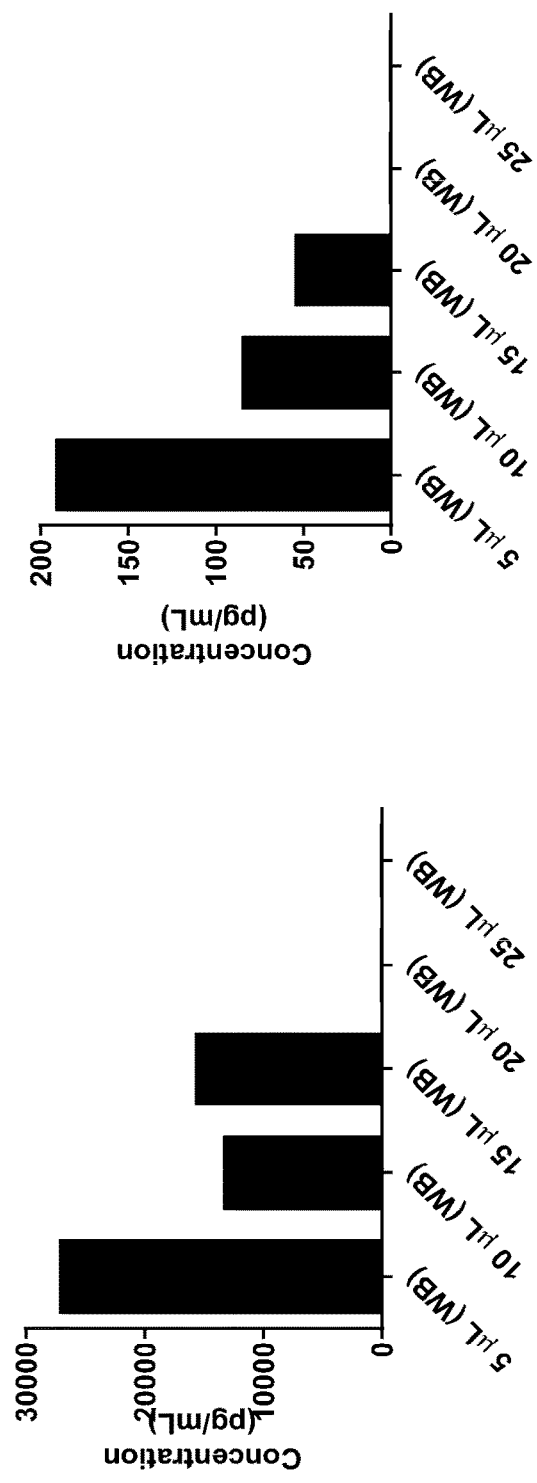
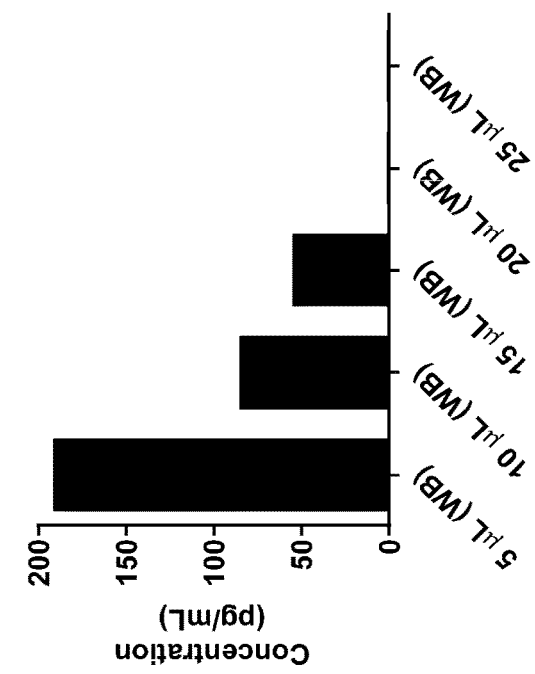
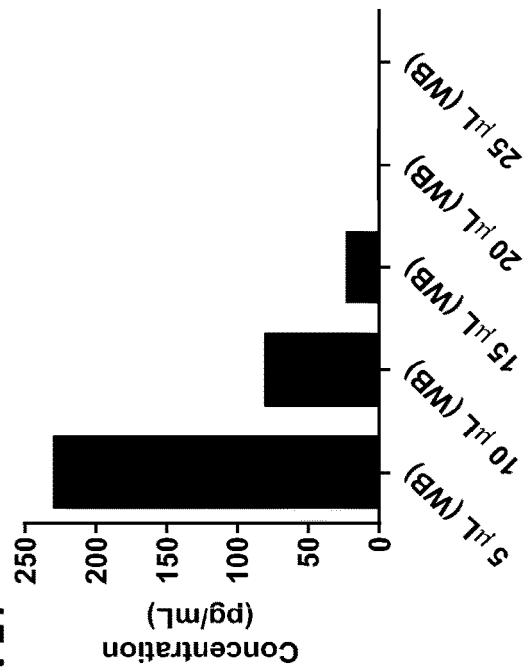
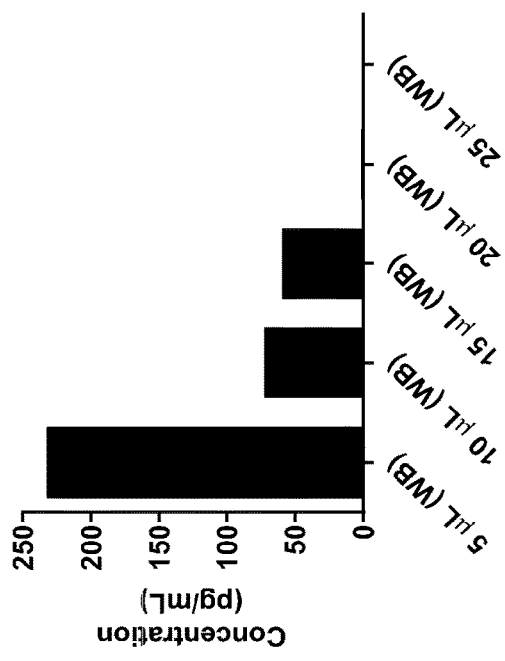
FIG. 1Q
FIG. 1R
FIG. 1S
FIG. 1T

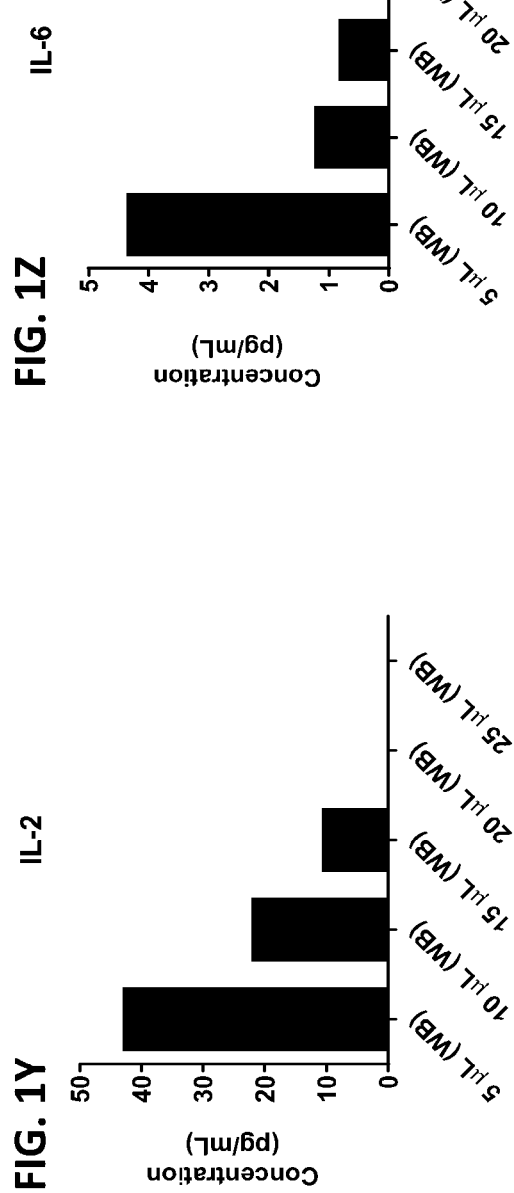
FIG. 1Y
FIG. 1Z
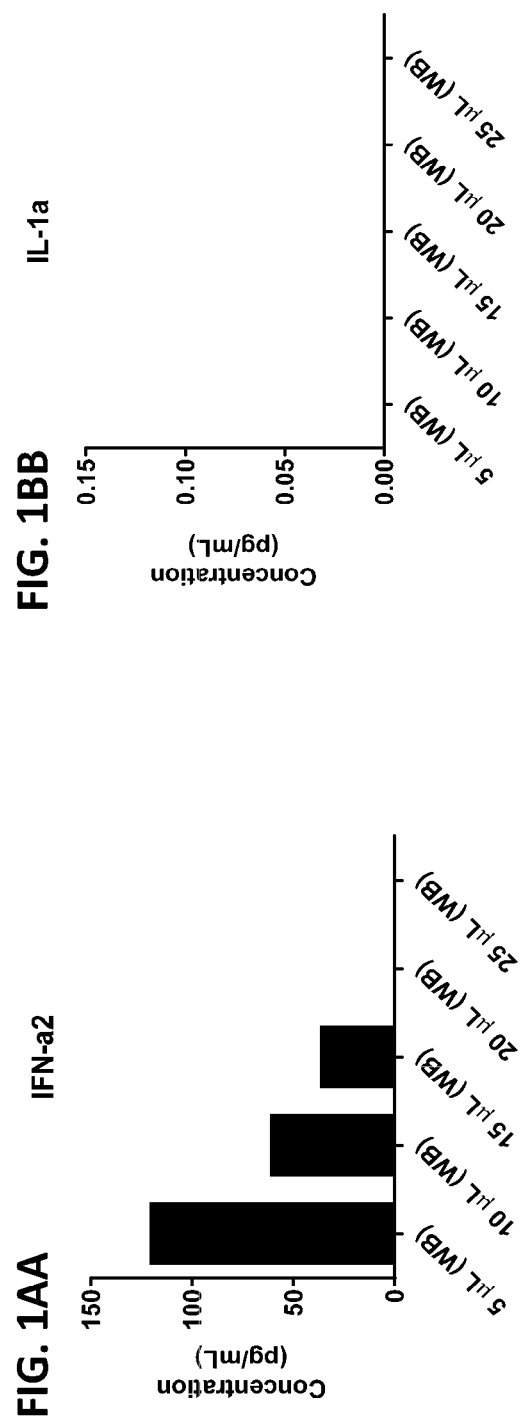
FIG. 1AA
FIG. 1BB

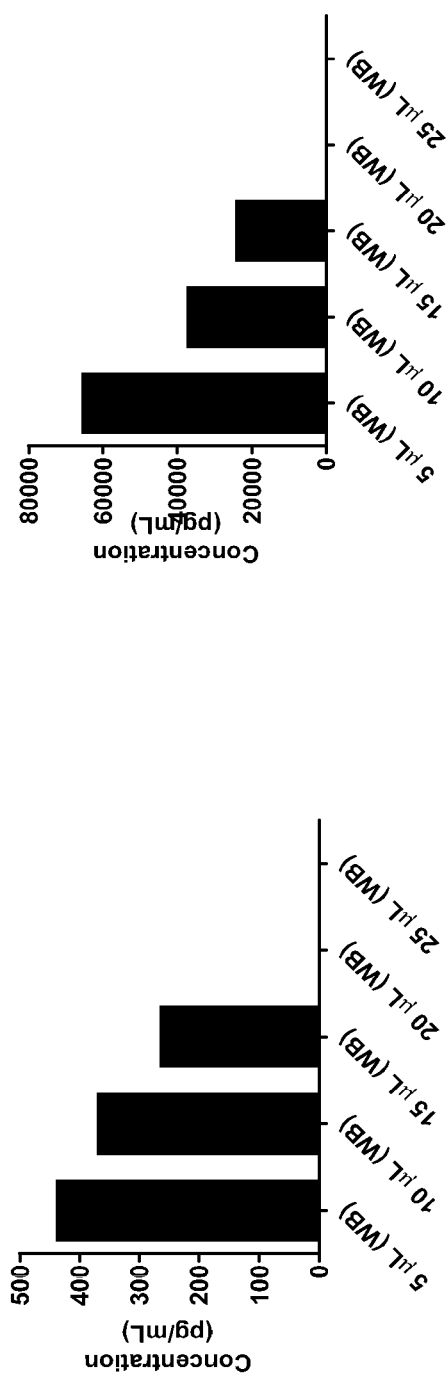
FIG. 1CC
FIG. 1DD
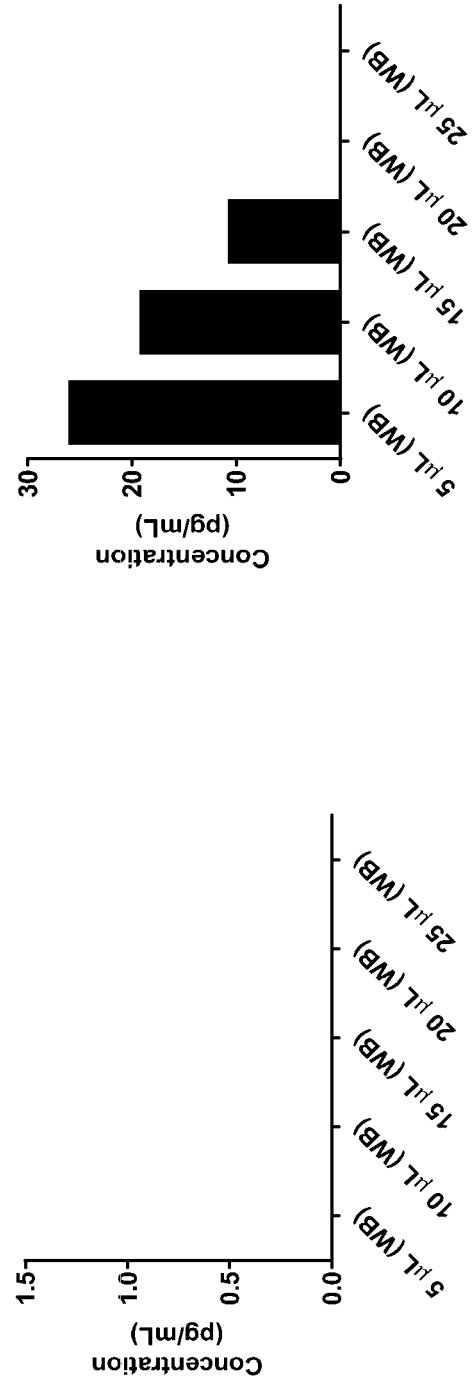
FIG. 1EE
FIG. 1FF

FIG. 5A

| Analyte | Plasma* pg/mL of whole blood | | | RBCs* pg/mL of whole blood | | | Fold change |
|---|---|---|---|---|---|---|---|
| | No. of subjects | Conc. | SD | No. of subjects | Conc. | SD | |
| | | | | Pro-inflammatory | | | |
| IFN-α2 | 3 | 24.4 | 18.9 | 3 | 251.5 | 32.4 | 14.97 |
| IFN-γ | 3 | 18.6 | 1.9 | 3 | 18.3 | 12.2 | 0.96 |
| IL-1α | 3 | 3.6 | 6.2 | 3 | 35.9 | 44.3 | 156.39 |
| IL-1β | 3 | 0.3 | 0.1 | 3 | 1.9 | 1.5 | 7.28 |
| IL-5 | 3 | 2.7 | 0.4 | 0 | - | - | - |
| IL-8 | 3 | 5.5 | 6.2 | 2 | 31.9 | 41.8 | 1.93 |
| IL-9 | 3 | 2.6 | 0.8 | 2 | 7.8 | 2.5 | 2.10 |
| IL-12(p70) | 3 | 5.2 | 5.6 | 3 | 15.3 | 5.6 | 6.11 |
| IL-15 | 3 | 1.3 | 0.7 | 3 | 53.6 | 20.3 | 62.29 |
| IL-17 | 3 | 19.1 | 14.4 | 3 | 132.8 | 26.2 | 9.75 |
| IL-18 | 3 | 67.0 | 91.9 | 3 | 1209.7 | 535.3 | 79.51 |
| MIF | 3 | 45.5 | 47.2 | 3 | 8348.1 | 4259.3 | 280.31 |
| TNF-α | 3 | 7.0 | 1.3 | 2 | 8.5 | 6.0 | 0.83 |
| TNF-β | 1 | 77.24 | - | 0 | - | - | - |
| TRAIL | 3 | 29.9 | 31.2 | 0 | - | - | - |

FIG. 5B

| Analyte | Plasma* | | | RBCs* | | | Fold change |
|---|---|---|---|---|---|---|---|
| | No. of subjects | pg/mL of whole blood | | No. of subjects | pg/mL of whole blood | | |
| | | Conc. | SD | | Conc. | SD | |
| Anti-inflammatory | | | | | | | |
| IL-1ra | 3 | 13.1 | 0.9 | 3 | 1182.4 | 970.5 | 87.35 |
| IL2-ra | 3 | 87.3 | 93.7 | 3 | 108.5 | 73.6 | 2.63 |
| IL-4 | 3 | 0.3 | 0.1 | - | - | - | - |
| IL-10 | 3 | 2.3 | 3.0 | 3 | 19.0 | 6.0 | 118.47 |
| IL-13 | 3 | 2.2 | 2.5 | 3 | 2.4 | 1.4 | 3.42 |
| Chemokines | | | | | | | |
| CTACK | 3 | 65.9 | 76.9 | 1 | 64.9 | - | 1.81 |
| Eotaxin | 3 | 20.9 | 26.3 | 3 | 38.6 | 23.1 | 3.67 |
| GRO-α | 3 | 32.9 | 33.7 | 3 | 217.6 | 98.0 | 10.11 |
| IL-16 | 3 | 361.8 | 461.0 | 3 | 3563.4 | 3915.3 | 12.29 |
| MCP-1 | 3 | 7.0 | 7.8 | 3 | 285.2 | 63.1 | 95.56 |
| MCP-3 | 2 | 6.3 | 6.5 | 0 | - | - | - |
| MIG | 3 | 249.7 | 285.1 | 0 | - | - | - |
| MIP-1α | 3 | 1.8 | 1.8 | 3 | 3.0 | 2.4 | 3.76 |
| MIP-1β | 3 | 10.4 | 8.2 | 3 | 4.6 | 1.8 | 0.87 |
| RANTES | 3 | 415.3 | 58.0 | 3 | 1717.1 | 398.8 | 4.10 |
| SDF-1α | 3 | 65.7 | 25.0 | 2 | 246.5 | 231.5 | 2.82 |

FIG. 5C

| Analyte | Plasma* | | | RBCs* | | | Fold change |
|---|---|---|---|---|---|---|---|
| | No. of subjects | pg/mL of whole blood | | No. of subjects | pg/mL of whole blood | | |
| | | Conc. | SD | | Conc. | SD | |
| Anti-inflammatory | | | | | | | |
| IL-1ra | 3 | 13.1 | 0.9 | 3 | 1182.4 | 970.5 | 87.35 |
| IL2-ra | 3 | 87.3 | 93.7 | 3 | 108.5 | 73.6 | 2.63 |
| IL-4 | 3 | 0.3 | 0.1 | - | - | - | - |
| IL-10 | 3 | 2.3 | 3.0 | 3 | 19.0 | 6.0 | 118.47 |
| IL-13 | 3 | 2.2 | 2.5 | 3 | 2.4 | 1.4 | 3.42 |
| Chemokines | | | | | | | |
| CTACK | 3 | 65.9 | 76.9 | 1 | 64.9 | - | 1.81 |
| Eotaxin | 3 | 20.9 | 26.3 | 3 | 38.6 | 23.1 | 3.67 |
| GRO-α | 3 | 32.9 | 33.7 | 3 | 217.6 | 98.0 | 10.11 |
| IL-16 | 3 | 361.8 | 461.0 | 3 | 3563.4 | 3915.3 | 12.29 |
| MCP-1 | 3 | 7.0 | 7.8 | 3 | 285.2 | 63.1 | 95.56 |
| MCP-3 | 2 | 6.3 | 6.5 | 0 | - | - | - |
| MIG | 3 | 249.7 | 285.1 | 0 | - | - | - |
| MIP-1α | 3 | 1.8 | 1.8 | 3 | 3.0 | 2.4 | 3.76 |
| MIP-1β | 3 | 10.4 | 8.2 | 3 | 4.6 | 1.8 | 0.87 |
| RANTES | 3 | 415.3 | 58.0 | 3 | 1717.1 | 398.8 | 4.10 |
| SDF-1α | 3 | 65.7 | 25.0 | 2 | 246.5 | 231.5 | 2.82 |

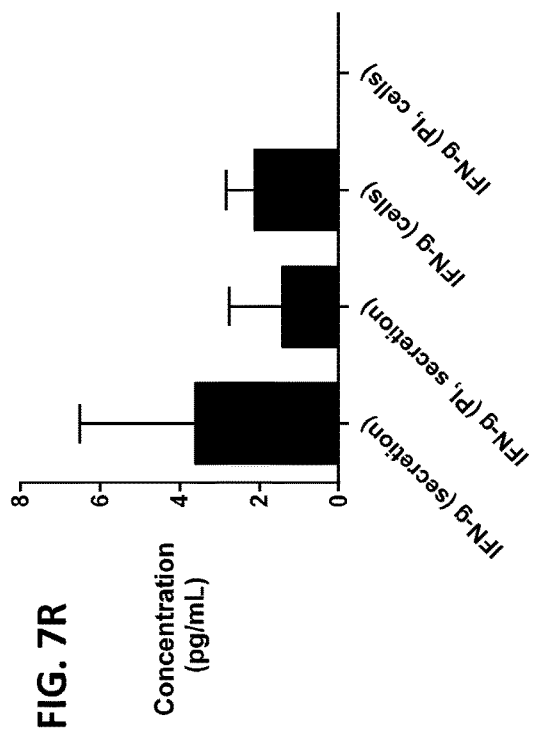
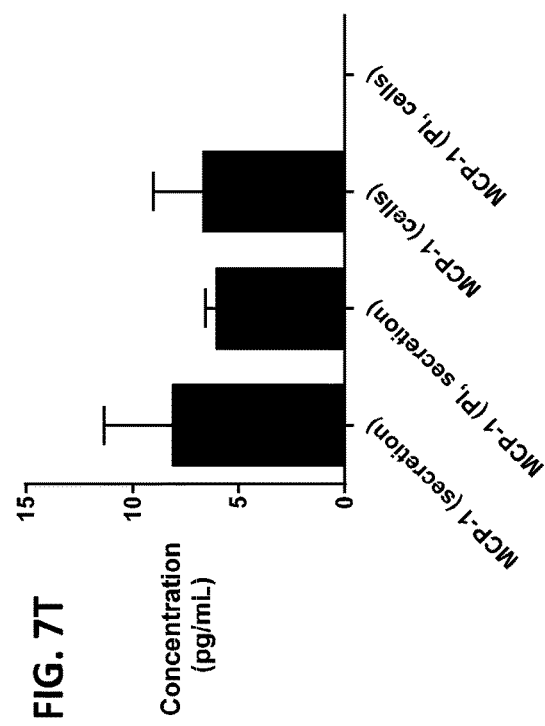
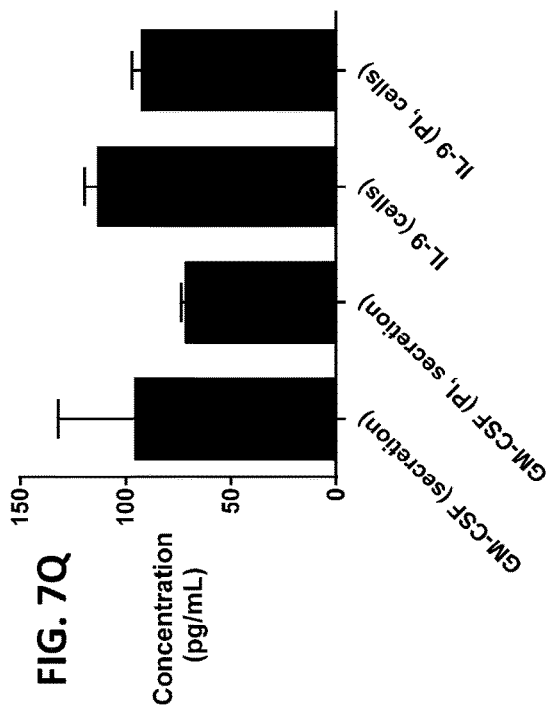
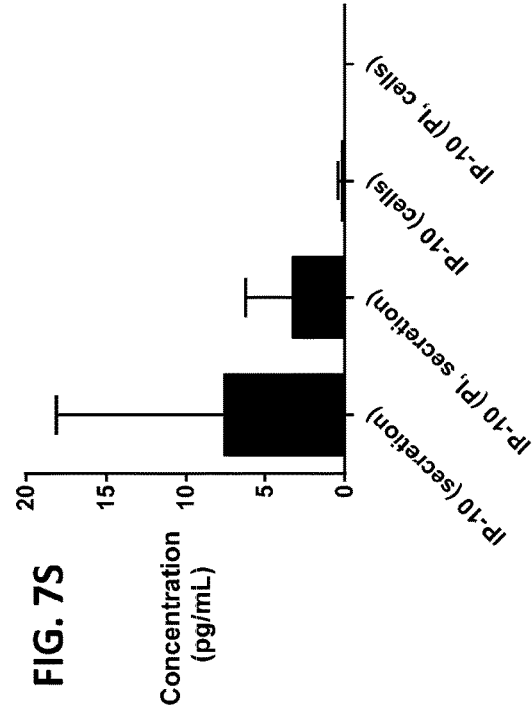

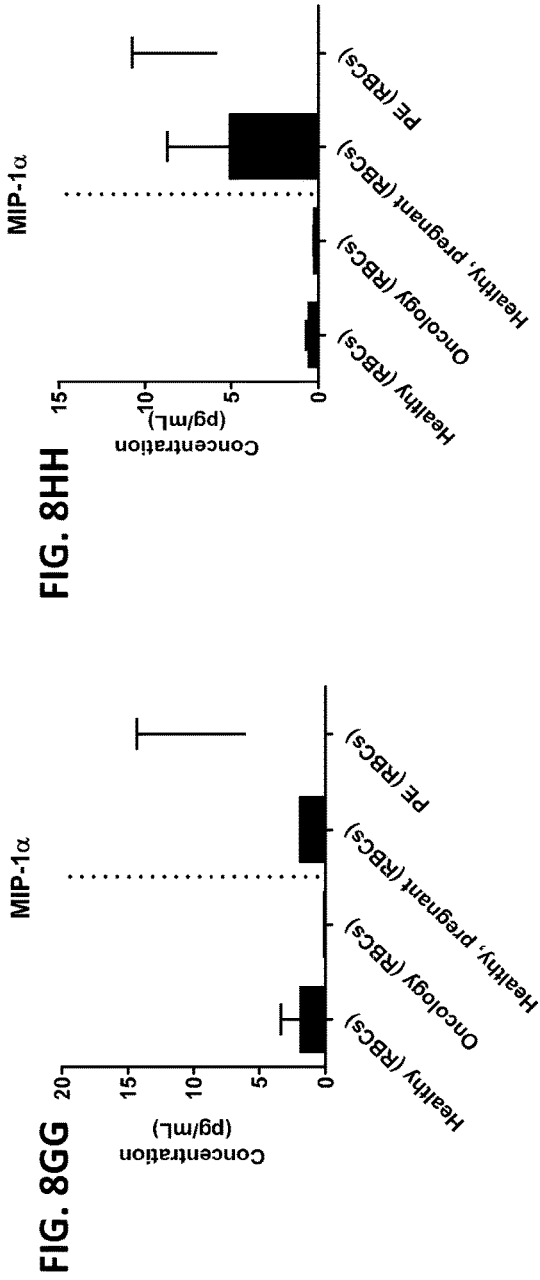
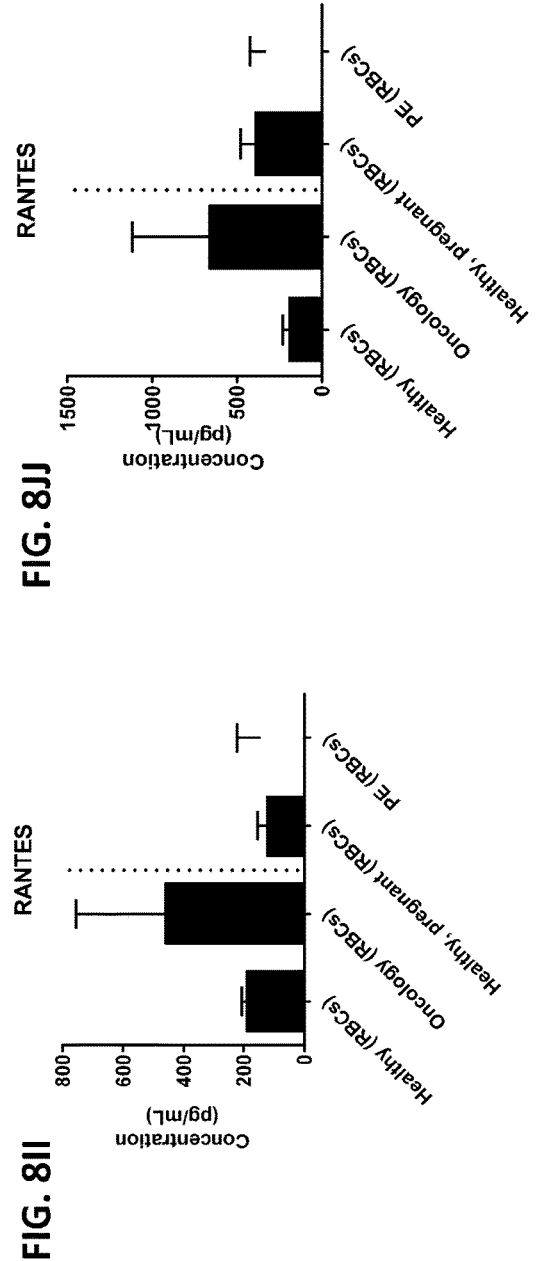
FIG. 8GG
FIG. 8HH
FIG. 8II
FIG. 8JJ

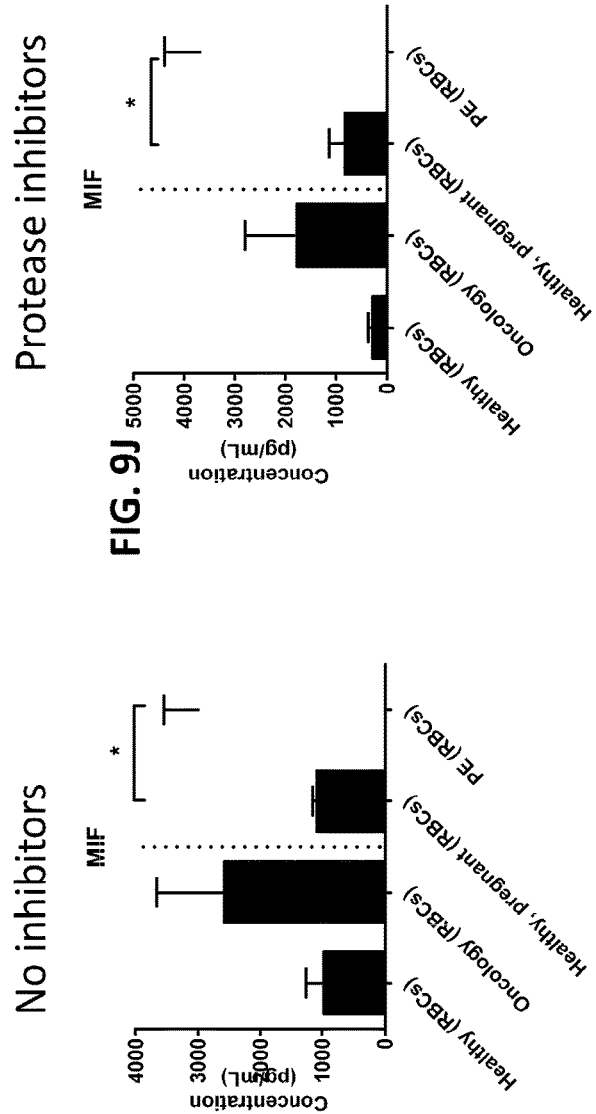
FIG. 9J
FIG. 9I
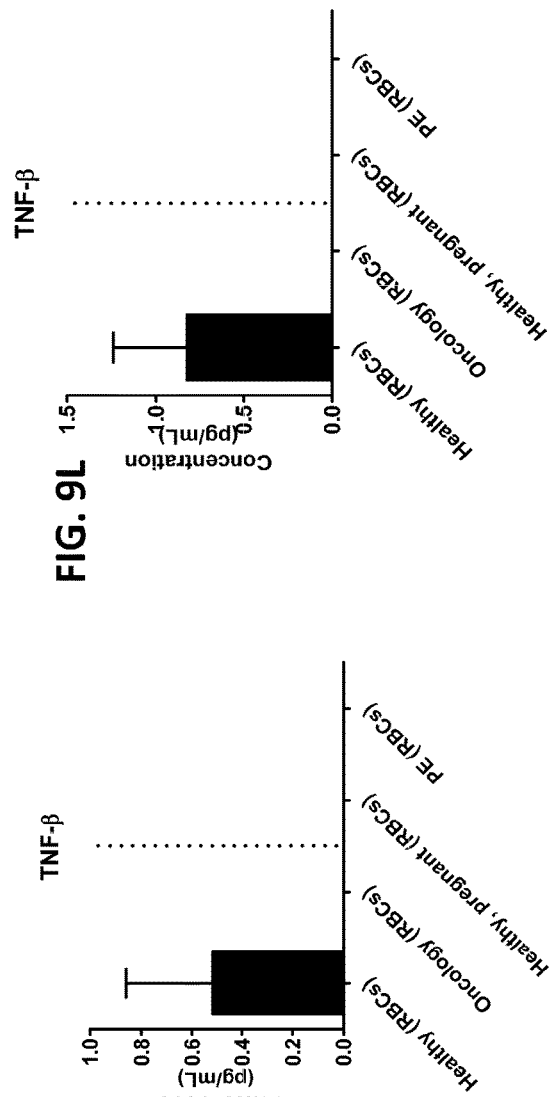
FIG. 9L
FIG. 9K

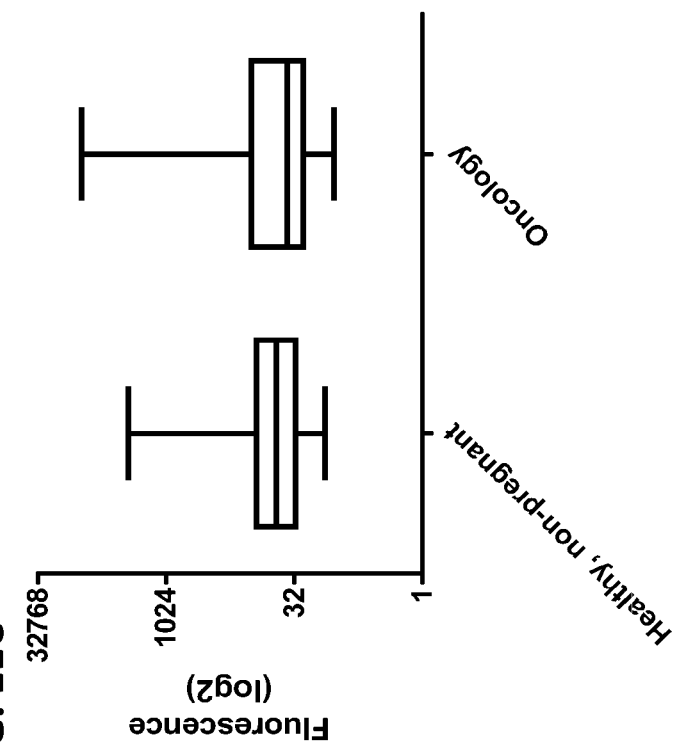
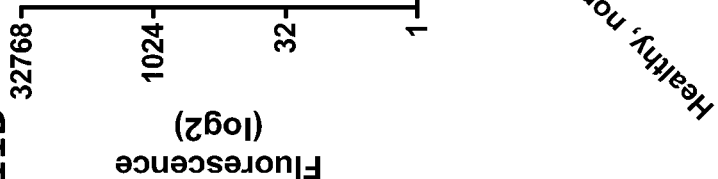
FIG. 11D
FIG. 11C

BLOOD PROFILING WITH PROTEASE INHIBITORS

CROSS REFERENCE TO RELATED APPLICATION

This application is the National Phase application of International Application No. PCT/AU2017/000282, filed Dec. 18, 2017, which designates the United States and was, published in English. This application also claims the benefit of priority from (1) U.S. Provisional Application No. 62/436,875 entitled "Blood Profiling with Protease Inhibitors" filed 20 Dec. 2016, (2) U.S. Provisional Application No. 62/482,582 entitled "Blood Profiling with Protease Inhibitors" filed 6 Apr. 2017, and (3) U.S. Provisional Application No. 62/523,489 entitled "Blood Profiling with Protease Inhibitors" filed 22 Jun. 2017. Each of the foregoing related applications, in their entirety, are incorporated herein by reference.

In addition, each of the following applications, in their entirety, are incorporated herein by reference: (1) Australian Application No. 2015904075 entitled "Blood Preparation and Profiling" filed 7 Oct. 2015; (2) International Application No. PCT/AU2016/000341, entitled "Blood Preparation and Profiling", filed 6 Oct. 2016, and (3) Australian Application No. 2015905309 entitled "Therapeutic Methods Using Erythrocytes" filed 22 Dec. 2015. In addition, the other references or publications referred to in the present disclosure are also hereby incorporated by reference in their entirety.

TECHNICAL FIELD

The present disclosure relates generally to the field of haematology. The present disclosure relates to protein profiling in the blood and methods for producing and/or generating blood protein profiles, including, for example, cytokine and/or chemokine profiles, from red blood cell-enriched blood samples and/or red blood cell components.

BACKGROUND

Protein profiling of blood is used for a variety of purposes. For example, the profiling of indicative proteins in peripheral blood mononuclear cells (PBMC) and serum/plasma is commonly used in disease diagnosis. Additionally, monitoring protein profiles within the blood may assist in directing more effective therapeutic interventions by providing a way of monitoring responsiveness to treatment and an indication of remission or regression.

Biological markers found in blood such as cytokines, chemokines and growth factors may provide insight into inflammation, immune responses, and repair. For example, the detection and quantification of pro- and/or anti-inflammatory cytokine and chemokine levels in blood is employed to gauge immune status. These cytokines and chemokines may be used to diagnose certain disease states, determine a predisposition to developing disease, and/or to predict prognostic outcomes. However, identifying proteins to serve as biological markers for various diseases can be time consuming and labor intensive.

Typically, the detection and quantification of various proteins in the blood may be performed using isolated serum/plasma, and/or PBMCs. Erythrocytes/red blood cells (RBCs), which are an abundant cellular component of blood and account typically for 40% to 50% of its volume, are routinely removed and discarded prior to conducting blood protein analyses because they are thought to, among other things, complicate current processing and assaying methods for blood. RBCs are also not believed to provide a significant contribution to the overall protein profile of the blood. Still, reliance on the less abundant blood components like plasma/serum and PBMCs to assay for blood proteins may, for example, increase inaccuracies in blood protein profiles and limit the ability to detect proteins and/or differences in protein levels under various circumstances. There are advantages to using RBCs in protein profiling and other evaluations of proteins from blood samples that have not been fully appreciated to date by those of ordinary skill in the art.

The present disclosure is directed to solving these and other problems disclosed herein. The present disclosure is also directed to overcoming and/or ameliorating at least one of the disadvantages of the prior art as will become apparent from the discussion herein. The present disclosure is also directed to pointing out one or more advantages to using RBCs.

SUMMARY OF THE DISCLOSURE

The present disclosure is directed to solving some of the aforementioned problems with blood protein profiles, surprisingly finding that RBCs are a source of a number of different proteins (e.g., cytokines, chemokines, and/or growth factors) at substantial levels. Moreover, the present inventors have found, among other things, that the addition of protease inhibitors to a red blood cell sample modulates the levels of various proteins in samples from those having a disease or disorder, yet does not similarly modulate the levels of those proteins in red blood cell samples from those not having the disease or disorder. Thus, the present inventors have created, among other things, new and useful laboratory techniques for producing a protein profile from whole blood, an enriched red blood cell sample and/or red blood cell components by evaluating the presence, level, or change in level of proteins in RBCs that have been contacted with various protease inhibitors. The new and useful laboratory techniques are an improvement over current techniques for producing a protein profile from blood and/or detecting a disease or disorder by increasing the ability to detect proteins and/or differentiate between those having a disease or disorder and healthy individuals. The present disclosure provides, among other things, improved methods, kits, and/or systems for producing protein profiles from whole blood, a red blood cell-enriched sample, red blood cell-enriched fraction, and/or red blood cell components using protease inhibitors, thereby providing one or more advantages including, but not limited to, reducing inaccuracies in protein detection and increasing protein detection and differential expression in relevant blood samples.

Certain non-limiting embodiments of the present disclosure are disclosed herein.

Certain embodiment are to methods for producing a protein profile, the methods comprising obtaining a blood sample; obtaining a red blood cell component from the blood sample; measuring the level of one or more proteins from the red blood cell component; contacting the red blood cell component with one or more protease inhibitors;

measuring the level of the one or more proteins from the red blood cell component contacted with the one or more protease inhibitors; and determining the change in the level of the one or more proteins from the red blood cell component before and after being contacted with the one or more protease inhibitors, wherein the protein profile produced comprises one or more proteins having a change in level before and after the red blood cell component is contacted with the one or more protease inhibitors.

Certain embodiments are to methods of producing a protein profile, the methods comprising obtaining blood sample or a red blood cell component from a blood sample; obtaining a first and second portion from the blood sample or the red blood cell component; contacting the second portion from the blood sample or the red blood cell component with one or more protease inhibitors; measuring the level of one or more proteins from the first and second portions of the blood sample or the red blood cell component, wherein the first portion has not been contacted with the one or more protease inhibitors; and determining the change in the level of the one or more proteins from the first portion of the blood sample or the red blood cell component and the second portion of the blood sample or the red blood cell component, wherein the protein profile produced comprises one or more proteins having a change in level of the one or more proteins from first portion of the blood sample or the red blood cell component and the second portion of the blood sample or the red blood cell component. In some embodiments, both a blood sample and a red blood cell component are obtained.

Certain embodiments are to methods of producing a protein profile, the methods comprising obtaining a blood sample that is from a subject not having a disease or disorder; obtaining a red blood cell component from the blood sample; measuring the level of one or more proteins from the red blood cell component; contacting the red blood cell component with one or more protease inhibitors; measuring the level of the one or more proteins from the red blood cell component contacted with the one or more protease inhibitors; and determining the change in the level of the one or more proteins from the red blood cell component before and after being contacted with the one or more protease inhibitors, wherein the protein profile produced comprises the change in the level of the one or more proteins from the red blood cell component before and after being contacted with one or more protease inhibitors.

Certain embodiments are to methods of producing a disease protein profile, the methods comprising obtaining from a subject having a disease or disorder a first protein profile produced according to one or more of the other embodiments; obtaining from a subject not having the disease or disorder a second protein profile produced according to one or more of the other embodiments, wherein the second protein profile is obtained from the same red blood cell component the first protein profile was obtained from; and comparing the difference between the change in the level of one or more proteins from the subject having the disease or disorder to the change in the level of the one or more proteins from the subject not having the disease or disorder, wherein the disease protein profile produced comprises one or more proteins for which there is a difference between the change in the level of the one or more proteins from the subject having the disease or disorder and the change in the level of the one or more proteins from the subject not having the disease or disorder.

In some embodiments, the red blood cell component is obtained from whole blood or isolated red blood cells. In other embodiments, the red blood cell component is red blood cells or red blood cell membranes. In other embodiments, the level of two or more proteins, three or more proteins, four or more proteins, five or more proteins, six or more proteins, seven or more proteins, eight or more proteins, nine or more proteins, or ten or more proteins is measured. In certain embodiments, the level of three or more proteins is measured. In certain other embodiments, the red blood cell component is contacted with one or more protease inhibitors, two or more protease inhibitors, three or more protease inhibitors, four or more protease inhibitors, five or more protease inhibitors, six or more protease inhibitors, seven or more protease inhibitors, eight or more protease inhibitors, nine or more protease inhibitors, or ten or more protease inhibitors. In other embodiments, the red blood component is contacted with a protease inhibitor cocktail comprising at least two protease inhibitors. In certain embodiments, the red blood cell component is contacted with the protease inhibitor cocktail A8127s. In some embodiments, the one or more protease inhibitors are selected from the group consisting of serine protease inhibitors, cysteine protease inhibitors, metalloprotease inhibitors, aspartic protease inhibitors, and aminopeptidase inhibitors. In other embodiments, the change in the level of the one or more proteins is determined by a statistical analysis selected from the group consisting of a Student T's test, an ANOVA test, a mixed-effects model, a Mann-Whitney test, a Wilcoxon rank sum, and a Spermans rank correlation. In certain embodiments, the change in the level of the one or more proteins is a fold change between 0-fold and 5-fold. In still other embodiments, the difference between the change in the level of the one or more proteins from the subject having a disease or disorder and the change in the level of the one or more proteins from the subject not having the disease or disorder is determined by a statistical analysis selected from the group consisting of a Student T's test, an ANOVA test, a mixed-effects model, a Mann-Whitney test, a Wilcoxon rank sum, and a Spermans rank correlation. In yet other embodiments, the difference between the change in the level of the one or more proteins from the subject having a disease or disorder and the change in the level of the one or more proteins from the subject not having the disease or disorder is an increase in the change in the level or a decrease in the change in the level. In certain other embodiments, the subject is a human or a non-human animal. In some embodiments, the level of the one or more proteins is measured using one or more antibodies. In other embodiments, the one or more proteins are selected from the group consisting of chemokines, cytokines, growth factors, receptors, intracellular signal transmitters, hormones, nuclear transcription factors, neurotransmitters, extracellular matrix components, glycoproteins, inflammatory proteins, and enzymes. In certain embodiments, the one or more proteins are selected from the group consisting of the proteins listed in Table 1 or the proteins listed in Table 2. In some embodiments, the disease or disorder is preeclampsia. In certain embodiments, the disease protein profile is a preeclampsia protein profile comprising one or more proteins selected from the group consisting of IL-1$\beta$, IL-8, TNF-$\alpha$, IL-1ra, MCP-1, G-CSG, GM-CSF, IL-6, IFN$\alpha$2, IL-1a, IL-18, MIF, IL-2ra, and HGF. In other embodiments, the disease or disorder is colorectal cancer. In still other embodiments, the disease protein profile is a cancer protein profile comprising one or more proteins selected from the group consisting of IL-6, IFN-$\gamma$, IL-4, IL-13, MIF, Eotaxin, RANTES, IL-7, IP-10, PDGF, and IL-12p40.

Certain embodiments are to methods of monitoring a disease or disorder in a subject, the methods comprising obtaining from the subject having a disease or disorder a first blood sample at a first point in time and a second blood sample at a second point in time; measuring the level of at least one protein from a disease protein profile produced according to one or more of the other embodiments for the disease or disorder in the first blood sample and second blood sample; and determining the difference between the change in the level of the at least one protein in the first blood sample and second blood sample, wherein a difference between the change in the level of the at least one protein in the first blood sample and second blood sample indicates a change in the disease or disorder.

Certain embodiments are to methods of monitoring the effect of a treatment in a subject, the methods comprising obtaining from the subject a first protein profile produced according to one or more of the other embodiments at a first point in time and a second protein profile produced according to one or more of the other embodiments at a second point in time; and comparing the change in the level of at least one protein from the first protein profile to the change in the level of the at least one protein from the second protein profile, wherein a difference between the change in the level of the at least one protein from the first protein profile and the change in the level of the at least one protein from the second protein profile indicates an effect of the treatment. In certain embodiments, the first point in time is before treatment and the second point in time is after treatment. In some embodiments, the first point in time is before treatment and the second point in time is during treatment. In other embodiments, the first point in time and the second point in time are during treatment. In still other embodiments, the first point in time is during treatment and the second point in time is after treatment. In other embodiments, the first point in time and the second point in time are after treatment. In yet other embodiments, the subject has received the same treatment. In other embodiments, the subject has received a different treatment. In certain embodiments, the blood sample is a small volume blood sample. In other embodiments, the subject is monitored a number of times selected from the group consisting of one or more times per day, two or more times per day, three or more times per day, four or more times per day, and five or more times per day. In still other embodiments, the subject is monitored a number of times selected from the group consisting of one or more times per week, two or more times per week, three or more times per week, four or more times per week, five or more times per week, six or more times per week, and seven or more times per week. In certain embodiments, the subject is monitored daily. In some embodiments, the subject is monitored a number of times selected from the group consisting of once a week, once every two weeks, once every three weeks, and once every four weeks.

Certain embodiments are to methods of diagnosing a disease or disorder, the methods comprising obtaining at least one disease protein profile produced according to one or more of the other embodiments; obtaining a blood sample that is from a subject; obtaining a red blood cell component from the blood sample; contacting at least a first portion of the red blood component with one or more protease inhibitors; measuring the level of at least one protein from the disease protein profile in the first portion of the red blood component and the level of the at least one protein in a second portion of the red blood component that has not been contacted with the one or more protease inhibitors; determining the change in the level between the at least one protein in the first portion of the red blood component and the at least one protein in a second portion of the red blood component; and comparing the change in the level between the at least one protein in the first portion of the red blood cell component and the second portion of the red blood cell component to the change in level of the at least one protein in the disease protein profile, wherein a same or similar change in the level of the at least one protein in the first portion of the red blood cell component and the second portion of the red blood cell component compared to the change in level of the at least one protein in the disease protein profile indicates that the subject has the disease or disorder.

Certain embodiments are to methods of diagnosing a disease or disorder in a subject, the methods comprising obtaining at least one protein profile for the subject produced according to one or more of the other embodiments; and comparing the change in the level of at least one protein from the at least one protein profile to the change in the level of the at least one protein from a disease protein profile produced according to one or more of the other embodiments, wherein a same or similar change in level of the at least one protein from the at least one protein profile for the subject to the change in the level of the at least one protein from the disease protein profile indicates that the subject has the disease or disorder.

Certain embodiments are to methods of diagnosing a disease or disorder in a subject, the methods comprising obtaining at least one protein profile produced according to one or more of the other embodiments for the subject; obtaining at least one protein profile produced according to one or more of the other embodiments for a subject not having a disease or disorder; and comparing the change in the level of at least one protein from the at least one protein profile for the subject to the change in the level of the at least one protein from the at least one protein profile produced according to one or more of the other embodiments for a subject not having a disease or disorder, wherein a difference between the change in the level of the at least one protein from the at least one protein profile for the subject and the change in the level of the at least one protein from the at least one protein profile produced according one or more of the other embodiments for a subject not having a disease or disorder indicates that the subject has the disease or disorder.

Certain embodiments are to kits for producing a protein profile of a blood sample, the kits comprising at least one reagent to obtain a red blood cell component; one or more protease inhibitors; and at least one reagent to measure the level of one or more proteins from the red blood cell component. In certain embodiments, the kit further comprises at least one reagent to obtain a blood sample from a subject. In other embodiments, the reagent to measure the level of one or more proteins is one or more antibodies. In still other embodiments, the reagent to detect the measure the level of one or more proteins is an enzyme-linked immunosorbent assay (ELISA) apparatus. In other embodiments, the one or more protease inhibitors comprise a protease inhibitor cocktail. In yet other embodiments, the protease inhibitor cocktail is A8127s.

Certain embodiments are to methods for producing a protein profile, the methods comprising obtaining a blood sample from a subject having a disease or disorder; leukodepleting at least a portion of the blood sample to produce a red blood cell-enriched sample; contacting the red blood cell-enriched sample with one or more protease inhibitors; and detecting the presence of one or more proteins in the red blood cell-enriched sample, wherein the protein profile produced comprises one or more proteins detected in the red blood cell-enriched sample.

Certain embodiments are to methods of producing a protein profile, the methods comprising obtaining a blood sample from a subject having a disease or disorder; leukodepleting at least a portion of the blood sample to produce a red blood cell-enriched sample; isolating red blood cells and plasma in the red blood cell-enriched sample; contacting the red blood cells with one or more protease inhibitors; measuring the level of one or more proteins in the red blood cells and the level of the one or more proteins in the plasma; and calculating a protein ratio comprising the level of the one or more proteins in the red blood cells to the level of the one or more proteins in the plasma, wherein the protein profile produced comprises one or more proteins that have a protein ratio of at least 2:1. In some embodiments, the one or more proteins have a protein ratio selected from the group consisting of at least 3:1, at least 4:1, at least 5:1, at least 10:1, at least 15:1, and at least 20:1.

Certain embodiments are to methods of producing a protein profile comprising obtaining a blood sample from a subject having a disease or disorder; leukodepleting at least a portion of the blood sample to produce a red blood cell-enriched sample; incubating the red blood cells in the red blood cell-enriched sample in a medium containing one or more protease inhibitors; and detecting one or more proteins in the medium, wherein the protein profile produced comprises one or more proteins detected in the medium.

In certain embodiments, the methods further comprise measuring the level of the one or more proteins detected in the red blood cell-enriched sample or the medium. In some embodiments, the presence of two or more proteins, three or more proteins, four or more proteins, five or more proteins, six or more proteins, seven or more proteins, eight or more proteins, nine or more proteins, or ten or more proteins, eleven or more proteins, twelve or more proteins, thirteen or more proteins, fourteen or more proteins, or fifteen or more proteins is detected or the level of two or more proteins, three or more proteins, four or more proteins, five or more proteins, six or more proteins, seven or more proteins, eight or more proteins, nine or more proteins, ten or more proteins, eleven or more proteins, twelve or more proteins, thirteen or more proteins, fourteen or more proteins, or fifteen or more proteins is measured. In some embodiments, the presence of three or more proteins is detected or the level of three or more proteins is measured. In other embodiments, the red blood cell-enriched sample is contacted with two or more protease inhibitors, three or more protease inhibitors, four or more protease inhibitors, five or more protease inhibitors, six or more protease inhibitors, seven or more protease inhibitors, eight or more protease inhibitors, nine or more protease inhibitors, or ten or more protease inhibitors. In other embodiments, the red blood cell-enriched sample is contacted with three or more protease inhibitors. In other embodiments, the red blood cell-enriched sample is contacted with three or more protease inhibitors and the presence of two or more proteins is detected or the level of two or more proteins is measured. In still other embodiments, the red blood cell-enriched sample is contacted with two or more protease inhibitors and the presence of three or more proteins is detected or the level of three or more proteins is measured. In certain embodiments, the one or more protease inhibitors are selected from the group consisting of serine protease inhibitors, cysteine protease iii inhibitors, metalloprotease inhibitors, and aspartic protease inhibitors.

In other embodiments, the subject is a human or a non-human animal. In still other embodiments, the presence of one or more proteins is detected or the level of one or more proteins is measured using one or more antibodies. In certain other embodiments, the one or more proteins are selected from the group consisting of chemokines, cytokines, growth factors, receptors, intracellular signal transmitters, hormones, nuclear transcription factors, neurotransmitters, and extracellular matrix components, and enzymes. In other embodiments, the one or more proteins are selected from the group consisting of the proteins listed in Table 1 or the proteins listed in Table 2. In some embodiments, the blood sample is leukodepleted by one or more methods selected from the group consisting of flow cytometry, magnetic bead separation, centrifugation, cellulose column, and dextran sedimentation. In some embodiments, the red blood cells are leukodepleted by dextran sedimentation.

Certain embodiments are to methods of monitoring a disease or disorder in a subject comprising obtaining at least one protein profile produced according to one or more of the other embodiments disclosed herein from the subject at a first point in time and a second point in time; and comparing the at least one protein profile of the subject at the first point in time to the at least one protein profile of the subject at the second point in time, wherein a difference in the presence or level of one or more proteins in the at least one protein profile of the subject at the first point in time compared to the at least one protein profile of the subject at the second point in time indicates a change in the disease or disorder.

Certain embodiments are to methods of monitoring treatment in a subject comprising obtaining at least one protein profile produced, according to the one or more of the other embodiments, from a subject before treatment and after treatment; and comparing the at least one protein profile of the subject before treatment to the at least one protein profile of the subject after treatment, wherein a difference in the presence or level of one or more proteins in the at least one protein profile of the subject before treatment compared to the at least one protein profile of the subject after treatment indicates an effect of the treatment on the subject. In some embodiments, the at least one protein profile of a subject who has received no treatment is compared to the at least one protein profile of the subject after receiving treatment. In some embodiments, the at least one protein profile of a subject who has received substantially no or little treatment is compared to the at least one protein profile of the subject after receiving treatment. In some embodiments, the at least one protein profile of a subject after treatment at one point in time is compared to the at least one protein profile of the subject after treatment at a different point in time. In other embodiments, the subject has received the same treatment. In other embodiments, the subject has received substantially the same treatment or similar treatment. In still other embodiments, the subject has received a different treatment. In some embodiments, the blood sample is a small volume blood sample. In some embodiments, the subject is monitored a number of times selected from the group consisting of one or more times per day, two or more times per day, three or more times per day, four or more times per day, and five or more times per day. In other embodiments, the subject is monitored a number of times selected from the group consisting of one or more times per week, two or more times per week, three or more times per week, four or more times per week, five or more times per week, six or more times per week, and seven or more times per week. In certain embodiments, the subject is monitored daily. In other embodiments, the subject is monitored a number of times selected from the group consisting of once a week, once every two weeks, once every three weeks, and once every four weeks.

Certain embodiments are to methods of producing a disease protein profile comprising obtaining a blood sample from a subject having a disease or disorder; leukodepleting at least a portion of the blood sample to produce a red blood cell-enriched sample; contacting a first portion of the red blood cell-enriched sample with one or more protease inhibitors; measuring the level of one or more proteins in the first portion of the red blood cell-enriched sample and the level of the one or more proteins in a second portion of the red blood cell-enriched sample that has not been contacted with the one or more protease inhibitors; and comparing the level of the one or more proteins in the first portion of the red blood cell-enriched sample to the level of the one or more proteins in the second portion of the red blood cell-enriched sample, wherein the disease protein profile produced comprises one or more proteins that have a different level in the first portion of the red blood cell-enriched sample compared to the level of the one or more proteins in the second portion of the red blood cell-enriched sample. In some embodiments, the difference in the level of the one or more proteins in the first portion of the red blood cell-enriched sample compared to the level of the one or more proteins in the second portion of the red blood cell-enriched sample is determined by a statistical analysis selected from the group consisting of a Student T's test, an ANOVA test, a mixed-effects model, a Mann-Whitney test, a Wilcoxon rank sum, and a Spermans rank correlation. In some embodiments, the level of two or more proteins, three or more proteins, four or more proteins, five or more proteins, six or more proteins, seven or more proteins, eight or more proteins, nine or more proteins, or ten or more proteins is measured. In certain embodiments, the level of three or more proteins is measured. In some embodiments, the disease or disorder is preeclampsia. In other embodiments, the disease protein profile is a preeclampsia protein profile comprising one or more proteins selected from the group consisting of IL-1β, IL-8, TNF-α, IL-1ra, MCP-1, G-CSG, GM-CSF, IL-6, IFNα2, IL-1a, IL-18, MIF, IL-2ra, and HGF. In still other embodiments, the disease or disorder is cancer. In other embodiments, the disease protein profile is a cancer protein profile comprising one or more proteins selected from the group consisting of IL-6, IFN-γ, IL-4, IL-13, MIF, Eotaxin, RANTES, IL-7, IP-10, PDGF, and IL-12p40.

Certain embodiments are to methods for diagnosing a disease or disorder comprising obtaining a blood sample from a subject; leukodepleting at least a portion of the blood sample to produce a red blood cell-enriched sample; contacting at least a first portion of the red blood cell-enriched sample with one or more protease inhibitors; measuring the level of one or more proteins in the first portion of the red blood cell-enriched sample and the level of the one or more proteins in a second portion of the red blood cell-enriched sample that has not been contacted with the one or more protease inhibitors; and comparing the level of the one or more proteins in the first portion of the red blood cell-enriched sample to the level of the one or more proteins in the second portion of the red blood cell-enriched sample, wherein a difference in the level of one or more proteins in the first portion of the red blood cell-enriched sample compared to the level of the one or more proteins in the second portion of the red blood cell-enriched sample indicates the subject has the disease or disorder. In some embodiments, no difference in the level of the one or more proteins indicates the subject does not have the disease or disorder.

Certain embodiments are to methods of determining whether a subject has a disease or disorder comprising obtaining a blood sample from the subject; leukodepleting at least a portion of the blood sample to produce a red blood cell-enriched sample; contacting at least a first portion of the red blood cell-enriched sample with one or more protease inhibitors; measuring the level of one or more proteins in the first portion of the red blood cell-enriched sample and the level of the one or more proteins in a second portion of the red blood cell-enriched sample that has not been contacted with the one or more protease inhibitors; and comparing the level of the one or more proteins in the first portion of the red blood cell-enriched sample to the level of the one or more proteins in the second portion of the red blood cell-enriched sample, wherein no difference in the level of the one or more proteins in the first portion of the red blood cell-enriched sample compared to the level of the one or more proteins in the second portion of the red blood cell-enriched sample indicates that the subject does not have the disease or disorder.

Certain embodiments are to methods of diagnosing a disease or disorder in a subject comprising obtaining at least one protein profile from the subject produced according to the methods provided herein; and comparing the at least one protein profile to at least one disease protein profile, wherein the presence or level of one or more proteins in the at least one protein profile that is similar to the presence or level of the one or more proteins in the at least one disease protein profile indicates the subject has the disease or disorder. In some embodiments, the at least one disease protein profile obtained is produced according to the one or more of the methods provided herein.

Certain embodiments are to methods of diagnosing a disease or disorder in a subject comprising obtaining at least one protein profile from the subject produced according to the methods provided herein; obtaining at least one protein profile from one or more subjects not having the disease or disorder; and comparing the at least one protein profile obtained from the subject to the at least one protein profile obtained from one or more subjects not having the disease or disorder, wherein a difference in the presence or level of the one or more proteins in the at least one protein profile obtained from the subject compared to presence or level of the one or more proteins in the at least one protein profile obtained from one or more subjects not having the disease or disorder indicates that the subject has the disease or disorder.

Certain embodiments are to kits for producing a protein profile of a blood sample, the kit comprising at least one reagent to leukodeplete a blood sample and produce a red blood cell-enriched sample; one or more protease inhibitors; and at least one reagent to detect the presence or measure the level of one or more proteins in the red blood cell-enriched sample. In some embodiments, the kit further comprises at least one reagent to obtain a blood sample from a subject. In other embodiments, the reagent to detect the presence or measure the level of one or more proteins is one or more antibodies. In still other embodiments, the reagent to detect the presence or measure the level of one or more proteins is an enzyme-linked immunosorbent assay (ELISA) apparatus.

As well as the embodiments discussed in the summary, other embodiments are disclosed in the specification, drawings and claims. The summary is not meant to cover each and every embodiment; combination or variations are contemplated with the present disclosure.

BRIEF DESCRIPTION OF THE DRAWINGS

Embodiments of the present disclosure are described, by way of example only, with reference to the accompanying figures.

FIG. 5A-5C is a chart indicating the ratio of the levels of various proteins in red blood cells to the levels in plasma isolated from oncology patients.

FIG. 11A-11D is a series of graphs showing the difference in the cumulative data of cytokines released from red blood cells from healthy individuals, healthy pregnant women, pregnant women with preeclampsia, and oncology patients in the presence or absence of protease inhibitors (PI).

DEFINITIONS

Figure 1A:
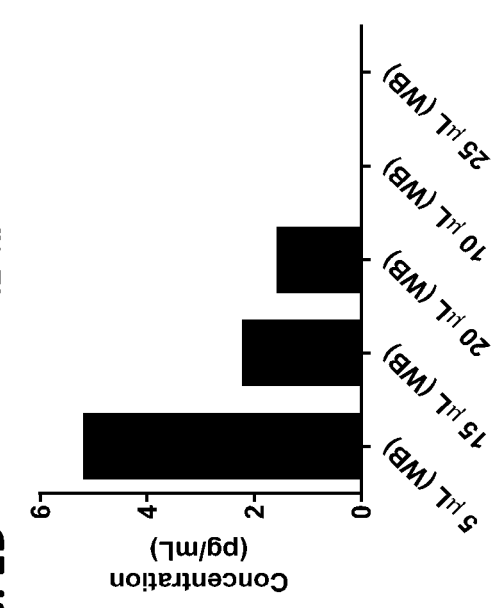
FIG. 1A-1TT is a series of graphs showing the levels of various proteins in small volumes of whole blood.
Figure 1B:
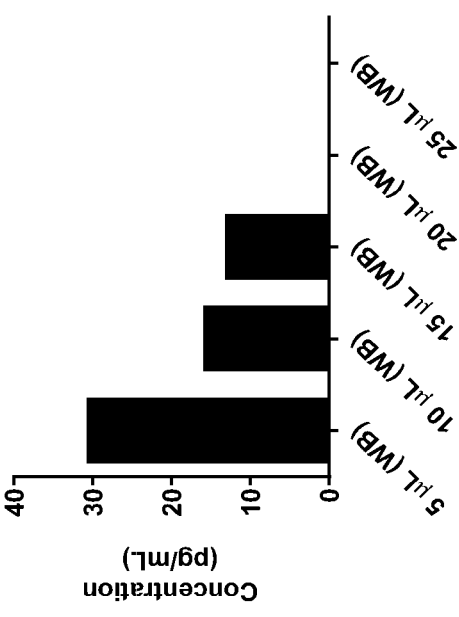
Figure 1C:
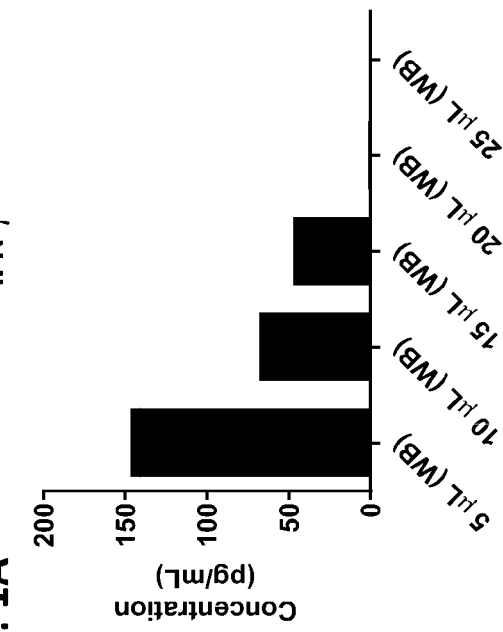
Figure 1D:
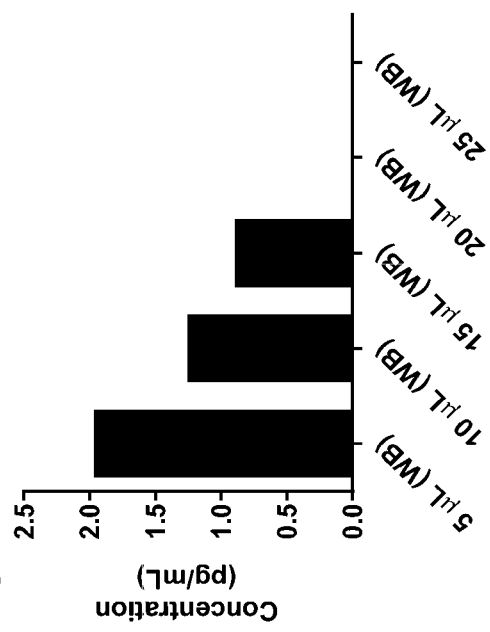
Figure 1F:
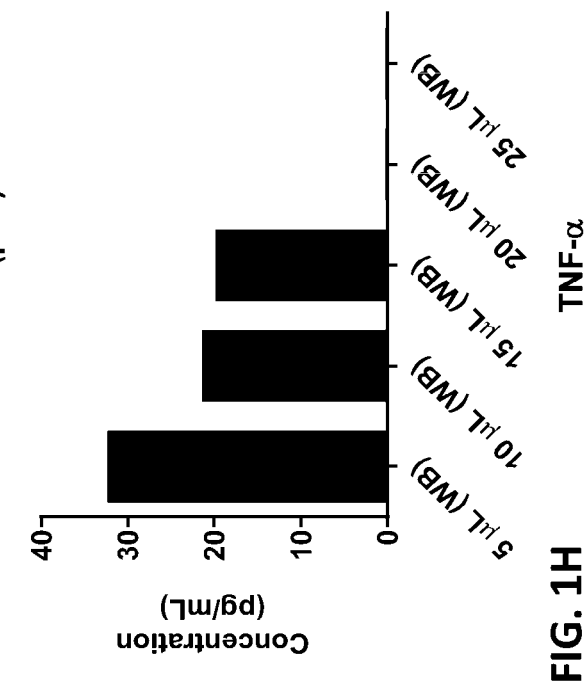
Figure 1H:
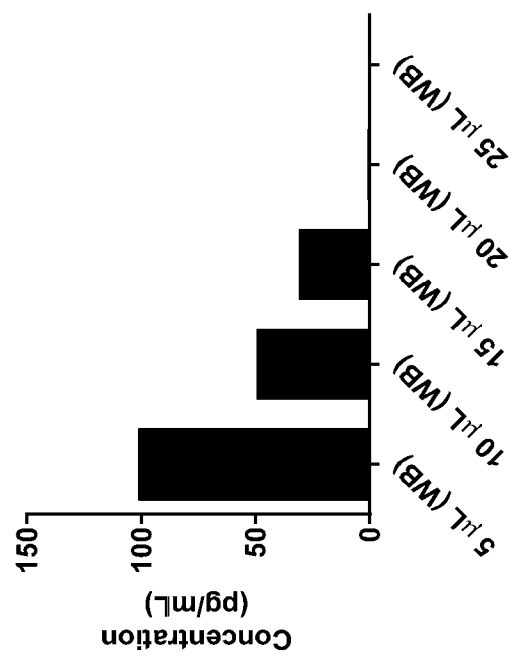
Figure 1E:
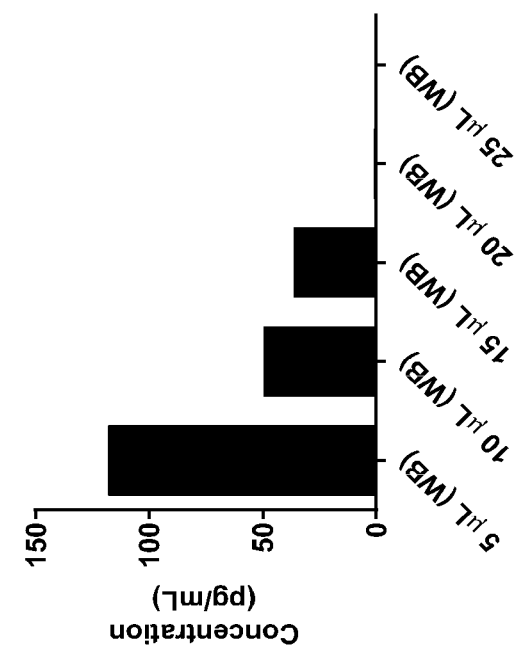
Figure 1G:
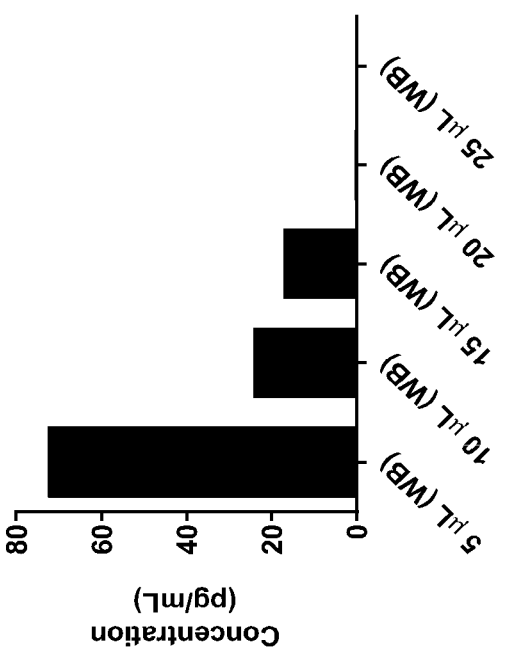
Figure 1I:
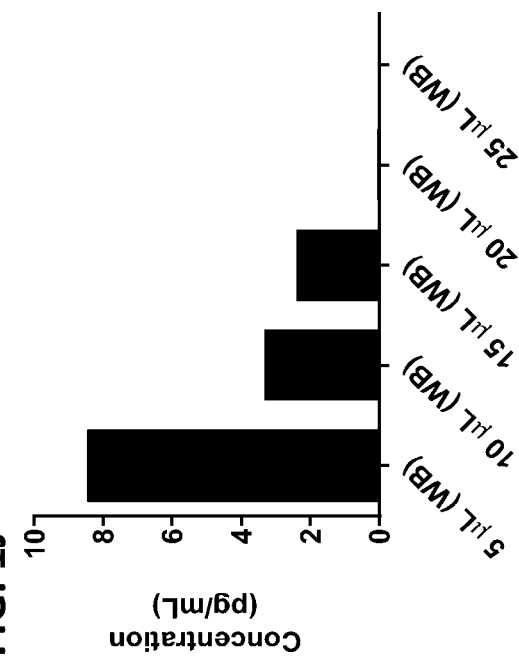
Figure 1J:
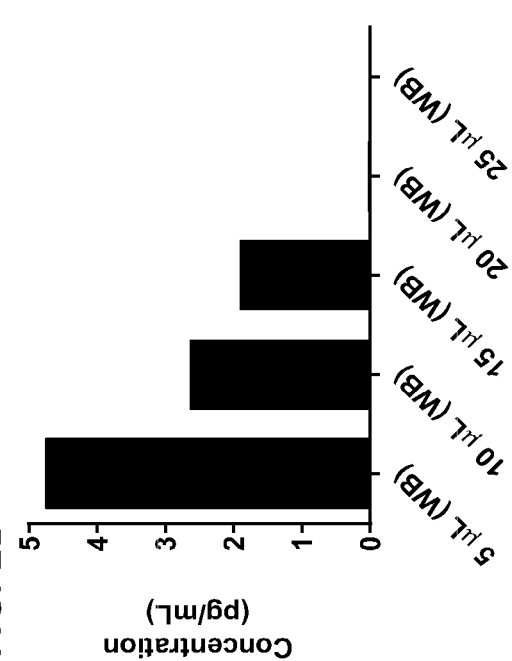
Figure 1K:
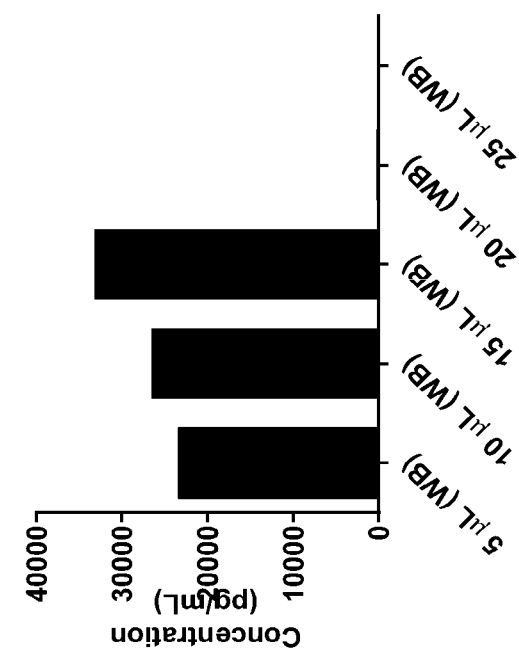
Figure 1L:
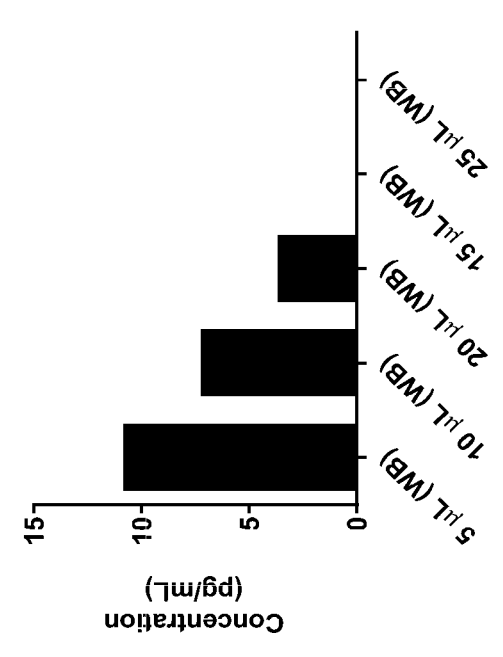
Figure 1M:
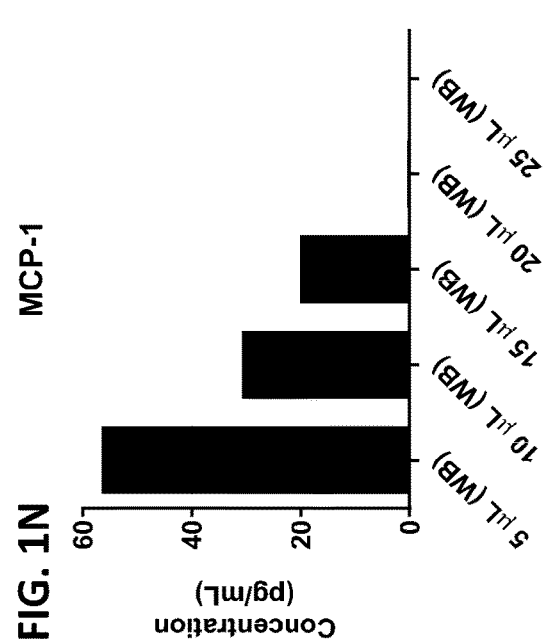
Figure 1N:
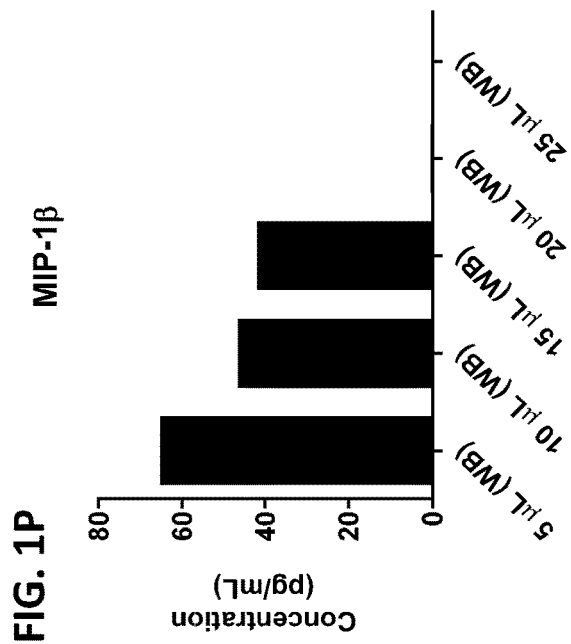
Figure 1O:
Figure 1P:
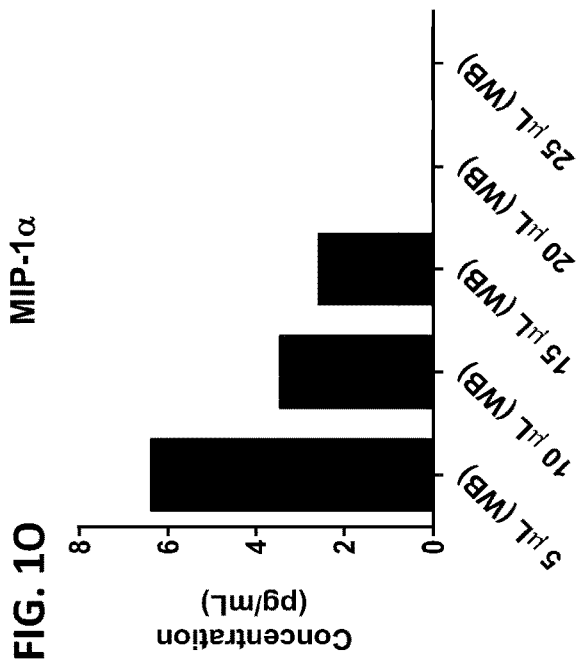
Figure 1U:
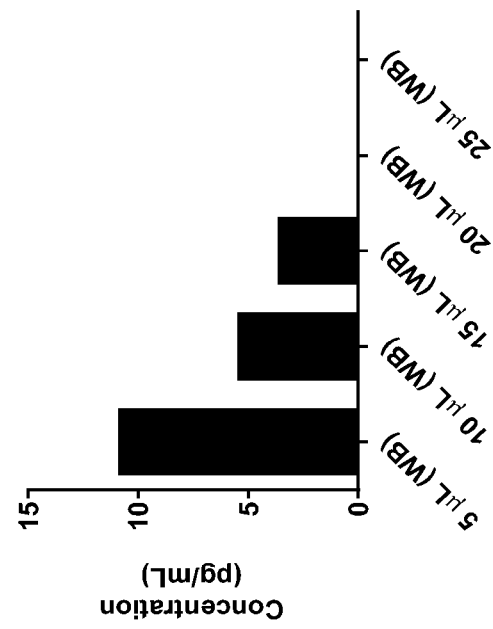
Figure 1V:
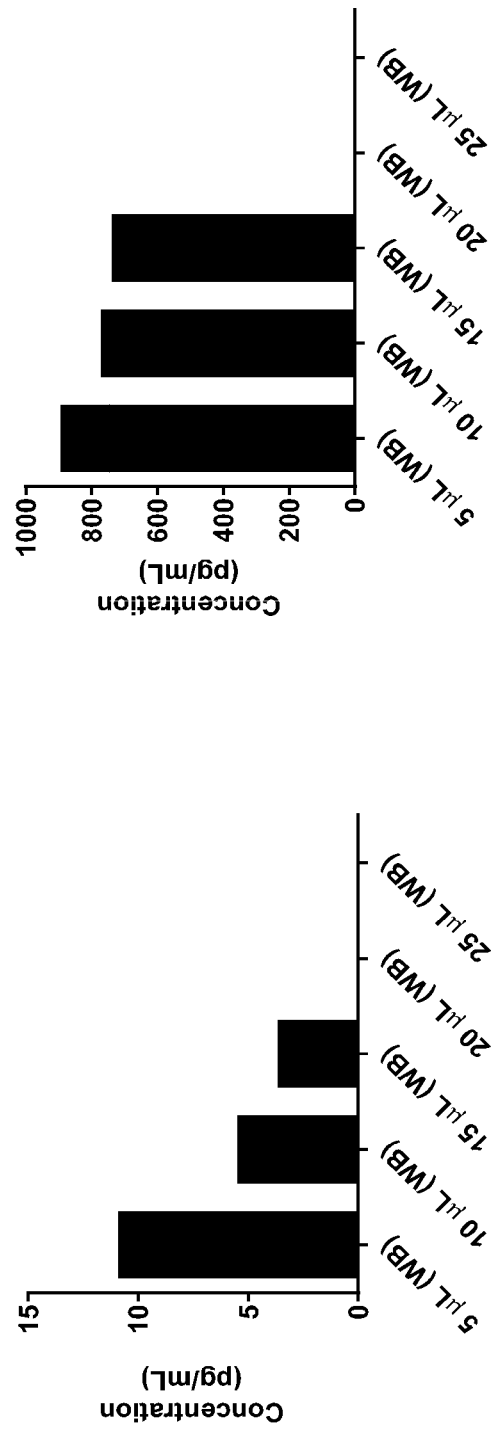
Figure 1W:
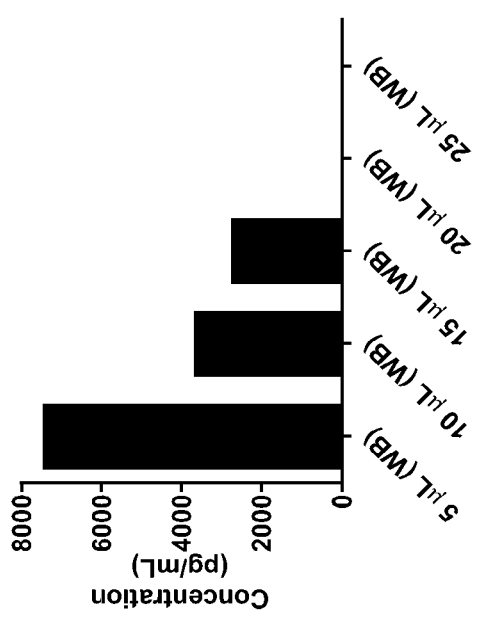
Figure 1X:
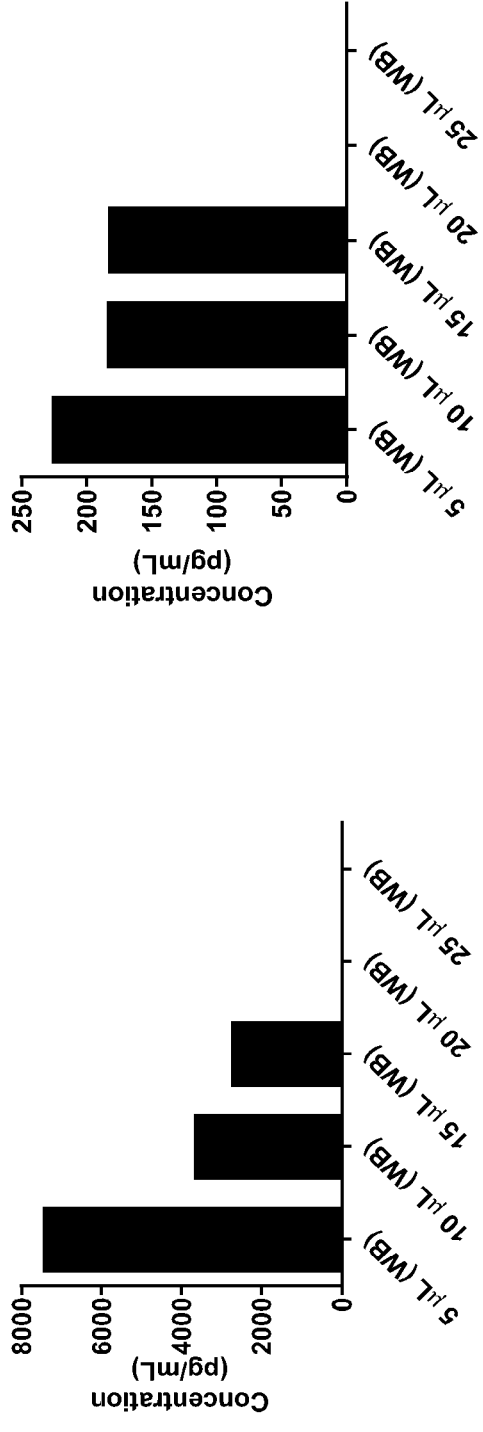
Figure 1G:
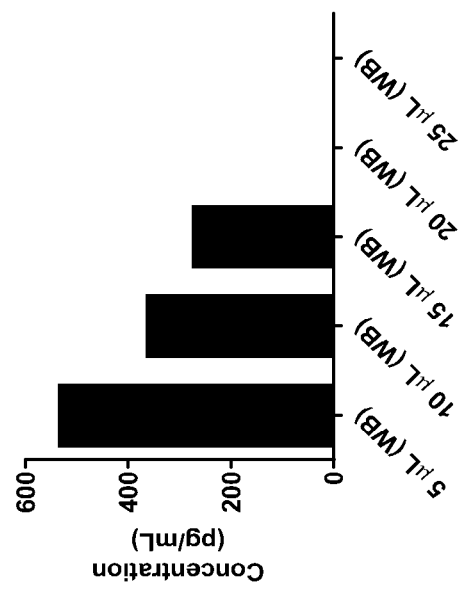
Figure 1I:
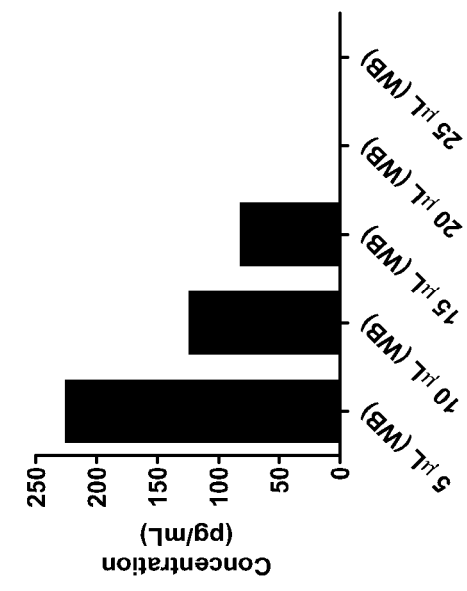
Figure 1H:
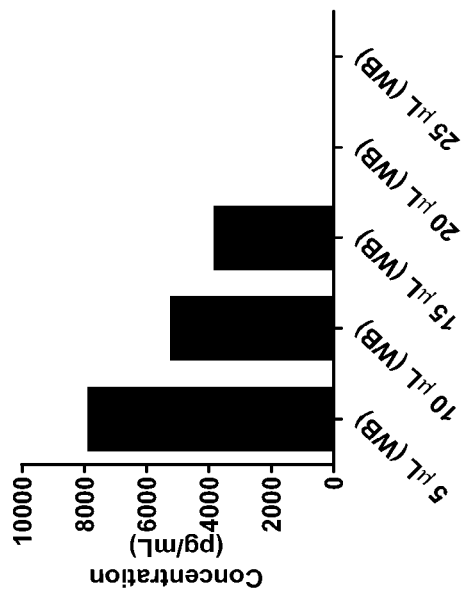
Figure 1J:
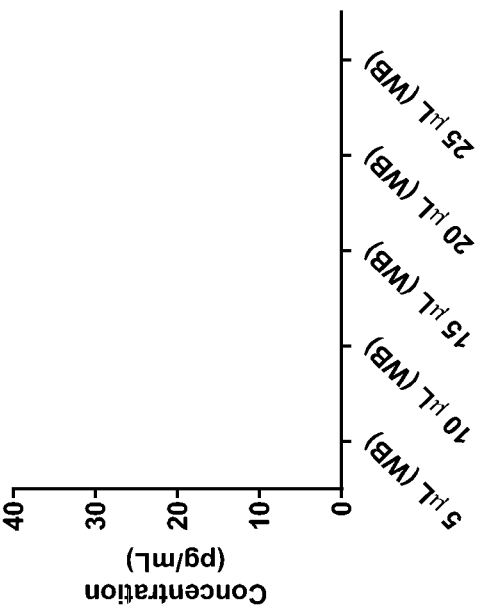
Figure 1L:
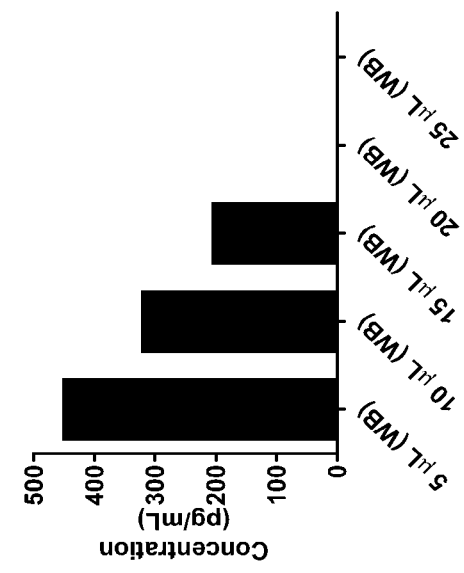
Figure 1N:
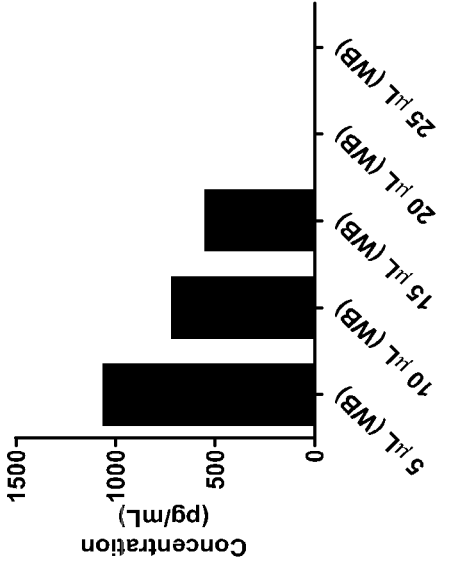
Figure 1K:
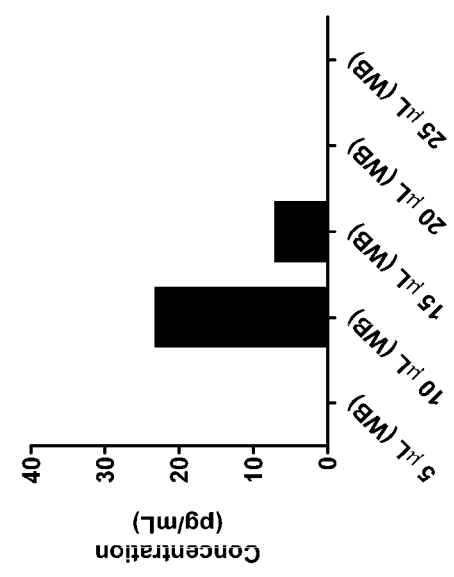
Figure 1M:
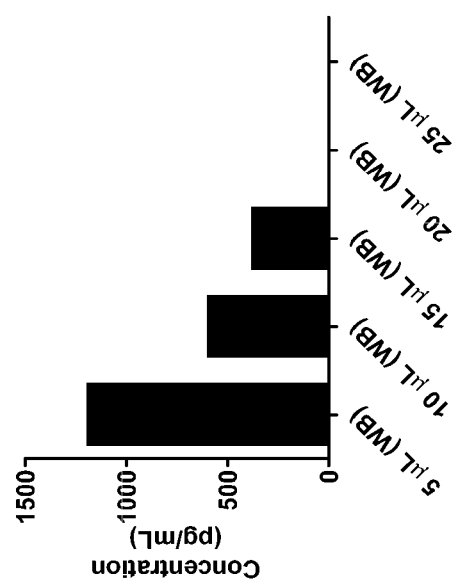
Figure 1O:
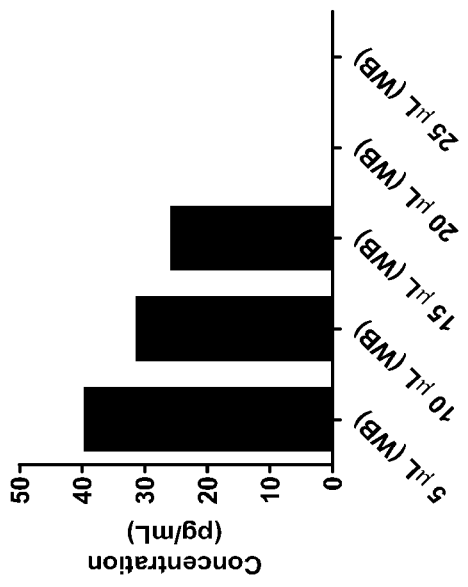
Figure 1P:

Figure 1Q:
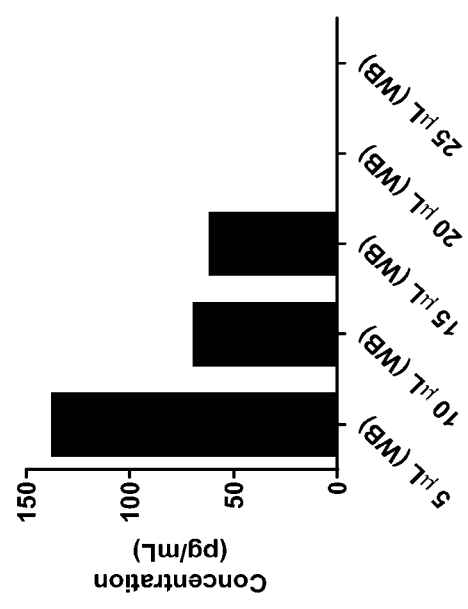
Figure 1R:
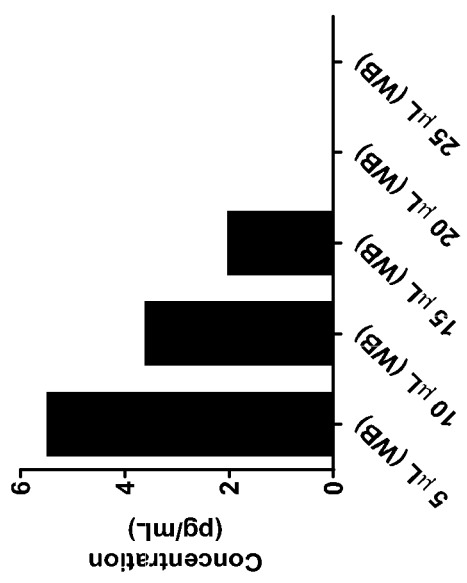

As used in this application, the singular form "a", "an" and "the" include plural references unless the context clearly dictates otherwise. For example, the term "a cell lysate" includes multiple cell lysates.

As used herein, the term "comprising" means "including." Variations of the word "comprising", such as "comprise" and "comprises," have correspondingly varied meanings. Thus, for example, a method "comprising" steps 'A' and 'B' may consist exclusively of steps 'A' and 'B' or may include one or more additional steps (e.g., steps 'A', 'B', and 'C').

The subject headings used in the detailed description are included for the ease of reference or the reader and should not be used to limit the subject matter found throughout the disclosure or the claims. The subject headings should not be used in construing the scope of the claims or the claim limitations.

As used herein, the term "subject" includes animals of economic, social or research importance including bovine, equine, ovine, primate, avian and rodent species. Hence, a "subject" may be a mammal such as, for example, a human or a non-human mammal.

As used herein, the terms "antibody" and "antibodies" include IgG (including IgG1, IgG2, IgG3, and IgG4), IgA (including IgA1 and IgA2), IgD, IgE, or IgM, and IgY, whole antibodies, including single-chain whole antibodies, and antigen-binding fragments thereof. Antigen-binding antibody fragments include, but are not limited to, Fab, Fab' and F(ab')2, Fd, single-chain Fvs (scFv), single-chain antibodies, disulfide-linked Fvs (sdFv) and fragments comprising either a VL or VH domain. The antibodies may be from animal origin. Antigen-binding antibody fragments, including single-chain antibodies, may comprise the variable region(s) alone or in combination with the entire or partial of the following: hinge region, CH1, CH2, and CH3 domains. Also included are combinations of variable region(s) and hinge region, CH1, CH2, and CH3 domains. Antibodies may be monoclonal, polyclonal, chimeric, multispecific, humanized, and human monoclonal and polyclonal antibodies which specifically bind the biological molecule.

As used herein, the term "protein" refers to a polymer made up of amino acids linked together by peptide bonds.

As used herein, the term "protease", "peptidase", or "proteinase" refers to an enzyme that breaks, cleaves, or proteolyzes the peptide bond(s) of a protein by hydrolysis. Proteases may include those that are specific to and/or specifically cleave a particular protein substrate (e.g., a particular protein), are specific to a type of protein substrate (e.g., a serine protease, cysteine protease, metalloprotease, or aspartic protease), or specific to more than one type of protein substrate (e.g., a cysteine and serine protease). Proteases may also include those that are non-specific or non-specifically cleave protein substrates (e.g., pepsin, proteinase K, elastase, exoproteases, endoproteases, and the like).

As used herein, the term "protease inhibitor" refers to a substance (e.g., protein or chemical substance) that blocks or reduces the catalytic (e.g., proteolytic) activity of a protease enzyme. A protease inhibitor may block the ability of a protease to cleave the peptide bond of a given protein, typically by blocking the active site of the protease and preventing its access to a substrate. By way of non-limiting example, protease inhibitors may include non-specific protease inhibitors (e.g., EDTA), specific protease inhibitors (including serine protease inhibitors, cysteine protease inhibitors, metalloprotease inhibitors, aspartic protease inhibitors, and aminopeptidase inhibitors), or dual-, multi- or pan-specific protease inhibitors (including serine and cysteine protease inhibitors).

As used herein, the term "protein profile" refers to protein(s) and/or protein fragment(s) present in a sample. The sample may or may not comprise cells. If the sample comprises cells, the proteins or protein fragments may exist intracellularly and/or partially or completely at the cell surface. Although not a requirement, the protein profile may also provide quantitative information for protein(s) and/or protein fragment(s) in the sample.

As used herein, the term "blood sample" refers to a sample comprising at least in part blood and/or blood components. The blood sample may be obtained directly from one or more subjects or from a pre-existing collection of blood from one or more subjects. The blood sample may be obtained from a human subject by a number of methods, for example, venipuncture (e.g., butterfly needle and Vacutainer, straight needle and Vacutainer, and butterfly needle and syringe) of a body part (e.g., arm, leg, ear) or by stick (e.g., finger, heel, or ear prick). The blood sample may be obtained from a non-human mammal subject by a number of methods, for example, venipuncture (e.g., needle and syringe) of a body part (e.g., tail, arm, leg (e.g., thigh), nose, face, ear, thorax, neck/throat, tongue, heart) or by stick (e.g., finger, heel, ear, or tail prick). The blood sample may be obtained from other non-human animals (e.g., chicken or birds) by a number of methods, for example, venipuncture (e.g., needle and syringe) of a body part (e.g., wing, throat, or heart).

As used herein, the term "blood cells" or "cell present in the blood sample" refers to cells in the sample, including red blood cells and white blood cells, but excludes, or substantially excludes, platelets.

As used herein, the term "red blood cell-enriched sample", "red blood cell sample", or "RBC-enriched fraction" refers to a sample or component of a sample in which the proportion of RBCs is increased compared to that of the blood sample prior to enriching. The proportion of RBCs may be increased, for example, by removing cell type(s) from the sample that are not RBCs (e.g., removal of leukocytes (leukodepletion) and/or removal of platelets), and/or by removing RBCs from other cell type(s) in the sample to provide a separate sample. The red blood cell-enriched sample may also be comprised of media, plasma/serum, supernatant, and/or cell wash. The RBC-enriched fraction may comprise more than 99.5%, more than 99.6%, more than 99.7%, more than 99.75%, more than 99.8%, more than 99.85%, more than 99.9%, more than 99.5%, approximately 100% red blood cells, or 100% red blood cells of the total blood cell number.

As used herein, the term "red blood cell component" refers to whole/intact red blood cells and a constituent part or element of red blood cells. For example, in certain embodiments a red blood cell component is red blood cells. In other embodiments, a red blood cell component is red blood cell membranes. The red blood cells may be obtained, for instance, from whole blood or a red blood cell-enriched sample. Red blood cell membranes may be obtained and/or produced from whole blood, a red blood cell-enriched sample, and/or isolated red blood cells.

As used herein, the term "snap freezing" refers to freezing blood cells (e.g., RBCs) and/or plasma/serum to a temperature below their freezing point generally within a rapid time period (for example, in a period of a few milliseconds, 1-2 seconds, 1-5 seconds, 1-10 seconds, 1-15 seconds, 1-20 seconds, 10-20 seconds, 10-30 seconds, 30-60 seconds, less than one minute, or less than two minutes).

As used herein, "leukodepletion" refers to reducing the proportion of leukocytes in a blood sample or a blood sample component, for example, by removing leukocytes from the blood sample or blood sample component, or alternatively by removing other blood constituent(s) from the blood sample or blood sample component to provide a separate leukodepleted sample. In some embodiments, leukodepletion includes platelet depletion.

As used herein, "platelet depletion" refers to reducing the proportion of platelets in a blood sample or a blood sample component, for example, by removing platelets from the blood sample or blood sample component or, alternatively, by isolating other blood constituent(s) from the blood sample or blood sample component to provide a separate platelet depleted sample.

As used herein, a "cell supernatant" will be understood to mean a cell culture medium in which a population of cells are incubated or cultured at a given temperature or a given range of temperatures for a given time period, for example, more than: 30 minutes, 1 hour, 2 hours, 3 hours, 6 hours, 12 hours, 24 hours, 48 hours, 72 hours, 96 hours, or 120 hours.

As used herein, a "cell wash" will be understood to mean a liquid that has been used to rinse a population of cells, and differs from a cell supernatant as defined above insofar as the cell wash is generally not used as a medium for cell culture. Accordingly, a fluid used to generate a "cell wash" may be mixed with the cell population for a period of less than: 30 minutes, 20 minutes, 15 minutes, 10 minutes, 5 minutes, 4, minutes, 3 minutes, 2 minutes, 1 minute, or 30 seconds.

As used herein, a "media" or "medium" refers to a composition having the ability to maintain the viability of cells within a blood sample, cells isolated from a blood sample, or cell components produced from cells isolated from a blood sample. The media may stimulate cell growth and proliferation or maintain cells at a particular and/or existing growth state. Non-limiting examples of media include isotonic salt solution, balanced salt solution, saline, phosphate buffered saline (PBS), hank's balanced salt solution (HBSS), Earles' balanced salt solution (EBSS), Roswell Park Memorial Institute medium (RPMI), minimum essential medium (MEM), Improved Minimum Essential Medium (IMEM), Eagle's minimal essential medium (EMEM), Dulbecco's modified Eagle's medium (DMEM), and Iscove's Modified Dulbecco's Media (IMDM).

As used herein, the term "small volume" refers to a volume of blood that is one millilitre or less. A small volume may be 1 µL to 100 µL, 100 µL to 200 µL, 200 µL to 300 µL, 300 µL to 400 µL, 400 µL to 500 µL, 500 µL to 600 µL, 600 µL to 700 µL, 700 µL to 800 µL, 800 µL to 900 µL and 900 µL to 1000 µL. In some embodiments, a small volume is 50 µL to 100 µL, 100 µL to 150 µL, 150 µL to 200 µL, 200 µL to 250 µL, 250 µL to 300 µL, 300 µL to 350 µL, 350 µL to 400 µL, 400 µL to 450 µL, 450 µL to 500 µL, 500 µL to 550 µL, 550 µL to 600 µL, 600 µL to 650 µL, 650 µL to 700 µL, 700 µL to 750 µL, 750 µL to 800 µL, 800 µL, to 850 µL, 850 µL to 900 µL, 900 µL to 950 µL, 950 µL to 1000 µL. In some embodiments, a small volume is 1 µL to 10 µL, 10 µL to 20 µL, 20 µL to 30 µL, 30 µL to 40 µL, 40 µL to 50 µL, 50 µL to 60 µL, 60 µL to 70 µL, 70 µL to 80 µL, 80 µL to 90 µL, or 90 µL to 100 µL. In other embodiments, a small volume is 0.1 µL to 0.5 µL, 0.5 µL to 1 µL, 1 µL to 5 µL, 5 µL to 10 µL, 10 µL to 15 µL, 15 µL to 20 µL, 20 µL to 25 µL, 25 µL to 30 µL, 30 µL to 35 µL, 35 µL to 40 µL, 40 µL to 45 µL, 45 µL to 50 µL, 50 µL to 55 µL, 55 µL to 60 µL, 60 µL to 65 µL, 65 µL to 70 µL, 70 µL to 75 µL, 75 µL to 80 µL, 80 µL to 85 µL, 85 µL to 90 µL, 90 µL to 95 µL, or 95 µL to 100 µL. In some embodiments, a small volume is 5 µL to 10 µL, 5 µL to 15 µL, 5 µL to 20 µL, 5 µL to 25 µL, 5 µL to 30 µL, 5 µL to 35 µL, 5 µL to 40 µL, 5 µL, to 45 µL, 5 µL to 50 µL, 5 µL to 55 µL, 5 µL to 60 µL, 5 µL to 65 µL, 5 µL to 70 µL, 5 µL to 75 µL, 5 µL to 80 µL, 5 µL to 85 µL, 5 µL to 90 µL, 5 µL to 95 µL, or 5 µL to 100 µL. In other embodiments, a small volume is 0.1 µL, 0.5 µL, 1 µL, 2 µL, 3 µL, 4 µL, 5 µL, 6 µL, 7 µL, 8 µL, 9 µL, 10 µL, 11 µL, 12 µL, 13 µL, 14 µL, 15 µL, 16 µL, 17 µL, 18 µL, 19 µL, 20 µL, 21 µL, 22 µL, 23 µL, 24 µL, 25 µL, 26 µL, 27 µL, 28 µL, 29 µL, 30 µL, 31 µL, 32 µL, 33 µL, 34 µL, 35 µL, 36 µL, 37 µL, 38 µL, 39 µL, 40 µL, 41 µL, 42 µL, 43 µL, 44 µL, 45 µL, 46 µL, 47 µL, 48 µL, 49 µL, or 50 µL.

As used herein, the term "detectable level" or "level of detection" refers to the ability of a composition or agent to indicate and/or signal the presence of a desired molecule, such as a protein, in a sample (e.g., a blood sample). In a red blood cell-enriched sample, for example, the detectable level of a protein may increase due to an increase in the protein available for detection. This increase may be due to one or more reasons, for example, through a disruption of protein-molecule interactions (e.g., protein-protein, protein-membrane, protein-nucleic acid) that prevent and/or decrease the detection of the protein.

As used herein, the term a "change in level" or "change in the level" of a protein(s) refers to an increase or decrease in the detectable level of the protein(s) that one of ordinary skill in the art would not consider to be the same, substantially the same, similar, or substantially similar protein level. Thus, the skilled artisan would recognize the increase or decrease in the detectable level of the protein as statistically significant by e.g., observation (e.g., chromatography), results of a statistical test (e.g., a Student T's test, an ANOVA test, a mixed-effects model, a Mann-Whitney test, a Wilcoxon rank sum, or a Spermans rank correlation) or a calculation of a relevant fold change (e.g., a statistically significant fold change (e.g., more than 0-fold change, more than 0.5-fold change, more than 1-fold change, or more than a 1.5-fold change)) in the protein(s) level measured.

As used herein, the term "no change" or "no difference" in the level of a protein(s) refers to either no increase or decrease in the protein(s) level (e.g., the protein level is the same) or a small enough increase or decrease in the protein(s) level that one of ordinary skill in the art would consider the protein level to be the same or substantially similar. Thus, the skilled artisan would recognize that the increase or decrease in the detectable level of the protein(s) as not statistically significant by e.g., observation (e.g., chromatography), results of a statistical test (e.g., a Student T's test, an ANOVA test, a mixed-effects model, a Mann-Whitney test, a Wilcoxon rank sum, or a Spermans rank correlation) or a calculation of a relevant fold change (e.g., a statistically significant fold change (e.g., less than 0.5-fold change, less than 1.0-fold change, or less than a 1.5-fold change)) in the protein levels measured.

As used herein, a "different change in level" or "difference between the change in level" refers to the change in the level of one or more proteins in one sample or subject that is not the same, not substantially the same, not similar, or not substantially similar to the change in the level of the one or more proteins in another sample or subject (e.g., a subject having a disease or disorder compared to a subject not having the disease or disorder). For example, a difference in a change in level of one or more proteins may include: an increase in protein levels in one subject compared to a decrease in the same protein levels in another subject; a larger or smaller magnitude of change in level of one or more proteins in one subject compared to that in another subject (e.g., an increase or decrease in protein levels in one subject that is larger or smaller than the increase or decrease in the protein levels in a different subject); or a change in level in one subject compared to no change in level in another subject (e.g., an increase or decrease in protein levels in one subject compared to no significant increase or decrease in the protein levels in the other subject). The difference in the change in level may be determined by data visualization (e.g., charts or graphs) or analysis methods, including statistical analyses (e.g., a Student T's test, an ANOVA test, a mixed-effects model, a Mann-Whitney test, a Wilcoxon rank sum, or a Spermans rank correlation).

As used herein, protein "release" from RBCs refers to proteins that have moved by active or inactive mechanisms from (i) the intracellular region or interior of a RBC to the surface and/or extracellular or exterior region of the RBC (e.g., plasma, serum, and/or medium) or (ii) moved from the extracellular or exterior region of the RBC (from, e.g., the plasma, serum and/or medium) to the surface and/or extracellular region or the exterior of the RBC. In some embodiments, the proteins may be bound to the surface of the RBCs by cell surface-protein binding interactions (e.g., receptors, covalent attachment, noncovalent attachment and/or adhesion). In other embodiments, the surface bound proteins may be released back into the extracellular or exterior region of the RBC (e.g., into the plasma, serum, and/or medium).

As used herein, "treatment" refers to one or more therapies, protocols, methods and/or agents that may be used in preventing, managing, alleviating, or ameliorating a disease, disorder, or condition, including in the prevention, alleviation, or amelioration of one or more symptoms of a disease, disorder, or condition and/or a symptom related thereto. In certain embodiments, the terms "treatment" and "treatments" refer to a biological therapy, supportive therapy, and/or other therapies useful in the prevention, management, alleviation, and/or amelioration of a disease, disorder, or condition.

As used herein, the phrase "substantially similar" or "substantially the same" denotes a sufficiently high degree of similarity between two numeric values such that one of skill in the art would consider the difference between the two values (e.g., protein concentration/level or change in level (e.g., fold change)) to be of little or no biological and/or statistical significance within the context of the biological characteristic measured by the values. For example, the difference between the two values may be less than about 50%, less than about 40%, less than about 30%, less than about 20%, less than about 10%, or less than about 5%.

As used herein, the term "kit" refers to a delivery system having the components useful for carrying out one or more of the embodiments described herein. By way of non-limiting example, the kits may comprise ways of: collecting blood, inhibiting proteases, increasing protein detection, preventing coagulation, stabilizing blood, obtaining red blood cell components, enrichment of RBC, removal/separation of non-RBC blood components, snap-freezing blood or component(s) thereof, lysing cells, washing cells, culturing cells, detecting specific target protein(s) intracellularly and/or extracellularly, or combinations thereof. In some embodiments, kits may comprise one or more of the following: device(s) for obtaining a blood sample from a subject (e.g., a syringe, needle, butterfly needle, tube, needle holder, blood collection set, transfer device, vacutainer, hemaPEN™); device(s) for obtaining a dried blood sample from a subject (e.g., filter paper, cards, HemaSpot™); device(s) for obtaining a red blood cell fraction, a leukocyte fraction, and/or a platelet fraction from a liquid blood sample (e.g., antibody coated magnetic beads); protease inhibitors; cationic salts; anticoagulants; protease inhibitors; protein denaturation agents; and the like. Such delivery systems may include systems that allow for the storage, transport, or delivery of reaction reagents (for example labels, reference samples, supporting material, etc. in the appropriate containers) and/or supporting materials (for example, buffers, written instructions for performing an assay etc.) from one location to another. For example, kits may include one or more enclosures, such as boxes, containing the relevant reaction reagents and/or supporting materials. The term "kit" includes both fragmented and combined kits.

As used herein, the term "fragmented kit" refers to a delivery system comprising two or more separate containers that contain a subportion of the total kit components. The containers may be delivered to the intended recipient together or separately. A delivery system comprising two or more separate containers that contain a subportion of the total kit components are included within the meaning of the term "fragmented kit".

As used herein, a "combined kit" refers to a delivery system containing the components of a reaction assay in a single container (e.g., in a single box housing each of the desired components).

Any description of prior art documents herein, or statements herein derived from or based on those documents, is not an admission that the documents or derived statements are part of the common general knowledge of the relevant art.

DETAILED DESCRIPTION

Currently used techniques for profiling protein levels in blood typically restrict the analysis to serum/plasma and/or PBMCs. Because RBCs are believed to interfere with blood processing and/or blood protein measurement, they are routinely removed and discarded during blood processing prior to generating protein profiles.

The present inventors have made the unexpected finding that RBCs provide a significant source of protein markers and that contacting a red blood cell-enriched sample with protease inhibitors modulates the detectable levels of protein markers in subjects having a disease or disorder, while leaving unchanged or differentially modulating protein levels in red blood cell samples from those not having the disease or disorder. Accordingly, a deficiency in current technologies has been identified in that RBCs were not previously recognised to provide a source of various protein markers described herein, and the exclusion of RBCs from protein profiling thus provides an inadequate and/or inaccurate assessment. (See also, Australian Application No.

AU2015904075 entitled "Blood Preparation and Profiling", filed on Oct. 7, 2015 and International Application No. PCT/AU2016/000341, entitled "Blood Preparation and Profiling", filed on Oct. 6, 2016). Moreover, current technologies do not lend themselves to simple and/or rapid delineation between a subject having a disease or disorder and a subject not having a disease or disorder based on a non-specific and/or specific change in the levels of red blood cell protein markers in response to the presence of protease inhibitors in a blood sample. The present disclosure remedies blood protein profiling deficiencies, providing a new and useful laboratory technique for generating protein profiles from blood that incorporate analyses of RBCs contacted with protease inhibitors to modulate protein levels/detection in subjects having a disease or disorder. The new and useful laboratory techniques provided herein have diagnostic, prognostic, and/or therapeutic applications.

The following description conveys exemplary embodiments of the present disclosure in sufficient detail to enable those of ordinary skill in the art to practice it. Features or limitations of the various embodiments described do not necessarily limit other embodiments of the present disclosure or the present disclosure as a whole. Hence, the following detailed description does not limit the scope of the present disclosure, which is defined by the claims.

Protein Profiling in Red Blood Cells (RBCs)

The present disclosure provides methods for generating a protein profile from a blood sample, red blood cell-enriched sample, red blood cell component, and/or blood sample component comprising RBCs using protease inhibitors. In some embodiments, the number of RBCs constitute more than: 0.5%, 1%, 5%, 10%, 20%, 30%, 40%, 50%, 60%, 70%, 80%, 90%, 95%, 97.5%, 98%, 99%, 99.5%, 99.75%, 99.9%, or 99.95%, of total number of blood cells present in the blood sample or the blood sample component.

Blood Samples

The blood sample obtained from a subject in the provided methods is as defined herein (see, e.g., "blood sample") and may be obtained from a subject or an existing collection of blood (e.g., blood previously obtained from one or more subjects and/or stored blood). The blood sample may be obtained from a subject using exemplary means available to those of ordinary skill in the art (see, for example, World Health Organisation, "*Requirements for the collection, processing and quality control of blood, blood components and plasma derivatives*", World Health Organisation Technical report Series, No. 840, 1994, Annex 2). By way of non-limiting example, the blood sample may be obtained from a subject using venous blood, capillary blood, arterial blood or, combinations thereof.

In certain embodiments, a small volume blood sample is obtained from a subject or an existing collection of blood. The small volume may be obtained from a subject by various methodologies including, for example, by stick (e.g., finger prick, heel prick, ear prick, or tail prick). In some embodiments, the small volume blood sample is obtained by finger prick, heel prick, or ear prick or dried blood spot (from, e.g., a human). In other embodiments, the small volume blood sample is obtained by tail prick (from, e.g., a mouse or rat). In other embodiments, the small volume blood sample is obtained by finger prick. In other embodiments, the small volume blood sample is obtained by heel prick (from, e.g., an infant). In still other embodiments, the small volume blood sample is obtained by ear prick. In further embodiments, the small volume blood sample is obtained by tail prick.

In some embodiments, the small volume is as defined herein (see, e.g., "small volume"). In other embodiments, the small volume is 1 µL to 10 µL, 5 µL to 100 µL or 5 µL to 50 µL. In other embodiments, the small volume is 5 µL to 20 µL or 5 µL to 10 µL. In still other embodiments, the small volume is 5 µL. In other embodiments, the small volume is 1 µL.

Obtaining a small volume blood sample allows for the more frequent sampling of, for example, a subject compared to a larger volume blood sample because taking a small volume blood sample decreases the harm to the subject (e.g., pain, blood loss, slow recovery of blood levels). For instance, using typical current methods, frequent blood sampling from small animals (e.g., rats, mice) is not achievable because a comprehensive blood analysis requires so much blood that the animal must be sacrificed. Similarly, to prevent harm from blood loss, infants may only be safely sampled frequently by stick (e.g., heel prick). In certain embodiments provided herein, a small volume blood sample is obtained. In certain embodiments, a small volume blood sample is obtained with a frequency of one or more times per day, two or more times per day, three or more times per day, four or more times per day, or five or more times per day. In other embodiments, a small volume blood sample is obtained one or more times per week, two or more times per week, three or more times per week, four or more times per week, five or more times per week, six or more times per week, or seven or more times per week. In other embodiments, a small volume blood sample is obtained daily. In still other embodiments, a small volume blood sample is obtained once a week, once every two weeks, once every three weeks, or once every four weeks. In certain embodiments, a small volume blood sample is obtained once a month.

Enriched Red Blood Cell Samples or Fractions

In some embodiments, the methods involve producing or generating a protein profile from a red blood cell-enriched sample, a red blood cell-enriched fraction, or red blood cells and determining the levels of one or more proteins in the red blood cell-enriched sample, red blood cell-enriched fraction, or red blood cells. The red blood cell-enriched sample and red blood cell-enriched fraction may be produced from a blood sample by, for example, leukodepletion and/or platelet depletion. Additionally or alternatively, RBCs may be removed from a sample to produce the red blood cell-enriched sample or red blood cell-enriched fraction.

Various methodologies for leukodepletion and platelet depletion are available (see, for example Wenz, B., "Methods for leukodepletion" in "Clinical Benefits of Leukodepleted Blood Products", pp 5-16, 1995, Springer Berlin Heidelberg; Novotny V., and Brand, A., "Leukocyte-Poor Blood and Platelet Transfusions" in "Modern Transfusion Medicine", pp 117-121, 1995, CRC Press, Inc.; White and Jennings, "Platelet Protocols: Research and Clinical Laboratory Procedures", 1999, Academic Press). Non-limiting examples of suitable techniques for leukodepletion include flow cytometry, dextran sedimentation, ficol/percol density gradient centrifugation, and the like.

The present disclosure also provides methods for increasing the sensitivity of the detection or measurement of one or more proteins in a blood sample by producing a red blood cell-enriched sample and detecting the presence or measuring the level of one or more proteins in the red blood cell-enriched sample. In certain embodiments, the ratio of blood to dextran is between 1:1 and 2:1, 1:1 and 3:1, 1:1 and 4:1, 1:1 and 5:1, 1:1 and 6:1, 1:1 and 7:1, 1:1 and 8:1, 1:1 and 9:1, or 1:1 and 10:1. In other embodiments, the ratio of blood to dextran is 1:1, 2:1, 3:1, 4:1, 5:1, 6:1, 7:1, 8:1, 9:1, or 10:1. In still other embodiments, the ratio of blood to dextran is 2:1. In further embodiments, the ratio of blood to dextran is 4:1.

By way of non-limiting example, the red blood cell-enriched sample or red blood cell-enriched fraction may be generated by leukodepletion of more than 90%, 92.5%, 95%, 97.5%, 99%, 99.5%, 99.75%, or 99.9% of the number of leukocytes that were present in the blood sample. 'Leukodepletion' in this context may be achieved by depleting leukocytes from the blood sample directly, and/or by removing RBCs from the sample to provide a separate leukodepleted (RBC-enriched) fraction. In some embodiments, leukodepletion includes platelet depletion.

Additionally or alternatively, the red blood cell-enriched sample or red blood cell-enriched fraction may be generated by platelet depletion of more than 90%, 92.5%, 95%, 97.5%, 99%, 99.5%, 99.75%, or 99.9% of the number of platelets that were present in the blood sample. 'Platelet depletion' in this context may be achieved by depleting platelets from the blood sample directly, and/or by removing RBCs from the sample to provide a separate platelet-depleted (RBC-enriched) fraction.

In some embodiments the red blood cell-enriched sample or red blood cell-enriched fraction may comprise more than 99.75%, more than 99.8%, more than 99.9%, more than 99.95%, approximately 100%, or 100% red blood cells (as a component of the total number of blood cells present within the RBC-enriched fraction).

The percentage of RBCs in a given enriched sample or red blood cell-enriched fraction may be assessed using methodologies available to those of ordinary skill in the art including, for example, flow cytometry, fluorescence microscopy, other antibody-based techniques, and the like.

Red Blood Cell Membranes

In certain embodiments, the methods provided herein involve producing or generating a protein profile from red blood cell membranes and/or red blood cell ghosts. Red blood cell membranes refer to RBCs from which some (e.g., more than: 10%, 20%, 30%, 40%, 50%, 60%, 70%, 80%, 90%, 95%, or 99%) of the cytoplasmic protein has been removed. The cytoplasmic protein may be removed, for example, by lysis, washing, and centrifugation of red blood cells, both isolated and found in whole blood. Red blood cells may be lysed to obtain red blood cell membranes by a number of methods including, for instance, hypotonic hemolysis. (see, for example, Bramley T A, Coleman R, Finean J B. Chemical, enzymological and permeability properties of human erythrocyte ghosts prepared by hypotonic lysis in media of different osmolarities. Biochimica et Biophysica Acta—Biomembranes, 241(3) 1971), freeze-thaw cycles, and the like. Freeze-thaw cycles may be repeated an appropriate number of times (e.g., at least two times, at least three times, at least four times, or at least five times) to achieve the desired level of cytoplasmic material associated with the red blood cell membrane (e.g., 95% free of cytoplamic protein). Because red blood cell membranes may be obtained by centrifugation (e.g., at 16,000 g) of lysed red blood cells, the membranes may be isolated from a sample that comprises red blood cells, even if the red blood cells are a small or minimal component of the sample.

Small Volume Red Blood Cell-Enriched Samples

The present disclosure also provides methods of producing a protein profile from a small volume of a red blood cell-enriched blood sample. A small volume may be obtained from a red blood cell-enriched blood sample by methods available in the art and as deemed appropriate by one of ordinary skill in the art for subsequent methods of protein detection or protein measurement in the red blood cell-enriched sample (see, e.g., protein profiling below). A small volume is a volume as defined herein (see, e.g., "small volume"). By way of non-limiting example, in other embodiments, the small volume may be 0.1 µL to 0.5 µL, 0.5 µL to 1 µL, 1 µL to 5 µL, 5 µL to 10 µL, 5 µL to 20 µL, 5 µL to 30 µL, 5 µL to 40 µL, 5 µL to 50 µL, 5 µL to 60 µL, 5 µL to 70 µL, 5 µL to 80 µL, 5 µL to 90 µL, or 5 µL to 100 µL. In some embodiments, the small volume is 5 µL to 100 µL. In other embodiments, the small volume is 5 µL to 50 µL or 5 µL to 20 µL. In still other embodiments, the small volume is 5 µL to 10 µL. In certain embodiments, the small volume is 5 µL.

Whole Blood Comprising RBCs

Other embodiments involve the analysis of a whole blood sample comprising RBCs. In these embodiments, the whole blood sample is analysed for a protein profile without, or substantially without, altering the relative proportions of blood cell types within the sample and without separating plasma/serum.

The whole blood sample may be obtained using exemplary means available to those of ordinary skill in the art (see, for example, World Health Organisation, "*Requirements for the collection, processing and quality control of blood, blood components and plasma derivatives*", World Health Organisation Technical report Series, No. 840, 1994, Annex 2). Methodology is also presented in the Examples of the present specification.

By way of non-limiting example, the whole blood sample may be obtained using venous blood, capillary blood, arterial blood, or combinations thereof.

In some embodiments, methods of the present disclosure involving the analysis of whole blood may be carried out using dried blood spot (DBS) sampling. Non-limiting advantages of DBS sampling include one or more of the following: sample stability, minimal volume requirements (e.g., 30-100 µL per spot), ease of sample collection (e.g., finger, toe or heel prick) and transport. A DBS sample obtained for use in the present disclosure may, for example, maintain stability for months to years under refrigeration and/or at ambient temperature.

Suitable methodologies for DBS are well available to those of ordinary skill in the art (see for example, McDade, et al; Demography 2007, 44: 899-925; De Jesus et al. Clin Chem 2009, 55:1; 158-164; Sharma et al. Drug Testing and Analysis, 2014, 6(5), 399-414).

Briefly, and again by way of non-limiting example only, whole blood may be obtained from a subject of interest (e.g., finger, heel or toe prick) using an appropriate instrument (e.g., a sterile surgical blade or disposable lancet) and spotted onto, for example, a membrane or paper (e.g., filter paper cards). For quantitative analyses, a measured volume of blood may be applied. The blood may then be allowed to dry for example, at room temperature and/or under nitrogen flow and/or controlled humidity. Drying time will generally depend at least in part on sample volume. DBS membranes or paper may be stored at ambient temperature or refrigerated, and may be appropriately packaged to avoid humidity. The DBS may then be extracted for analysis at a suitable time (e.g., using an extraction solvent or similar).

Analyses of Additional Blood Compartments

In addition to protein profiling of enriched RBCs sample, RBC fractions or whole blood samples comprising RBCs, the methods of the present disclosure may further comprise conducting protein profile analyses of one or more additional blood compartment(s).

For example, protein profile analyses may be conducted on one or more additional blood compartment(s) selected from plasma, serum, platelets, leukocytes, an enriched platelet fraction, an enriched leukocyte fraction, platelet-rich plasma, leukocyte-rich plasma, a mixture of platelets and leukocytes, specific leukocyte(s) (e.g., one or more of T lymphocytes (e.g., CD4+ T lymphocytes, CD8+ T lymphocytes), B lymphocytes, NK cells, monocytes, neutrophils, eosinophils, basophils, and the like), and combinations thereof.

The additional blood compartment(s) for analysis may be prepared using available techniques. For example, cellular components may be isolated by flow cytometry, magnetic bead separation, centrifugation, and the like. Plasma/serum separation techniques are also available in the art. Many standard texts and protocols are available and widely used for these purposes, and by way of non-limiting example reference is made to: World Health Organisation, "Requirements for the collection, processing and quality control of blood, blood components and plasma derivatives", World Health Organisation Technical report Series, No. 840, 1994, Annex 2; Wenz, B., "Methods for leukodepletion" in "Clinical Benefits of Leukodepleted Blood Products", pp 5-16, 1995, Springer Berlin Heidelberg; Novotny V., and Brand, A. "Leukocyte-Poor Blood and Platelet Transfusions" in "Modern Transfusion Medicine", pp 117-121, 1995, CRC Press, Inc.; White and Jennings, "Platelet Protocols: Research and Clinical Laboratory Procedures", 1999, Academic Press).

Lysate Analyses

In some embodiments, the methods of the present disclosure comprise generating a protein profile from a cellular lysate.

By way of non-limiting example only, an enriched RBC sample or RBC fraction prepared in accordance with the one or more of the methods of the present disclosure may be treated to provide a lysate in which the levels of one or more proteins are determined. The lysate may also be produced from one or more other blood compartment(s) selected from whole blood, plasma, serum, platelets, leukocytes, an enriched platelet fraction, an enriched leukocyte fraction, platelet-rich plasma, leukocyte-rich plasma, a mixture of platelets and leukocytes, specific leukocyte(s) (e.g., one or more of T lymphocytes (e.g., CD4+ T lymphocytes, CD8+ T lymphocytes), B lymphocytes, NK cells, monocytes, neutrophils, eosinophils, basophils, and the like), and combinations thereof.

Additionally or alternatively, other cellular components of blood that are not RBCs, or that contain minimal amounts of RBCs (e.g., less than: 10%, 5%, 4%, 3%, 2%, 1%, or 0.5% RBCs) may be treated to provide a lysate in which the levels of one or more proteins are determined.

Cell lysates for use in the methods of the disclosure may be produced using suitable means including, for example, liquid homogenization, mechanical disruption, freeze/thaw cycles, high frequency sound waves, manual grinding, chemical permeabilisation, enzymatic permeabilisation, permeabilisation using streptolysin, and the like.

In some embodiments, cell lysates are prepared by one, two, three, four, five, or more than five cycles of freeze/thawing. This technique offers the potential benefit of providing a means of stabilising a blood sample or component(s) thereof at the point of freezing and allowing storage prior to lysing and analysis of protein content. Typically, the snap freezing may be performed at a temperature of at or below: $-10°$ C., $-20°$ C., $-30°$ C., $-40°$ C., $-50°$ C., $-60°$ C., $-70°$ C., $-75°$ C., $-80°$ C., $-90°$ C., $-100°$ C., $-120°$ C., $-140°$ C., $-160°$ C., $-180°$ C., $-190°$ C., $-195°$ C., or $-196°$ C. In still other embodiments, snap freezing is performed at a temperature of below: $-5°$ C., $-10°$ C., $-20°$ C., $-30°$ C., $-40°$ C., $-50°$ C., $-60°$ C., $-70°$ C., $-75°$ C., $-80°$ C., $-90$, $-100°$ C., $-120°$ C., $-104°$ C., $-160°$ C., $-180°$ C., $-190°$ C., $-200°$ C. In still other embodiments, snap-freezing is performed at a temperature below: $-190°$ C., $-191°$ C., $-192°$ C., $-193°$ C., $-194°$ C., $-195°$ C., $-196°$ C., $-197°$ C., $-198°$ C., or $-199°$ C. A whole blood sample, a RBC-enriched sample, a RBC-enriched fraction, and/or other different cellular components may be snap frozen to stabilise the cells. This may reduce or prevent, for example, the sequestration and/or release of proteins from RBCs and/or other cell types present during processing.

Analyses of Cell Washes and Supernatants

In some embodiments, the methods of the present disclosure comprise generating a protein profile from a cell wash and/or a cell supernatant.

The cell wash and/or cell supernatant may be produced from a blood sample or blood sample component comprising RBCs. In some embodiments, the number of RBCs constitute more than: 0.5%, 1%, 5%, 10%, 20%, 30%, 40%, 50%, 60%, 70%, 80%, 90%, 95%, 97.5%, 98%, 99%, 99.5%, 99.75%, 99.9%, or 99.95%, of total number of blood cells present in the blood sample or the blood sample component.

In some embodiments, the cell wash may be produced by washing RBC-enriched cells and/or by separately washing one or more cellular blood compartment(s) selected from whole blood, platelets, leukocytes, an enriched platelet fraction, an enriched leukocyte fraction, platelet-rich plasma, leukocyte-rich plasma, mixtures of platelets and leukocytes, specific leukocyte(s) (e.g., one or more of T lymphocytes (e.g., CD4+ T lymphocytes, CD8+ T lymphocytes), B lymphocytes, NK cells, monocytes, neutrophils, eosinophils, basophils, and the like), or combinations thereof.

In some embodiments, the cell supernatant may be produced by incubating or culturing RBC-enriched cells and/or by separately incubating or culturing one or more cellular blood compartment(s) selected from platelets, leukocytes, an enriched platelet fraction, an enriched leukocyte fraction, platelet-rich plasma, leukocyte-rich plasma, mixtures of platelets and leukocytes, specific leukocyte(s) (e.g., one or more of T lymphocytes (e.g., CD4+ T lymphocytes, CD8+ T lymphocytes), B lymphocytes, NK cells, monocytes, neutrophils, eosinophils, basophils, and the like), or combinations thereof. Cell supernatant may then be separated from the cells and analysed for proteins released (intracellularly and/or from the cell surface) by the incubated or cultured cells. Optionally, cells remaining after removal of the supernatant may be washed and used to generate a protein profile. The cell wash may be combined with the cell supernatant to generate the protein profile, or alternatively individual protein profiles may be generated from the cell wash and the cell supernatant separately. This will allow comparison of the two individual profiles if desired.

A series of cell supernatants may be produced by culturing cells as above for a time period and collecting a series of supernatants at different time points. The supernatant may be analysed for protein content to provide a protein profile analysis over multiple time points. Optionally, the incubation or culture conditions (e.g., content of media, temperature, etc.) may be varied between time points sampling of supernatants. Optionally, cells remaining after removal of the supernatant at one or more time points may be washed and used to generate a protein profile. The cell wash may be combined with the cell supernatant of a given time point (e.g., the same time point) to generate the protein profile.

Alternatively, individual protein profiles may be generated from individual cell washes and individual cell supernatants. Alternatively, cell washes from multiple time points may be pooled and analysed to generate the protein profile. Likewise, cell supernatants from multiple time points may be pooled and analysed to generate the protein profile.

Suitable exemplary protocols and/or media for incubating or culturing the RBC-enriched cells and/or separately incubating or culturing the other cellular blood compartment(s) are available to those of ordinary skill in the art (see, for example, Koller, Palsson, Masters, (Eds) "Human Cell Culture: Vol IV. Primary Hematopoietic cells", 2006, Springer Science and Business Media; Mirty and Hughes (Eds) 2001, "Human Cell Culture Protocols, Third edition", 2011, Humana Press). Methodology is also presented in the Examples of the present specification.

Cell washes may be performed using suitable media such as, for example, phosphate buffered saline (PBS), an isotonic salt solution, a growth medium, a culture medium, or combinations thereof.

Non-limiting examples of suitable media for use as cell wash liquid, cell culture media, or cell incubation media in the methods of the present disclosure include isotonic salt solution, balanced salt solution, saline, phosphate buffered saline (PBS), hank's balanced salt solution (HBSS), Earles' balanced salt solution (EBSS), Roswell Park Memorial Institute medium (RPMI), minimum essential medium (MEM), Improved Minimum Essential Medium (IMEM), Eagle's minimal essential medium (EMEM), Dulbecco's modified Eagle's medium (DMEM), and Iscove's Modified Dulbecco's Media (IDMM), or combinations thereof. In some embodiments, the media is PBS or HBSS to maintain the RBCs in a non-growth or proliferation state. In other embodiments, the media is RPMI to stimulate the growth or proliferation of RBCs.

Blood Stabilising Agents and Anticoagulants

Without limitation to specific mechanistic features, it is hypothesised that RBCs may have a capacity to sequester and release different proteins (e.g., cytokines and chemokines), and the degree of protein release (or alternatively sequestration) by RBCs is thought to be influenced by various factors arising during blood collection and processing.

In some embodiments a blood sample or a component thereof used in certain embodiments may be mixed with a blood stabilising agent. Agents having a capacity to stabilise RBCs are useful so as to reduce or prevent the sequestration and/or release of proteins from RBCs during processing.

The blood cell stabilising agent may be mixed with the blood sample at the time of collecting the blood sample from the subject and/or during subsequent processing of the blood sample or component(s) thereof. By way of non-limiting example, the blood stabilising agent may be mixed with the blood sample or a component thereof within 1 second, 2 seconds, 3 seconds, 4 seconds, 5 seconds, 10 seconds, 20 seconds, 30 seconds, 1 minute, 2 minutes, 3 minutes, 4 minutes, 5 minutes, 10 minutes, 15 minutes, 30 minutes, 45 minutes, 1 hour, 2 hours, 3 hours, 4 hours, 5 hours, 7.5 hours or 10 hours of the blood sample being obtained from the subject.

Non-limiting examples of suitable blood stabilising agents include protease inhibitors, anticoagulants, RNA stabilisers (e.g., RNALater—Thermo Fisher Scientific), protein denaturation agents, or combinations thereof. In certain embodiments, the blood stabilising agent is not a protease inhibitor.

In exemplary embodiments, the blood stabilising agent is an anticoagulant. The anticoagulant may be mixed with the anticoagulant at the time of collecting the blood sample from the subject (e.g., a vessel or container into which the blood sample is collected may contain the anticoagulant), and/or during subsequent processing of the blood sample or component(s) thereof.

Non-limiting examples of suitable anticoagulants include heparin, ethylenediaminetetraacetic acid (EDTA), EDTA disodium salt, EDTA tetrasodium salt, EDTA dipotassium salt, EDTA diammonium salt, ethylenebis(oxyethylenenitrilo)tetraacetic acid (EGTA), EDTA trisodium salt, EDTA tripotassium salt, ethylene glycol-O,O-bis(2-aminoethyl)-N, N,N,N-tetraacetic acid, N-(2-hydroxyethyl)ethylenediamine-N,N,N-triacetic acid trisodium salt, citrate, acid-citrate-dextrose, di-ammonium hydrogen citrate, di-ammonium tartrate, warfarin, N-(2-bis(carboxymethyl) aminoethyl)-N-(2-hydroxyethyl)glycin salt dihydrate, citric acid, citric acid monosodium salt, citric acid disodium salt, citric acid trisodium salt, citric acid monopotassium salt, citric acid tripotassium salt, protein C/protein S, nitrilotriacetic acid, potassium sodium tartrate, potassium hydrogen D-tartrate, L-tartaric acid monosodium salt, L-tartaric acid disodium salt, L-tartaric acid dipotassium salt, streptokinase, protamine sulfate, tris(carboxymethyl)amine, anti-thrombin III, phenprocoumon, hirudin, nicoumalone, Coumadin, glycosaminoglymays, ibuprofen, acetylsalicylic acid, indomethacin, prostaglandins, sulfinpyrazone, urokinase, hirulog, tissue plasminogen activator, coumarin, or combinations thereof.

An anticoagulant may be beneficial to use, for example, when, in addition to the analysis of a RBC-enriched fraction, protein profiling of one or more of leukocytes (white blood cells), platelets and/or plasma is desirable. An anticoagulant may also be beneficial to use if it is desirable to conduct protein profiling of the full cellular component of blood (i.e., a mixed population of blood cells minus the plasma component).

In other embodiments, a blood sample used in the methods of the present disclosure may not be mixed with an anticoagulant when, for example, protein profiling is to be conducted on RBCs, enriched RBCs, or a whole blood sample. In such cases, other stabilising agents without anti-coagulant activity or with only a nominal amount of anticoagulant activity may be mixed with the blood sample or a component thereof. In other embodiments, a blood sample or a component thereof used in the methods of the present disclosure may be stabilised by freezing (e.g., snap freezing) or by drying (e.g., dried blood spot).

Use of Protease Inhibitors

In certain embodiments, the methods comprise contacting a whole blood sample, a red blood cell-enriched sample, or a red blood cell component (e.g., red blood cells or red blood cell membranes) with one or more protease inhibitors that modulate the level of one or more proteins in the sample or component. A red blood cell-enriched sample, or a red blood cell component may be contacted with one or more protease inhibitors by, for example, incubating the red blood cell-enriched sample, or a red blood cell component in a medium (e.g., PBS, HBSS, EBSS, RPMI, MEM, IMEM, EMEM, DMEM, IDMM) containing one or more protease inhibitors. The blood sample or component may be obtained from a subject having a disease or disorder and/or a subject not having a disease or disorder (e.g., a healthy subject). For example, the blood sample or component may be contacted by one or more protease inhibitors that differentially modulate the level of one or more proteins in a sample or component from a subject having a disease or disorder in comparison to the modulation of the level of the one or more proteins in a blood sample or component from a subject that does not have the disease or disorder.

Numerous protease inhibitors may be used in the methods provided herein, either individually or in combination, with suitable protease inhibitors for use in the methods determined by one of ordinary skill in the art. For example, by determining the effect (e.g., magnitude of increase or decrease, or lack of a significant increase or decrease) of individual protease inhibitors on the levels of protein(s) from a red blood cell component, one of skill in the art may choose to use a particular protease inhibitor based on a desired modulation of protein levels. Protease inhibitors suitable for use in the methods may include those that inhibit proteases from various protease families, including, in some embodiments, serine protease inhibitors, cysteine protease inhibitors, metalloproteases inhibitors, aspartic protease inhibitors, and aminopeptidase inhibitors. Protease inhibitors may be specific to the inhibition of a particular protease, or a particular family of proteases, or non-specific, inhibiting a general/common proteolytic mechanism (e.g., EDTA). Protease inhibitors may also include those that inhibit proteases from more than one protease family, for instance, a protease inhibitor that inhibits both serine and cysteine proteases (e.g., leupeptin, phenylmethylsulfonyl fluoride (PMSF), squamous cell carcinoma antigen-1 (SCCA-1)). The protease inhibitors may include those that are endogenous (e.g., endogenous proteins) or synthetic (e.g., chemically synthesized).

Serine protease inhibitors suitable for use in the provided methods may include, for example, alpha-1-antichymotrypsin, C1 Inhibitor (C1INH), alpha-1-antitrypsin, antithrombin III, alpha-1-antiplasmin, plasminogen activator inhibitor-1 (PAI-1), pancreatic trypsin inhibitor, SCCA-1, other members of the SERPIN superfamily that inhibit serine protease activity, aprotinin, chymostatin, leupeptin, antipain dihydrochloride, PMSF (Thermo Fisher Scientific), diisopropyl fluorophosphate (DSF), E-64 (N—(N-L-3-trans-carbonyl)-L-leucyl)-agmatine), Pefabloc® SC (Roche/Sigma-Aldrich), TLCK (CAS 131918-97-3), cathespin (e.g., cathepsin A and G) inhibitors, trypsin inhibitors, and the like.

Cysteine (thiol) protease inhibitors suitable for use in the methods provided herein may include, for example, caspase inhibitors, calpain inhibitors (e.g., calpain inhibitor I, calpain inhibitor II, calpastatin), cathepsin (e.g., cathepsin B, C, F, H, K, S, L, O, S, V, X, and W) (e.g., papain) inhibitors (e.g., cystatins (e.g., stefins, cystatins, kininogens), thyropins, serpins, E-64 (N—(N-L-3-trans-carbonyl)-L-leucyl)-agmatine)), SCCA-1, chymostatin, antipain dihydrochloride, N-Ethylmaleimide, leupeptin, α2-macroglobulin, PMSF, and the like.

Metalloprotease (metalloproteinase) inhibitors suitable for use in the methods provided herein may include, for example, bestatin, phosphoramidon, α2-macroglobulin, tissue inhibitors of metalloproteinases (e.g., TIMP1-TIMP4), EDTA, 2,2'-bipyridyl ReagentPlus®, ethylenediaminetetraacetic acid disodium salt dehydrate, 1,10-phenanthroline monohydrate, phosphoramidon disodium salt, and other synthetic inhibitors (e.g, hydroxamate-based, thiol-based, pyrimidine-based, hydroxyprone-based, phosphorus-based, and tetracycline-based, and metalloendopeptidase inhibitors (e.g., phosphoramidon, SCH 39370), and the like.

Aspartic/aspartyl protease inhibitors suitable for use in the methods provided herein may include, for example, α2-macroglobulin, pepstatin, pepstatin A, cathepsin (e.g., cathepsin D and E) inhibitors, and the like.

Aminopeptidase inhibitors suitable for use in the methods provided herein may include, for example, bestatin hydrochloride, actinonin, arphamenine A, aspstatin, amastatin hydrochloride, arphamenine B, ebelactone A, epiamastatin hydrochloride, aminopeptidase N inhibitor, bestatin methyl ester, 1-glutamic acid gamma-(7-amido-4-methylcoumarin), CHR 2797, captopril, fumagillin, HFI 142, SC 57461A, and the like.

Also suitable for use in the methods provided herein are protease inhibitor cocktails (PIC). In certain embodiments, the protease inhibitor cocktail is A8127s, which comprises antipain-dihydrochloride, bestatin, E-64, leupeptin, pepstatin, phosphoramidon, pefabloc SC, EDTA-Na$_2$, and aprotinin. In other embodiments, PICs such as cOmplete® Protease Inhibitor Cocktail Tablets (Roche), protease inhibitor cocktail powder (Sigma Aldrich, Cat. No. SRE0055), SIGMAFAST protease inhibitor tablets (Sigma Aldrich, Cat. No. S8820), protease inhibitor cocktail (Sigma Aldrich, Cat. No. P8340), animal component free protease inhibitor cocktail (Sigma Aldrich, Cat. No. 13786), Halt Protease and phosphate inhibitor cocktails (Thermo Fisher), Abcam's protease inhibitor (Abcam), Protease inhibitor cocktails (Promega), and the like may be used in the methods provided herein. Moreover, a protease inhibitor cocktail may be customized to enhance the change in the level of protein(s) of interest by determining the effect of individual protease inhibitors on the change in the level of the protein(s) of interest (e.g., proteins in a protein profile). A protease inhibitors may be included in or eliminated from a particular protease inhibitor cocktail based on its effect on the expression of proteins(s) being measured, for instance, for a particular disease protein profile.

In some embodiments, a whole blood sample, a red blood cell-enriched sample, and/or red blood cell component is contacted with one or more protease inhibitors. In other embodiments, a whole blood sample, a red blood cell-enriched sample, and/or red blood cell component is contacted with a combination of the foregoing protease inhibitors (e.g., a combination of serine protease inhibitors, cysteine protease inhibitors, metalloproteases inhibitors, aspartic protease inhibitors, and/or aminopeptidase inhibitors). In some embodiments, a whole blood sample, a red blood cell-enriched sample, and/or red blood cell component is contacted with one or more serine protease inhibitors, one or more cysteine protease inhibitors, one or more metalloprotease inhibitors, one or more aspartic protease inhibitors and/or one or more aminopeptidase inhibitors. In other embodiments, a whole blood sample, a red blood cell-enriched sample, and/or red blood cell component is contacted with one or more serine protease inhibitors and one or more cysteine protease inhibitors. In other embodiments, a whole blood sample, a red blood cell-enriched sample, and/or red blood cell component is contacted with one or more serine protease inhibitors and one or more metalloprotease inhibitors. In some embodiments, a whole blood sample, a red blood cell-enriched sample, and/or red blood cell component is contacted with one or more serine protease inhibitors and one or more aspartyl protease inhibitors. In still other embodiments, a whole blood sample, a red blood cell-enriched sample, and/or red blood cell component is contacted with one or more serine protease inhibitors and one or more aminopeptidase inhibitors. In yet other embodiments, a whole blood sample, a red blood cell-enriched sample, and/or red blood cell component is contacted with one or more serine protease inhibitors, one or more cysteine protease inhibitors, and one or more metalloprotease inhibitors. In other embodiments, a whole blood sample, a red blood cell-enriched sample, and/or red blood cell component is contacted with one or more serine protease inhibitors, one or more cysteine protease inhibitors, and one or more aspartic protease inhibitors. In other embodiments, a whole blood sample, a red blood cell-enriched sample, and/or red blood cell component is contacted with one or more serine protease inhibitors, one or more cysteine protease inhibitors, and one or more aminopeptidase inhibitors. In yet other embodiments, a whole blood sample, a red blood cell-enriched sample, and/or red blood cell component is contacted with one or more cysteine protease inhibitors and one or more metalloprotease inhibitors. In some other embodiments, a whole blood sample, a red blood cell-enriched sample, and/or red blood cell component is contacted with one or more cysteine protease inhibitors and one or more aspartic protease inhibitors. In certain embodiments, a whole blood sample, a red blood cell-enriched sample, and/or red blood cell component is contacted with one or more cysteine protease inhibitors and one or more aminopeptidase inhibitors. In still other embodiments, a whole blood sample, a red blood cell-enriched sample, and/or red blood cell component is contacted with one or more cysteine protease inhibitors, one or more metalloprotease inhibitors and/or one or more aspartic protease inhibitors. In still other embodiments, a whole blood sample, a red blood cell-enriched sample, and/or red blood cell component is contacted with one or more cysteine protease inhibitors, one or more metalloprotease inhibitors and/or one or more aminopeptidase inhibitors. In other embodiments, a whole blood sample, a red blood cell-enriched sample, and/or red blood cell component is contacted with one or more cysteine protease inhibitors, one or more metalloprotease inhibitors, one or more aspartic protease inhibitors, and/or one or more aminopeptidase inhibitors. In other embodiments, a whole blood sample, a red blood cell-enriched sample, and/or red blood cell component is contacted with one or more metalloprotease inhibitors and one or more aspartic protease inhibitors. In still other embodiments, a whole blood sample, a red blood cell-enriched sample, and/or red blood cell component is contacted with one or more metalloprotease inhibitors and one or more aminopeptidase inhibitors. In still other embodiments, a whole blood sample, a red blood cell-enriched sample, and/or red blood cell component is contacted with one or more metalloprotease inhibitors, one or more aspartic protease inhibitors, and one or more aminopeptidase inhibitors. In still other embodiments, a whole blood sample, a red blood cell-enriched sample, and/or red blood cell component is contacted with one or more aspartic protease inhibitors and one or more aminopeptidase inhibitors.

In yet other embodiments, a whole blood sample, a red blood cell-enriched sample, and/or red blood cell component is contacted with one or more protease inhibitors that inhibit both serine and cysteine proteases. In still other embodiments, a whole blood sample, a red blood cell-enriched sample, and/or red blood cell component is contacted with one or more protease inhibitors that inhibit both serine and cysteine proteases and one or more metalloproteases. In other embodiments, a whole blood sample, a red blood cell-enriched sample, and/or red blood cell component is contacted with one or more protease inhibitors that inhibit both serine and cysteine proteases and one or more aspartic proteases. In still other embodiments, a whole blood sample, a red blood cell-enriched sample, and/or red blood cell component is contacted with one or more protease inhibitors that inhibit both serine and cysteine proteases and one or more aminopeptidases. In other embodiments, a whole blood sample, a red blood cell-enriched sample, and/or red blood cell component is contacted with one or more protease inhibitors that inhibit both serine and cysteine proteases, one or more metalloproteases, and one or more aspartic proteases. In other embodiments, a whole blood sample, a red blood cell-enriched sample, and/or red blood cell component is contacted with one or more protease inhibitors that inhibit both serine and cysteine proteases, one or more metalloproteases, one or more aspartic acid proteases, and one or more aminopeptidases. In certain embodiments, a whole blood sample, a red blood cell-enriched sample, and/or red blood cell component is contacted with one or more specific protease inhibitors (e.g., serine, cysteine, metalloprotease, aspartyl protease, or aminopeptidase inhibitors) and one or more non-specific protease inhibitors (e.g., EDTA). In some embodiments, a whole blood sample, a red blood cell-enriched sample, and/or red blood cell component is contacted with one or more of the foregoing protease inhibitors that comprise a protease inhibitor cocktail. In a certain embodiments, a whole blood sample, a red blood cell-enriched sample, and/or red blood cell component is contacted with the protease inhibitor cocktail A8127s.

A number of the foregoing protease inhibitors may be used in combination in certain embodiments. For instance, in some embodiments, a whole blood sample, a red blood cell-enriched sample, and/or red blood cell component may be contacted with one or more protease inhibitors, two or more protease inhibitors, three or more protease inhibitors, four or more protease inhibitors, five or more protease inhibitors, six or more protease inhibitors, seven or more protease inhibitors, eight or more protease inhibitors, nine or more protease inhibitors, ten or more protease inhibitors, eleven or more protease inhibitors, twelve or more protease inhibitors, thirteen or more protease inhibitors, fourteen or more protease inhibitors, fifteen or more protease inhibitors, sixteen or more protease inhibitors, seventeen or more inhibitors, eighteen or more protease inhibitors, nineteen or more protease inhibitors or twenty or more protease inhibitors. In other embodiments, a whole blood sample, a red blood cell-enriched sample, and/or red blood cell component is contacted with two or more protease inhibitors. In other embodiments, a whole blood sample, a red blood cell-enriched sample, and/or red blood cell component is contacted with three or more protease inhibitors. In still other embodiments, a whole blood sample, a red blood cell-enriched sample, and/or red blood cell component is contacted with four or more protease inhibitors. In some other embodiments, a whole blood sample, a red blood cell-enriched sample, and/or red blood cell component is contacted with five or more protease inhibitors. In other embodiments, a whole blood sample, a red blood cell-enriched sample, and/or red blood cell component is contacted with six or more protease inhibitors. In some other embodiments, a whole blood sample, a red blood cell-enriched sample, and/or red blood cell component is contacted with seven or more protease inhibitors. In yet other embodiments, a whole blood sample, a red blood cell-enriched sample, and/or red blood cell component is contacted with eight or more protease inhibitors. In still other embodiments, a whole blood sample, a red blood cell-enriched sample, and/or red blood cell component is contacted with nine or more protease inhibitors. In other embodiments, a whole blood sample, a red blood cell-enriched sample, and/or red blood cell component is contacted with ten or more protease inhibitors. In other embodiments, a whole blood sample, a red blood cell-enriched sample, and/or red blood cell component is contacted with fifteen or more protease inhibitors. In yet other embodiments, a whole blood sample, a red blood cell-enriched sample, and/or red blood cell component is contacted with twenty or more protease inhibitors.

Use of Cationic Salts

Certain embodiments further comprise contacting a red blood cell-enriched sample with at least one cationic salt that increases and/or enhances the detectable level of one or more proteins in the sample. The cationic salt may be one or more that are suitable for use in the methods, as determined by one of ordinary skill in the art. The cationic salt, in some embodiments, is a monovalent or multivalent (e.g., divalent, trivalent) metal ion salt. In other embodiments, the cationic salt is an ammonium salt.

Monovalent metal cationic salts suitable for use in the methods may include, for example, a sodium salt, a potassium salt, a lithium salt, and the like, or combinations thereof. Suitable sodium salts may include, for example, sodium chloride, sodium citrate, sodium sulfate, sodium lactate, sodium acetate, sodium bicarbonate, sodium carbonate, sodium stearate, sodium ascorbate, sodium benzoate, sodium biphosphate, dibasic sodium phosphate, sodium phosphate, sodium bisulfite, sodium borate, sodium gluconate, sodium metasilicate, sodium propionate and the like, or combinations thereof. Suitable potassium salts may include, for example, potassium chloride, potassium citrate, potassium bromide, potassium iodide, potassium bicarbonate, potassium nitrite, potassium persulfate, potassium sulfite, potassium sulfate, potassium bisulfite, potassium phosphate, potassium acetate, potassium citrate, potassium glutamate, dipotassium guanylate, potassium gluconate, potassium malate, potassium ascorbate, potassium sorbate, potassium succinate, potassium tartrate and combinations thereof. Suitable lithium salts include, for example, lithium chloride, lithium bromide, lithium carbonate, lithium nitrate, lithium sulfate, lithium acetate, lithium lactate, lithium citrate, lithium aspartate, lithium gluconate, lithium malate, lithium ascorbate, lithium orotate, lithium succinate or combinations thereof.

Divalent metal cation salts suitable for use in the methods may include, for example, a calcium salt, a potassium salt, a beryllium salt, a strontium salt, a barium salt, a radium salt, an iron (ferrous) salt, and the like, or combinations thereof. Suitable calcium salts include, for example, calcium chloride, calcium sulfate, calcium lactate, calcium citrate, calcium carbonate, calcium acetate, calcium phosphate, calcium alginite, calcium stearate, calcium sorbate, calcium gluconate and the like, or combinations thereof. Suitable magnesium salts may include, for example, magnesium fluoride, magnesium chloride, magnesium bromide, magnesium iodide, magnesium lactate, magnesium phosphate, magnesium sulfate, magnesium sulfite, magnesium carbonate, magnesium oxide, magnesium nitrate, magnesium borate, magnesium acetate, magnesium citrate, magnesium gluconate, magnesium maleate, magnesium succinate, magnesium malate, magnesium taurate, magnesium orotate, magnesium glycinate, magnesium naphthenate, magnesium acetylacetonate, magnesium formate, magnesium hydroxide, magnesium stearate, magnesium hexafluorsilicate, magnesium salicylate or combinations thereof. Suitable beryllium salts may include, for example, beryllium phosphate, beryllium acetate, beryllium tartrate, beryllium citrate, beryllium gluconate, beryllium maleate, beryllium succinate, sodium beryllium malate, beryllium alpha brom camphor sulfonate, beryllium acetylacetonate, beryllium formate or combinations thereof. Suitable strontium salts may include, for example, strontium chloride, strontium phosphate, strontium sulfate, strontium carbonate, strontium oxide, strontium nitrate, strontium acetate, strontium tartrate, strontium citrate, strontium gluconate, strontium maleate, strontium succinate, strontium malate, strontium aspartate in either L and/or D-form, strontium fumarate, strontium glutamate in either L- and/or D-form, strontium glutarate, strontium lactate, strontium L-threonate, strontium malonate, strontium ranelate (organic metal chelate), strontium ascorbate, strontium butyrate, strontium clodronate, strontium ibandronate, strontium salicylate, strontium acetyl salicylate or combinations thereof. Suitable barium salts may include, for example, barium hydroxide, barium fluoride, barium chloride, barium bromide, barium iodide, barium sulfate, barium sulfide (S), barium carbonate, barium peroxide, barium oxide, barium nitrate, barium acetate, barium tartrate, barium citrate, barium gluconate, barium maleate, barium succinate, barium malate, barium glutamate, barium oxalate, barium malonate, barium naphthenate, barium acetylacetonate, barium formate, barium benzoate, barium p-t-butylbenzoate, barium adipate, barium pimelate, barium suberate, barium azelate, barium sebacate, barium phthalate, barium isophthalate, barium terephthalate, barium anthranilate, barium mandelate, barium salicylate, barium titanate or combinations thereof. Suitable radium salts may include, for example, radium fluoride, radium chloride, radium bromide, radium iodide, radium oxide, radium nitride or combinations thereof. Suitable radium salts included, for example, radium fluoride, radium chloride, radium bromide, radium iodide, radium oxide, radium nitride, and the like. Suitable iron (ferrous) salts may include, for example, ferrous sulfate, ferrous oxides, ferrous acetate, ferrous citrate, ferrous ammonium citrate, ferrous gluconate, ferrous oxalate, ferrous fumarate, ferrous maleate, ferrous malate, ferrous lactate, ferrous ascorbate, ferrous erythrobate, ferrous glycerate, ferrous pyruvate, and the like, or combinations thereof.

In certain embodiments, the cationic salt is one that may prevent and/or minimize pH change in the red blood cell-enriched sample (e.g., a chloride or carbonate salt). Thus, in certain embodiments, the cationic salt is a carbonate salt. In further embodiments, the cationic salt may also prevent or minimize damage to cell membranes (e.g., RBC membranes). In certain embodiments, the cationic salt is a chloride salt. In other embodiments, the cationic salt is calcium chloride, potassium chloride, strontium chloride, barium chloride, radium chloride, or combinations thereof. In still other embodiments, the cationic salt is sodium chloride, potassium chloride, rubidium chloride, cesium chloride, lithium chloride, or combinations thereof. In other embodiments, the cationic salt is lithium chloride. In other embodiments, the cationic salt may be sodium chloride. In certain embodiments, the cationic salt may be calcium carbonate, potassium carbonate, strontium carbonate, barium carbonate, or radium carbonate. In still other embodiments, the cationic salt is sodium carbonate, potassium carbonate, rubidium carbonate, cesium carbonate, lithium carbonate, or combinations thereof. In yet other embodiments, the cationic salt is lithium carbonate. In other embodiments, the cationic salt is sodium carbonate.

Salts other than monovalent or divalent metal cation salts may be used in the methods, including, for example, a trivalent or other multivalent salt, such as aluminum, silicon, scandium, titanium, vanadium, chromium, cobalt, nickel, copper, manganese, zinc, tin, silver and the like, or combinations thereof.

Ammonium salts may also be used in the methods with suitable ammonium salts including ammonium carbonate, ammonium chloride, ammonium nitrate, ammonium acetate, ammonium biorate, ammonium bromide, ammonium carbamate, ammonium cerium (IV) sulphate, ammonium chromate, ammonium dichromate, ammonium dihydrogen phosphate, ammonium fluoride, ammonium formate, ammonium phosphate, ammonium sodium phosphate dibasic tetrahydrate, ammonium thiosulfate, ammonium zirconium, and the like, or combinations thereof.

In certain embodiments, the cationic salt is ammonium chloride. In other embodiments, the cationic salt is ammonium carbonate.

In certain embodiments, the red blood cell-enriched sample is contacted with one or more combinations of the foregoing cationic salts to increase and/or enhance the detectable level of one or more protein in the sample. In some embodiments, the red blood cell-enriched sample is contacted with at least one cationic salt. In other embodiments, the red blood cell-enriched sample is contacted with at least two cationic salts. In still other embodiments, the red blood cell-enriched sample is contacted with at least three cationic salts.

In certain embodiments, the blood sample is contacted with one or more combinations of the foregoing cationic salts to increase and/or enhance the detectable level of one or more proteins in the sample prior to the red blood cell enriching of the blood sample. In some embodiments, the blood sample is contacted with at least one cationic salt. In other embodiments, the blood sample is contacted with at least two cationic salts. In still other embodiments, the blood sample is contacted with at least three cationic salts.

The references to salts (e.g., sodium containing salts) herein include anhydrous forms and hydrated forms of the salt.

In certain embodiments, a whole blood sample is contacted with at least one of the foregoing cationic salts to produce a protein profile. The whole blood sample may be obtained from venous blood, capillary blood, arterial blood or combinations thereof, using methods available to one of ordinary skill in the art.

In other embodiments, one or more additional blood compartment(s) selected from plasma, serum, platelets, leukocytes, an enriched platelet fraction, an enriched leukocyte fraction, platelet-rich plasma, leukocyte-rich plasma, a mixture of platelets and leukocytes, specific leukocyte(s) (e.g., one or more of T lymphocytes (e.g., CD4+ T lymphocytes, CD8+ T lymphocytes), B lymphocytes, NK cells, monocytes, neutrophils, eosinophils, basophils, and the like), and combinations thereof, are contacted by at least one of the foregoing cationic salts to produce a protein profile. The additional blood compartment(s) for analysis may be prepared using available techniques (e.g., flow cytometry, magnetic bead separation, centrifugation, and the like).

Protein Detection and Profiling

The present disclosure provides methods for producing a protein profile from a blood sample comprising a RBC component (e.g., an RBC-enriched sample, RBC-enriched fraction or a whole blood sample). The production of such profiles may provide insight into biological processes including, but not limited to inflammation, immune responses, and/or cellular repair, and/or disease state.

While not imparting particular limitations to the type(s) of proteins that may be detected or measured in generating a protein profile by the methods of the present disclosure, non-limiting examples include signalling molecules, e.g., chemokines, cytokines, other inflammatory proteins, glycoproteins, growth factors, receptors, intracellular signal transmitters, hormones, nuclear transcription factors, neurotransmitters, and extracellular matrix components, and enzymes. For instance, growth factors may include those that stimulate the growth, proliferation, healing, or differentiation of, for example, skin cells (e.g., epidermal growth factor (EGF), keratinocyte growth factor (KGF), migration stimulating factor (MSF)), nerve cells/nervous system (e.g., neuregulins (e.g., neuregulin 1-4) and neurotrophins (e.g., nerve growth factor (NGF), brain-derived neurotrophic factor (BDNF), neurotrophin-3 (NT-3), neurotrophin-4 (NT-4))), connective tissue and mesenchymal cells (e.g., fibroblast growth factor (FGF)), blood vessel cells (e.g., platelet-derived growth factor (PDGF), placental growth factor (PGF), vascular endothelial growth factor (VEGF)), blood cells (e.g., erythropoietin, granulocyte colony stimulating factor (G-CSF), granulocyte macrophage colony-stimulating factor (GM-CSF)), and cell proliferation (e.g., insulin-like growth factor (IGF-1), insulin-like growth factor-2 (IGF-2)) along with pleitropic growth factors (e.g, transforming growth factor-beta (TGF-$\beta$), transforming growth factor-beta (TGF-$\alpha$), tumor necrosis factor (TNF)).

Receptors may include intracellular receptors (e.g., nuclear (e.g., transcription factors), cytoplasmic (e.g., steroid), and endoplasmic recticulum (e.g., IP3) receptors), cell surface receptors (e.g., ion channel-linked, G-protein-linked, enzyme-linked, toll gate, and ligand gated receptors, integrins), soluble receptors (e.g., soluble cytokine receptors), and scavenger receptors (e.g., SR-A1, SR-A2, SCARA1-SCARA5, SCARB1-SCARB3, CD68, dSR-C1, LOX-1, sPD-1, sCTLA-4). Hormones may include lipid-derived (e.g., prostaglandins, leukotrienes, prostacylins, thromboxane); amino acid-derived (e.g., epinephrine, melatonin, thyroxine); peptide (e.g., amylin, adiponenctin, angiotensinogen, calcitonin, brain natriuretic peptide (BNP), erythropoietin, follicle-stimulating hormone (FSH), ghrelin, glucagon-like peptide-1 (GLP-1), human chorionic gonadotropin (hCG), insulin, insulin-like growth factor (IGF), and the like); and steroids (e.g., androgen, estrogen, glucocorticoid, progestogen, secosteroid, and the like). Intracellular signal transmitters or transducers may include families of proteins and protein kinases (e.g., Ras and Src families), and Wnt signalling family proteins. Neurotransmitters may include amino acids, peptides (e.g., $\beta$-endorphin, opioid), monoamines, trace amines, purines, and gasotransmitters. Nuclear transcription factors may include modulators of DNA transcription (e.g., fos, myc, N-myc), and modulators of mRNA transcription, and suppressors of cell division (e.g., p53, pRb). Enzymes may include oxidoreductases (e.g., alcohol, aldehyde, amino acid, sulphur, diphenol, peroxidises, and the like) NADH, NADPH, nucleases, proteases, kinases, transferases, hydrolases, lyases, isomerases, and ligases. Chemokines and cytokines are numerous may include, for example, those listed in Table 1 and Table 2 below.

In certain embodiments, the methods comprise producing a protein profile consisting of, or comprising, a single protein or combinations of proteins as set out in Tables 1 and 2 below. The profile may be generated from a blood sample comprising an RBC component (e.g., a red blood cell-enriched sample, RBC-enriched fraction, or a whole blood sample). Additional profile(s) may be generated from other cellular compartment(s) including, but not limited to, plasma, serum, platelets, leukocytes, an enriched platelet fraction, an enriched leukocyte fraction, platelet-rich plasma, leukocyte-rich plasma, a mixture of platelets and leukocytes, specific leukocyte(s) (e.g., one or more of T lymphocytes (e.g., CD4+ T lymphocytes, CD8+ T lymphocytes), B lymphocytes, NK cells, monocytes, neutrophils, eosinophils, basophils, and the like), or combinations thereof.

TABLE 1

Non-limiting examples of individual proteins that may be included in a protein profile generated by the methods of the present disclosure. The protein profile may comprise or consist of one or more of the proteins listed.

| Single Protein (acronym) | Single Protein (full name) |
| --- | --- |
| basic FGF | basic fibroblast growth factor |
| CTACK (CCL27) | cutaneous T cell-attracting chemokine |
| Eotaxin 1 | CCL11 #1 |
| G-CSF (GCSF) | granulocyte-colony stimulating factor |
| GM-CSF (CSF2) | granulocyte-macrophage colony-stimulating factor |
| HGF | hepatocyte growth factor |
| IFN-α2 | interferon alpha subtype α2 |
| IFN-γ | interferon gamma |
| IL-10 | interleukin 10 |
| IL-12 (IL-12p70) | interleukin 12 p35 and p40 heterodimer |
| IL-13 | interleukin 13 |
| IL-12p40 | interleukin 12 p40 subunit |
| IL-15 | interleukin 15 |
| IL-16 | interleukin 16 |
| IL-17A | interleukin 17A |
| IL-18 | interleukin 18 |
| IL-1α | interleukin 1 alpha |
| IL-1β | interleukin 1 beta |
| IL-2 | interleukin 2 |
| IL-2ra | interleukin 2 receptor alpha chain |
| IL-3 | interleukin 3 |
| IL-5 | interleukin 5 |
| IL-6 | interleukin 6 |
| IL-7 | interleukin 7 |
| IL-9 | interleukin 9 |
| IP-10 (CXCL10) | interferon gamma-induced protein 10 |
| LIF | leukaemia inhibitory factor |
| M-CSF (CSF1) | macrophage colony-stimulating factor |
| MIG (CXCL9) | monokine induced by IFN-γ, Chemokine (C-X-C motif) ligand 9 |
| MIP-1α (CCL3) | macrophage inflammatory protein-1 alpha |
| MIP-1β (CCL4) | macrophage inflammatory protein-1 alpha |
| PDGF-BB | platelet-derived growth factor B chain homodimer |
| SDF-1α (CXCL12) | stromal cell-derived factor 1 |
| TNF-α (cachexin) | tumour necrosis factor alpha |
| TNF-β (lymphotoxin) | tumour necrosis factor-beta |
| TRAIL | TNF-related apoptosis-inducing ligand |
| VEGF | vascular endothelial growth factor |
| IL-8 | interleukin 8 |
| MCP-1 (CCL2) | monocyte chemoattractant protein-1 |
| MGSA | maintenance of genome stability protein A |
| PGE-2 | prostaglandin E2 |
| RANTES (CCL5) | regulated on activation, normal T cell expressed and secreted |
| MIF (MMIF) | macrophage migration inhibitory factor |
| GRO-α (CXCL1) | Growth-regulated oncogene α |
| CRP | C-reactive protein |
| DDT (MIF-2) | D-dopachrome tautomerase |
| IGF-1 | insulin like growth factor 1 |
| sEGFR | epidermal growth factor receptor |
| sHER-2/neu (CD340) | receptor tyrosine-protein kinase erbB-2 |
| sIL-6Ra | interleukin-6 receptor |
| Leptin | |
| Osteopontin | |
| PECAM-1 (CD31) | platelet endothelial cell adhesion molecule precursor |
| PDGF-AB/BB | platelet-derived growth factor AB/platelet derived growth factor BB |
| Prolactin | prolactin |
| sTIE-1 | tyrosine kinase with Ig and EGF homology domains-1 |
| sTIE-2 | tyrosine kinase with Ig and EGF homology domains-2 |
| sVEGFR-1 | vascular endothelial growth factor receptor-1 |
| sVEGFR-2 | vascular endothelial growth factor receptor-2 |
| APRIL/TNFSF13 | A proliferation-inducing ligand/tumor necrosis factor ligand superfamily member 13 |
| BAFF/TNFSF13B | B-cell activating factor/tumor necrosis factor ligand superfamily member 13B |
| TNFRSF8 (CD30) | TNF receptor superfamily member 8 |
| sCD163 | cluster of differentiation 163 |
| CHI3L1 | Chitinase-3-like 1 |
| gp130/sIL-6Rβ | glycoprotein 130/interleukin-6 receptor beta |
| IL-11 | interleukin-11 |
| IL-19 | interleukin-19 |
| IL-20 | interleukin-20 |
| IL-22 | interleukin-22 |
| IL-26 | interleukin-26 |
| IL-27(p28) | interleukin-27(p28) |
| IL-28A/IFN-λ2 | interleukin-28/interferon gamma 2 |
| IL-29/IFN-λ1 | interleukin-29/interferon gamma 1 |
| IL-32 | interleukin-32 |
| IL-34 | interleukin-34 |
| IL-35 | interleukin-35 |
| TNFSF14/LIGHT | tumor necrosis factor superfamily member 14/homologous to lymphotoxin, exhibits inducible expression and competes with HSV glycoprotein D for binding to herpersvirus entry mediator, a receptor expressed on T lymphocytes/ |
| MMP-1 | matrix metalloproteinase-1 |
| MMP-2 | matrix metalloproteinase-2 |
| MMP-3 | matrix metalloproteinase-3 |
| Osteocalcin | |
| Pentraxin-3 | |
| sTNF-R1 | tumor necrosis factor receptor 1 |
| sTNF-R2 | tumor necrosis factor receptor 2 |
| TSLP | thymic stromal lymphopoietin |
| TWEAK/TNFSF12 | TNF-related weak inducer of apoptosis/tumor necrosis factor superfamily member 12 |
| 4-1BB (CD137) | |
| CTLA-4 (CD152) | cytotoxic T-lymphocyte associated protein 4 |
| Lag-3 (CD223) | lymphocyte-activation gene 3 |
| CD27 | |
| HVEM/TNFRSF14 (CD270) | herpesvirus entry mediator/tumor necrosis factor superfamily member 14 |
| BTLA (CD272) | B- and T-lymphocyte associated |
| PD-1 (CD279) | programmed cell death protein 1 |
| CD28 | |
| GITR/TNFRSF18 (CD357) | glucocorticoid-induced TNFR family related gene/ tumor necrosis factor superfamily member 18 |
| B7-1 (CD80) | |
| TIM3 | T-cell immunoglobulin domain and mucin domain 3 |

TABLE 2

Non-limiting examples of protein pairs that may be included in a protein profile generated by the methods of the present disclosure. The protein profile may comprise or consist of one or more protein pairs listed.

| Protein #1 | Protein #2 | Protein #1 | Protein #2 | Protein #1 | Protein #2 | Protein #1 | Protein #2 |
|---|---|---|---|---|---|---|---|
| basic FGF | CTACK | CTACK | Eotaxin 1 | Eotaxin 1 | G-CSF | G-CSF | GM-CSF |
| basic FGF | Eotaxin 1 | CTACK | G-CSF | Eotaxin 1 | GM-CSF | G-CSF | HGF |
| basic FGF | G-CSF | CTACK | GM-CSF | Eotaxin 1 | HGF | G-CSF | IFN-α2 |
| basic FGF | GM-CSF | CTACK | HGF | Eotaxin 1 | IFN-α2 | G-CSF | IFN-γ |
| basic FGF | HGF | CTACK | IFN-α2 | Eotaxin 1 | IFN-γ | G-CSF | IL-10 |
| basic FGF | IFN-α2 | CTACK | IFN-γ | Eotaxin 1 | IL-10 | G-CSF | IL-12 |
| basic FGF | IFN-γ | CTACK | IL-10 | Eotaxin 1 | IL-12 | G-CSF | IL-13 |
| basic FGF | IL-10 | CTACK | IL-12 | Eotaxin 1 | IL-13 | G-CSF | IL-12p40 |
| basic FGF | IL-12 | CTACK | IL-13 | Eotaxin 1 | IL-12p40 | G-CSF | IL-15 |
| basic FGF | IL-13 | CTACK | IL-12p40 | Eotaxin 1 | IL-15 | G-CSF | IL-16 |
| basic FGF | IL-12p40 | CTACK | IL-15 | Eotaxin 1 | IL-16 | G-CSF | IL-17A |
| basic FGF | IL-15 | CTACK | IL-16 | Eotaxin 1 | IL-17A | G-CSF | IL-18 |
| basic FGF | IL-16 | CTACK | IL-17A | Eotaxin 1 | IL-18 | G-CSF | IL-1α |
| basic FGF | IL-17A | CTACK | IL-18 | Eotaxin 1 | IL-1α | G-CSF | IL-1β |
| basic FGF | IL-18 | CTACK | IL-1α | Eotaxin 1 | IL-1β | G-CSF | IL-2 |
| basic FGF | IL-1α | CTACK | IL-1β | Eotaxin 1 | IL-2 | G-CSF | IL-2ra |
| basic FGF | IL-1β | CTACK | IL-2 | Eotaxin 1 | IL-2ra | G-CSF | IL-3 |
| basic FGF | IL-2 | CTACK | IL-2ra | Eotaxin 1 | IL-3 | G-CSF | IL-5 |
| basic FGF | IL-2ra | CTACK | IL-3 | Eotaxin 1 | IL-5 | G-CSF | IL-6 |
| basic FGF | IL-3 | CTACK | IL-5 | Eotaxin 1 | IL-6 | G-CSF | IL-7 |
| basic FGF | IL-5 | CTACK | IL-6 | Eotaxin 1 | IL-7 | G-CSF | IL-9 |
| basic FGF | IL-6 | CTACK | IL-7 | Eotaxin 1 | IL-9 | G-CSF | IP-10 |
| basic FGF | IL-7 | CTACK | IL-9 | Eotaxin 1 | IP-10 | G-CSF | LIF |
| basic FGF | IL-9 | CTACK | IP-10 | Eotaxin 1 | LIF | G-CSF | M-CSF |
| basic FGF | IP-10 | CTACK | LIF | Eotaxin 1 | M-CSF | G-CSF | MIG |
| basic FGF | LIF | CTACK | M-CSF | Eotaxin 1 | MIG | G-CSF | MIP-1α |
| basic FGF | M-CSF | CTACK | MIG | Eotaxin 1 | MIP-1α | G-CSF | MIP-1β |
| basic FGF | MIG | CTACK | MIP-1α | Eotaxin 1 | MIP-1β | G-CSF | PDGF-BB |
| basic FGF | MIP-1α | CTACK | MIP-1β | Eotaxin 1 | PDGF-BB | G-CSF | SDF-1α |
| basic FGF | MIP-1β | CTACK | PDGF-BB | Eotaxin 1 | SDF-1α | G-CSF | TNF-α |
| basic FGF | PDGF-BB | CTACK | SDF-1α | Eotaxin 1 | TNF-α | G-CSF | TNF-β |
| basic FGF | SDF-1α | CTACK | TNF-α | Eotaxin 1 | TNF-β | G-CSF | TRAIL |
| basic FGF | TNF-α | CTACK | TNF-β | Eotaxin 1 | TRAIL | G-CSF | VEGF |
| basic FGF | TNF-β | CTACK | TRAIL | Eotaxin 1 | VEGF | G-CSF | IL-8 |
| basic FGF | TRAIL | CTACK | VEGF | Eotaxin 1 | IL-8 | G-CSF | MCP-1 |
| basic FGF | VEGF | CTACK | IL-8 | Eotaxin 1 | MCP-1 | G-CSF | MGSA |
| basic FGF | IL-8 | CTACK | MCP-1 | Eotaxin 1 | MGSA | G-CSF | PGE-2 |
| basic FGF | MCP-1 | CTACK | MGSA | Eotaxin 1 | PGE-2 | G-CSF | RANTES |
| basic FGF | MGSA | CTACK | PGE-2 | Eotaxin 1 | RANTES | G-CSF | MIF |
| basic FGF | PGE-2 | CTACK | RANTES | Eotaxin 1 | MIF | G-CSF | GRO-α |
| basic FGF | RANTES | CTACK | MIF | Eotaxin 1 | GRO-α | G-CSF | CRP |
| basic FGF | MIF | CTACK | GRO-α | Eotaxin 1 | CRP | G-CSF | DDT |
| basic FGF | GRO-α | CTACK | CRP | Eotaxin 1 | DDT | | |
| basic FGF | CRP | CTACK | DDT | | | | |
| basic FGF | DDT | | | | | | |
| GM-CSF | HGF | HGF | IFN-α2 | IFN-α2 | IFN-γ | IFN-γ | IL-10 |
| GM-CSF | IFN-α2 | HGF | IFN-γ | IFN-α2 | IL-10 | IFN-γ | IL-12 |
| GM-CSF | IFN-γ | HGF | IL-10 | IFN-α2 | IL-12 | IFN-γ | IL-13 |
| GM-CSF | IL-10 | HGF | IL-12 | IFN-α2 | IL-13 | IFN-γ | IL-12p40 |
| GM-CSF | IL-12 | HGF | IL-13 | IFN-α2 | IL-12p40 | IFN-γ | IL-15 |
| GM-CSF | IL-13 | HGF | IL-12p40 | IFN-α2 | IL-15 | IFN-γ | IL-16 |
| GM-CSF | IL-12p40 | HGF | IL-15 | IFN-α2 | IL-16 | IFN-γ | IL-17A |
| GM-CSF | IL-15 | HGF | IL-16 | IFN-α2 | IL-17A | IFN-γ | IL-18 |
| GM-CSF | IL-16 | HGF | IL-17A | IFN-α2 | IL-18 | IFN-γ | IL-1α |
| GM-CSF | IL-17A | HGF | IL-18 | IFN-α2 | IL-1α | IFN-γ | IL-1β |
| GM-CSF | IL-18 | HGF | IL-1α | IFN-α2 | IL-1β | IFN-γ | IL-2 |
| GM-CSF | IL-1α | HGF | IL-1β | IFN-α2 | IL-2 | IFN-γ | IL-2ra |
| GM-CSF | IL-1β | HGF | IL-2 | IFN-α2 | IL-2ra | IFN-γ | IL-3 |
| GM-CSF | IL-2 | HGF | IL-2ra | IFN-α2 | IL-3 | IFN-γ | IL-5 |
| GM-CSF | IL-2ra | HGF | IL-3 | IFN-α2 | IL-5 | IFN-γ | IL-6 |
| GM-CSF | IL-3 | HGF | IL-5 | IFN-α2 | IL-6 | IFN-γ | IL-7 |
| GM-CSF | IL-5 | HGF | IL-6 | IFN-α2 | IL-7 | IFN-γ | IL-9 |
| GM-CSF | IL-6 | HGF | IL-7 | IFN-α2 | IL-9 | IFN-γ | IP-10 |
| GM-CSF | IL-7 | HGF | IL-9 | IFN-α2 | IP-10 | IFN-γ | LIF |
| GM-CSF | IL-9 | HGF | IP-10 | IFN-α2 | LIF | IFN-γ | M-CSF |
| GM-CSF | IP-10 | HGF | LIF | IFN-α2 | M-CSF | IFN-γ | MIG |
| GM-CSF | LIF | HGF | M-CSF | IFN-α2 | MIG | IFN-γ | MIP-1α |
| GM-CSF | M-CSF | HGF | MIG | IFN-α2 | MIP-1α | IFN-γ | MIP-1β |
| GM-CSF | MIG | HGF | MIP-1α | IFN-α2 | MIP-1β | IFN-γ | PDGF-BB |
| GM-CSF | MIP-1α | HGF | MIP-1β | IFN-α2 | PDGF-BB | IFN-γ | SDF-1α |
| GM-CSF | MIP-1β | HGF | PDGF-BB | IFN-α2 | SDF-1α | IFN-γ | TNF-α |
| GM-CSF | PDGF-BB | HGF | SDF-1α | IFN-α2 | TNF-α | IFN-γ | TNF-β |
| GM-CSF | SDF-1α | HGF | TNF-α | IFN-α2 | TNF-β | IFN-γ | TRAIL |
| GM-CSF | TNF-α | HGF | TNF-β | IFN-α2 | TRAIL | IFN-γ | VEGF |

TABLE 2-continued

Non-limiting examples of protein pairs that may be included in a protein profile generated by the methods of the present disclosure. The protein profile may comprise or consist of one or more protein pairs listed.

| Protein #1 | Protein #2 | Protein #1 | Protein #2 | Protein #1 | Protein #2 | Protein #1 | Protein #2 |
|---|---|---|---|---|---|---|---|
| GM-CSF | TNF-β | HGF | TRAIL | IFN-α2 | VEGF | IFN-γ | IL-8 |
| GM-CSF | TRAIL | HGF | VEGF | IFN-α2 | IL-8 | IFN-γ | MCP-1 |
| GM-CSF | VEGF | HGF | IL-8 | IFN-α2 | MCP-1 | IFN-γ | MGSA |
| GM-CSF | IL-8 | HGF | MCP-1 | IFN-α2 | MGSA | IFN-γ | PGE-2 |
| GM-CSF | MCP-1 | HGF | MGSA | IFN-α2 | PGE-2 | IFN-γ | RANTES |
| GM-CSF | MGSA | HGF | PGE-2 | IFN-α2 | RANTES | IFN-γ | MIF |
| GM-CSF | PGE-2 | HGF | RANTES | IFN-α2 | MIF | IFN-γ | GRO-α |
| GM-CSF | RANTES | HGF | MIF | IFN-α2 | GRO-α | IFN-γ | CRP |
| GM-CSF | MIF | HGF | GRO-α | IFN-α2 | CRP | IFN-γ | DDT |
| GM-CSF | GRO-α | HGF | CRP | IFN-α2 | DDT | | |
| GM-CSF | CRP | HGF | DDT | | | | |
| GM-CSF | DDT | | | | | | |
| IL-10 | IL-12 | IL-12 | IL-13 | IL-13 | IL-12p40 | IL-12p40 | IL-15 |
| IL-10 | IL-13 | IL-12 | IL-12p40 | IL-13 | IL-15 | IL-12p40 | IL-16 |
| IL-10 | IL-12p40 | IL-12 | IL-15 | IL-13 | IL-16 | IL-12p40 | IL-17A |
| IL-10 | IL-15 | IL-12 | IL-16 | IL-13 | IL-17A | IL-12p40 | IL-18 |
| IL-10 | IL-16 | IL-12 | IL-17A | IL-13 | IL-18 | IL-12p40 | IL-1α |
| IL-10 | IL-17A | IL-12 | IL-18 | IL-13 | IL-1α | IL-12p40 | IL-1β |
| IL-10 | IL-18 | IL-12 | IL-1α | IL-13 | IL-1β | IL-12p40 | IL-2 |
| IL-10 | IL-1α | IL-12 | IL-1β | IL-13 | IL-2 | IL-12p40 | IL-2ra |
| IL-10 | IL-1β | IL-12 | IL-2 | IL-13 | IL-2ra | IL-12p40 | IL-3 |
| IL-10 | IL-2 | IL-12 | IL-2ra | IL-13 | IL-3 | IL-12p40 | IL-5 |
| IL-10 | IL-2ra | IL-12 | IL-3 | IL-13 | IL-5 | IL-12p40 | IL-6 |
| IL-10 | IL-3 | IL-12 | IL-5 | IL-13 | IL-6 | IL-12p40 | IL-7 |
| IL-10 | IL-5 | IL-12 | IL-6 | IL-13 | IL-7 | IL-12p40 | IL-9 |
| IL-10 | IL-6 | IL-12 | IL-7 | IL-13 | IL-9 | IL-12p40 | IP-10 |
| IL-10 | IL-7 | IL-12 | IL-9 | IL-13 | IP-10 | IL-12p40 | LIF |
| IL-10 | IL-9 | IL-12 | IP-10 | IL-13 | LIF | IL-12p40 | M-CSF |
| IL-10 | IP-10 | IL-12 | LIF | IL-13 | M-CSF | IL-12p40 | MIG |
| IL-10 | LIF | IL-12 | M-CSF | IL-13 | MIG | IL-12p40 | MIP-1α |
| IL-10 | M-CSF | IL-12 | MIG | IL-13 | MIP-1α | IL-12p40 | MIP-1β |
| IL-10 | MIG | IL-12 | MIP-1α | IL-13 | MIP-1β | IL-12p40 | PDGF-BB |
| IL-10 | MIP-1α | IL-12 | MIP-1β | IL-13 | PDGF-BB | IL-12p40 | SDF-1α |
| IL-10 | MIP-1β | IL-12 | PDGF-BB | IL-13 | SDF-1α | IL-12p40 | TNF-α |
| IL-10 | PDGF-BB | IL-12 | SDF-1α | IL-13 | TNF-α | IL-12p40 | TNF-β |
| IL-10 | SDF-1α | IL-12 | TNF-α | IL-13 | TNF-β | IL-12p40 | TRAIL |
| IL-10 | TNF-α | IL-12 | TNF-β | IL-13 | TRAIL | IL-12p40 | VEGF |
| IL-10 | TNF-β | IL-12 | TRAIL | IL-13 | VEGF | IL-12p40 | IL-8 |
| IL-10 | TRAIL | IL-12 | VEGF | IL-13 | IL-8 | IL-12p40 | MCP-1 |
| IL-10 | VEGF | IL-12 | IL-8 | IL-13 | MCP-1 | IL-12p40 | MGSA |
| IL-10 | IL-8 | IL-12 | MCP-1 | IL-13 | MGSA | IL-12p40 | PGE-2 |
| IL-10 | MCP-1 | IL-12 | MGSA | IL-13 | PGE-2 | IL-12p40 | RANTES |
| IL-10 | MGSA | IL-12 | PGE-2 | IL-13 | RANTES | IL-12p40 | MIF |
| IL-10 | PGE-2 | IL-12 | RANTES | IL-13 | MIF | IL-12p40 | GRO-α |
| IL-10 | RANTES | IL-12 | MIF | IL-13 | GRO-α | IL-12p40 | CRP |
| IL-10 | MIF | IL-12 | GRO-α | IL-13 | CRP | IL-12p40 | DDT |
| IL-10 | GRO-α | IL-12 | CRP | IL-13 | DDT | | |
| IL-10 | CRP | IL-12 | DDT | | | | |
| IL-10 | DDT | | | | | | |
| IL-15 | IL-16 | IL-16 | IL-17A | IL-17A | IL-18 | IL-18 | IL-1α |
| IL-15 | IL-17A | IL-16 | IL-18 | IL-17A | IL-1α | IL-18 | IL-1β |
| IL-15 | IL-18 | IL-16 | IL-1α | IL-17A | IL-1β | IL-18 | IL-2 |
| IL-15 | IL-1α | IL-16 | IL-1β | IL-17A | IL-2 | IL-18 | IL-2ra |
| IL-15 | IL-1β | IL-16 | IL-2 | IL-17A | IL-2ra | IL-18 | IL-3 |
| IL-15 | IL-2 | IL-16 | IL-2ra | IL-17A | IL-3 | IL-18 | IL-5 |
| IL-15 | IL-2ra | IL-16 | IL-3 | IL-17A | IL-5 | IL-18 | IL-6 |
| IL-15 | IL-3 | IL-16 | IL-5 | IL-17A | IL-6 | IL-18 | IL-7 |
| IL-15 | IL-5 | IL-16 | IL-6 | IL-17A | IL-7 | IL-18 | IL-9 |
| IL-15 | IL-6 | IL-16 | IL-7 | IL-17A | IL-9 | IL-18 | IP-10 |
| IL-15 | IL-7 | IL-16 | IL-9 | IL-17A | IP-10 | IL-18 | LIF |
| IL-15 | IL-9 | IL-16 | IP-10 | IL-17A | LIF | IL-18 | M-CSF |
| IL-15 | IP-10 | IL-16 | LIF | IL-17A | M-CSF | IL-18 | MIG |
| IL-15 | LIF | IL-16 | M-CSF | IL-17A | MIG | IL-18 | MIP-1α |
| IL-15 | M-CSF | IL-16 | MIG | IL-17A | MIP-1α | IL-18 | MIP-1β |
| IL-15 | MIG | IL-16 | MIP-1α | IL-17A | MIP-1β | IL-18 | PDGF-BB |
| IL-15 | MIP-1α | IL-16 | MIP-1β | IL-17A | PDGF-BB | IL-18 | SDF-1α |
| IL-15 | MIP-1β | IL-16 | PDGF-BB | IL-17A | SDF-1α | IL-18 | TNF-α |
| IL-15 | PDGF-BB | IL-16 | SDF-1α | IL-17A | TNF-α | IL-18 | TNF-β |
| IL-15 | SDF-1α | IL-16 | TNF-α | IL-17A | TNF-β | IL-18 | TRAIL |
| IL-15 | TNF-α | IL-16 | TNF-β | IL-17A | TRAIL | IL-18 | VEGF |
| IL-15 | TNF-β | IL-16 | TRAIL | IL-17A | VEGF | IL-18 | IL-8 |
| IL-15 | TRAIL | IL-16 | VEGF | IL-17A | IL-8 | IL-18 | MCP-1 |
| IL-15 | VEGF | IL-16 | IL-8 | IL-17A | MCP-1 | IL-18 | MGSA |
| IL-15 | IL-8 | IL-16 | MCP-1 | IL-17A | MGSA | IL-18 | PGE-2 |

TABLE 2-continued

Non-limiting examples of protein pairs that may be included in a protein profile generated by the methods of the present disclosure. The protein profile may comprise or consist of one or more protein pairs listed.

| Protein #1 | Protein #2 | Protein #1 | Protein #2 | Protein #1 | Protein #2 | Protein #1 | Protein #2 |
|---|---|---|---|---|---|---|---|
| IL-15 | MCP-1 | IL-16 | MGSA | IL-17A | PGE-2 | IL-18 | RANTES |
| IL-15 | MGSA | IL-16 | PGE-2 | IL-17A | RANTES | IL-18 | MIF |
| IL-15 | PGE-2 | IL-16 | RANTES | IL-17A | MIF | IL-18 | GRO-α |
| IL-15 | RANTES | IL-16 | MIF | IL-17A | GRO-α | IL-18 | CRP |
| IL-15 | MIF | IL-16 | GRO-α | IL-17A | CRP | IL-18 | DDT |
| IL-15 | GRO-α | IL-16 | CRP | IL-17A | DDT | | |
| IL-15 | CRP | IL-16 | DDT | | | | |
| IL-15 | DDT | | | | | | |
| IL-1α | IL-1β | IL-1β | IL-2 | IL-2 | IL-2ra | IL-2ra | IL-3 |
| IL-1α | IL-2 | IL-1β | IL-2ra | IL-2 | IL-3 | IL-2ra | IL-5 |
| IL-1α | IL-2ra | IL-1β | IL-3 | IL-2 | IL-5 | IL-2ra | IL-6 |
| IL-1α | IL-3 | IL-1β | IL-5 | IL-2 | IL-6 | IL-2ra | IL-7 |
| IL-1α | IL-5 | IL-1β | IL-6 | IL-2 | IL-7 | IL-2ra | IL-9 |
| IL-1α | IL-6 | IL-1β | IL-7 | IL-2 | IL-9 | IL-2ra | IP-10 |
| IL-1α | IL-7 | IL-1β | IL-9 | IL-2 | IP-10 | IL-2ra | LIF |
| IL-1α | IL-9 | IL-1β | IP-10 | IL-2 | LIF | IL-2ra | M-CSF |
| IL-1α | IP-10 | IL-1β | LIF | IL-2 | M-CSF | IL-2ra | MIG |
| IL-1α | LIF | IL-1β | M-CSF | IL-2 | MIG | IL-2ra | MIP-1α |
| IL-1α | M-CSF | IL-1β | MIG | IL-2 | MIP-1α | IL-2ra | MIP-1β |
| IL-1α | MIG | IL-1β | MIP-1α | IL-2 | MIP-1β | IL-2ra | PDGF-BB |
| IL-1α | MIP-1a | IL-1β | MIP-1β | IL-2 | PDGF-BB | IL-2ra | SDF-1α |
| IL-1α | MIP-1β | IL-1β | PDGF-BB | IL-2 | SDF-1α | IL-2ra | TNF-α |
| IL-1α | PDGF-BB | IL-1β | SDF-1α | IL-2 | TNF-α | IL-2ra | TNF-β |
| IL-1α | SDF-1α | IL-1β | TNF-α | IL-2 | TNF-β | IL-2ra | TRAIL |
| IL-1α | TNF-α | IL-1β | TNF-β | IL-2 | TRAIL | IL-2ra | VEGF |
| IL-1α | TNF-β | IL-1β | TRAIL | IL-2 | VEGF | IL-2ra | IL-8 |
| IL-1α | TRAIL | IL-1β | VEGF | IL-2 | IL-8 | IL-2ra | MCP-1 |
| IL-1α | VEGF | IL-1β | IL-8 | IL-2 | MCP-1 | IL-2ra | MGSA |
| IL-1α | IL-8 | IL-1β | MCP-1 | IL-2 | MGSA | IL-2ra | PGE-2 |
| IL-1α | MCP-1 | IL-1β | MGSA | IL-2 | PGE-2 | IL-2ra | RANTES |
| IL-1α | MGSA | IL-1β | PGE-2 | IL-2 | RANTES | IL-2ra | MIF |
| IL-1α | PGE-2 | IL-1β | RANTES | IL-2 | MIF | IL-2ra | GRO-α |
| IL-1α | RANTES | IL-1β | MIF | IL-2 | GRO-α | IL-2ra | CRP |
| IL-1α | MIF | IL-1β | GRO-α | IL-2 | CRP | IL-2ra | DDT |
| IL-1α | GRO-α | IL-1β | CRP | IL-2 | DDT | | |
| IL-1α | CRP | IL-1β | DDT | | | | |
| IL-1α | DDT | | | | | | |
| IL-3 | IL-5 | IL-5 | IL-6 | IL-6 | IL-7 | IL-7 | IL-9 |
| IL-3 | IL-6 | IL-5 | IL-7 | IL-6 | IL-9 | IL-7 | IP-10 |
| IL-3 | IL-7 | IL-5 | IL-9 | IL-6 | IP-10 | IL-7 | LIF |
| IL-3 | IL-9 | IL-5 | IP-10 | IL-6 | LIF | IL-7 | M-CSF |
| IL-3 | IP-10 | IL-5 | LIF | IL-6 | M-CSF | IL-7 | MIG |
| IL-3 | LIF | IL-5 | M-CSF | IL-6 | MIG | IL-7 | MIP-1α |
| IL-3 | M-CSF | IL-5 | MIG | IL-6 | MIP-1α | IL-7 | MIP-1β |
| IL-3 | MIG | IL-5 | MIP-1α | IL-6 | MIP-1β | IL-7 | PDGF-BB |
| IL-3 | MIP-1α | IL-5 | MIP-1β | IL-6 | PDGF-BB | IL-7 | SDF-1α |
| IL-3 | MIP-1β | IL-5 | PDGF-BB | IL-6 | SDF-1α | IL-7 | TNF-α |
| IL-3 | PDGF-BB | IL-5 | SDF-1α | IL-6 | TNF-α | IL-7 | TNF-β |
| IL-3 | SDF-1α | IL-5 | TNF-α | IL-6 | TNF-β | IL-7 | TRAIL |
| IL-3 | TNF-α | IL-5 | TNF-β | IL-6 | TRAIL | IL-7 | VEGF |
| IL-3 | TNF-β | IL-5 | TRAIL | IL-6 | VEGF | IL-7 | IL-8 |
| IL-3 | TRAIL | IL-5 | VEGF | IL-6 | IL-8 | IL-7 | MCP-1 |
| IL-3 | VEGF | IL-5 | IL-8 | IL-6 | MCP-1 | IL-7 | MGSA |
| IL-3 | IL-8 | IL-5 | MCP-1 | IL-6 | MGSA | IL-7 | PGE-2 |
| IL-3 | MCP-1 | IL-5 | MGSA | IL-6 | PGE-2 | IL-7 | RANTES |
| IL-3 | MGSA | IL-5 | PGE-2 | IL-6 | RANTES | IL-7 | MIF |
| IL-3 | PGE-2 | IL-5 | RANTES | IL-6 | MIF | IL-7 | GRO-α |
| IL-3 | RANTES | IL-5 | MIF | IL-6 | GRO-α | IL-7 | CRP |
| IL-3 | MIF | IL-5 | GRO-α | IL-6 | CRP | IL-7 | DDT |
| IL-3 | GRO-α | IL-5 | CRP | IL-6 | DDT | | |
| IL-3 | CRP | IL-5 | DDT | | | | |
| IL-3 | DDT | | | | | | |
| IL-9 | IP-10 | IP-10 | LIF | LIF | M-CSF | M-CSF | MIG |
| IL-9 | LIF | IP-10 | M-CSF | LIF | MIG | M-CSF | MIP-1α |
| IL-9 | M-CSF | IP-10 | MIG | LIF | MIP-1α | M-CSF | MIP-1β |
| IL-9 | MIG | IP-10 | MIP-1α | LIF | MIP-1β | M-CSF | PDGF-BB |
| IL-9 | MIP-1α | IP-10 | MIP-1β | LIF | PDGF-BB | M-CSF | SDF-1α |
| IL-9 | MIP-1β | IP-10 | PDGF-BB | LIF | SDF-1α | M-CSF | TNF-α |
| IL-9 | PDGF-BB | IP-10 | SDF-1α | LIF | TNF-α | M-CSF | TNF-β |
| IL-9 | SDF-1α | IP-10 | TNF-α | LIF | TNF-β | M-CSF | TRAIL |
| IL-9 | TNF-α | IP-10 | TNF-β | LIF | TRAIL | M-CSF | VEGF |
| IL-9 | TNF-β | IP-10 | TRAIL | LIF | VEGF | M-CSF | IL-8 |
| IL-9 | TRAIL | IP-10 | VEGF | LIF | IL-8 | M-CSF | MCP-1 |
| IL-9 | VEGF | IP-10 | IL-8 | LIF | MCP-1 | M-CSF | MGSA |

TABLE 2-continued

Non-limiting examples of protein pairs that may be included in a protein profile generated by the methods of the present disclosure. The protein profile may comprise or consist of one or more protein pairs listed.

| Protein #1 | Protein #2 | Protein #1 | Protein #2 | Protein #1 | Protein #2 | Protein #1 | Protein #2 |
|---|---|---|---|---|---|---|---|
| IL-9 | IL-8 | IP-10 | MCP-1 | LIF | MGSA | M-CSF | PGE-2 |
| IL-9 | MCP-1 | IP-10 | MGSA | LIF | PGE-2 | M-CSF | RANTES |
| IL-9 | MGSA | IP-10 | PGE-2 | LIF | RANTES | M-CSF | MIF |
| IL-9 | PGE-2 | IP-10 | RANTES | LIF | MIF | M-CSF | CRP |
| IL-9 | RANTES | IP-10 | MIF | LIF | GRO-α | M-CSF | DDT |
| IL-9 | MIF | IP-10 | GRO-α | LIF | CRP | | |
| IL-9 | GRO-α | IP-10 | CRP | LIF | DDT | | |
| IL-9 | CRP | IP-10 | DDT | | | | |
| IL-9 | DDT | | | | | | |
| MIG | MIP-1α | MIP-1α | MIP-1β | MIP-1β | PDGF-BB | PDGF-BB | SDF-1α |
| MIG | MIP-1β | MIP-1α | PDGF-BB | MIP-1β | SDF-1α | PDGF-BB | TNF-α |
| MIG | PDGF-BB | MIP-1α | SDF-1α | MIP-1β | TNF-α | PDGF-BB | TNF-β |
| MIG | SDF-1α | MIP-1α | TNF-α | MIP-1β | TNF-β | PDGF-BB | TRAIL |
| MIG | TNF-α | MIP-1α | TNF-β | MIP-1β | TRAIL | PDGF-BB | VEGF |
| MIG | TNF-β | MIP-1α | TRAIL | MIP-1β | VEGF | PDGF-BB | IL-8 |
| MIG | TRAIL | MIP-1α | VEGF | MIP-1β | IL-8 | PDGF-BB | MCP-1 |
| MIG | VEGF | MIP-1α | IL-8 | MIP-1β | MCP-1 | PDGF-BB | MGSA |
| MIG | IL-8 | MIP-1α | MCP-1 | MIP-1β | MGSA | PDGF-BB | PGE-2 |
| MIG | MCP-1 | MIP-1α | MGSA | MIP-1β | PGE-2 | PDGF-BB | RANTES |
| MIG | MGSA | MIP-1α | PGE-2 | MIP-1β | RANTES | PDGF-BB | MIF |
| MIG | PGE-2 | MIP-1α | RANTES | MIP-1β | MIF | PDGF-BB | GRO-α |
| MIG | RANTES | MIP-1α | MIF | MIP-1β | GRO-α | PDGF-BB | CRP |
| MIG | MIF | MIP-1α | GRO-α | MIP-1β | CRP | PDGF-BB | DDT |
| MIG | GRO-α | MIP-1α | CRP | MIP-1β | DDT | | |
| MIG | CRP | MIP-1α | DDT | | | | |
| MIG | DDT | | | | | | |
| SDF-1α | TNF-α | TNF-α | TNF-β | TNF-β | TRAIL | TRAIL | VEGF |
| SDF-1α | TNF-β | TNF-α | TRAIL | TNF-β | VEGF | TRAIL | IL-8 |
| SDF-1α | TRAIL | TNF-α | VEGF | TNF-β | IL-8 | TRAIL | MCP-1 |
| SDF-1α | VEGF | TNF-α | IL-8 | TNF-β | MCP-1 | TRAIL | MGSA |
| SDF-1α | IL-8 | TNF-α | MCP-1 | TNF-β | MGSA | TRAIL | PGE-2 |
| SDF-1α | MCP-1 | TNF-α | MGSA | TNF-β | PGE-2 | TRAIL | RANTES |
| SDF-1α | MGSA | TNF-α | PGE-2 | TNF-β | RANTES | TRAIL | MIF |
| SDF-1α | PGE-2 | TNF-α | RANTES | TNF-β | MIF | TRAIL | GRO-α |
| SDF-1α | RANTES | TNF-α | MIF | TNF-β | GRO-α | TRAIL | CRP |
| SDF-1α | MIF | TNF-α | GRO-α | TNF-β | CRP | TRAIL | DDT |
| SDF-1α | GRO-α | TNF-α | CRP | TNF-β | DDT | | |
| SDF-1α | CRP | TNF-α | DDT | | | | |
| SDF-1α | DDT | | | | | | |
| VEGF | IL-8 | IL-8 | MCP-1 | MCP-1 | MGSA | MGSA | PGE-2 |
| VEGF | MCP-1 | IL-8 | MGSA | MCP-1 | PGE-2 | MGSA | RANTES |
| VEGF | MGSA | IL-8 | PGE-2 | MCP-1 | RANTES | MGSA | MIF |
| VEGF | PGE-2 | IL-8 | RANTES | MCP-1 | MIF | MGSA | GRO-α |
| VEGF | RANTES | IL-8 | MIF | MCP-1 | GRO-α | MGSA | CRP |
| VEGF | MIF | IL-8 | GRO-α | MCP-1 | CRP | MGSA | DDT |
| VEGF | GRO-α | IL-8 | CRP | MCP-1 | DDT | | |
| VEGF | CRP | IL-8 | DDT | | | | |
| VEGF | DDT | | | | | | |
| PGE-2 | RANTES | RANTES | MIF | MIF | GRO-α | GRO-α | CRP |
| PGE-2 | MIF | RANTES | GRO-α | MIF | CRP | GRO-α | DDT |
| PGE-2 | GRO-α | RANTES | CRP | MIF | DDT | | |
| PGE-2 | CRP | RANTES | DDT | | | | |
| PGE-2 | DDT | | | | | | |
| CRP | DDT | | | | | | |

In certain embodiments, the presence, level, or change in level of one or more, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty-one or more, twenty-two or more, twenty-three or more, twenty-four or more, twenty-five or more, twenty-six or more, twenty-seven or more, twenty-eight or more, twenty-nine or more or thirty or more proteins is detected or measured in a red blood cell-enriched sample and/or a red blood cell component.

In certain other embodiments, the presence of one or more proteins is detected, the level of one or more proteins is measured, or the change in level of one or more proteins is determined from a red blood cell-enriched sample or red blood cell component. In other embodiments, the presence of two or more proteins is detected, the level of two or more proteins is measured, or the change in level of two or more proteins is determined from a red blood cell-enriched sample or red blood cell component. In other embodiments, the presence of three or more proteins is detected, the level of three or more proteins is measured, or the change in level of three or more proteins is determined from a red blood cell-enriched sample or red blood cell component. In other embodiments, the presence of four or more proteins is detected, the level of four or more proteins is measured, or the change in level of four or more proteins is determined from a red blood cell-enriched sample or red blood cell component. In yet other embodiments, the presence of five or more proteins is detected, the level of five or more proteins is measured, or the change in level of five or more proteins is determined from a red blood cell-enriched sample or red blood cell component. In other embodiments, the presence of six or more proteins is detected, the level of six or more proteins is measured, or the change in level of six or more proteins is determined from a red blood cell-enriched sample or red blood cell component. In other embodiments, the presence of seven or more proteins is detected, the level of seven or more proteins is measured, or the change in level of seven or more proteins is determined from a red blood cell-enriched sample or red blood cell component. In still other embodiments, the presence of eight or more proteins is detected, the level of eight or more proteins is measured, or the change in level of eight or more proteins is determined from a red blood cell-enriched sample or red blood cell component. In other embodiments, the presence of nine or more proteins is detected, the level of nine or more proteins is measured, or the change in level of nine or more proteins is determined from a red blood cell-enriched sample or red blood cell component. In still other embodiments, the presence of ten or more proteins is detected, the level of ten or more proteins is measured, or the change in level of ten or more proteins is determined from a red blood cell-enriched sample or red blood cell component. In yet other embodiments, the presence of eleven or more proteins is detected, the level of eleven or more proteins is measured, or the change in level of eleven or more proteins is determined from a red blood cell-enriched sample or red blood cell component. In some embodiments, the presence of twelve or more proteins is detected, the level of twelve or more proteins is measured, or the change in level of twelve or more proteins is determined from a red blood cell-enriched sample or red blood cell component. In other embodiments, the presence of thirteen or more proteins is detected, the level of thirteen or more proteins is measured, or the change in level of thirteen or more proteins is determined from a red blood cell-enriched sample or red blood cell component. In yet other embodiments, the presence of fourteen or more proteins is detected, the level of fourteen or more proteins is measured, or the change in level of fourteen or more proteins is determined from a red blood cell-enriched sample or red blood cell component. In further embodiments, the presence of fifteen or more proteins is detected, the level of fifteen or more proteins is measured, or the change in level of fifteen or more proteins is determined from a red blood cell-enriched sample or red blood cell component. In other embodiments, the presence of sixteen or more proteins is detected, the level of sixteen or more proteins is measured, or the change in level of sixteen or more proteins is determined from a red blood cell-enriched sample or red blood cell component. In still other embodiments, the presence of seventeen or more proteins is detected, the level of seventeen or more proteins is measured, or the change in level of seventeen or more proteins is determined from a red blood cell-enriched sample or red blood cell component. In yet other embodiments, the presence of eighteen or more proteins is detected, the level of eighteen or more proteins is measured, or the change in level of eighteen or more proteins is determined from a red blood cell-enriched sample or red blood cell component. In other embodiments, the presence of nineteen or more proteins is detected, the level of nineteen or more proteins is measured, or the change in level of nineteen or more proteins is determined in a red blood cell-enriched sample. In still other embodiments, the presence of twenty or more proteins is detected, the level of twenty or more proteins is measured, or the change in level of twenty or more proteins is determined from a red blood cell-enriched sample or red blood cell component. In yet other embodiments, the presence of twenty-one or more proteins is detected, the level of twenty-one or more proteins is measured, or the change in level of twenty-one or more proteins is determined from a red blood cell-enriched sample or red blood cell component. In other embodiments, the presence of twenty-two or more proteins is detected, the level of twenty-two or more proteins is measured, or the change in level of twenty-two or more proteins is determined from a red blood cell-enriched sample or red blood cell component. In other embodiments, the presence of twenty-three or more proteins is detected, the level of twenty-three or more proteins is measured, or the change in level of twenty-three or more proteins is determined from a red blood cell-enriched sample or red blood cell component. In still other embodiments, the presence of twenty-four or more proteins is detected, the level of twenty-four or more proteins is measured, or the change in level of twenty-four or more proteins is determined from a red blood cell-enriched sample or red blood cell component. In yet other embodiments, the presence of twenty-five or more proteins is detected, the level of twenty-five or more proteins is measured, or the change in level of twenty-five or more proteins is determined from a red blood cell-enriched sample or red blood cell component. In still other embodiments, the presence of twenty-six or more proteins is detected, the level of twenty-six or more proteins is measured, or the change in level of twenty-six or more proteins is determined from a red blood cell-enriched sample or red blood cell component. In still other embodiments, the presence of twenty-seven or more proteins is detected, the level of twenty-seven or more proteins is measured, or the change in level of twenty-seven or more proteins is determined from a red blood cell-enriched sample or red blood cell component. In other embodiments, the presence of twenty-eight or more proteins is detected or the level or change in level of twenty-eight or more proteins is measure is detected, the level of twenty-eight or more proteins is measured, or the change in level of twenty-eight or more proteins is determined from a red blood cell-enriched sample or red blood cell component. In other embodiments, the presence of twenty-nine or more proteins is detected, the level of twenty-nine or more proteins is measured, or the change in level of twenty-nine or more proteins is determined from a red blood cell-enriched sample or red blood cell component. In still other embodiments, the presence of thirty or more proteins is detected, the level of thirty or more proteins is measured, or the change in level of thirty or more proteins is determined from a red blood cell-enriched sample or red blood cell component.

A protein profile may be produced or generated for example, by detecting the presence of one or more proteins in a lysate, cell wash, cell supernatant, or a combination thereof prepared according to one or more of the methods of the present disclosure. The protein(s) detected may also be quantified (e.g., levels measured) to produce or generate the protein profile. In other embodiments, a protein profile may be produced according to the methods provided herein by measuring the change in the level of one or more proteins, where the protein profile may comprise one or more proteins having a change in level and/or the measurement of the change in level of the one or more proteins.

Methods for the detection and/or quantification of proteins in single or mixed blood cell populations and plasma/serum are available to those of ordinary skill in the art. Non-limiting examples of suitable methods include antibody-based methods generally, flow cytometry, ELISA, lateral flow, immunostaining, immunofluorescence, immunoelectrophoresis (including, e.g., Western blot), and the like. Alternatively, proteins may be detected and/or quantified using mass spectrometry, spectroscopy, chromatography, electrophoresis, bicinchoninic acid assay (BCA), enzyme assay and the like. Again by way of example only, protein quantification methods are described in U.S. Pat. Nos. 7,501,286, 8,530,182, and United States Patent Publication Number 2013028838. Methodology is also presented in the Examples of the present specification.

The present disclosure also provides methods for producing a protein profile from a red blood cell-enriched sample or red blood cell component by calculating a protein ratio comprising the level of one or more proteins in red blood cells to the level of those same one or more proteins in plasma. The protein ratio maybe calculated by normalizing the measured protein concentration in the RBCs and the plasma and then dividing the concentration of the protein(s) in the RBCs by the concentration of the protein(s) in the plasma. The concentration of the protein(s) in the RBCs and plasma are normalized by calculating their relative concentration per millilitre in whole blood (e.g., percent in whole blood).

In certain embodiments, the protein ratio comprising the level of one or more proteins in red blood cells to the level of those one or more proteins in the plasma is at least 2:1, at least 10:1, at least 20:1, at least 30:1, at least 40:1, at least 50:1, at least 60:1, at least 70:1, at least 80:1, at least 90:1, at least 100:1, at least 110:1, at least 120:1, at least 130:1, at least 140:1, at least 150:1, at least 160:1, at least 170:1, at least 180:1, at least 190:1, or at least 200:1. In other embodiments, the protein ratio is at least 3:1, at least 4:1, at least 5:1, at least 6:1, at least 7:1, at least 8:1, at least 9:1, at least 10:1, at least 11:1, at least 12:1, at least 13:1, at least 14:1, at least 15:1, at least 16:1, at least 17:1, at least 18:1, at least 19:1, at least 20:1, at least 21:1, at least 22:1, at least 23:1, at least 24:1, at least 25:1, at least 26:1, at least 27:1, at least 28:1, at least 29:1, at least 30:1, at least 31:1, at least 32:1, at least 33:1, at least 34:1, at least 35:1, at least 36:1, at least 37:1, at least 38:1, at least 39:1 or at least 40:1.

Disease Profiling and Evaluation

The present disclosure provides methods herein for producing a disease protein profile in a blood sample (e.g., a whole blood sample or a red blood cell-enriched sample or red blood cell-enriched fraction). In certain embodiments, a disease profile may be produced for a disease or disorder for which there is a difference in the presence and/or levels of one or more proteins associated with a red blood cell-enriched sample or red blood cell component that has been contacted with protease inhibitors compared to a sample that has not been contacted with protease inhibitors. Alternatively or in addition, a disease protein profile may be produced for a disease or disorder for which there is a difference in the presence and/or levels of one or more proteins associated with a red blood cell-enriched sample or red blood cell component contacted with protease inhibitors from a subject having a disease or disorder compared to a red blood cell-enriched sample or red blood cell component (e.g., a sample contacted with protease inhibitors) from a subject not having a disease or disorder. In yet other embodiments, a disease protein profile may be produced for a disease or disorder for which there is a difference between the change in level of one or more proteins from a protein profile for a subject having a disease or disorder and the change in levels of the one or more proteins from a protein profile for a subject not having the disease or disorder. By way of non-limiting example, a disease profile maybe produced for a disease or disorder for which there is a difference in the presence or level of one or more of the proteins set out in Table 1 or one or more combinations of proteins set out in Table 2.

In certain embodiments, a disease protein profile(s) is produced by obtaining at least one protein profile according to the methods provided herein from one or more subjects having a disease or disorder and comparing the presence, level, or change in level of one of more proteins in red blood cell enriched samples that have and have not been contacted with protease inhibitors. In other embodiments, a disease protein profile(s) is produced by obtaining at least one protein profile from one or more subjects not having a disease or disorder according to the methods and comparing the presence or level of one of more proteins in the at least one protein profile obtained according to the methods from one or more subjects having a disease or disorder. In certain embodiments, at least one protein profile is obtained from a subject having a disease or disorder. In other embodiments, at least one profile is obtained from a subject not having the disease or disorder. In further embodiments, at least one protein profile is obtained from a subject having a disease or disorder and at least one protein profile is obtained from a subject not having the disease or disorder. In other embodiments, the blood samples are obtained from one or more subjects having a disease or disorder and pooled. In other embodiments, blood samples are obtained from one or more subjects not having the disease or disorder and pooled. A protein profile may be obtained according to the methods from the pooled blood samples of the one or more subjects having the disease or disorder and/or one or more subjects not having the disease or disorder. The protein profiles may be obtained at a time prior to determining the proteins that would comprise the disease protein profile by comparing the presence or level of one or more proteins in the protein profiles.

In some embodiments, a disease protein profile is comprised of one or more proteins that have a different presence, level, or change in level in a red blood cell-enriched sample or red blood cell component from a subject having a disease or disorder that has been contacted with protease inhibitors compared to a red blood cell-enriched sample or red blood cell component from the subject that has not been contacted with protease inhibitors. In other embodiments, a disease protein profile is produced according to the methods and comprises one or more proteins that have a different presence, level, or change in level in a red blood cell-enriched sample or red blood cell component from a subject having a disease or disorder compared to a red blood cell-enriched sample or red blood cell component from a subject not having a disease or disorder. One of skill in the art may determine whether a protein has a different (e.g., changed or altered) presence and/or level (e.g., higher or lower level), or different change in level (e.g., fold change) using an analysis that determines a statistically relevant difference in the presence and/or level of the proteins.

In certain embodiments, the disease protein profile comprises one or more proteins that are present in a blood sample (e.g., whole blood sample or red blood cell-enriched sample) or red blood cell component from a subject having a disease or disorder that has been contacted with one or more protease inhibitors that are not present in the blood sample from the subject that has not been contacted with protease inhibitors. In other embodiments, the disease protein profile comprises one or more proteins that are not present in a blood sample or red blood cell component from a subject having a disease or disorder that has been contacted with one or more protease inhibitors that are present in the blood sample or red blood cell component from the subject that has not been contacted with protease inhibitors. In other embodiments, the disease protein profile comprises one or more proteins that have a higher level in a blood sample or red blood cell component from a subject having a disease or disorder that has been contacted with protease inhibitors compared to a blood sample or red blood cell component from the subject that has not been contacted with protease inhibitors. In still other embodiments, the disease protein profile comprises one or more proteins that have a lower level in a blood sample or red blood cell component from a subject having a disease or disorder that has been contacted with protease inhibitors compared to a blood sample from the subject that has not been contacted with protease inhibitors.

In yet other embodiments, the disease protein profile produced according to the methods comprises one or more proteins that have a different change in level in a subject having a disease or disorder compared to a subject not having the disease or disorder. In other embodiments, the change in the level of the one or more proteins in a subject having the disease or disorder is an increase in level compared to a decrease in the level of the one or more proteins in a subject not having the disease or disorder. In still other embodiments, the change in the level of the one or more proteins in a subject having the disease or disorder is a decrease in level compared an increase in the level of the one or more proteins in a subject not having the disease or disorder. In other embodiments, the magnitude of the increase or decrease of the change in the level of one or more protein is larger in a subject having a disease or disorder compared to the magnitude of the increase or decrease in the change in level of the one or more proteins in a subject not having the disease or disorder. In other embodiments, the magnitude of the increase or decrease of the change in level of the one or more protein is smaller in a subject having a disease or disorder compared to the magnitude of the increase in the change of level of the one or more proteins in a subject not having the disease or disorder. In other embodiments, there is no significant change in the level of the one or more proteins in a subject having a disease or disorder compared to the change in the level of the one or more proteins in a subject not having the disease or disorder. In yet other embodiments, there is no significant change in the level of the one or more proteins in a subject not having a disease or disorder compared to the change in the level of the one or more proteins in a subject having the disease or disorder.

In other embodiments, the disease protein profile comprises combinations of the foregoing—for example, it comprises one or more proteins that have a higher level and one or more proteins that have a lower level in a blood sample or red blood cell component from a subject having a disease or disorder that has been contacted with protease inhibitors compared to the level of those one or more proteins in a blood sample or red blood cell component from the subject that has not been contacted with protease inhibitors. In certain embodiments, a disease protein profile comprises one or more proteins that have a different level in a blood sample or red blood cell component from a subject having a disease or disorder that has been contacted with protease inhibitors compared to the level of those one or more proteins in a blood sample or red blood cell component from the subject that has not been contacted with protease inhibitors.

In other embodiments, the disease protein profile comprises one or more proteins that are present in a subject having a disease or disorder but not present in a subject not having the disease or disorder. In other embodiments, the disease protein profile comprises one or more proteins that are not present in a subject having a disease or disorder but are present in a subject not having the disease or disorder. In some other embodiments, the disease protein profile comprises one or more proteins that have a higher level in a subject having a disease or disorder compared to the one or more proteins in a subject not having the disease or disorder. In yet other embodiments, the disease protein profile comprises one or more proteins that have a lower level in a subject having a disease or disorder compared to the one or more proteins in a subject not having a disease or disorder. In still other embodiments, the disease protein profile comprises combinations of the foregoing—for instance, one or more proteins having a higher level and one or more proteins having a lower level in a subject having a disease or disorder compared to the one or more proteins in a subject not having the disease or disorder. In certain embodiments, a disease protein profile comprises one or more proteins that have a different level in a subject having a disease or disorder compared to the one or more proteins in a subject not having the disease or disorder. In still other embodiments, a disease protein profile comprises one or more proteins that have a different change in level in a subject having a disease or disorder compared to the change in level of the one or more proteins in a subject not having a disease or disorder.

In certain embodiments, the disease protein profile is a cancer protein profile comprising one or more proteins selected from the group consisting of IL-6, IFN-γ, IL-4, IL-13, MIF, Eotaxin, RANTES, IL-7, IP-10, PDGF, and IL-12p40. In other embodiments, the disease protein profile is a preeclampsia protein profile comprising one or more proteins selected from the group consisting of IL-10, IL-8, TNF-α, IL-1ra, MCP-1, G-CSG, GM-CSF, IL-6, IFNα2, IL-1a, IL-18, MIF, IL-2ra, and HGF.

The present disclosure also provides methods for determining whether a subject has a disease or disorder using a disease protein profile produced by the methods provided herein. At least one protein profile may be obtained from a subject that has been produced by one of the methods provided herein. The protein profile(s) of the subject may be compared to a disease protein profile produced by the methods provided herein for similarities between the two protein profiles (in, e.g., protein presence, protein levels, or change in protein levels). Similarities between a subject's protein profile and a disease protein profile may indicate that the subject has the disease or disorder. In certain embodiments, there are similarities between at least one protein, at least two proteins, at least three proteins, at least four proteins, at least five proteins, at least six proteins, at least seven proteins, at least eight proteins, at least nine proteins, at least ten proteins, at least eleven proteins, at least twelve proteins, at least thirteen proteins, at least fourteen proteins, at least fifteen proteins, at least sixteen proteins, at least seventeen proteins, at least eighteen proteins, at least nineteen proteins, at least twenty proteins, at least twenty-one proteins, at least twenty-two proteins, at least twenty-three proteins, at least twenty-four proteins, at least twenty-five proteins, at least twenty-six proteins, at least twenty-seven proteins, at least twenty-eight proteins, at least twenty-nine proteins, or at least thirty proteins in the subject's protein profile compared to the disease protein profile. In other embodiments, there are similarities between at least one protein in the subject's protein profile compared to at least one protein in the disease protein profile. In yet other embodiments, there are similarities between at least 3 proteins in the subject's protein profile compared to the disease protein profile. In still other embodiments, there are similarities between at least 5 proteins in the subject's protein profile compared to the disease protein profile. In still other embodiments, there are similarities between at least 10 proteins in the subject's protein profile compared to the disease protein profile. In yet other embodiments, there are similarities between at least 15 proteins in the subject's protein profile compared to the disease protein profile. In other embodiments, there are similarities between at least 20 proteins in the subject's protein profile compared to the disease protein profile. In other embodiments, there are similarities between at least 30 proteins in the subject's protein profile compared to the disease protein profile.

In certain embodiments, a subject's protein profile and a disease protein profile have the same or similar presence, level, or change in level, indicating that the subject may have the disease or disorder. The same or substantially the same level or change in level of one or more proteins may range from, for example, protein levels that are the same (e.g., within a relevant statistical analysis as determined by one of skill in the art) to protein levels less than those determined to be different by a person of ordinary skill in the art by, for example, a statistical analysis or a threshold fold difference (e.g., protein levels less than two-fold different). In some embodiments, the level or change in level of one or more proteins of a subject's protein profile and a disease protein profile are the same. In yet other embodiments, the level or change in level of one or more proteins of a subject's protein profile and a disease protein profile are substantially similar. In other embodiments, the difference in the level or change in level of one or more proteins of a subject's protein profile and a disease protein profile is substantially similar as determined by statistical methods available to one skilled in the art (e.g., a Student's T-test with a p-value of 0.05 or less). In yet other embodiments, the difference in the level of one or more proteins of a subject's protein profile and a disease protein profile is determined by comparison to a predetermined reference range (e.g., a healthy or normal concentration range of the proteins) available to those of skill in the art or determined by one of skill in the art. In other embodiments, the level of one or more proteins of a subject's protein profile and a disease protein profile is less than 0.5 fold different. In certain other embodiments, the level of one or more proteins of a subject's protein profile and a disease protein profile is less than 1-fold different. In yet other embodiments, the level of one or more proteins of a subject's protein profile and a disease protein profile is less than 1.5-fold different. In still other embodiments, the level of one or more proteins of a subject's protein profile and a disease protein profile is less than 2-fold different.

In other embodiments, a subject's protein profile and a disease protein profile have a different presence, level, or change in level of proteins, indicating that the subject does not have the disease or disorder. In certain embodiments, a subject's protein profile and a disease protein profile comprise one or more different proteins. In other embodiments, a subject's protein profile and a disease protein profile have a different or substantially different level of one or more proteins. The different or substantially different level or change in level of one or more proteins may range from, for example, protein levels that are different (e.g., not within a relevant statistical analysis as determined by one of skill in the art) to protein levels that are more than those determined to be similar by a person of ordinary skill in the art by, for example, a statistical analysis or a threshold fold difference (e.g., proteins levels more than two-fold different). In some embodiments, the level or change in level of one or more proteins of a subject's protein profile and a disease protein profile are different. In yet other embodiments, the level or change in level of one or more proteins of a subject's protein profile and a disease protein profile are substantially different. In other embodiments, the difference in the level or change in level of one or more proteins of a subject's protein profile and a disease protein profile is substantially different as determined by statistical methods available to one skilled in the art (e.g., a Student's T-test with a p-value of 0.05 or higher). In yet other embodiments, the difference in the level or change in level of one or more proteins of a subject's protein profile and a disease protein profile is determined by comparison to a predetermined reference range (e.g., a healthy or normal concentration range of the proteins) available to those of skill in the art or determined by one of skill in the art. In certain embodiments, the level or change in level of one or more proteins of a subject's protein profile and a disease protein profile is between 0-fold and 5-fold different. In other embodiments, the level or change in level of one or more proteins of a subject's protein profile and a disease protein profile is more than 0.5 fold different. In other embodiments, the level or change in level of one or more proteins of a subject's protein profile and a disease protein profile is more than 1.0 fold different. In certain other embodiments, the level or change in level of one or more proteins of a subject's protein profile and a disease protein profile is more than 1.5-fold different. In yet other embodiments, the level or change in level of one or more proteins of a subject's protein profile and a disease protein profile is more than 2.0-fold different. In still other embodiments, the level or change in level of one or more proteins of a subject's protein profile and a disease protein profile is more than 2.5-fold different. In other embodiments, the level or change in level of one or more proteins of a subject's protein profile and a disease protein profile is more than 3.0-fold different. In other embodiments, the level or change in level of one or more proteins of a subject's protein profile and a disease protein profile is more than 3.5 fold different. In still other embodiments, the level or change in level of one or more proteins of a subject's protein profile and a disease protein profile is more than 4.0 fold different. In further embodiments, the level or change in level of one or more proteins of a subject's protein profile and a disease protein profile is more than 4.5 fold different. In other embodiments, the level or change in level of one or more proteins of a subject's protein profile and a disease protein profile is more than 5.0 fold different.

Treatment Evaluation

The present disclosure also provides methods for monitoring treatment in a subject using a protein profile produced by the methods provided herein. In certain embodiments a protein profile produced according to the methods provided herein is obtained from a subject before treatment and after treatment and the protein profiles compared for differences between the two (in, e.g., protein presence, levels, or change in levels). In other embodiments, a protein profile produced according to the methods provided herein is obtained from a subject before treatment and during treatment and the protein profiles compared for differences between the two. In still other embodiments, a protein profile produced according to the methods provided herein is obtained from a subject during treatment and after treatment and the protein profiles compared for differences between the two. In other embodiments, a protein profile produced according to the methods provided herein is obtained from a subject after treatment completion and at subsequent time after treatment completion and the protein profiles compared for differences between the two.

In certain embodiments, the subject receiving treatment may be undergoing one or more treatments or a number of treatments. In other embodiments, the subject has received and/or is receiving a particular treatment. In certain embodiments, the protein profile obtained before treatment may be obtained from a subject who has had no treatment and is compared to the protein profile of the subject after treatment. In other embodiments, a protein profile is obtained during the course of a treatment where at least one protein profile of the subject obtained at one point in time during the treatment is compared to at least one protein profile of the subject obtained at a different point in time during the treatment. In certain embodiments, the protein profiles before treatment and after treatment are obtained from a subject that is undergoing the same treatment during the course of a treatment. In other embodiments, the protein profiles before treatment and after treatment are obtained from a subject that is undergoing a different treatment during the course of a treatment (e.g., a subject that has switched treatments). Differences between a subject's protein profile (e.g., protein presence, levels, or change in levels) obtained before treatment compared to the subject's protein profile after treatment may indicate that the treatment has had an effect on the subject. Differences between a subject's protein profiles obtained at different points in time during treatment may indicate that the treatment has had an effect on the subject. Differences between a subject's protein profiles obtained during and after treatment may indicate that the treatment has had an effect on the subject.

In certain embodiments, there are differences between at least one protein, at least two proteins, at least three proteins, at least four proteins, at least five proteins, at least six proteins, at least seven proteins, at least eight proteins, at least nine proteins, at least ten proteins, at least eleven proteins, at least twelve proteins, at least thirteen proteins, at least fourteen proteins, at least fifteen proteins, at least sixteen proteins, at least seventeen proteins, at least eighteen proteins, at least nineteen proteins, at least twenty proteins, at least twenty-one proteins, at least twenty-two proteins, at least twenty-three proteins, at least twenty-four proteins, at least twenty-five proteins, at least twenty-six proteins, at least twenty-seven proteins, at least twenty-eight proteins, at least twenty-nine proteins, or at least thirty proteins in the protein profiles before and after treatment.

In certain embodiments, there are differences between at least one protein in the protein profile before treatment compared to the protein profile after treatment. In yet other embodiments, there are differences between at least 3 proteins in the protein profile before treatment compared to the protein profile after treatment. In still other embodiments, there are differences between at least 5 proteins in the protein profiles before treatment compared to the protein profile after treatment. In still other embodiments, there are differences between at least 10 proteins in the protein profiles before treatment compared to the protein profiles after treatment. In yet other embodiments, there are differences between at least 15 proteins in the protein profiles before treatment compared to the protein profiles after treatment. In other embodiments, there are differences between at least 20 proteins in the protein profiles before treatment compared to the protein profiles after treatment. In other embodiments, there are differences between at least 30 proteins in the protein profiles before treatment compared to the protein profiles after treatment. In certain embodiments, there are differences between at least one protein in the protein profile at one point in time during treatment compared to the protein profile at another point in time during treatment. In yet other embodiments, there are differences between at least 3 proteins in the protein profile at one point in time during treatment compared to the protein profile at another point in time during treatment. In still other embodiments, there are differences between at least 5 proteins in the protein profiles at one point in time during treatment compared to the protein profile at another point in time during treatment. In still other embodiments, there are differences between at least 10 proteins in the protein profiles at one point in time during treatment compared to the protein profile at another point in time during treatment. In yet other embodiments, there are differences between at least 15 proteins in the protein profiles at one point in time during treatment compared to the protein profile at another point in time during treatment. In other embodiments, there are differences between at least 20 proteins in the protein profiles at one point in time during treatment compared to the protein profile at another point in time during treatment. In other embodiments, there are differences between at least 30 proteins in the protein profiles at one point in time during treatment compared to the protein profile at another point in time during treatment. In certain other embodiments, there are differences between at least one protein in the protein profile during treatment compared to the protein profile after treatment. In yet other embodiments, there are differences between at least 3 proteins in the protein profile during treatment compared to the protein profile after treatment. In still other embodiments, there are differences between at least 5 proteins in the protein profiles during treatment compared to the protein profile after treatment. In still other embodiments, there are differences between at least 10 proteins in the protein profiles during treatment compared to the protein profiles after treatment. In yet other embodiments, there are differences between at least 15 proteins in the protein profiles during treatment compared to the protein profiles after treatment. In other embodiments, there are differences between at least 20 proteins in the protein profiles during treatment compared to the protein profiles after treatment. In other embodiments, there are differences between at least 30 proteins in the protein profiles during treatment compared to the protein profiles after treatment.

In certain embodiments, a subject's protein profile obtained before treatment comprises different protein(s) than the protein profile obtained after treatment, indicating that the treatment may have had an effect on the subject. In other embodiments, a subject's protein profile obtained before treatment has different levels of one or more proteins compared to the protein profile obtained after treatment, indicating that the treatment may have had an effect on the subject. The difference in levels of the one or more proteins may be appropriately determined by one of skill in the art as previously described (e.g., using a statistical analysis or measuring and comparing protein levels to determine a statistically significant difference in protein presence or levels). The different levels of one or more proteins may include, for example, levels that are greater than a 1-fold difference. In certain embodiments, the difference in the level of one or more proteins of a subject's protein profile before and after treatment is greater than 1-fold, greater than 1.5 fold, greater than 2-fold, greater than 2.5 fold, greater than 3-fold, greater than 3.5-fold, greater than 4-fold, greater than 4.5 fold, greater than 5-fold, greater than 5.5 fold, greater than 6-fold, greater than 6.5-fold, greater than 7-fold, greater than 7.5-fold, greater than 8-fold, greater than 8.5-fold, greater than 9-fold, greater than 9.5-fold, or greater than 10-fold. In some embodiments, the difference in the level of one or more proteins of a subject's protein profile before and after treatment is greater than 1.5-fold. In other embodiments, the difference in the level of one or more proteins of a subject's protein profile before and after treatment is greater than 2-fold. In other embodiments, the difference in the level of one or more proteins of a subject's protein profile before and after treatment is greater than 2.5-fold. In still other embodiments, the difference in the level of one or more proteins of a subject's protein profile before and after treatment is greater than 3-fold. In still other embodiments, the difference in the level of one or more proteins of a subject's protein profile before and after treatment is greater than 4-fold. In other embodiments, the difference in the level of one or more proteins of a subject's protein profile before and after treatment is greater than 5-fold. In other embodiments, the difference in the level of one or more proteins of a subject's protein profile before and after treatment is greater than 6-fold. In still other embodiments, the difference in the level of one or more proteins of a subject's protein profile before and after treatment is greater than 7-fold. In other embodiments, the difference in the level of one or more proteins of a subject's protein profile before and after treatment is greater than 8-fold. In yet other embodiments, the difference in the level of one or more proteins of a subject's protein profile before and after treatment is greater than 9-fold. In still other embodiments, the difference in the level of one or more proteins of a subject's protein profile before and after treatment is greater than 10-fold.

In certain embodiments, a small volume blood sample is obtained to produce the protein profiles before treatment and after treatment in order to monitor treatment of a subject. A small volume blood sample allows the subject to be sampled frequently and, consequently, allows for treatment monitoring at a frequency not previously achievable. In some embodiments, a small volume blood sample may be obtained at a frequency of one or more times per day, two or more times per day, three or more times per day, four or more times per day, or five or more times per day. In other embodiments, a small volume blood sample is obtained one or more times per week, two or more times per week, three or more times per week, four or more times per week, five or more times per week, six or more times per week, or seven or more times per week. In other embodiments, a small volume blood sample is obtained daily. In still other embodiments, a small volume blood sample is obtained once a week, once every two weeks, once every three weeks, or once every four weeks. In certain embodiments, a small volume blood sample is obtained once a month.

The present disclosure also provides methods for determining the effectiveness of a treatment in a subject using protein profiles produced by the methods provided herein. In certain embodiments, at least one protein profile is obtained from a subject that has undergone a treatment. In other embodiments, at least one protein profile is obtained from a subject that has not undergone a treatment and the at least one protein profile of the subject that has undergone treatment is compared to the at least one protein profile of the subject that has not undergone treatment. In other embodiments, the protein profile is produced using blood samples obtained from one or more subjects who have not undergone treatment and the blood samples are pooled. In other embodiments, a protein profile is produced using one or more blood samples obtained from a subject who has undergone treatment and the blood samples are pooled. A protein profile may be obtained from the pooled blood samples of the one or more subjects that have not undergone treatment and/or the one or more blood samples from a subject that has not undergone treatment. In other embodiments, one or more protein profiles are obtained from one or more subjects that have not undergone treatment and/or one or more protein profiles are obtained from a subject that has undergone treatment, and a statistical analysis is performed by means available in the art to determine the proteins that will comprise (by statistically significant difference in presence and/or level) the protein profile of a subject that has not undergone treatment and/or a reference range from healthy individual(s) is compared to the protein profile of a subject that has undergone treatment. The protein profile of a subject that has undergone a treatment and the protein profile of a subject that has not undergone a treatment may be produced at a time prior to comparison of the two protein profiles.

Similarities in the presence, level, or change in level of one or more proteins between the protein profile of the subject that has undergone treatment, compared to the protein profile of the subject that has not undergone treatment may indicate the effectiveness of the treatment. In certain embodiments, there are similarities between at least one protein, at least two proteins, at least three proteins, at least four proteins, at least five proteins, at least six proteins, at least seven proteins, at least eight proteins, at least nine proteins, at least ten proteins, at least eleven proteins, at least twelve proteins, at least thirteen proteins, at least fourteen proteins, at least fifteen proteins, at least sixteen proteins, at least seventeen proteins, at least eighteen proteins, at least nineteen proteins, at least twenty proteins, at least twenty-one proteins, at least twenty-two proteins, at least twenty-three proteins, at least twenty-four proteins, at least twenty-five proteins, at least twenty-six proteins, at least twenty-seven proteins, at least twenty-eight proteins, at least twenty-nine proteins, or at least thirty proteins. In other embodiments, there are similarities between at least one protein. In yet other embodiments, there are similarities between at least 3 proteins. In still other embodiments, there are similarities between at least 5 proteins. In still other embodiments, there are similarities between at least 10 proteins. In yet other embodiments, there are similarities between at least 15 proteins. In other embodiments, there are similarities between at least 20 proteins. In other embodiments, there are similarities between at least 30 proteins.

In certain embodiments, the protein profile of a subject that has undergone treatment and the protein profile of a subject that has not undergone treatment have the same one or more proteins present, indicating that the treatment may have been effective. In other embodiments, the protein profile of a subject that has undergone treatment and the protein profile of a subject that has not undergone treatment have the same or substantially similar level or change in level of one or more proteins, indicating that the treatment may have been effective. The same or substantially similar level or change in level of one or more proteins may include, for example, protein level or change in level that are the same (e.g., within a relevant statistical analysis as determined by one of skill in the art) to protein levels that are determined to be sufficiently different by a person of ordinary skill in the art by, for example, a statistical analysis or a determined threshold fold difference (e.g., less than a two-fold difference). In some embodiments, the level or change in level of one or more proteins of the protein profile of a subject that has undergone treatment and the protein profile of a subject that has not undergone treatment are the same. In yet other embodiments, the level or change in level of one or more proteins of the protein profile of a subject that has undergone treatment and the protein profile of a subject that has not undergone treatment are substantially similar. In other embodiments, the difference in the level or change in level of one or more proteins of the protein profile of a subject that has undergone treatment and the protein profile of a subject that has not undergone treatment is determined by statistical methods available to one skilled in the art (e.g., a Student's T-test with a p-value of 0.05 of less). In yet other embodiments, the difference in the level or change in level of one or more proteins of the protein profile of a subject that has undergone treatment and the protein profile of a subject that has not undergone treatment is determined by comparison to a predetermined reference range (e.g., a healthy or normal concentration range) available to those of skill in the art or determined by one of skill in the art. In other embodiments, the level or change in level of one or more proteins of the protein profile of a subject that has undergone treatment and the protein profile of a subject that has not undergone treatment is less than 0.5 fold different. In other embodiments, the level or change in level of one or more proteins of the protein profile of a subject that has undergone treatment and the protein profile of a subject that has not undergone treatment is less than 1-fold different. In still other embodiments, the level or change in level of one or more proteins of the protein profile of a subject that has undergone treatment and the protein profile of a subject that has not undergone treatment is less than 1.5-fold different. In still other embodiments, the level or change in level of one or more proteins of the protein profile of a subject that has undergone treatment and the protein profile of a subject that has not undergone treatment is less than 2-fold different.

Subjects

Certain embodiments relate to determining the protein profile of a blood sample or component thereof from a subject.

The subject may be an animal in which blood comprises red blood cells (e.g., a mammal, bird, fish, reptile, or amphibian). Non-limiting examples of suitable subjects include bovine, equine, ovine, primate, avian and rodent species. Hence, in some embodiments, the subject may be a human or a non-human animal. In other embodiments, the subject may be a mouse, rat, hamster, ferret, gerbil, rabbit, monkey, chimpanzee, horse, pony, donkey, sheep, pig, chicken, goat, cat, or dog.

Kits

The present disclosure also provides kits comprising components necessary for carrying out the methods described herein.

By way of non-limiting example, the kits may comprise means for: collecting blood, inhibiting proteases, preventing blood coagulation, stabilising blood, enriching RBCs, obtaining red blood cell components, the removal/separation of non-RBCs blood components, snap-freezing blood or component(s) thereof, lysing cells, washing cells, culturing cells, detecting specific target protein(s) intracellularly and/or extracellularly, measuring the level of specific proteins, and/or combinations thereof. In certain embodiments, the kits comprise at least one reagent to leukodeplete a blood sample and produce a red blood cell-enriched sample and at least one reagent to detect the presence or measure the level of one or more proteins in a small volume red blood cell-enriched sample. In certain embodiments, the reagent to detect the presence or measure the level of one or more proteins is an ELISA apparatus. In other embodiments, the kit further comprises at least one reagent to obtain a blood sample from a subject.

In some embodiments, kits according to the present disclosure may comprise one or more of the following: device(s) for obtaining a blood sample from a subject (e.g., a syringe, needle, butterfly needle, tube, needle holder, blood collection set, transfer device, vacutainer, hemaPEN™), device(s) for obtaining a dried blood sample from a subject (e.g., filter paper, cards, HemaSpot™); device(s) for obtaining a red blood cell fraction, a leukocyte fraction, and/or a platelet fraction from a liquid blood sample (e.g., antibody coated magnetic beads); protease inhibitors; anticoagulants; protein denaturation agents; and the like and combinations thereof.

EXAMPLES

The present disclosure will now be described with reference to specific example(s), which should not be construed as in any way limiting.

Example 1. Measurement of Protein Levels in a Small Blood Volume

The discovery of a high level of various proteins in red blood cells as compared to their levels in an equivalent volume in plasma, for example, suggested that a small volume of whole blood and/or RBCs may be used to identify protein markers. The levels of numerous proteins were analyzed in a small volume of whole blood and RBCs.

Whole blood was collected from healthy volunteers by finger prick (n=1) directly into EDTA solution (3 mg/mL). For multiplex analysis (BioPlex analysis) the samples were stored at −80° C. and were subjected to 3 freeze-thaw cycles at −80° C. to ensure complete cellular lysis prior to analysis. The red blood cells were subjected to 3 freeze-thaw cycles to ensure complete cellular lysis. Following lysis, the whole blood was analysed on the multiplex cytokine assay at 5 µL whole blood (in 45 µL PBS), 10 µL whole blood (in 40 µL PBS), 15 µL whole blood (in 35 µL PBS), 20 µL whole blood (in 30 µL, PBS), or 25 µL whole blood (in 25 µL PBS). Two multiplex assays were utilised. The first was the 27-plex human cytokine panel that assays for FGF basic, Eotaxin, G-CSF, GM-CSF, IFN-γ, IL-1β, IL-1ra, IL-2, IL-4, IL-5, IL-6, IL-7, IL-8, IL-9, IL-10, IL-12(p70), IL-13, IL-15, IL-17, IP-10, MCP-1, MIP-1α, MIP-1β, PDGF-BB, RANTES, TNF-α, and VEGF, and the second was the 21-plex human cytokine panel that assays for IL-1α, IL-2Ra, IL-3, IL-12, IL-16, IL-18, CTACK, GRO-α, HGF, IFN-α2, LIF, MCP-3, M-CSF, MIF, MIG, β-NGF, SCF, SCGF-β, SDF-1α, TNF-β, TRAIL (Bio-Plex Pro 27-plex and 21-plex, Bio-Rad). The assays were performed according to manufacturer's instructions using an automated magnetic wash station (BioPlex Pro II, Bio-Rad) for the washing steps. The assays were run on the Luminex® 200™ system (Bio-Rad) and fluorescent values were collected. The calibration curve for each cytokine was analysed with 5 parametric logistic curve regression using BioPlex manager software (ver. 5.0, Bio-Rad, USA).

Figure 1T:
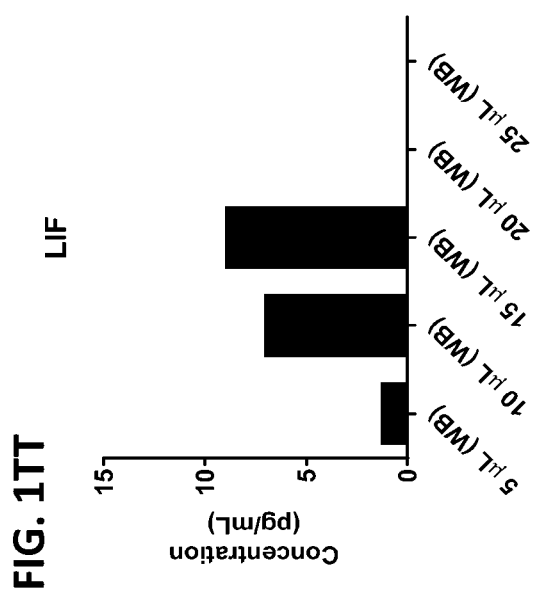
Figure 1S:
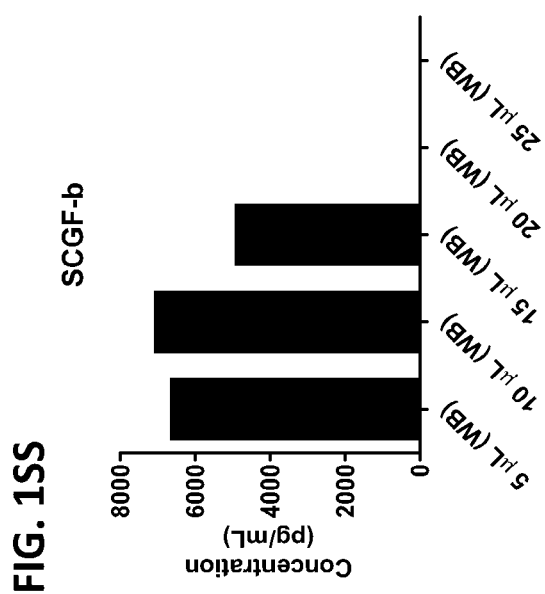

The concentration of the indicated proteins in whole blood at various dilutions (1:10, 1:5, 1:3.3, 1:2.5, 1:2) are shown in FIG. 1A-1TT (calculated back to the undiluted concentration). Analysis of whole blood revealed the presence of a number of proteins and these proteins were also present at a range of dilutions. However, there was no dilution linearity for many of the analysed proteins, which is not unique to whole blood; it is also observed in the analysis of plasma on Luminex platforms such as BioPlex (more protein is typically detected with dilution). The results indicate that proteins may be monitored in small volumes of whole blood (down to 5 µL). The ease of detection of numerous proteins in whole blood demonstrates that very small blood volumes (obtained from e.g., the fingertip) could be collected and used for analysis of protein levels.

Example 2. Presence of Proteins in Fingertip Versus Venous Blood Samples

To further explore the detection of proteins in small blood volumes, the levels of numerous proteins in a finger prick was compared to their levels in venous blood collected by available methods.

Whole blood was collected from healthy volunteers by venipuncture or by finger prick (n>12) directly into EDTA vacutainers ($k_2$EDTA vacutainers, BD Biosciences) or EDTA solution (3 mg/mL). The fractions of blood were collected and processed at room temperature within 4 hours of collection. For multiplex analysis (BioPlex analysis) the samples were stored at −80° C. and were subjected to 3 freeze-thaw cycles at −80° C. to ensure complete cellular lysis prior to analysis. The plasma and red blood cells were isolated using dextran sedimentation as follows. Whole blood was centrifuged (1500 g, 10 minutes) and the upper plasma layer was collected. The remaining cell pellet was resuspended in an equal volume of sodium chloride (0.15 M). Dextran (6% w/v in 0.15 M sodium chloride) was then added to this cellular suspension at a 1:4 ratio (dextran:cell suspension). This solution was left at room temperature for 30 minutes for red blood cell sedimentation to the bottom of the tube. After this time the upper white blood cell rich layer was discarded and the lower red blood cell fraction was isolated. The red blood cell fraction was washed twice in phosphate buffered saline (PBS, 500 g, 5 minutes) and the remaining red blood cell pellet was counted (Coulter Act Diff, Beckman Coulter) and then frozen (−80° C.) until analysis.

The red blood cells were subjected to 3 freeze-thaw cycles to ensure complete cellular lysis. Following lysis, the red blood cell lysates were diluted in PBS to the equivalent of 400 million cells/mL. These lysates were then analysed on the multiplex cytokine assay. One multiplex assay was utilised. It was the 27-plex human cytokine panel that assays for FGF basic, Eotaxin, G-CSF, GM-CSF, IFN-γ, IL-1β, IL-1ra, IL-2, IL-4, IL-5, IL-6, IL-7, IL-8, IL-9, IL-10, IL-12(p70), IL-13, IL-15, IL-17, IP-10, MCP-1, MIP-1α, MIP-1β, PDGF-BB, RANTES, TNF-α, and VEGF (Bio-Plex Pro 27-plex, Bio-Rad). The assays were performed according to manufacturer's instructions using an automated magnetic wash station (BioPlex Pro II, Bio-Rad) for the washing steps. The assays were run on the Luminex® 200™ system (Bio-Rad) and fluorescent values were collected. The calibration curve for each cytokine was analysed with 5 parametric logistic curve regression using BioPlex manager software (ver. 5.0, Bio-Rad, USA).

Figure 2B:
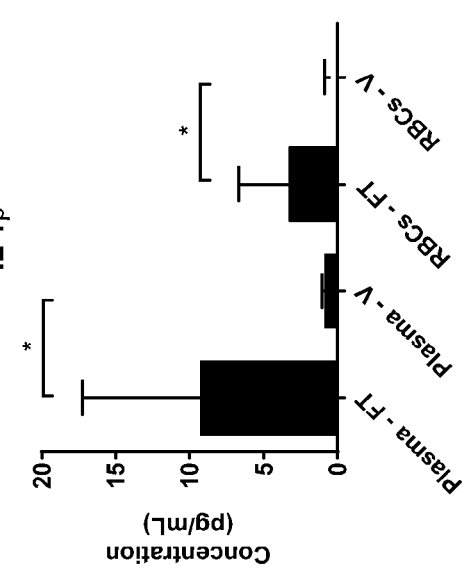
FIG. 2A-2AA is a series of graphs showing the levels of various proteins in red blood cells isolated from whole blood samples obtained from healthy subjects by finger prick (FT) or venipuncture (V).
Figure 2D:
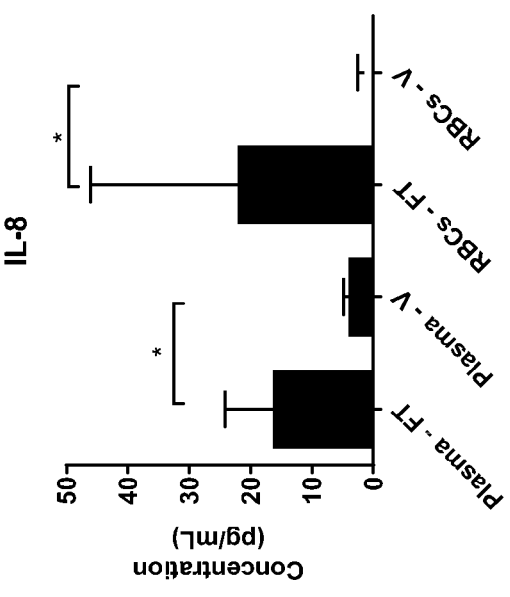
Figure 2A:
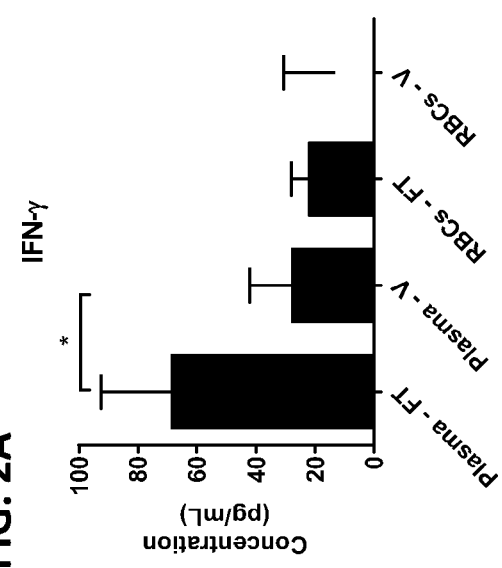
Figure 2C:
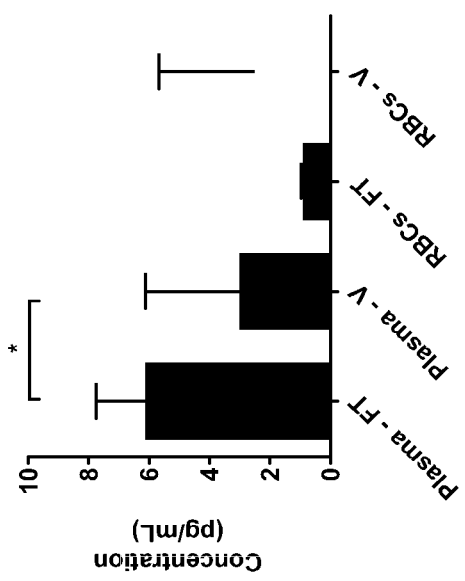
Figure 2F:
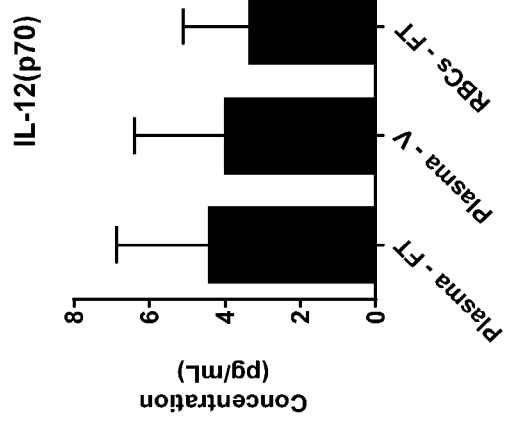
Figure 2E:
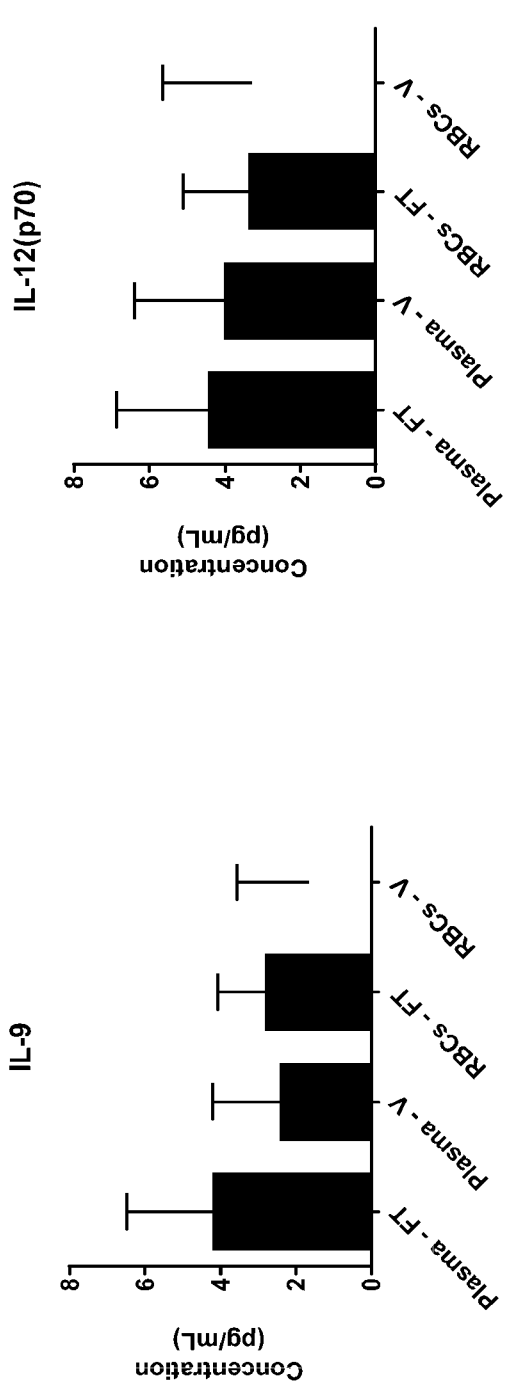
Figure 2H:
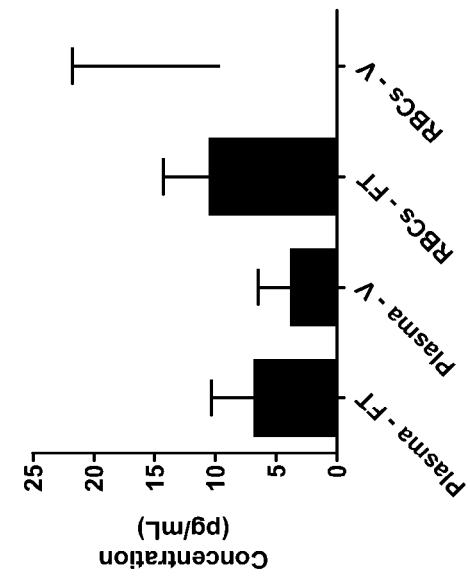
Figure 2G:
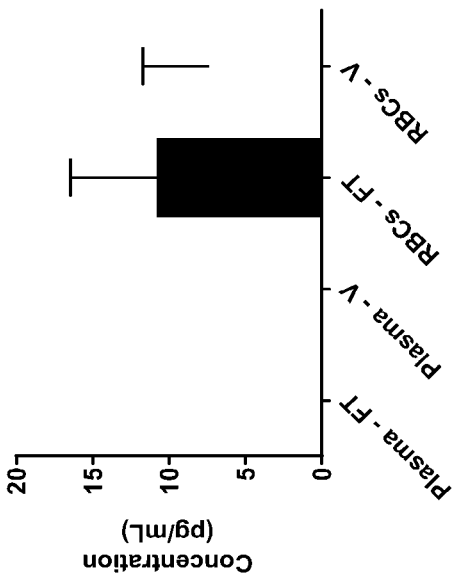
Figure 2J:
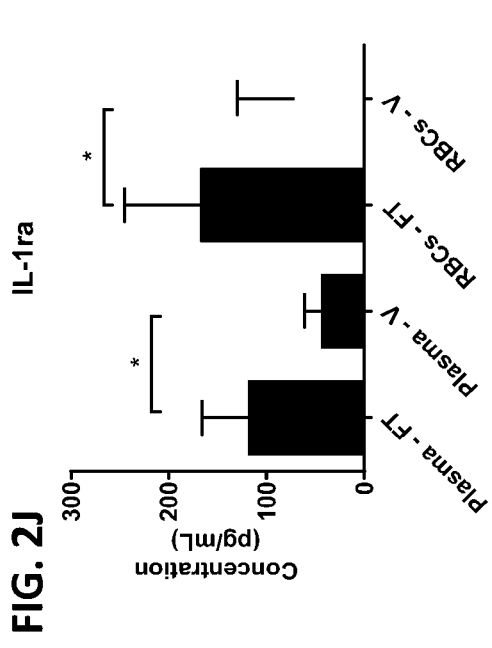
Figure 2L:
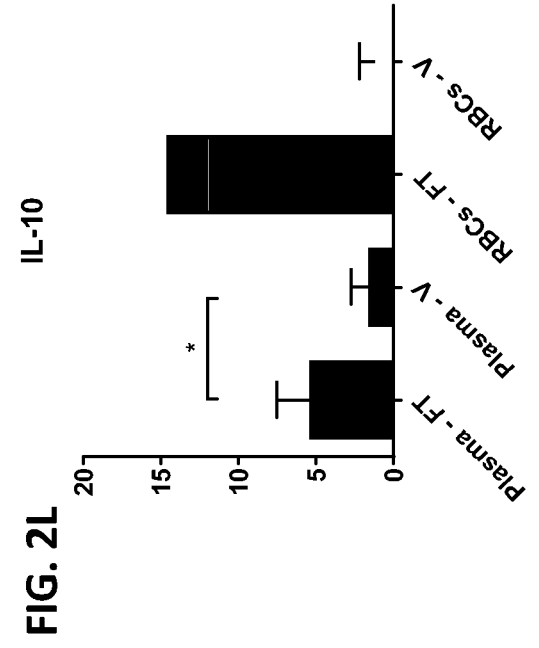
Figure 2I:
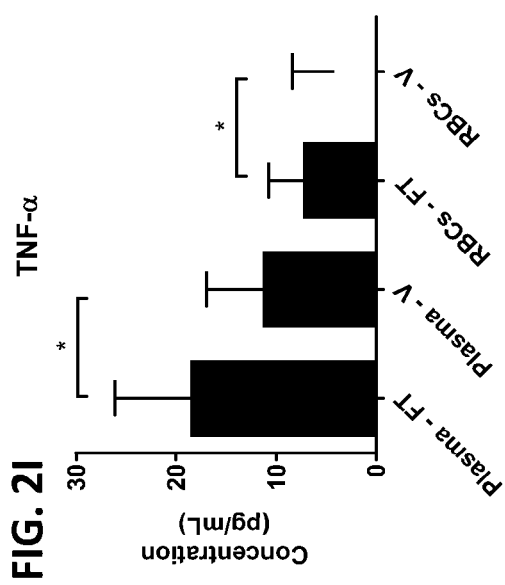
Figure 2K:
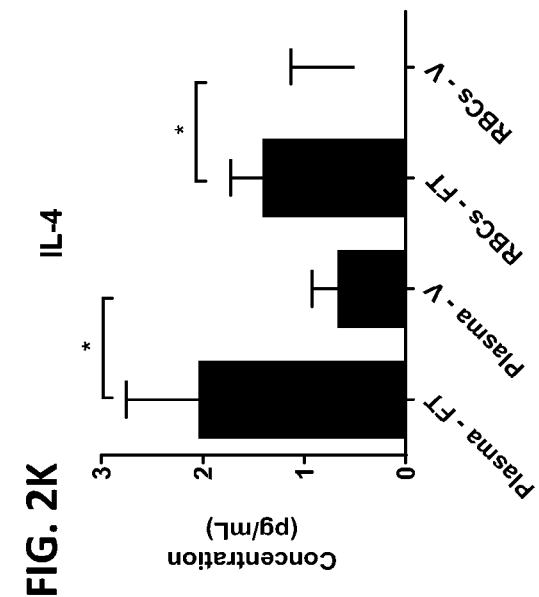
Figure 2M:
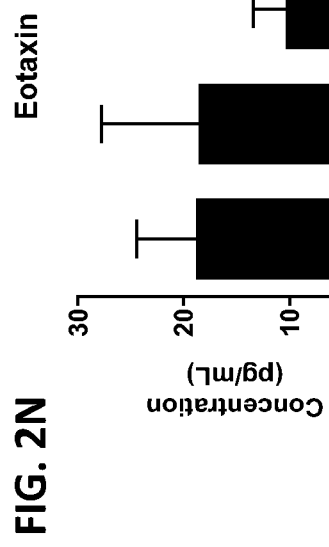
Figure 2N:
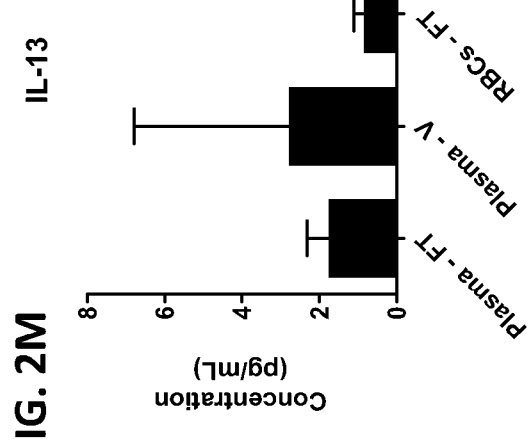
Figure 2O:
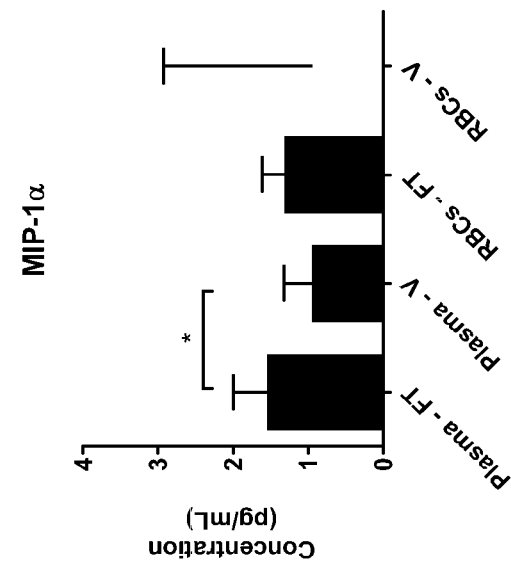
Figure 2P:
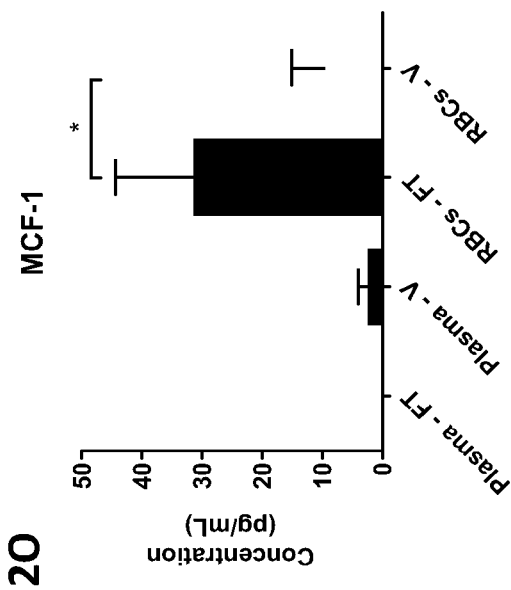
Figure 2Q:
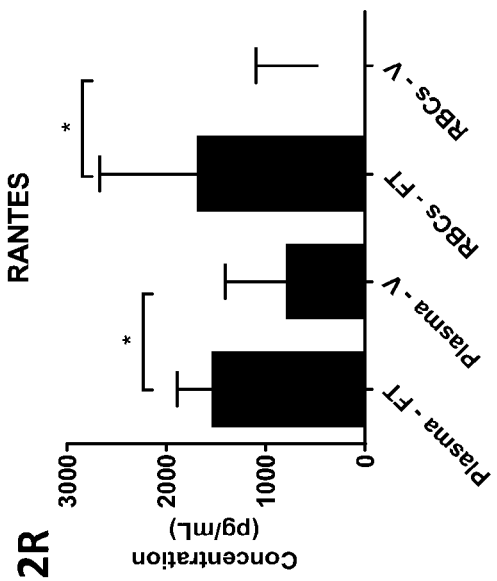
Figure 2R:
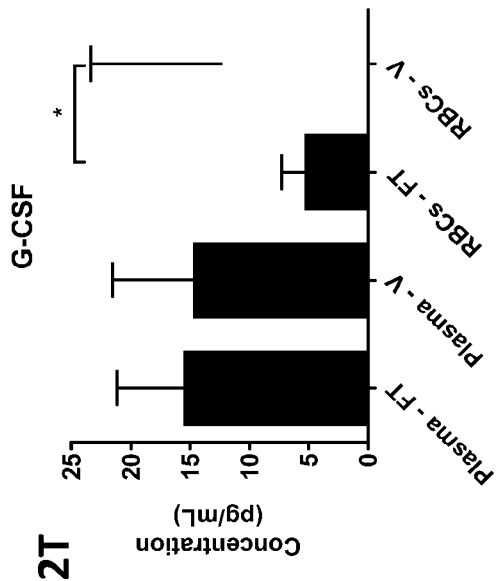
Figure 2S:
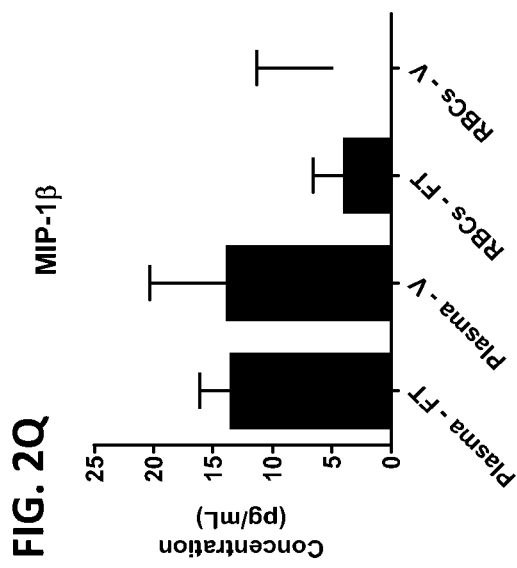
Figure 2T:
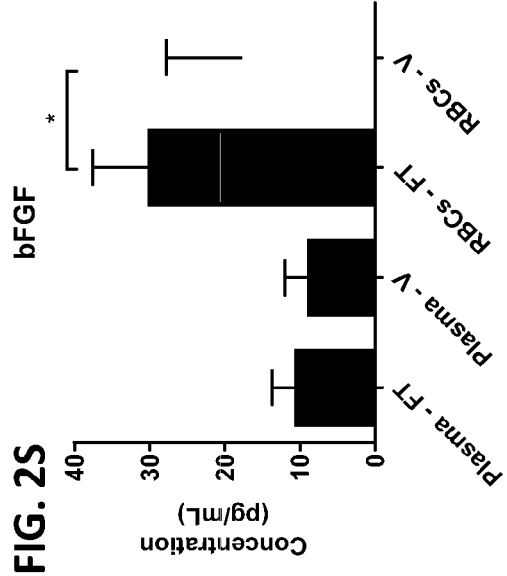
Figure 2V:
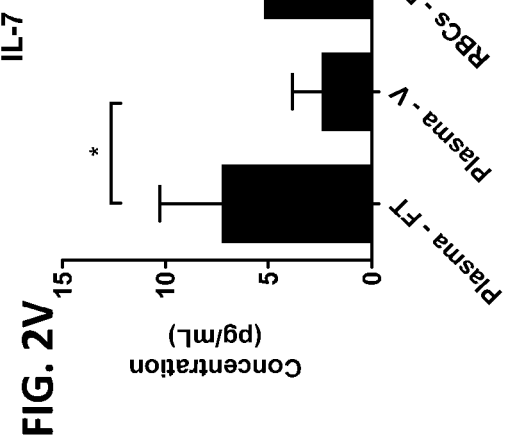
Figure 2X:
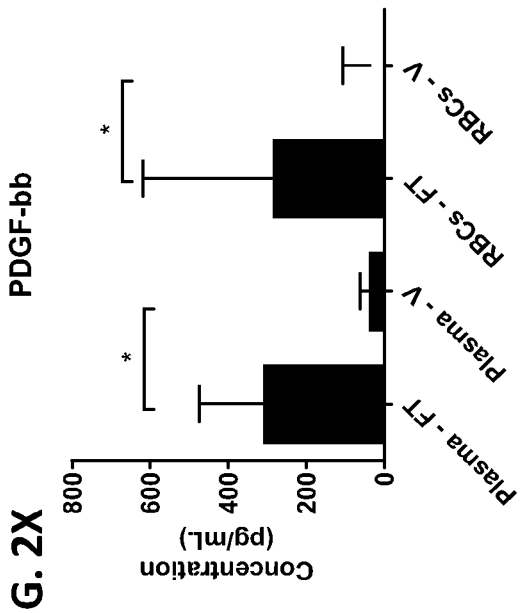
Figure 2U:
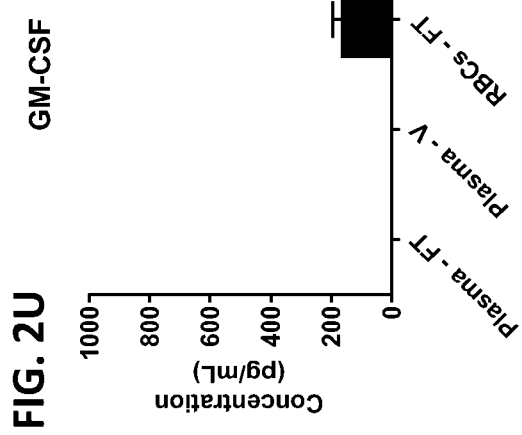
Figure 2W:
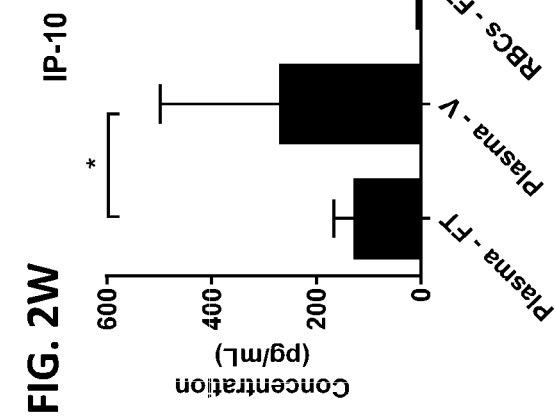
Figure 2Z:
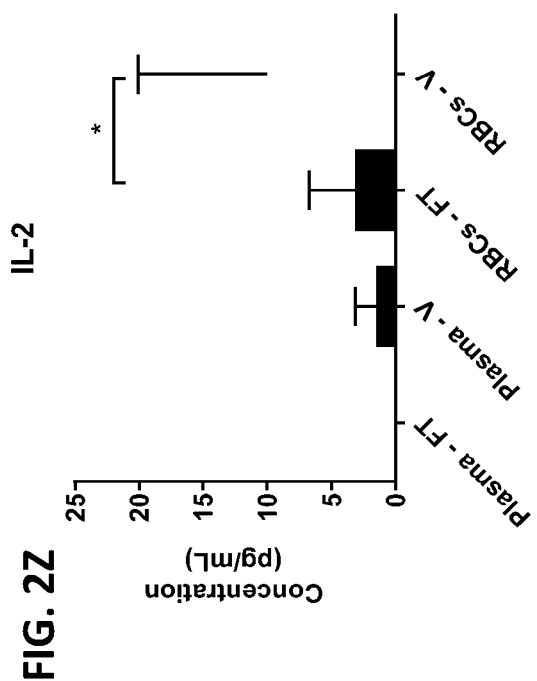
Figure 2Y:
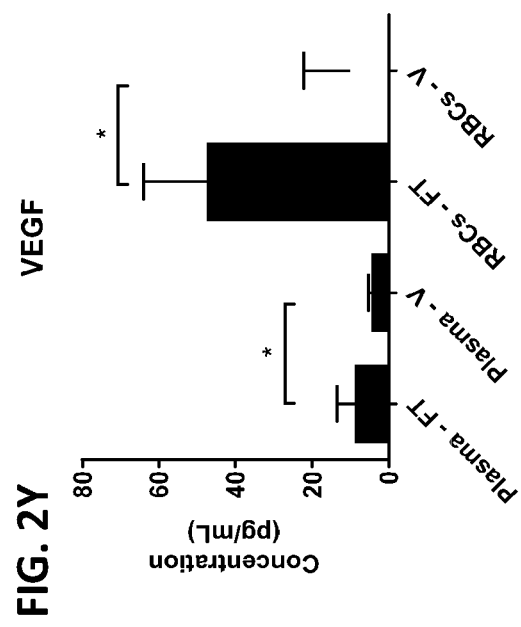
Figure 2A:
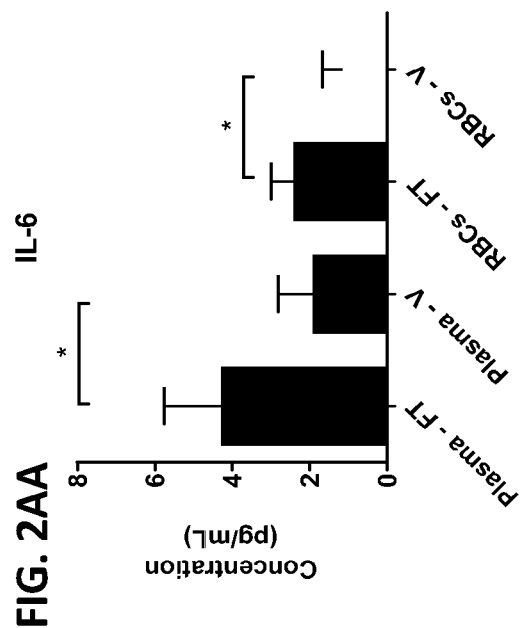
Figure 3A:
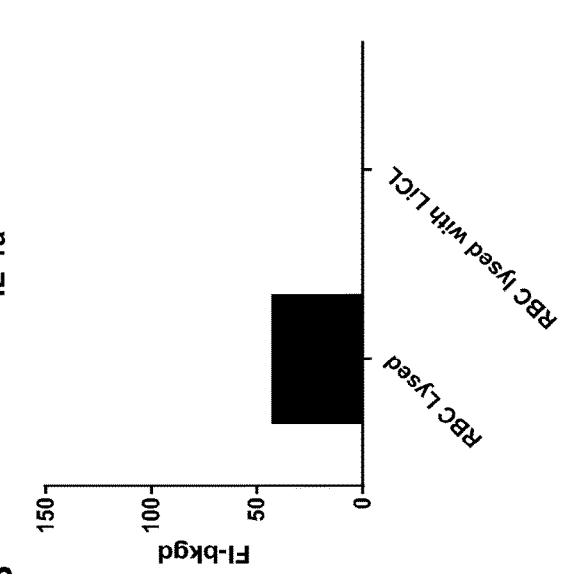
FIG. 3A-3G is a series of graphs showing the levels of various proteins in red blood cells contacted with lithium chloride.
Figure 3B:
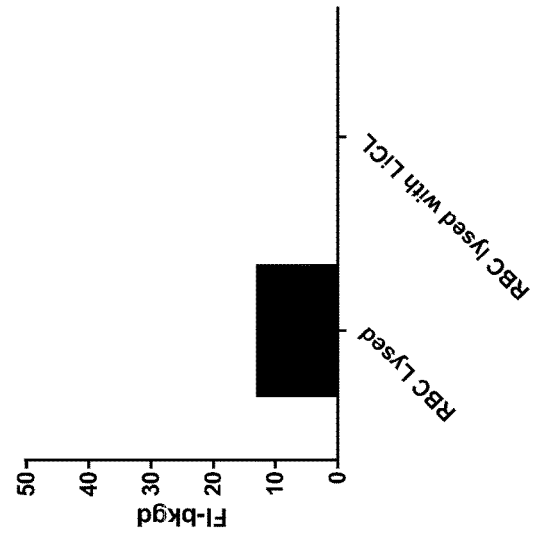
Figure 3C:
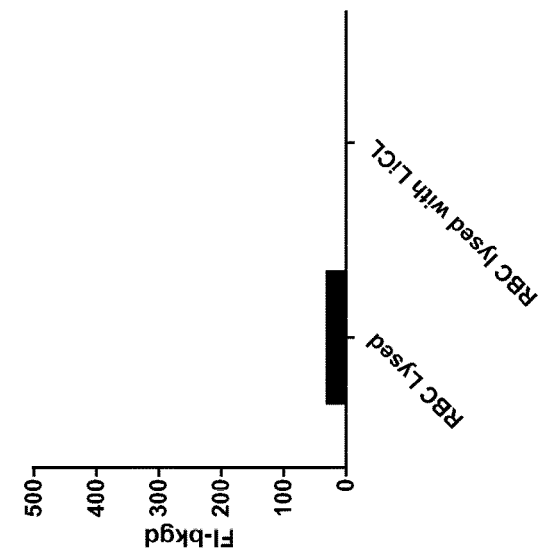
Figure 3D:
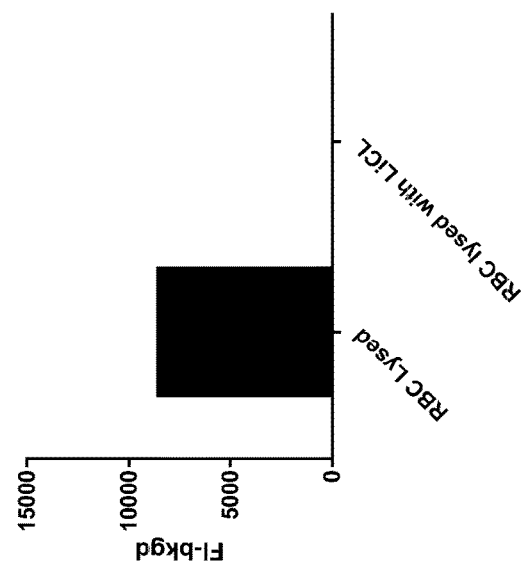
Figure 3F:
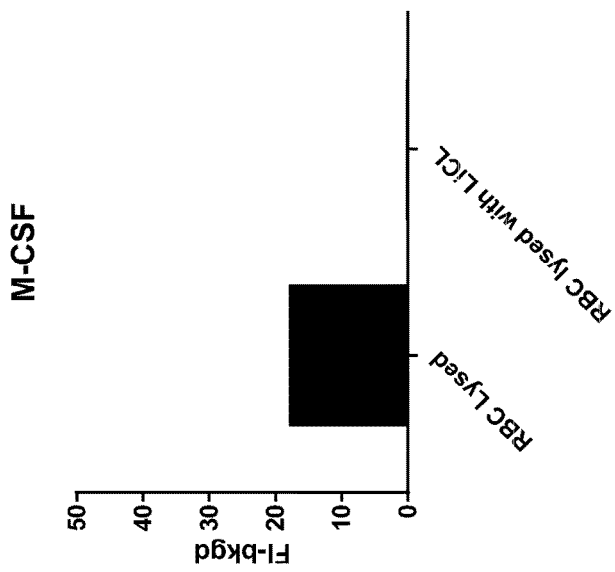
Figure 3E:
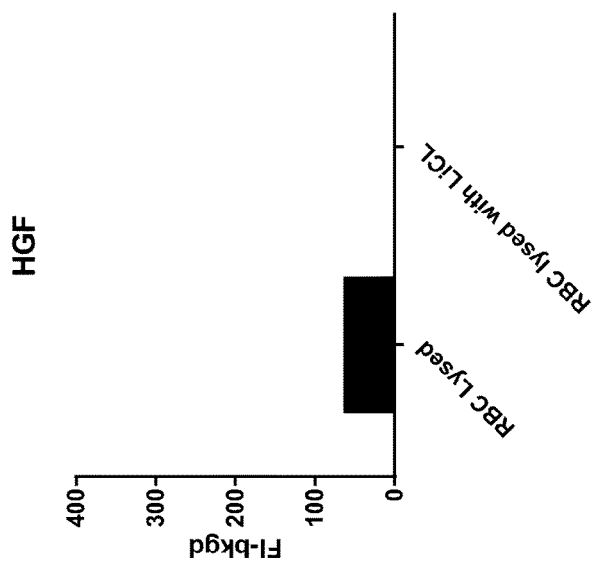
Figure 3G:
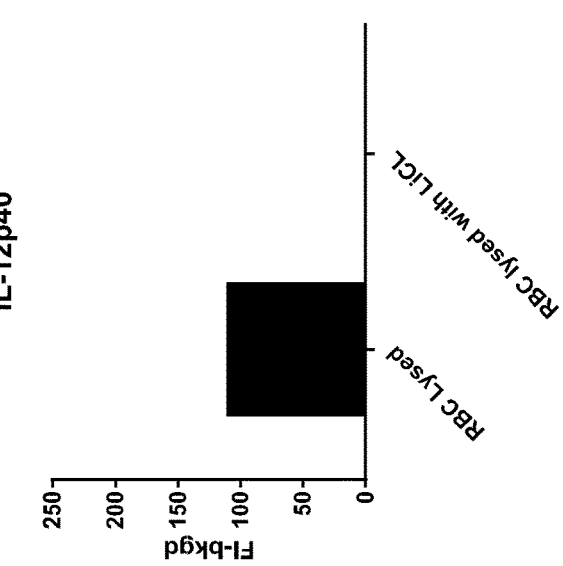

The concentration of the indicated proteins in the plasma isolated from venous blood and fingertip blood, or the lysate of red blood cells isolated from venous blood and fingertip blood are depicted in FIG. 2A-2AA. Significant differences (p<0.05) were determined using Student T-tests. There were consistent trends between levels of proteins in the plasma and the red blood cells when fingertip blood and venous blood were compared. For example, the concentration of IL-6 was at a significantly higher concentration in the plasma isolated from the fingertip as opposed to that in venous plasma. This same trend was observed with the red blood cells, with significantly higher levels of proteins observed in the cells isolated from fingertip blood. This trend was observed for a number of proteins including, for example, IL-2, RANTES, and IP-10. For a number of proteins, higher concentrations were observed in the plasma and red blood cells isolated from fingertip blood, including, for instance, IL-1β, IL-8, and TNF-α.

For the red blood cells, the biological variation (standard deviation) was lower in the fingertip samples than the venous samples (e.g., MIP-1β, G-CSF). This suggested that analysis of the red blood cells collected from the fingertip would be more reproducible than analysis of venous blood. The opposite was observed for a number of proteins in plasma, where venous plasma was less variable than the fingertip blood (e.g., IL-7, PDGF-bb). These results supported the case for isolating and analysing red blood cells from the fingertip, where frequent blood collection may be used.

Example 3. Protein Profile in RBCs Using Cationic Salts

Red blood cells were isolated using dextran sedimentation as follows. Whole blood was centrifuged (1500 g, 10 minutes) and the upper plasma layer was discarded. The remaining cell pellet was resuspended in an equal volume of sodium chloride (0.15 M). Dextran (6% w/v in 0.15 M sodium chloride) was then added to this cellular suspension at a 1:4 ratio (dextran:cell suspension). This solution was left at room temperature for 30 minutes for red blood cell sedimentation to the bottom of the tube. After this time the upper white blood cell rich layer and the lower red blood cell fraction were separated and the white blood cells discarded. The lower red blood cell fraction was washed twice in phosphate buffered saline (PBS, 500 g, 5 minutes). The supernatant was discarded, and the red blood cell pellet resuspended in either PBS or PBS containing 100 mM LiCl.

The red blood cells were subjected to 3 freeze-thaw cycles to ensure complete cellular lysis. Following lysis, the red blood cell lysates were diluted in PBS to the equivalent of 400 million cells/mL. The red blood cell lysates were analysed on a 21-plex human cytokine panel that assays for IL-1α, IL-2Ra, IL-3, IL-12, IL-16, IL-18, CTACK, GRO-α, HGF, IFN-α2, LIF, MCP-3, M-CSF, MIF, MIG, β-NGF, SCF, SCGF-β, SDF-1α, TNF-β, TRAIL (Bio-Plex Pro 27-plex and 21-plex, Bio-Rad). The assays were performed according to manufacturer's instructions using an automated magnetic wash station (BioPlex Pro II, Bio-Rad) for the washing steps. The assays were run on the Luminex® 200™ system (Bio-Rad) and fluorescent values were collected. The calibration curve for each cytokine was analysed with 5 parametric logistic curve regression using BioPlex manager software (ver. 5.0, Bio-Rad, USA).

As seen in FIG. 3A-FIG. 3G, lithium chloride increased and/or enhanced the level of several of the proteins in the assay.

Example 4. Protein Profile in RBCs from Healthy Individuals Versus Individuals Having Preeclampsia or Cancer The difference in the levels of proteins in the blood of healthy individuals compared to those with a disease or disorder was measured. Whole blood was collected from four groups of people including: 1) healthy volunteers, 2)

healthy, pregnant women, 3) pregnant women with preeclampsia, and 4) oncology patients (see Table 1). The healthy, pregnant controls were matched with the preeclampsia samples according to gestation. Blood was collected from each volunteer by venipuncture (n≥3) directly into EDTA vacutainers (k₂EDTA vacutainers, BD Biosciences).

TABLE 1

Participant summary.

| Subject | Condition | Relevant information |
|---|---|---|
| OBS-101 | Lymphoma | Chemotherapy and radiation therapy |
| OBS-102 | Lymphoma | Chemotherapy |
| OBS-103 | Cancer (specific type unknown) | Chemotherapy |
| PE-001 | Preeclampsia | 3$^{rd}$ trimester |
| PE-002 | Preeclampsia | 3$^{rd}$ trimester |
| PE-003 | Preeclampsia | 3$^{rd}$ trimester |

The fractions of blood were collected and processed at room temperature within 4 hours of collection. For multiplex analysis (BioPlex analysis) the samples were stored at −80° C. and were subjected to 3 freeze-thaw cycles at −80° C. to ensure complete cellular lysis prior to analysis.

The plasma and red blood cells were isolated using dextran sedimentation as follows. Whole blood was centrifuged (1500 g, 10 minutes) and the upper plasma layer was collected. The remaining cell pellet was resuspended in an equal volume of sodium chloride (0.15 M). Dextran (6% w/v in 0.15 M sodium chloride) was then added to this cellular suspension at a 1:4 ratio (dextran:cell suspension). This solution was left at room temperature for 30 minutes for red blood cell sedimentation to the bottom of the tube. After this time the upper white blood cell rich layer was discarded and the lower red blood cell fraction was isolated. The red blood cell fraction was washed twice in phosphate buffered saline (PBS, 500 g, 5 minutes) and the remaining red blood cell pellet was counted (Coulter Act Diff, Beckman Coulter) and then frozen (−80° C.) until analysis.

The red blood cells were subjected to 3 freeze-thaw cycles to ensure complete cellular lysis. Following lysis, the red blood cell lysates were diluted in PBS to the equivalent of 400 million cells/mL. These lysates and the plasma samples (undiluted) were then analysed on the multiplex cytokine assays. Two multiplex assays were utilised. The first was the 27-plex human cytokine panel that assays for FGF basic, Eotaxin, G-CSF, GM-CSF, IFN-γ, IL-1β, IL-1ra, IL-2, IL-4, IL-5, IL-6, IL-7, IL-8, IL-9, IL-10, IL-12(p70), IL-13, IL-15, IL-17, IP-10, MCP-1, MIP-1α, MIP-1β, PDGF-BB, RANTES, TNF-α, and VEGF, and the second was the 21-plex human cytokine panel that assays for IL-1α, IL-2Ra, IL-3, IL-12, IL-16, IL-18, CTACK, GRO-α, HGF, IFN-α2, LIF, MCP-3, M-CSF, MIF, MIG, β-NGF, SCF, SCGF-β, SDF-1α, TNF-β, TRAIL (Bio-Plex Pro 27-plex and 21-plex, Bio-Rad). The assays were performed according to manufacturer's instructions using an automated magnetic wash station (BioPlex Pro II, Bio-Rad) for the washing steps. The assays were run on the Luminex® 200™ system (Bio-Rad) and fluorescent values were collected. The calibration curve for each cytokine was analysed with 5 parametric logistic curve regression using BioPlex manager software (ver. 5.0, Bio-Rad, USA).

Figure 4A:
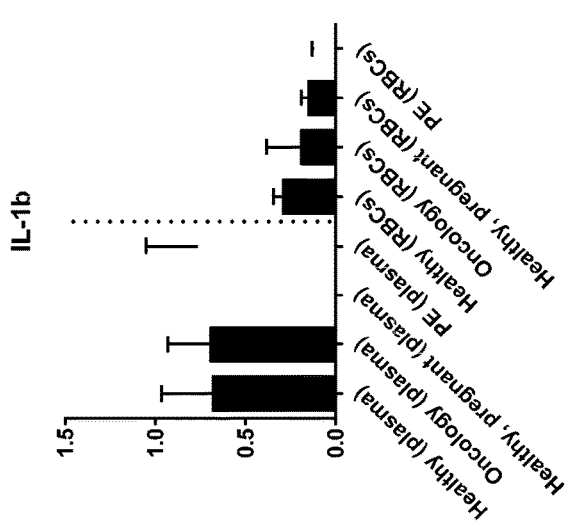
FIG. 4A-4VV is a series of graphs showing the difference in the level of various proteins in red blood cells isolated from healthy individuals, healthy pregnant women, pregnant women with preeclampsia, and oncology patients.
Figure 4B:
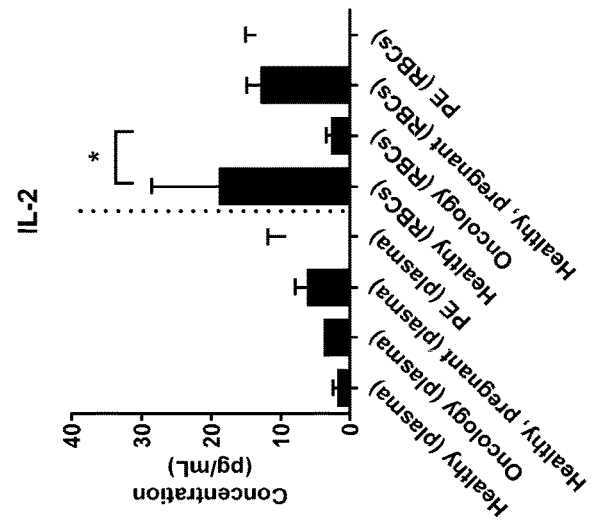
Figure 4C:
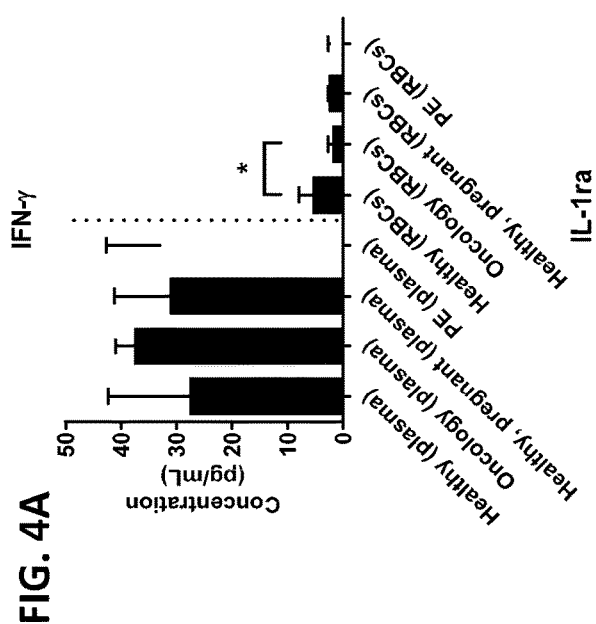
Figure 4D:
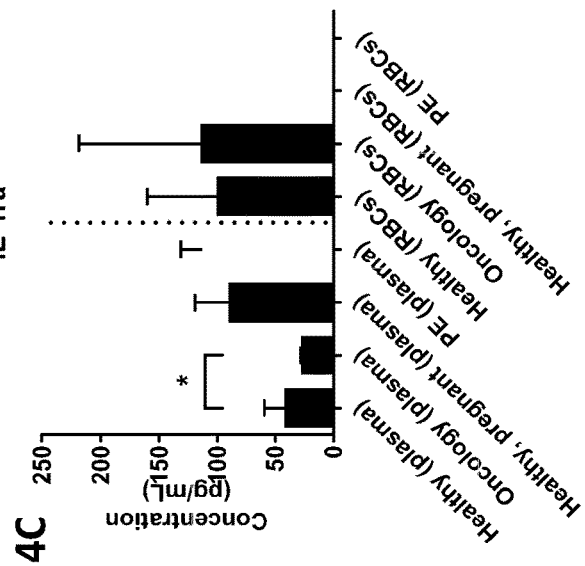
Figure 4E:
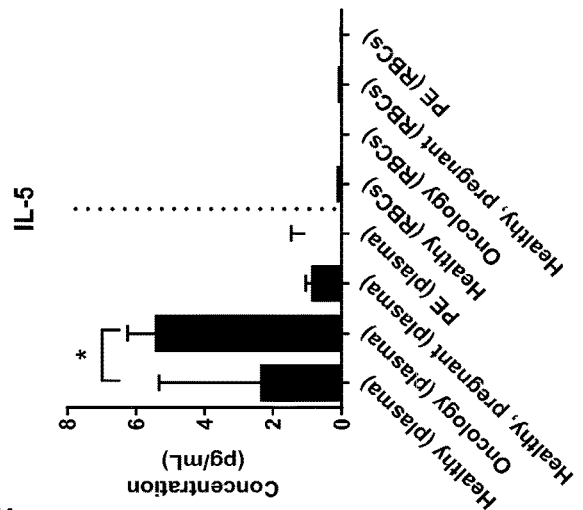
Figure 4F:
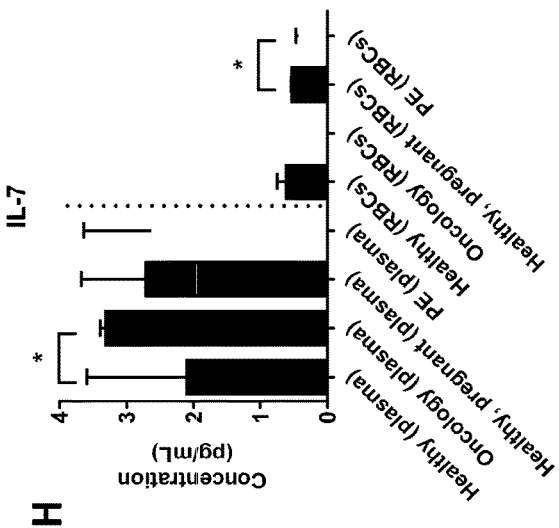
Figure 4G:
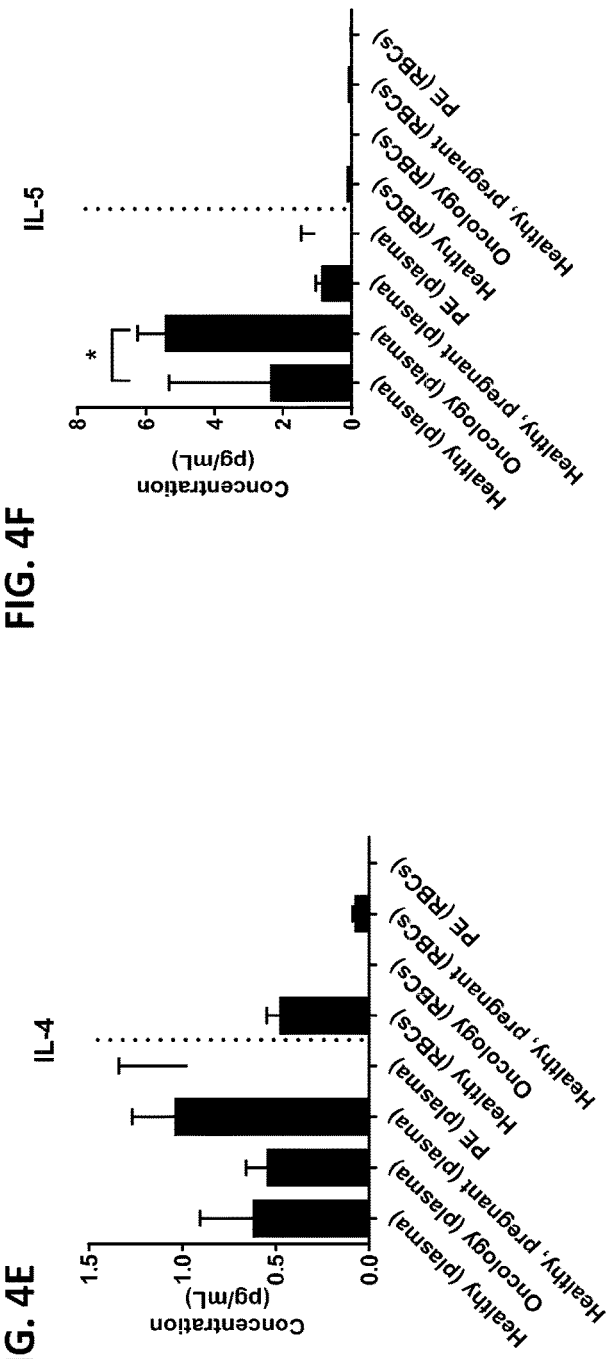
Figure 4H:
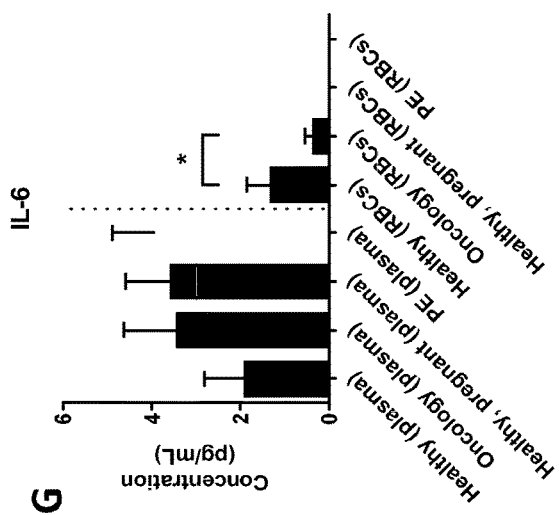
Figure 4I:
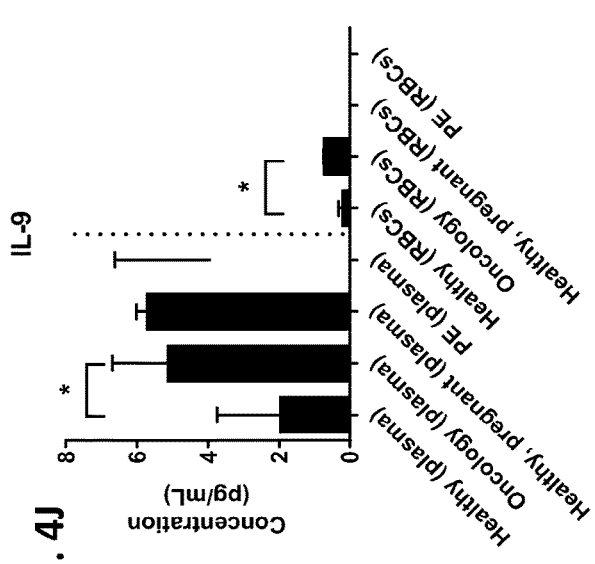
Figure 4J:
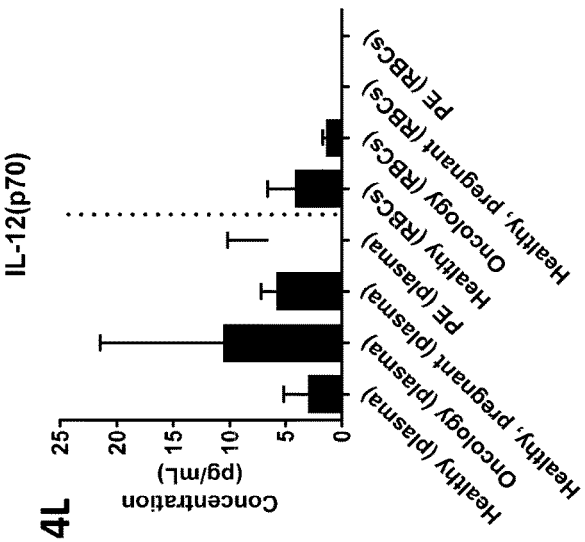
Figure 4K:
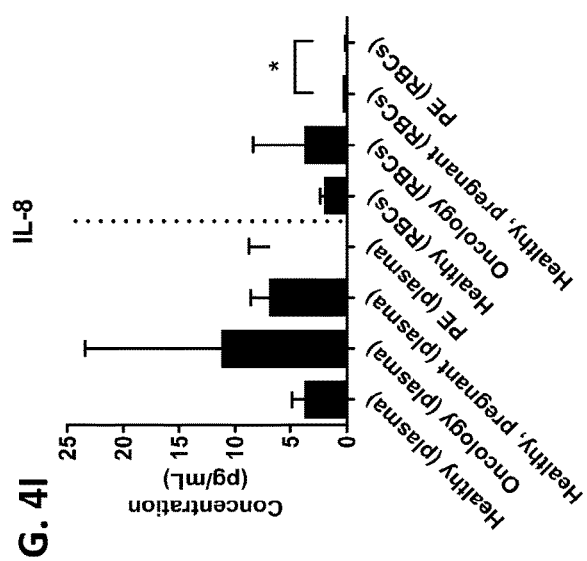
Figure 4L:
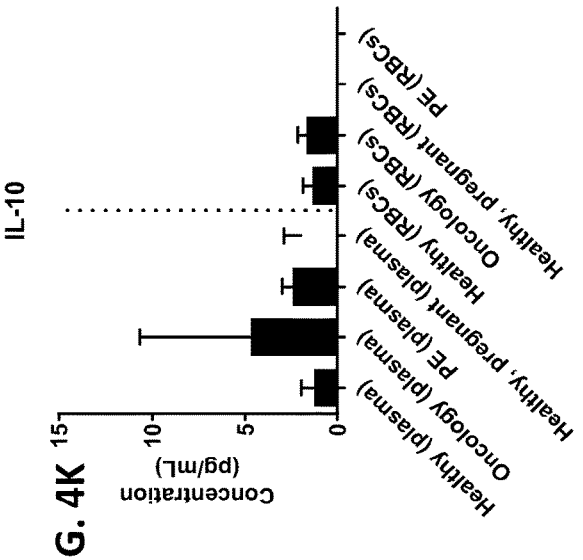
Figure 4M:
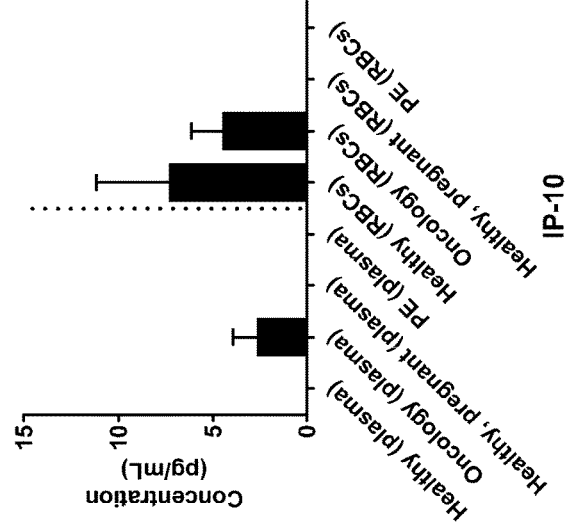
Figure 4N:
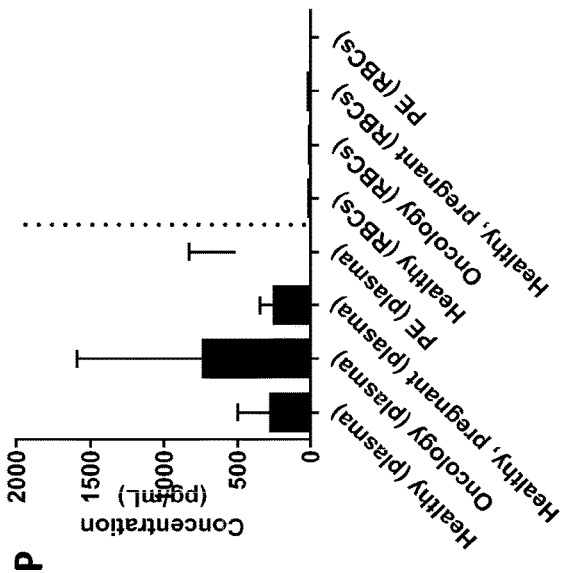
Figure 4O:
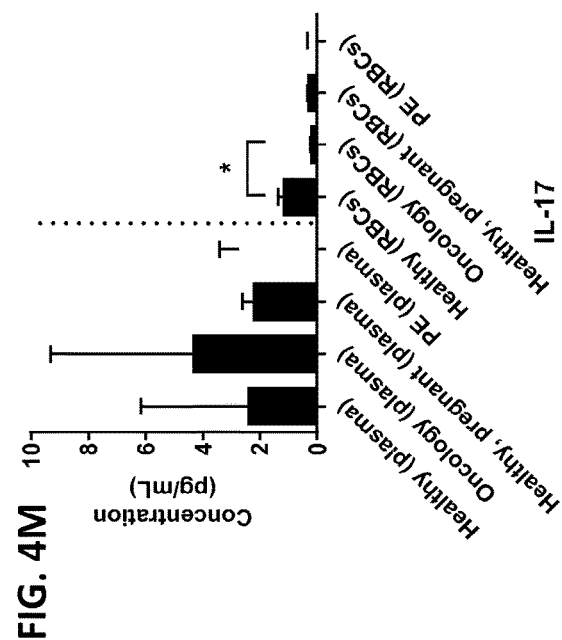
Figure 4P:
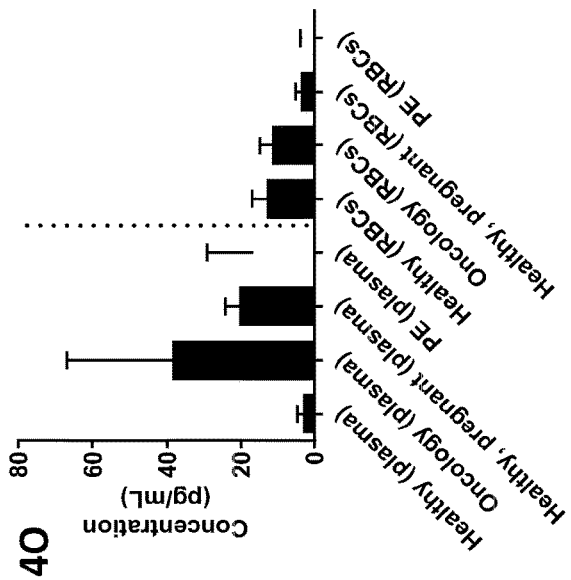
Figure 4Q:
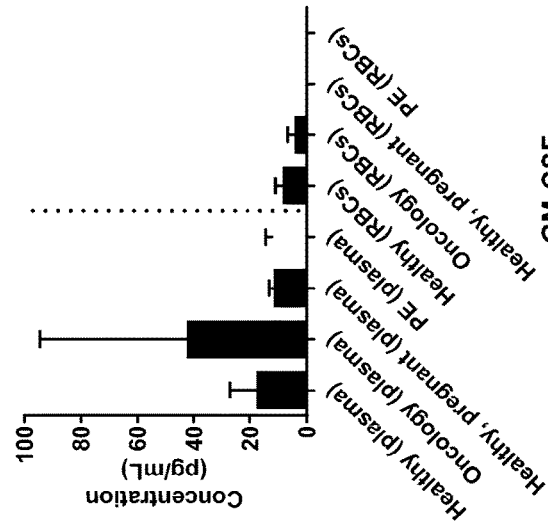
Figure 4R:
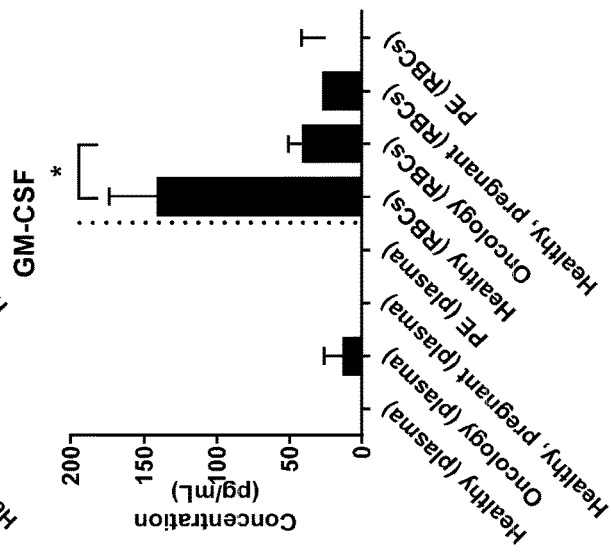
Figure 4S:
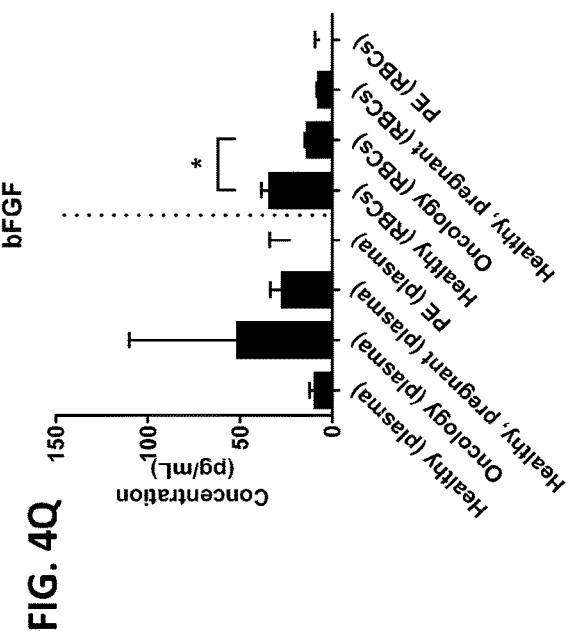
Figure 4T:
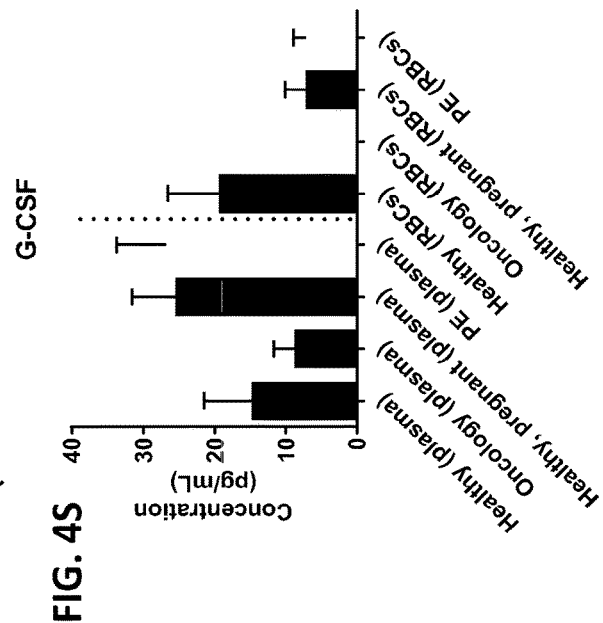
Figure 4V:
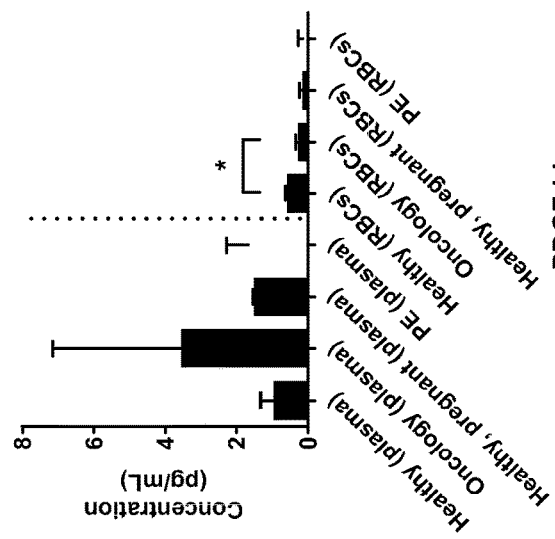
Figure 4X:
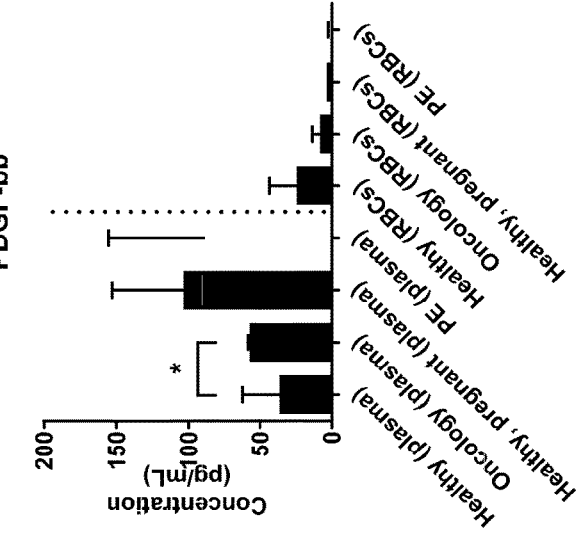
Figure 4U:
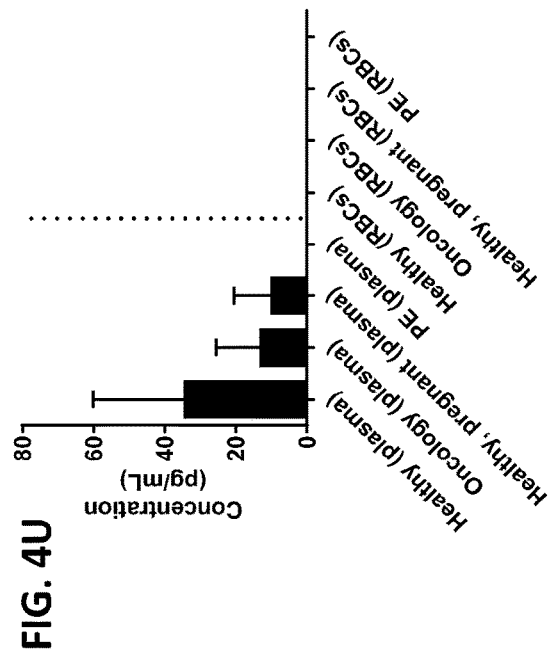
Figure 4W:
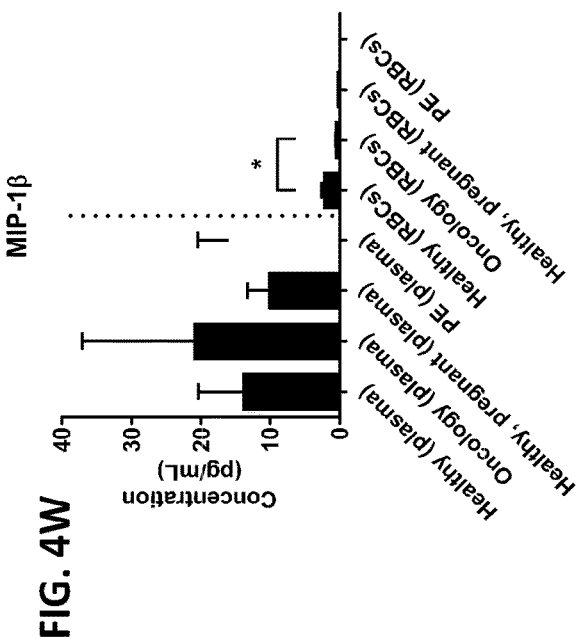
Figure 4Z:
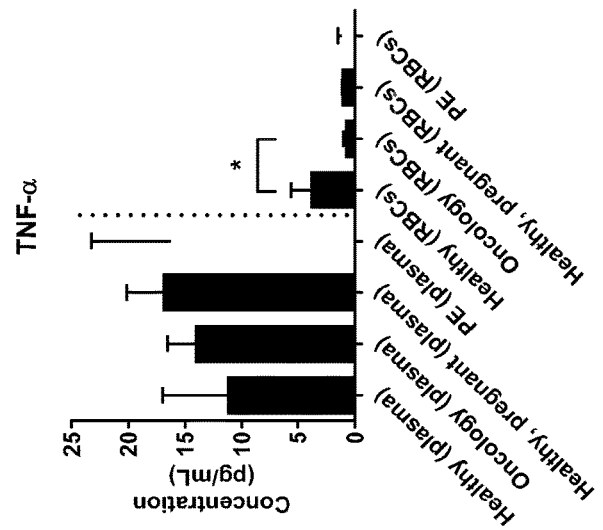
Figure 4B:
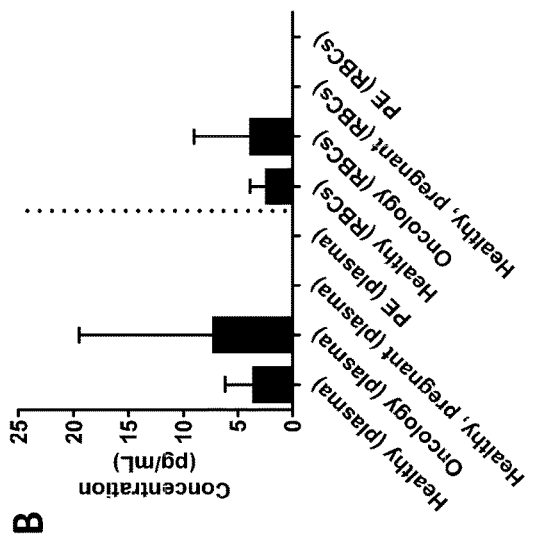
Figure 4Y:
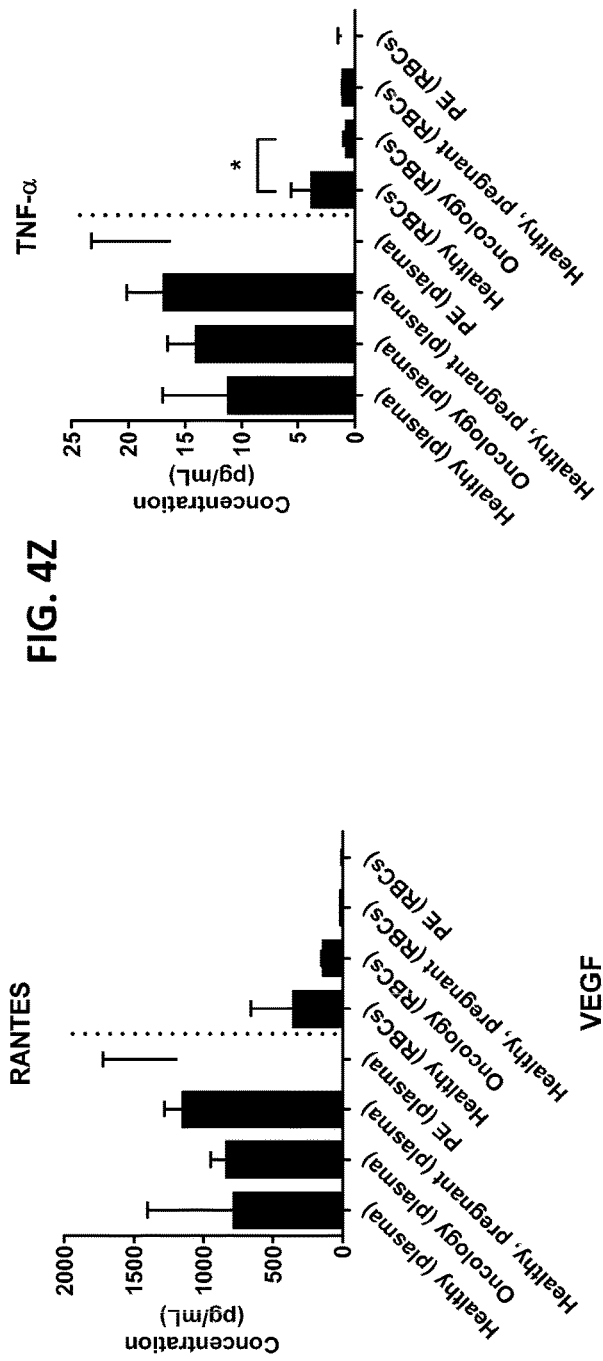
Figure 4A:
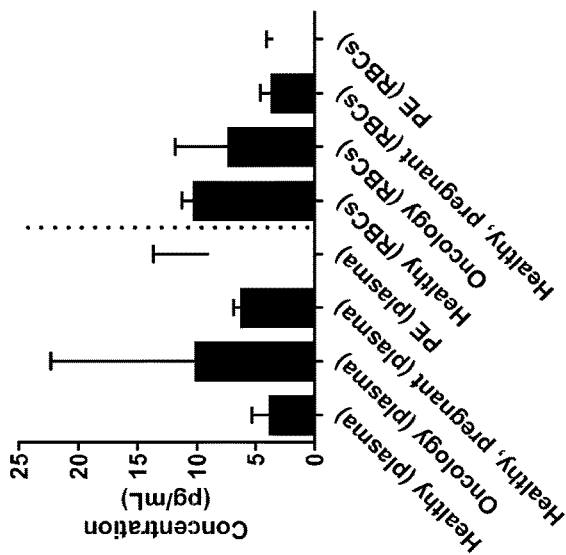
Figure 4D:
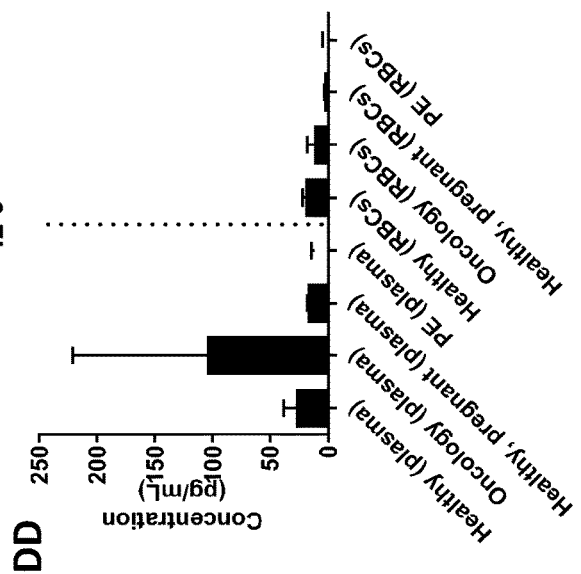
Figure 4F:
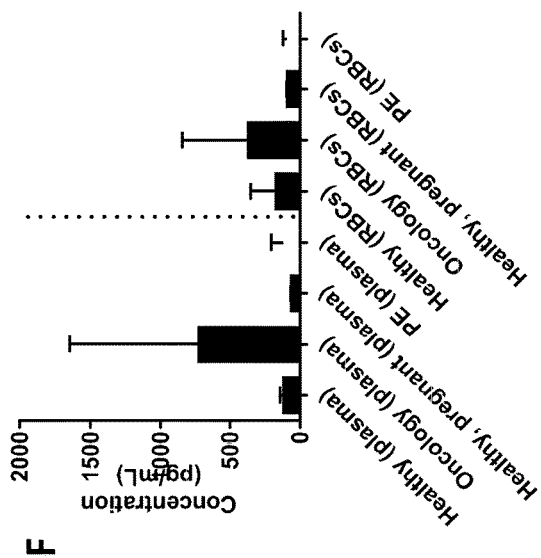
Figure 4C:
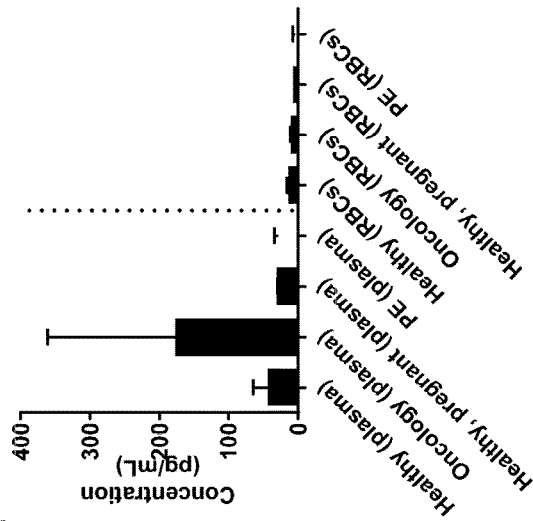
Figure 4E:
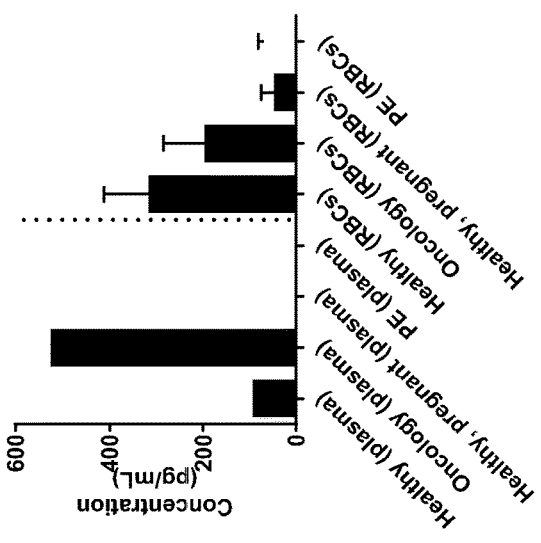
Figure 4G:
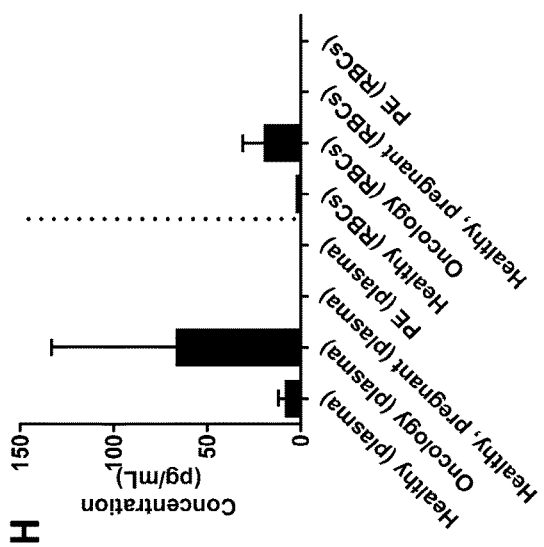
Figure 4H:
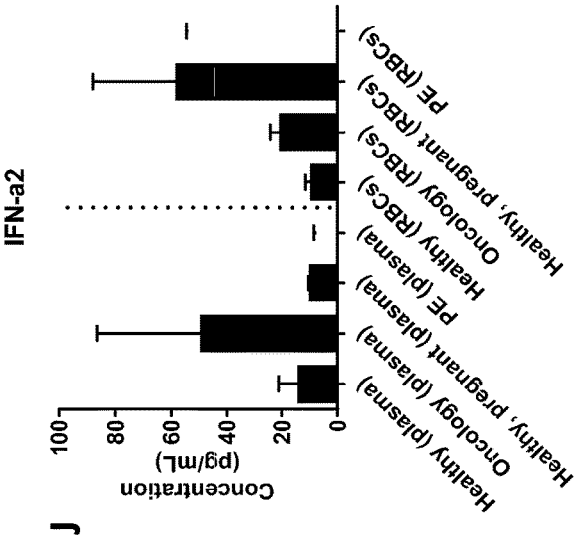
Figure 4I:
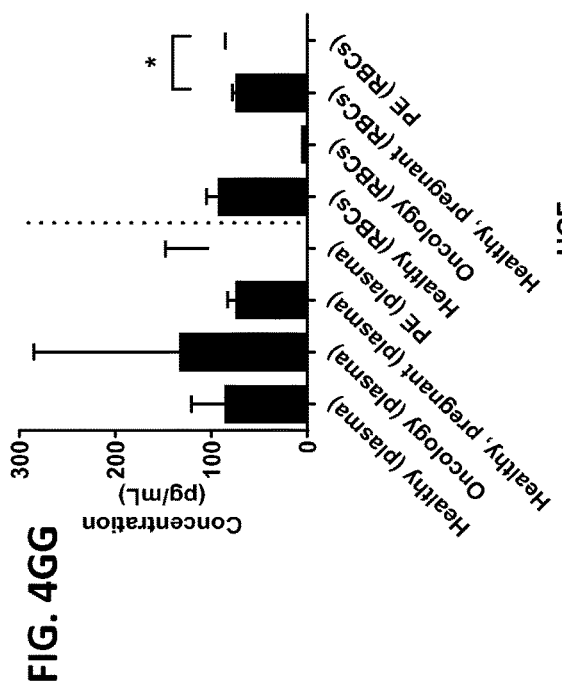
Figure 4J:
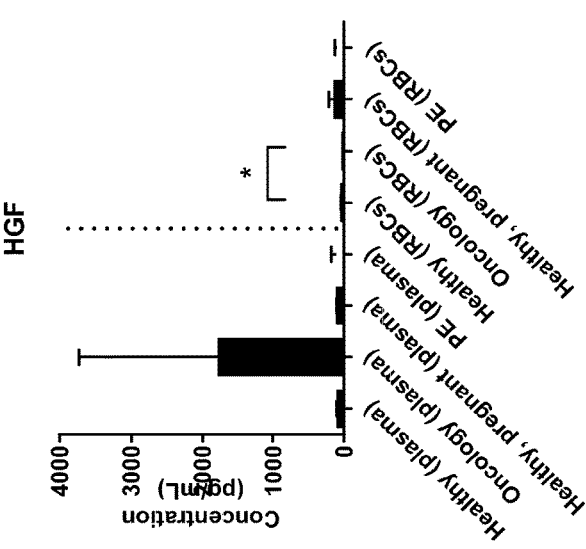
Figure 4L:
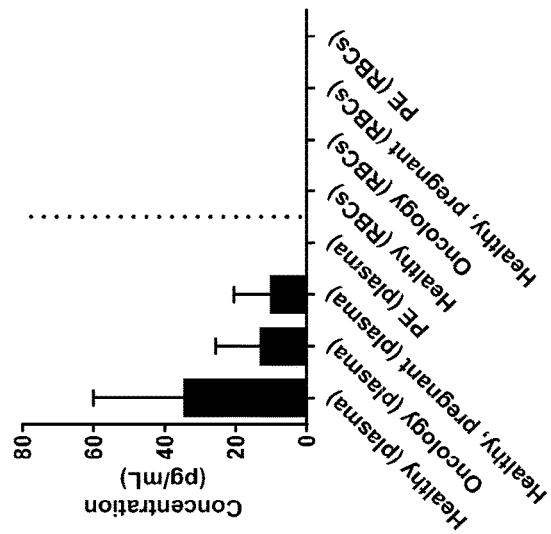
Figure 4N:
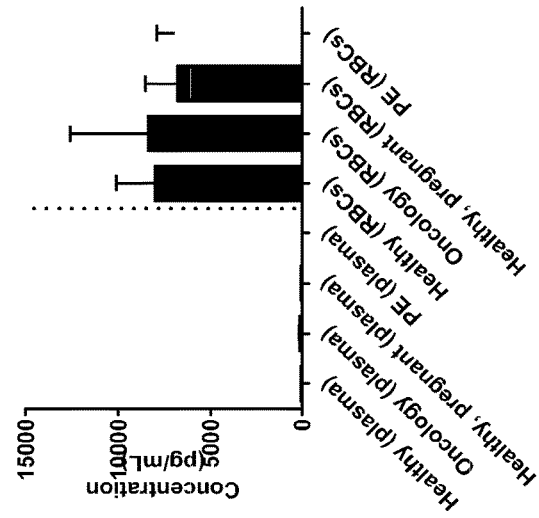
Figure 4K:
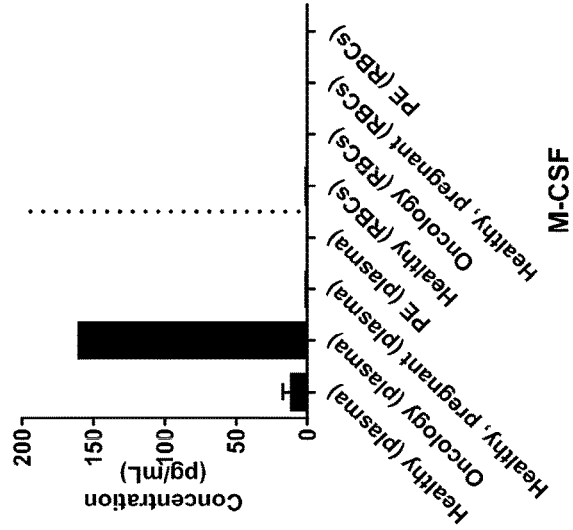
Figure 4M:
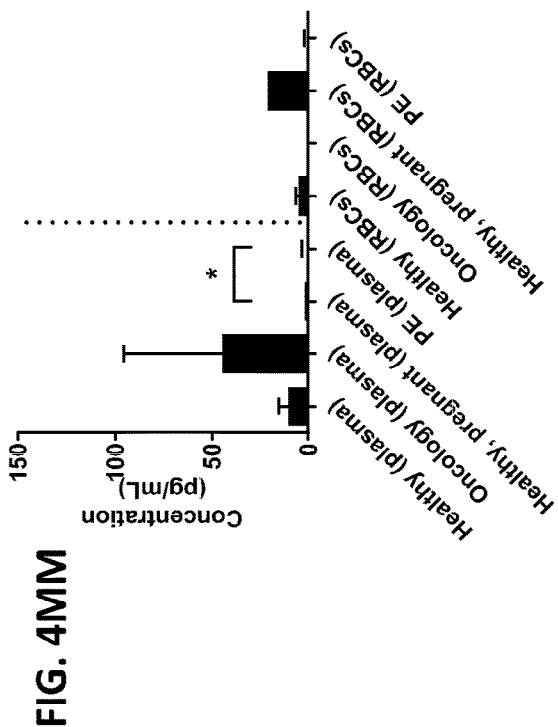
Figure 4O:
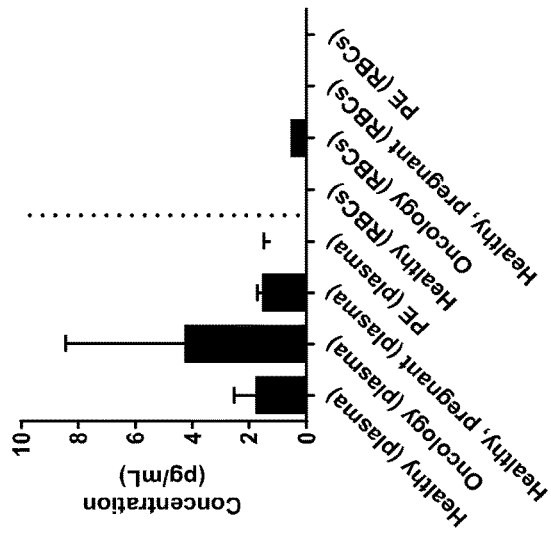
Figure 4P:
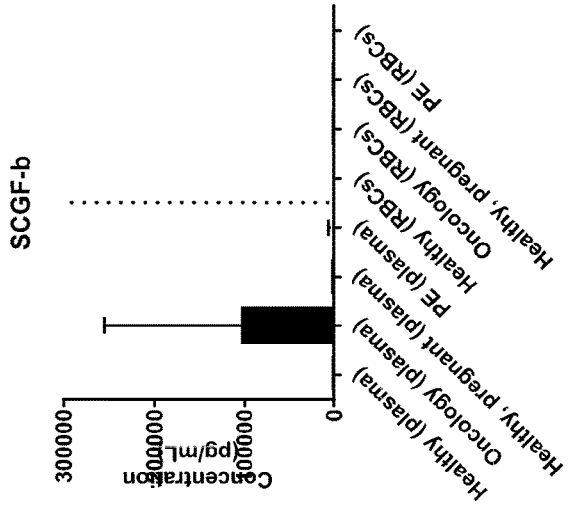
Figure 4Q:
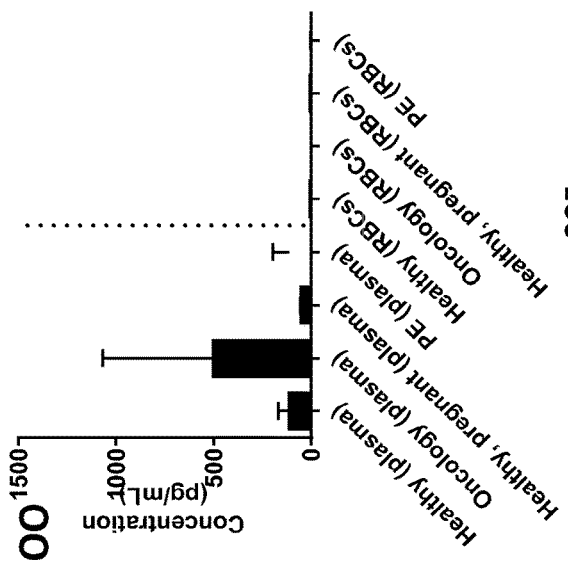
Figure 4R:
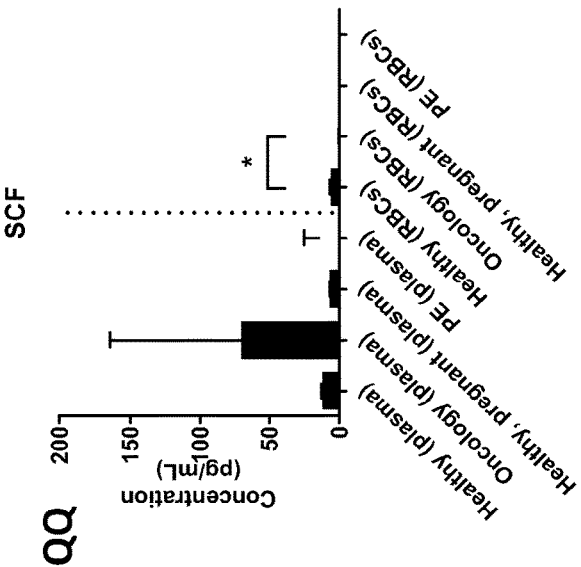
Figure 4S:
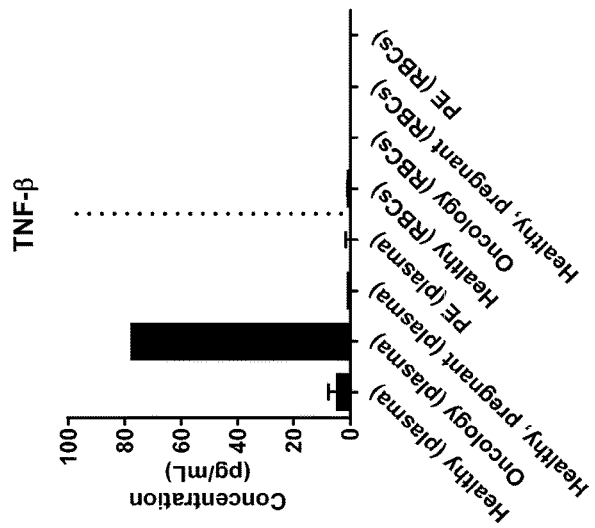
Figure 4T:
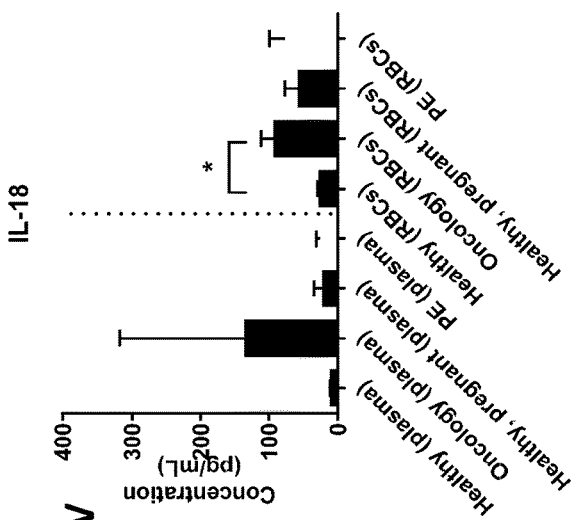
Figure 4U:
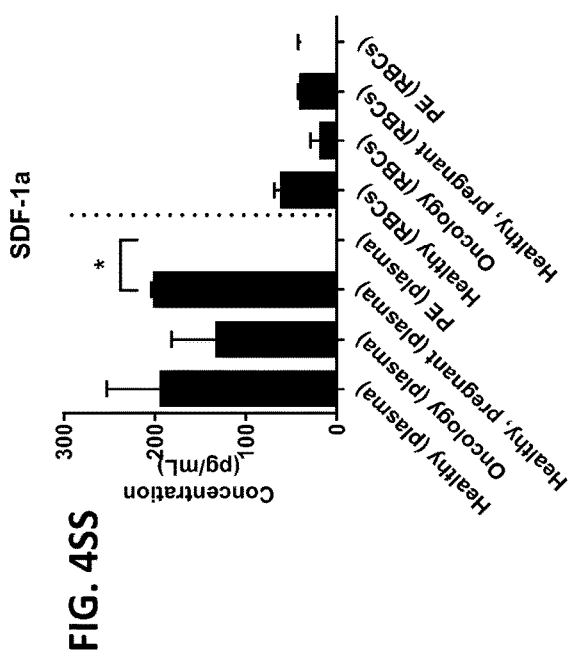
Figure 4V:
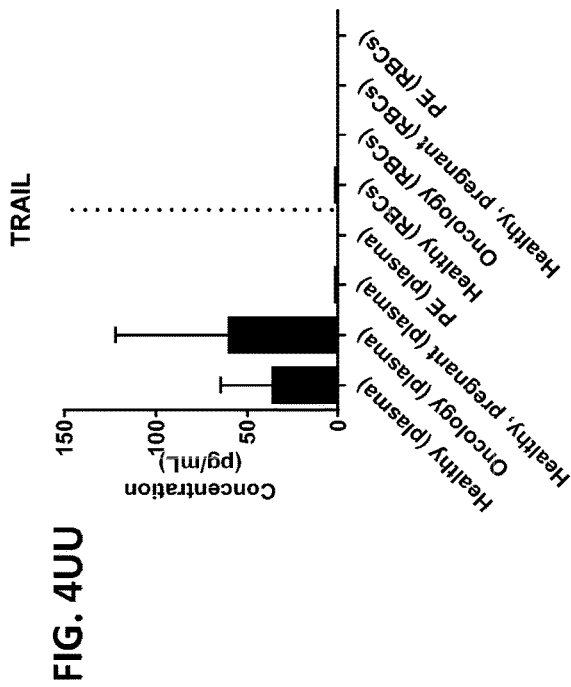

FIG. 4A-FIG. 4VV shows the concentration of the indicated proteins in the plasma and the lysate of red blood cells (400 million cells/mL) from participant groups calculated back to the relative concentration per mL of whole blood (approximately 5×10⁹ cells/mL). Significant differences ($p<0.05$) were determined using Student T-tests. The protein levels in the blood of healthy (non-pregnant) individuals were compared to the oncology patients and that of healthy, pregnant individuals was compared to that of pregnant individuals with preeclampsia. FIG. 5A-FIG. 5C shows the fold difference between the concentrations of the proteins in red blood cell as opposed to plasma.

There were significant differences between the protein levels in healthy control individuals and that in the individuals with a disease or disorder in a collection of proteins. For example, IL-2 was significantly lower (approximately 10-fold lower) in the red blood cells collected from the oncology group than in the healthy group and the chemokine CTACK was significantly higher in the red blood cells collected from the preeclampsia group than the healthy, pregnant group. In addition, twenty-eight of the 48 cytokines had a level of protein in RBCs that substantially exceeded the plasma level (greater than 2:1), with the fold change ranging from 2:1 to ~280:1 (RBC:plasma ratio). The median RBC-plasma ratio was 5.9:1. The results of the study demonstrated that red blood cells may be a useful tool for identifying biomarkers in disease. Moreover, analysis of red blood cells in conjunction with plasma may provide more information about the disease state that is currently unachievable, for example, in instances in which there are no clear differences in protein levels in plasma alone, but identifiable differences in red blood cells (e.g., bFGF) or between red blood cells and plasma.

Example 5. Protein Profile in RBCs and RBC Protein Release from Healthy Individuals Versus Individuals Having Preeclampsia or Cancer The levels of proteins released by red blood cells was evaluated in healthy individuals and those with a disease or disorder. Whole blood was collected from four groups of people including: 1) healthy volunteers, 2) healthy, pregnant women, 3) pregnant women with pre-eclampsia, and 4) oncology patients (Table 2).

TABLE 2

Participant summary

| Subject | Condition | Relevant information |
|---|---|---|
| OBS-101 | Lymphoma | Chemotherapy and radiation therapy |
| OBS-102 | Lymphoma | Chemotherapy |
| OBS-103 | Cancer (specific type unknown) | Chemotherapy |
| PE-001 | Preeclampsia | 3$^{rd}$ trimester |
| PE-002 | Preeclampsia | 3$^{rd}$ trimester |
| PE-003 | Preeclampsia | 3$^{rd}$ trimester |

The healthy, pregnant control samples were matched with the preeclampsia samples according to gestation. Blood was collected from each volunteer by venipuncture (n≥3) directly into EDTA vacutainers (k₂EDTA vacutainers, BD Biosciences). The fractions of blood were collected and processed at room temperature within 4 hours of collection. For multiplex analysis (BioPlex analysis) the samples were stored at −80° C. and were subjected to 3 freeze-thaw cycles at −80° C. to ensure complete cellular lysis prior to analysis.

The red blood cells were isolated using dextran sedimentation as follows. Whole blood was centrifuged (1500 g, 10 minutes) and the upper plasma layer was discarded. The remaining cell pellet was resuspended in an equal volume of sodium chloride (0.15 M). Dextran (6% w/v in 0.15 M sodium chloride) was then added to this cellular suspension at a 1:4 ratio (dextran:cell suspension). This solution was left at room temperature for 30 minutes for red blood cell sedimentation to the bottom of the tube. After this time the upper white blood cell rich layer was discarded and the lower red blood cell fraction was isolated. The red blood cell fraction was washed twice in phosphate buffered saline (PBS, 500 g, 5 minutes) and the remaining red blood cell pellet was counted (Coulter Act Diff, Beckman Coulter). The red blood cells were then diluted to 400 million cells/mL in PBS and were incubated at 37° C. and 5% $CO_2$ for 24 hours. After incubation, the resulting conditioned PBS was isolated by centrifugation (500 g, 5 minutes). The samples were stored at −80° C., and underwent 3 freeze/thaw cycles before analysis. The conditioned PBS samples were then analysed on the multiplex cytokine assays. Two multiplex assays were utilised. The first was the 27-plex human cytokine panel that assays for FGF basic, Eotaxin, G-CSF, GM-CSF, IFN-γ, IL-1β, IL-1ra, IL-2, IL-4, IL-5, IL-6, IL-7, IL-8, IL-9, IL-10, IL-12(p70), IL-13, IL-15, IL-17, IP-10, MCP-1, MIP-1α, MIP-1β, PDGF-BB, RANTES, TNF-α, and VEGF, and the second was the 21-plex human cytokine panel that assays for IL-1α, IL-2Ra, IL-3, IL-12, IL-16, IL-18, CTACK, GRO-α, HGF, IFN-α2, LIF, MCP-3, M-CSF, MIF, MIG, β-NGF, SCF, SCGF-β, SDF-1α, TNF-β, TRAIL (Bio-Plex Pro 27-plex and 21-plex, Bio-Rad). The assays were performed according to the manufacturer's instructions using an automated magnetic wash station (BioPlex Pro II, Bio-Rad) for the washing steps. The assays were run on the Luminex® 200™ system (Bio-Rad) and fluorescent values were collected. The calibration curve for each cytokine was analysed with 5 parametric logistic curve regression using BioPlex manager software (ver. 5.0, Bio-Rad, USA).

Figure 6B:
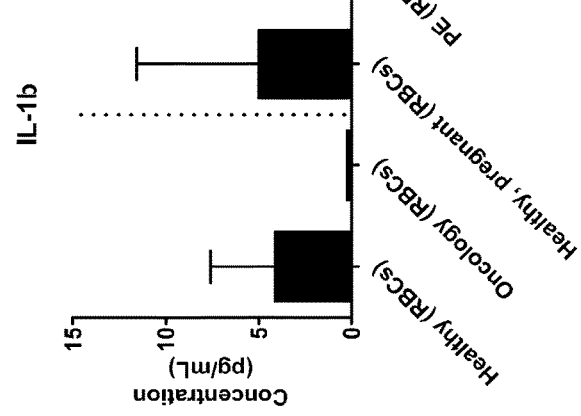
FIG. 6A-6RR is a series of graphs showing the levels of various proteins from red blood cells isolated from healthy individuals, healthy pregnant women, pregnant women with preeclampsia, and oncology patients.
Figure 6D:
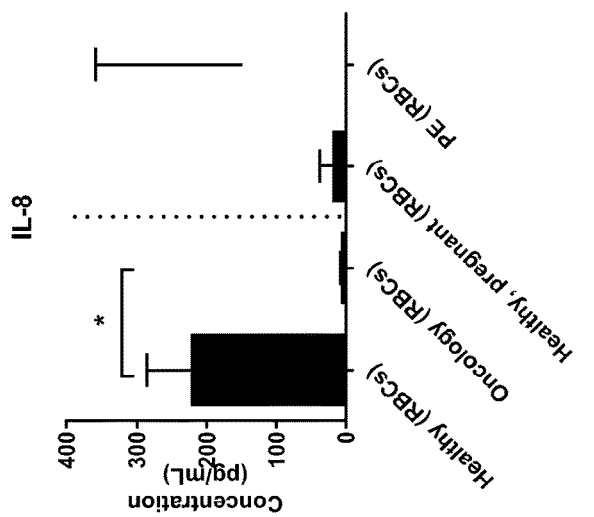
Figure 6A:
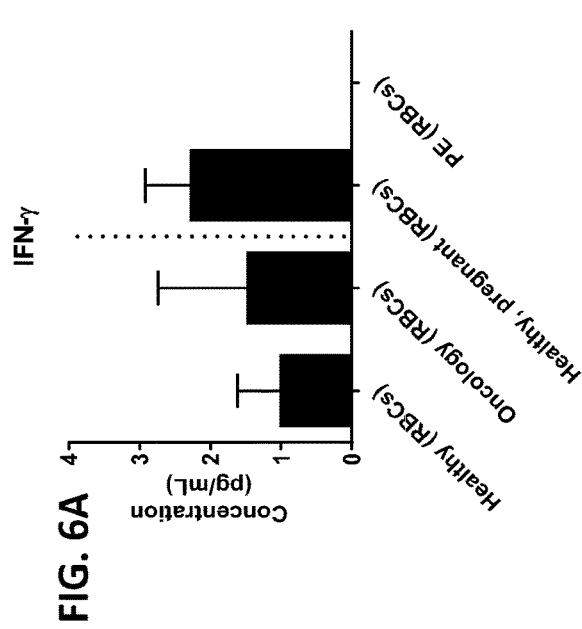
Figure 6C:
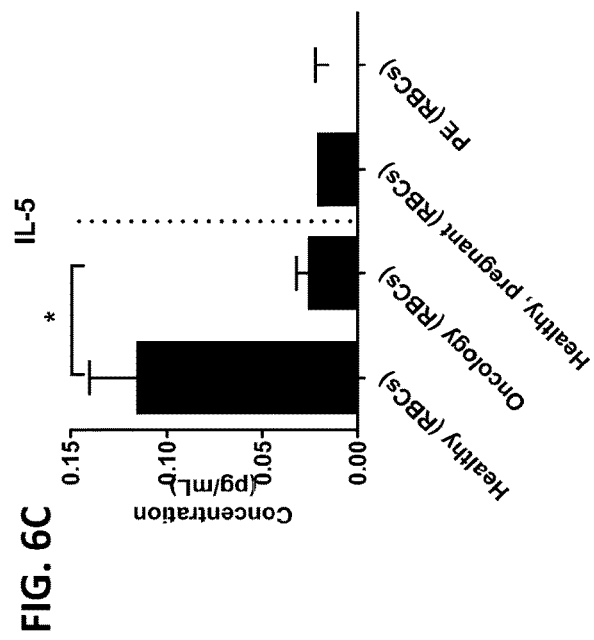
Figure 6E:
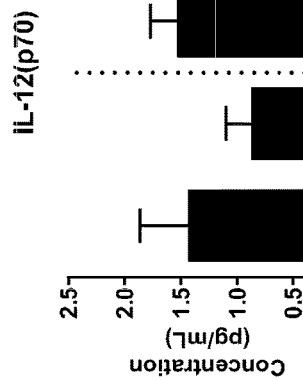
Figure 6F:
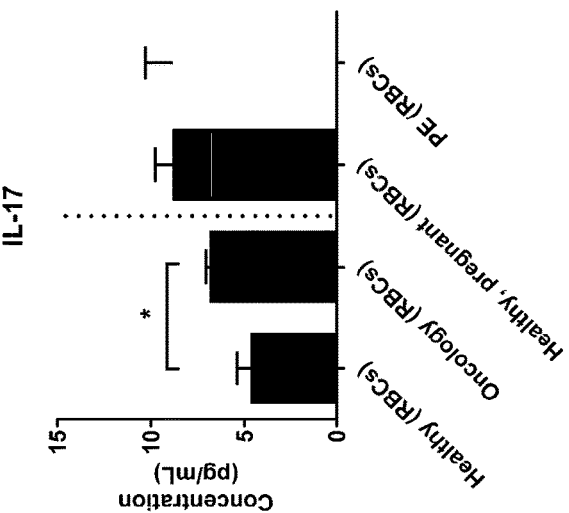
Figure 6G:
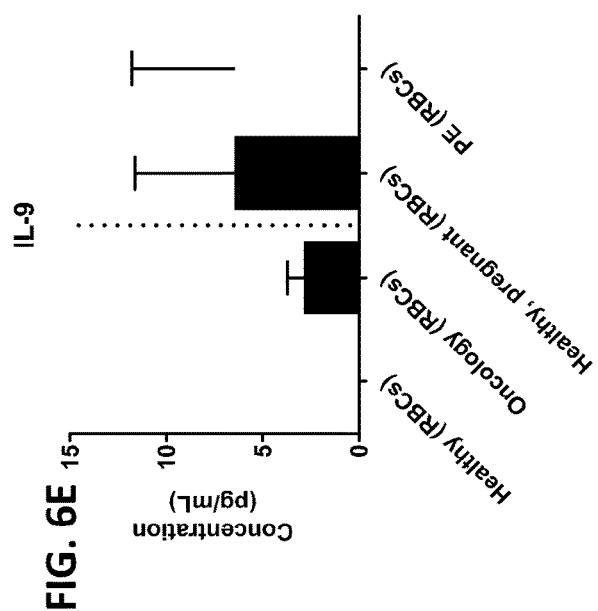
Figure 6H:
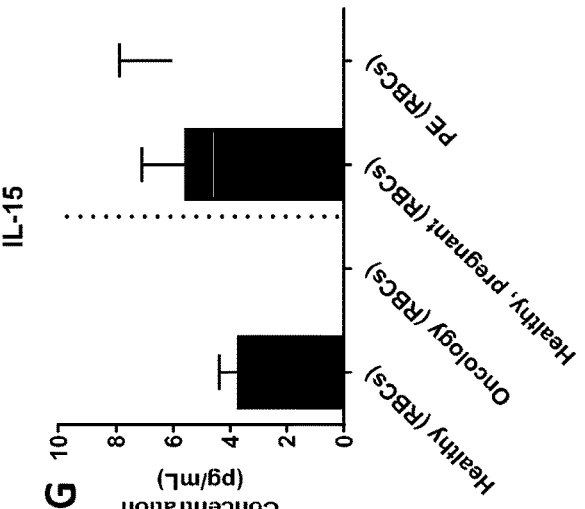
Figure 6J:
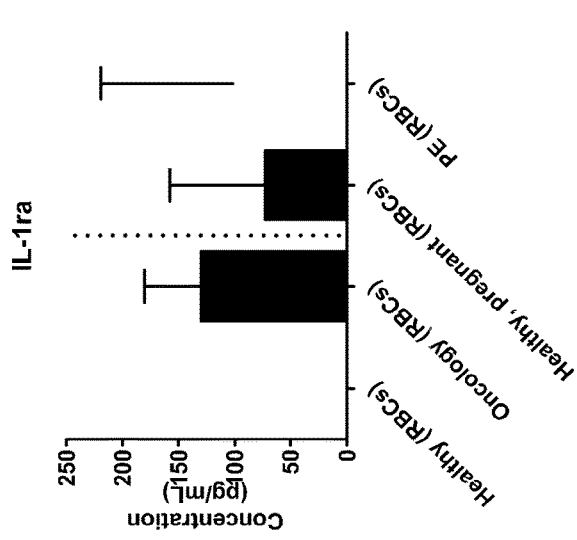
Figure 6L:
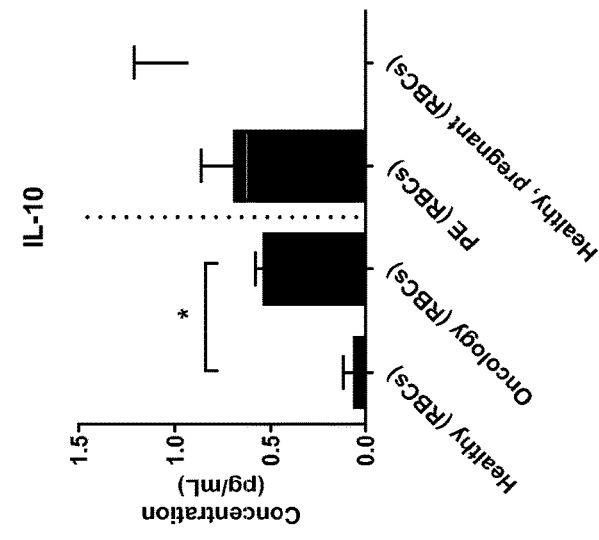
Figure 6I:
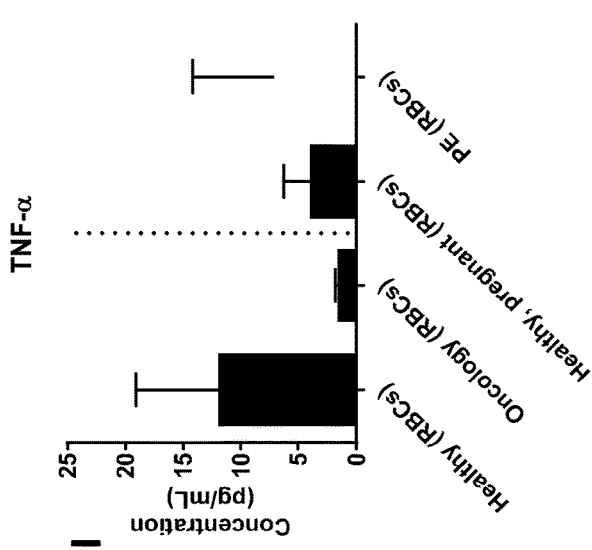
Figure 6K:
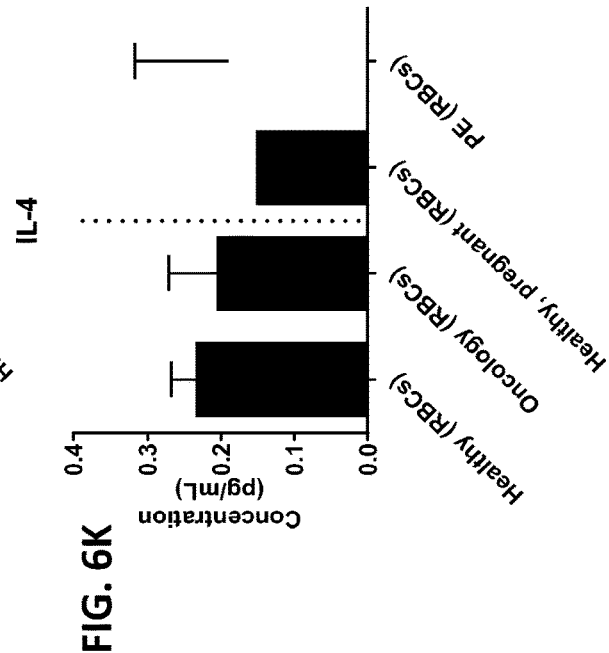
Figure 6M:
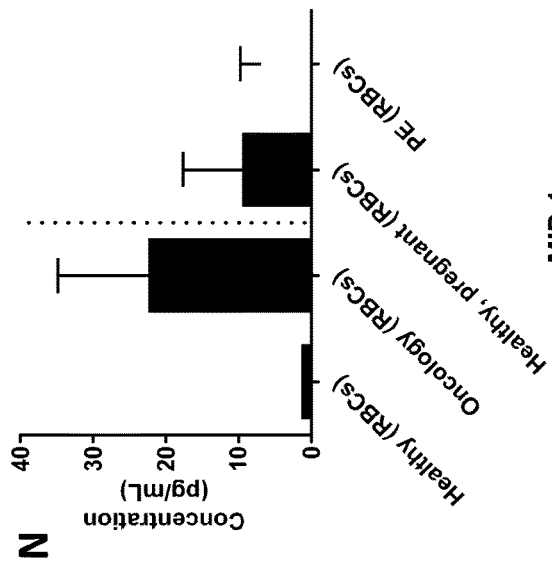
Figure 6N:
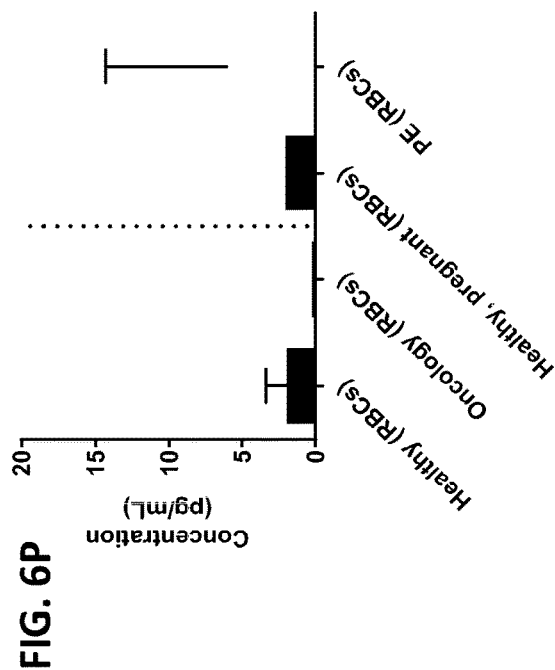
Figure 6O:
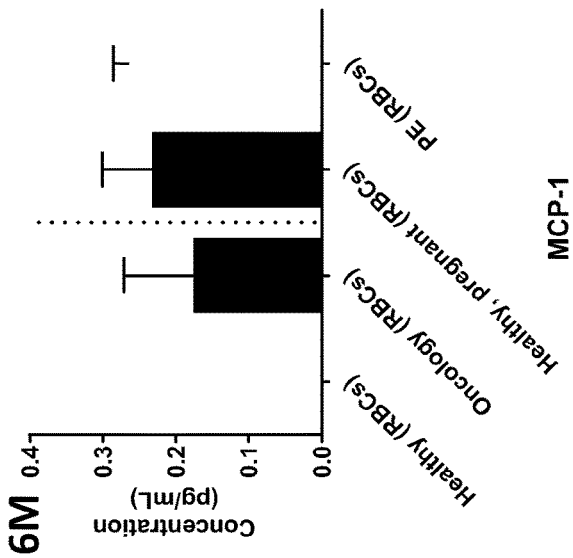
Figure 6P:
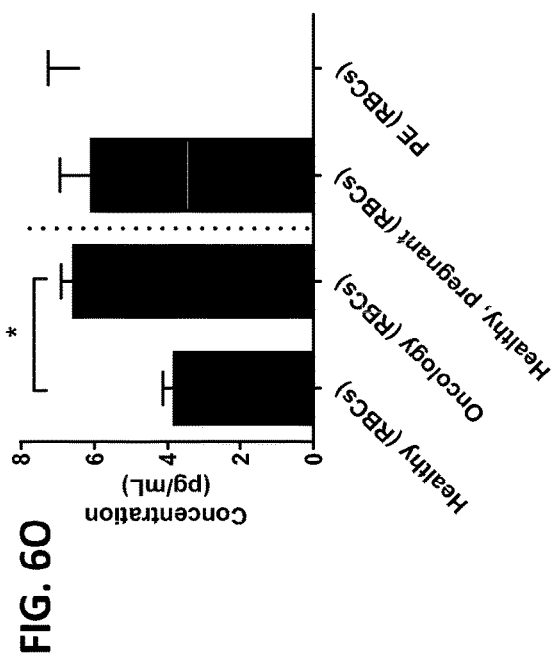
Figure 6Q:
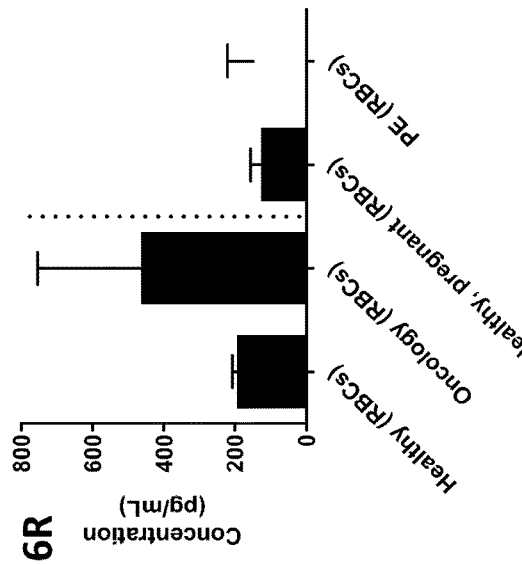
Figure 6R:
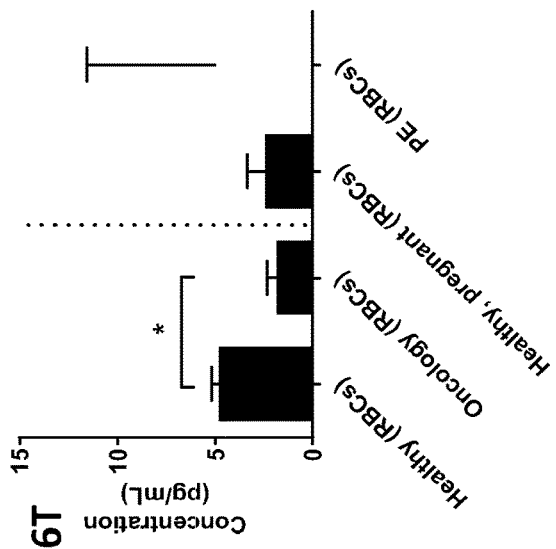
Figure 6S:
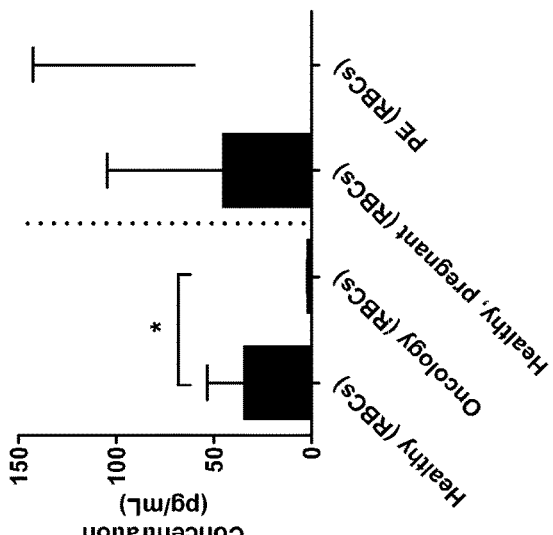
Figure 6T:
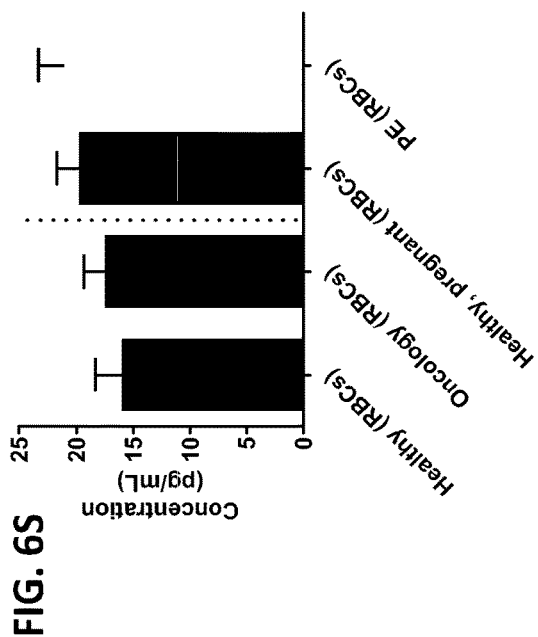
Figure 6U:
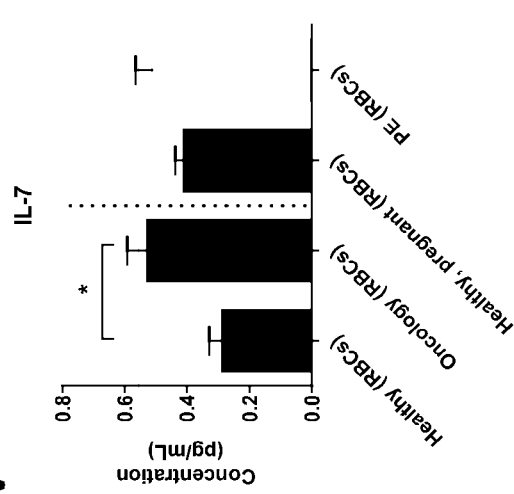
Figure 6V:
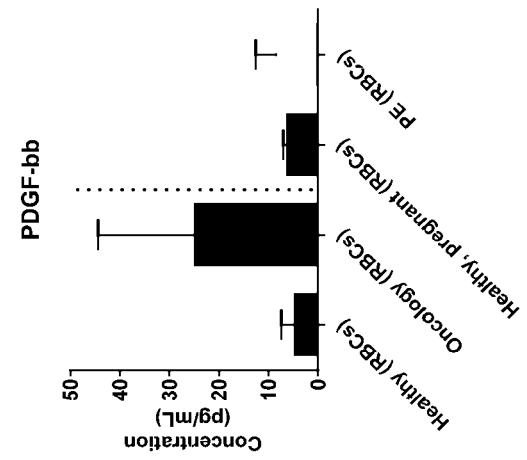
Figure 6W:
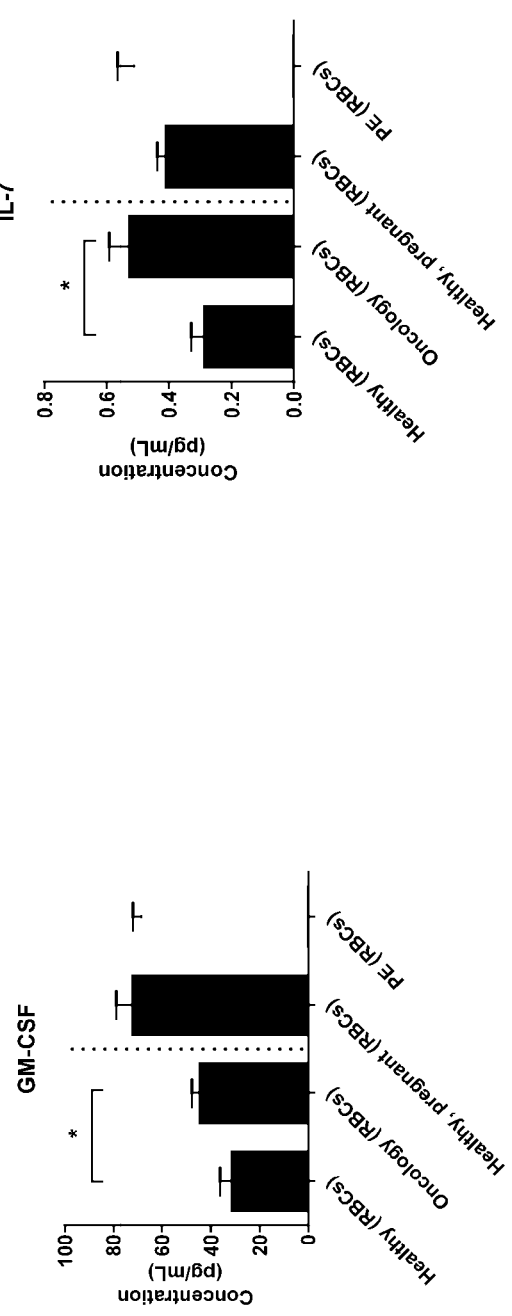
Figure 6X:
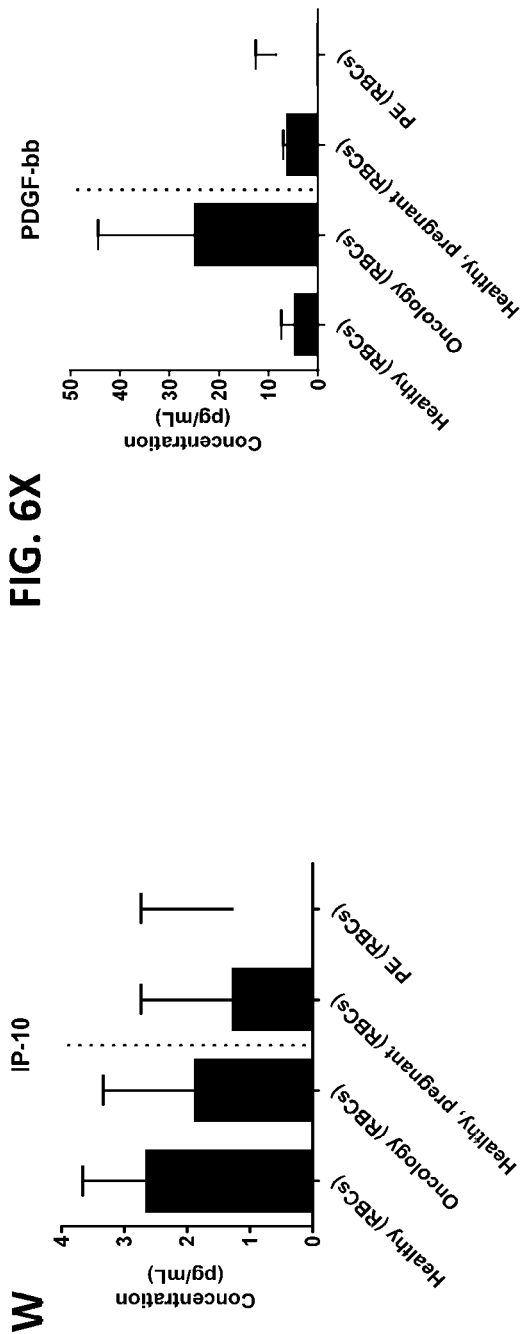
Figure 6Y:
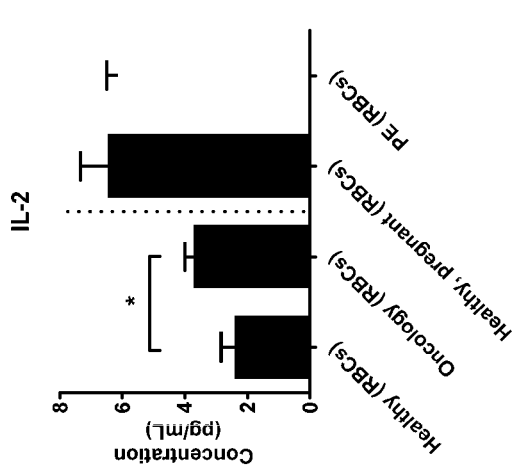
Figure 6Z:
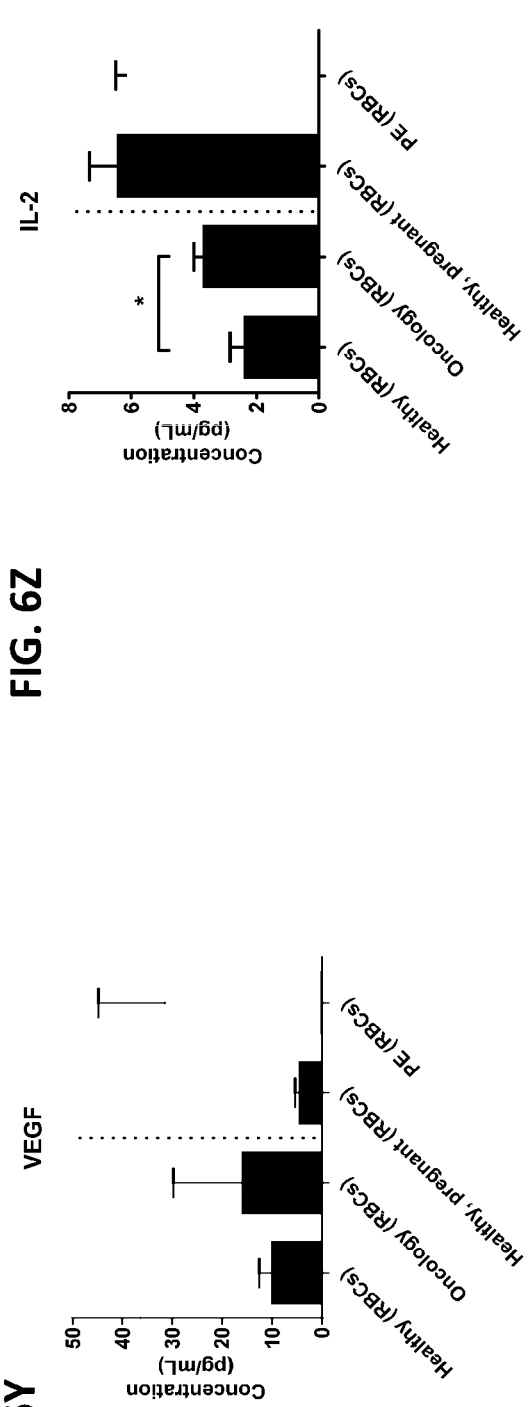
Figure 6A:
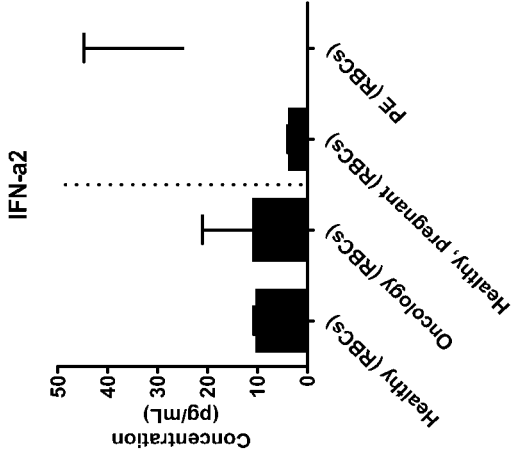
Figure 6B:
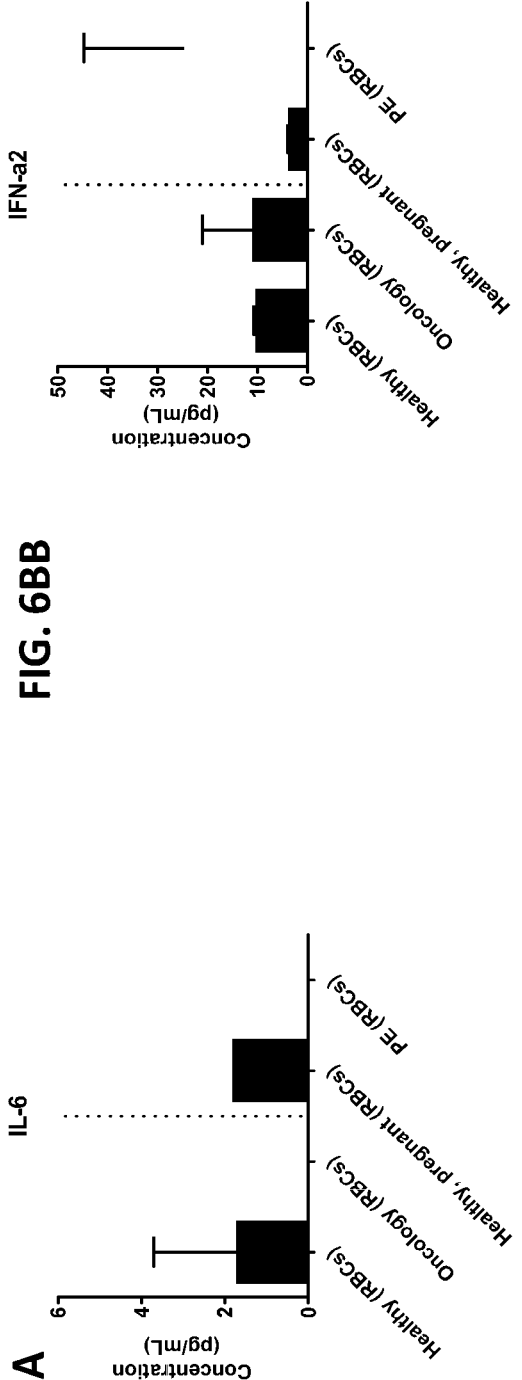
Figure 6C:
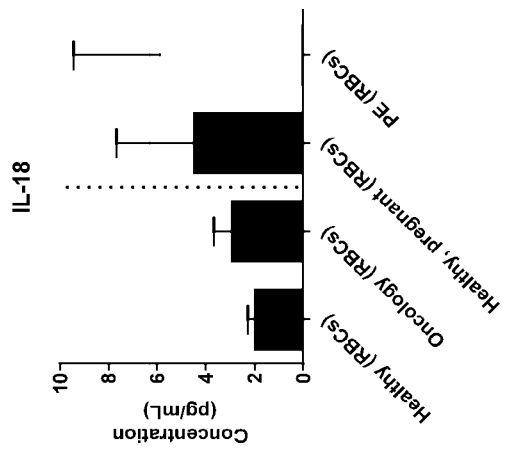
Figure 6D:
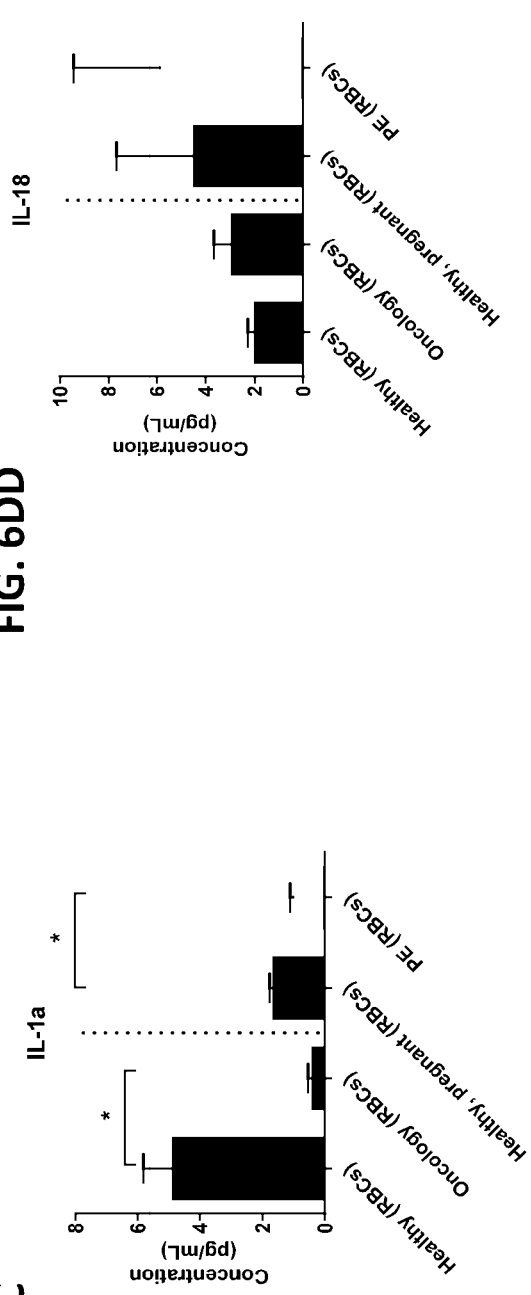
Figure 6E:
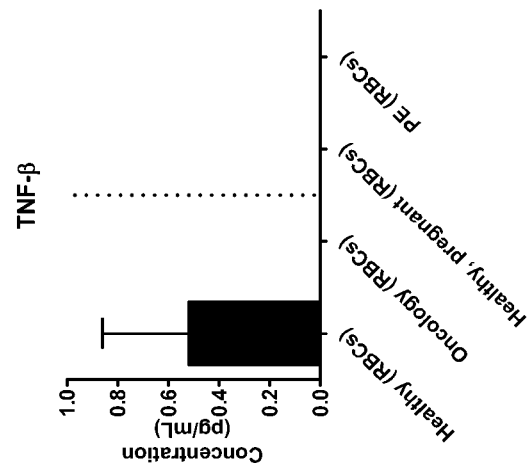
Figure 6F:
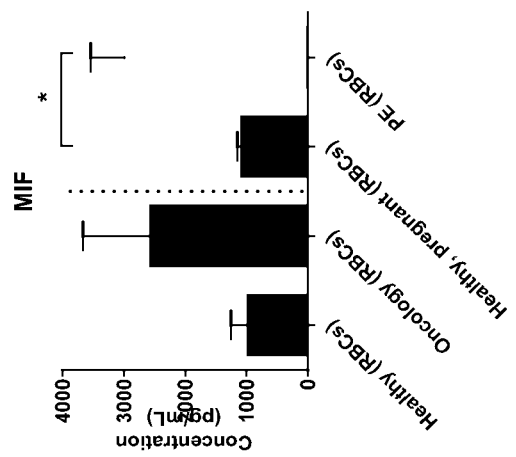
Figure 6H:
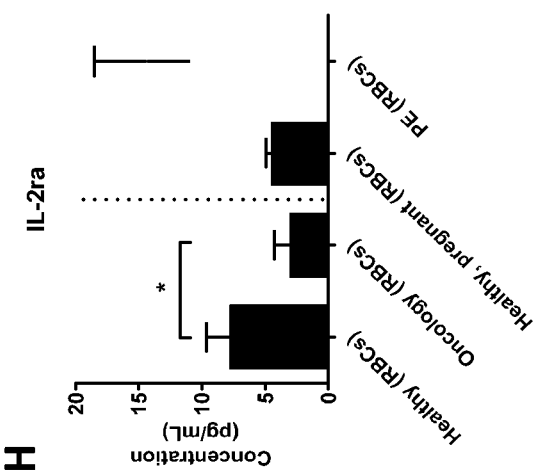
Figure 6J:
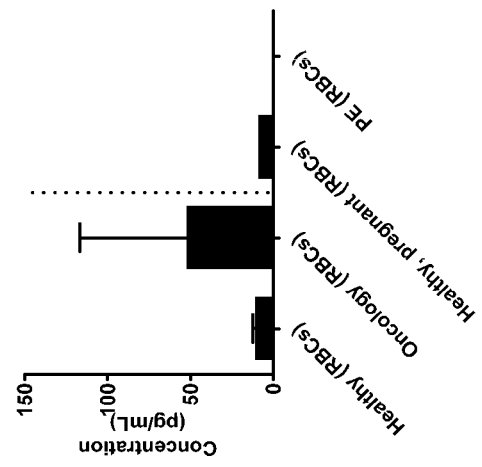
Figure 6G:
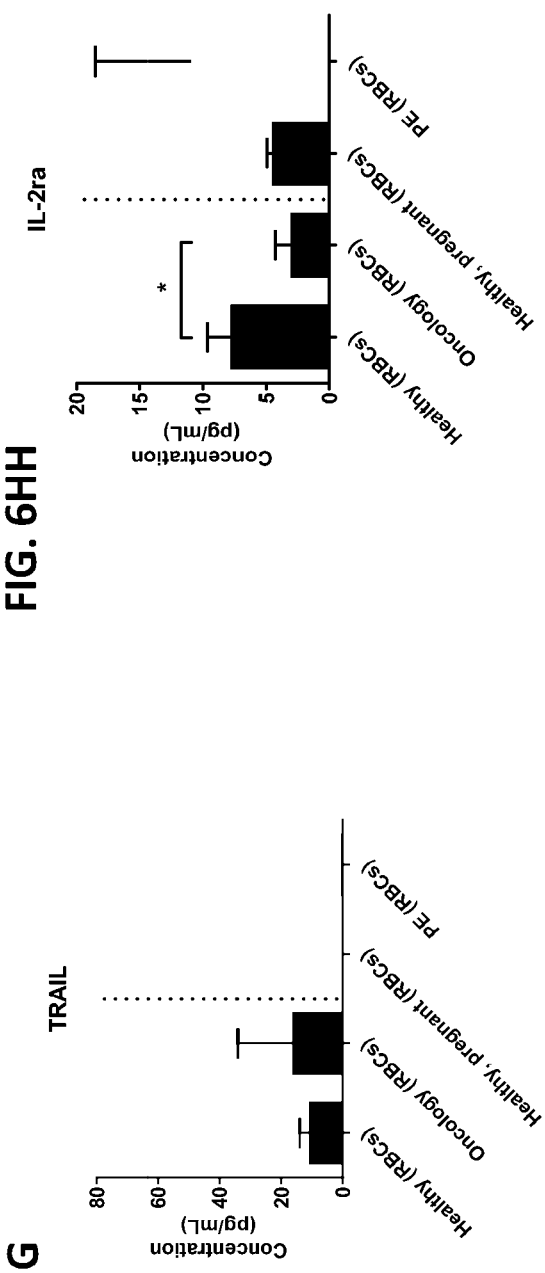
Figure 6I:
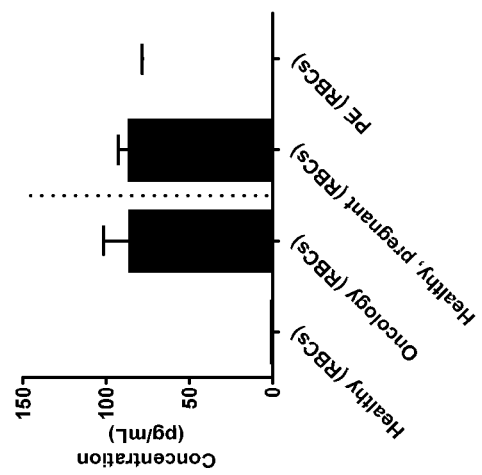
Figure 6L:
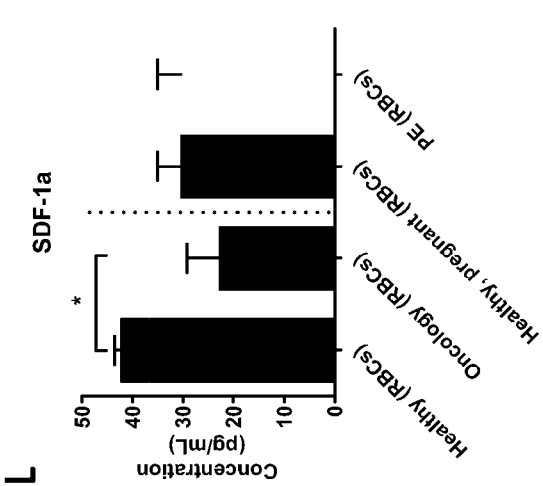
Figure 6N:
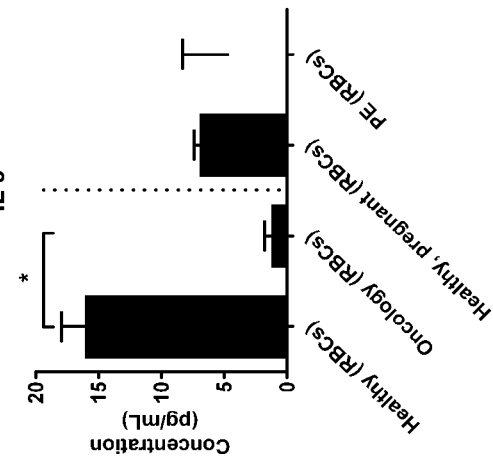
Figure 6K:
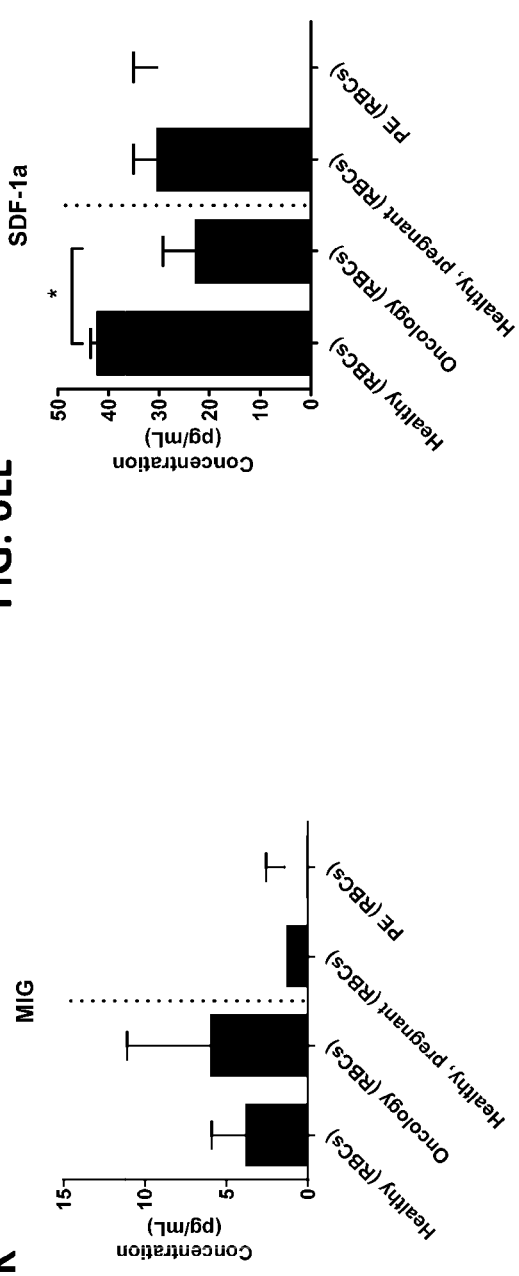
Figure 6M:
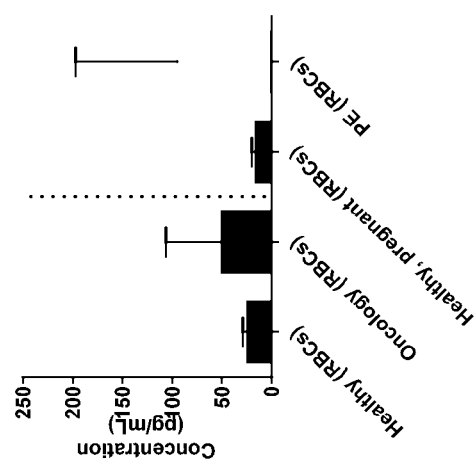
Figure 6O:
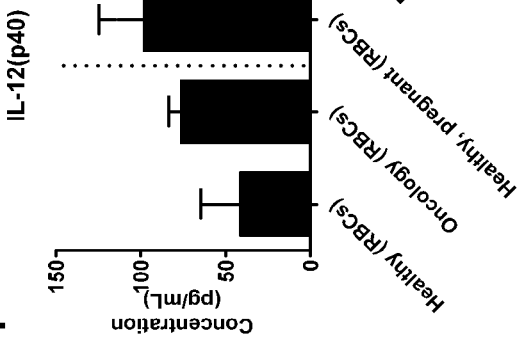
Figure 6P:
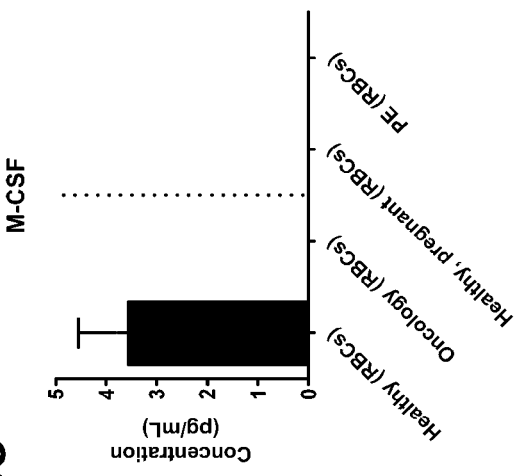
Figure 6Q:
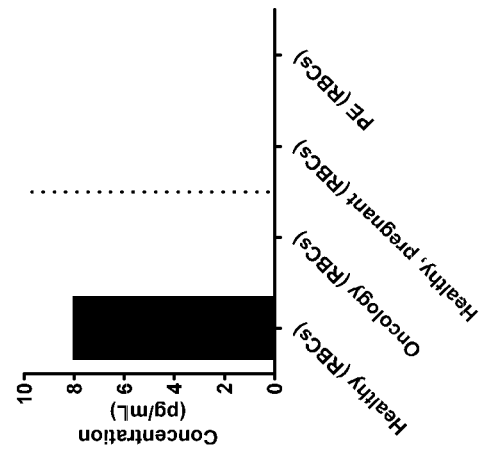
Figure 6R:
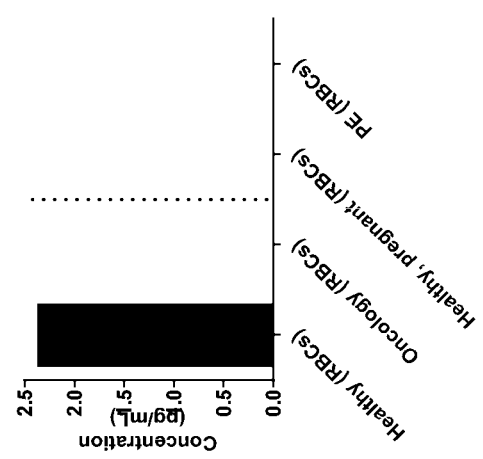

FIG. 6A-FIG. 6RR shows the concentration of the indicated proteins in the red blood cell conditioned PBS from the participant groups. The conditioned PBS was produced following red blood cell incubation for 24 hours at 37° C. Significant differences (p<0.05) were determined using Student T-tests. There were significant differences in protein levels between the healthy control individuals and individuals in the disease groups. For example, significantly less IL-1α and GCS-F was released from red blood cells isolated from people with cancer when compared to the healthy controls, and significantly more IL-12(p40) and Eotaxin was released from the red blood cells isolated from cancer patients than healthy individuals. Similarly, a few cytokines were significantly different between the healthy pregnant group and the group with preeclampsia, such as MIF The results suggested that analysis of the secretome of red blood cells may be a useful diagnostic tool for identifying and tracking biomarkers in disease. Analysis of the secretion of red blood cells (red blood cell protein release) may provide additional information regarding disease state.

Example 6. Effect of Protease Inhibitors on Proteins Present in RBCs

Whole blood was collected by venous collection into EDTA vacutainers. Plasma was collected after centrifugation and cells were isolated using either FACS or dextran sedimentation as described above. Isolated cells and whole blood were pelleted by centrifugation (2000 g, 10 minutes) and were resuspended to set concentrations. Samples were frozen at −80° C., and subjected 3 times to freeze/thaw cycles to lyse the cells. Samples were analyzed on a Hu 27-plex BioPlex. In addition, proteins released or secreted by RBCs were analyzed. Whole blood was collected by venous collection into EDTA vacutainers and RBCs isolated by dextran sedimentation as described previously. Isolated RBCs were aliquoted to 20 million cells in 100 uL of PBS or PBS+protease inhibitors (PI) (1×) and cells were incubated at 37° C. with 5% CO2 for 24 hours. After incubation, supernatant and cells were separated by centrifugation, samples were frozen at −80° C., and subjected to 3 times freeze/thaw cycles to lyse the cells. The samples were analyzed on Hu 27-plex BioPlex.

The addition of protease inhibitors during RBCs culture altered protein release or secretion (24 hours at 37° C.).

Incubation conditions were as follows:
1. RBCs+PBS (20 million RBCs in 100 uL PBS)
2. RBCs+PBS+protease inhibitors (PI) (20 million RBCs in 100 uL PBS+PI)

Figure 7B:
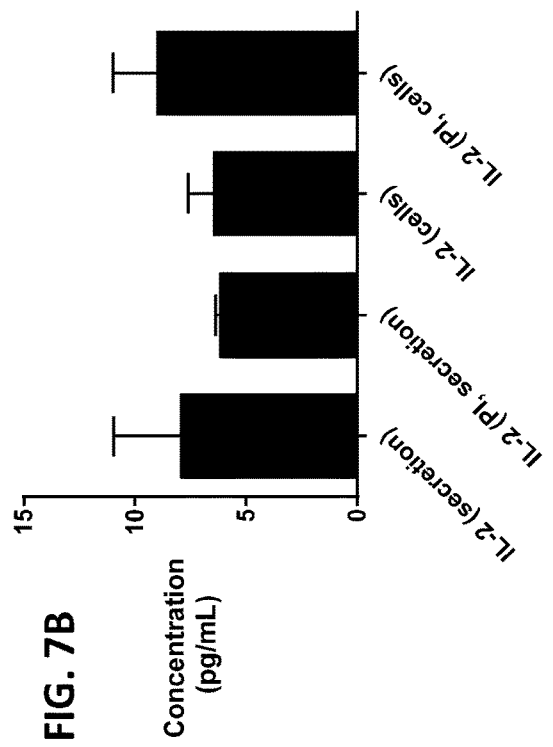
FIG. 7A-7Z is a series of graphs showing the effect of protease inhibitors (PI) on the concentration of proteins released from RBCs (black columns) and the concentration of proteins remaining in the cells after incubation (grey columns).
Figure 7D:
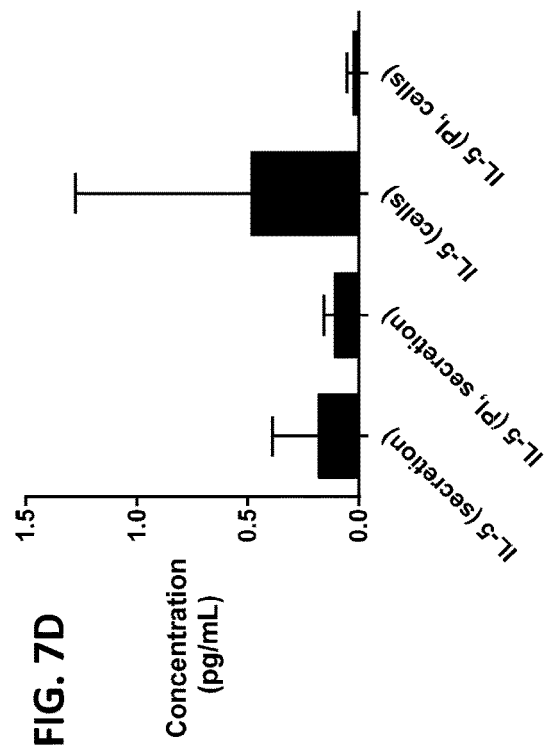
Figure 7A:
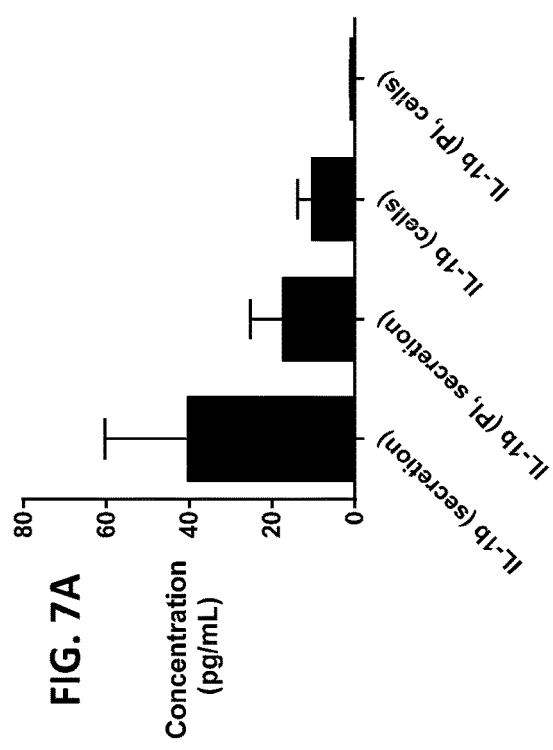
Figure 7C:
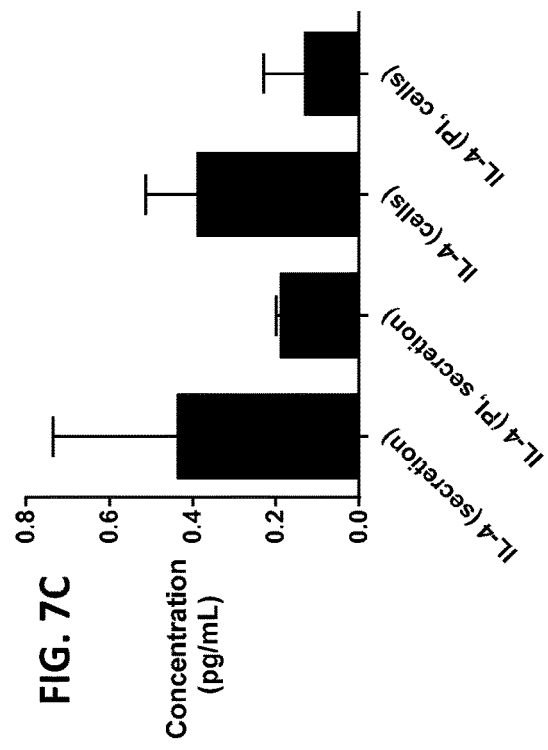
Figure 7E:
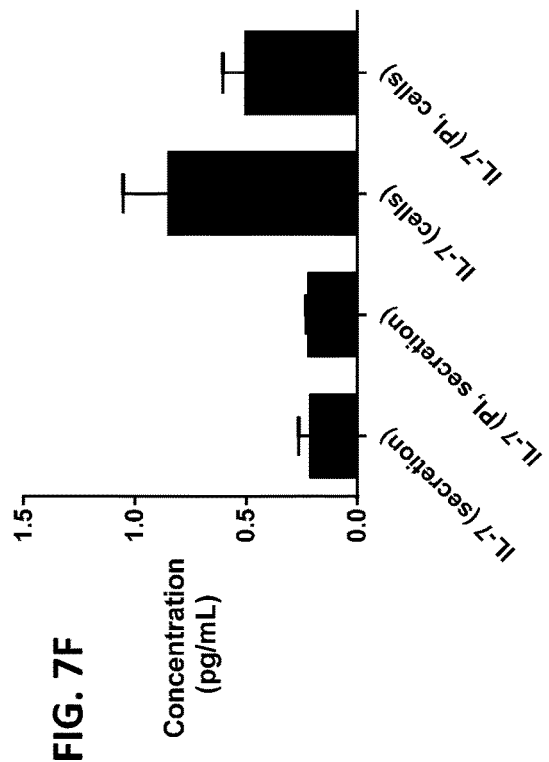
Figure 7F:
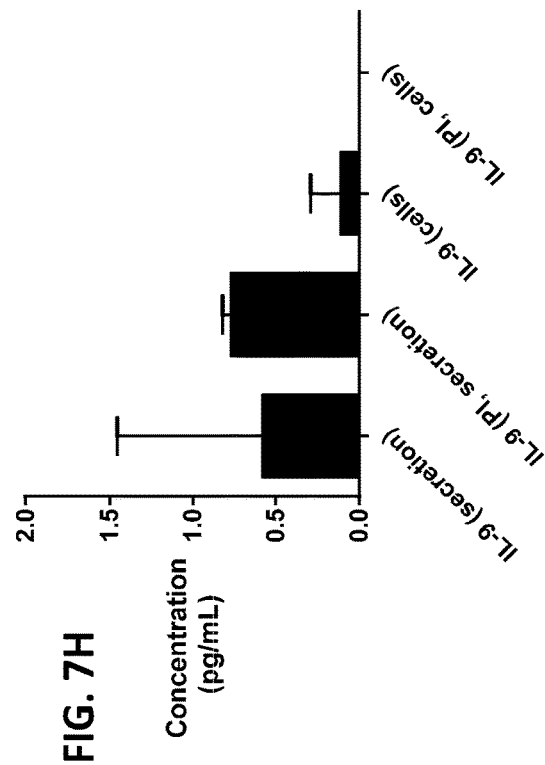
Figure 7G:
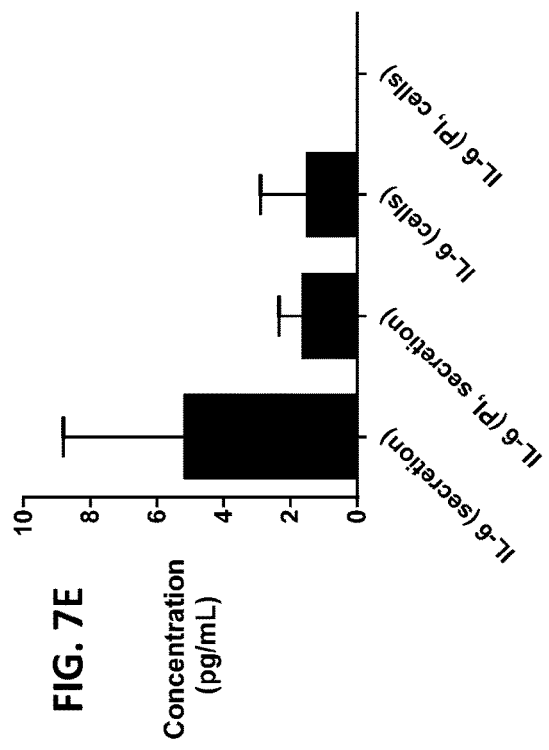
Figure 7H:
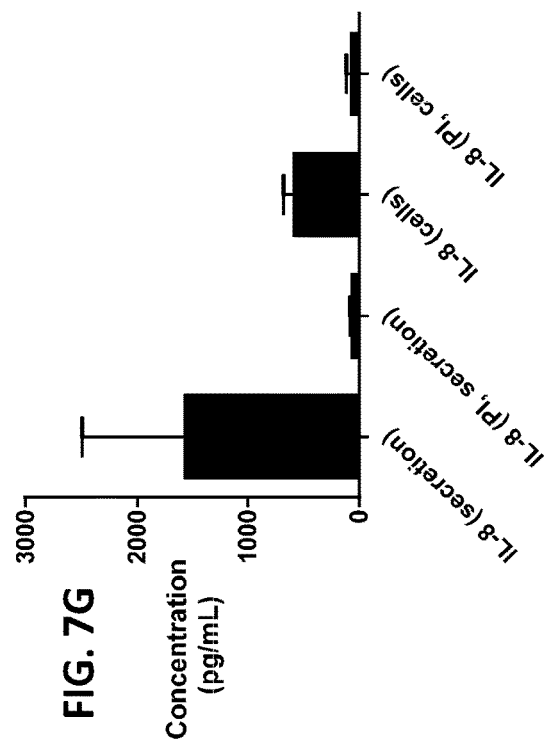
Figure 7J:
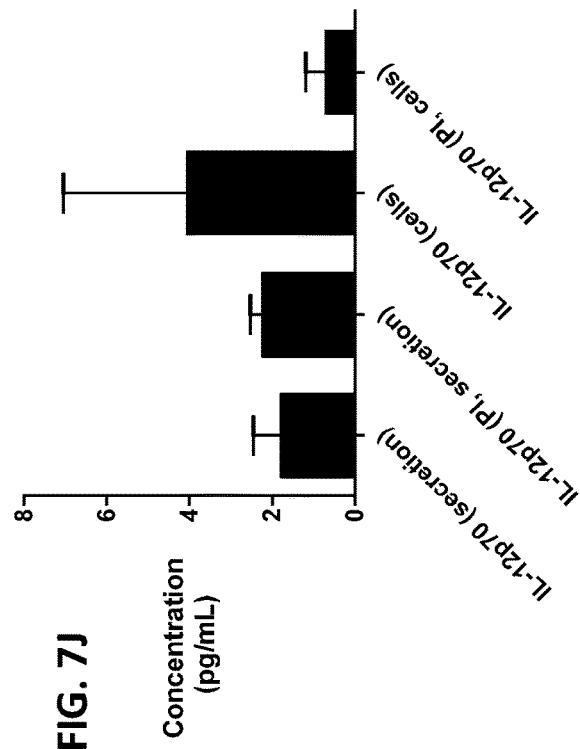
Figure 7L:
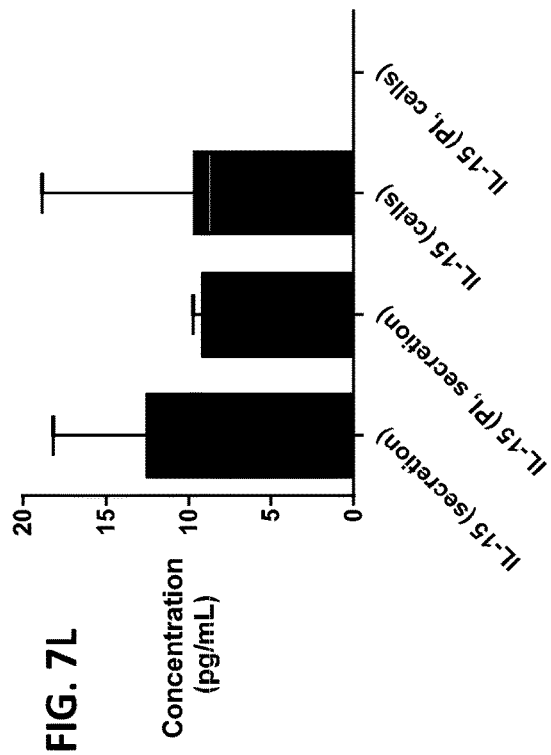
Figure 7I:
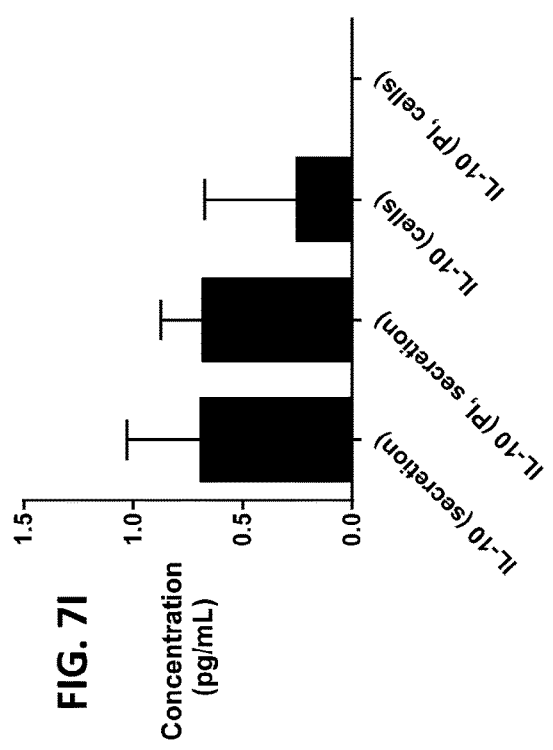
Figure 7K:
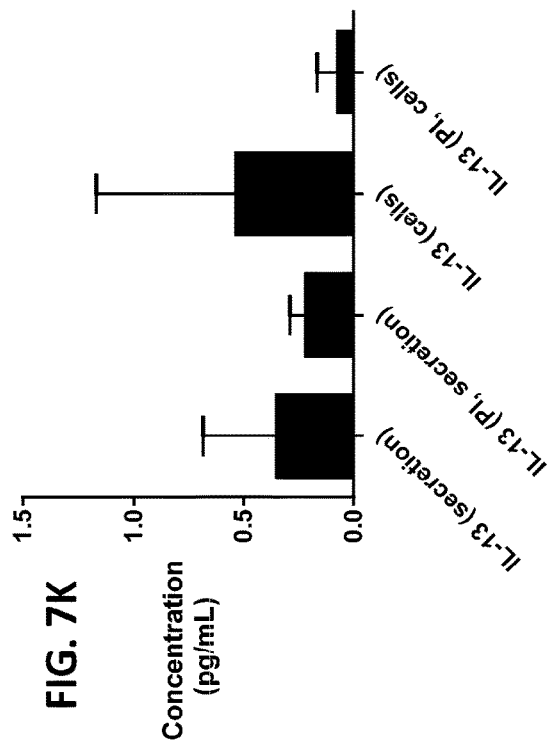
Figure 7M:
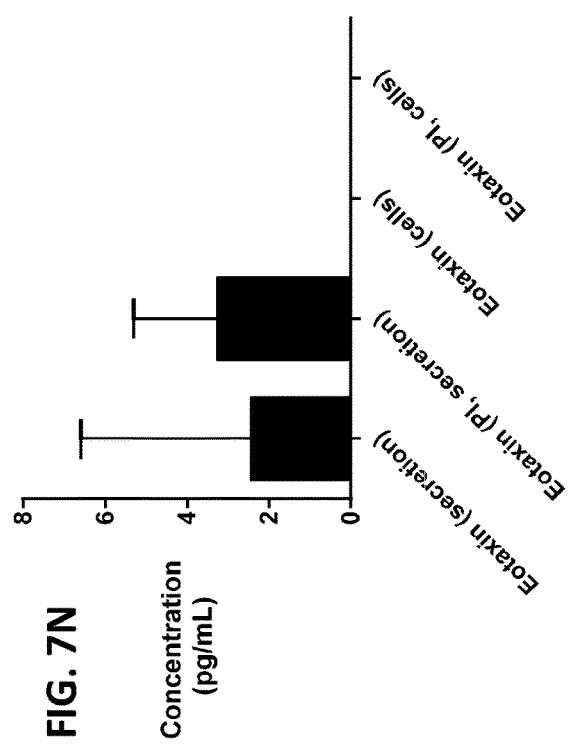
Figure 7N:
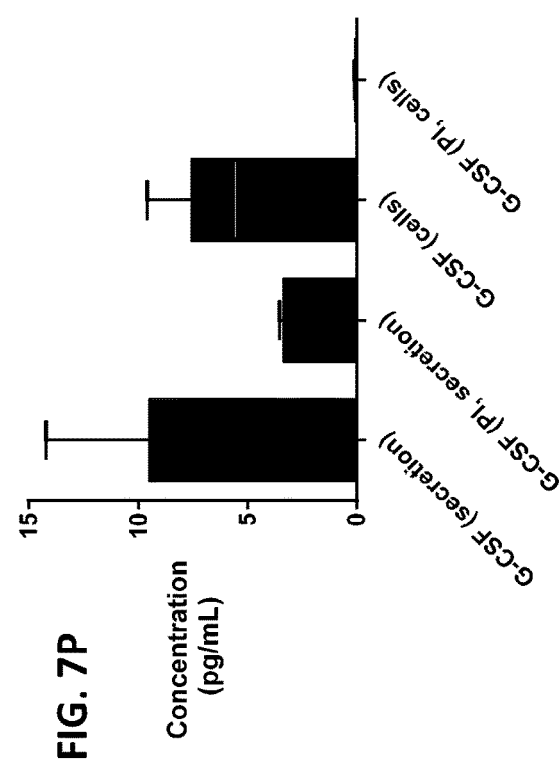
Figure 7O:
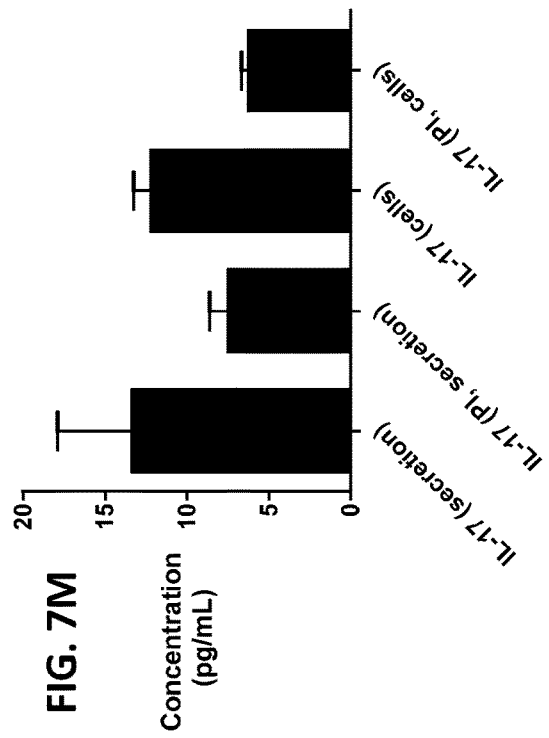
Figure 7P:
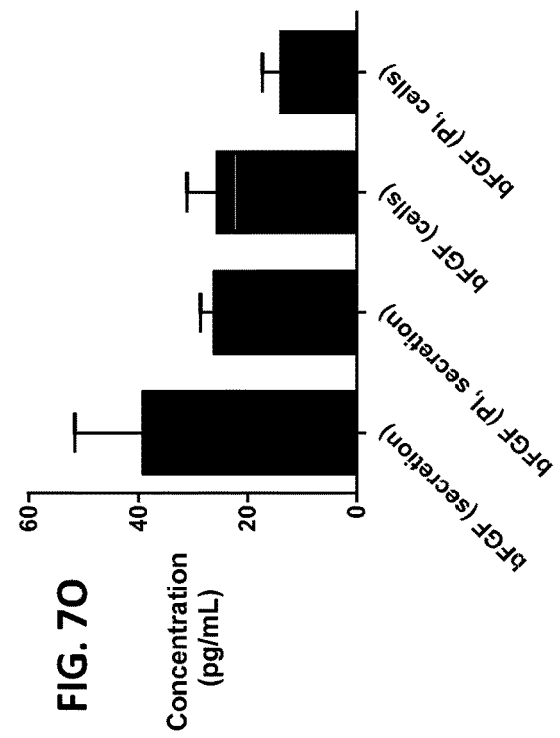
Figure 7V:
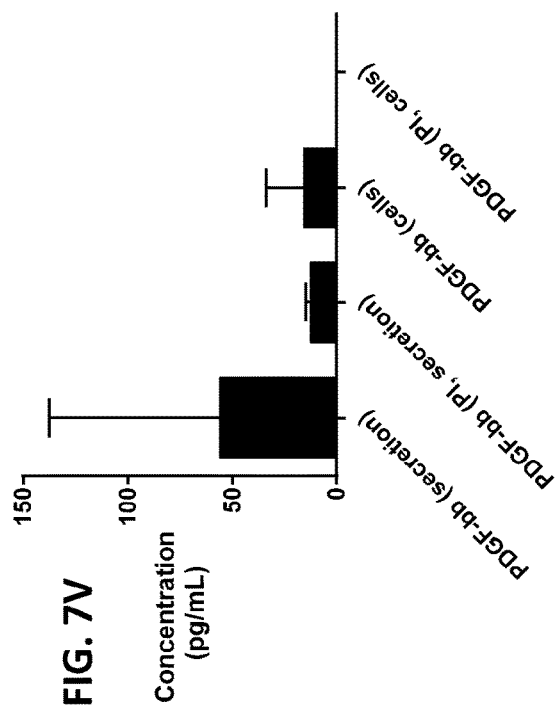
Figure 7X:
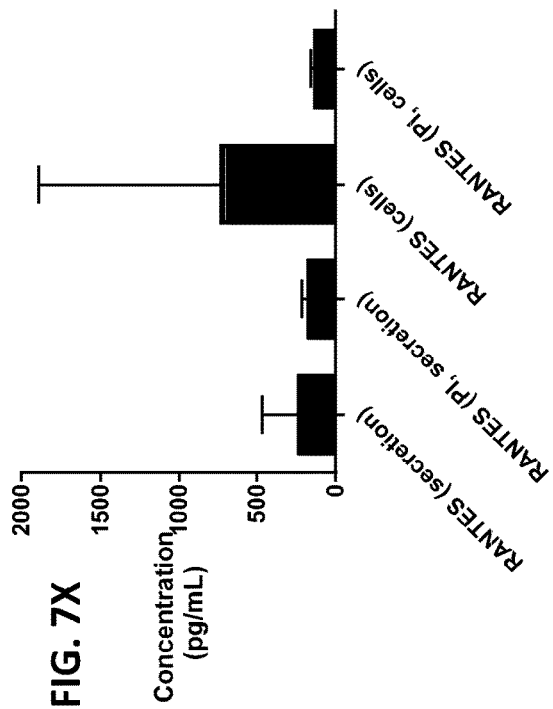
Figure 7U:
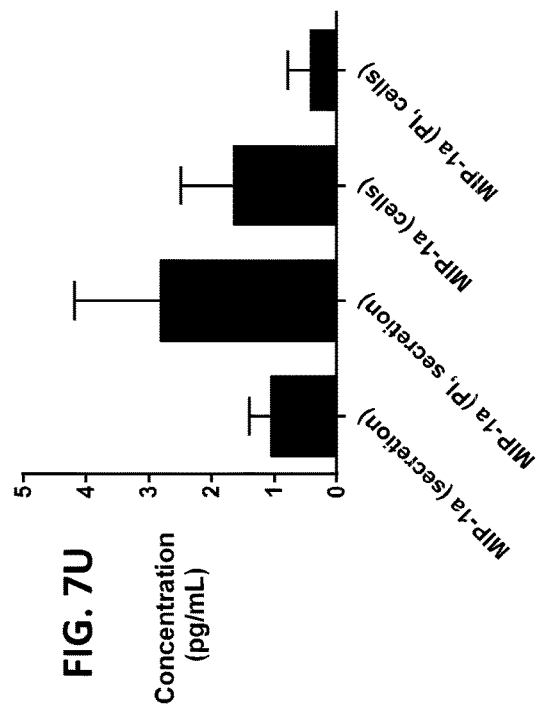
Figure 7W:
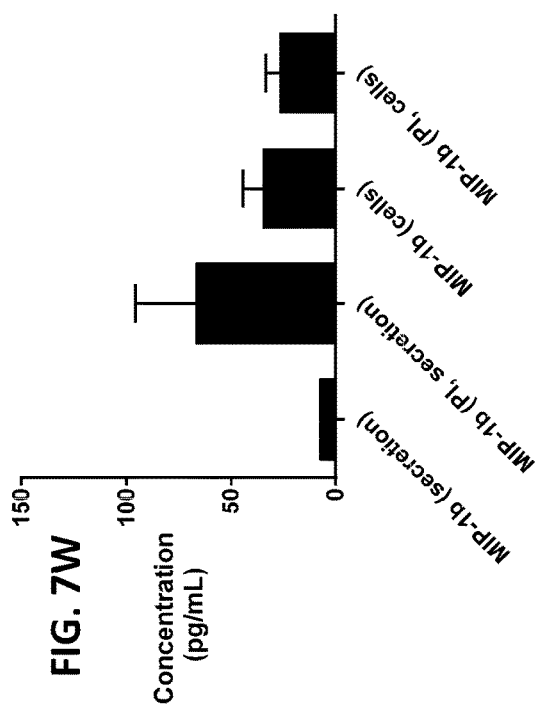
Figure 7Z:
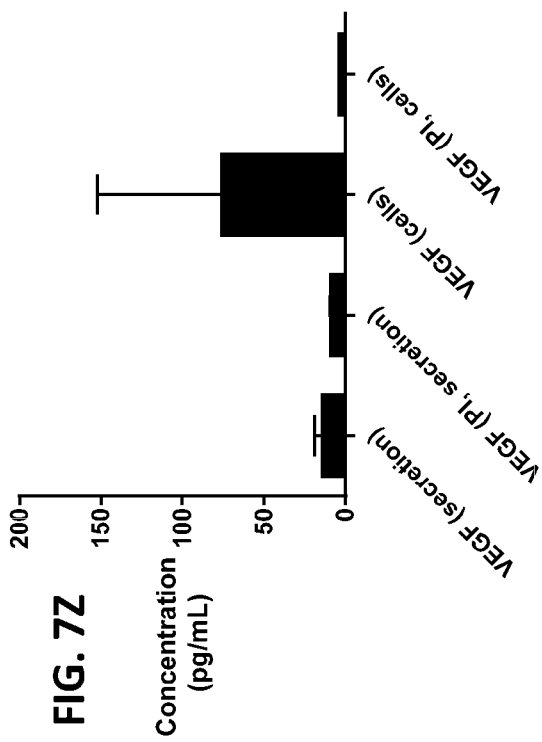
Figure 7Y:
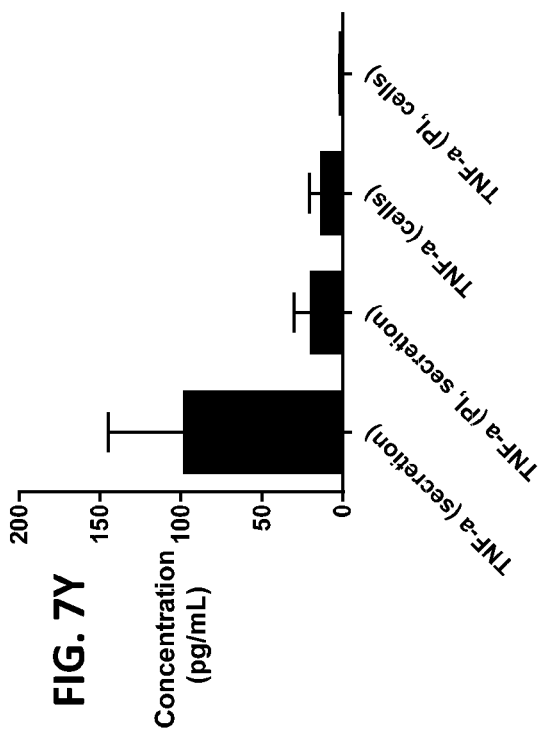

The series of graphs shown in FIG. 7A-7Z depict the effect of protease inhibitors (PI) on the concentration of proteins released or secreted from RBCs (black columns) and the concentration of proteins remaining in the cells after release or secretion (grey columns). Inclusion of protease inhibitors in the culture solution typically resulted in a lower detectable concentration for both release or secretion and cell lysate, although there were some exceptions (i.e., MIP-1b). Data presented as mean±standard deviation (SD).

Example 7. Effect of Protease Inhibitors on Protein Levels in RBCs from Healthy Individuals Versus Individuals Having Preeclampsia or Cancer The levels of proteins released by red blood cells were evaluated in red blood cells from healthy individuals and from those with a disease or disorder. Whole blood was collected from four groups of people including: 1) healthy volunteers, 2) healthy, pregnant women, 3) pregnant women with pre-eclampsia, and 4) oncology patients (Table 3).

TABLE 3

Participant summary

| Subject | Condition | Relevant information |
|---|---|---|
| OBS-101 | Lymphoma | Chemotherapy and radiation therapy |
| OBS-102 | Lymphoma | Chemotherapy |
| OBS-103 | Cancer (specific type unknown) | Chemotherapy |
| PE-001 | Preeclampsia | $3^{rd}$ trimester |
| PE-002 | Preeclampsia | $3^{rd}$ trimester |
| PE-003 | Preeclampsia | $3^{rd}$ trimester |

The healthy, pregnant control samples were matched with the preeclampsia samples according to gestation. Blood was collected from each volunteer by venipuncture (n≥3) directly into EDTA vacutainers ($k_2$EDTA vacutainers, BD Biosciences). The fractions of blood were collected and processed at room temperature within 4 hours of collection. For multiplex analysis (BioPlex analysis) the samples were stored at −80° C. and were subjected to 3 freeze-thaw cycles at −80° C. to ensure complete cellular lysis prior to analysis.

Whole blood was centrifuged (1500 g, 10 minutes) and the upper plasma layer was discarded. Then, red blood cells were isolated using dextran sedimentation as follows. Whole blood was centrifuged (1500 g, 10 minutes) and the upper plasma layer was discarded. The remaining cell pellet was resuspended in an equal volume of sodium chloride (0.15 M). Dextran (6% w/v in 0.15 M sodium chloride) was then added to this cellular suspension at a 1:4 ratio (dextran:cell suspension). This solution was left at room temperature for 30 minutes for red blood cell sedimentation to the bottom of the tube. After this time the upper white blood cell rich layer was discarded and the lower red blood cell fraction was isolated. The red blood cell fraction was washed twice in phosphate buffered saline (PBS, 500 g, 5 minutes) and the remaining red blood cell pellet was counted (Coulter Act Diff, Beckman Coulter). The red blood cells were then diluted to 400 million cells/mL in PBS and were incubated at 37° C. and 5% $CO_2$ for 24 hours.

In one instance, the whole blood sample was divided into two aliquots and one aliquot was treated with a protease inhibitor cocktail (1×), mini cOmplete protease inhibitor cocktail tablets, Roche) during the overnight incubation for each group (healthy volunteers, healthy pregnant, pre-eclampsia, oncology) as indicated in Table 4. The red blood cells were then isolated from the whole blood using dextran sedimentation. In another instance, red blood cells were first isolated from whole blood by dextran sedimentation and the red blood cell fraction divided into two aliquots and treated with a protease inhibitor cocktail (1×, mini cOmplete protease inhibitor cocktail tablets, Roche) during the overnight incubation for each group (healthy volunteers, healthy pregnant, pre-eclampsia, oncology) as indicated in Table 4.

TABLE 4

| Experimental conditions | | |
|---|---|---|
| RBCs (200 million cells per mL) | PBS | Protease Inhibitors |
| Condition 1 (none) | ✓ | x |
| Condition 2 (PI) | ✓ | ✓ |

After incubation, the resulting conditioned PBS was isolated by centrifugation (500 g, 5 minutes). The samples were stored at −80° C., and underwent 3 freeze/thaw cycles before analysis. The conditioned PBS samples were then analysed on the multiplex cytokine assays. Two multiplex assays were utilised. The first was the 27-plex human cytokine panel that assays for FGF basic, Eotaxin, G-CSF, GM-CSF, IFN-γ, IL-1β, IL-1ra, IL-2, IL-4, IL-5, IL-6, IL-7, IL-8, IL-9, IL-10, IL-12(p70), IL-13, IL-15, IL-17, IP-10, MCP-1, MIP-1α, MIP-1β, PDGF-BB, RANTES, TNF-α, and VEGF, and the second was the 21-plex human cytokine panel that assays for IL-1α, IL-2Ra, IL-3, IL-12, IL-16, IL-18, CTACK, GRO-α, HGF, IFN-α2, LIF, MCP-3, M-CSF, MIF, MIG, β-NGF, SCF, SCGF-β, SDF-1α, TNF-β, TRAIL (Bio-Plex Pro 27-plex and 21-plex, Bio-Rad). The assays were performed according to the manufacturer's instructions using an automated magnetic wash station (BioPlex Pro II, Bio-Rad) for the washing steps. The assays were run on the Luminex® 200™ system (Bio-Rad) and fluorescent values were collected. The calibration curve for each cytokine was analysed with 5 parametric logistic curve regression using BioPlex manager software (ver. 5.0, Bio-Rad, USA).

Figure 8A:
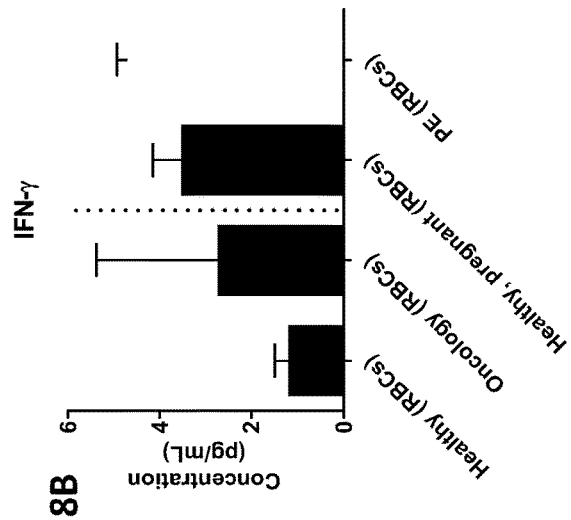
FIG. 8A-8ZZ is a series of graphs showing the effect of protease inhibitors (PI) on the concentration of proteins from red blood cells isolated from healthy individuals, healthy pregnant women, pregnant women with preeclampsia, and oncology patients.
Figure 8B:
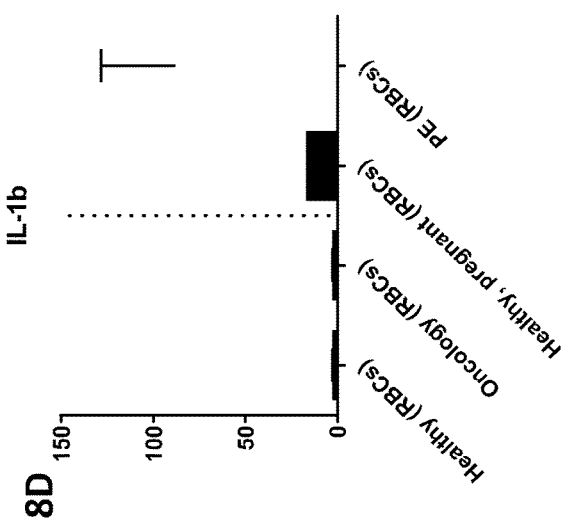
Figure 8C:
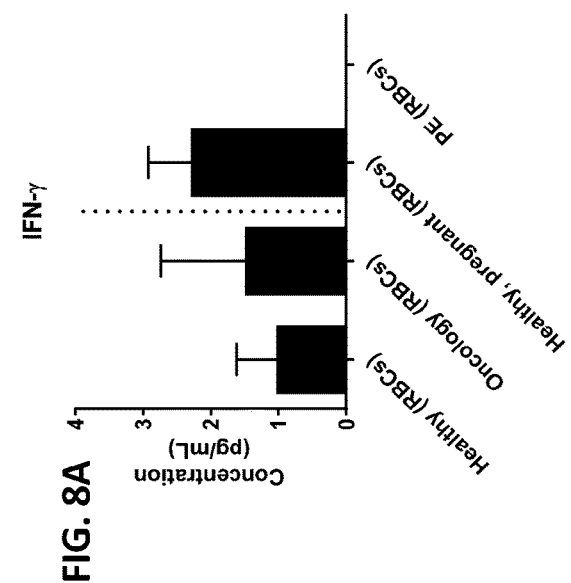
Figure 8D:
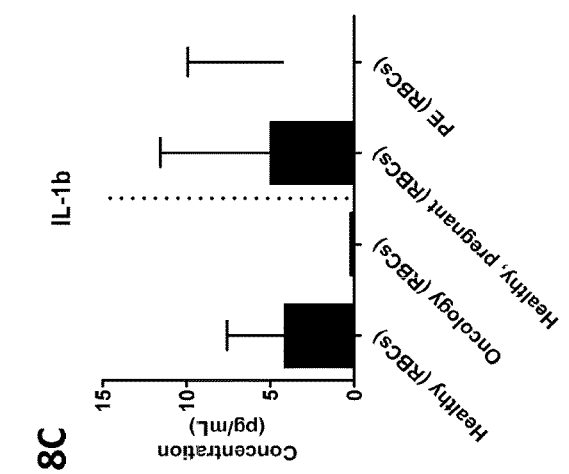
Figure 8E:
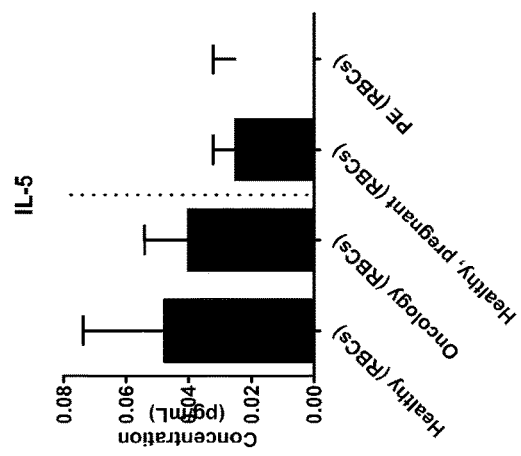
Figure 8F:
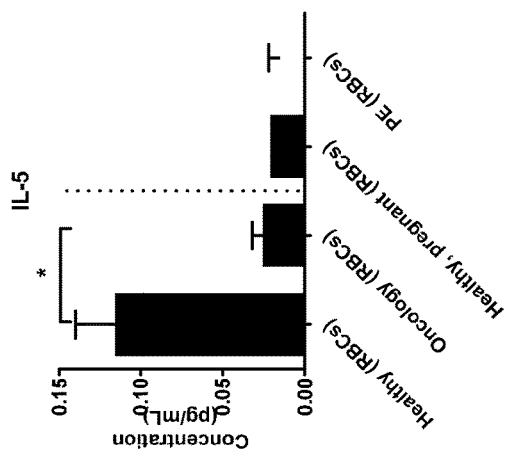
Figure 8G:
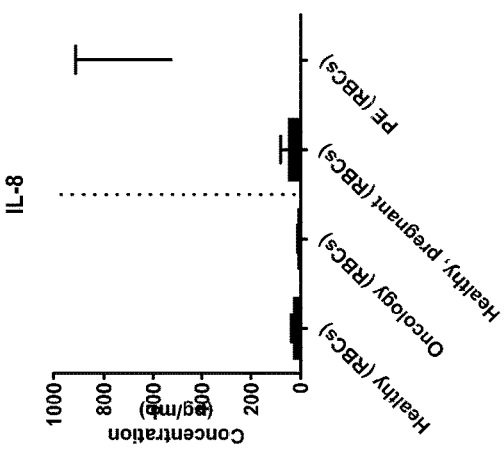
Figure 8H:
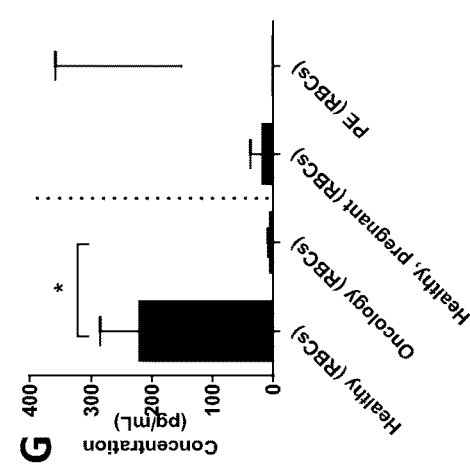
Figure 8J:
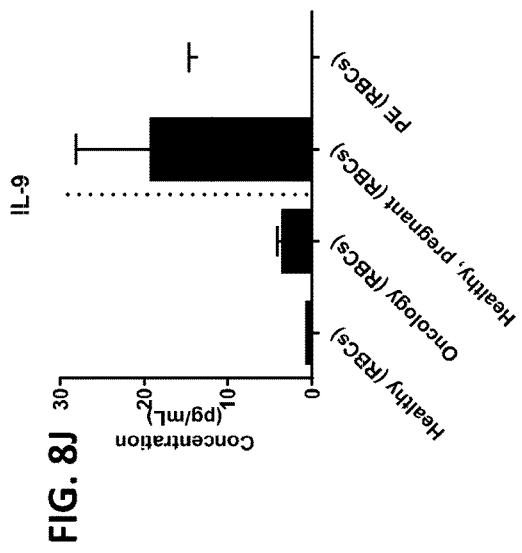
Figure 8L:
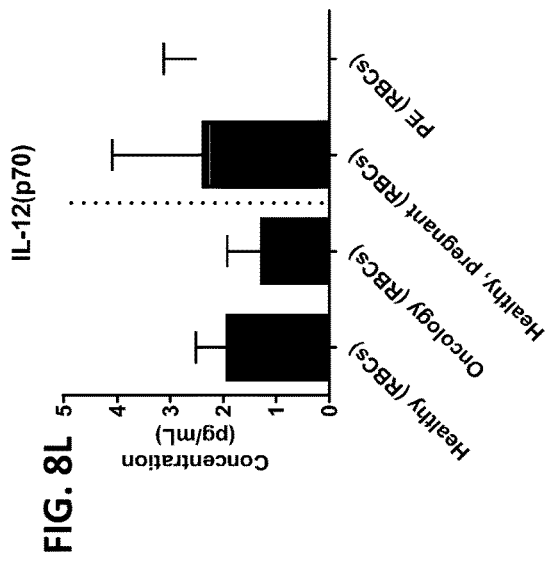
Figure 8I:
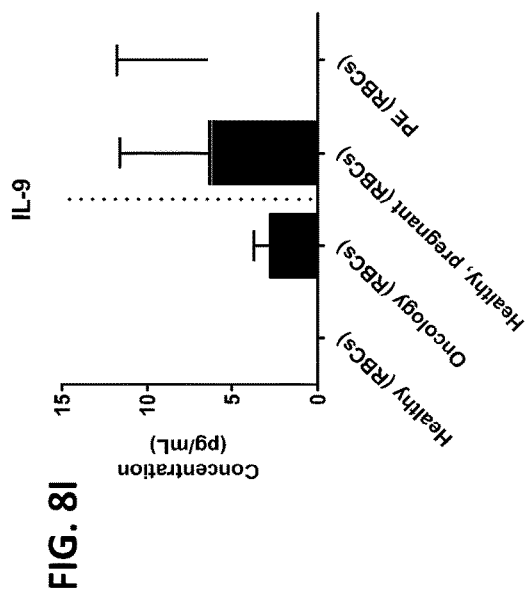
Figure 8K:
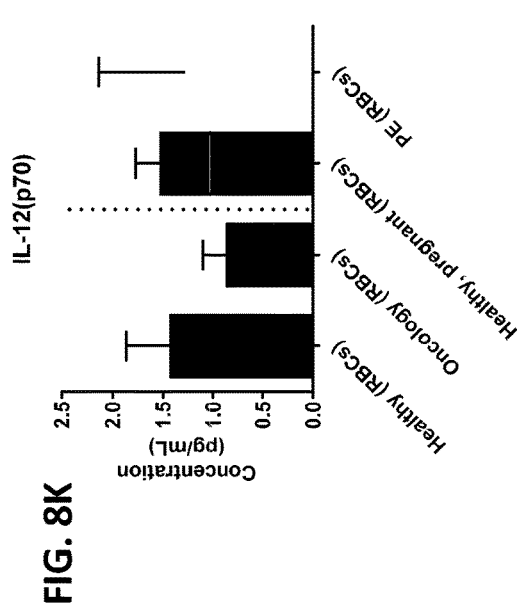
Figure 8M:
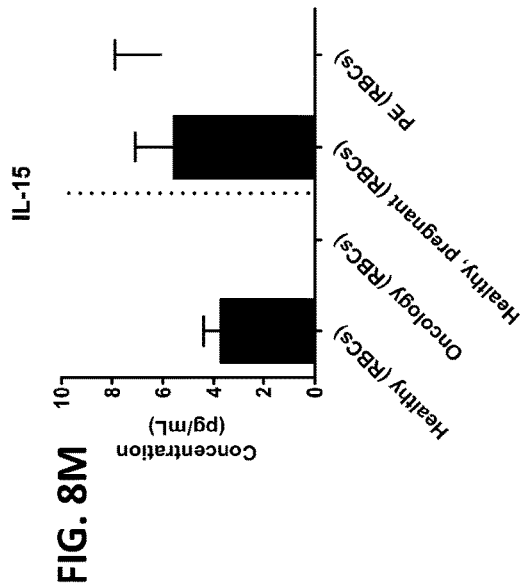
Figure 8N:
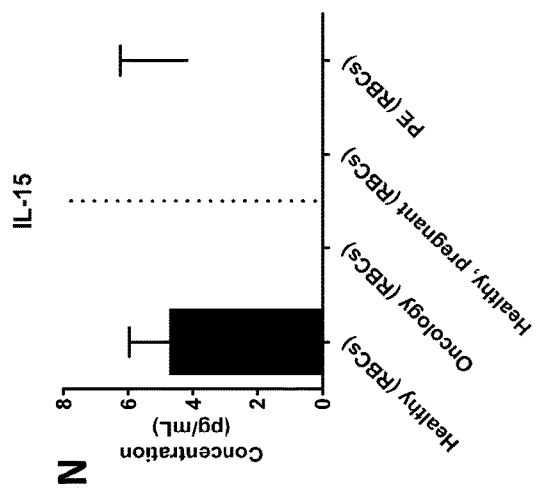
Figure 8O:
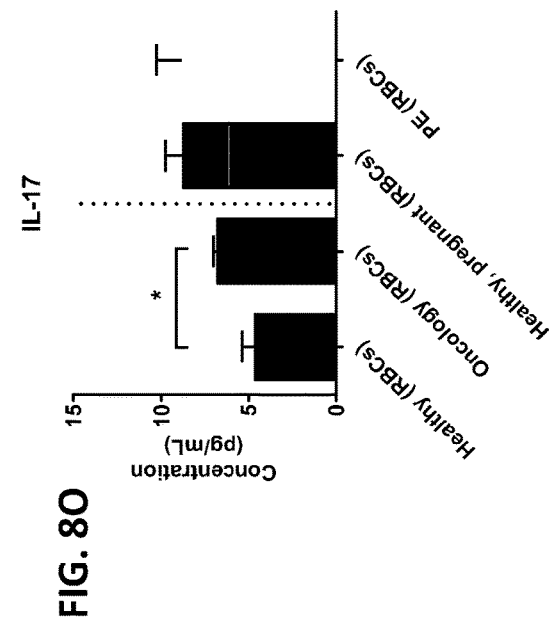
Figure 8P:
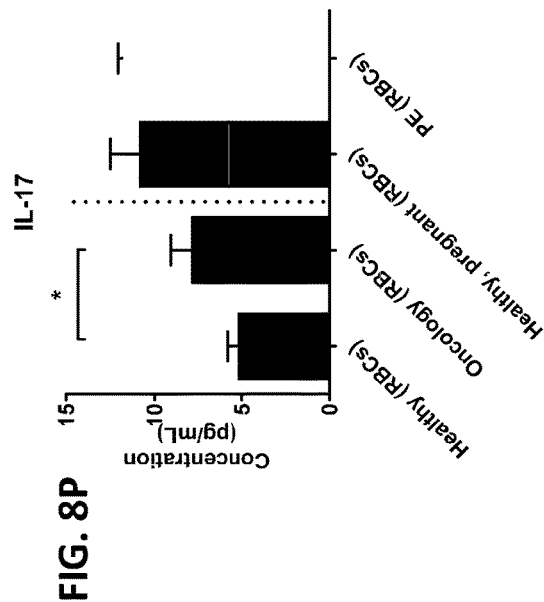
Figure 8Q:
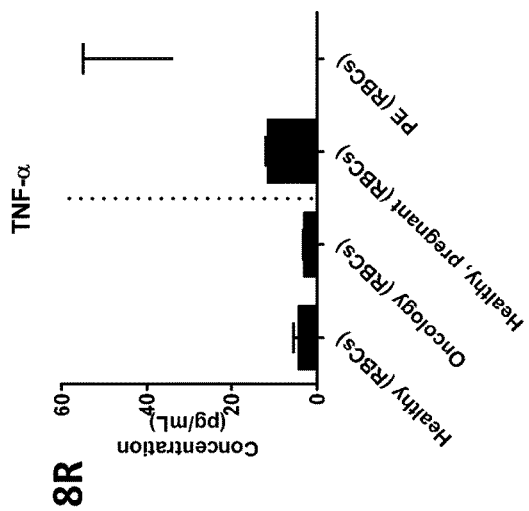
Figure 8R:
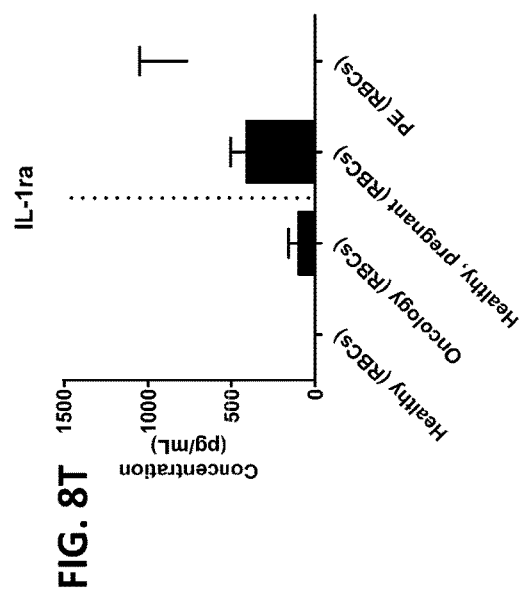
Figure 8S:
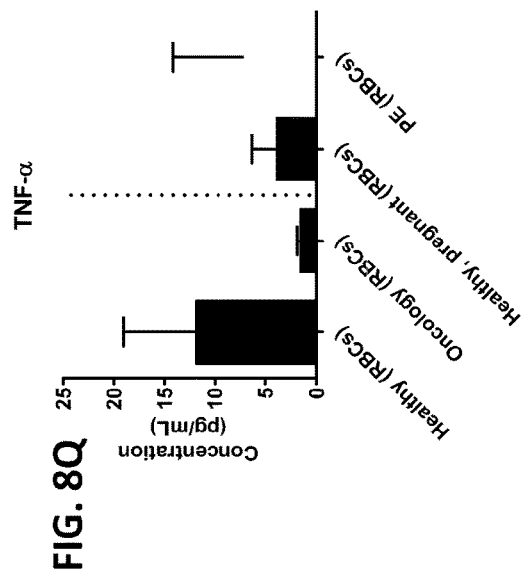
Figure 8T:
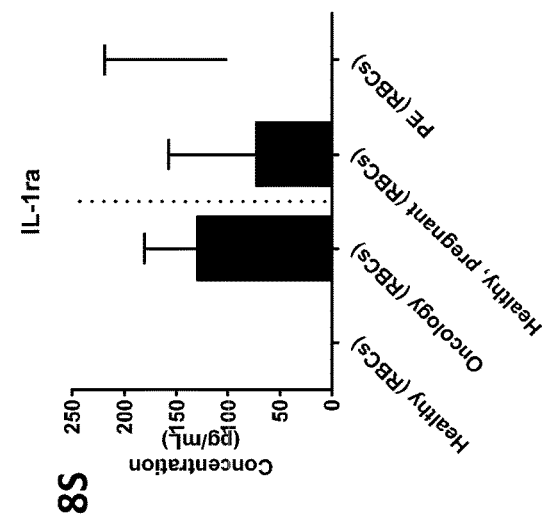
Figure 8U:
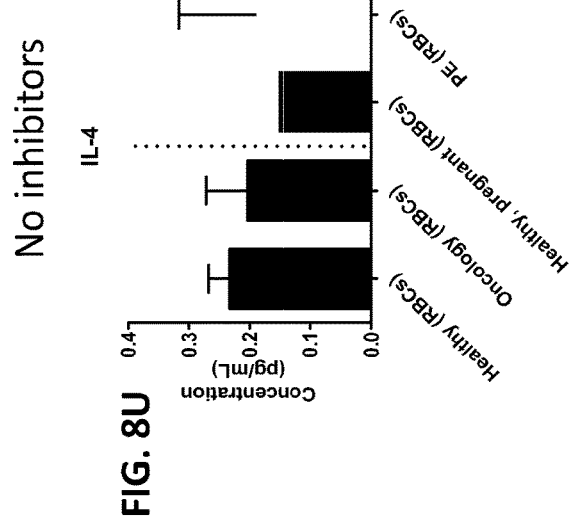
Figure 8V:
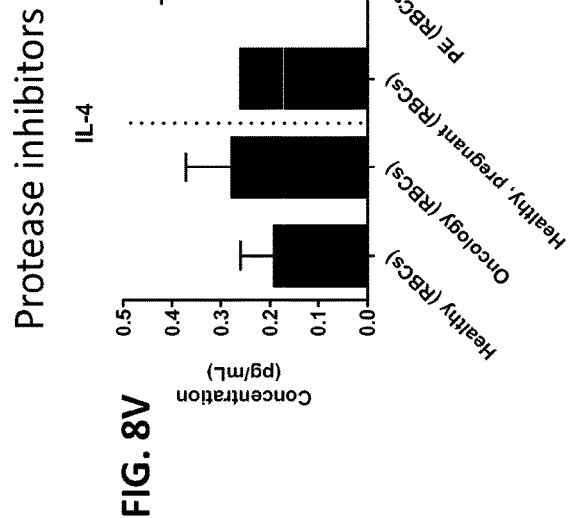
Figure 8W:
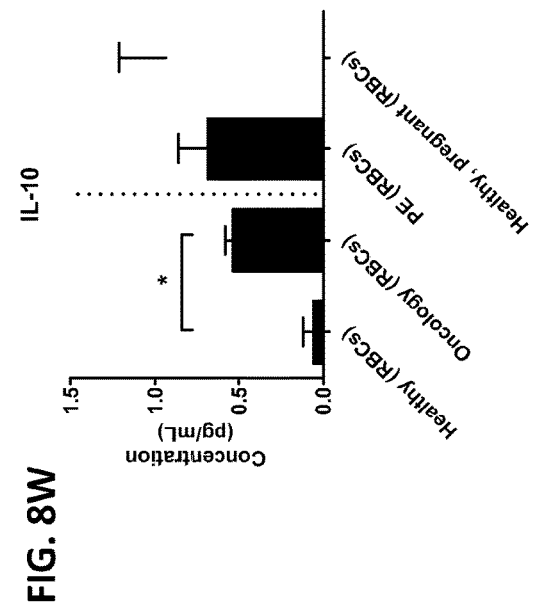
Figure 8X:
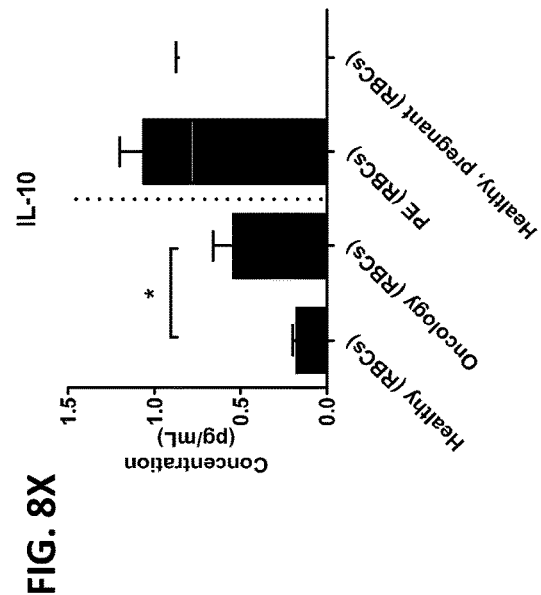
Figure 8Z:
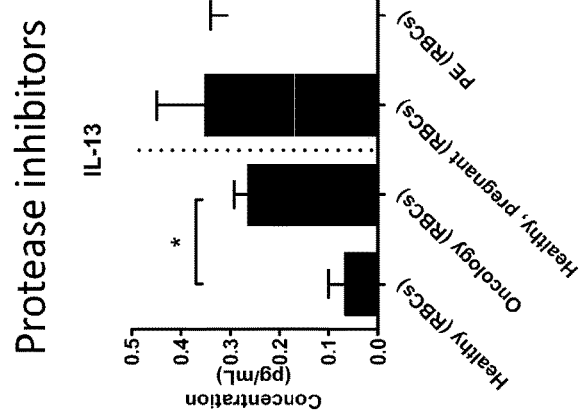
Figure 8B:
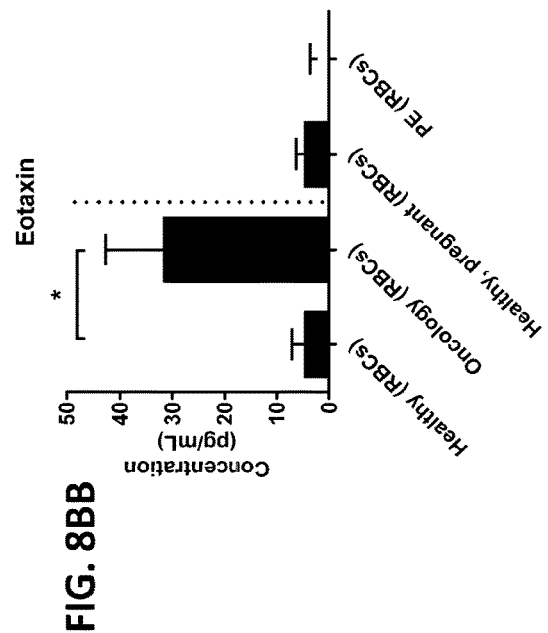
Figure 8Y:
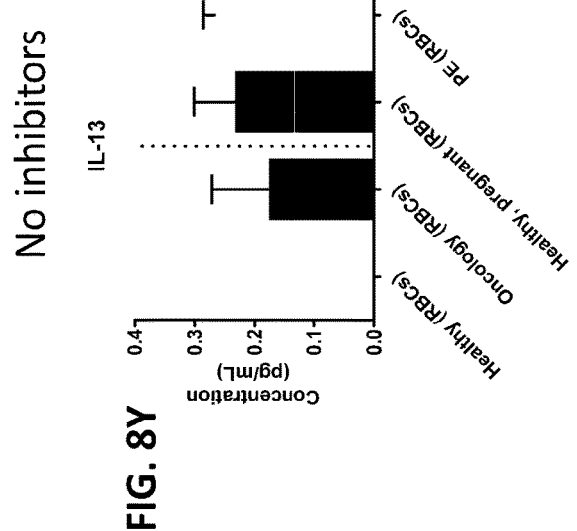
Figure 8A:
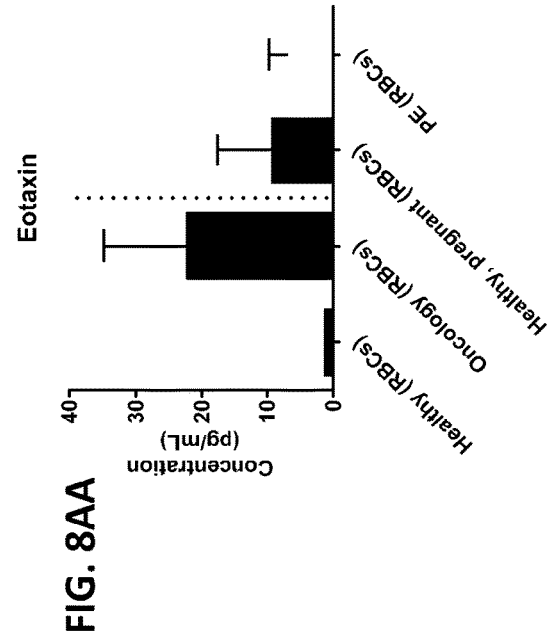
Figure 8D:
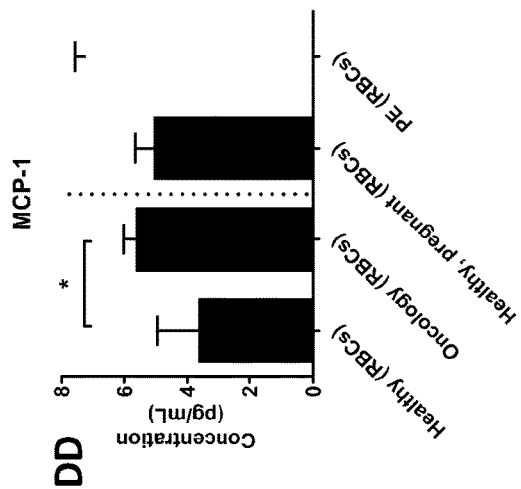
Figure 8C:
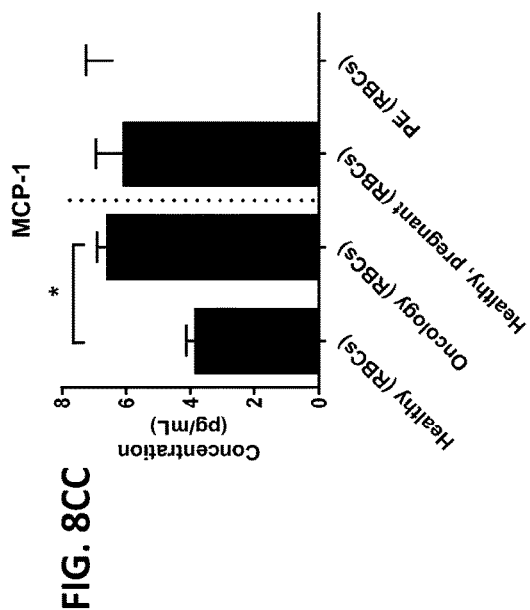
Figure 8F:
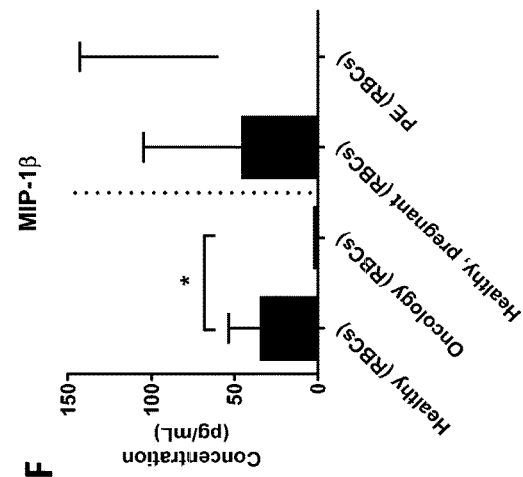
Figure 8E:
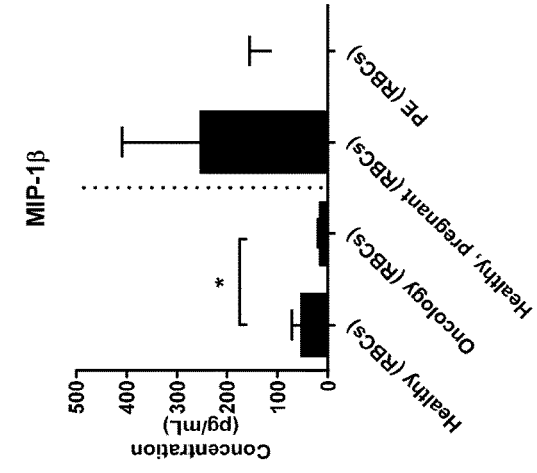
Figure 8K:
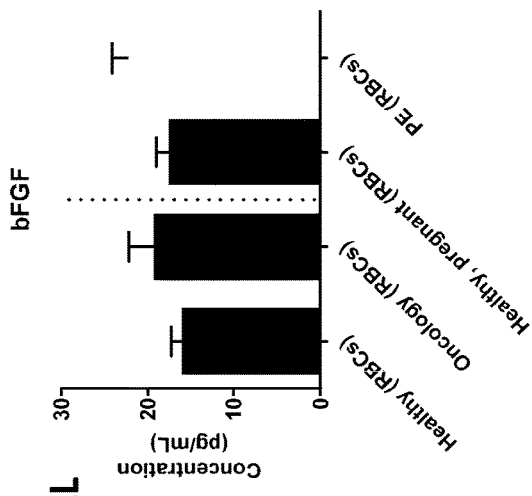
Figure 8L:
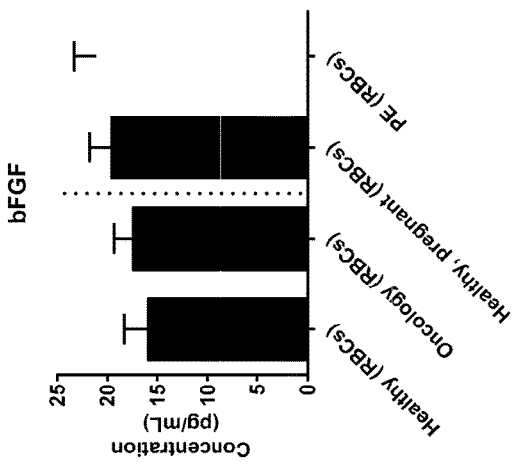
Figure 8M:
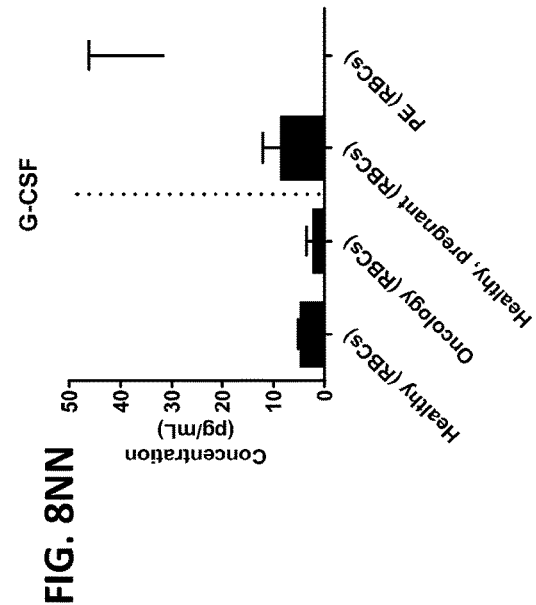
Figure 8N:
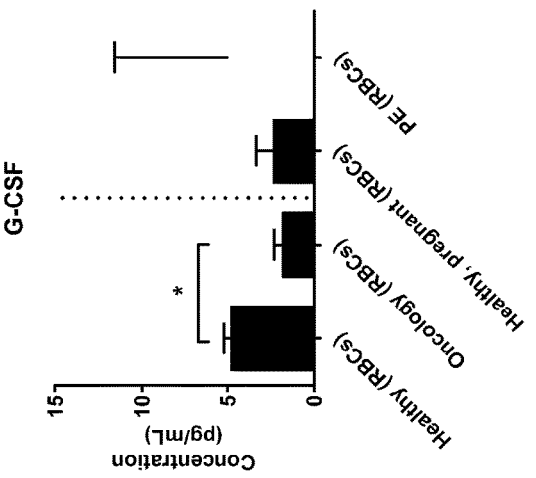
Figure 8P:
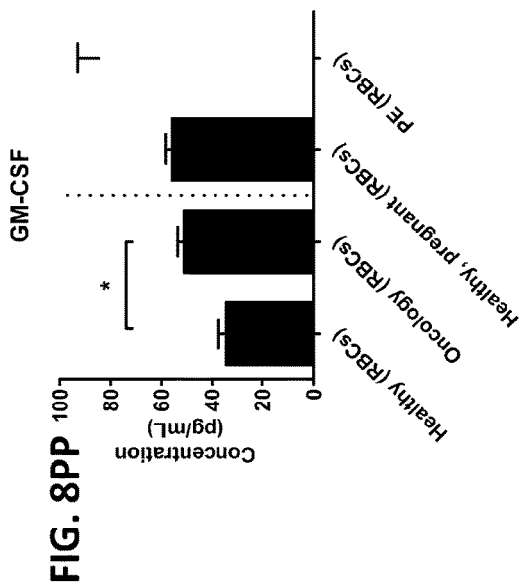
Figure 8R:
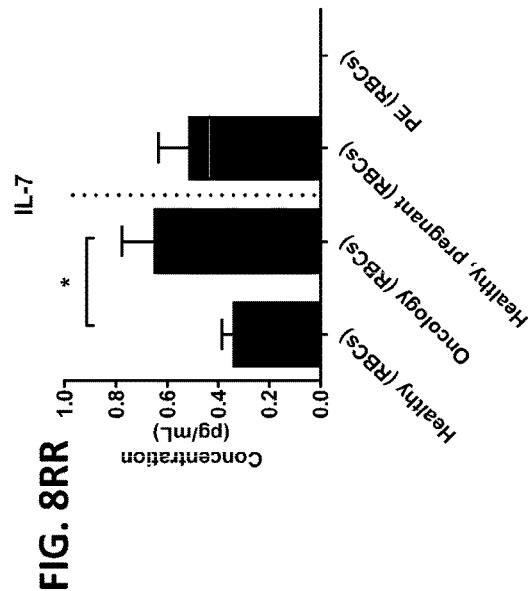
Figure 8O:
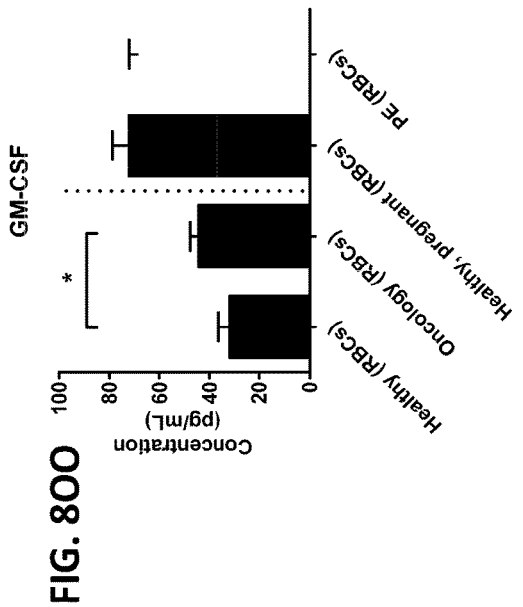
Figure 8Q:
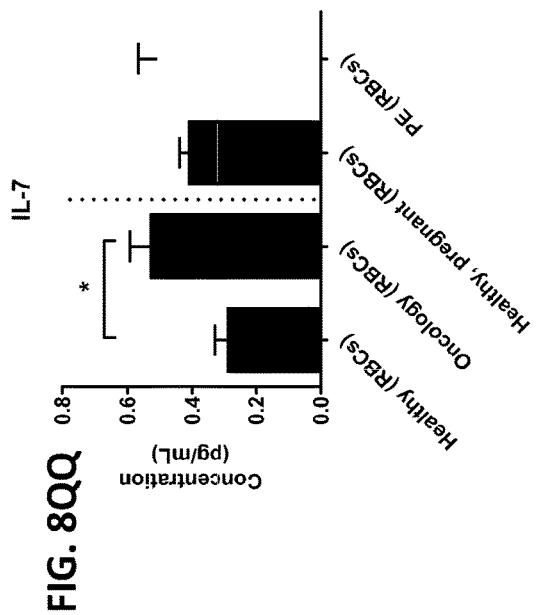
Figure 8T:
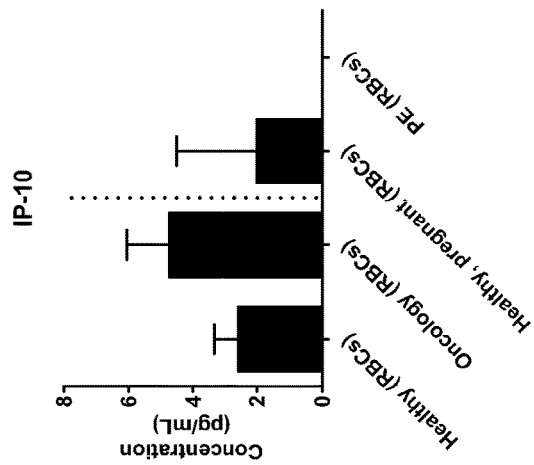
Figure 8V:
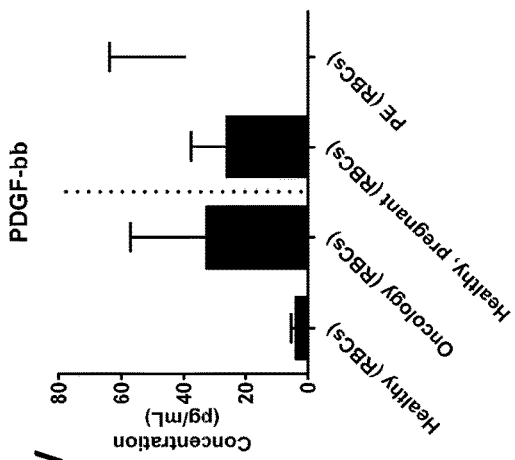
Figure 8S:
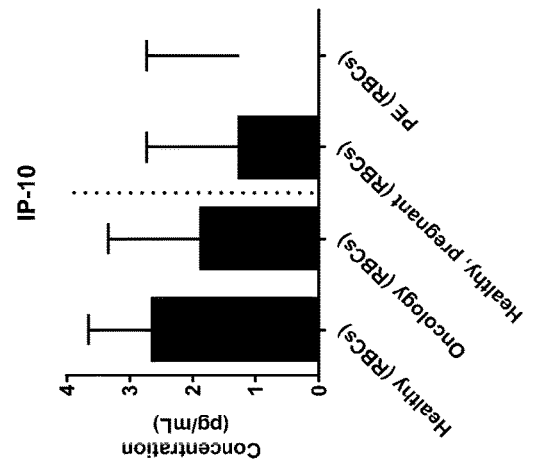
Figure 8U:
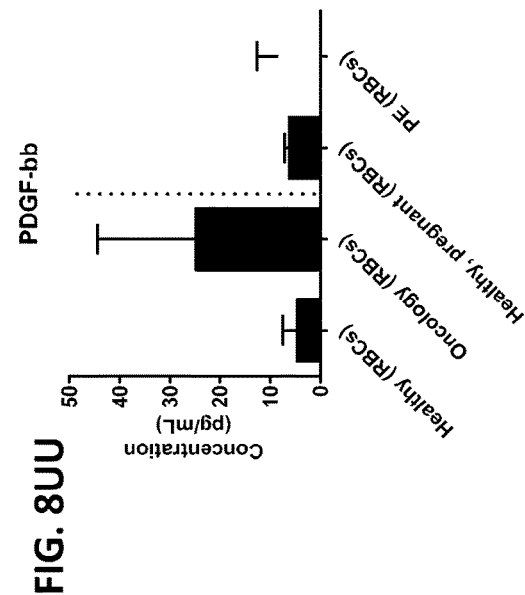
Figure 8X:
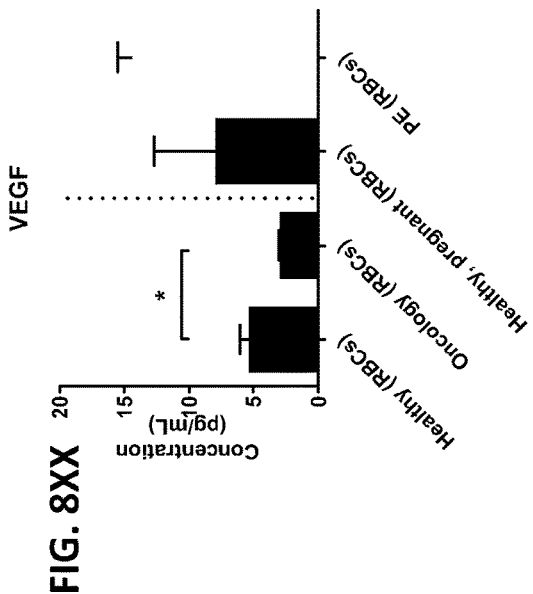
Figure 8Z:
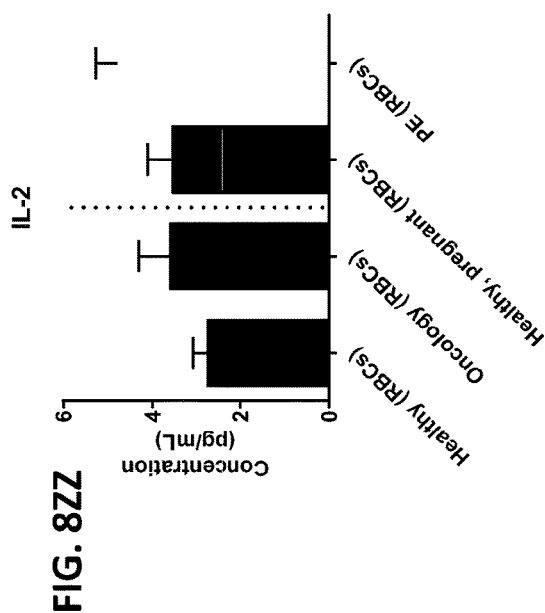
Figure 8W:
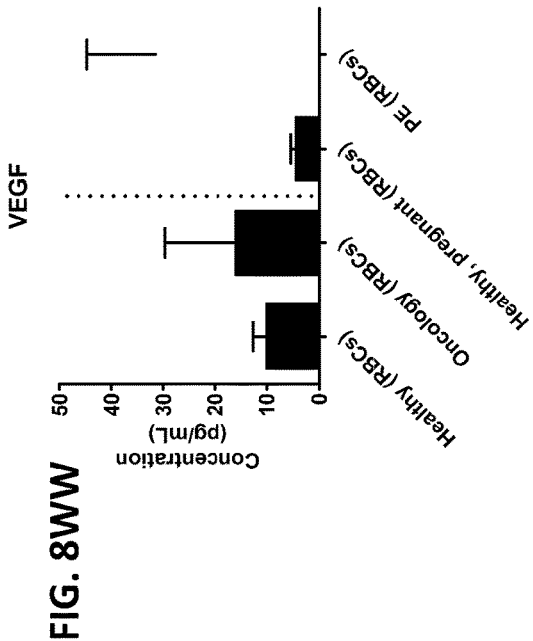
Figure 8Y:
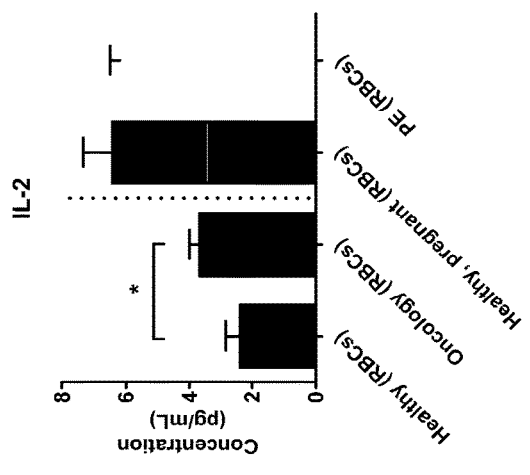
Figure 9A:
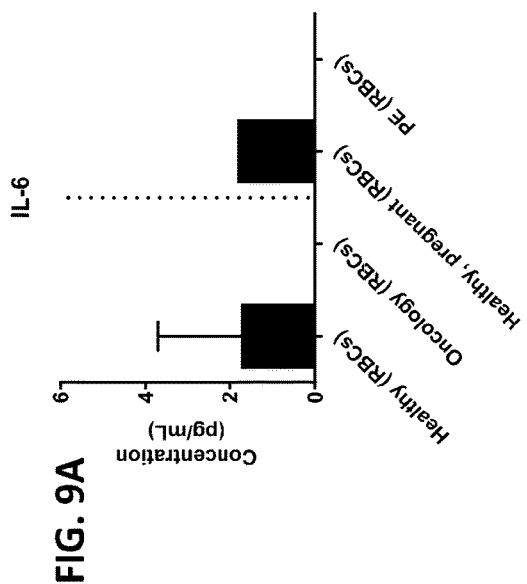
FIG. 9A-9FF is a series of graphs showing the effect of protease inhibitors (PI) on the concentration of proteins from red blood cells isolated from healthy individuals, healthy pregnant women, pregnant women with preeclampsia, and oncology patients.
Figure 9B:
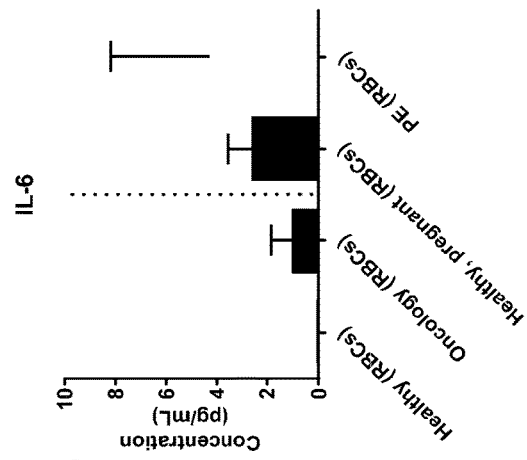
Figure 9C:
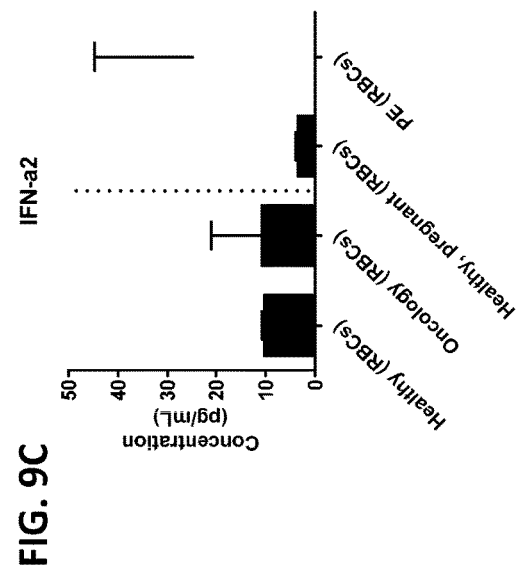
Figure 9D:
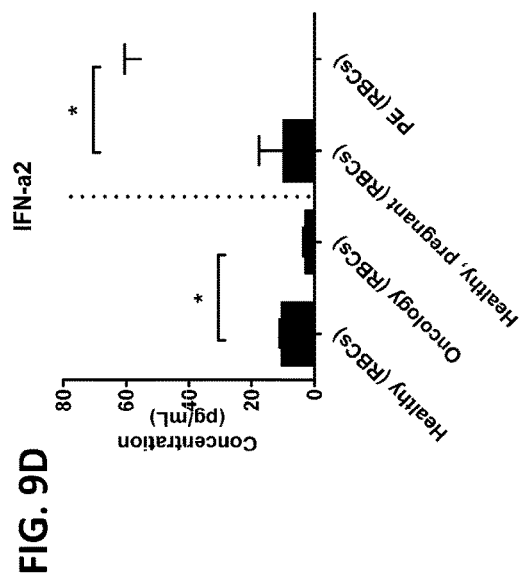
Figure 9E:
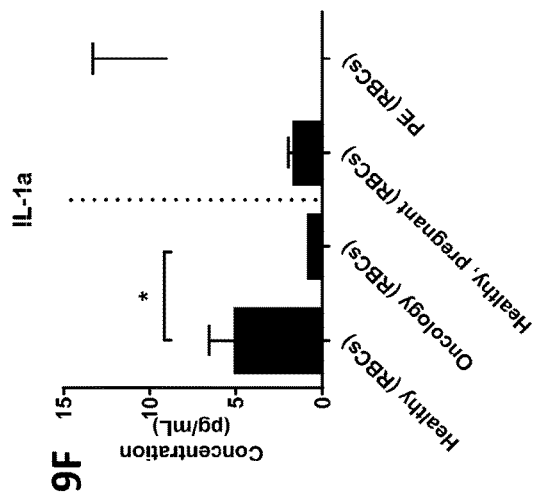
Figure 9F:
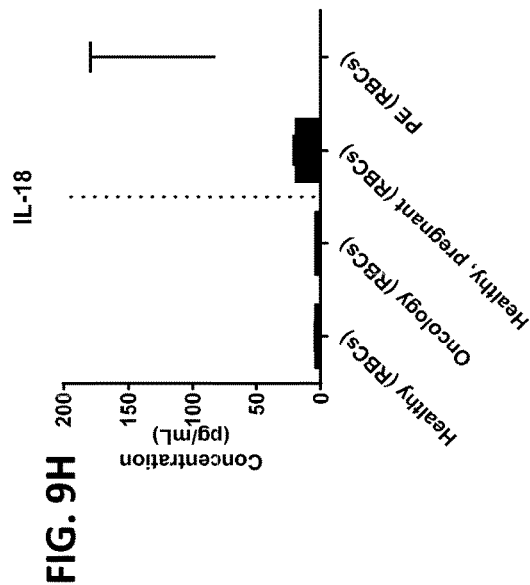
Figure 9G:
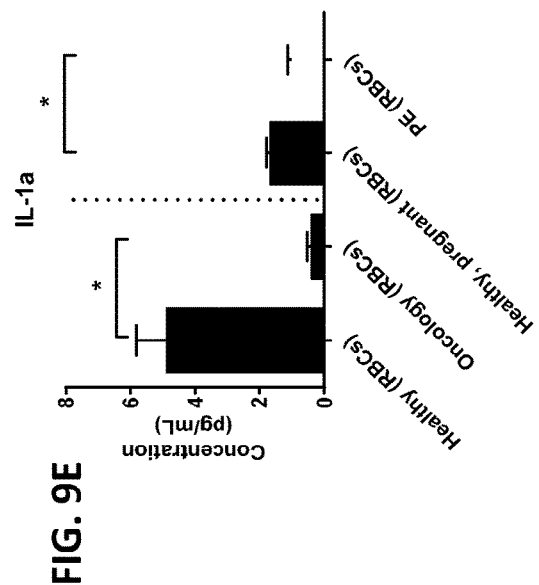
Figure 9H:
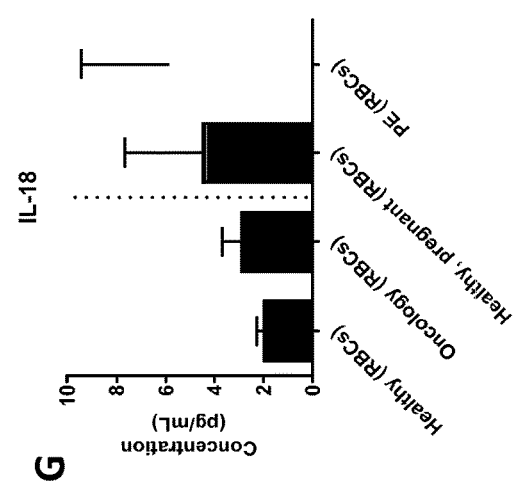
Figure 9M:
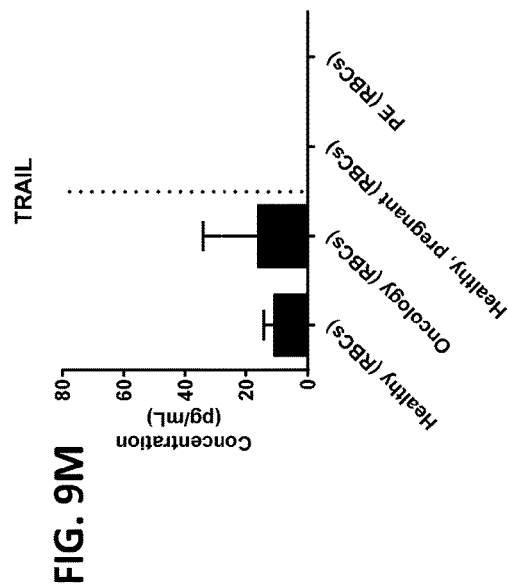
Figure 9N:
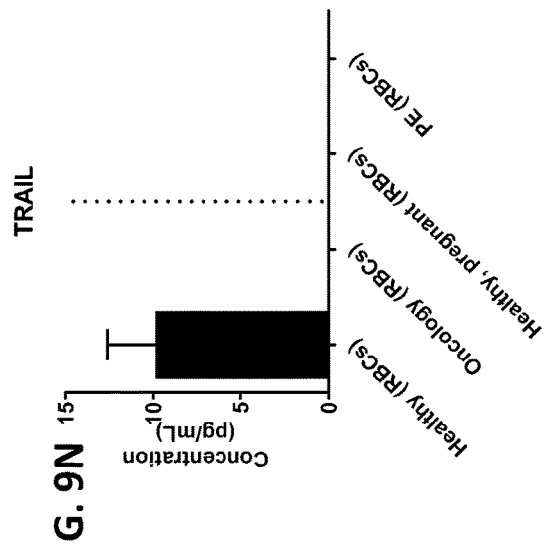
Figure 9O:
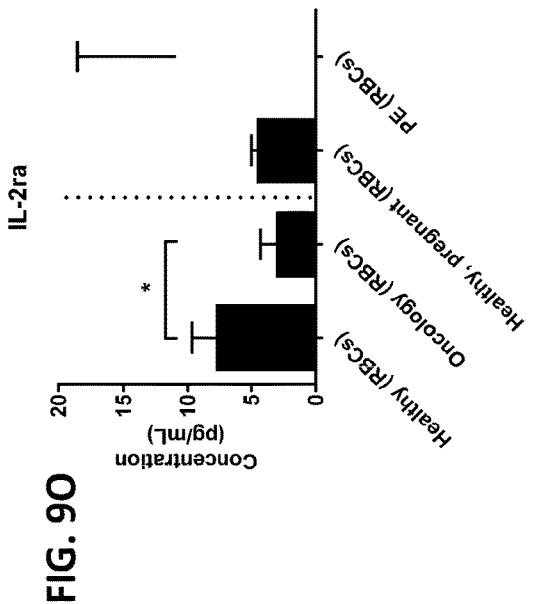
Figure 9P:
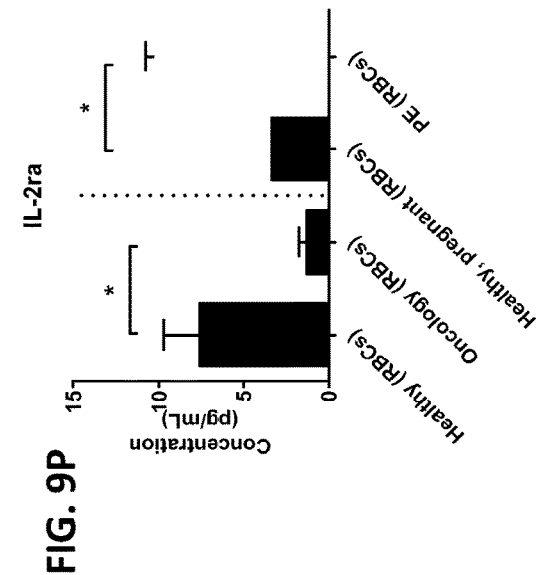
Figure 9Q:

Figure 9R:
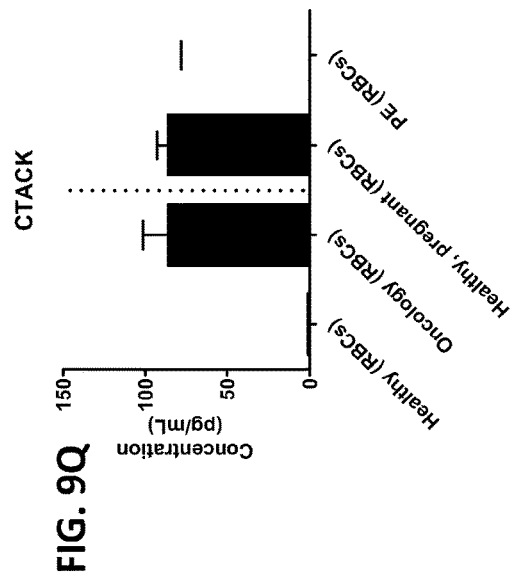
Figure 9S:
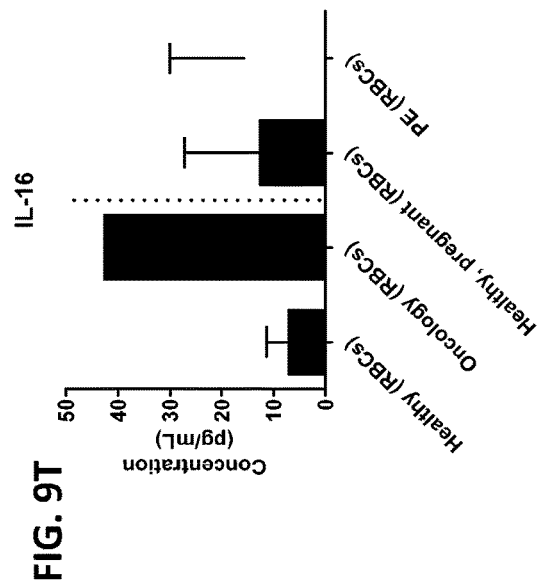
Figure 9T:
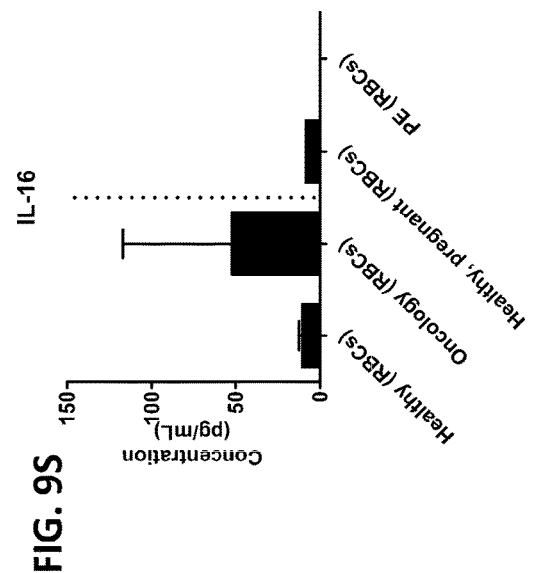
Figure 9U:
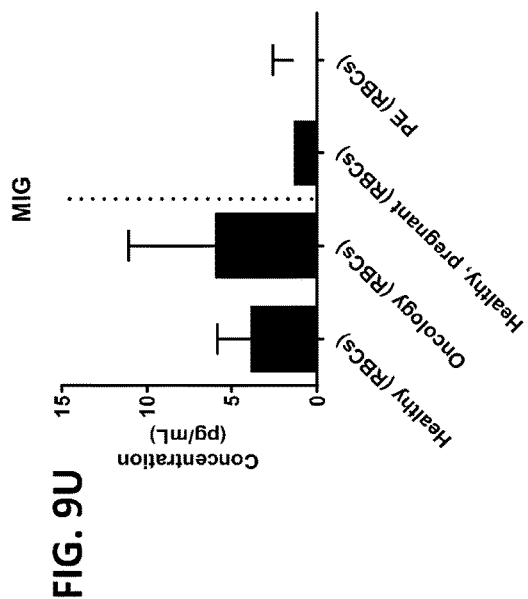
Figure 9V:
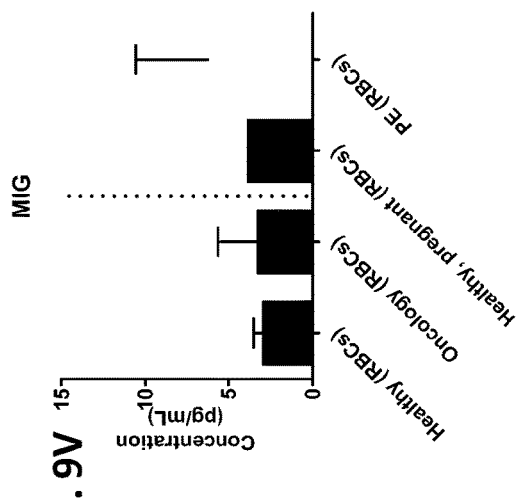
Figure 9W:
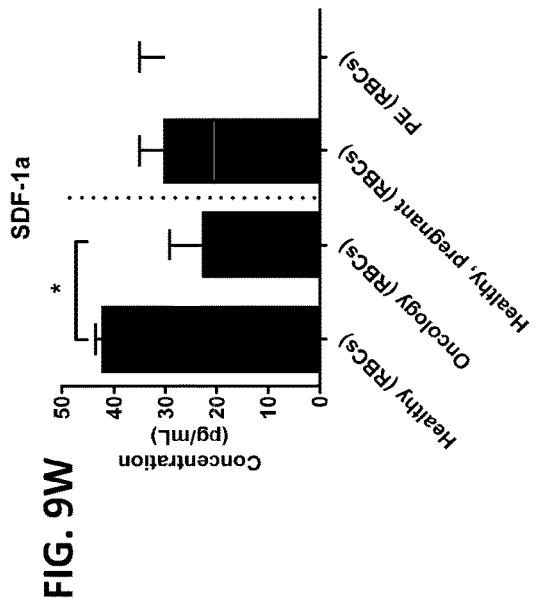
Figure 9X:
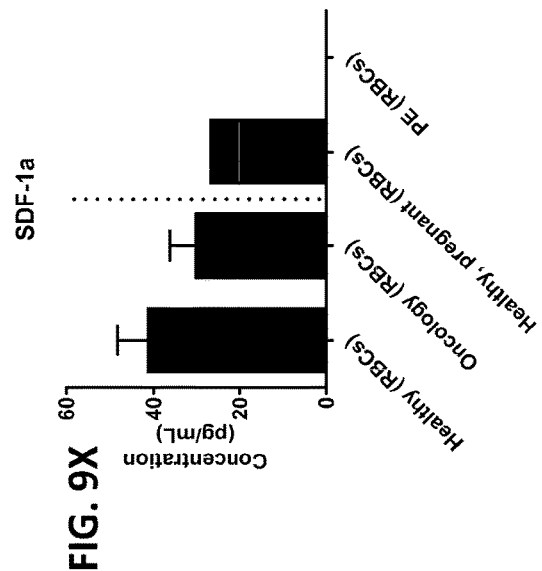
Figure 9Y:
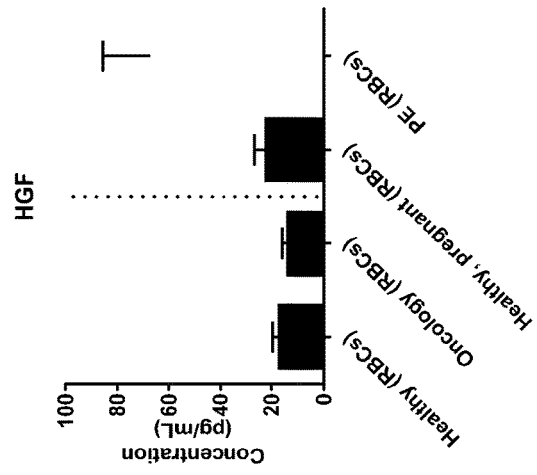
Figure 9Z:
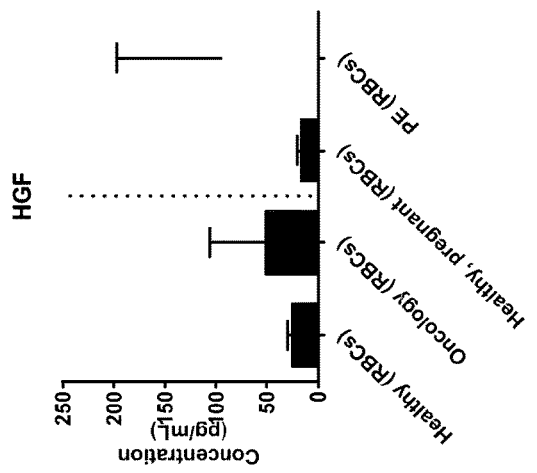
Figure 9A:
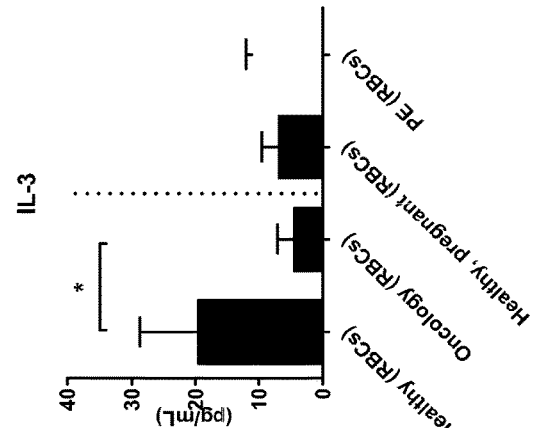
Figure 9B:
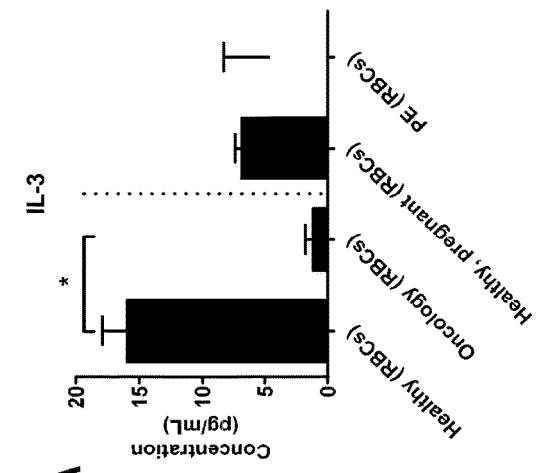
Figure 9C:
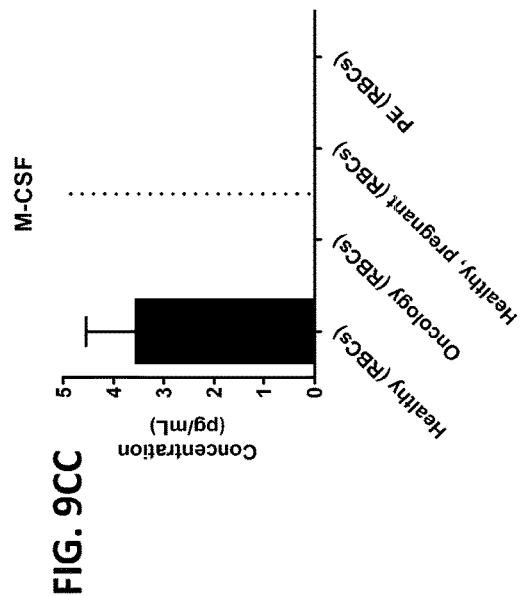
Figure 9D:
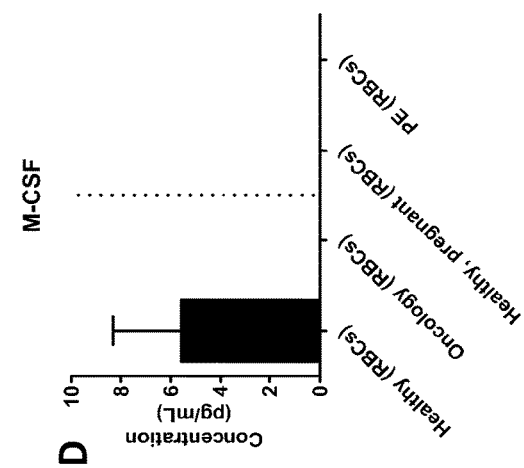
Figure 9E:
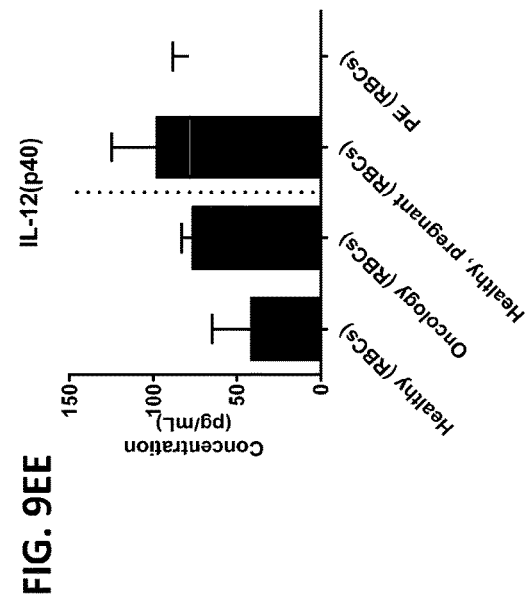
Figure 9F:
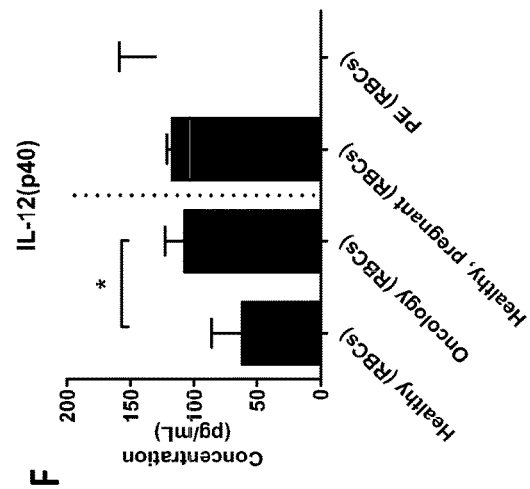
Figure 10B:
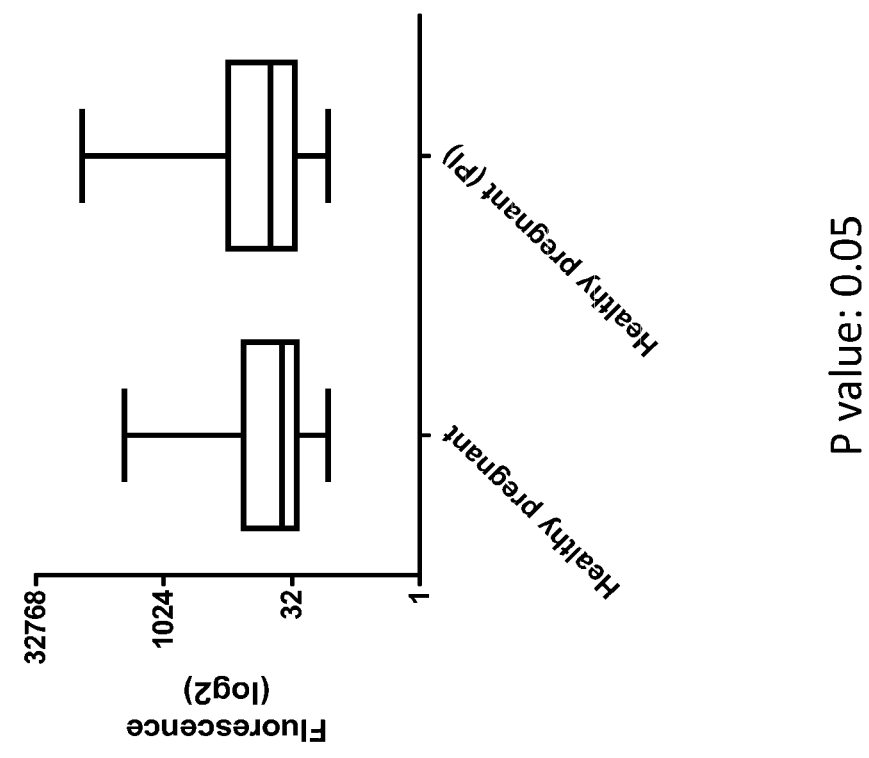
FIG. 10A-10D is a series of graphs showing the effect of protease inhibitors (PI) on the cumulative data of cytokines released from red blood cells from healthy individuals, healthy pregnant women, pregnant women with preeclampsia, and oncology patients.
Figure 10A:
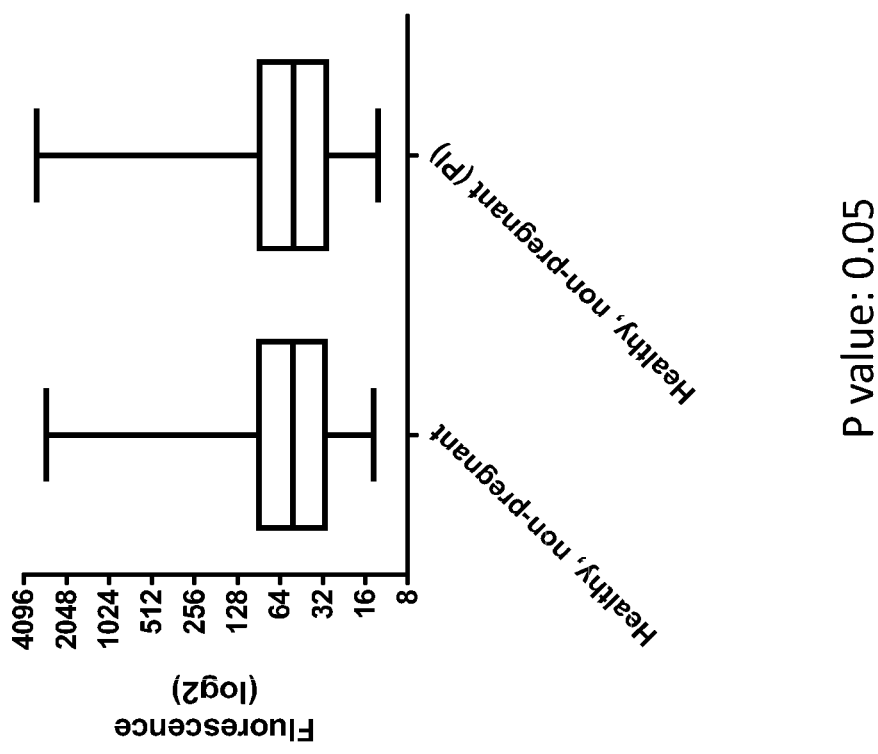
Figure 10D:
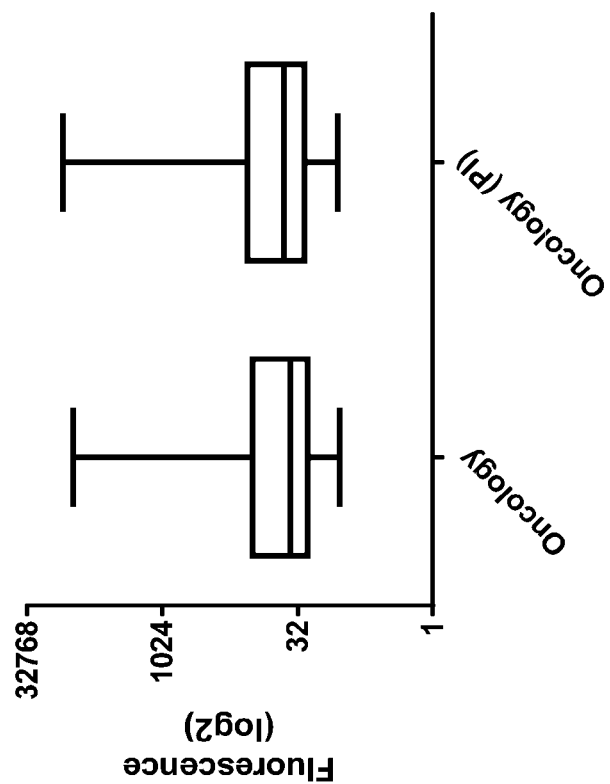
Figure 10C:
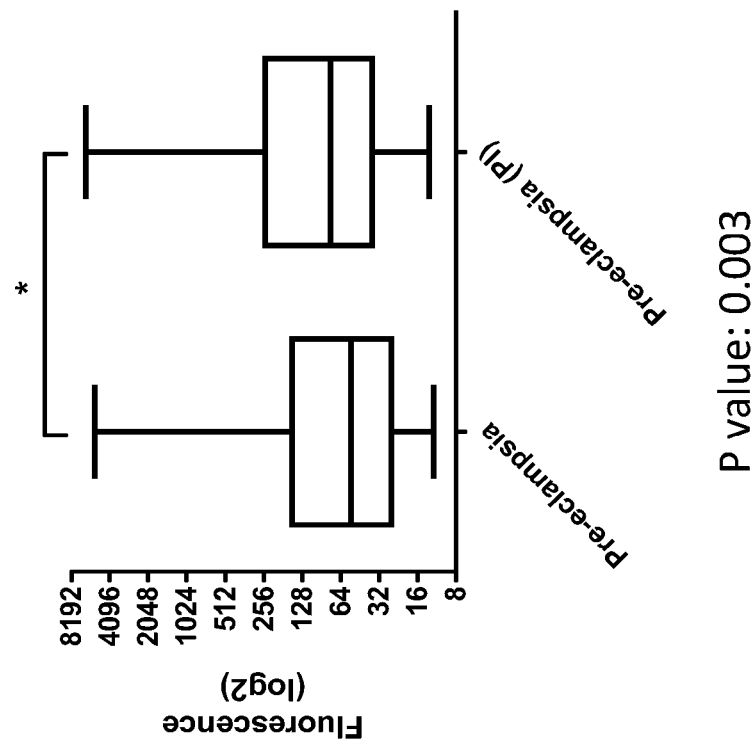

FIG. 8A-FIG. 8ZZ and FIG. 9A-FIG. 9FF shows the concentration of the indicated proteins in the red blood cell conditioned PBS either in the presence or absence of protease inhibitors from the participant groups. The conditioned PBS was produced following red blood cell incubation for 24 hours at 37° C. Significant differences (p<0.05) were determined using Student T-tests. As opposed to blood samples from healthy subjects in which protein levels generally decreased in the presence of protease inhibitors (see FIG. 7A-7Z), there was a trend for similar or increased levels of proteins when the blood samples of subjects having preeclampsia or cancer were incubated with protease inhibitors. The results suggest that one may differentiate between healthy and diseased blood samples by contacting either blood sample with protease inhibitors and detecting/measuring a change in protein levels.

Figure 11A:
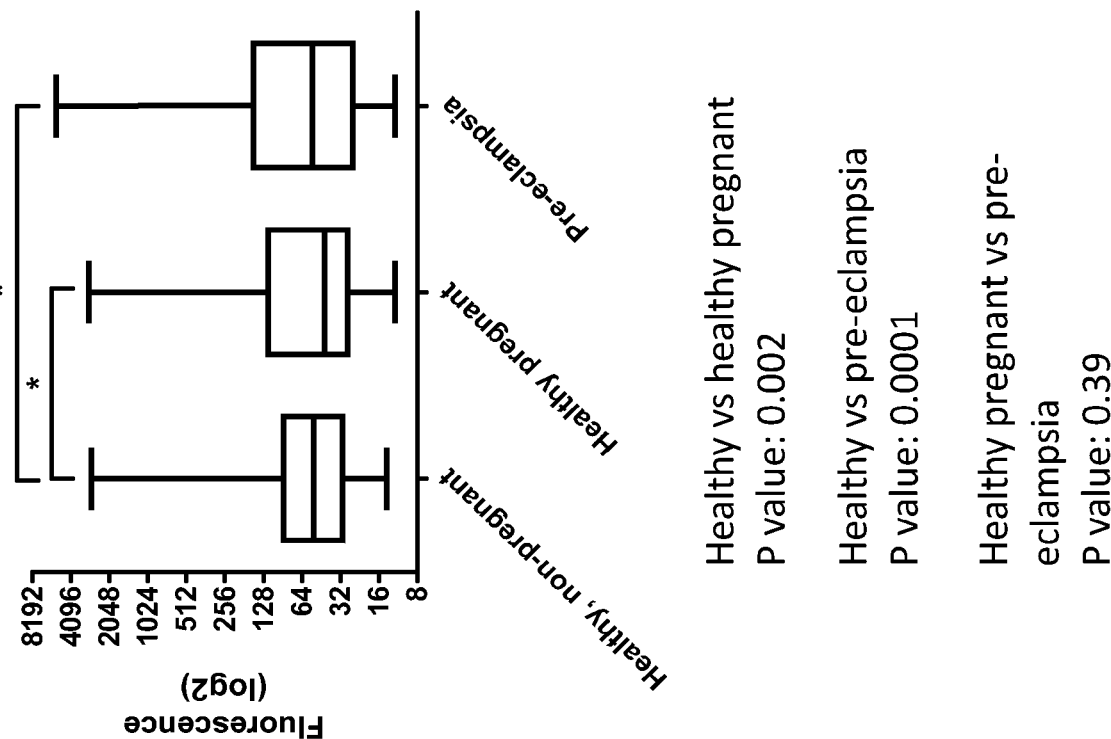
Figure 11B:
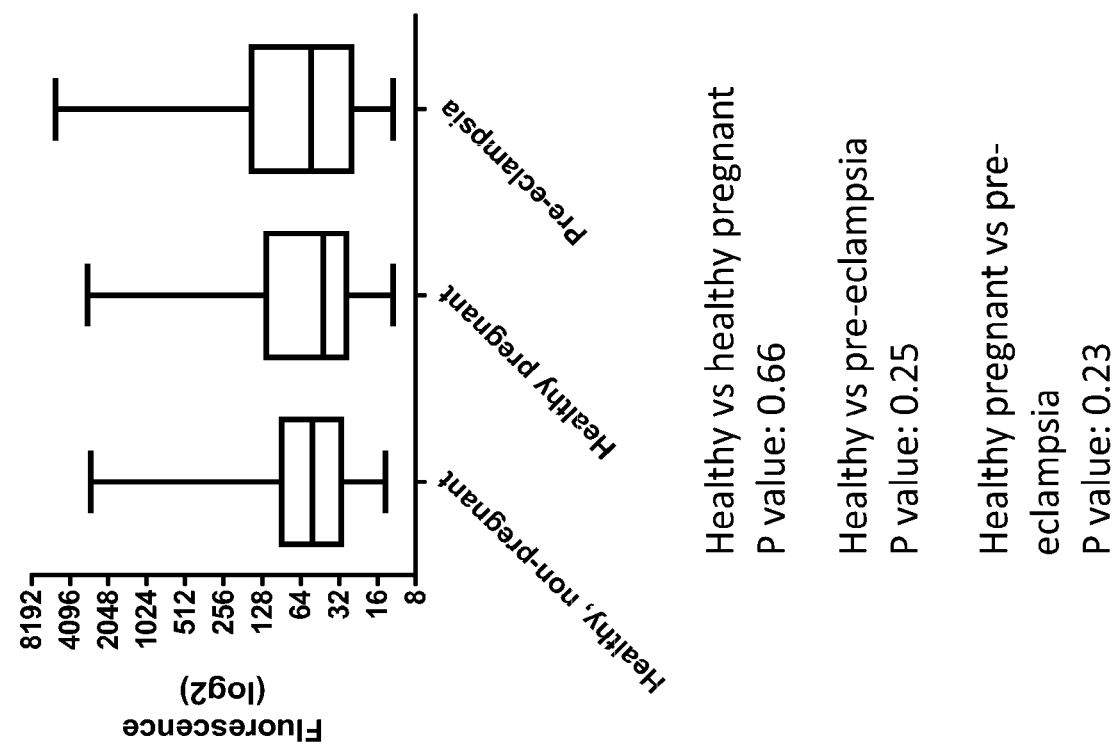

FIG. 10A-FIG. 10D and FIG. 11A-FIG. 11D shows the cumulative fluorescence data (log 2) of the cytokine analyses in the red blood cell conditioned PBS either in the presence or absence of protease inhibitors from the participant groups. The conditioned PBS was produced following red blood cell incubation for 24 hours at 37° C. Significant differences (p<0.05) were determined using Student T-tests. These data show that red blood cells isolated from women with pre-eclampsia released significantly more cytokines when treated with protease inhibitors compared to their absence (see FIG. 10C). In comparison, no significant difference was observed with and without protease inhibitors for healthy non-pregnant participants (see FIG. 10A) or for healthy pregnant participants (see FIG. 10B). Similarly, there was a significant difference between the level of cytokines with protease inhibitor treatment between healthy non-pregnant and healthy pregnant individuals (FIG. 10B), and a trend towards significance between healthy participants and oncology patients (FIG. 11D). The results suggest that the use of protease inhibitors to treat blood samples may aid in the discrimination between healthy and diseased groups.

Example 8. Effect of Specific Protease Inhibitors on Proteins from Red Blood Cells from Healthy Individuals Blood samples from healthy volunteers were used to evaluate the effect of specific protease inhibitors on proteins from red blood cells. Whole blood was collected from healthy volunteers by venepuncture (n≥3) directly into EDTA vacutainers ($k_2$EDTA vacutainers, BD Biosciences). The fractions of blood were collected and processed at room temperature within 4 hours of collection. For multiplex analysis (BioPlex analysis) the samples were stored at −80° C.

The red blood cells were isolated using dextran sedimentation as follows. Whole blood was centrifuged (1500 g, 10 minutes) and the upper plasma layer was discarded. The remaining cell pellet was resuspended in an equal volume of sodium chloride (0.15 M). Dextran (6% w/v in 0.15 M sodium chloride) was then added to this cellular suspension at a 1:4 ratio (dextran:cell suspension). The solution was left at room temperature for 30 minutes for red blood cell sedimentation to the bottom of the tube. The upper white blood cell rich layer was then discarded and the lower red blood cell fraction isolated. The red blood cell fraction was washed once in phosphate buffered saline (PBS, 500 g, 5 minutes) and the remaining red blood cell pellet was counted (Coulter Act Diff, Beckman Coulter). The red blood cells were then diluted to 400 million cells/mL in PBS and were incubated at 37° C. and 5% $CO_2$ for 24 hours. Some samples were also incubated with the protease inhibitors indicated in Table 5 during the PBS incubation.

TABLE 5

| Protease inhibitors | | | |
|---|---|---|---|
| Sample ID | Protease Inhibitors | Concentration | Specificity |
| 1 | None | — | — |
| 2 | cOmplete protease inhibitor cocktail (Roche) | 1× | Serine, cysteine, and metallo-proteases |

TABLE 5-continued

Protease inhibitors

| Sample ID | Protease Inhibitors | Concentration | Specificity |
|---|---|---|---|
| 3 | Antipain-dihydrochloride | 50 µg/mL | Papain, trypsin, cathepsin A and B |
| 4 | Bestatin | 40 µg/mL | Aminopeptidases |
| 5 | E-64 | 10 µg/mL | Cysteine proteases |
| 6 | Leupeptin | 5 µg/mL | Serine and cysteine proteases |
| 7 | Pepstatin | 0.7 µg/mL | Aspartate proteases |
| 8 | Phosphoramidon | 330 µg/mL | Metallo-endopeptidases |
| 9 | Pefabloc SC | 1 mg/mL | Serine proteases |
| 10 | EDTA-Na$_2$ | 0.5 mg/mL | Metalloproteases |
| 11 | Aprotinin | 2 µg/mL | Serine proteases |
| 12 | A8127s protease inhibitor cocktail | 1× | Serine, cysteine, and aspartic proteases, aminopeptidases, metalloproteases |

After incubation, the resulting conditioned PBS was isolated by centrifugation (500 g, 5 minutes) and then stored at −80° C. The conditioned PBS samples were then analysed on the multiplex cytokine assays. Two multiplex assays were utilised. The first was a 27-plex human cytokine panel that assays for FGF basic, Eotaxin, G-CSF, GM-CSF, IFN-γ, IL-1β, IL-1ra, IL-2, IL-4, IL-5, IL-6, IL-7, IL-8, IL-9, IL-10, IL-12(p70), IL-13, IL-15, IL-17, IP-10, MCP-1, MIP-1α, MIP-1β, PDGF-BB, RANTES, TNF-α, and VEGF, and the second was a 21-plex human cytokine panel that assays for IL-1α, IL-2Ra, IL-3, IL-12, IL-16, IL-18, CTACK, GRO-α, HGF, IFN-α2, LIF, MCP-3, M-CSF, MIF, MIG, β-NGF, SCF, SCGF-β, SDF-1α, TNF-β, TRAIL (Bio-Plex Pro 27-plex and 21-plex, Bio-Rad). The assays were performed according to manufacturer's instructions using an automated magnetic wash station (BioPlex Pro II, Bio-Rad) for the washing steps. The assays were run on the Luminex® 200™ system (Bio-Rad) and fluorescent values were collected. The calibration curve for each cytokine was analysed with 5 parametric logistic curve regression using BioPlex manager software (ver. 5.0, Bio-Rad, USA).

The fold change was determined for proteins in red blood cell-conditioned PBS at 400 million cells/mL following incubation at 37° C. for 24 hours with protease inhibitor cocktail or individual protease inhibitors from healthy participants. Values significantly different from untreated control if $p<0.05$ (* for $p=0.05$-$0.01$;  for $p=0.01$-$0.001$; * for $p<0.001$). Values with a fold change of >1 indicated that the protein was higher in the sample incubated with protease inhibitor(s) compared to one that was not (control), and values with a fold change of <1 indicated that the protein had a lower concentration in the sample incubated with protease inhibitor(s) compared to one that was not (control). Significant differences ($p<0.05$) were determined using Student T-tests.

TABLE 6

Fold change of proteins in red blood cells due to protease inhibitors

| Protein | Protease Inhibitor Sample ID | | | | | | | | | |
|---|---|---|---|---|---|---|---|---|---|---|
| | 2 | 3 | 4 | 5 | 6 | 7 | 8 | 9 | 10 | 11 |
| IFN-α2 | 0.64** | | 3.81** | 0.53* | | 0.46* | | | | 1.50* |
| IL-1α | 1.28*** | 1.43* | | 1.14* | | | | | | |
| IL-18 | | 2.01* | 1.45** | | | | | | | |
| MIF | 0.59*** | | 0.83* | 1.42** | | 1.39* | | | 0.82* | 0.77** |
| TNF-β | 1.22*** | | | | | | | | 0.93** | |
| TRAIL | 1.45** | | 1.69* | | | | | | | |
| IL-2ra | | | | | | 0.81** | | | | |
| CTACK | | 7.39* | | | | 1.61* | | 2.31* | | |
| GRO-a | 1.13** | | | | 1.08*** | | | | | |
| IL-16 | | | | | | 0.84* | | 0.59* | | |
| MCP-3 | 1.83*** | 4.07* | | 1.24* | | | | | | |
| MIG | 1.07** | | | | | | | | | 1.07* |
| SDF-1α | | | | | 1.55* | | | | | |
| HGF | | | 9.10*** | 0.43** | | 0.47* | | | | |
| IL-3 | 1.73*** | 6.06* | | | | 1.45* | | | | |
| M-CSF | 1.24** | 2.35* | | | | | | | | |
| β-NGF | 1.13** | | | 1.16* | | | | | | |
| SCF | 1.13*** | 2.55* | | | | | | | | |
| IL-12p40 | 1.38*** | 2.17* | 1.11* | 1.34* | | | | | | |
| LIF | 1.09* | | | | | | | | | |
| IL-9 | | | | | | | | 0.64** | | |
| IL-15 | | 3.85** | | | | | | | | |
| IL-17 | 1.34** | 3.50* | | | | | | | | |
| IL-1ra | | | | | | | | | | |
| IL-10 | | | | 0.46* | | 0.50** | | | 0.45* | 1.32* |
| Eotaxin | | | | | | | | 0.63** | | |
| MCP-1 | 0.93** | | | 0.66* | | 0.81* | | | 0.70* | |
| MIP-1β | | 3.99* | | | | | | | | |
| bFGF | 1.16* | | | | | | | | | |
| G-CSF | | | | | | | | | | 1.66** |
| GM-CSF | 1.20* | 1.37* | | | 1.07* | | | | | |
| VEGF | | | | 0.44* | | 0.47* | 0.60** | | | |
| IL-2 | 1.40* | 9.01* | | | | | | | 0.06* | |

The use of individual protease inhibitors changed the concentration of a variety of cytokines that were released from the red blood cells when compared to control cells (no protease inhibitor(s)) (See Table 6). Although multiple protease inhibitors changed the concentration of the same cytokine, the direction of this change was variable. For example, bestatin and pepstatin are prime examples of the complex effects of different protease inhibitors on release of proteins from red blood cell. Incubating red blood cells with bestatin, which is an amino peptidase inhibitor, alters the concentration of released IFN-a2, IL-18, MIF, TRAIL, HGF, and IL12-p40. Pepstatin, an aspartate protease, also affects the concentration of IFN-a2, MIF, and HGF. However in each of those instances, pepstatin produced the opposite effect of bestatin. Similarly, the concentration of HGF was dramatically increased following red blood cell incubation with bestatin, but HGF concentration was significantly decreased following red blood cell incubation with pepstatin (Table 6). The complex nature of this interaction between specific protease inhibitors and the concentration of multiple cytokines provided compelling evidence that more than the inhibition of non-specific proteolysis of cytokines was causing the protease inhibitor-mediated protein concentration effects.

Figure 12A:
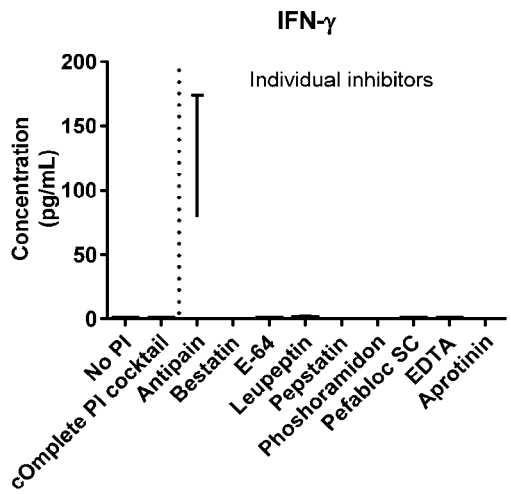
FIG. 12A-12VV is a series of graphs showing the effect of individual protease inhibitors on cytokines released from red blood cells from healthy individuals.
Figure 12B:
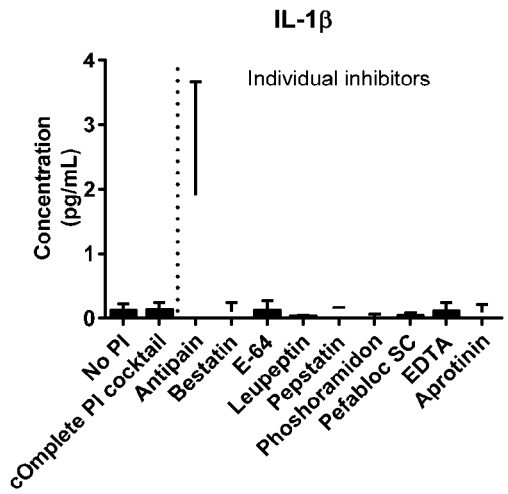
Figure 12C:
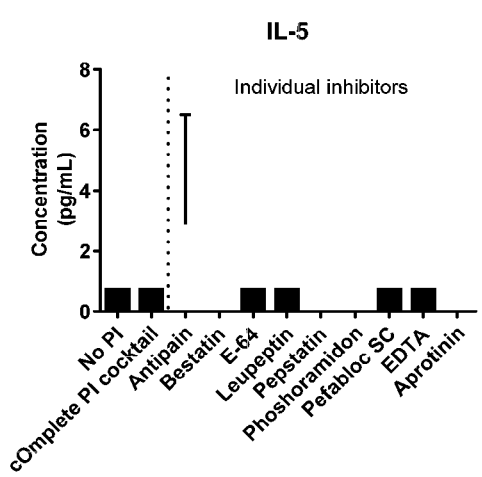
Figure 12D:
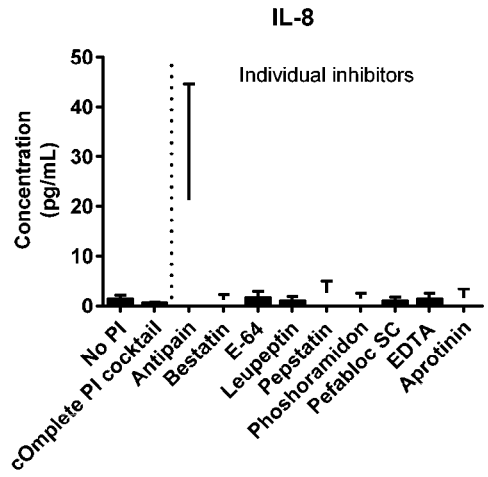
Figure 12E:
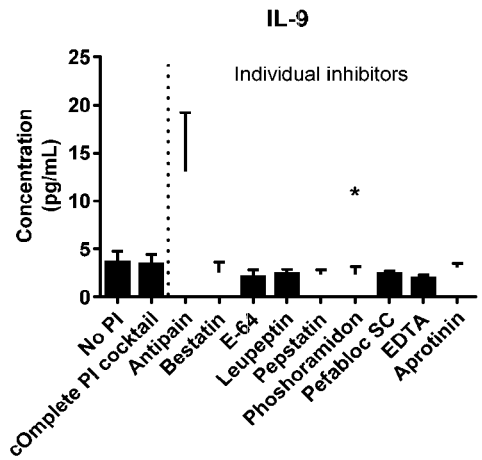
Figure 12F:
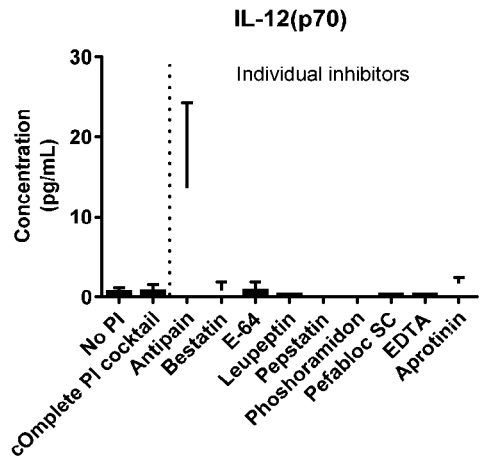
Figure 12G:
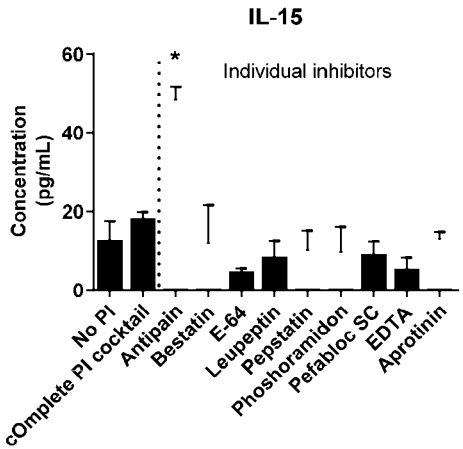
Figure 12H:
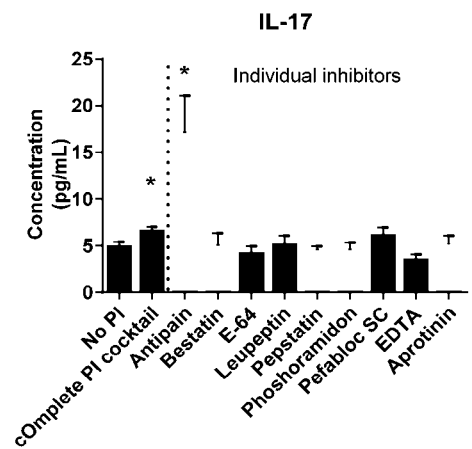
Figure 12I:
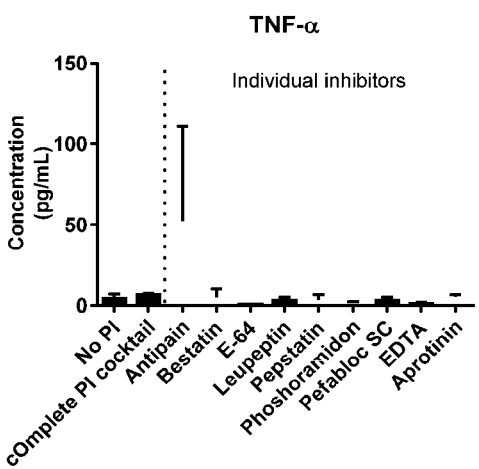
Figure 12J:
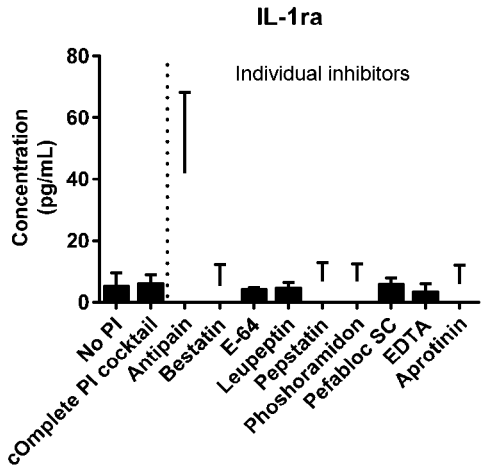
Figure 12K:
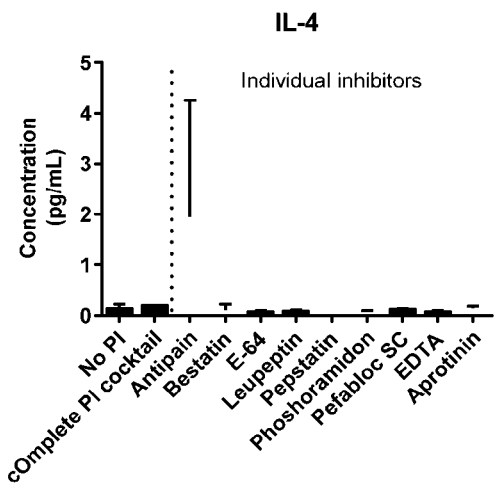
Figure 12L:
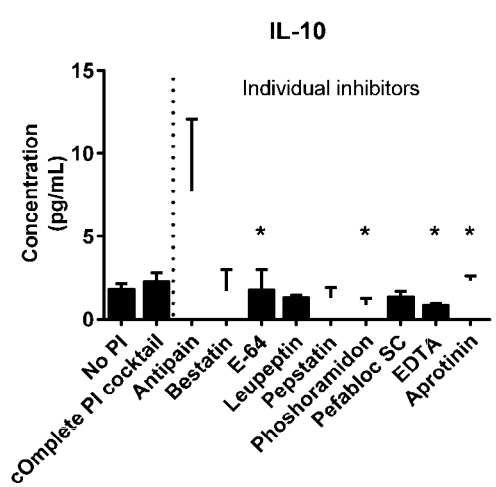
Figure 12M:
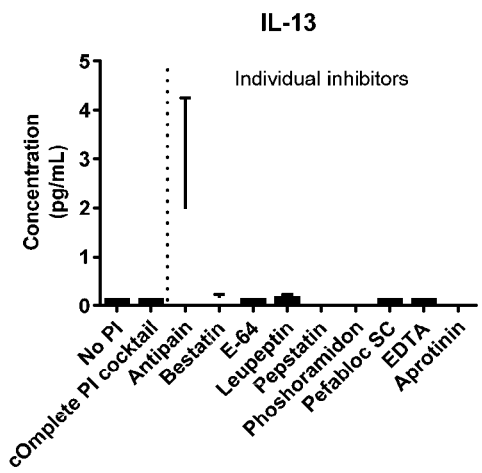
Figure 12N:
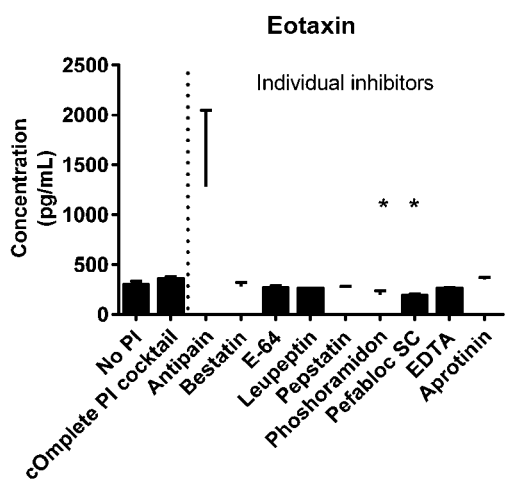
Figure 12O:
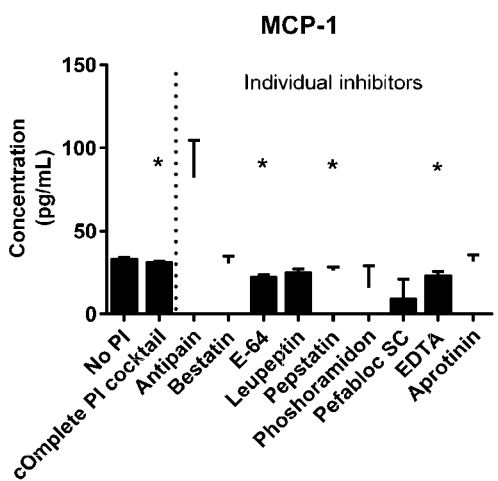
Figure 12P:
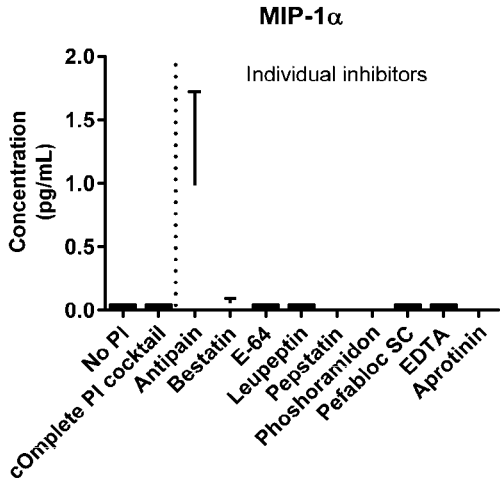
Figure 12Q:
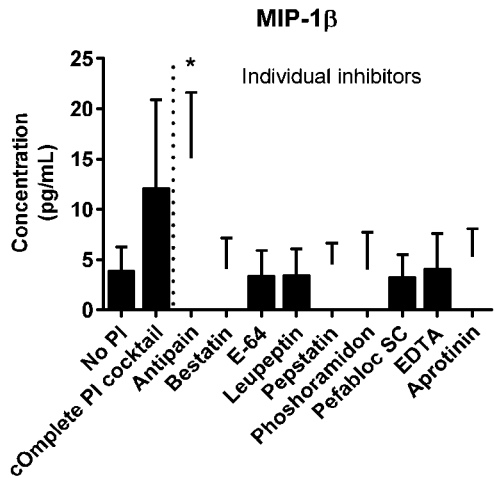
Figure 12R:
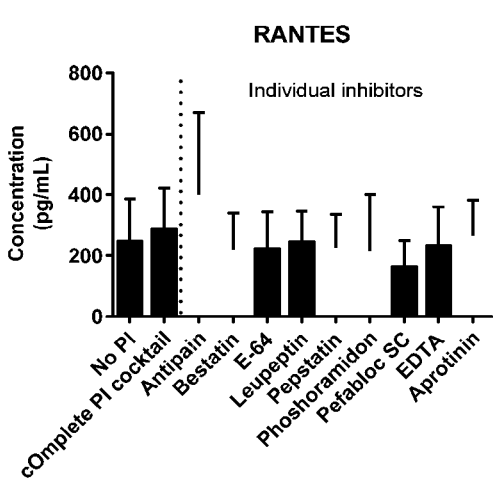
Figure 12S:
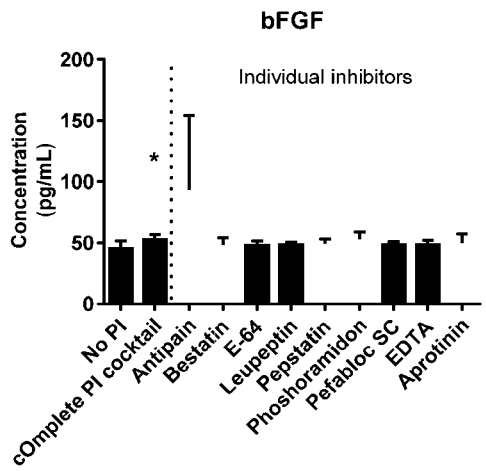
Figure 12T:
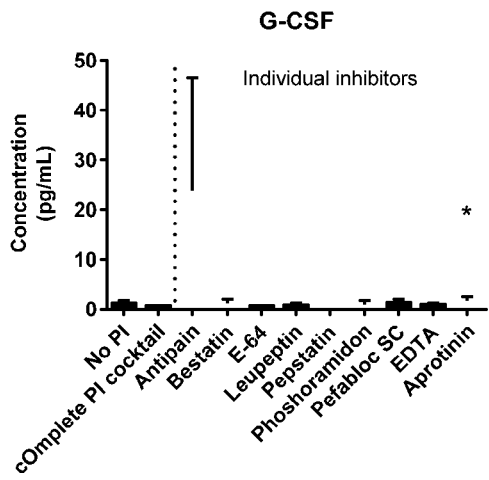
Figure 12U:
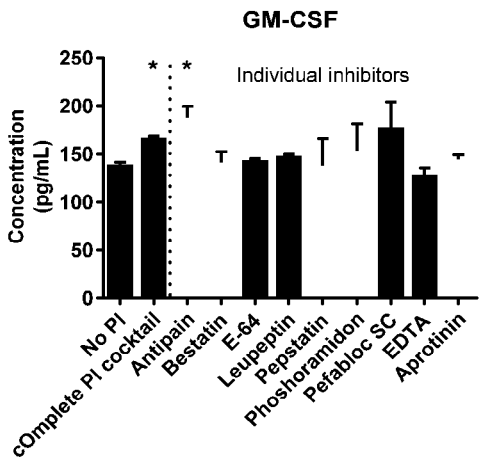
Figure 12V:
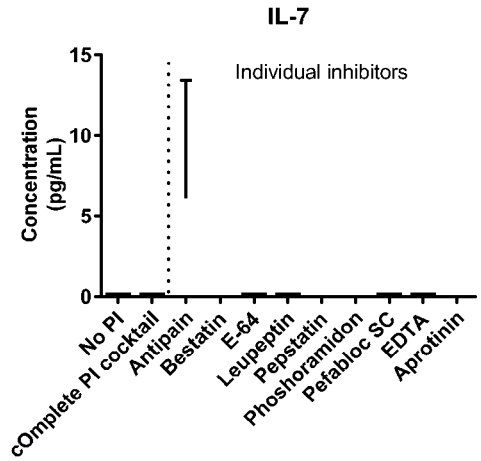
Figure 12W:
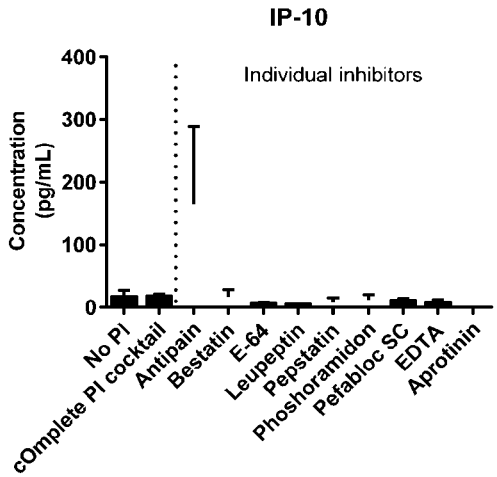
Figure 12X:
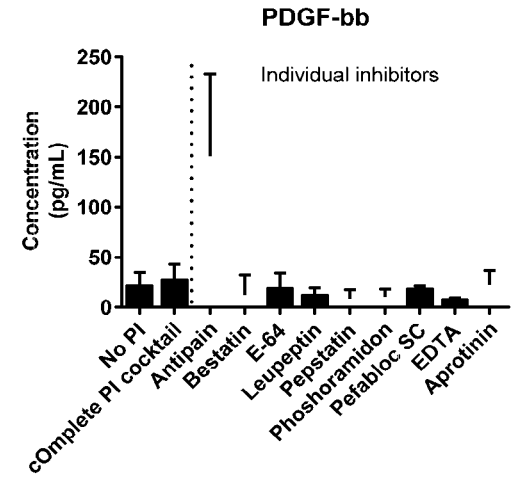
Figure 12Y:
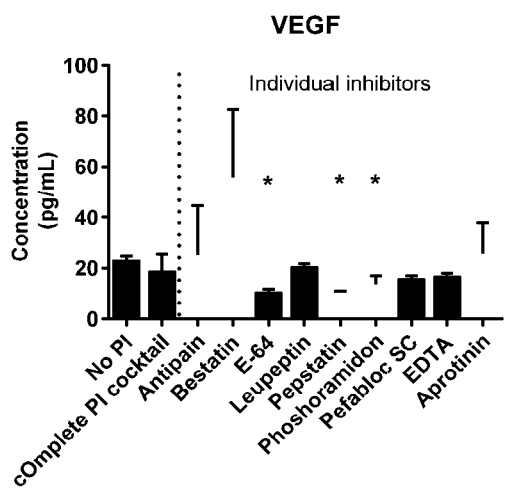
Figure 12Z:
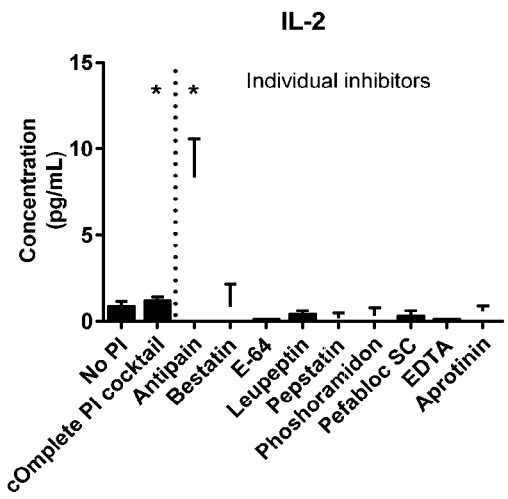
Figure 12A:
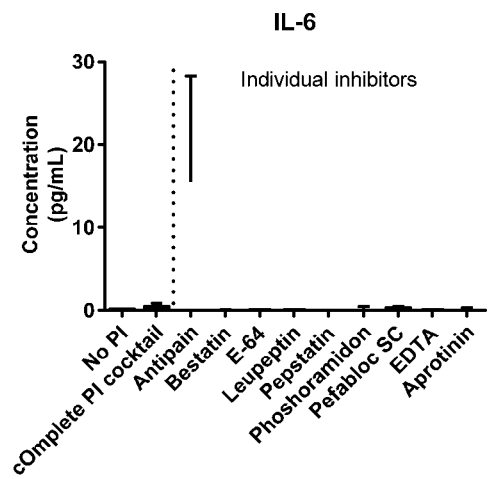
Figure 12B:
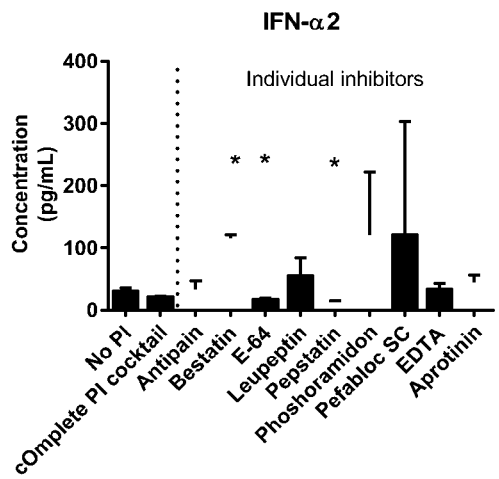
Figure 12C:
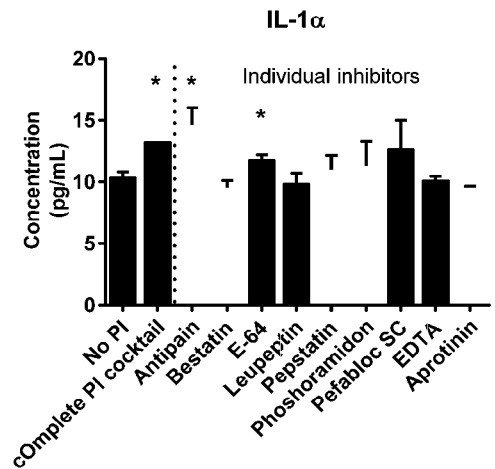
Figure 12D:
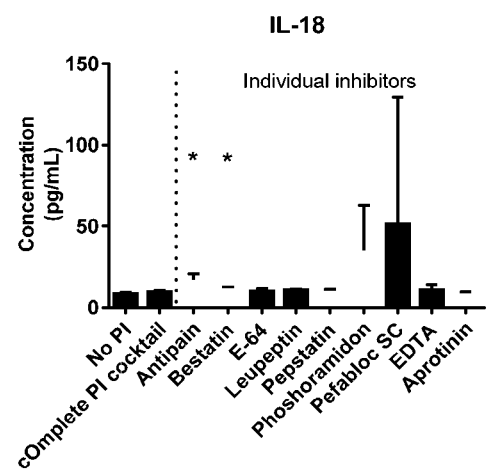
Figure 12E:
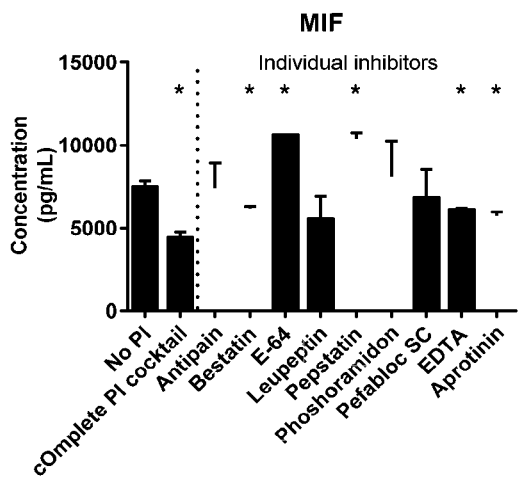
Figure 12F:
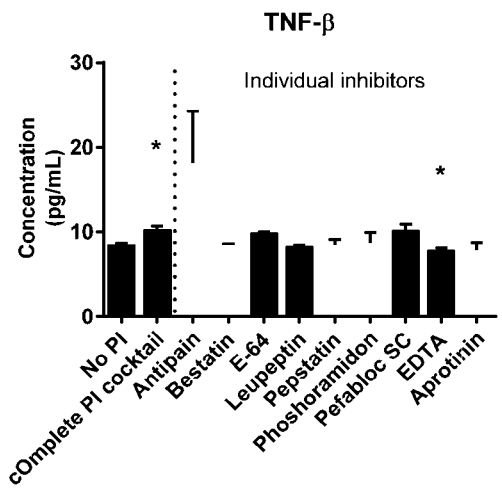
Figure 12G:
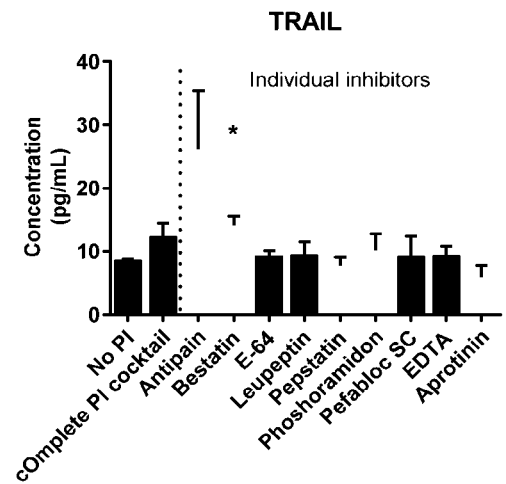
Figure 12H:
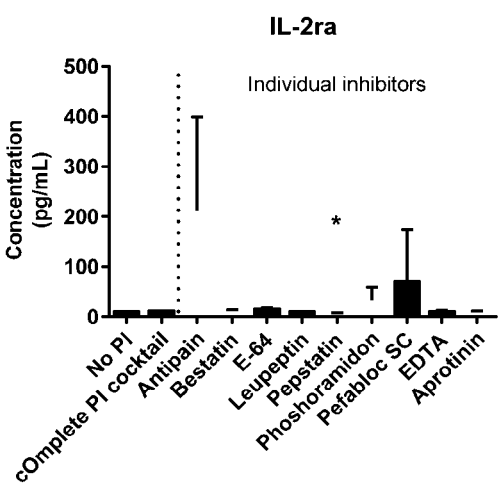
Figure 12I:
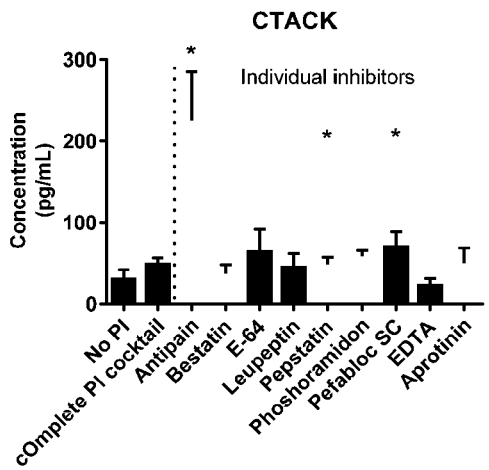
Figure 12J:
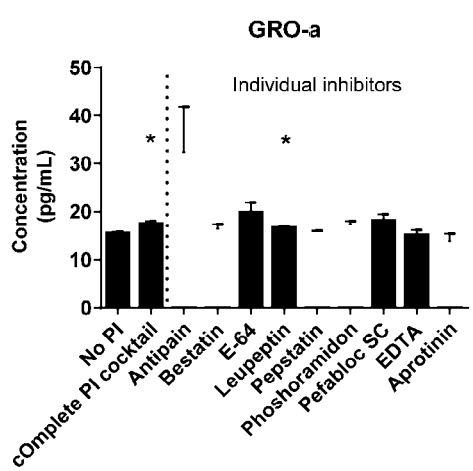
Figure 12K:
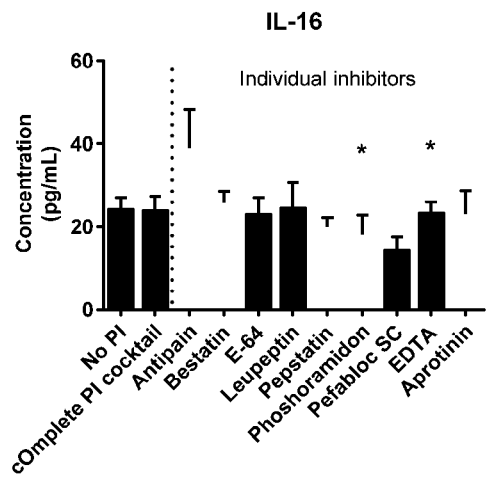
Figure 12L:
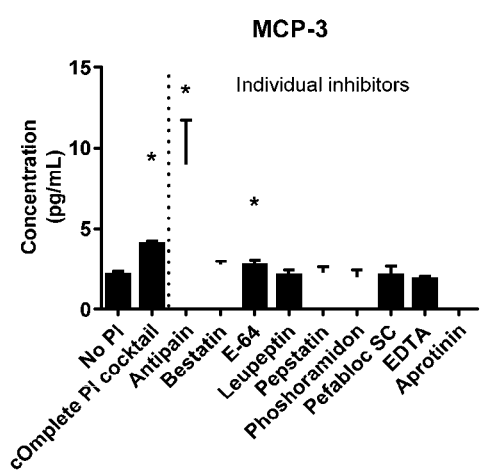
Figure 12M:
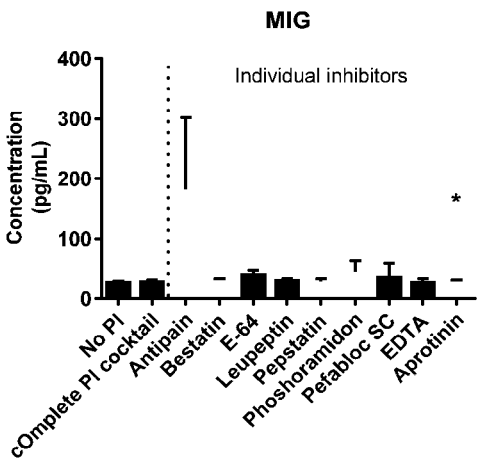
Figure 12N:
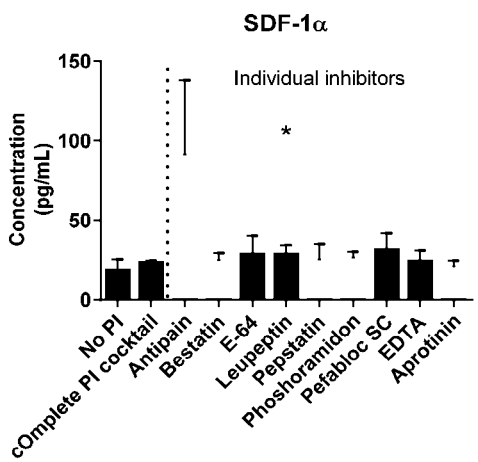
Figure 12O:
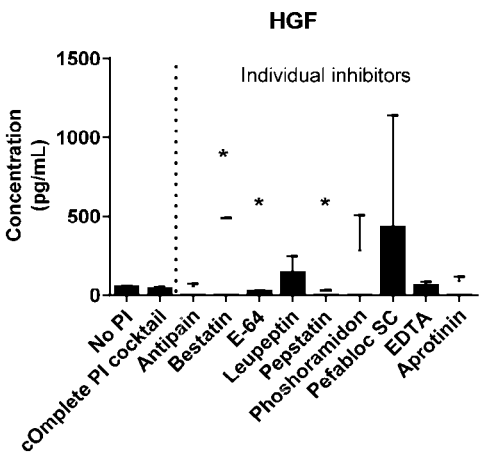
Figure 12P:
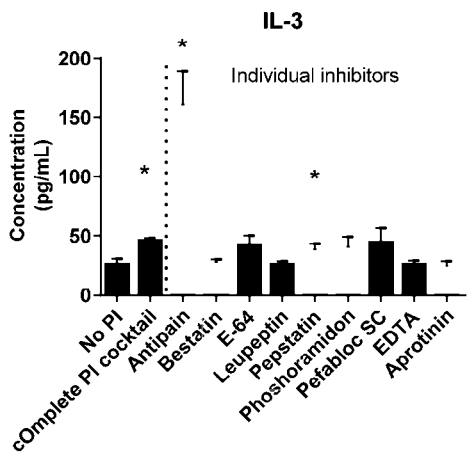
Figure 12Q:
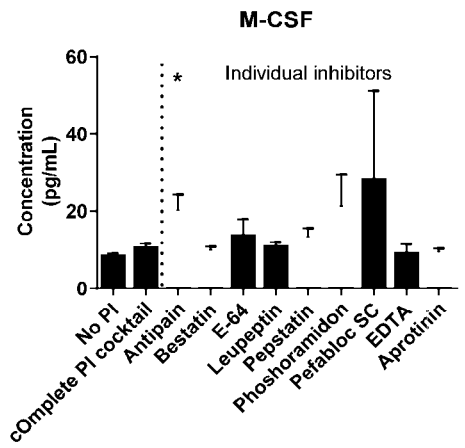
Figure 12R:
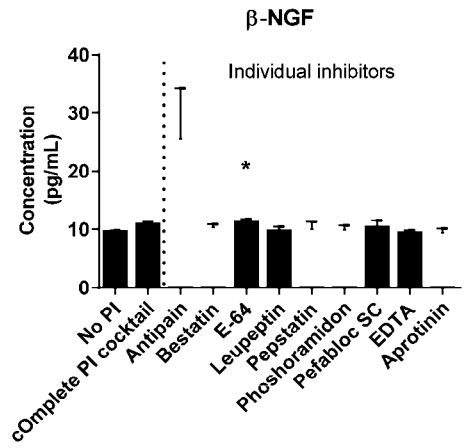
Figure 12S:
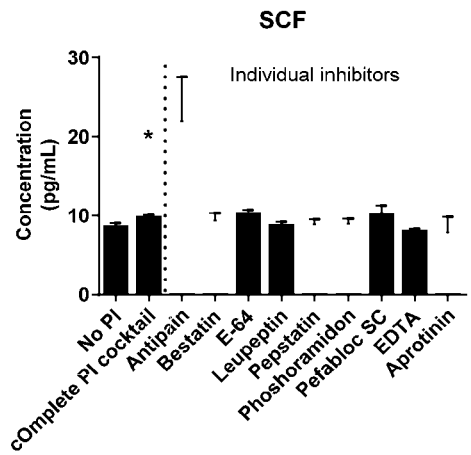
Figure 12T:
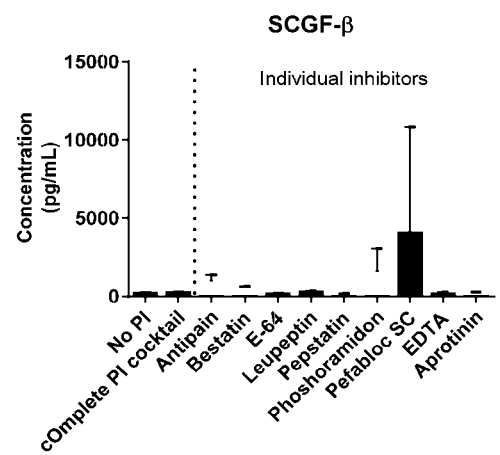
Figure 12U:
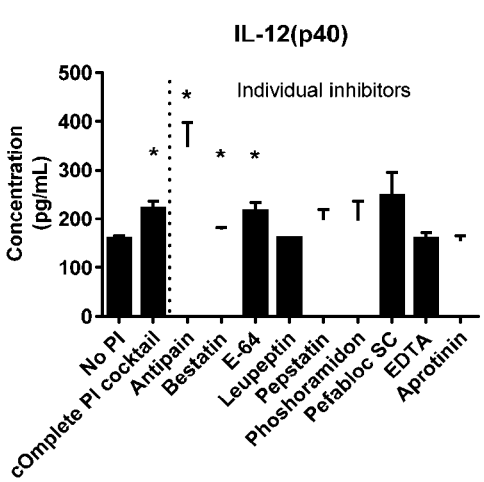
Figure 12V:
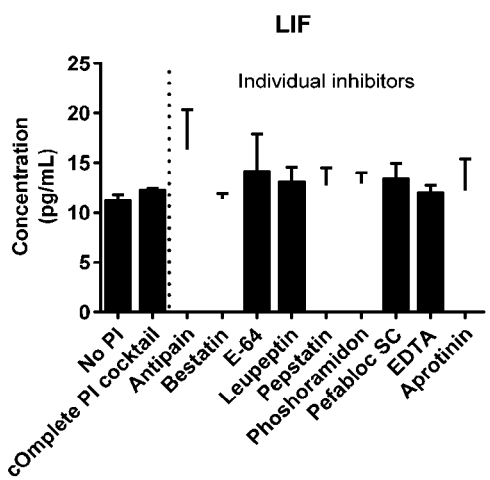
Figure 13A:
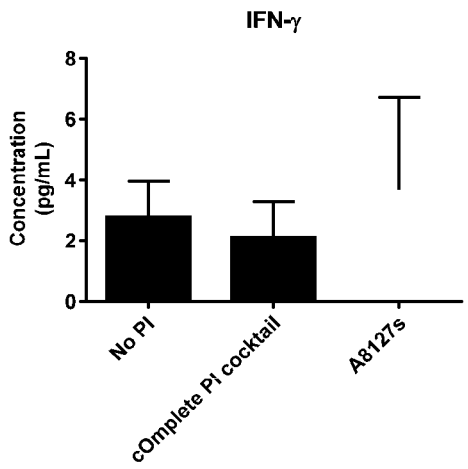
FIG. 13A-13VV is a series of graphs showing the effect of protease inhibitor cocktails on cytokines released from red blood cells from healthy individuals.
Figure 13B:
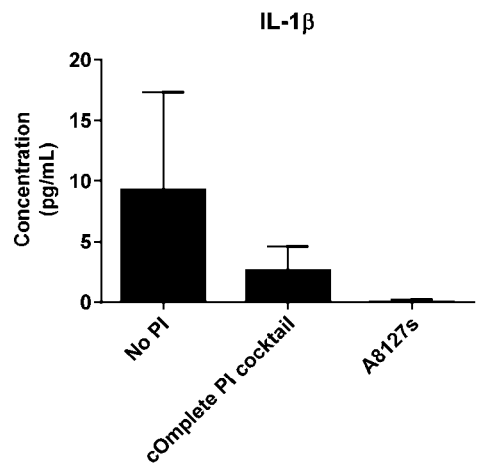
Figure 13C:
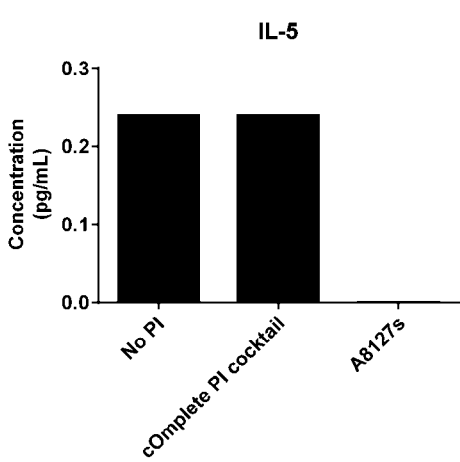
Figure 13D:
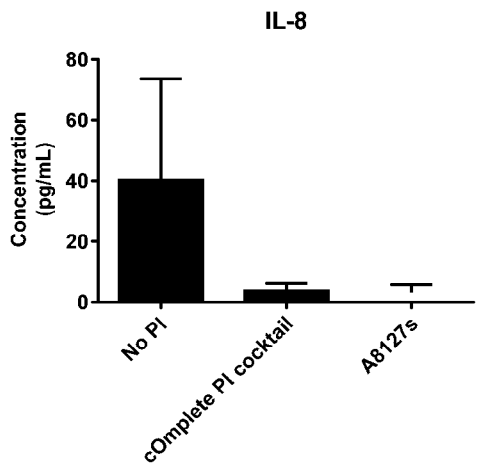
Figure 13E:
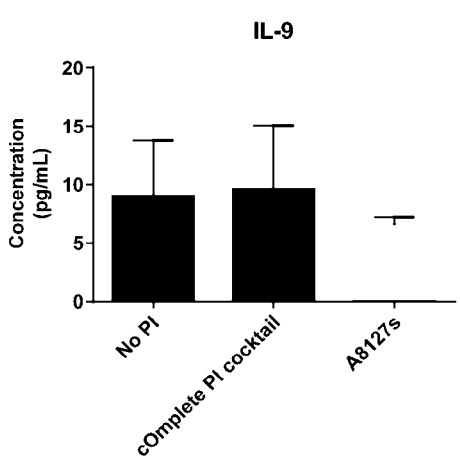
Figure 13F:
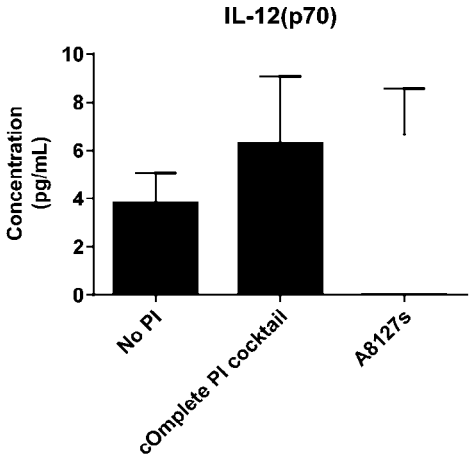
Figure 13G:
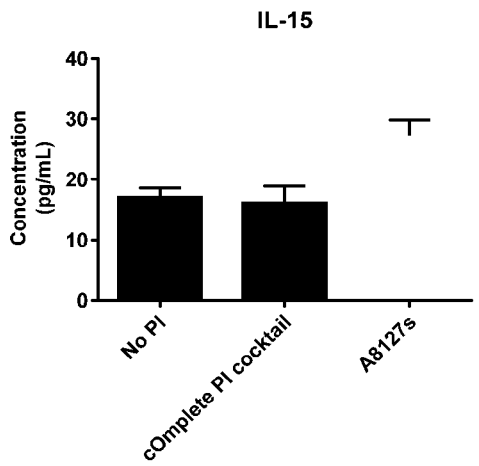
Figure 13H:
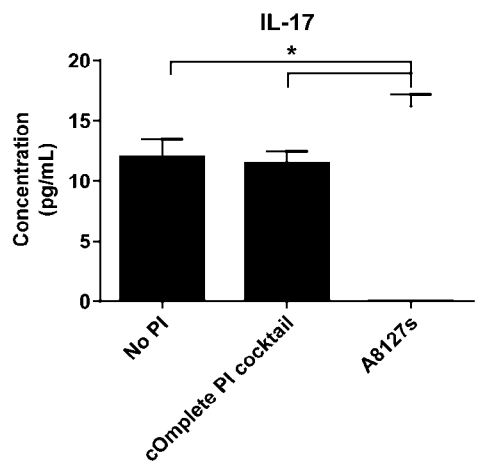
Figure 13I:
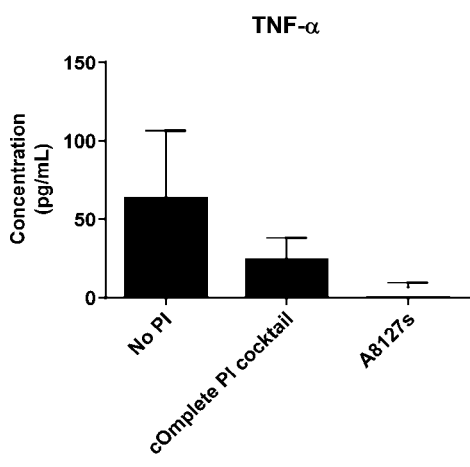
Figure 13J:
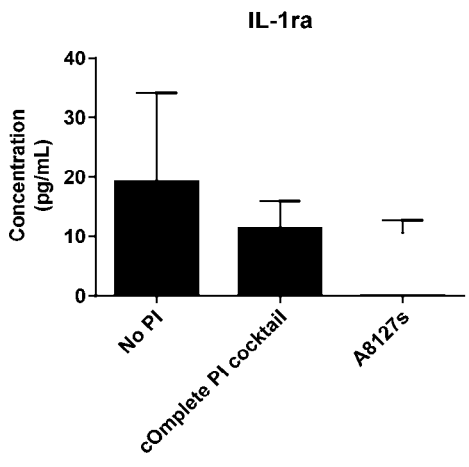
Figure 13K:
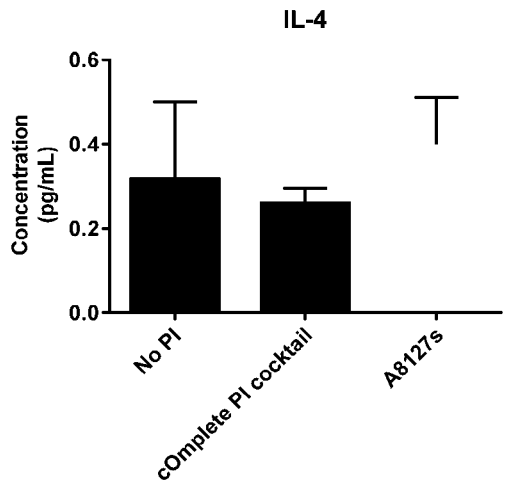
Figure 13L:
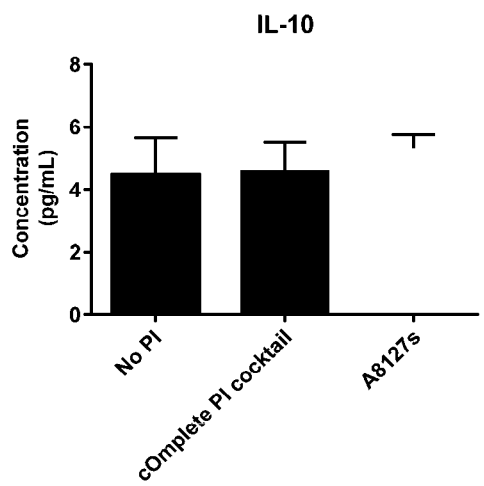
Figure 13M:
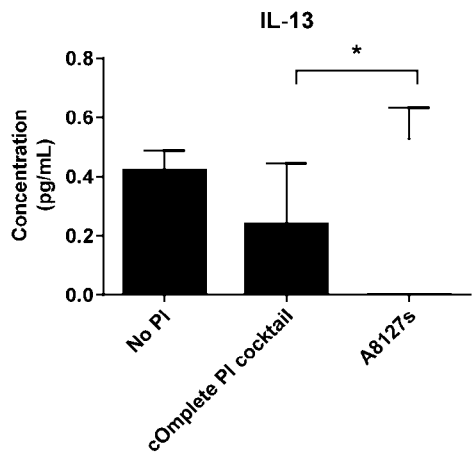
Figure 13N:
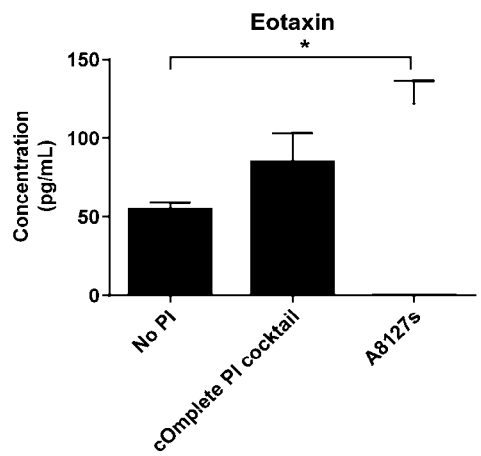
Figure 13O:
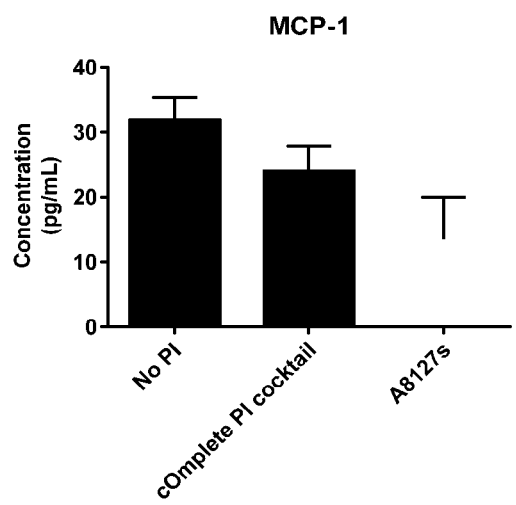
Figure 13P:
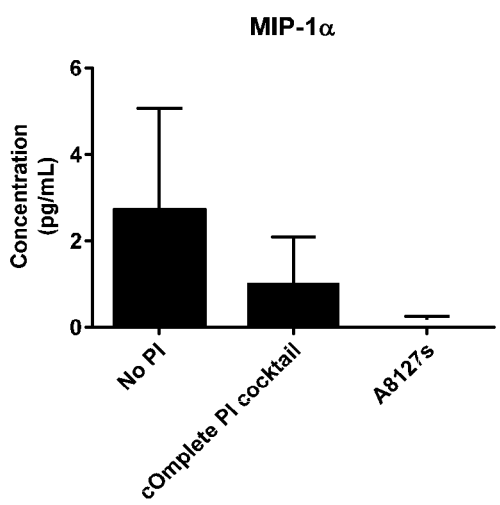
Figure 13Q:
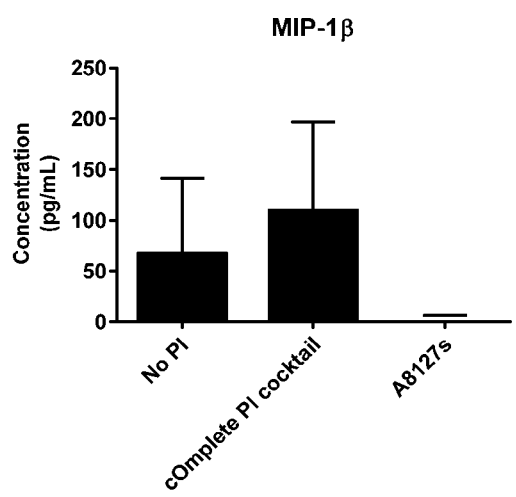
Figure 13R:
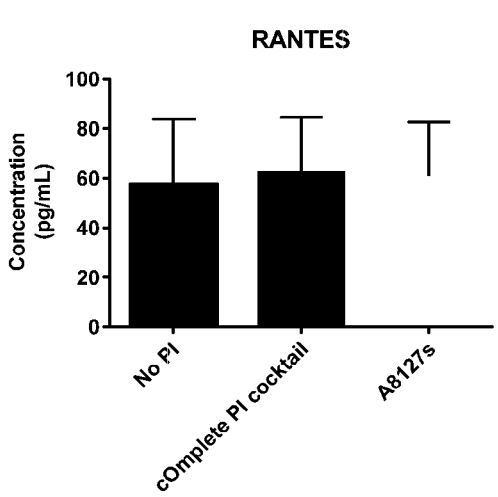
Figure 13S:
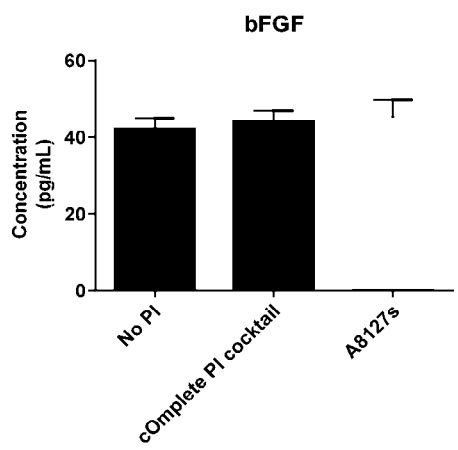
Figure 13T:
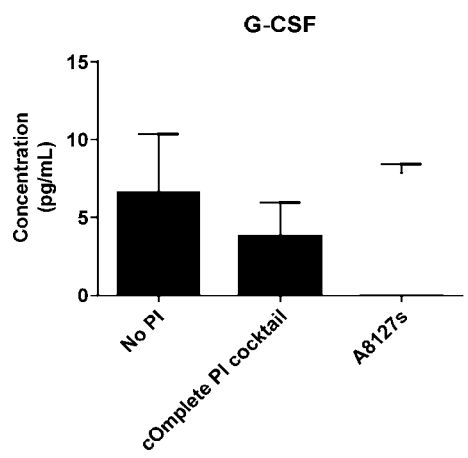
Figure 13U:
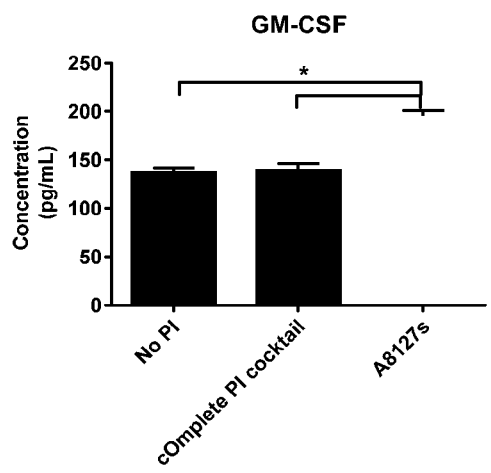
Figure 13V:
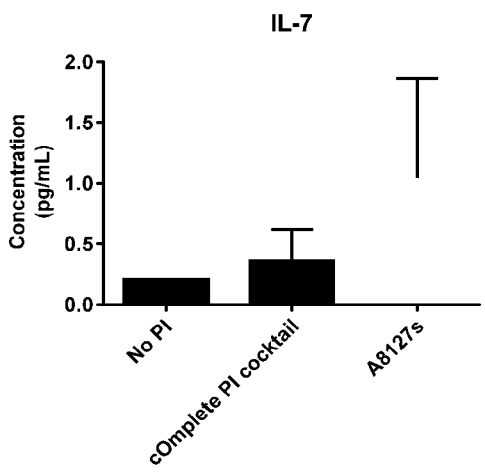
Figure 13W:
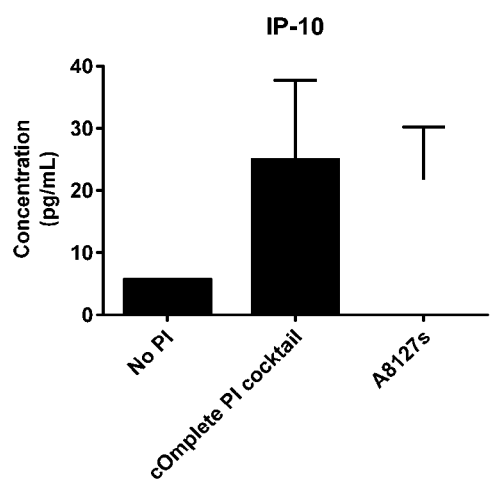
Figure 13X:
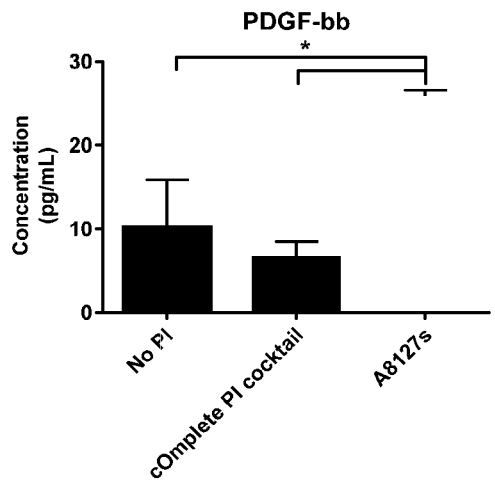
Figure 13Y:
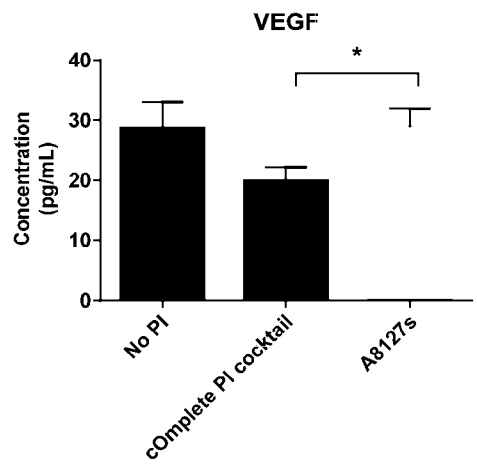
Figure 13Z:
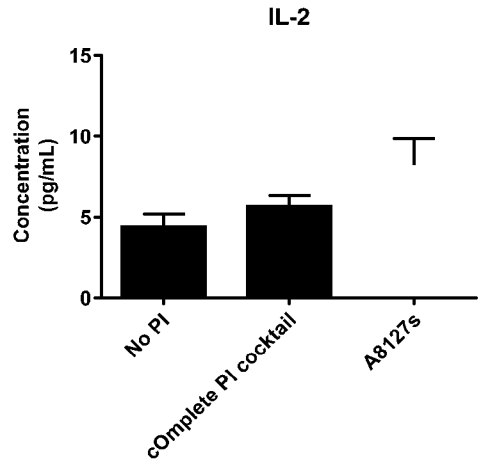
Figure 13A:
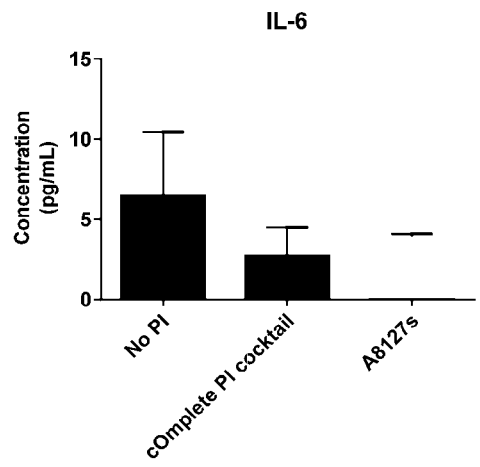
Figure 13B:
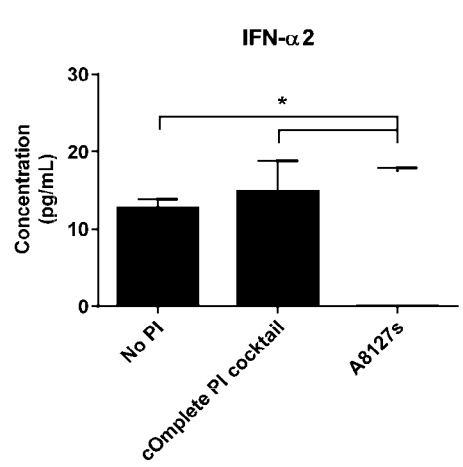
Figure 13C:
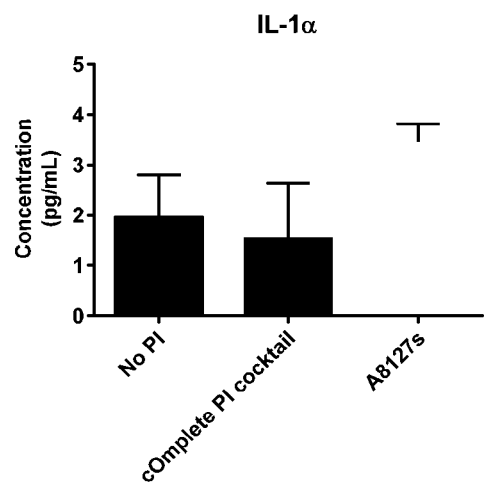
Figure 13D:
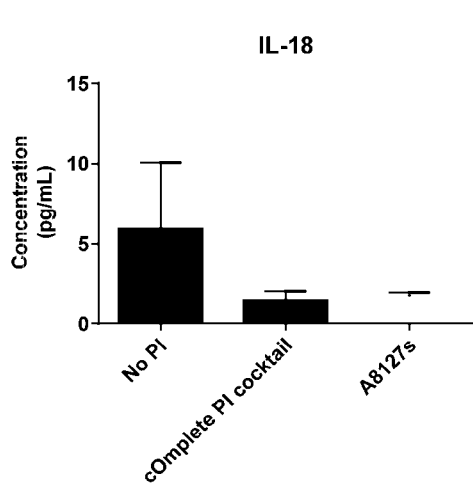
Figure 13E:
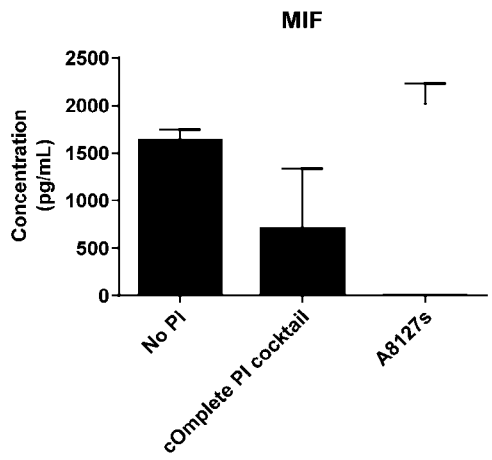
Figure 13F:
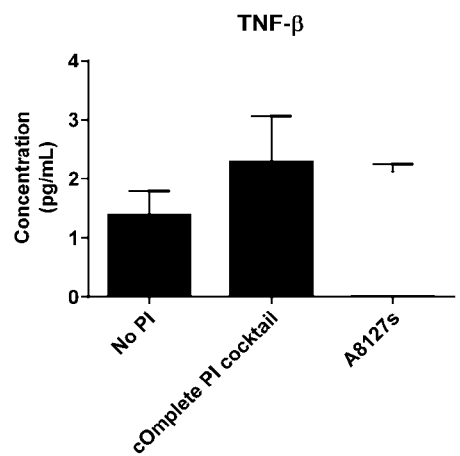
Figure 13G:
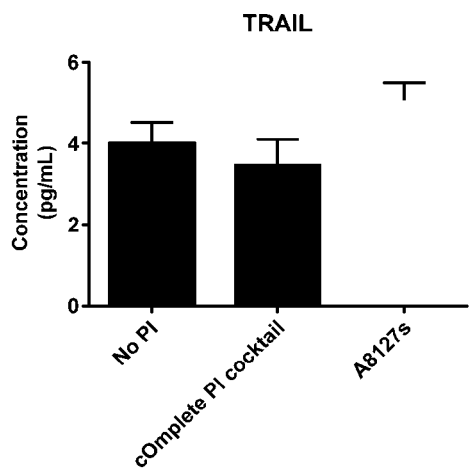
Figure 13H:
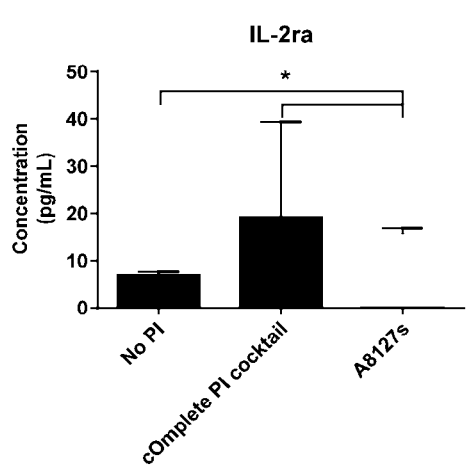
Figure 13I:
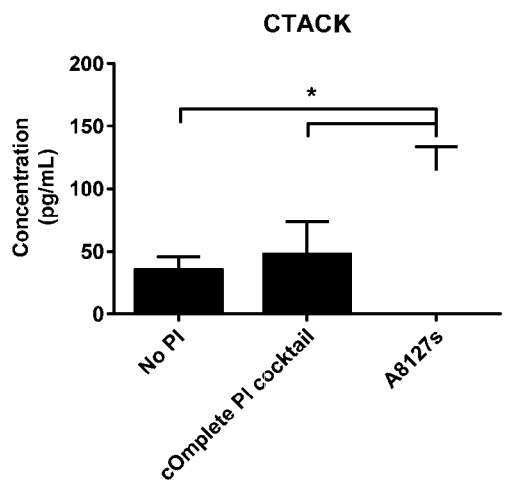
Figure 13J:
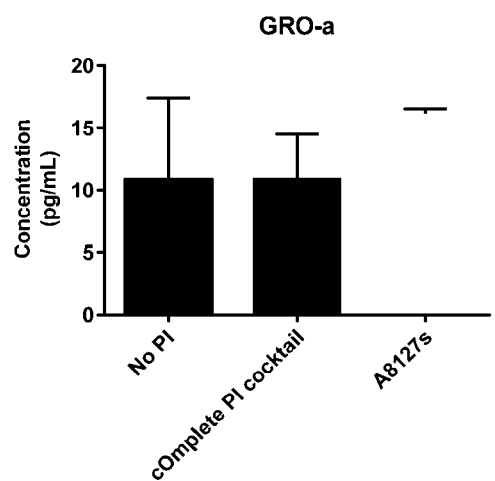
Figure 13K:
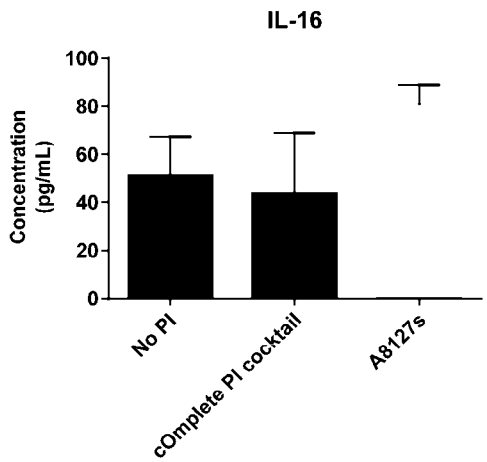
Figure 13L:
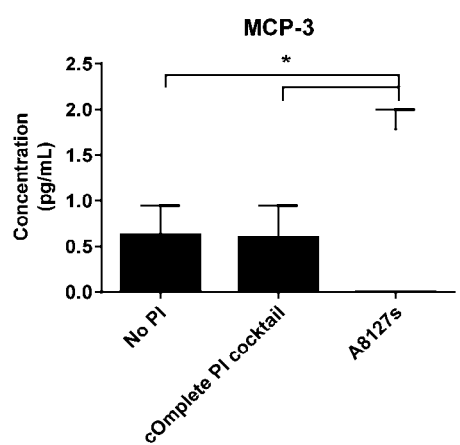
Figure 13M:
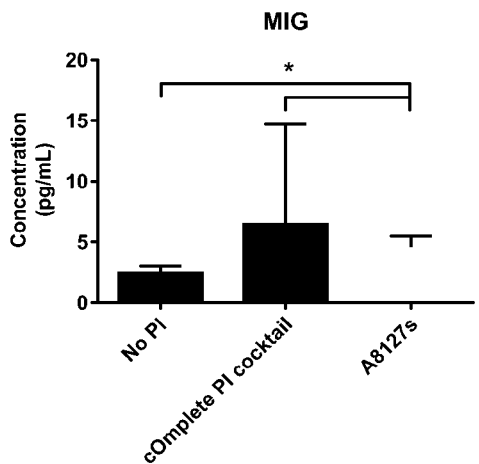
Figure 13N:
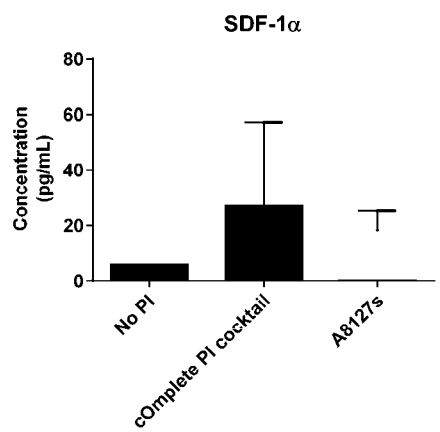
Figure 13O:
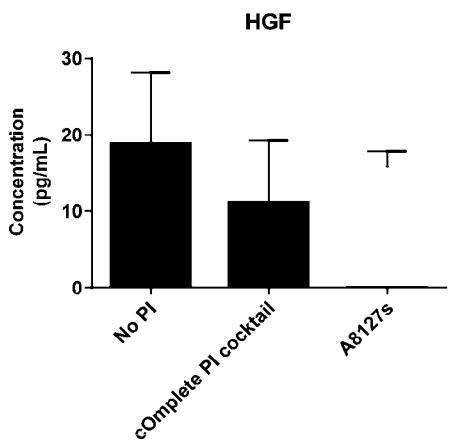
Figure 13P:
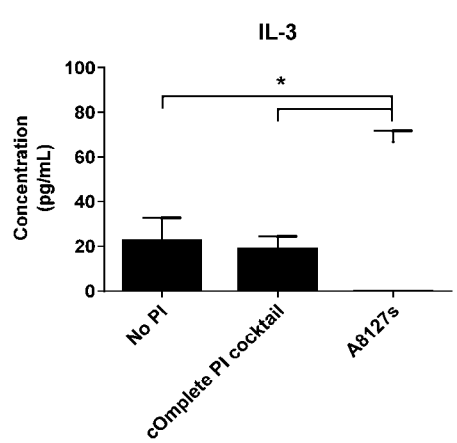
Figure 13Q:
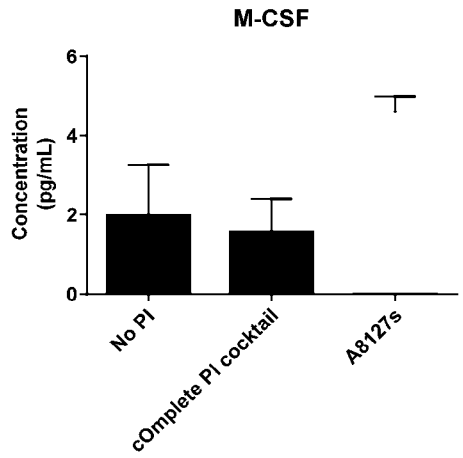
Figure 13R:
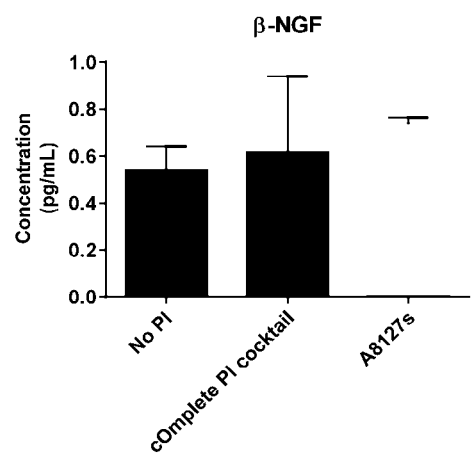
Figure 13S:
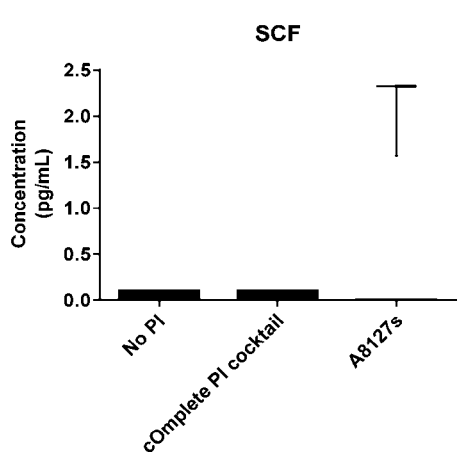
Figure 13T:
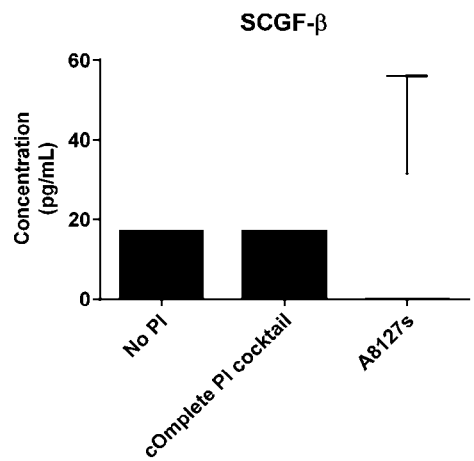
Figure 13U:
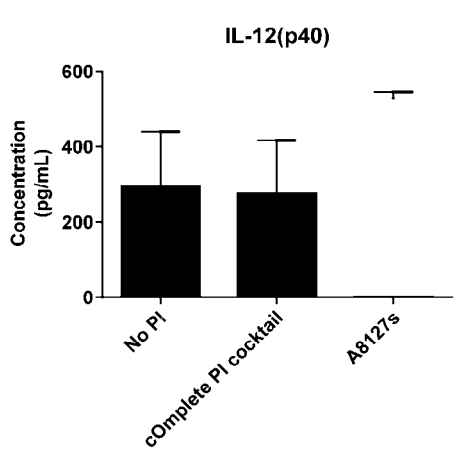
Figure 13V:
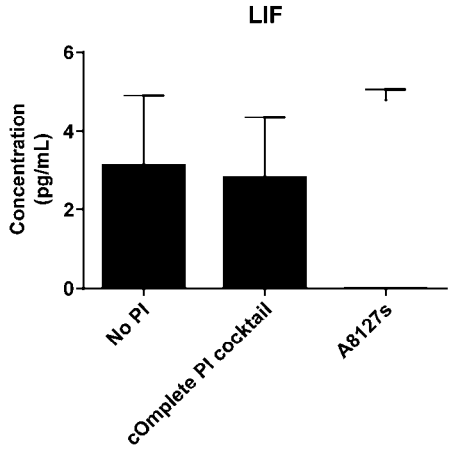

To determine the effect of a combination of protease inhibitors on the release of proteins from red blood cells, a protein profile was obtained from healthy red blood cells incubated with protease inhibitor cocktails. The protease inhibitor cocktail A8127s was produced by combining the individual protease inhibitors in Table 5 (antipain-dihydrochloride 50 µg/mL; bestatin 40 µg/mL; E-64 10 µg/mL; leupeptin 5 µg/mL; pepstatin 0.7 µg/mL; phosphoramidon 330 µg/mL; Pefabloc SC 1 mg/mL; EDTA-Naz 0.5 mg/mL; aprotinin 2 µg/mL), each of which had a significant effect on cytokine release from healthy red blood cells individually (Table 6 and FIG. 12A-FIG. 12VV). Healthy red blood cells were incubated with A8127s and the cOmplete protease inhibitor cocktail (Roche). A8127s produced statistically significant changes in IL-17, Eotaxin, GM-CSF, PDGF-bb, INF-a2, IL-2ra, CTACK, MCP-3, MIG and IL-3 (FIG. 13A-FIG. 13VV), while the cOmplete protease inhibitor cocktail did not produce significant changes to cytokine concentration in the experiment.

Overall, the data demonstrated that protease inhibitors produced significant changes in the concentration of cytokines released from red blood cells isolated from healthy individuals. The complex relationship between individual proteases and changes in cytokine concentrations indicated that such effects were unlikely to be only related to the inhibition of non-specific proteolysis of the cytokines. Moreover, comparison of a commercial inhibitor cocktail (Roche complete) and the A8127s protease inhibitor cocktail showed that A8127s has a greater capacity to produce significant changes in the concentration/profile of cytokines released from red blood cells isolated from healthy participants.

Example 9. Effect of Protease Inhibitors on Proteins from Red Blood Cell Membranes To determine if protease inhibitors had an effect on the release of proteins from red blood cell membranes, red blood cell membranes were obtained from isolated red blood cells and whole blood and then incubated with protease inhibitors. Whole blood was collected from healthy volunteers by venepuncture directly into EDTA vacutainers ($k_2$EDTA vacutainers, BD Biosciences). The fractions of blood were collected and processed at room temperature within 4 hours of collection. For multiplex analysis (BioPlex analysis) the samples were stored at −80° C. prior to analysis.

An aliquot of whole blood was collected and frozen at −80° C. The red blood cells were isolated from remaining fresh whole blood using dextran sedimentation as follows. Whole blood was centrifuged (1500 g, 10 minutes) and the upper plasma layer was discarded. The remaining cell pellet was resuspended in an equal volume of sodium chloride (0.15 M). Dextran (6% w/v in 0.15 M sodium chloride) was then added to the cellular suspension at a 1:4 ratio (dextran:cell suspension). The solution was left at room temperature for 30 minutes for red blood cell sedimentation to the bottom of the tube. Then the upper white blood cell rich layer was discarded and the lower red blood cell fraction isolated. The red blood cell fraction was washed once in phosphate buffered saline (PBS, 500 g, 5 minutes), the remaining red blood cell pellet was counted (Coulter Act Diff, Beckman Coulter), and an aliquot of the cells were frozen at −80° C.

For the isolation of red blood cell membranes, frozen aliquots of both whole blood and the isolated red blood cells were subjected to 3 freeze thaw cycles to ensure complete cellular lysis. An aliquot of the lysates (volume equivalent to 40 million red blood cells per 100 µL) was added to PBS at a 1:20 ratio (lysate:PBS). The red blood cell membranes were then isolated by centrifugation out of solution (16,000 g, 20 mins, 4° C.). The upper fraction was then discarded and the resulting membranes were then diluted to 400 million cells/mL in PBS and were incubated at 37° C. and 5% $CO_2$ for 24 hours. Some samples were also incubated with the protease inhibitors in Table 5.

After incubation, the resulting conditioned PBS was isolated by centrifugation (16,000 g, 20 minutes, 4° C.). The samples were stored at −80° C. until analysis. The conditioned PBS samples were then analysed on a multiplex cytokine assay. The 27-plex human cytokine panel assays for FGF basic, Eotaxin, G-CSF, GM-CSF, IFN-γ, IL-1β, IL-1ra, IL-2, IL-4, IL-5, IL-6, IL-7, IL-8, IL-9, IL-10, IL-12(p70), IL-13, IL-15, IL-17, IP-10, MCP-1, MIP-1α, MIP-1β, PDGF-BB, RANTES, TNF-α, and VEGF. The assay was performed according to manufacturer's instructions using an automated magnetic wash station (BioPlex Pro II, Bio-Rad) for the washing steps. The assay was run on the Luminex® 200™ system (Bio-Rad) and fluorescent values were collected. The calibration curve for each cytokine was analysed with 5 parametric logistic curve regression using BioPlex manager software (ver. 5.0, Bio-Rad, USA).

Figure 14A:
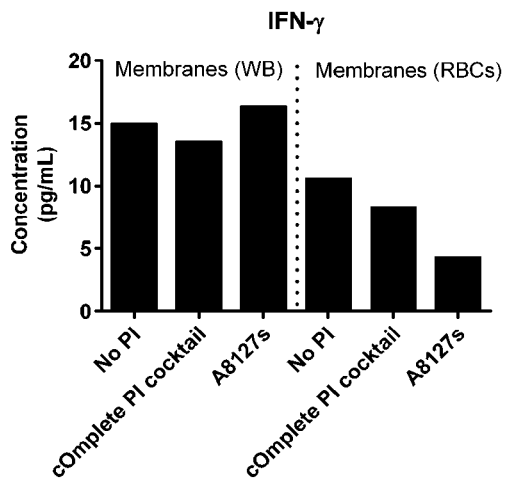
FIG. 14A-14AA is a series of graphs showing the effect of protease inhibitor cocktails on cytokines released from red blood cell membranes from healthy individuals.
Figure 14B:
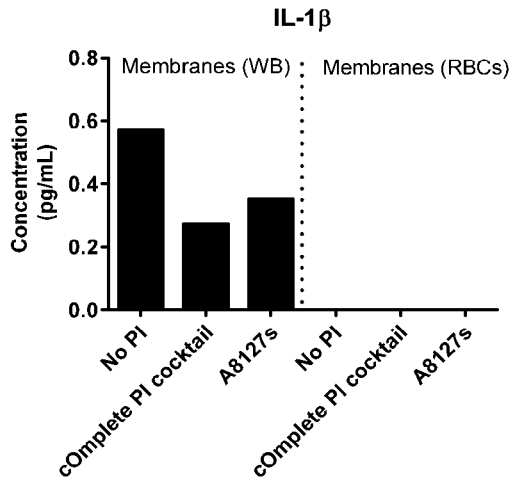
Figure 14C:
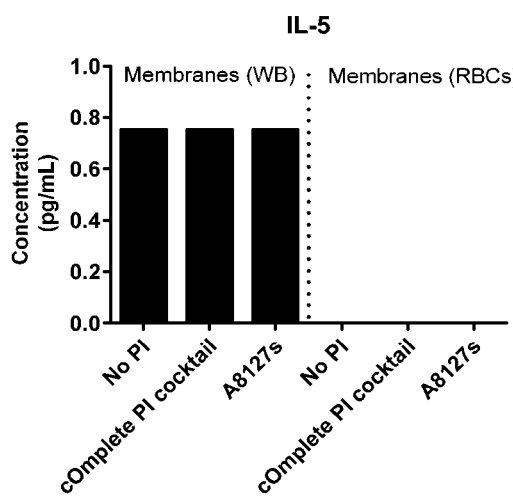
Figure 14D:
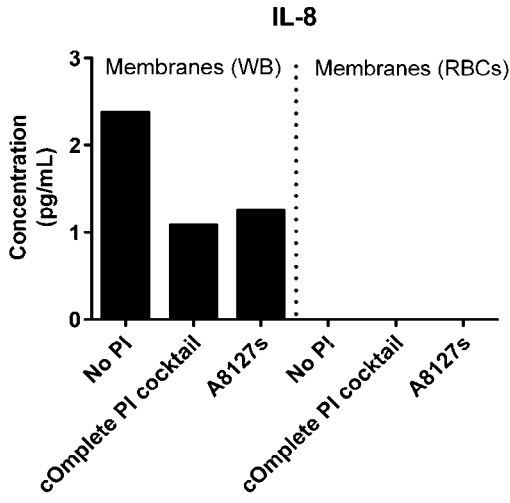
Figure 14E:
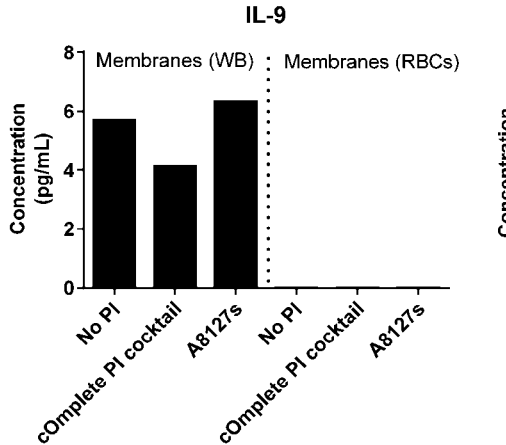
Figure 14F:
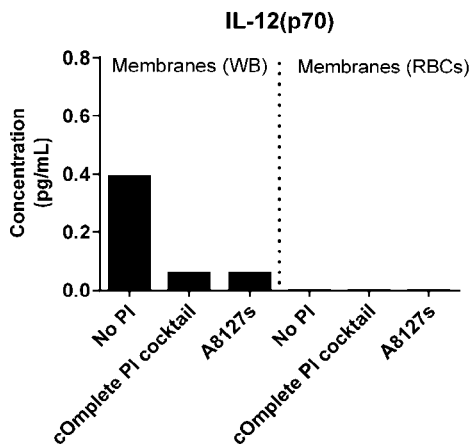
Figure 14G:
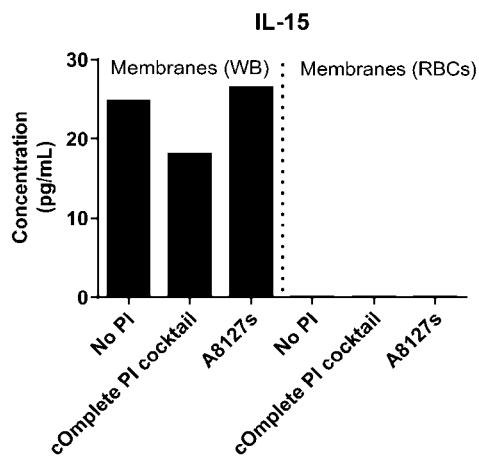
Figure 14H:
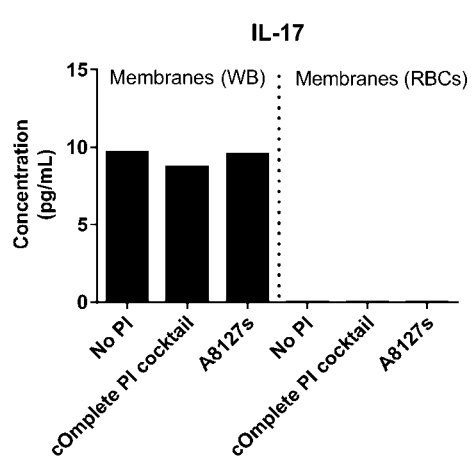
Figure 14I:
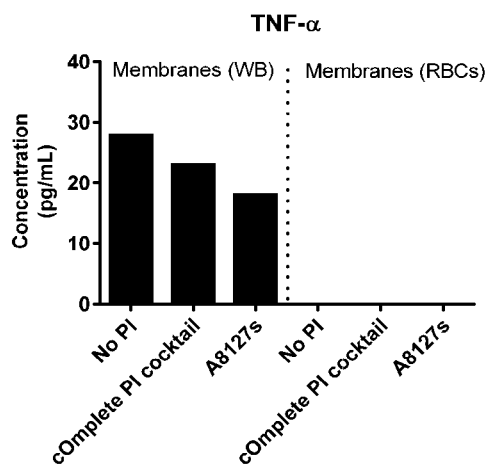
Figure 14J:
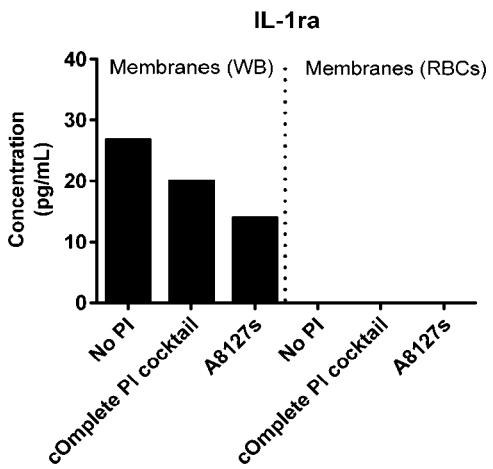
Figure 14K:
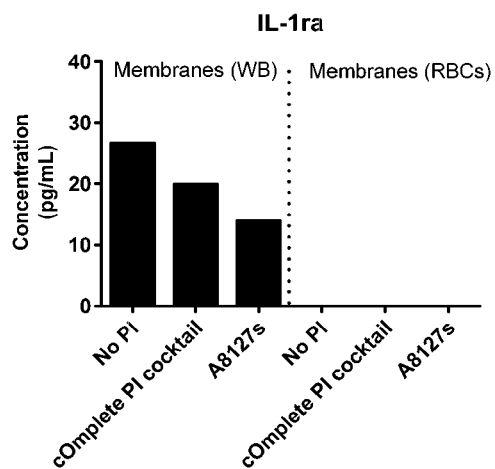
Figure 14L:
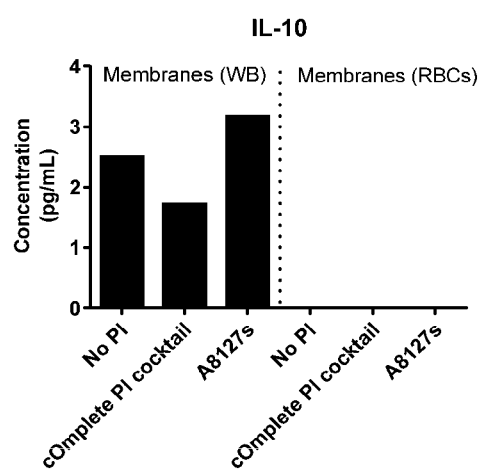
Figure 14M:
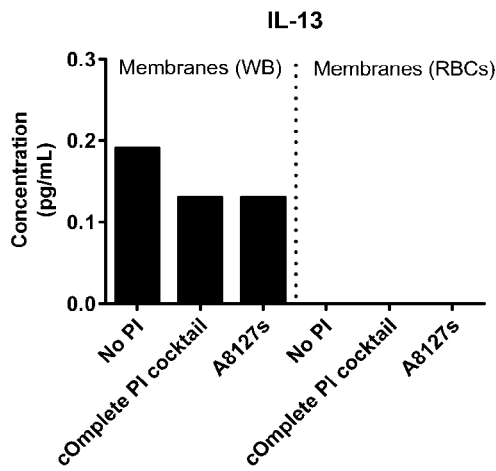
Figure 14N:
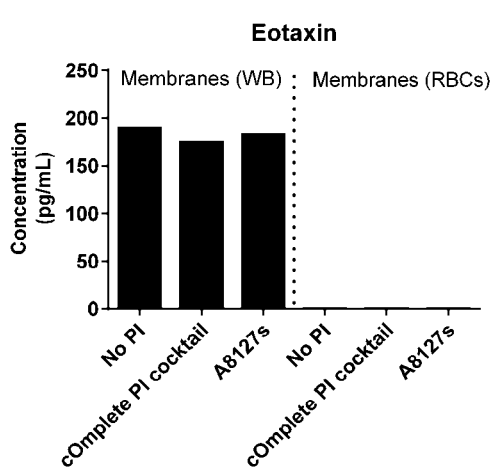
Figure 14O:
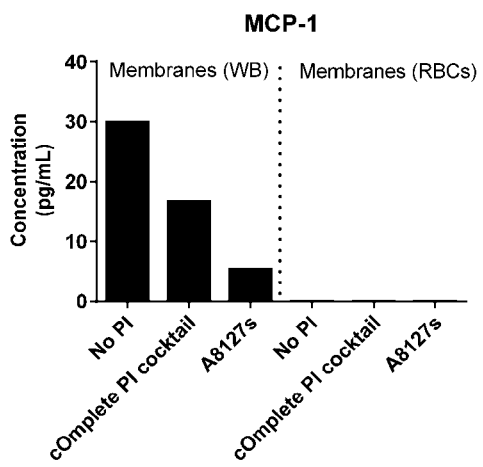
Figure 14P:
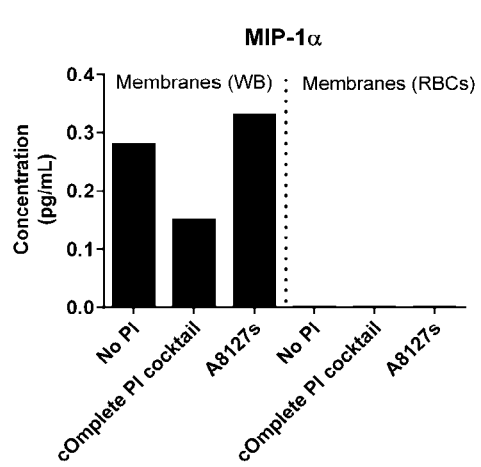
Figure 14Q:
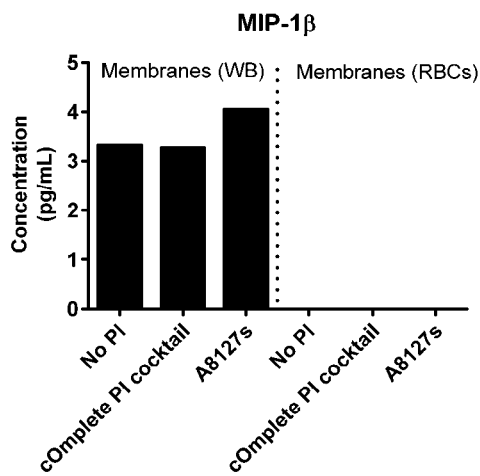
Figure 14R:
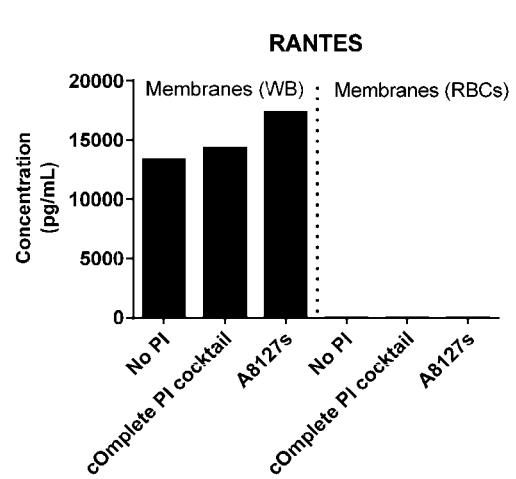
Figure 14S:
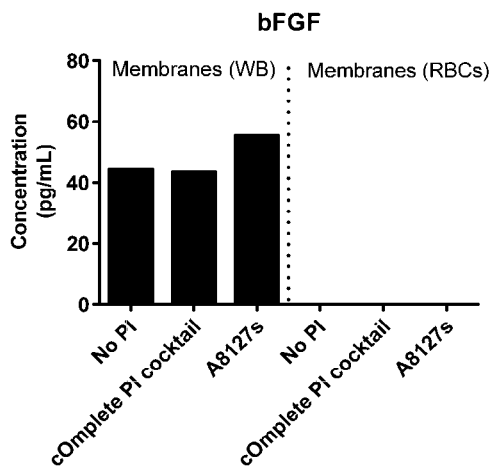
Figure 14T:
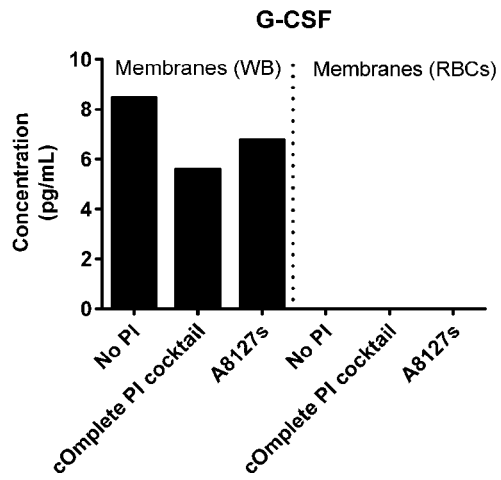
Figure 14U:
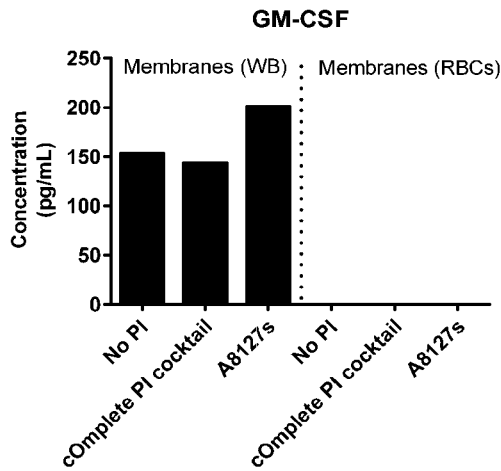
Figure 14V:
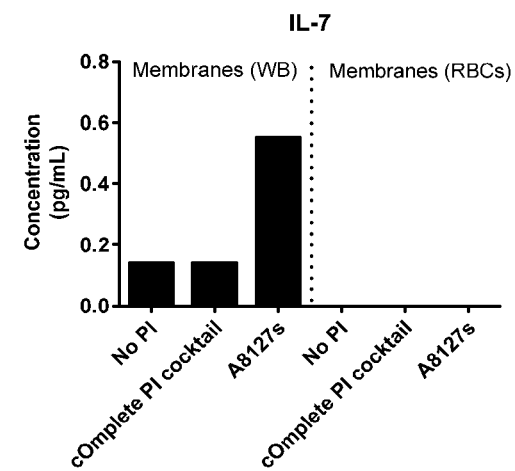
Figure 14W:
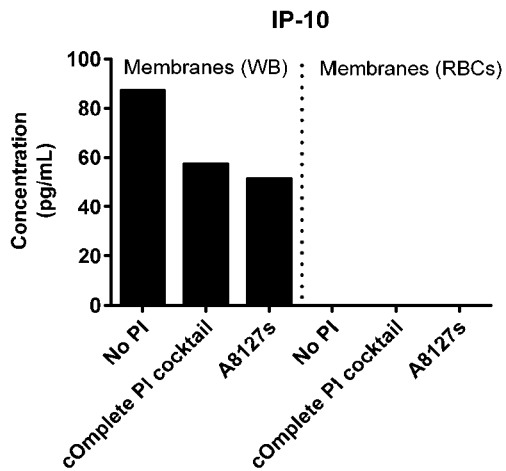
Figure 14X:
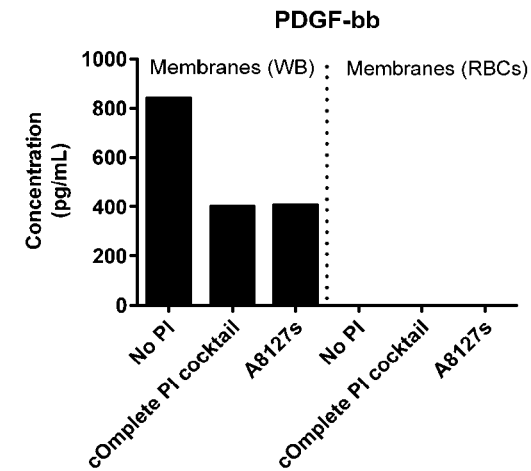
Figure 14Y:
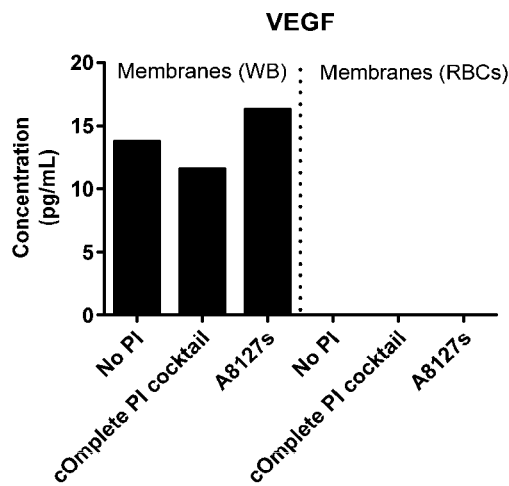
Figure 14Z:
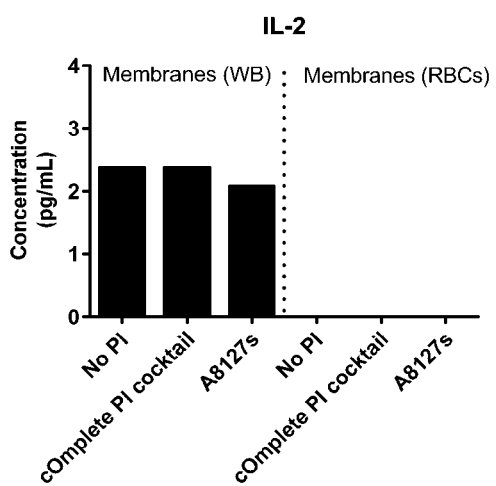
Figure 14A:
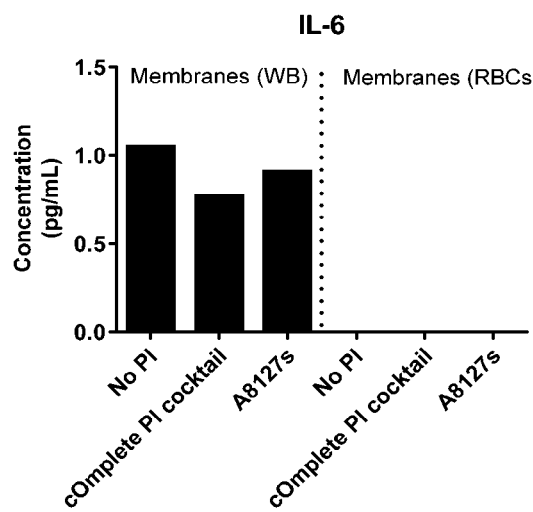

FIG. 14A-FIG. 14AA shows the concentration of several proteins in the red blood cell membranes incubated in conditioned PBS in either the presence or absence of protease inhibitor cocktails (A8127s and cOmplete (Roche)). The data demonstrated that even at lower red blood cell numbers, a significant number of cytokines were still present at readily detectable levels in red blood cell membrane-conditioned PBS (from both whole blood and enriched red blood cell lysates). The concentration of 400 million red blood cells per mL, was equivalent to only 80 µL of whole blood per mL (assuming a normal concentration of $5 \times 10^9$ red blood cells per mL of fresh whole blood). Because the experiment was carried out in only 200 µL of the 400 million cells/mL solution, it follow that a starting sample of only 16 µL of whole blood would be sufficient to detect the cytokine concentrations observed above.

Example 10. Effect of Protease Inhibitors on Red Blood Cell Proteins from Cancer Cohorts A change in the presence or levels of numerous proteins characterizes a variety of diseases. In particular, cancer is a disease involving differential levels of, among other proteins, inflammatory proteins (e.g., cytokines). Thus, the concentration of proteins from the red blood cells from those having colorectal cancer and lymphoma was investigated.

Whole blood was collected from volunteers with by venepuncture directly into EDTA vacutainers ($k_2$EDTA vacutainers, BD Biosciences). The fractions of blood were collected and processed at room temperature within 4 hours of collection. For multiplex analysis (BioPlex analysis) the samples were stored at −80° C. prior to analysis. The red blood cells were isolated using dextran sedimentation as follows. Whole blood was centrifuged (1500 g, 10 minutes) and the upper plasma layer was discarded. The remaining cell pellet was resuspended in an equal volume of sodium chloride (0.15 M). Dextran (6% w/v in 0.15 M sodium chloride) was then added to this cellular suspension at a 1:4 ratio (dextran:cell suspension). The solution was left at room temperature for 30 minutes for red blood cell sedimentation to the bottom of the tube. The upper white blood cell rich layer was discarded and the lower red blood cell fraction was isolated. The red blood cell fraction was washed once in phosphate buffered saline (PBS, 500 g, 5 minutes) and the remaining red blood cell pellet was counted (Coulter Act Diff, Beckman Coulter). The red blood cells were then diluted to 400 million cells/mL in PBS and incubated at 37° C. and 5% $CO_2$ for 24 hours. Some samples were also incubated with the individual protease inhibitors in Table 5, a commercial protease inhibitor cocktail (cOmplete, Roche), or the A8127s protease inhibitor cocktail during the PBS incubation. The A8127s protease inhibitor cocktail comprised antipain-dihydrochloride (50 µg/mL); bestatin (40 µg/mL); E-64 (10 µg/mL); leupeptin (5 µg/mL); pepstatin (0.7 µg/mL); phosphoramidon (330 µg/mL); Pefabloc SC (1 mg/mL); EDTA-$Na_2$ (0.5 mg/mL); and aprotinin (2 µg/mL).

After incubation, the resulting conditioned PBS was isolated by centrifugation (500 g, 5 minutes). The samples were stored at −80° C. The conditioned PBS samples were then analysed on a 27-plex human cytokine panel that assays for FGF basic, Eotaxin, G-CSF, GM-CSF, IFN-γ, IL-1β, IL-1ra, IL-2, IL-4, IL-5, IL-6, IL-7, IL-8, IL-9, IL-10, IL-12(p70), IL-13, IL-15, IL-17, IP-10, MCP-1, MIP-1α, MIP-1β, PDGF-BB, RANTES, TNF-α, and VEGF (Bio-Plex Pro 27-plex, Bio-Rad). The assay was performed according to manufacturer's instructions using an automated magnetic wash station (BioPlex Pro II, Bio-Rad) for the washing steps. The assay was run on the Luminex® 200™ system (Bio-Rad) and fluorescent values were collected. The calibration curve for each cytokine was analysed with 5 parametric logistic curve regression using BioPlex manager software (ver. 5.0, Bio-Rad, USA).

10.1 Colorectal Cancer

Figure 15A:
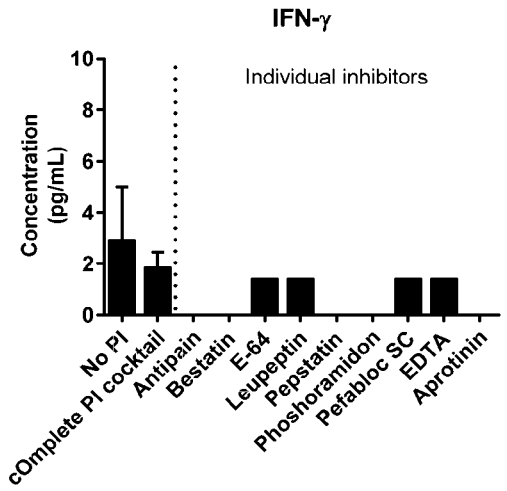
FIG. 15A-15AA is a series of graphs showing the effect of individual protease inhibitors and a protease inhibitor cocktail on cytokines released from red blood cells from individuals having colorectal cancer.
Figure 15B:
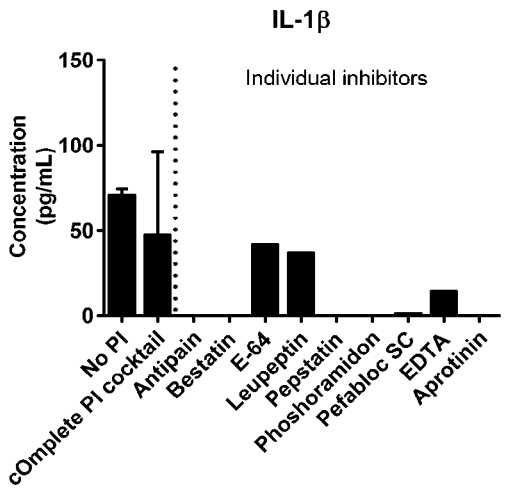
Figure 15C:
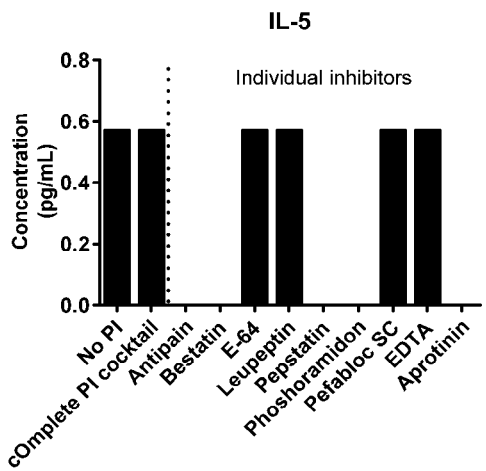
Figure 15D:
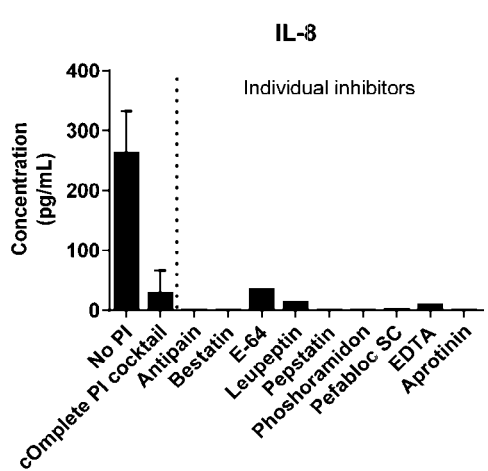
Figure 15E:
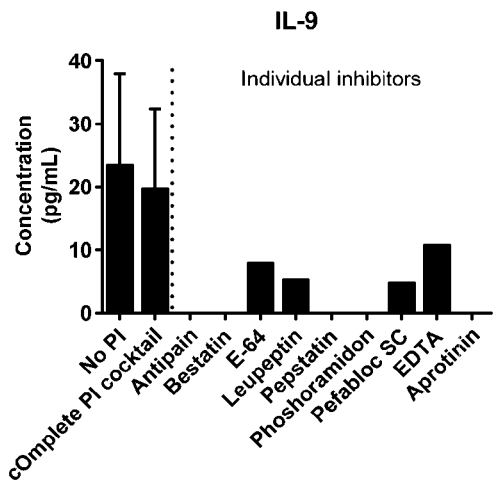
Figure 15F:
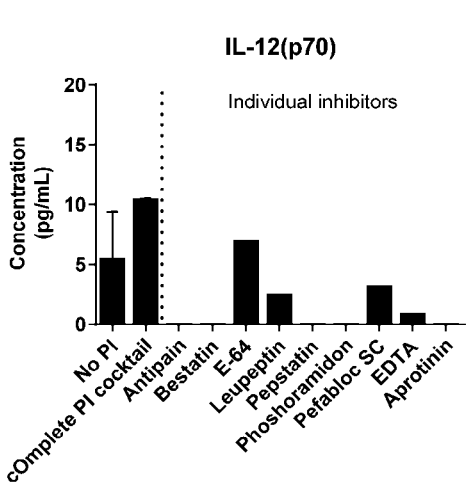
Figure 15G:
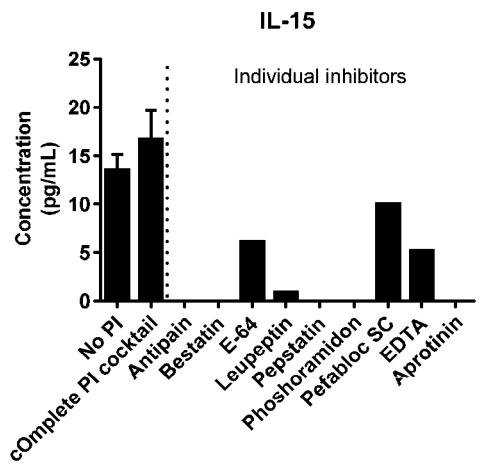
Figure 15H:
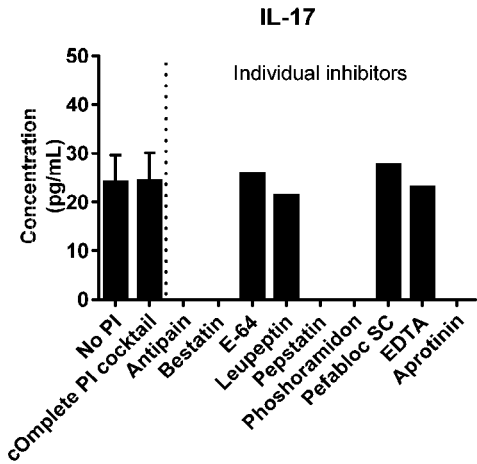
Figure 15I:
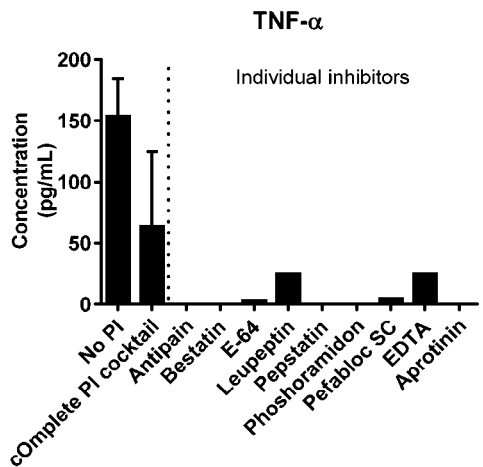
Figure 15J:
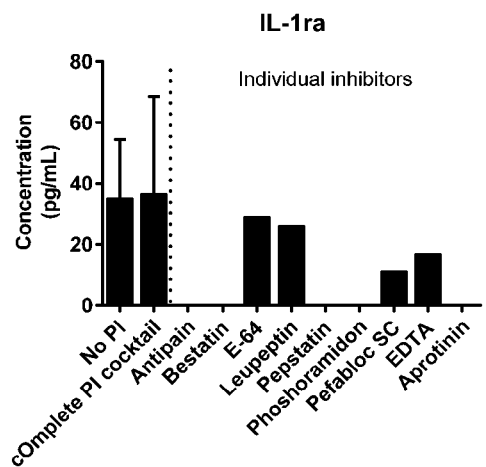
Figure 15K:
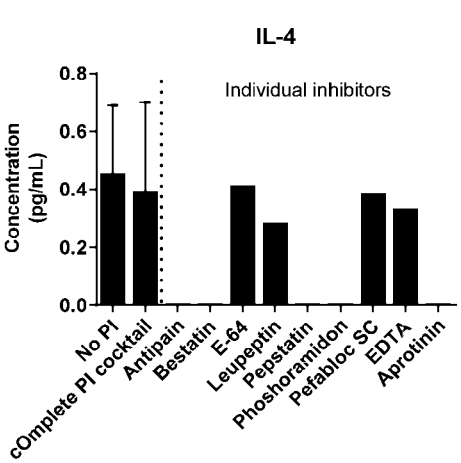
Figure 15L:
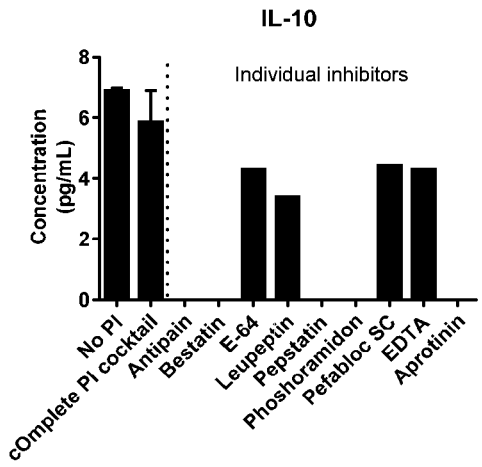
Figure 15M:
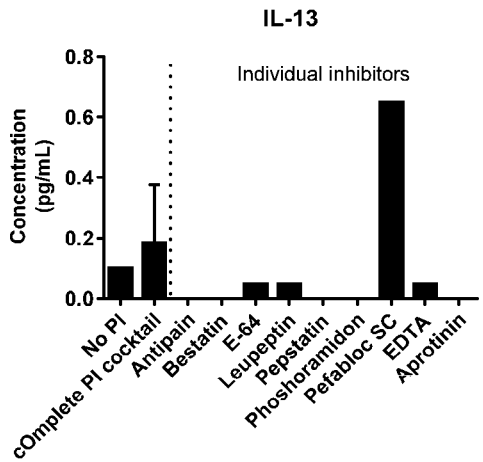
Figure 15N:
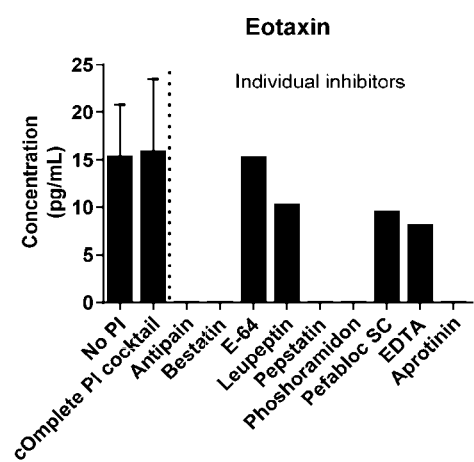
Figure 15O:
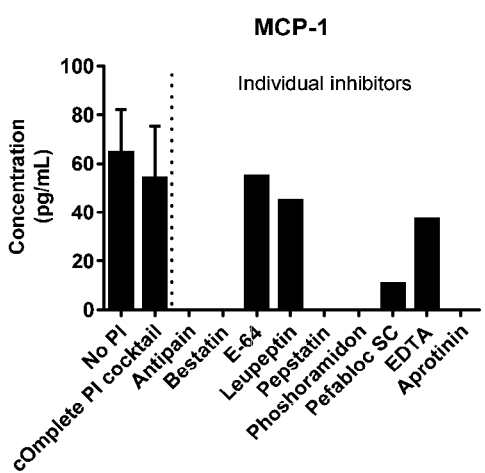
Figure 15P:
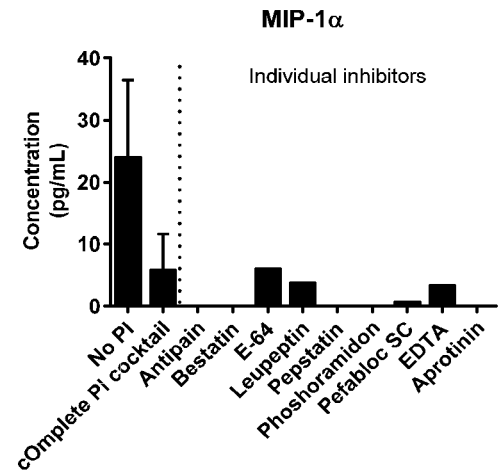
Figure 15Q:
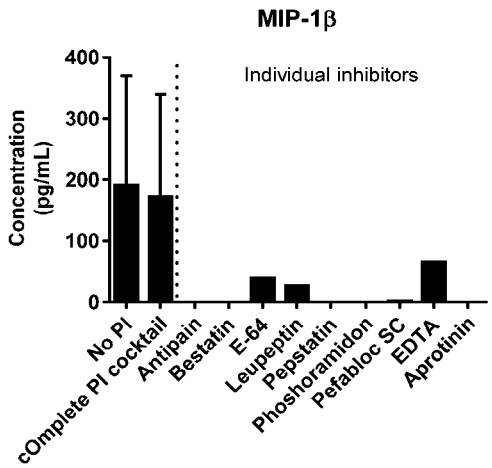
Figure 15R:
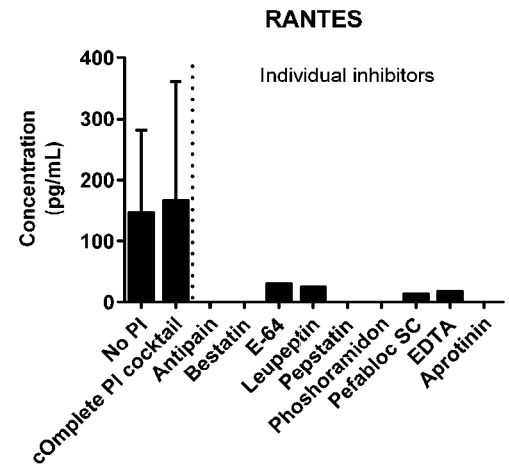
Figure 15S:
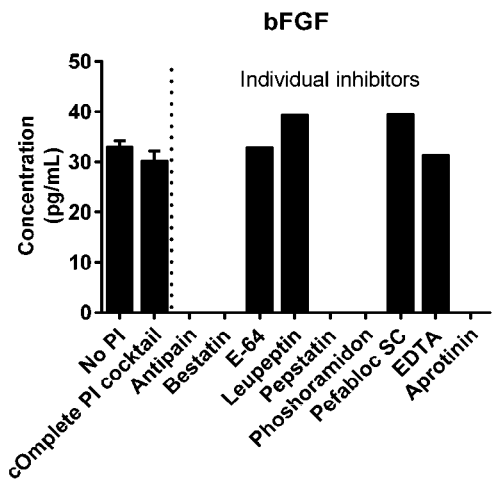
Figure 15T:
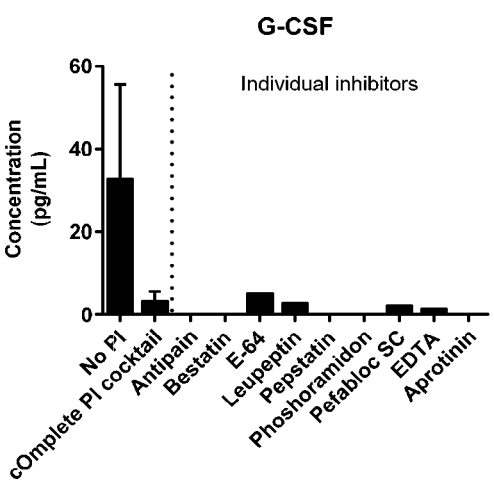
Figure 15U:
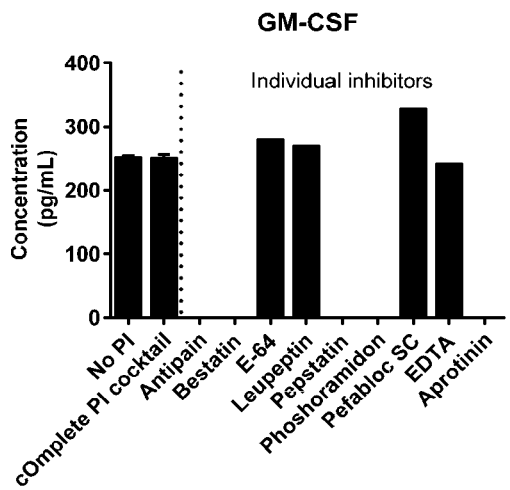
Figure 15V:
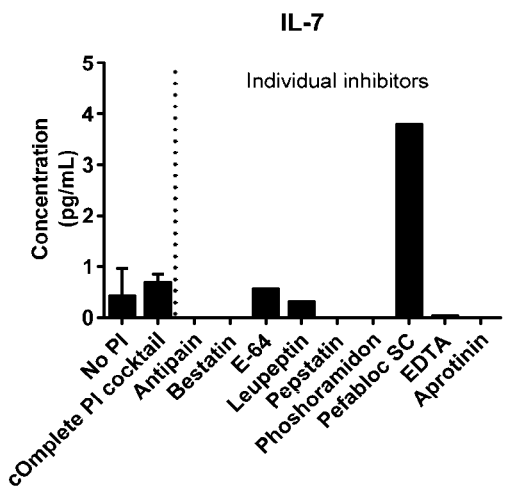
Figure 15W:
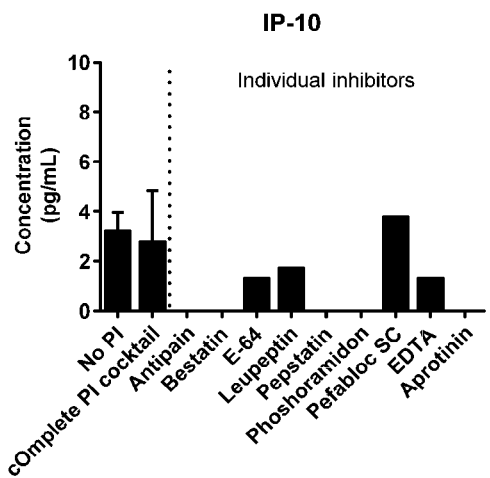
Figure 15X:
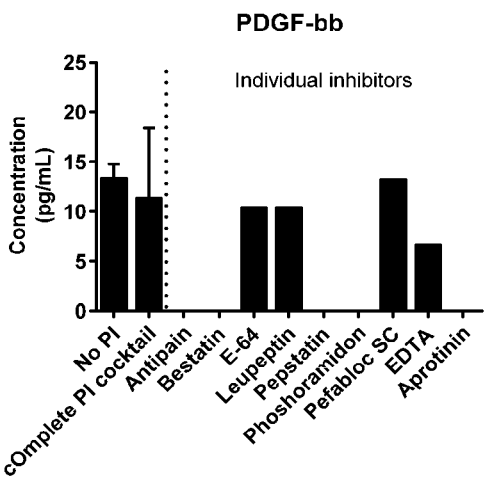
Figure 15Y:
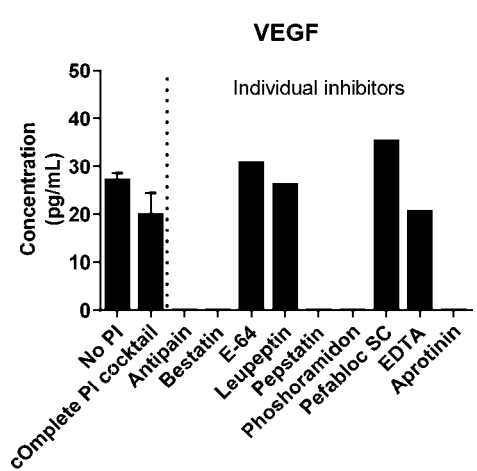
Figure 15Z:
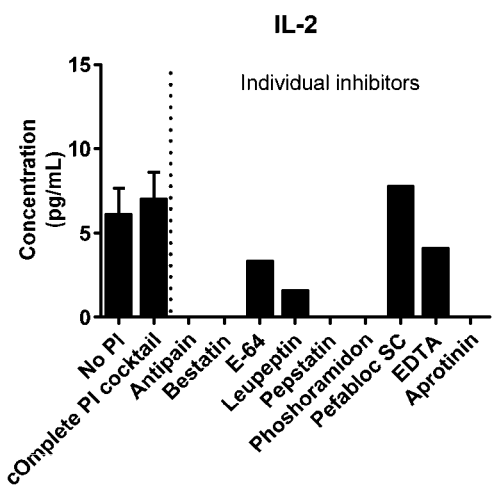
Figure 15A:
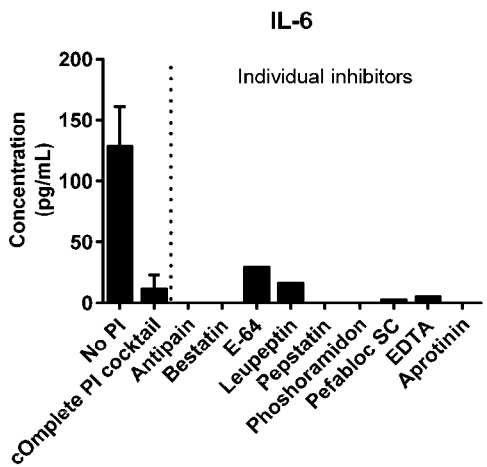
Figure 16A:
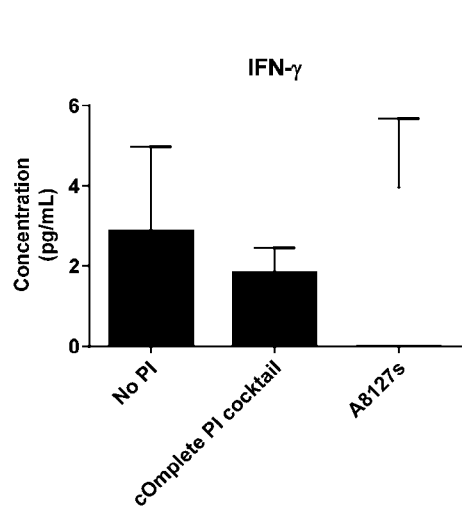
FIG. 16A-16AA is a series of graphs showing the effect of protease inhibitor cocktails on cytokines released from red blood cells from individuals having colorectal cancer.
Figure 16B:
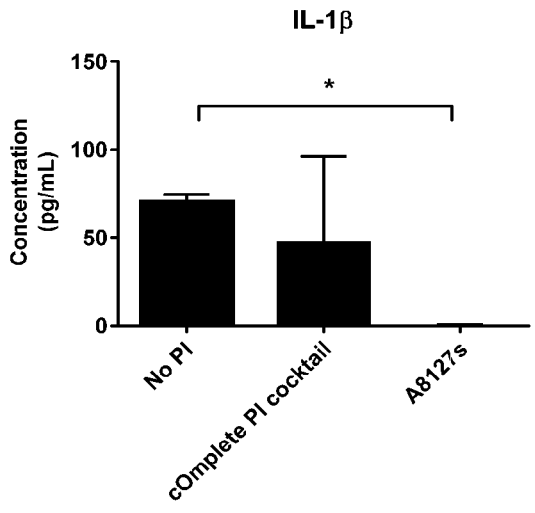
Figure 16C:
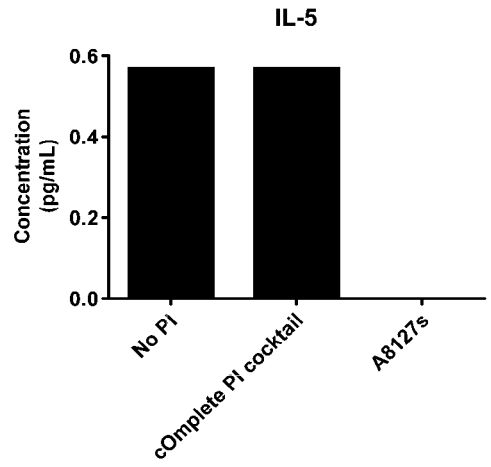
Figure 16D:
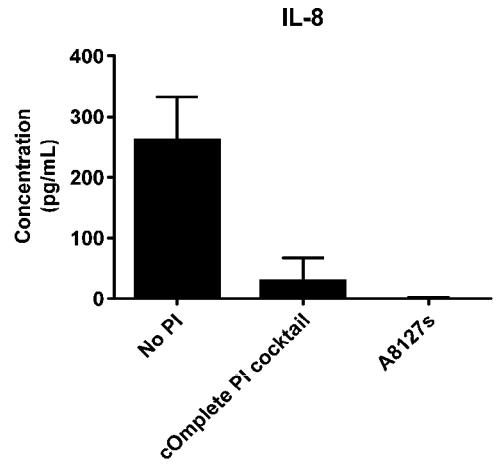
Figure 16E:
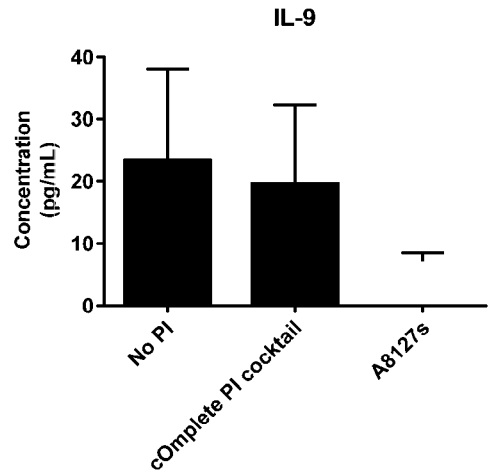
Figure 16F:
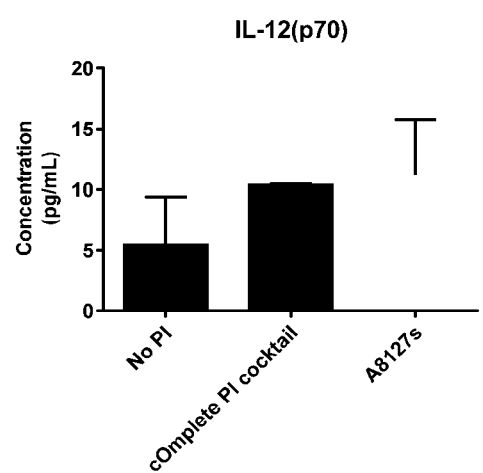
Figure 16G:
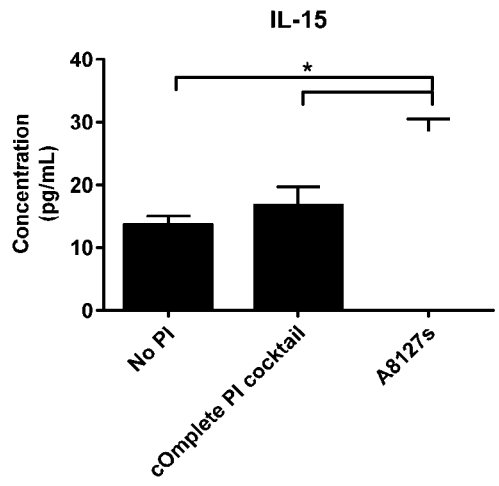
Figure 16H:
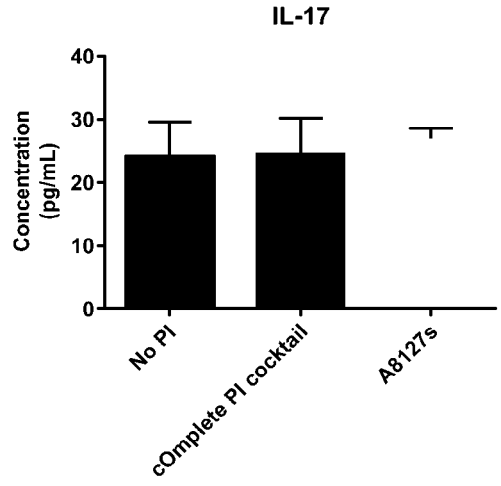
Figure 16I:
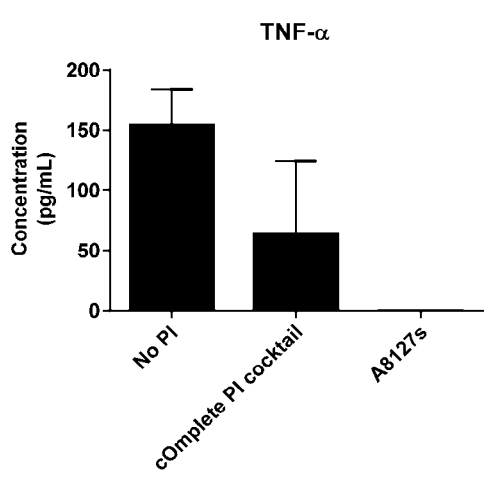
Figure 16J:
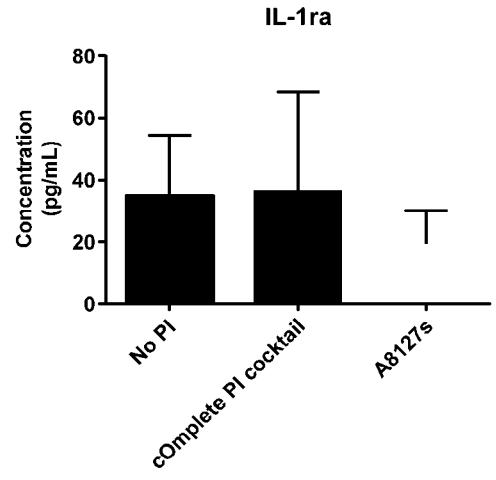
Figure 16K:
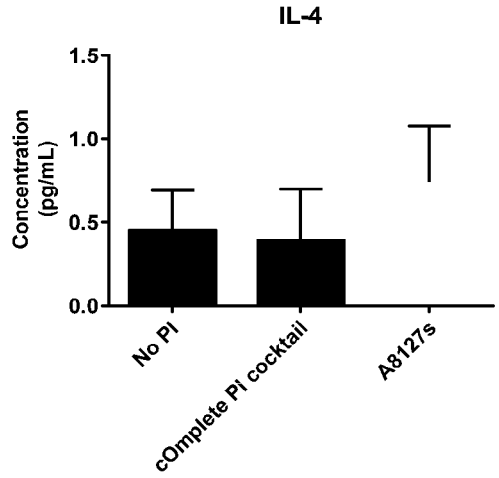
Figure 16L:
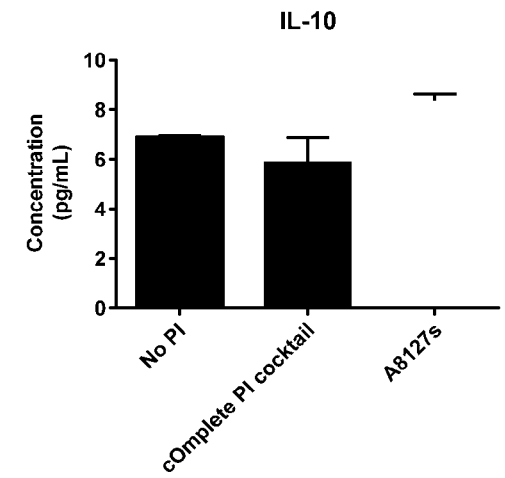
Figure 16M:
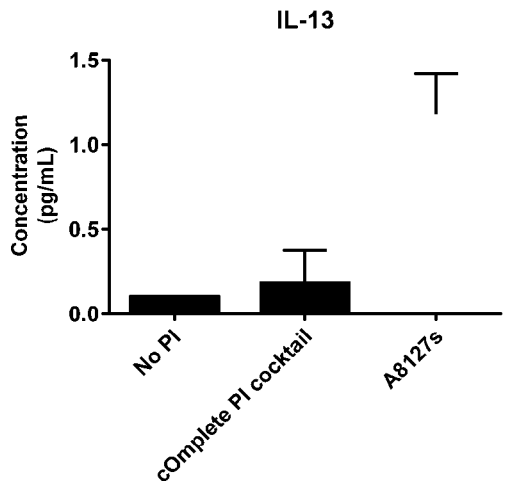
Figure 16N:
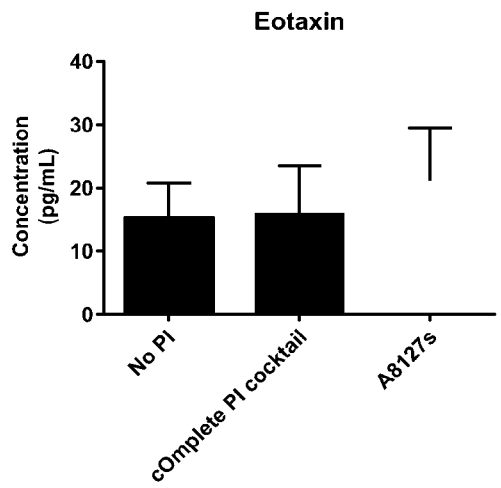
Figure 16O:
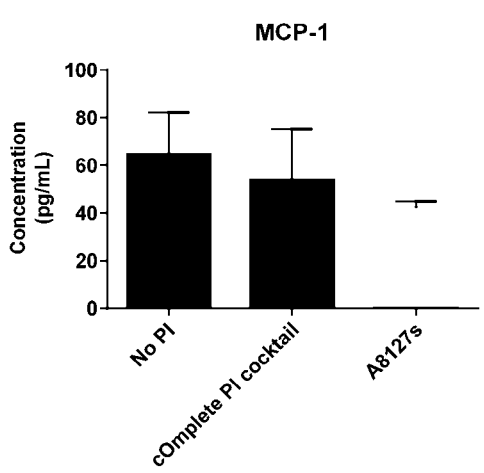
Figure 16P:
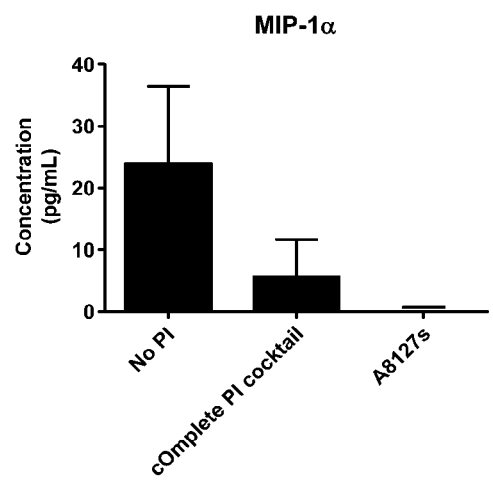
Figure 16Q:
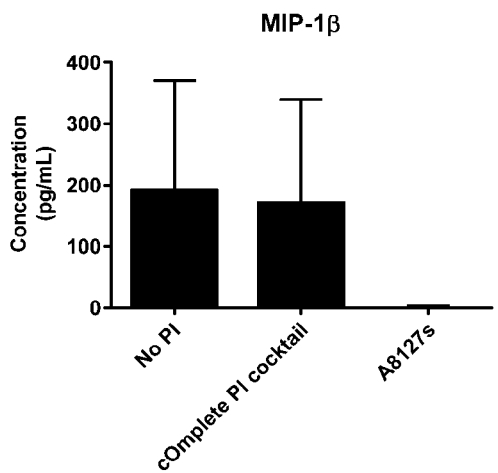
Figure 16R:
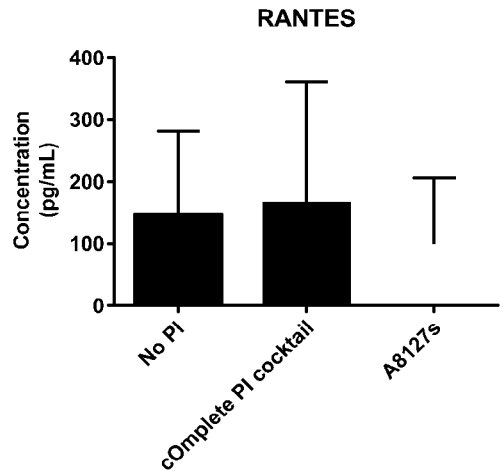
Figure 16S:
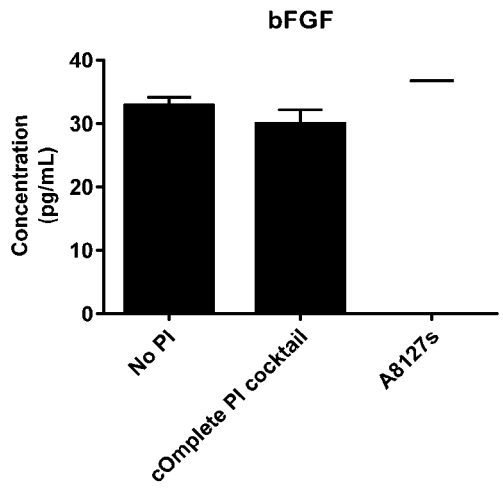
Figure 16T:
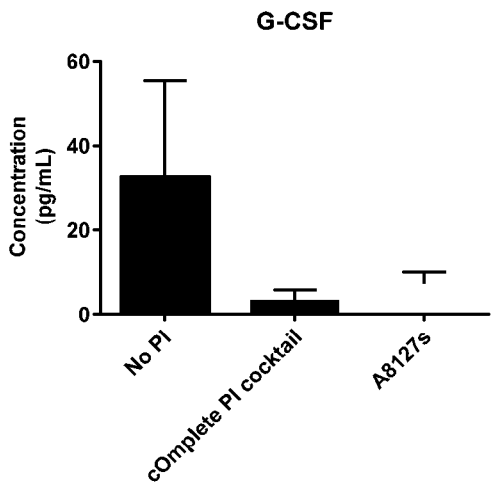
Figure 16U:
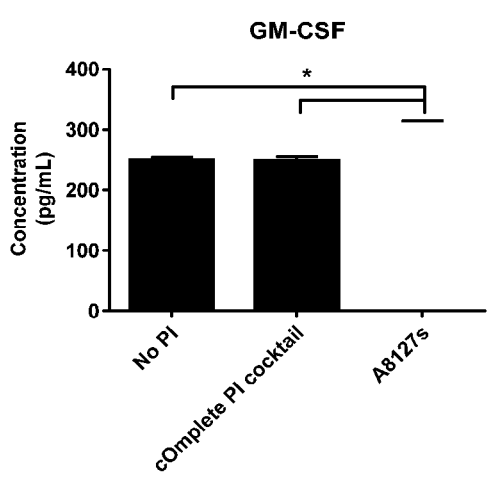
Figure 16V:
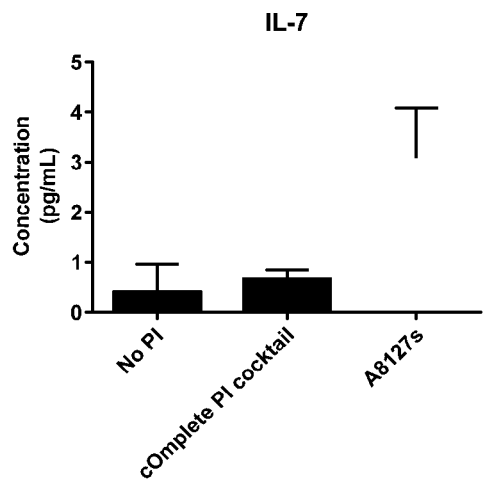
Figure 16W:
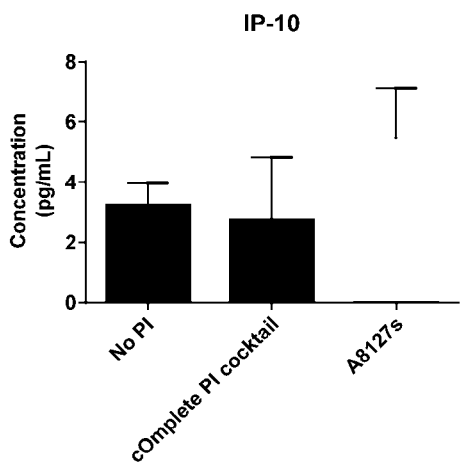
Figure 16X:
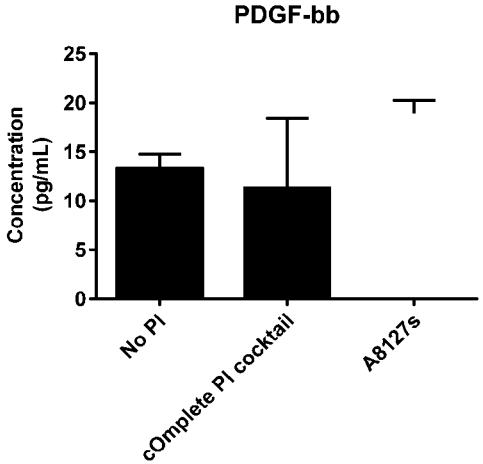
Figure 16Y:
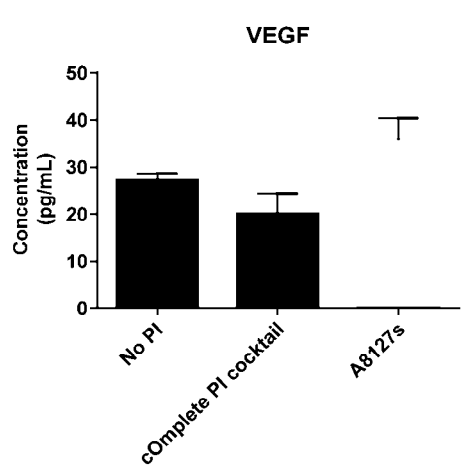
Figure 16Z:
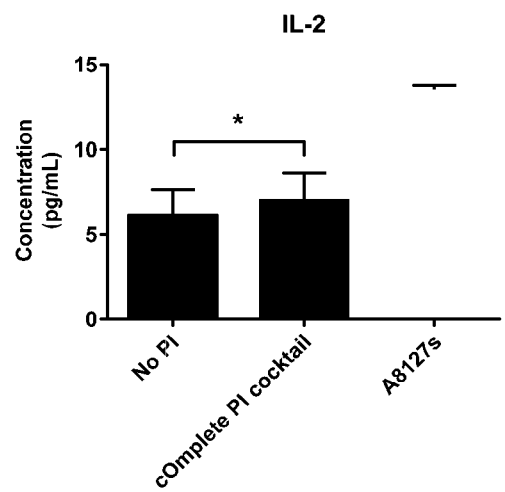
Figure 16A:
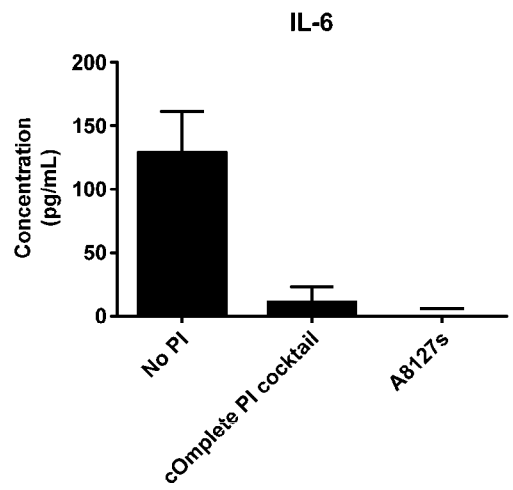

FIG. 15A-FIG. 15AA shows the concentration of the indicated proteins released from red blood cells from individuals having colorectal cancer, where the red blood cells had been incubated with individual protease inhibitors or a commercial protease inhibitor cocktail (cOmplete, Roche). Significant differences (p<0.05) were determined using Student T-tests. Individual protease inhibitors changed the concentration of a variety of cytokines that were released from the red blood cells from colorectal cancer participants when compared to the control (no protease inhibitors). Individual protease inhibitors changed the released cytokine profile in very different ways. For example, treating red blood cells with antipain-dihydrochloride (an inhibitor of papain, trypsin and cathepsin) increased the concentration of released IFN-γ, IL-12(p70), IL-15, IL-17, IL-13, IL-7, IP-10, PDGF-bb and IL-2, while decreasing the concentration IL-1β, IL-8, TNF-α, MIP-1α, G-CSF and IL-6. In contrast, Pefabloc SC (a serine protease inhibitor) increased the released concentration of only IL-13 and IL-7, while decreasing the concentration of IL-1β, IL-8, IL-9, TNF-α, IL-1ra, MCP-1, MIP-1α, G-CSF and IL-6. The complex nature of the interaction between specific protease inhibitors and the release of multiple cytokines provided compelling evidence that more than the inhibition of non-specific proteolysis of cytokines was causing protease inhibitor-mediated effects on protein levels. FIG. 16A-FIG. 16AA shows the concentration of proteins released from red blood cells from individuals having colorectal cancer into conditioned PBS containing either a commercial protease inhibitor cocktail (cOmplete, Roche) or A8127s. The cOmplete protease inhibitor cocktail only significantly changed the concentration of IL-2 when compared to control samples. In contrast, incubation of red blood cells with the A8127s protease inhibitor cocktail significantly changed the concentration of IL-1β, IL-15 and GM-CSF when compared to control samples. The data demonstrated that exposure of red blood cells isolated from colorectal cancer patients to protease inhibitors resulted in significant changes to the concentration of the cytokines released into the conditioned PBS. Moreover, comparison of the cOmplete protease inhibitor cocktail and the A8127s protease inhibitor cocktail showed that the A8127s cocktail had a greater capacity to produce significant changes in the profile of released cytokines from red blood cells isolated from colorectal cancer participants.

Figure 17A:
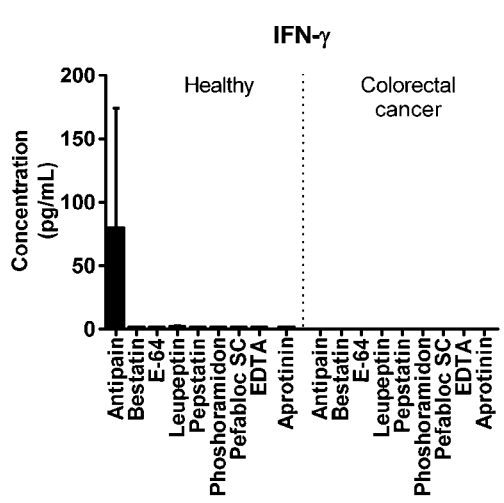
FIG. 17A-17AA is a series of graphs showing the effect of individual protease inhibitors on cytokines released from red blood cells from healthy individuals compared to cytokines released from red blood cells from individuals with colorectal cancer.
Figure 17B:
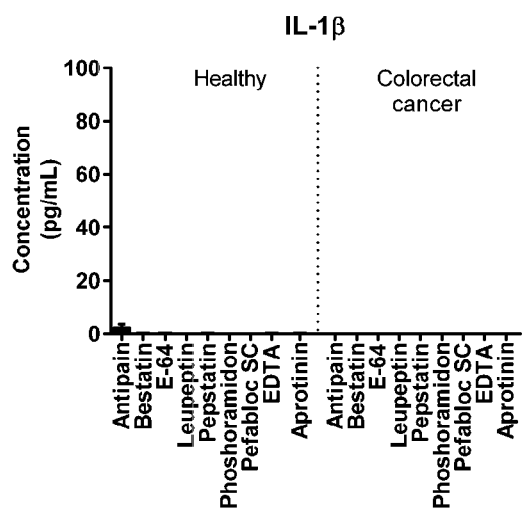
Figure 17C:
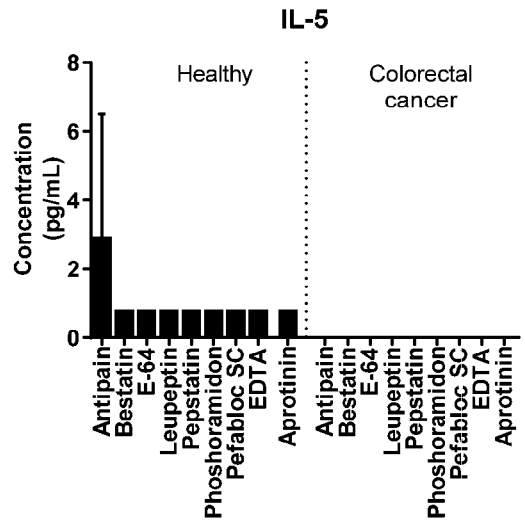
Figure 17D:
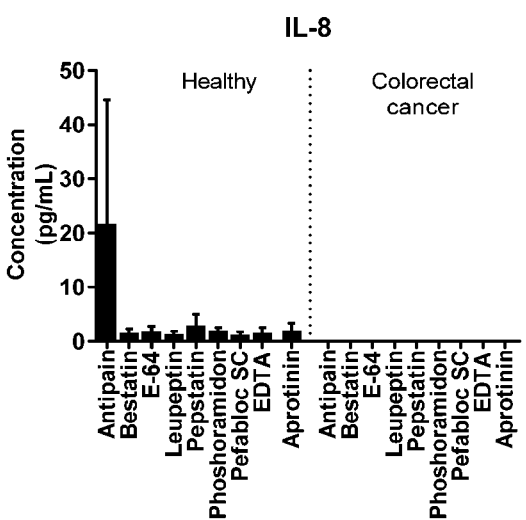
Figure 17E:
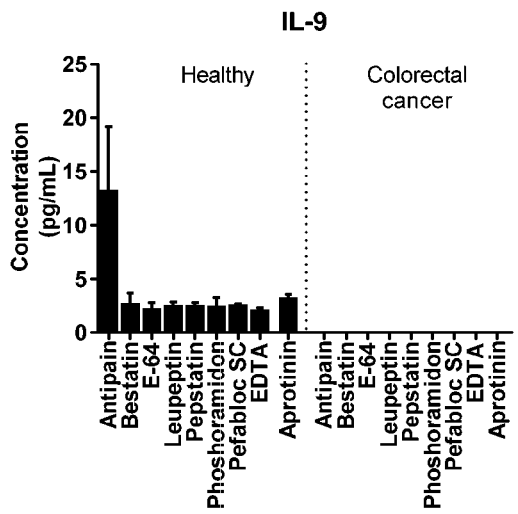
Figure 17F:
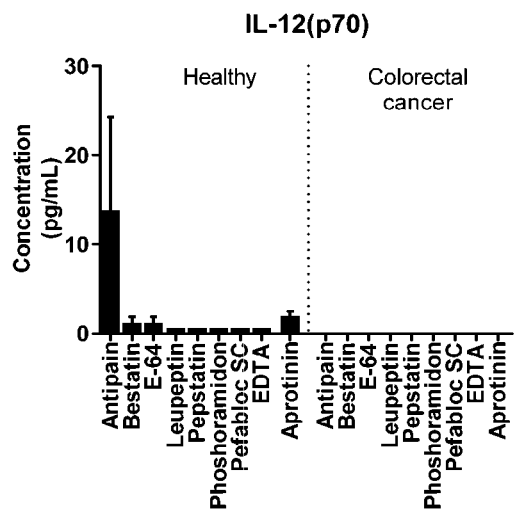
Figure 17G:
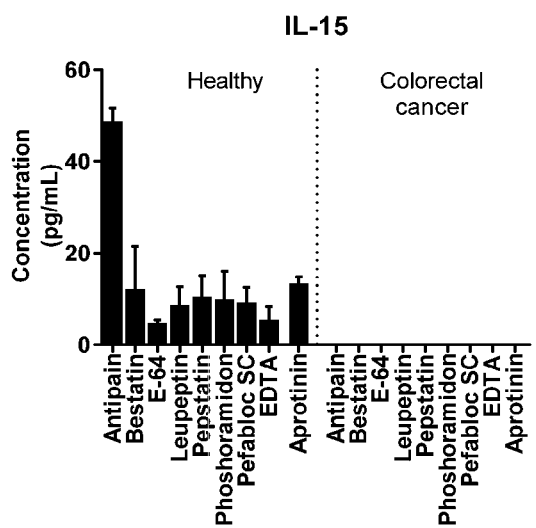
Figure 17H:
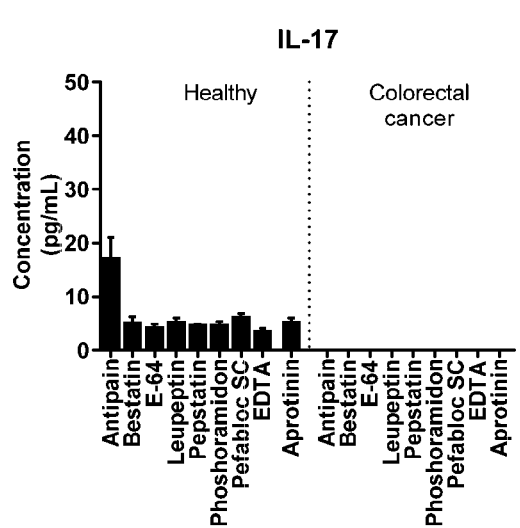
Figure 17I:
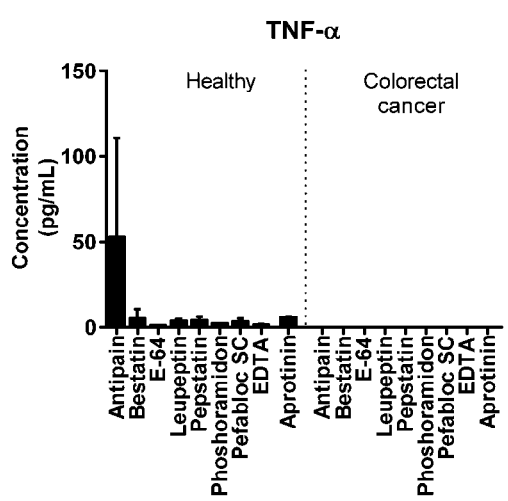
Figure 17J:
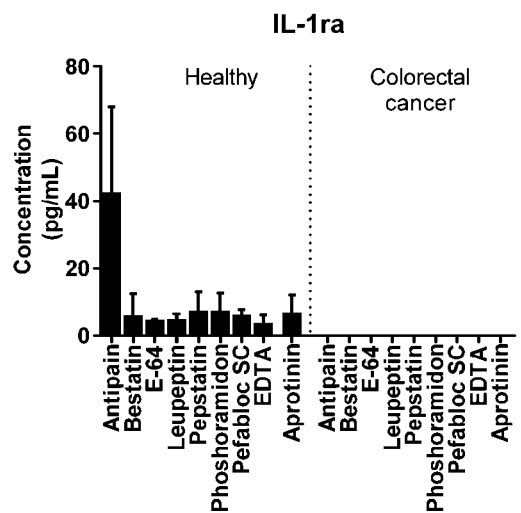
Figure 17K:
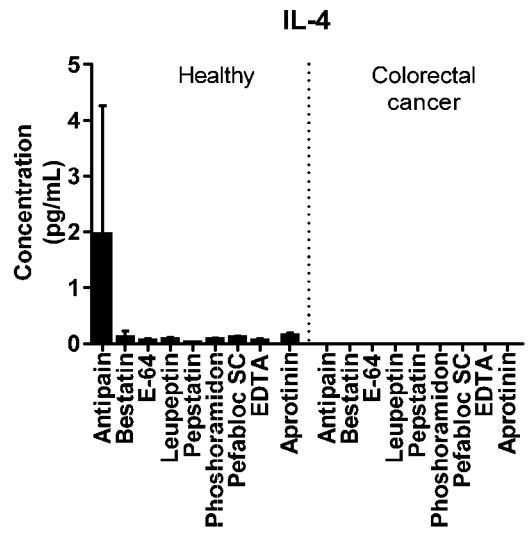
Figure 17L:
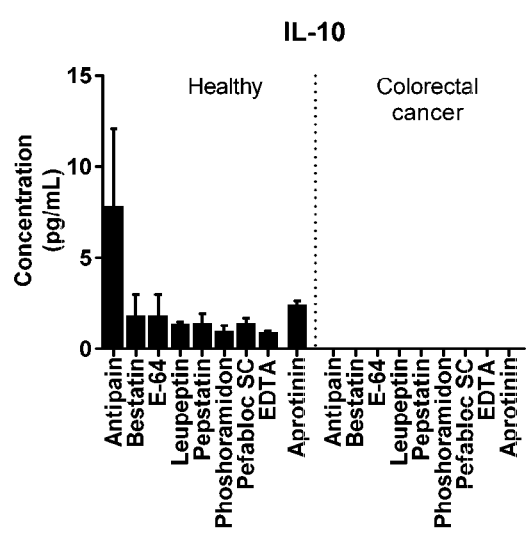
Figure 17M:
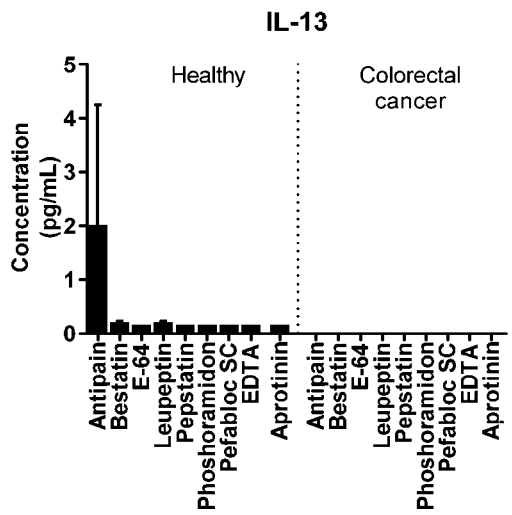
Figure 17N:
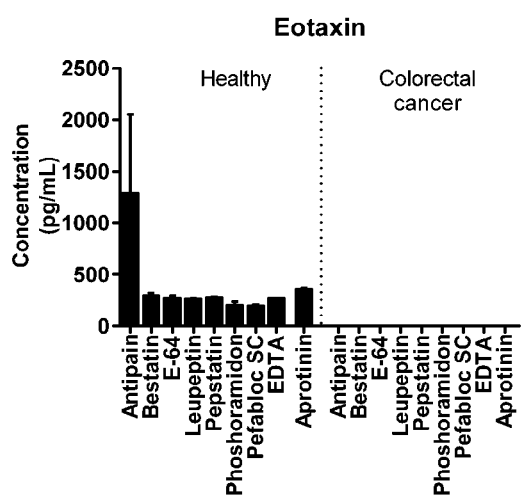
Figure 17O:
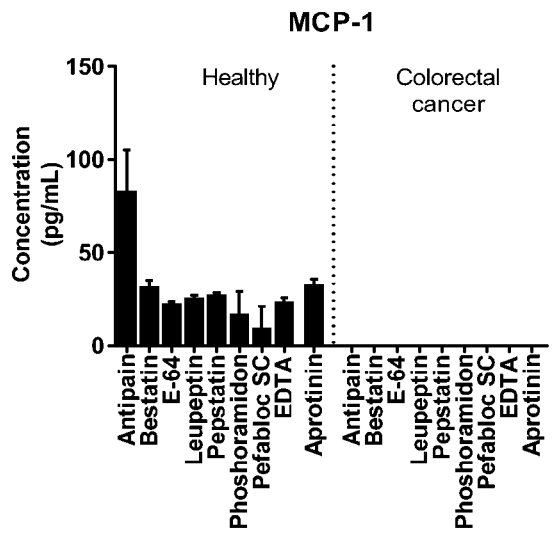
Figure 17P:
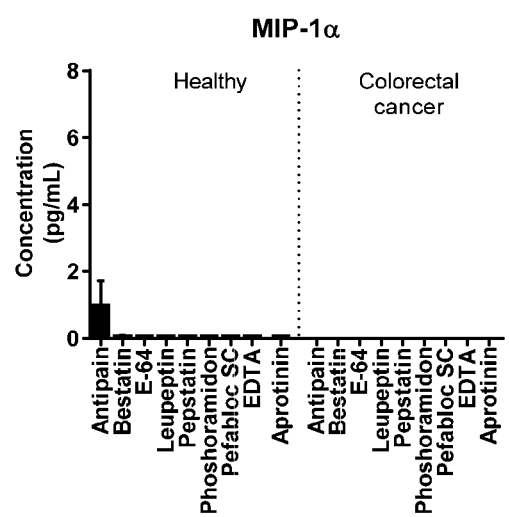
Figure 17Q:
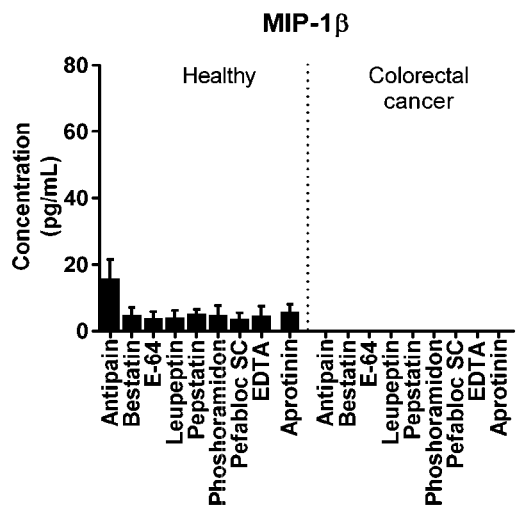
Figure 17R:
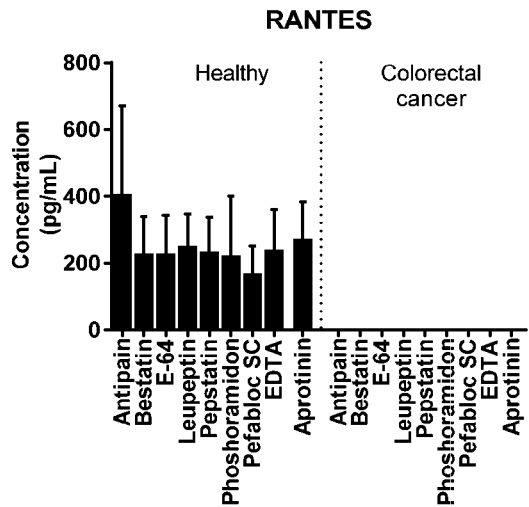
Figure 17S:
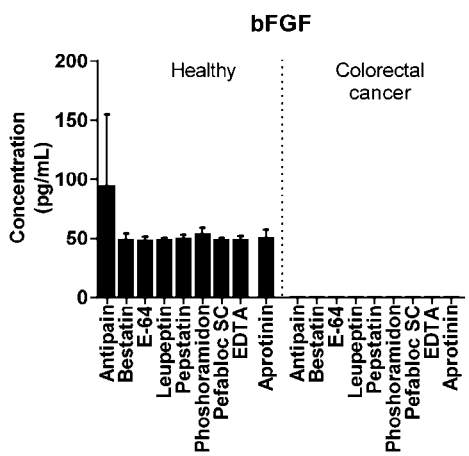
Figure 17T:
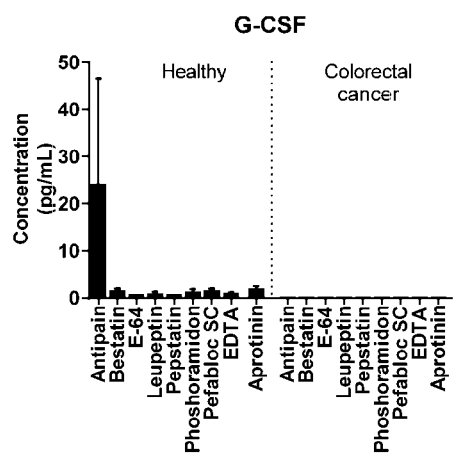
Figure 17U:
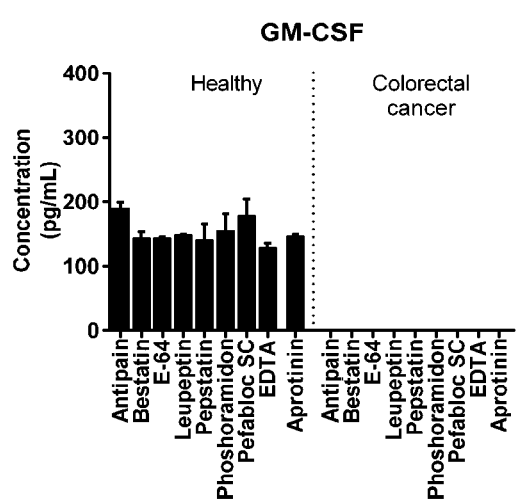
Figure 17V:
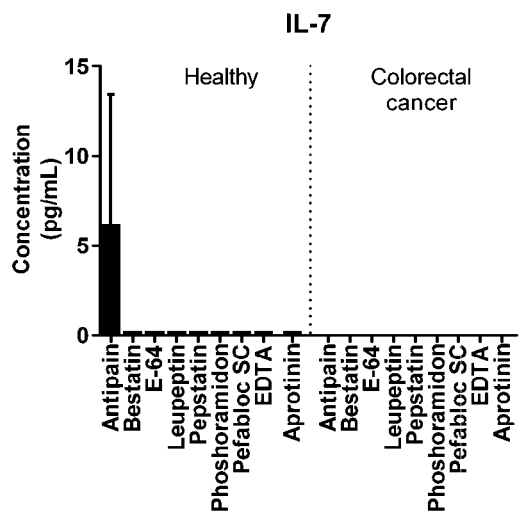
Figure 17W:
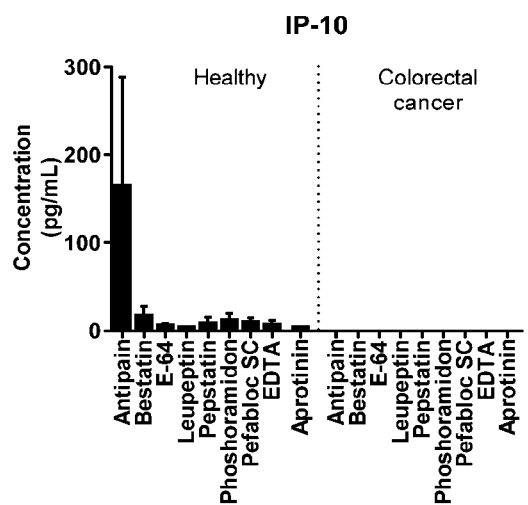
Figure 17X:
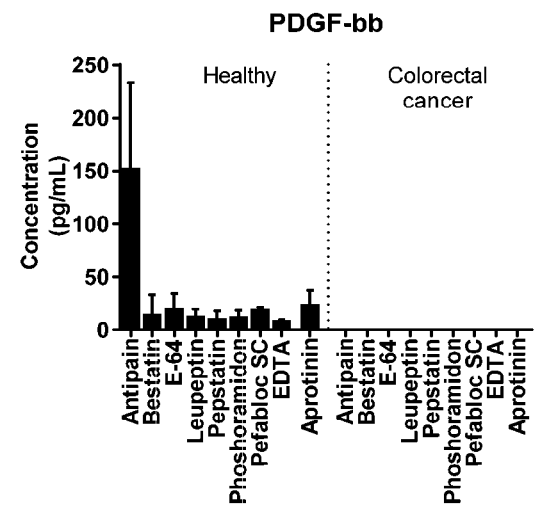
Figure 17Y:
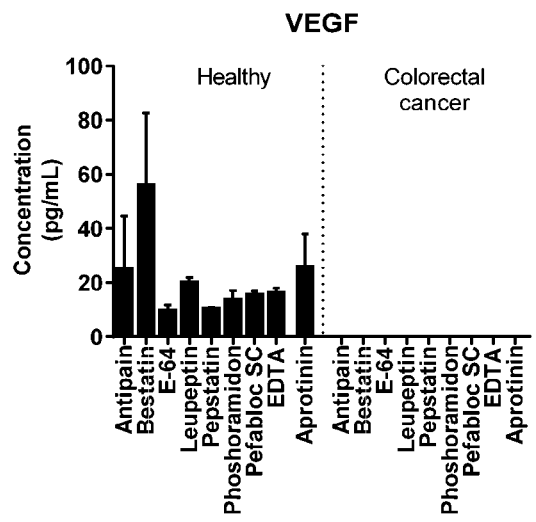
Figure 17Z:
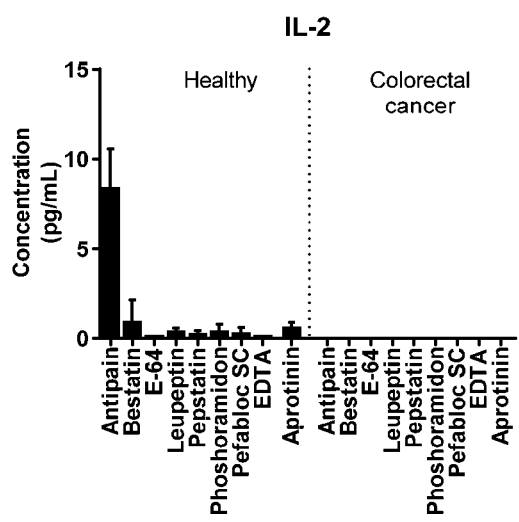
Figure 17A:
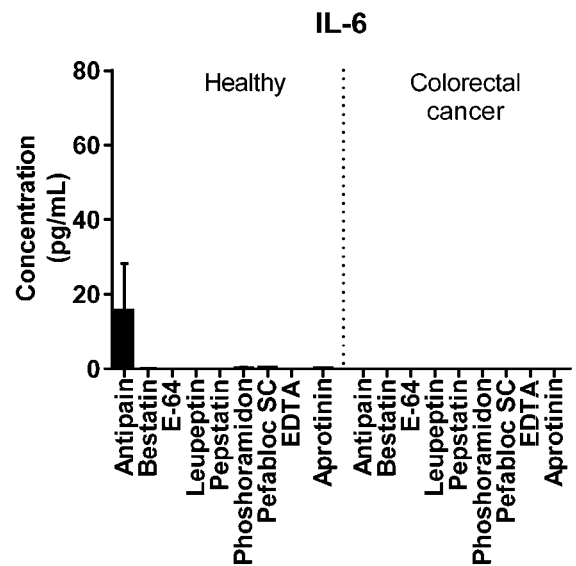

Next, the difference in the effect of protease inhibitors on proteins released from red blood cells from healthy individuals compared their effect on proteins released from the red blood cells of those with colorectal cancer was assessed. The concentration of proteins from red blood cells incubated with the individual protease inhibitors in Table 5 is shown in FIG. 17A-FIG. 17AA. The data provide a method by which a protease inhibitor cocktail may be optimized for a specific disease state. The cytokines IL-8, IL-15, TNF-α, MIP-1α, MIP-1β and IL-6 were identified as having a statistically significant change in red blood cells incubated with A8127s from colorectal cancer participants. The individual protease inhibitor data showed that Pefabloc SC affected healthy and colorectal cancer participants in the same way for IL-8, IL-15, TNF-α, MIP-1α, MIP-1β and IL-6. Therefore, the removal of Pefabloc SC from the A8127s protease cocktail may increase the differences observed between the healthy and colorectal cancer cytokine profiles.

Figure 18A:
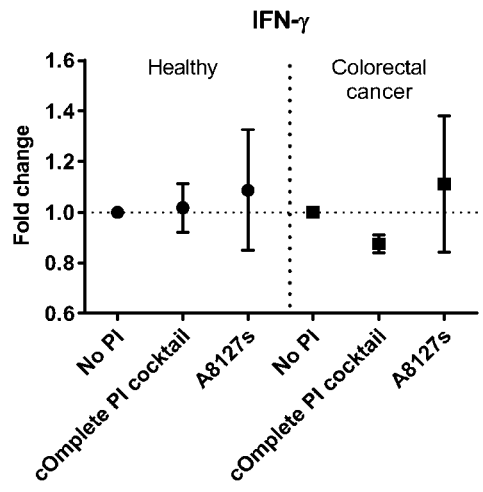
FIG. 18A-18AA is a series of graphs showing the effect of protease inhibitor cocktails on the fold change of cytokines released from red blood cells from healthy individuals compared to cytokines released from red blood cells from individuals with colorectal cancer.
Figure 18B:
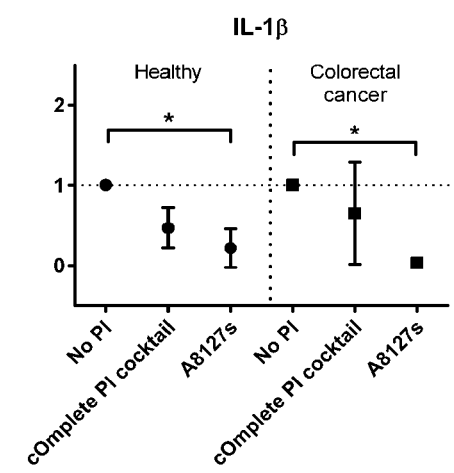
Figure 18C:
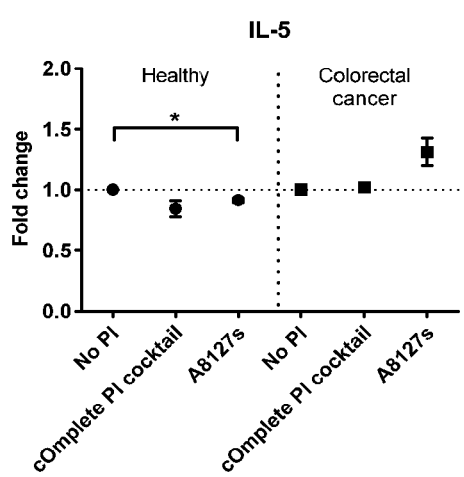
Figure 18D:
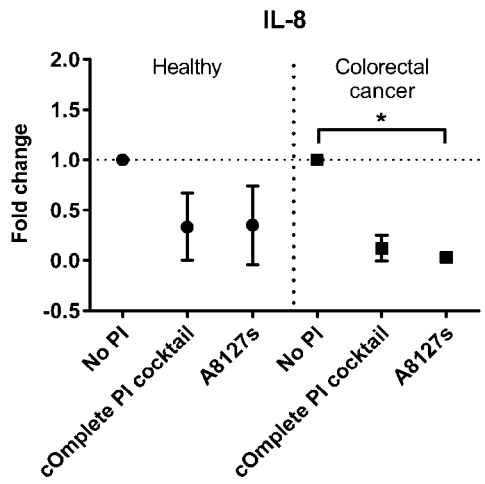
Figure 18E:
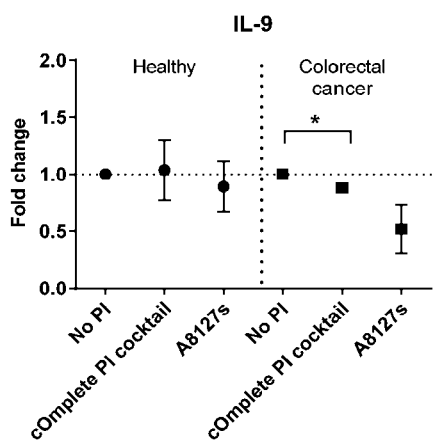
Figure 18F:
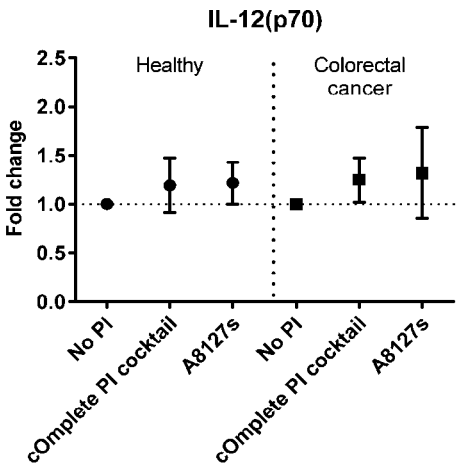
Figure 18G:
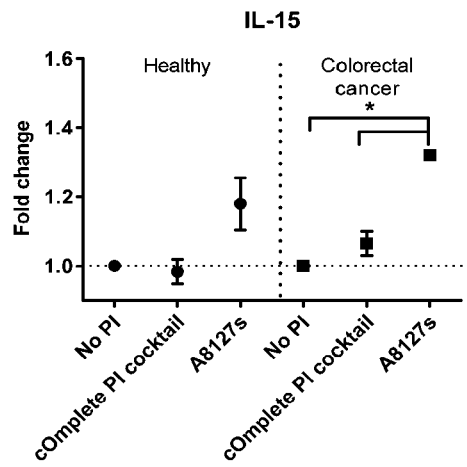
Figure 18H:
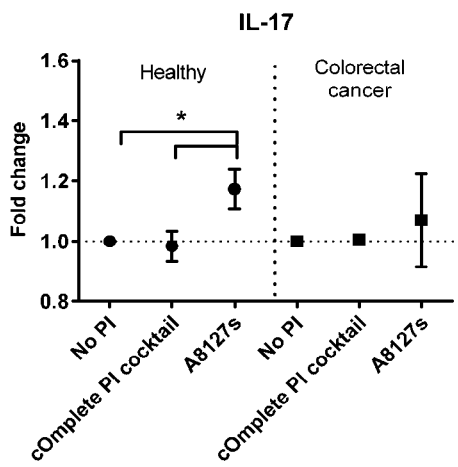
Figure 18I:
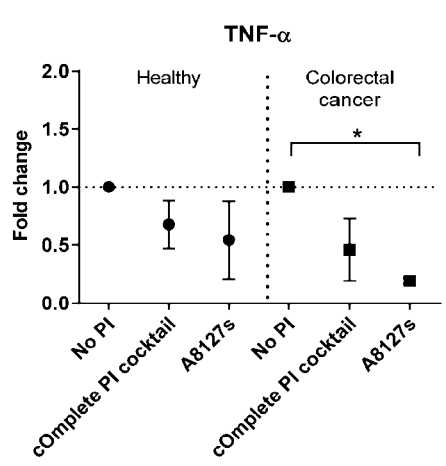
Figure 18J:
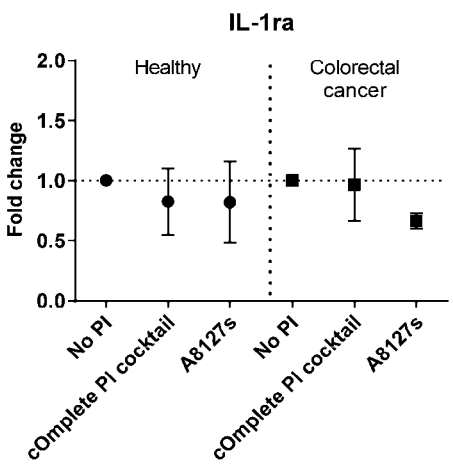
Figure 18K:
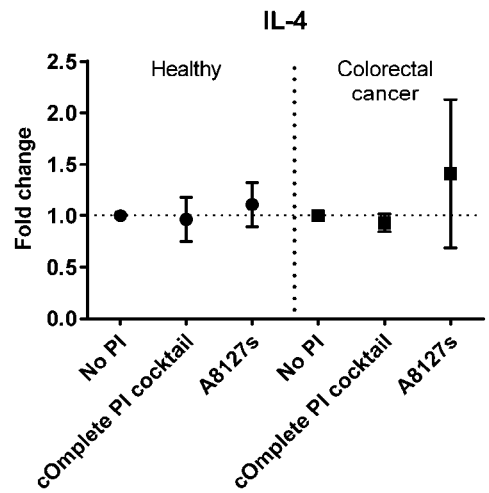
Figure 18L:
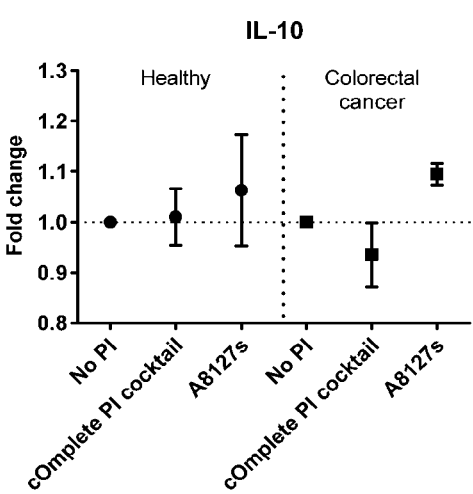
Figure 18M:
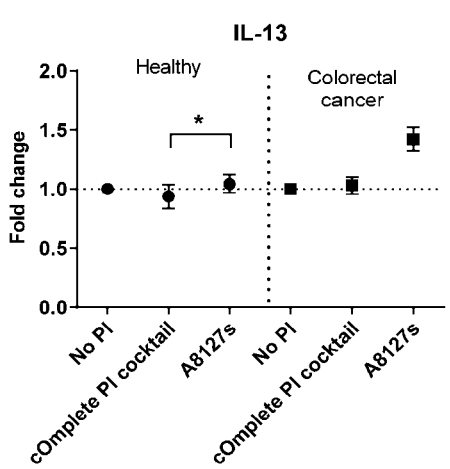
Figure 18N:
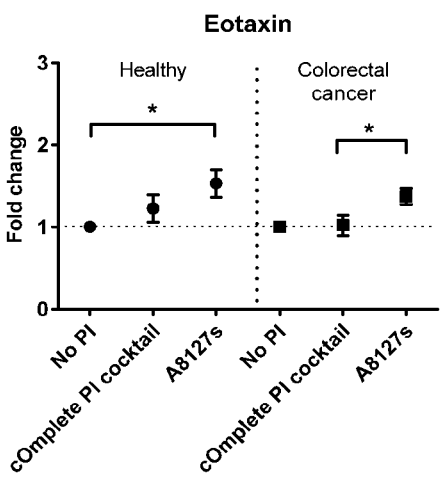
Figure 18O:
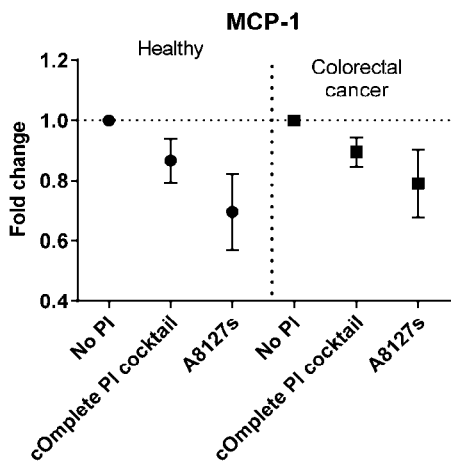
Figure 18P:
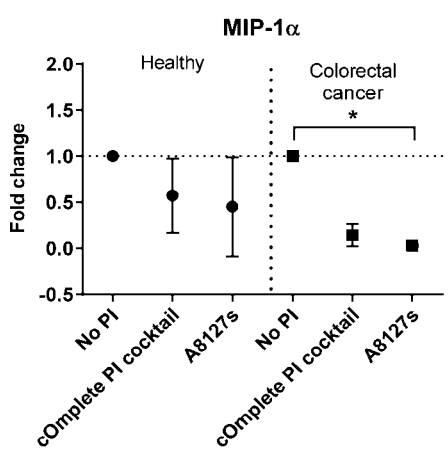
Figure 18Q:
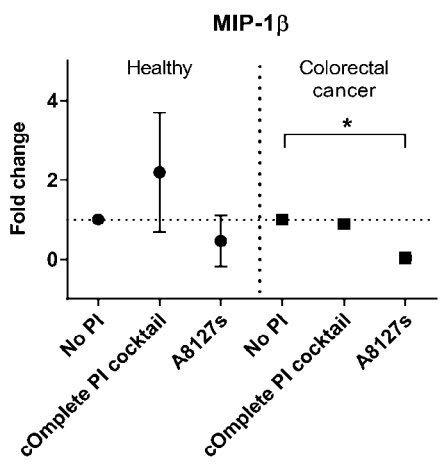
Figure 18R:
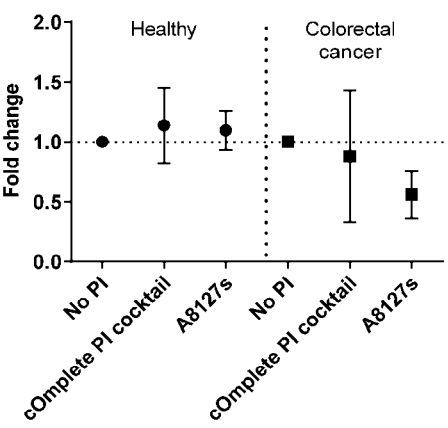
Figure 18S:
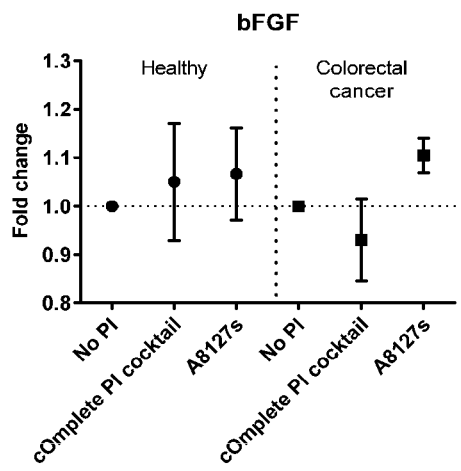
Figure 18T:
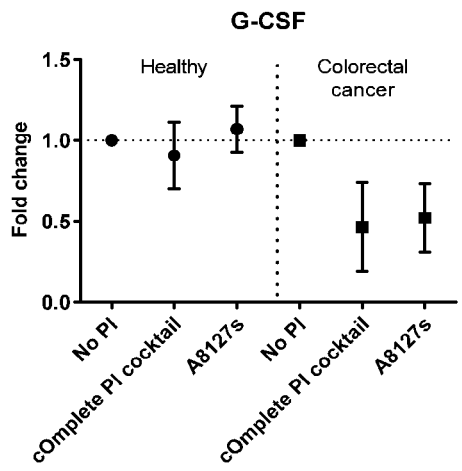
Figure 18U:
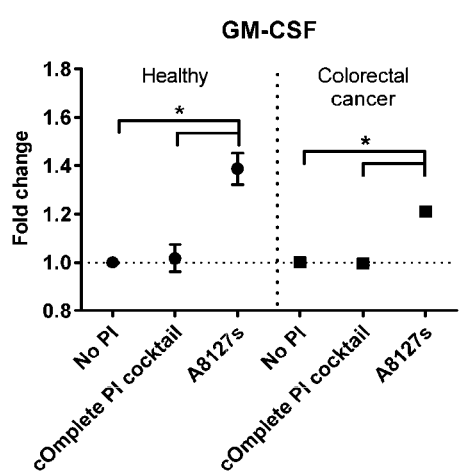
Figure 18V:
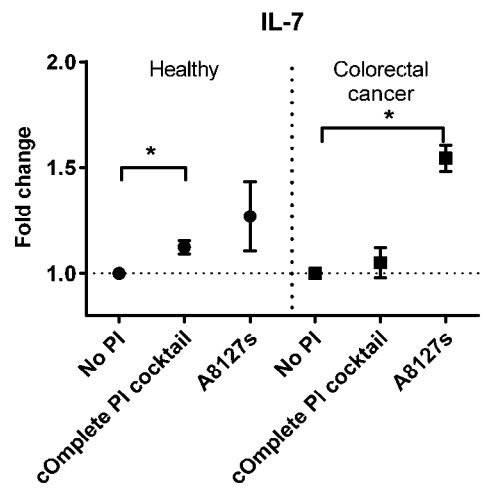
Figure 18W:
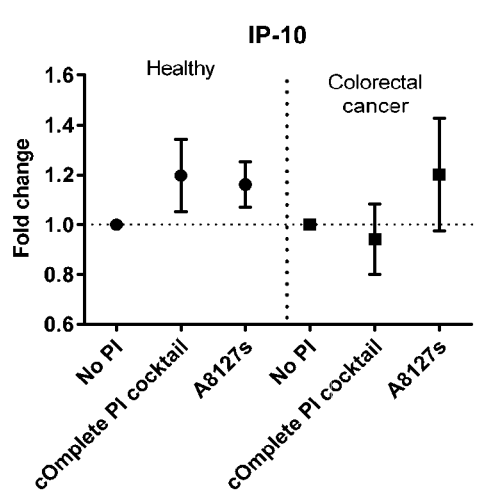
Figure 18X:
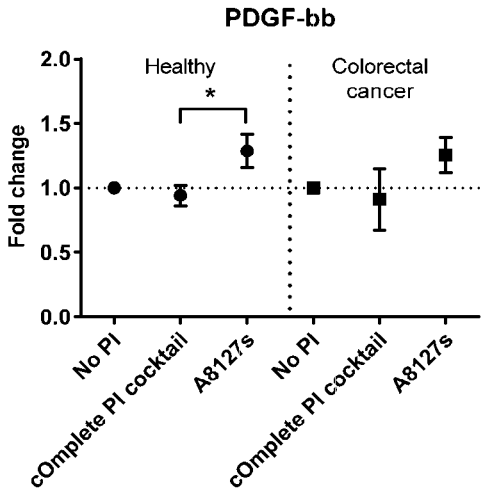
Figure 18Y:
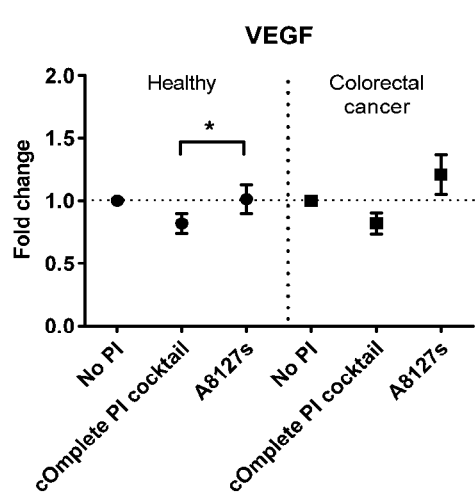
Figure 18Z:
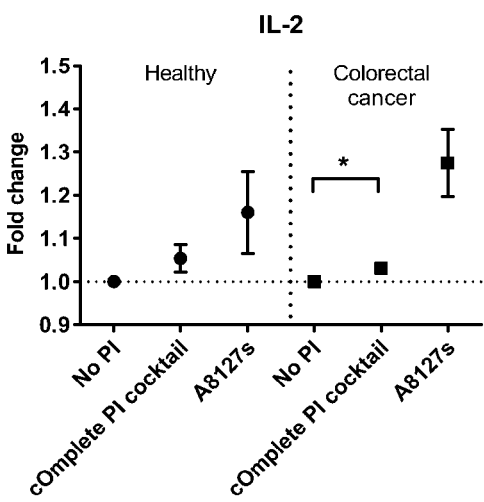
Figure 18A:
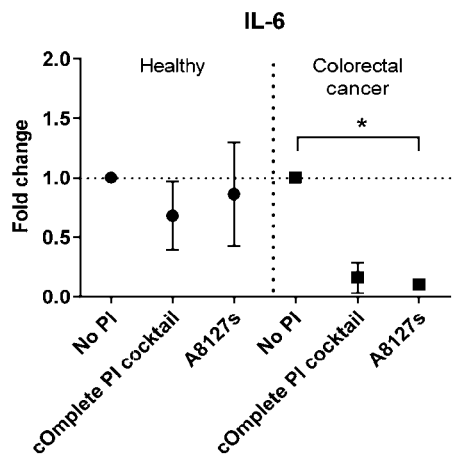

FIG. 18A-FIG. 18AA illustrates the fold change in protein concentration in red blood cells from healthy individuals versus colorectal cancer participants when the red blood cells were incubated with protease inhibitor cocktails (A8127s and cOmplete (Roche)). The results indicated that incubation of red blood cells with protease inhibitors resulted in significant changes to the cytokine profile of red blood cell conditioned PBS from both healthy and colorectal cancer participant groups. The A8127s protease inhibitor cocktail produced the largest number of statistically significant changes in cytokine levels when compared to untreated samples for both healthy and colorectal cancer participants. The results were consistent with previous data in healthy individuals, which showed that the A8127s protease inhibitor cocktail resulted in more significant changes in the cytokine profile than the cOmplete protease inhibitor cocktail.

Samples isolated from the healthy and colorectal cancer cohorts differed in how they responded to the protease inhibitors. There were a number of cytokines that changed significantly when intact red blood cells from colorectal cancer patients were incubated with the A8127s protease inhibitor cocktail-IL-8, IL-15, TNF-α, MIP-1α, MIP-1β and IL-6. In contrast, no significant change was detected when intact red blood cells were isolated from healthy participants and incubated with A8127s. This indicated that intact red blood cells incubated with or without the A8127s protease inhibitor cocktail may be valuable in identifying cytokine profiles that are specific to colorectal cancer. Table 7 summarizes the number of cytokines that significantly changed in healthy and colorectal cancer participants with each protease inhibitor cocktail.

TABLE 7

Number of proteins having significantly changed concentrations after incubation of red blood cells with protease inhibitor cocktails.
Intact red blood cell secretions

| Healthy | | Colorectal cancer | |
| --- | --- | --- | --- |
| cOmplete PI cocktail | A8127s | cOmplete PI cocktail | A8127s |
| 1 | 5 | 2 | 9 |

Figure 19A:
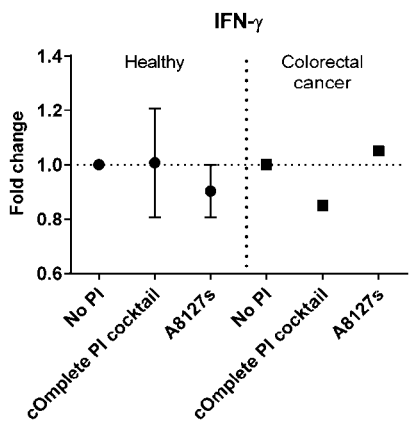
FIG. 19A-19VV is a series of graphs showing the effect of protease inhibitor cocktails on the fold change of cytokines released from red blood cell membranes from healthy individuals compared to cytokines released from red blood cell membranes from individuals with colorectal cancer.
Figure 19B:
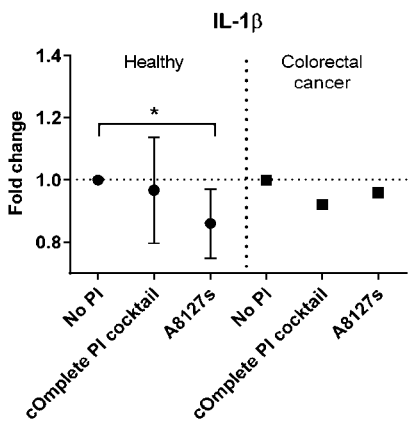
Figure 19C:
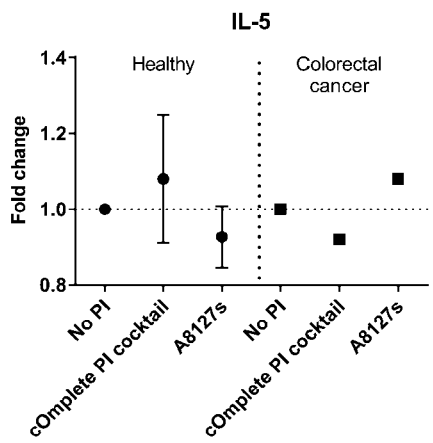
Figure 19D:
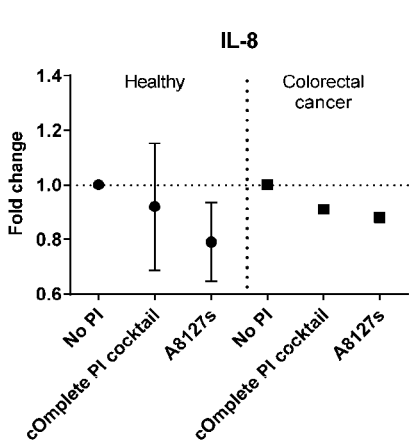
Figure 19E:
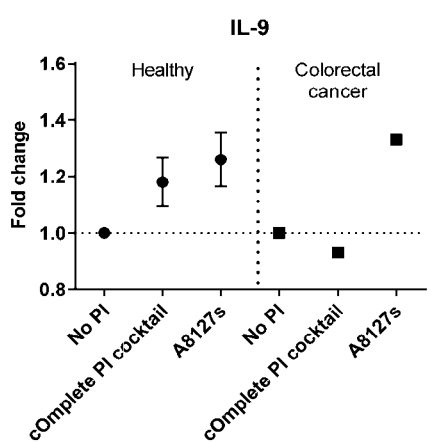
Figure 19F:
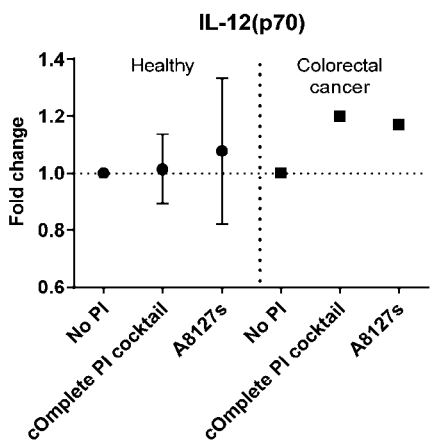
Figure 19G:
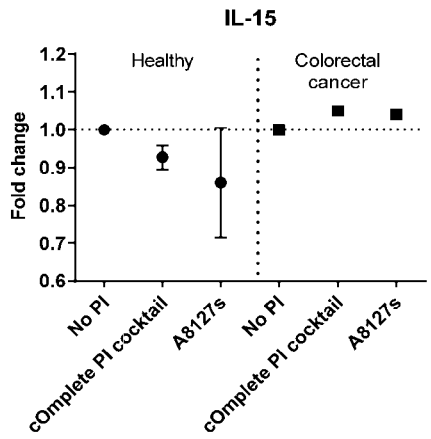
Figure 19H:
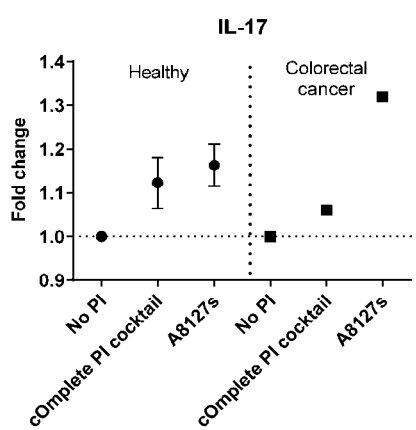
Figure 19I:
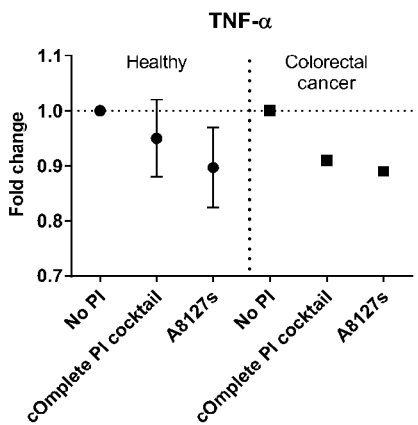
Figure 19J:
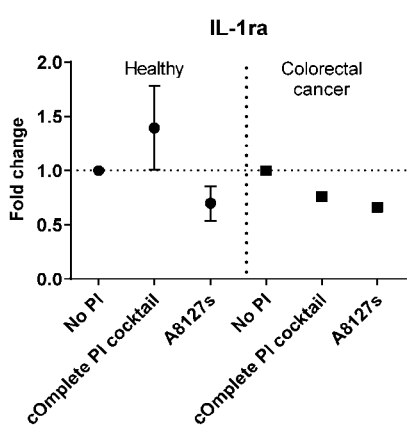
Figure 19K:
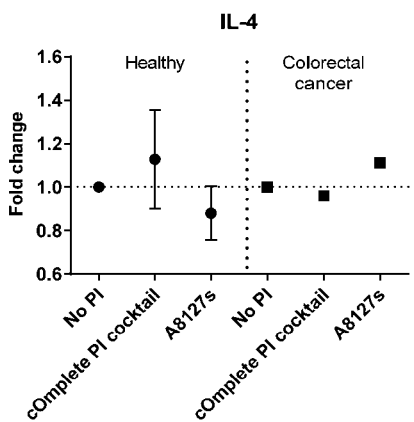
Figure 19L:
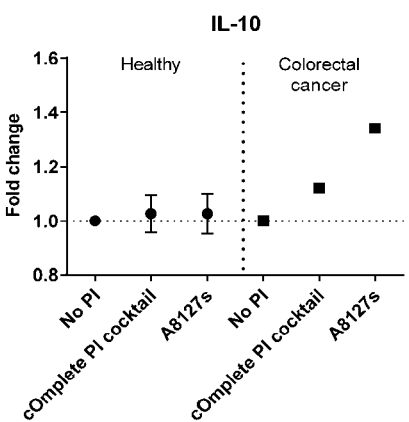
Figure 19M:
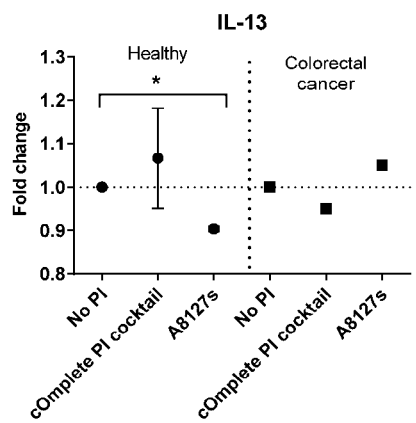
Figure 19N:
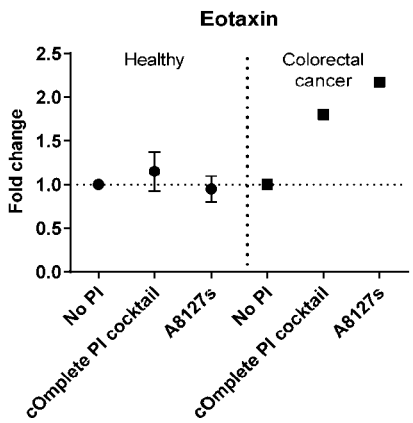
Figure 19O:
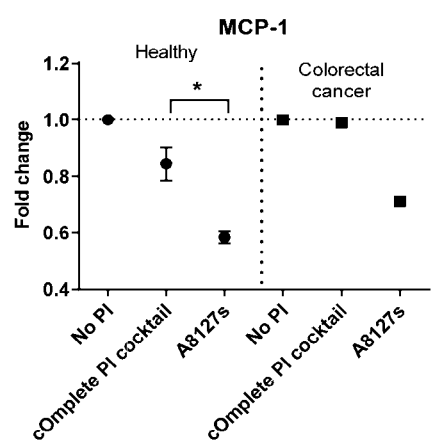
Figure 19P:
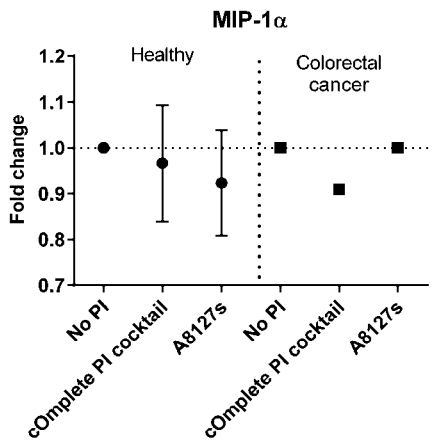
Figure 19Q:
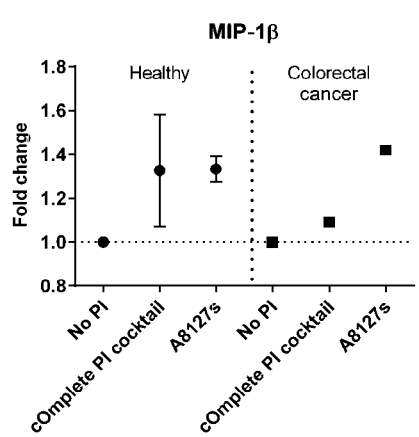
Figure 19R:
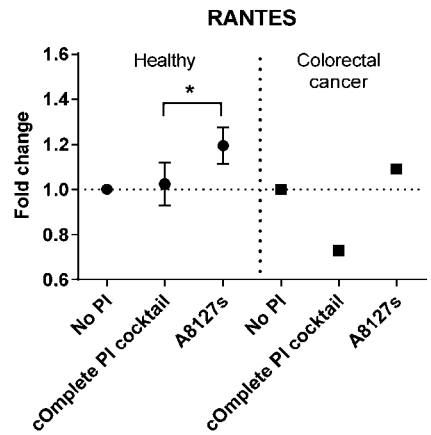
Figure 19S:
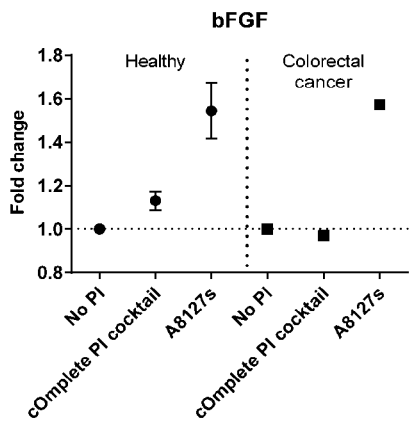
Figure 19T:
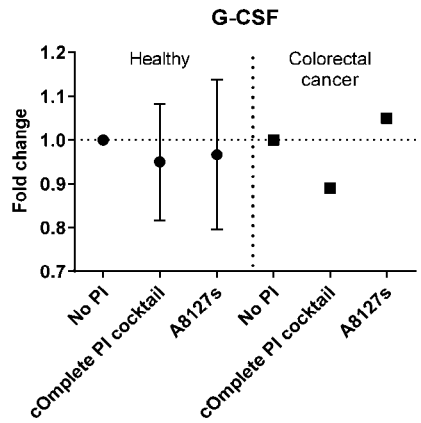
Figure 19U:
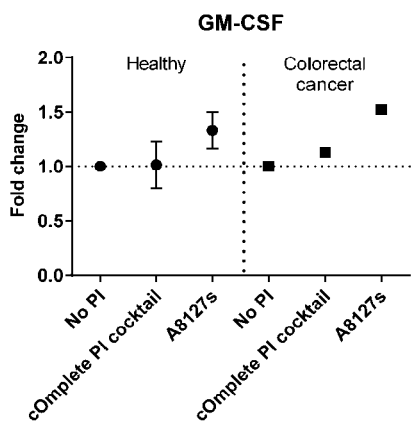
Figure 19V:
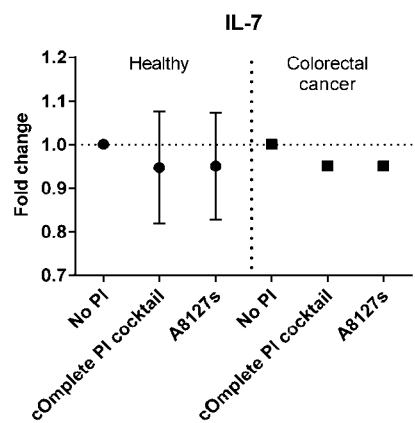
Figure 19W:
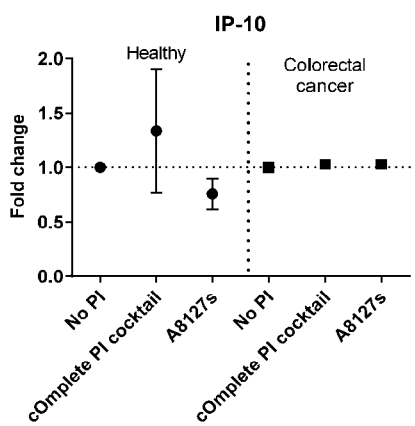
Figure 19X:
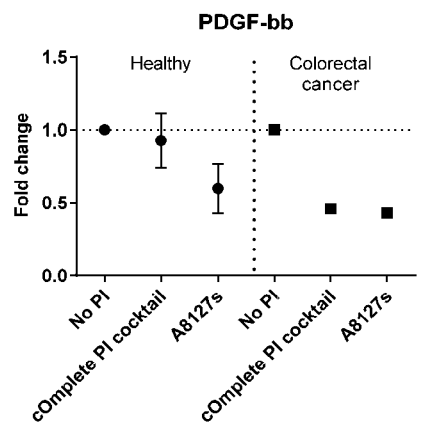
Figure 19Y:
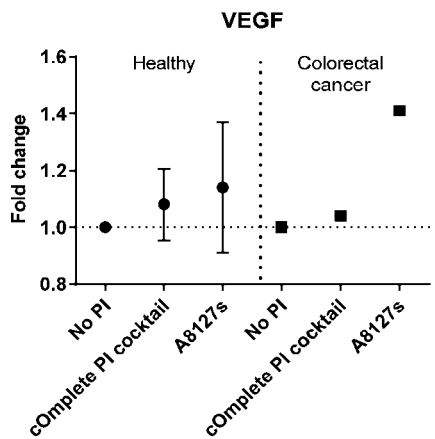
Figure 19Z:
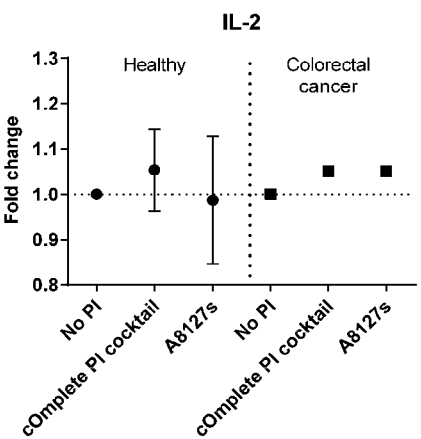
Figure 19A:
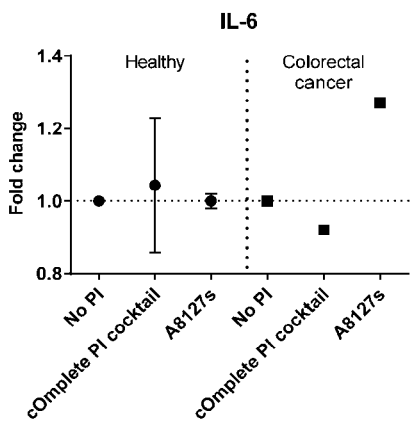
Figure 19B:
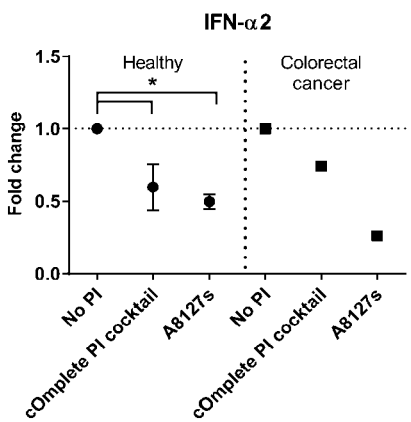
Figure 19C:
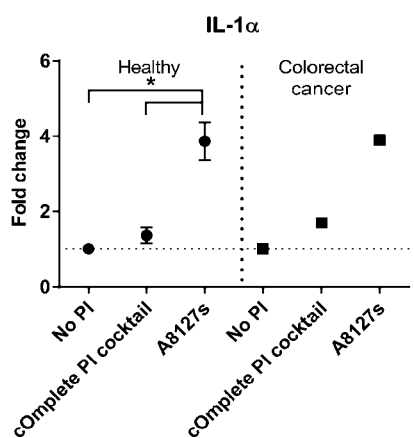
Figure 19D:
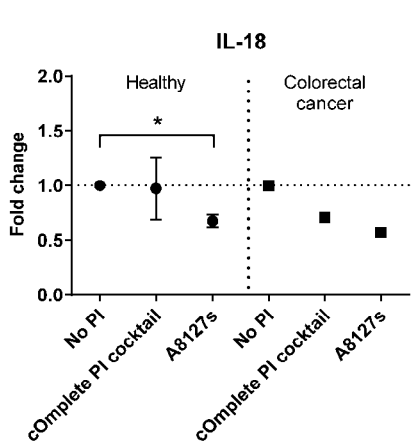
Figure 19E:
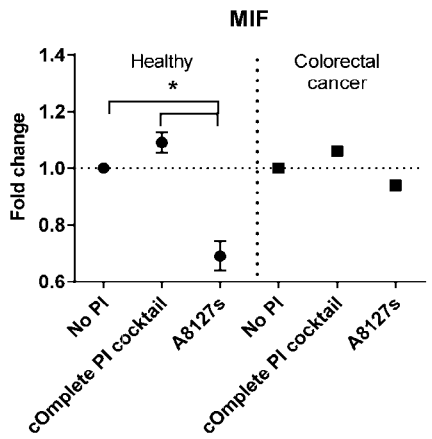
Figure 19F:
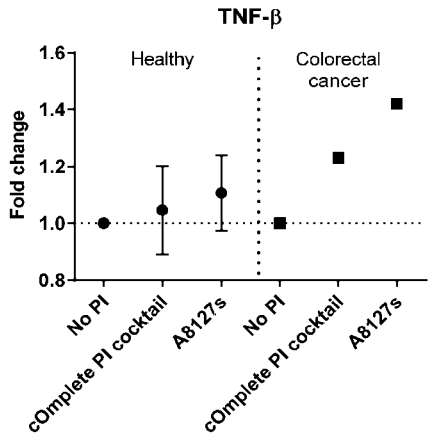
Figure 19G:
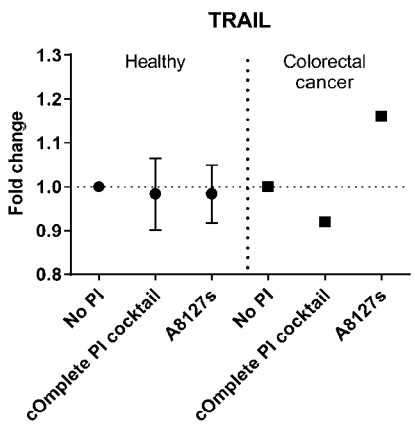
Figure 19H:
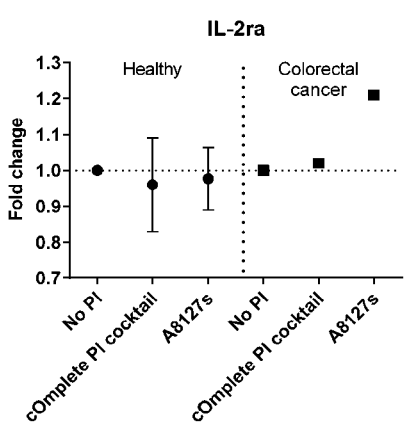
Figure 19I:
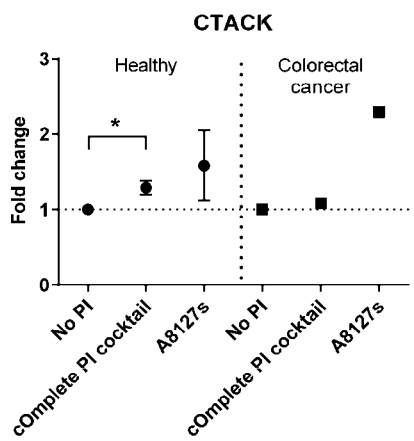
Figure 19J:
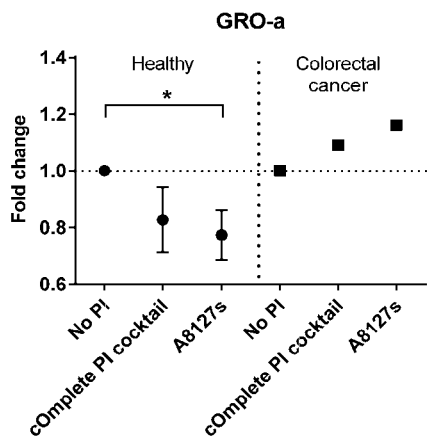
Figure 19K:
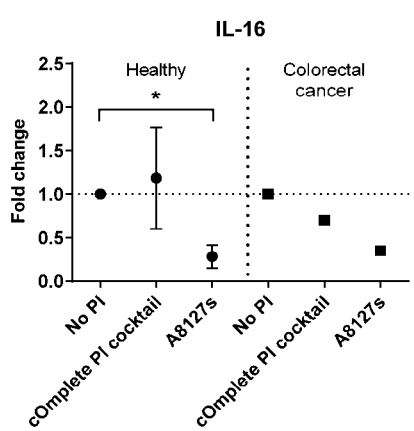
Figure 19L:
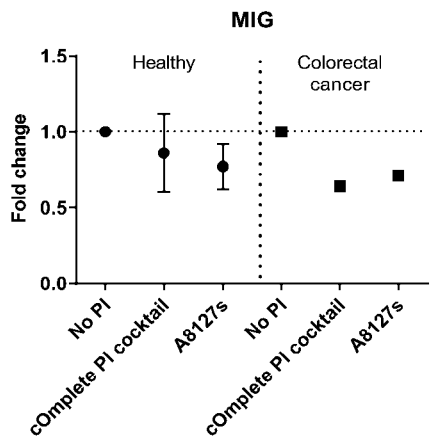
Figure 19M:
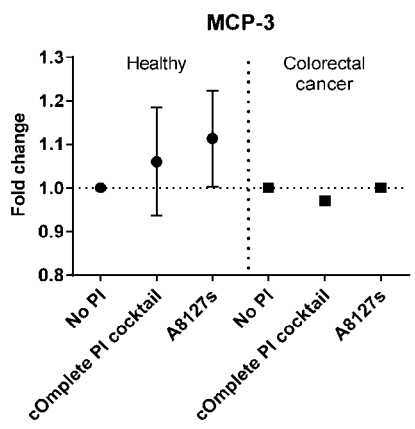
Figure 19N:
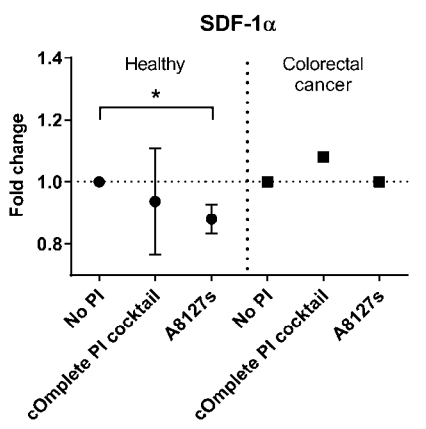
Figure 19O:
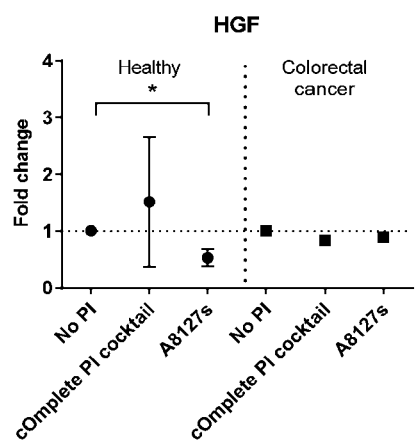
Figure 19P:
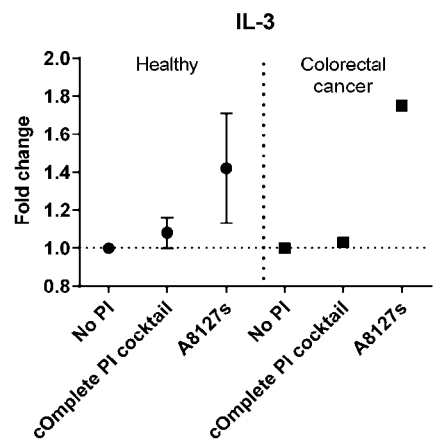
Figure 19Q:
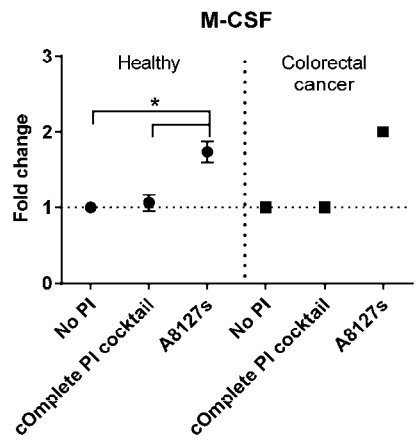
Figure 19R:
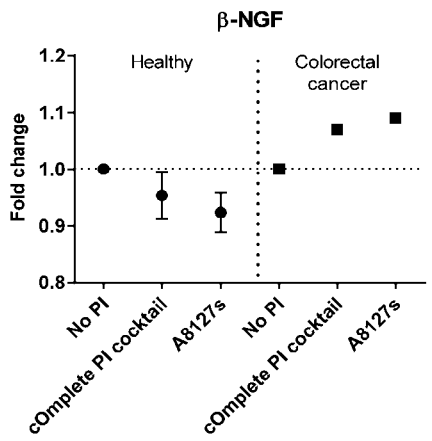
Figure 19S:
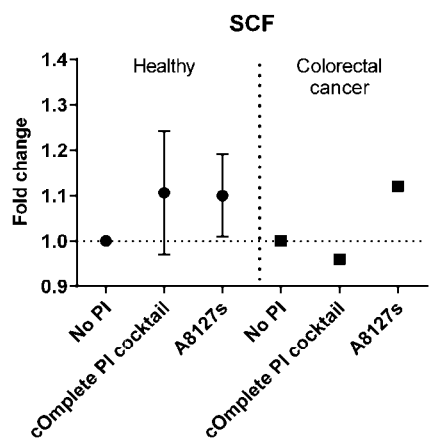
Figure 19T:
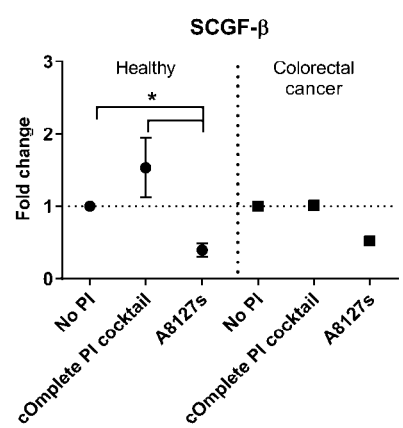
Figure 19U:
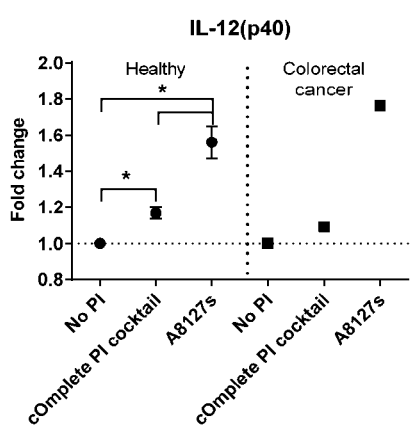
Figure 19V:
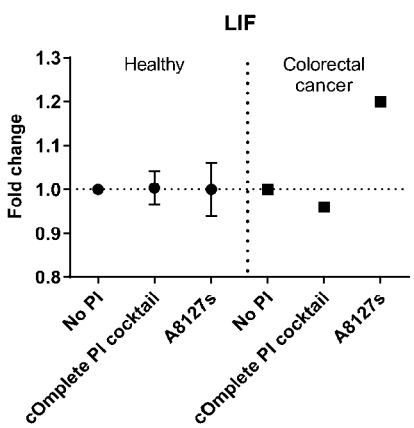
Figure 20A:
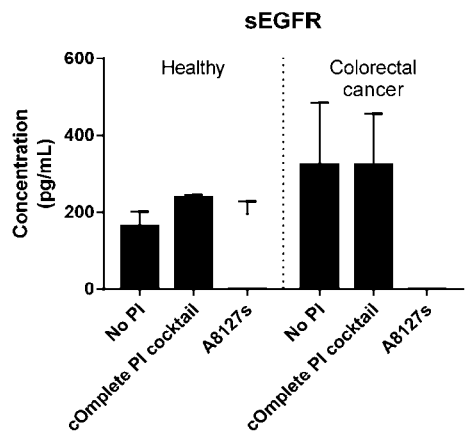
FIG. 20A-20LL is a series of graphs showing the effect of individual protease inhibitors and protease inhibitor cocktails on other proteins released from red blood cells from healthy individuals.
Figure 20B:
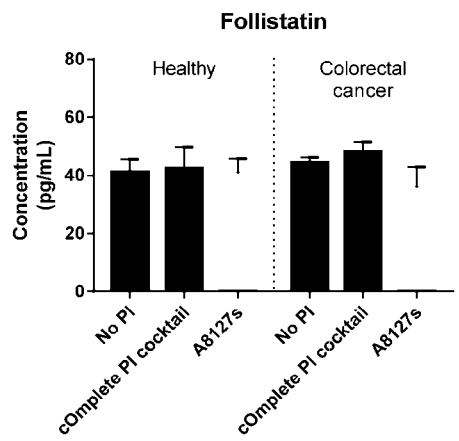
Figure 20C:
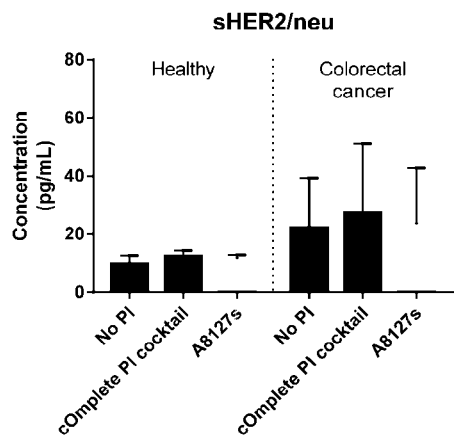
Figure 20D:
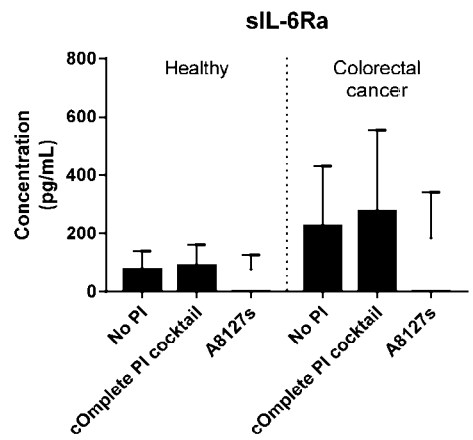
Figure 20E:
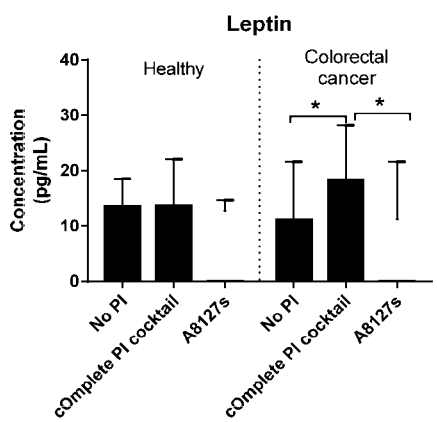
Figure 20F:
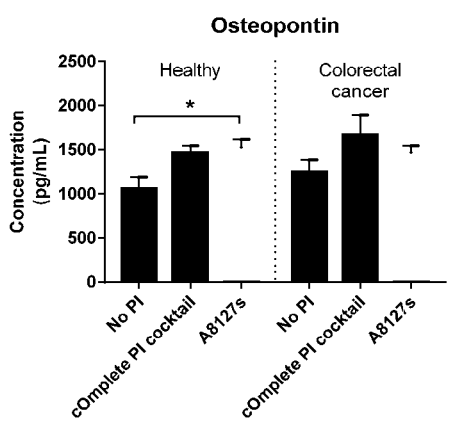
Figure 20G:
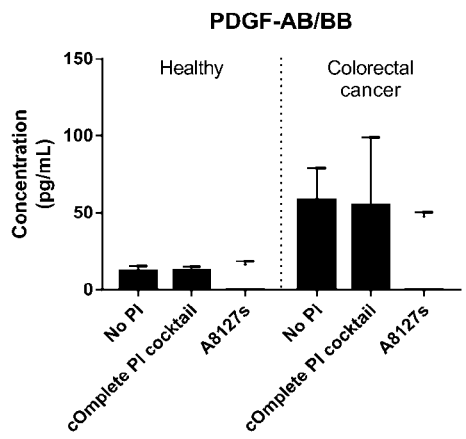
Figure 20H:
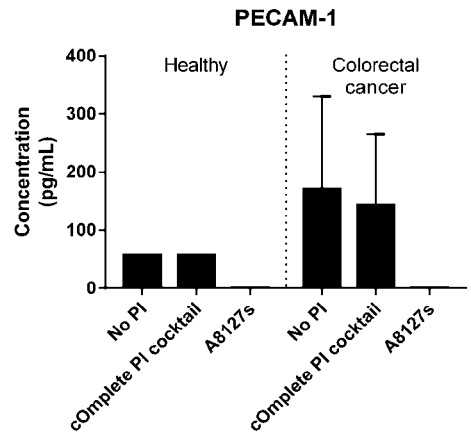
Figure 20I:
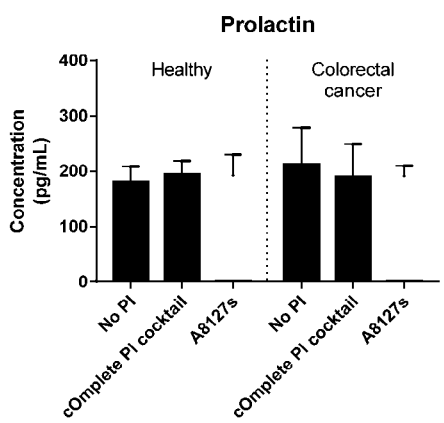
Figure 20J:
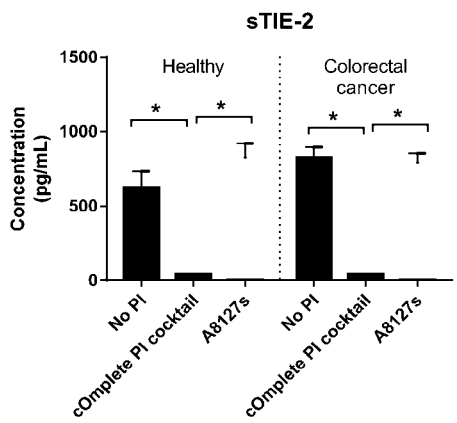
Figure 20K:
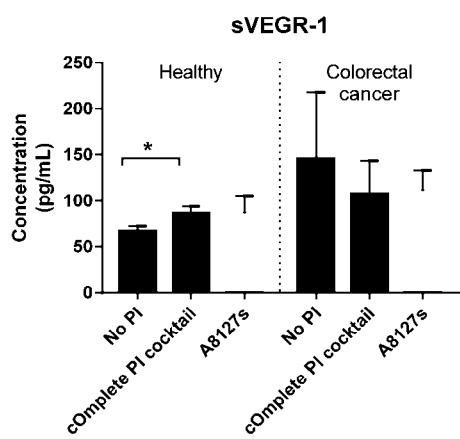
Figure 20L:
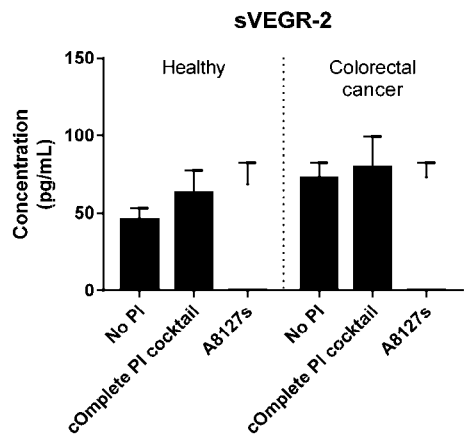
Figure 20M:
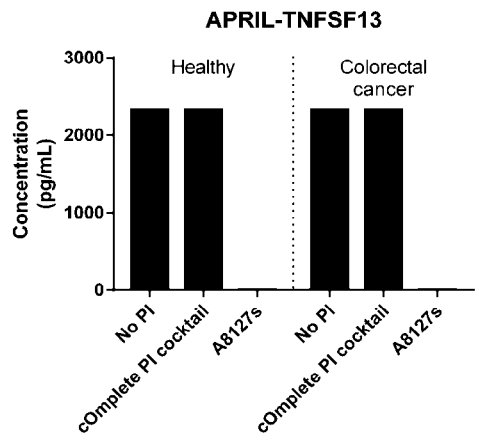
Figure 20N:
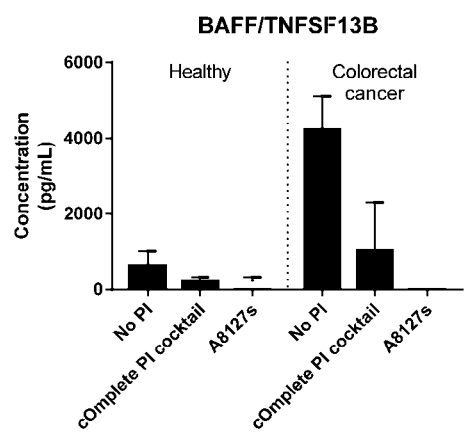
Figure 20O:
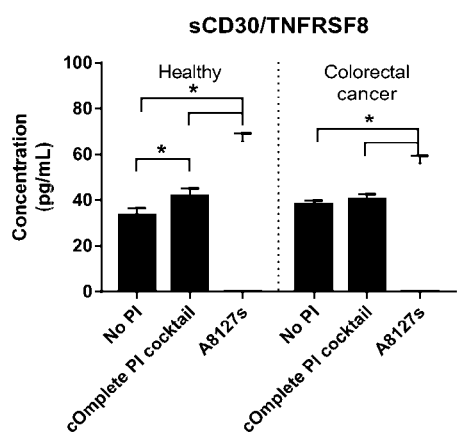
Figure 20P:
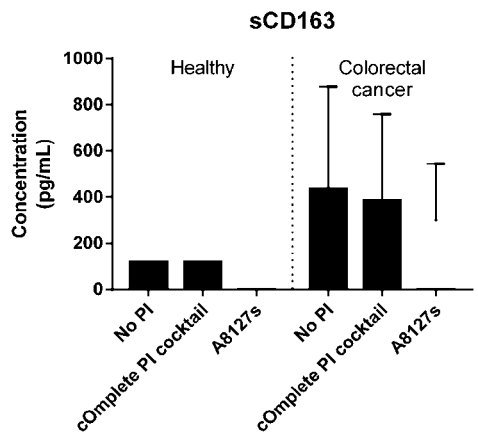
Figure 20Q:
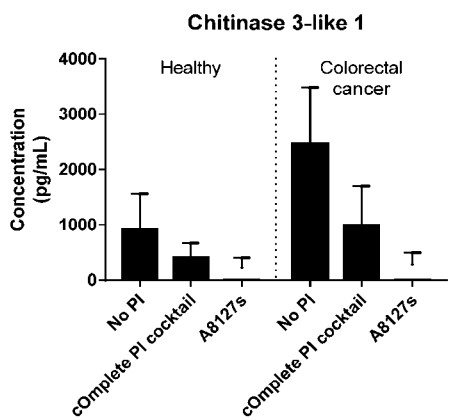
Figure 20R:
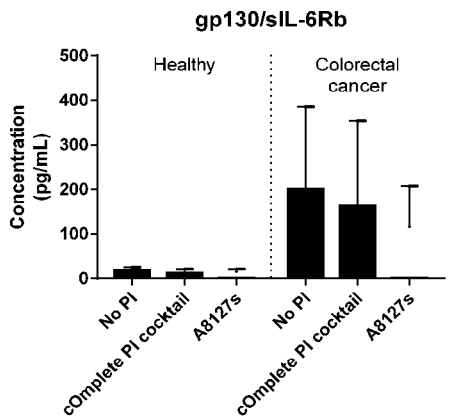
Figure 20S:
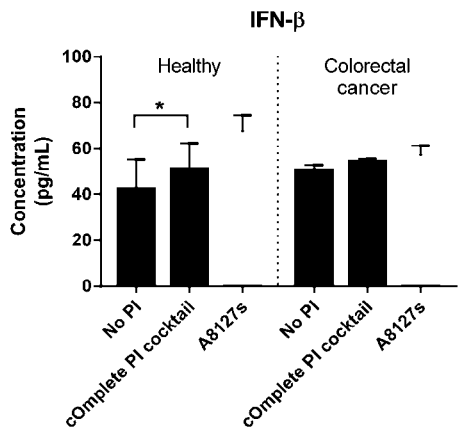
Figure 20T:
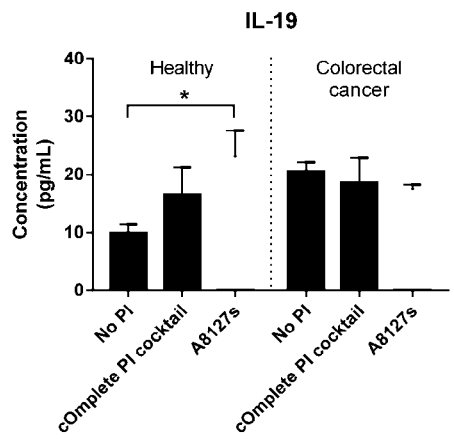
Figure 20U:
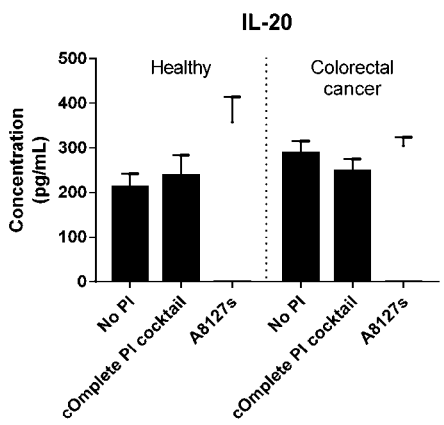
Figure 20V:
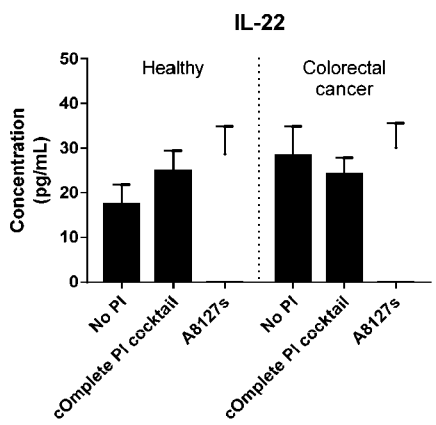
Figure 20W:
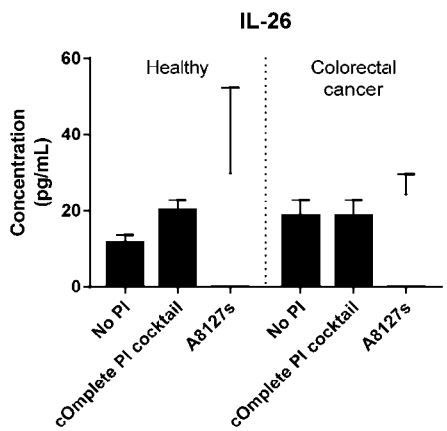
Figure 20X:
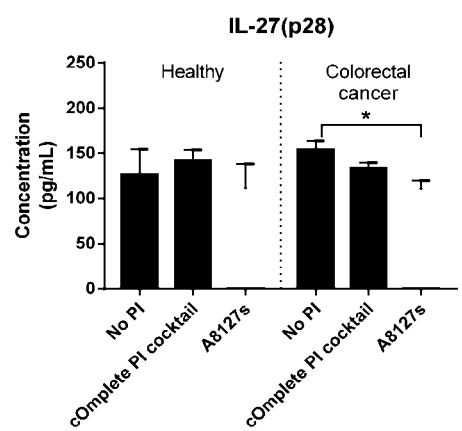
Figure 20Y:
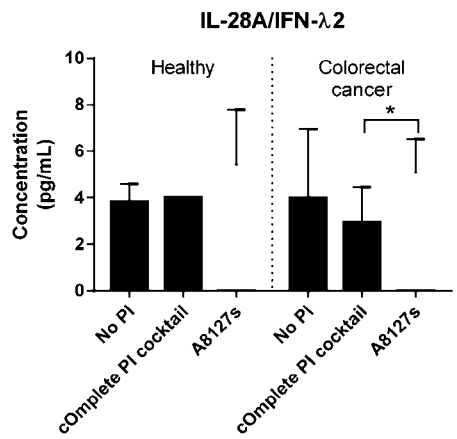
Figure 20Z:
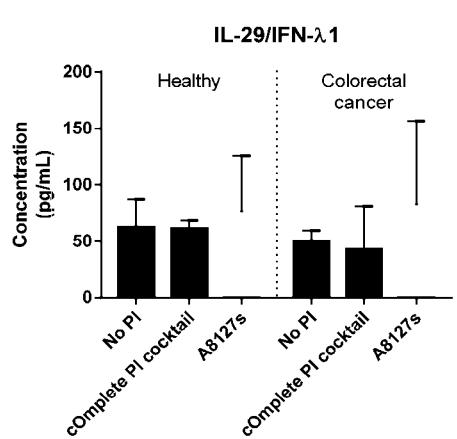
Figure 20A:
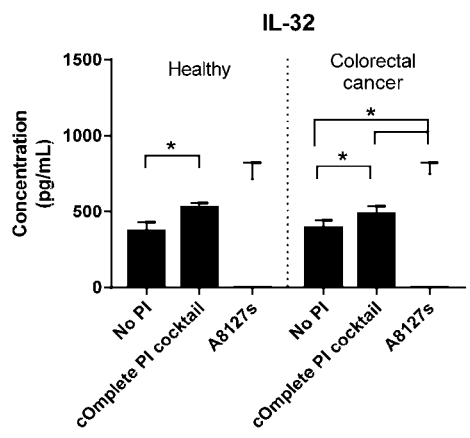
Figure 20B:
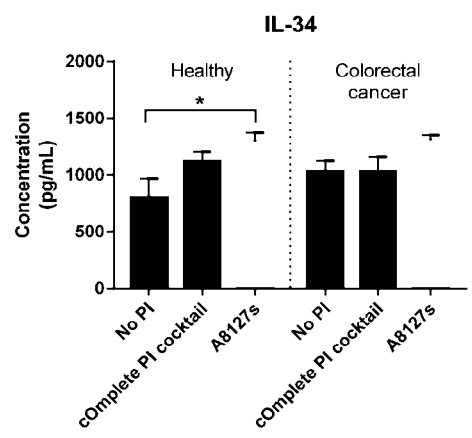
Figure 20C:
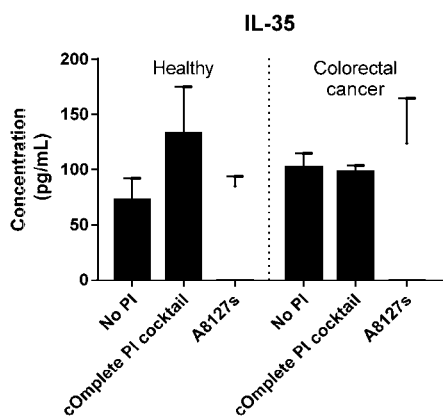
Figure 20D:
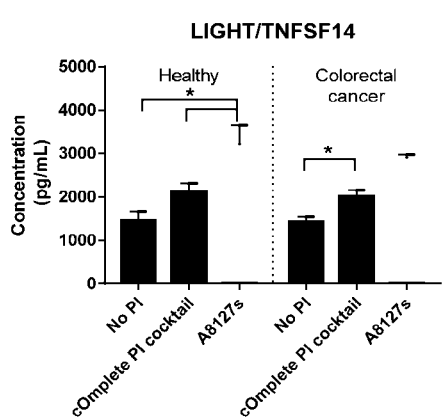
Figure 20E:
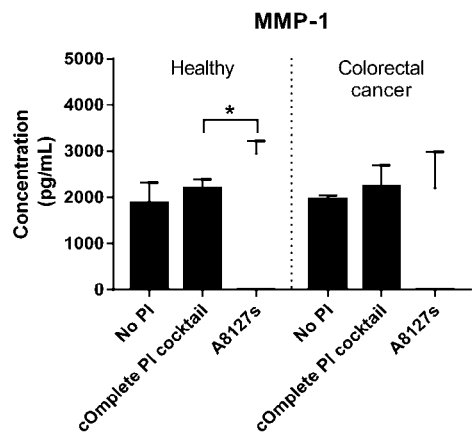
Figure 20F:
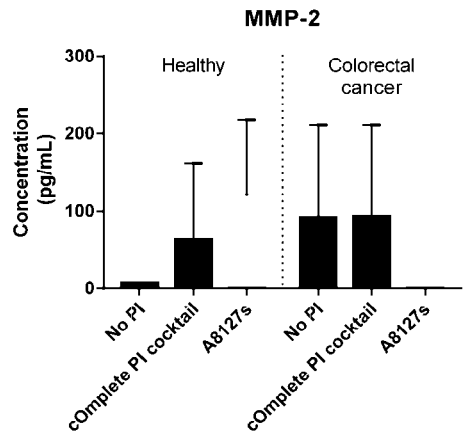
Figure 20G:
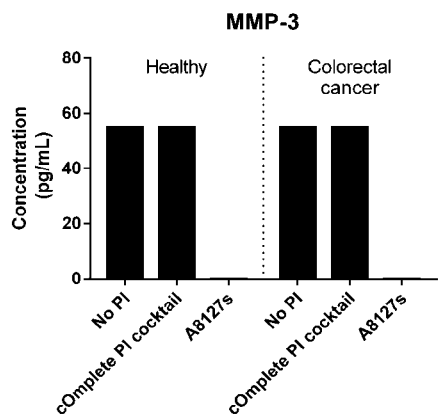
Figure 20H:
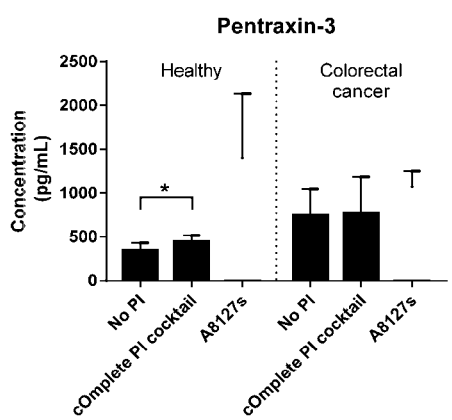
Figure 20I:
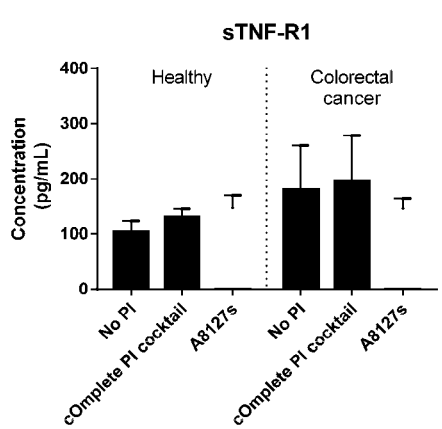
Figure 20J:
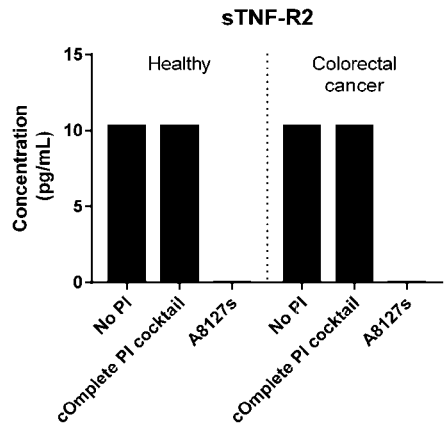
Figure 20K:
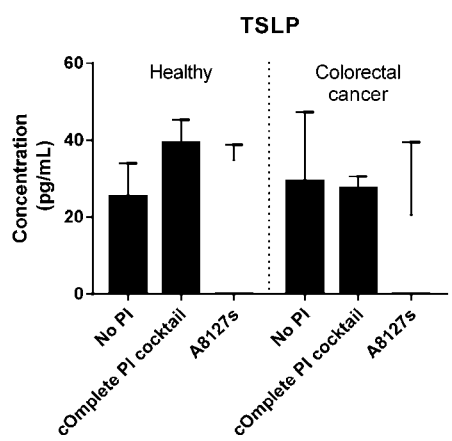
Figure 20L:
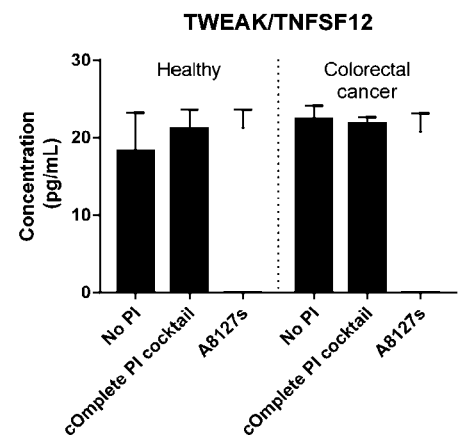
Figure 21A:
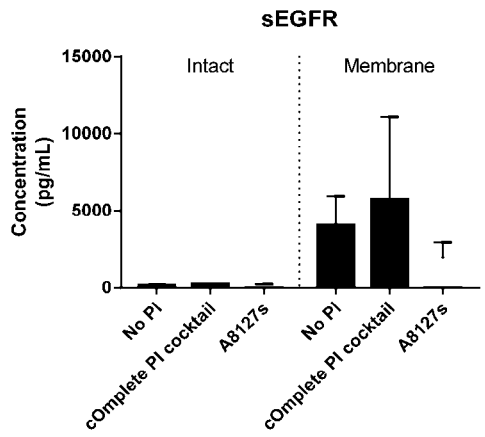
FIG. 21A-21LL is a series of graphs showing the effect of protease inhibitor cocktails on cytokines released from red blood cells from healthy individuals compared to cytokines released from red blood cell membranes from healthy individuals.
Figure 21B:
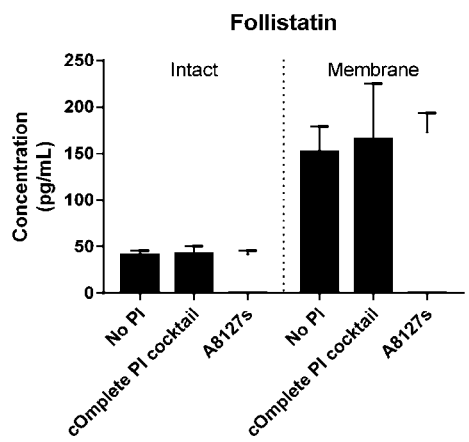
Figure 21C:
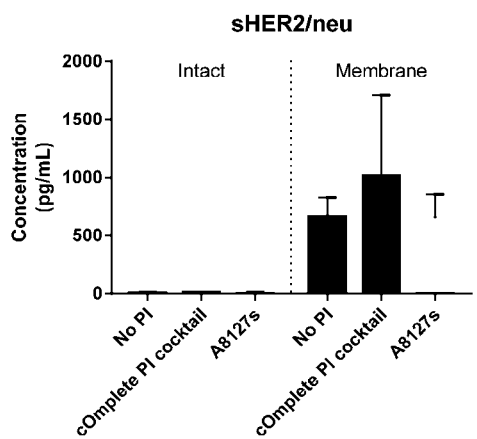
Figure 21D:
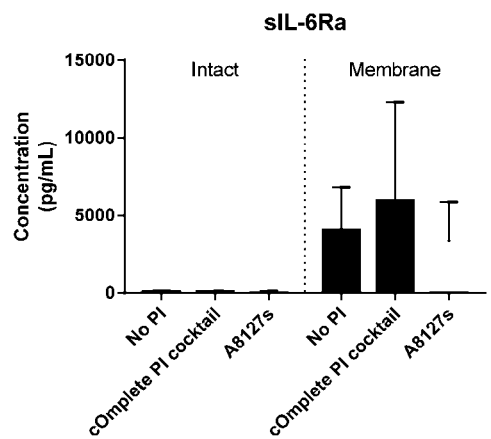
Figure 21E:
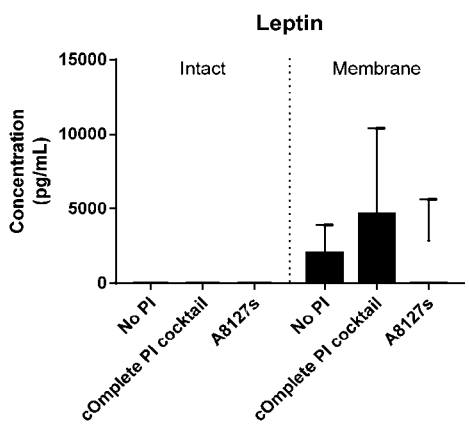
Figure 21F:
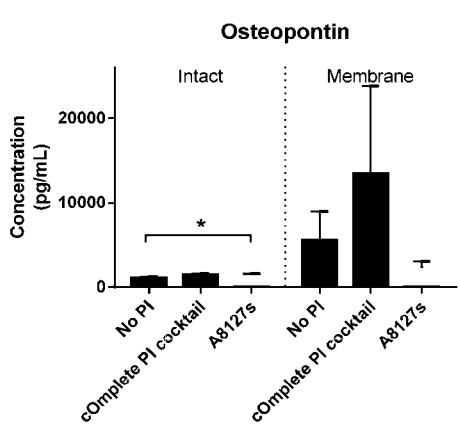
Figure 21G:
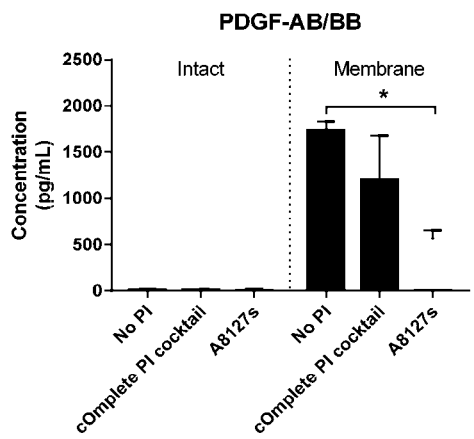
Figure 21H:
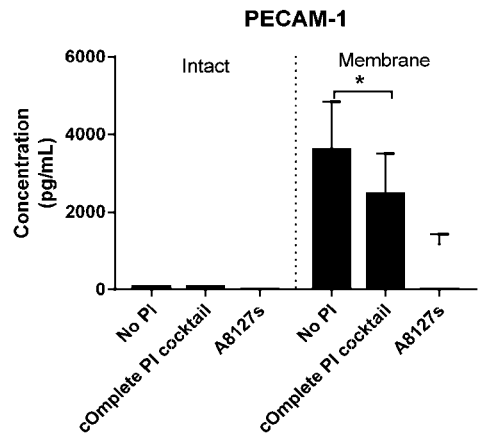
Figure 21I:
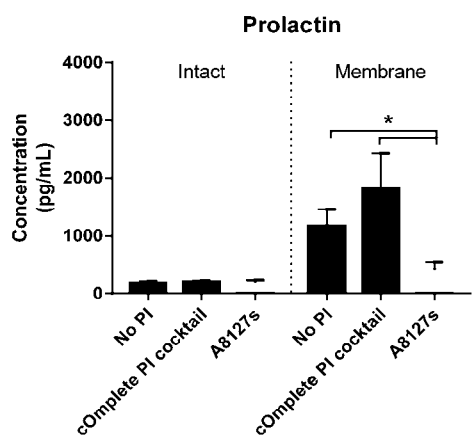
Figure 21J:
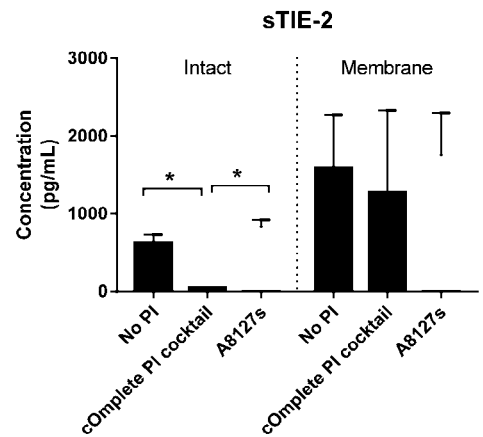
Figure 21K:
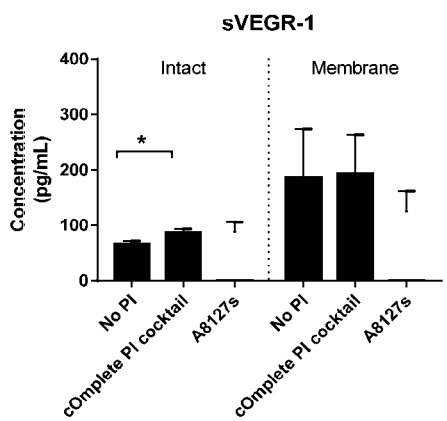
Figure 21L:
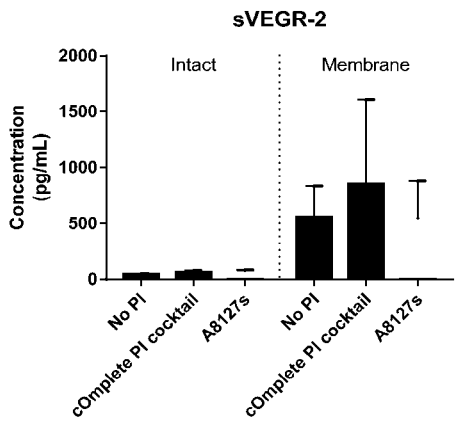
Figure 21M:
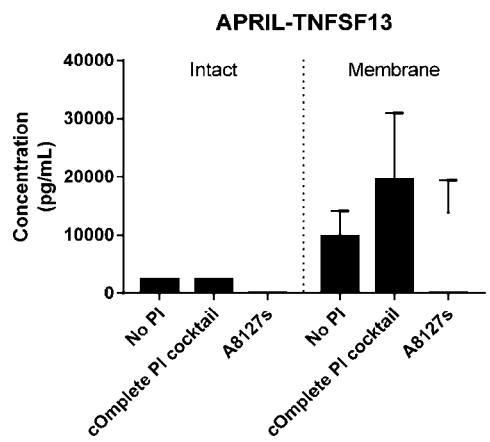
Figure 21N:
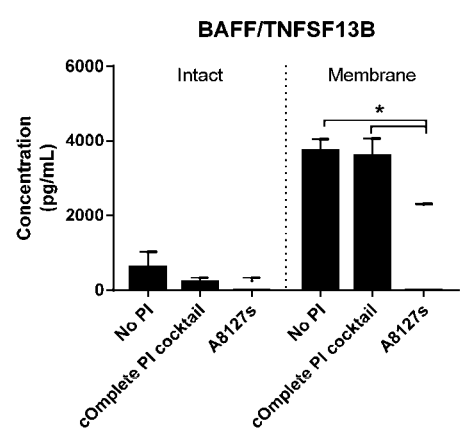
Figure 21O:
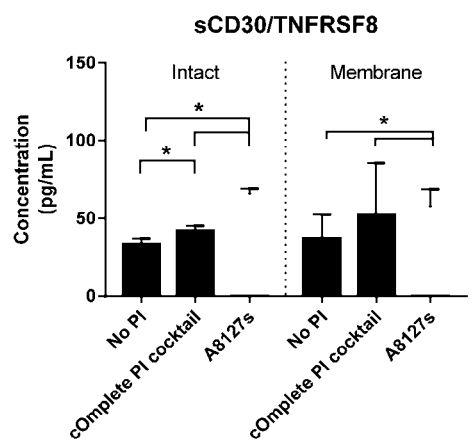
Figure 21P:
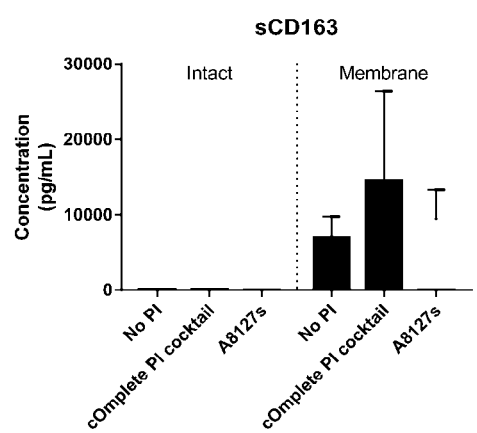
Figure 21Q:
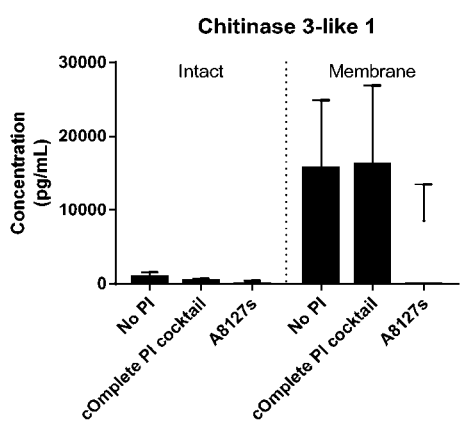
Figure 21R:
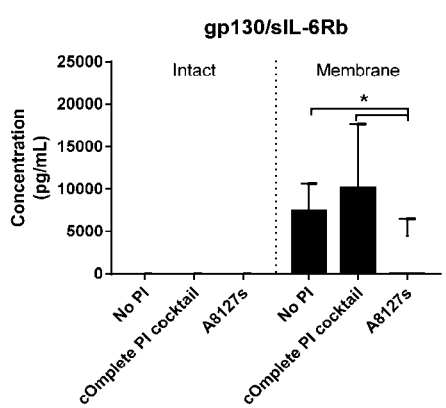
Figure 21S:
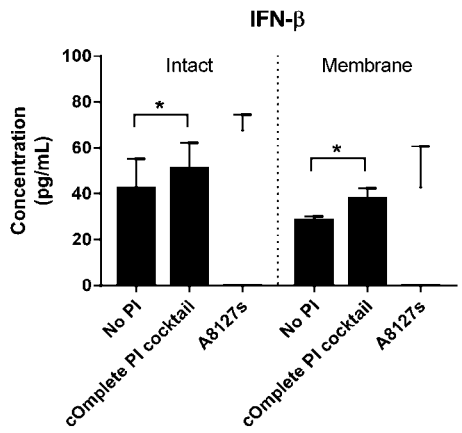
Figure 21T:
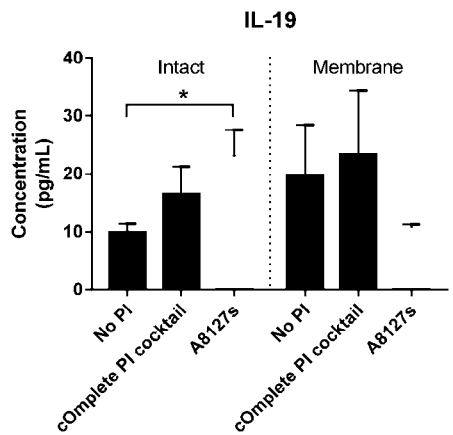
Figure 21U:
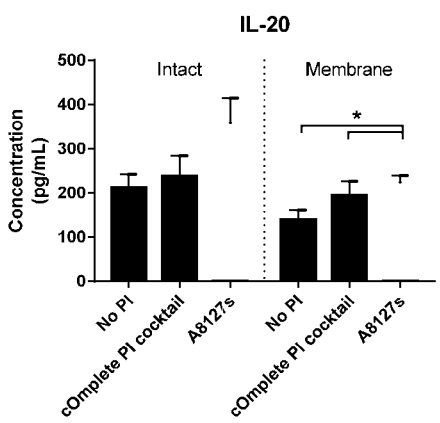
Figure 21V:
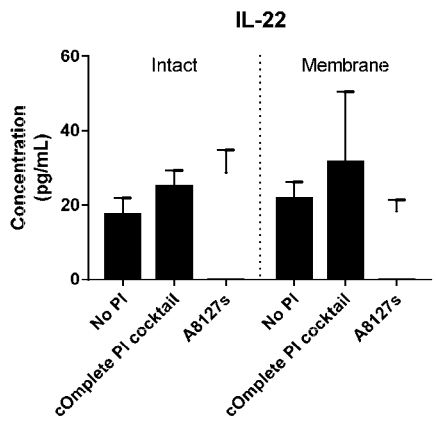
Figure 21W:
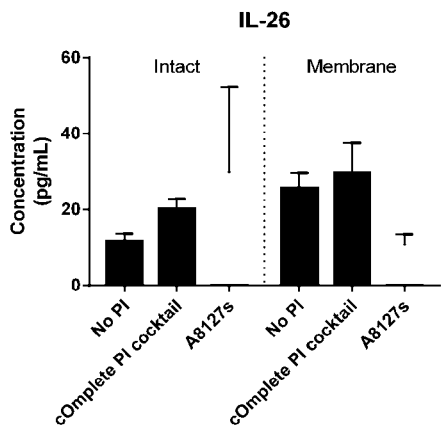
Figure 21X:
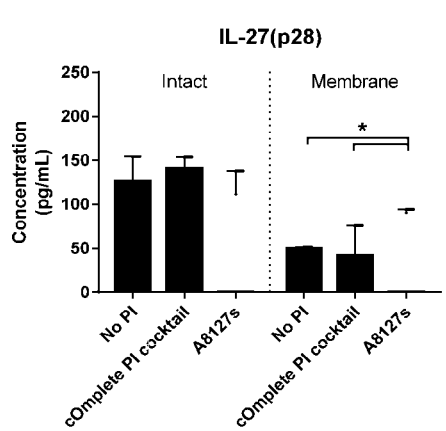
Figure 21Y:
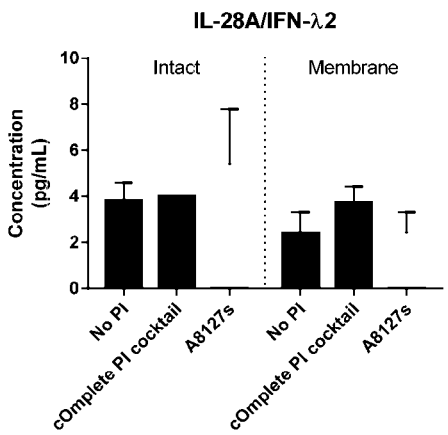
Figure 21Z:
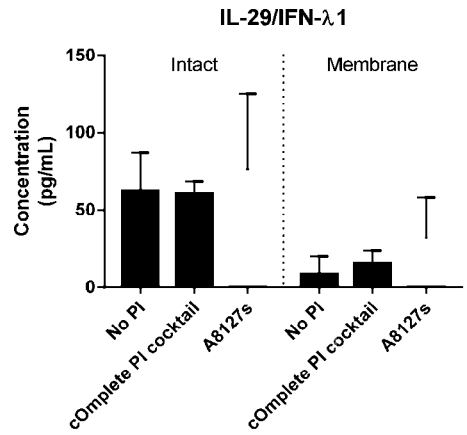
Figure 21A:
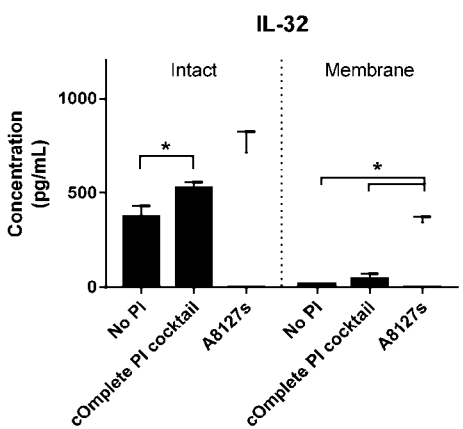
Figure 21B:
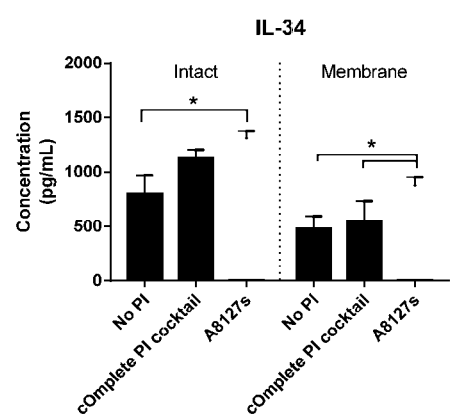
Figure 21C:
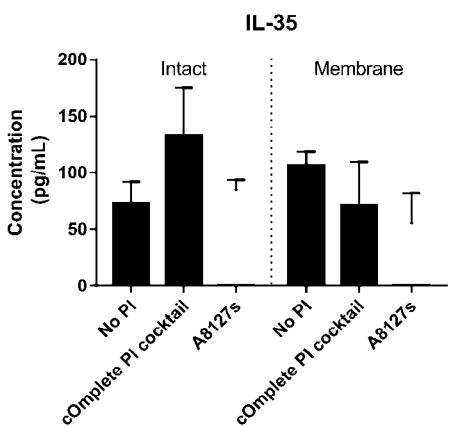
Figure 21D:
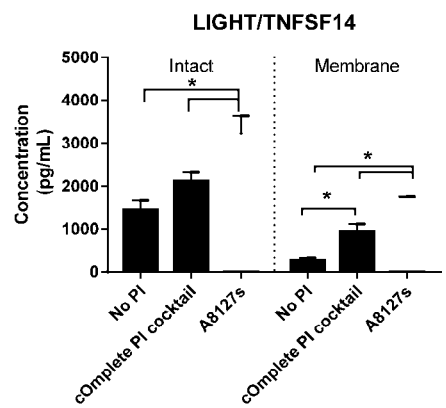
Figure 21E:
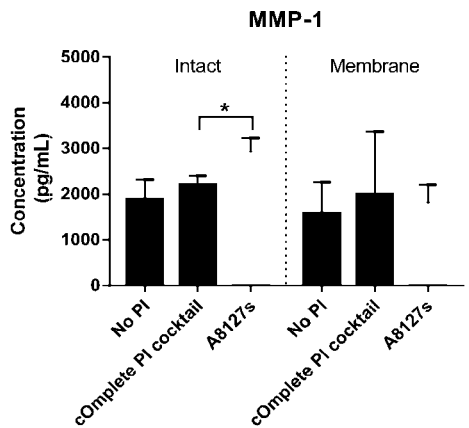
Figure 21F:
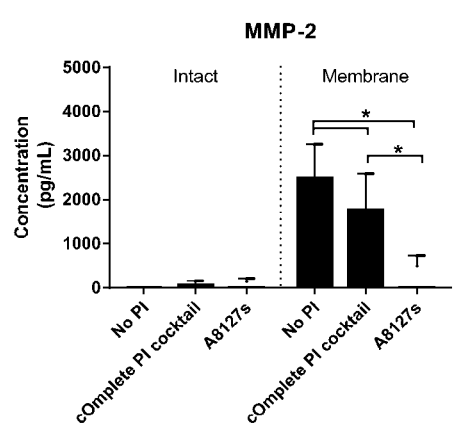
Figure 21G:
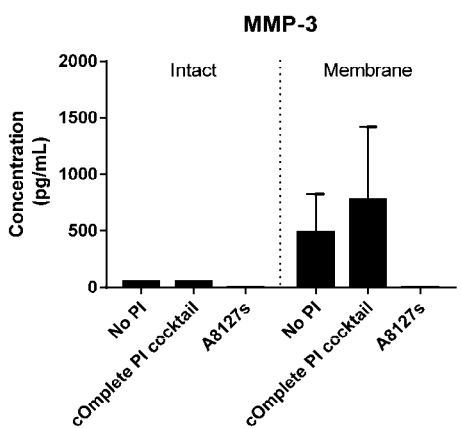
Figure 21H:
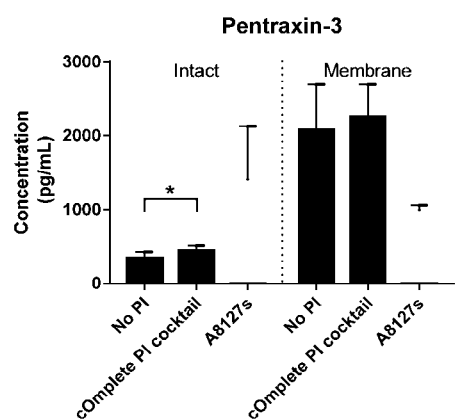
Figure 21I:
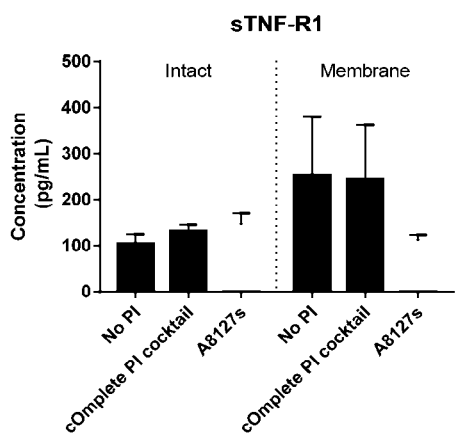
Figure 21J:
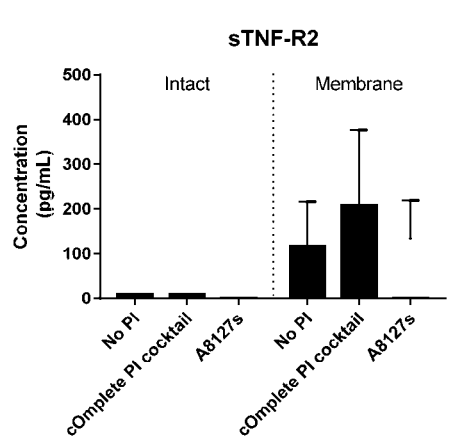
Figure 21K:
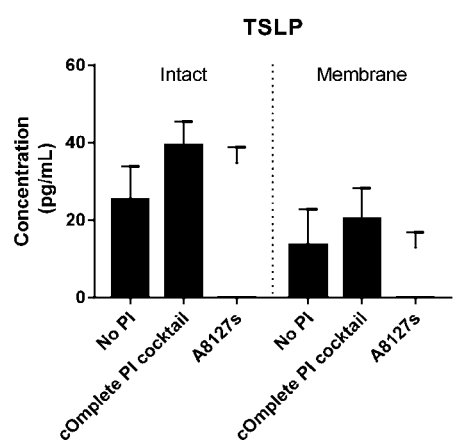
Figure 21L:
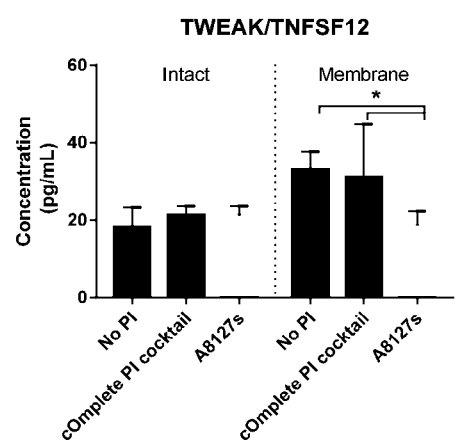

Proteins released from red blood cell membranes from healthy and colorectal cancer cohorts also had a differential concentration in the presence and absence of protease inhibitors. For the isolation of red blood cell membrane, the frozen aliquots of the whole blood were subjected to 3 freeze thaw cycles to ensure complete cellular lysis. Following this, an aliquot of the lysates (volume equivalent to 120 million red blood cells per 100 μL) was added to PBS at a 1:20 ratio (lysate:PBS). The red blood cell membranes were then isolated by centrifugation out of solution (16,000 g, 20 mins, 4° C.). The upper fraction was then discarded and the resulting membranes were then diluted to 1,200 million cells/mL in PBS and were incubated at 37° C. and 5% $CO_2$ for 24 hours. The fold change of proteins in red blood cell membrane-conditioned PBS (isolated from whole blood lysates) at 1,200 million cells/mL following incubation at 37° C. for 24 hours with protease inhibitors compared to no protease inhibitor incubation of red blood cell membranes from healthy participants or participants with colorectal cancer. Values significantly different (*) if p<0.05. Data are mean±standard deviation. FIG. 19A-19VV shows that eight cytokines had a differential response to the protease inhibitor cocktail A8127s in red blood cell membranes from individuals having colorectal cancer compared to that of healthy individuals.

The concentration of additional proteins were analyzed in red blood cells incubated with protease inhibitors from healthy individuals and those having colorectal cancer. A 16-plex human cancer biomarker panel 1 that assays for sEGFR, FGF-basic, G-CSF, HGF, sHER-2/neu, sIL-6Ra, Leptin, Osteopontin, PECAM-1, PDGF-AB/BB, Prolactin, SCF, sTIE-2, sVEGFR-1, and sVEGFR-2, and a 37-plex human inflammation cytokine panel that assays for APRIL/TNFSF13, BAFF/TNFSF13B, sCD30/TNFRF8, sCD163, Chitinase-3-like 1, gp130/sIL-6β, IFN-α2, IFN-γ, IL-2, sIL-6Rα, IL-8, IL-10, IL-11, IL-12(p40), IL-12(p70), IL-19, IL-20, IL-22, IL-26, IL-27(p28), IL-28A/IFN-λ2, IL-29/IFN-λ1, IL-32, IL-34, IL-35, LIGHT/TNFSF14, MMP-1, MMP-2, MMP-3, Osteocalcin, Osteopontin, Pentraxin-3, sTNF-R1, sTNF-R2, TSLP, and TWEAK/TNFSF12 (Bio-Plex cancer biomarker 16-plex panel and inflammation 37-plex panel, Bio-Rad) were used. The assays were performed according to manufacturer's instructions using an automated magnetic wash station (BioPlex Pro II, Bio-Rad) for the washing steps. The assays were run on the Luminex® 200™ system (Bio-Rad) and fluorescent values were collected. The calibration curve for each cytokine was analysed with 5 parametric logistic curve regression using BioPlex manager software (ver. 5.0, Bio-Rad, USA).

FIG. 20A-20LL shows the concentration of proteins in red blood cell-conditioned PBS at 400 million cells/mL following incubation at 37° C. for 24 hours with either no protease inhibitors and protease inhibitor cocktails for healthy participants (n=3) or participants with colorectal cancer (n=2). Values were significantly different (*) if p<0.05. Data are presented as mean±standard deviation. The data demonstrated that protease inhibitors have an effect on the concentration of a range of hormones, soluble receptors, proteins, and cytokines that are released from red blood cells. High concentrations of molecules, such as osteopontin, chitinase 3-like 1, and MMP-1, were released from red blood cells isolated from healthy individuals that were incubated for 24 hours at 37° C. in PBS (FIG. 20A-20LL). The addition of protease inhibitor cocktails to the red blood cells, resulted in an alteration in protein concentration. For example, sCD30/TNFRSF8, IL-19, and LIGHT/TNFSF14 were significantly higher with A8127s incubation in comparison to the control (no protease inhibitors) (FIG. 20A-20LL). The observed changes following protease inhibitor incubation was different between red blood cells isolated from healthy participants and those isolated from participants with colorectal cancer. For instance, the concentration of osteopontin was significantly increased with A8127s incubation of red blood cells from the healthy group, but it did not change under the same conditions in the colorectal cancer group. Conversely, the concentration of IL-27(p28) significantly decreased with A8127s in the colorectal cancer group, but did not change in the healthy group. The trend of one cohort having a significantly changed protein concentration in the presence of protease inhibitors while in the other cohort protein concentration moved in the opposite direction or did not change, occurred in 10 proteins.

Next, whether proteins released from the red blood cell membranes were at differential concentrations in red blood cells compared to red blood cell membranes incubated with protease inhibitor cocktails was assessed for healthy individuals. To obtain red blood cell membranes, frozen aliquots of whole blood were subjected to 3 freeze thaw cycles to ensure complete cellular lysis. Following this, an aliquot of the lysates (volume equivalent to 120 million red blood cells per 100 μL) was added to PBS at a 1:20 ratio (lysate:PBS). The red blood cell membranes were then isolated by centrifugation out of solution (16,000 g, 20 mins, 4° C.). The upper fraction was then discarded and the resulting membranes were then diluted to 1,200 million cells/mL in PBS and were incubated at 37° C. and 5% $CO_2$ for 24 hours. Some samples were treated with the protease inhibitor cocktails (complete or A8127s) during the PBS incubation. Concentration of proteins in red blood cell-conditioned PBS at 400 million cells/mL (intact red blood cells) or red blood cell membrane-conditioned PBS at 1,200 million cells/mL (red blood cell membranes) following incubation at 37° C. for 24 hours with either no protease inhibitors and protease inhibitor cocktails from healthy participants (n=3) or participants with colorectal cancer (n=2). Values were significantly different (*) if p<0.05. Data are presented as mean±standard deviation.

As seen in FIG. 21A-21LL, there was a stark difference in the protein profile of intact red blood cells and red blood cell membranes from healthy participants. In the control (no protease inhibitors), the concentration of proteins released by red blood cell membranes was significantly higher than that released by intact red blood cells for 16 proteins, and was significantly lower for 6 proteins. There were also differences in how the protease inhibitors altered the proteins profile of the conditioned PBS in both intact cells and red blood cell membranes. For example, PDGF-AB/BB was significantly lower in the red blood cell membranes incubated with A8127s compared to the control, but was unchanged in the intact cell group. A similar trend was observed for prolactin, gp130/sIL-6Rb, BAFF/TNFSF13B, MMP-2, and TWEAK/TNFSF12 amongst others (see FIG. 21A-21LL). In other instances, the inclusion of protease inhibitor cocktails significantly changed the concentration of proteins in the conditioned PBS of intact red blood cells but did not affect the release of proteins from red blood cell membranes. Examples of this included osteopontin, sVEGR-1, IL-19, MMP-1, and pentraxin-3. The results indicated that the mechanisms regulating the response to protease inhibitors and the concentration of proteins in conditioned PBS was substantially changed in red blood cell membranes compared to intact red blood cells.

10.2 Lymphoma

To further explore the effect of protease inhibitors on the concentration of proteins released from red blood cell components from those having cancer, the change in concentration of proteins from red blood cell membranes of healthy individuals and those having lymphoma was assessed. For the isolation of red blood cell membranes, frozen aliquots of the whole blood and red blood cells were subjected to 3 freeze thaw cycles to ensure complete cellular lysis. Following this, an aliquot of the lysates (volume equivalent to 120 million red blood cells per 100 μL) was added to PBS at a 1:20 ratio (lysate:PBS). The red blood cell membranes were then isolated by centrifugation out of solution (16,000 g, 20 mins, 4° C.). The upper fraction was then discarded and the resulting membranes were then diluted to 1,200 million cells/mL in PBS and were incubated at 37° C. and 5% $CO_2$ for 24 hours. Some samples were treated with protease inhibitor cocktails (cOmplete or A8127s) during the PBS incubation period.

Figure 22A:
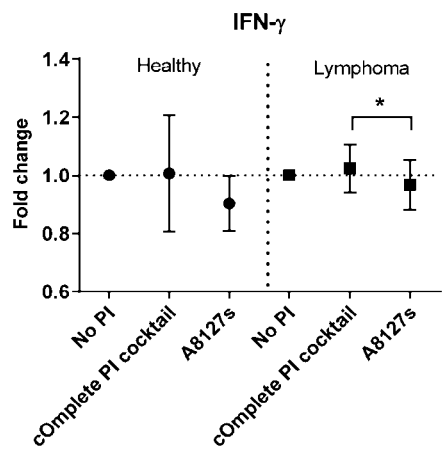
FIG. 22A-22VV is a series of graphs showing the effect of protease inhibitor cocktails on cytokines released from red blood cell membranes obtained from whole blood lysates from healthy individuals compared to individuals having lymphoma.
Figure 22B:
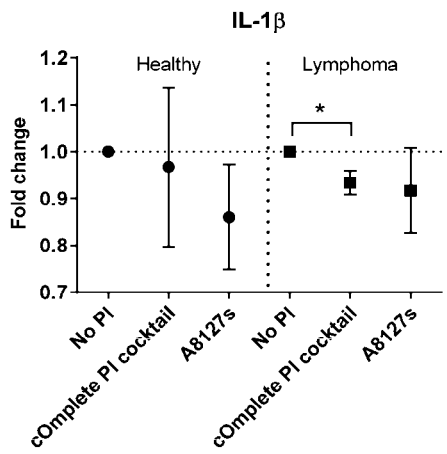
Figure 22C:
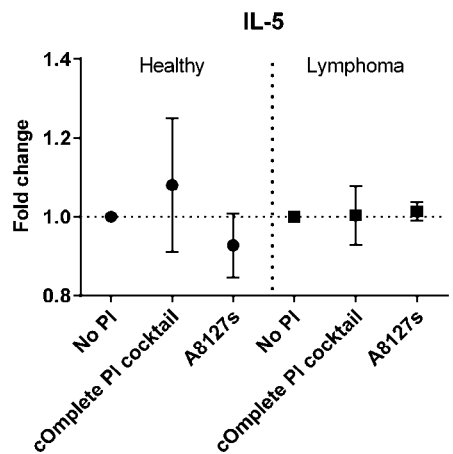
Figure 22D:
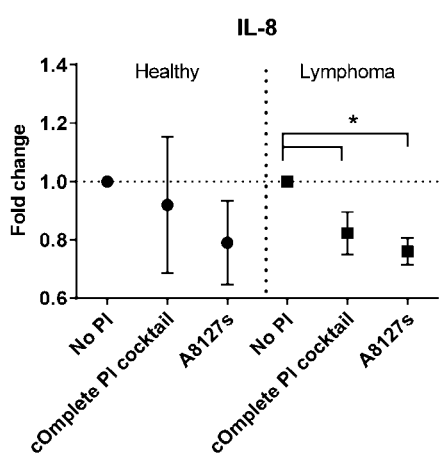
Figure 22E:
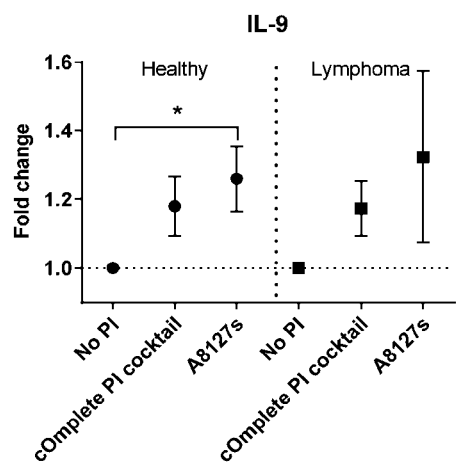
Figure 22F:
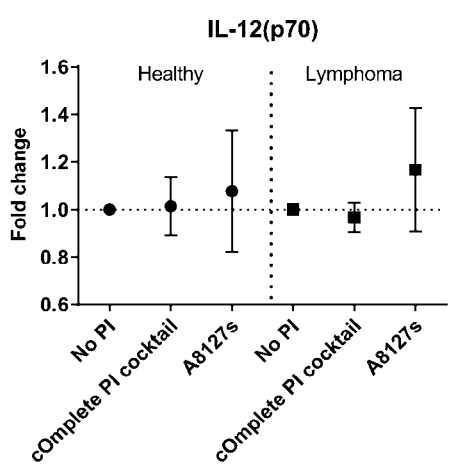
Figure 22G:
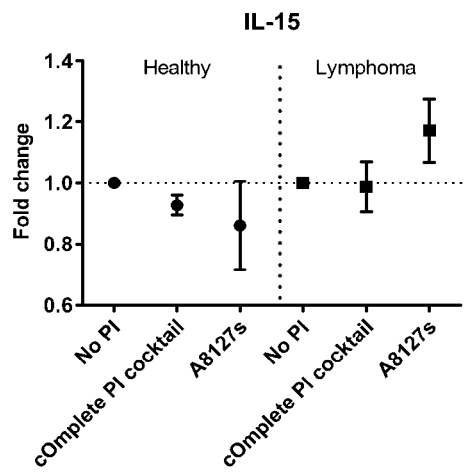
Figure 22H:
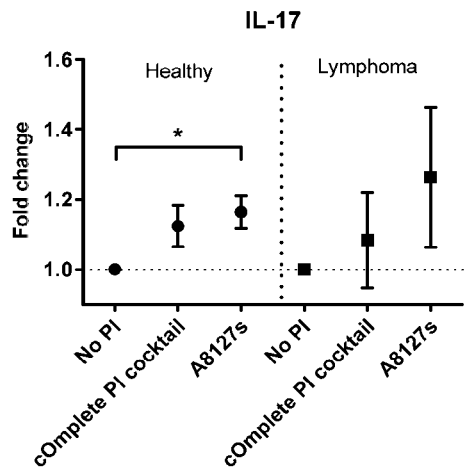
Figure 22I:
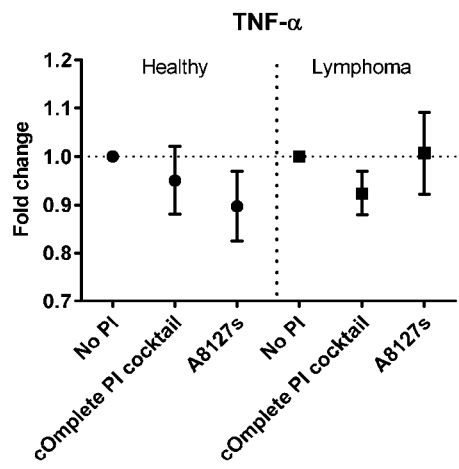
Figure 22J:
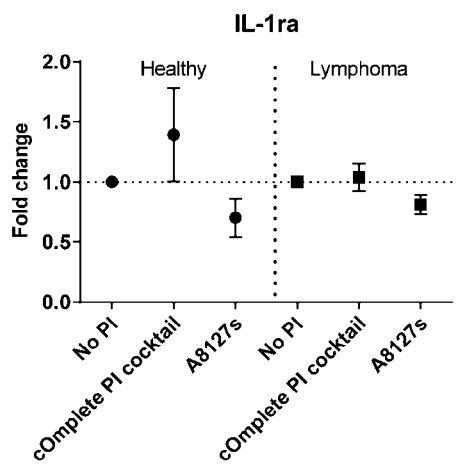
Figure 22K:
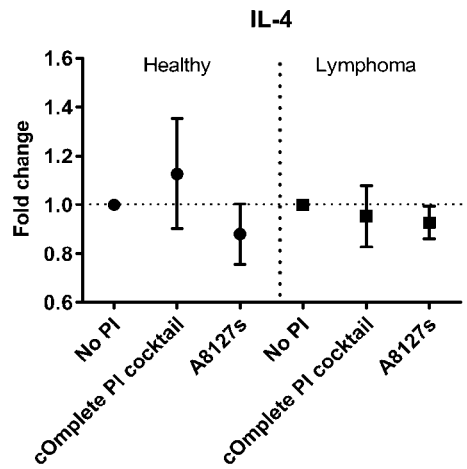
Figure 22L:
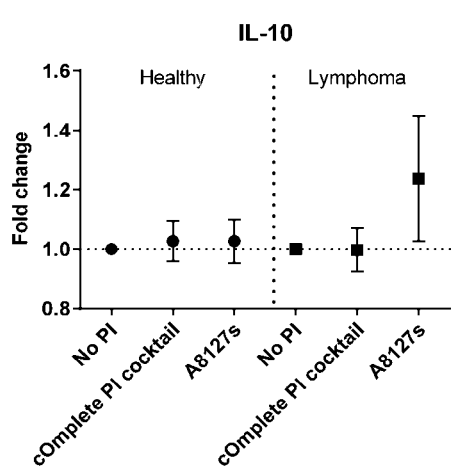
Figure 22M:
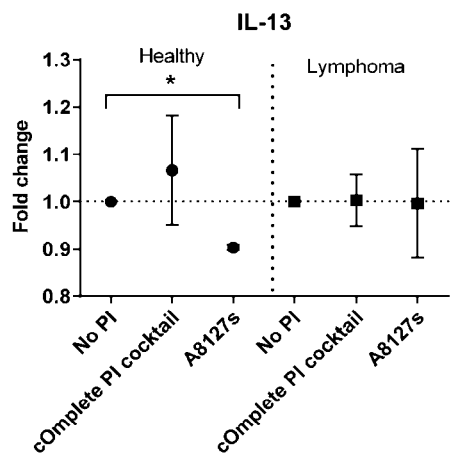
Figure 22N:
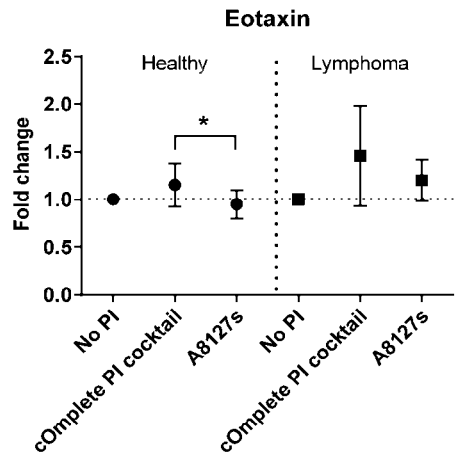
Figure 22O:
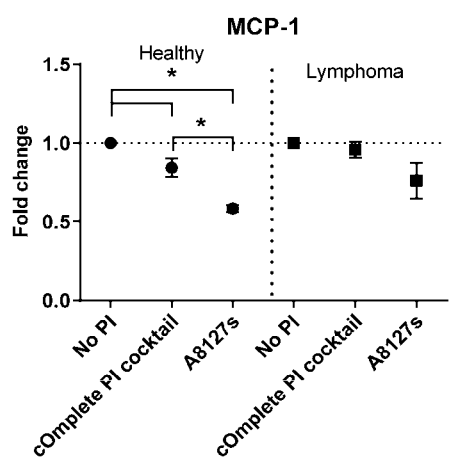
Figure 22P:
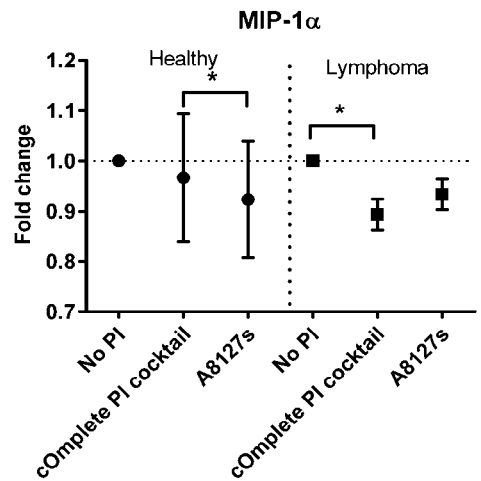
Figure 22Q:
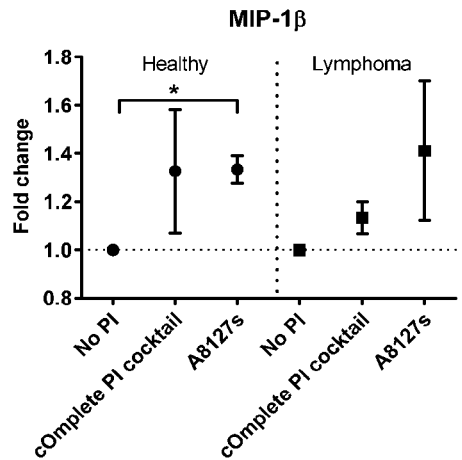
Figure 22R:
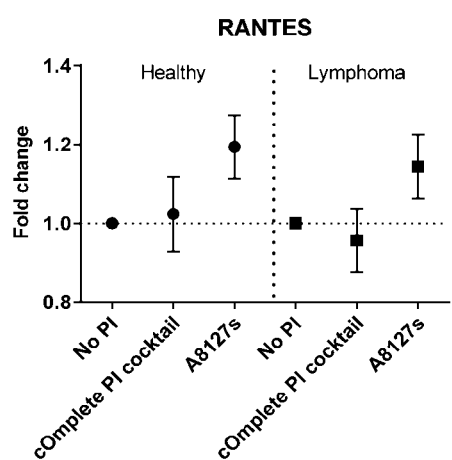
Figure 22S:
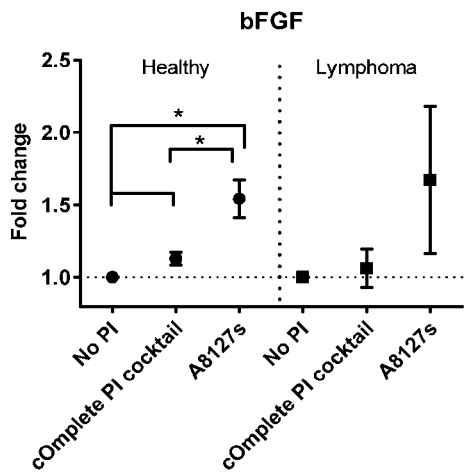
Figure 22T:
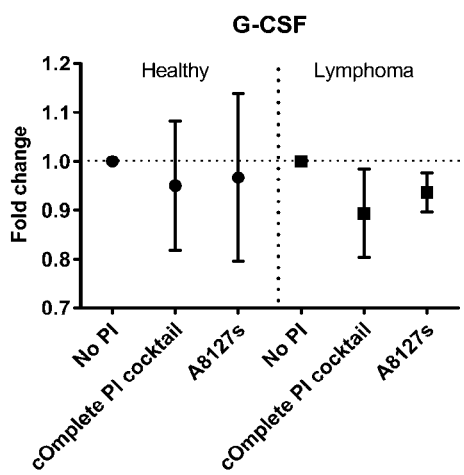
Figure 22U:
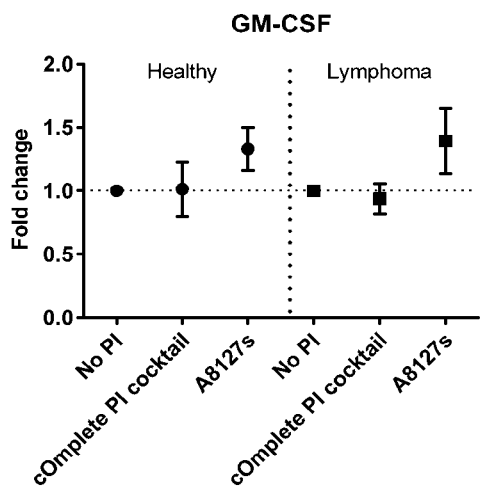
Figure 22V:
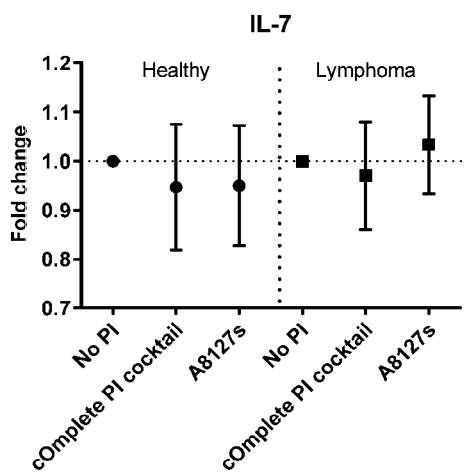
Figure 22W:
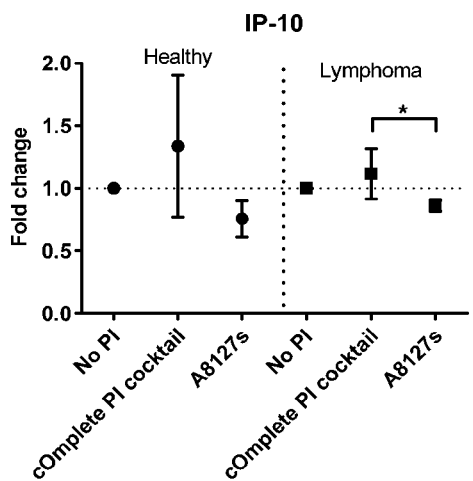
Figure 22X:
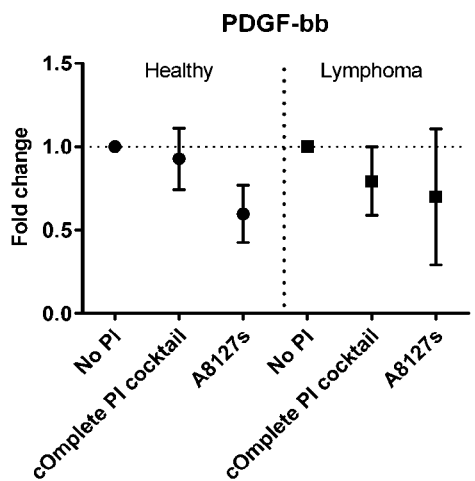
Figure 22Y:
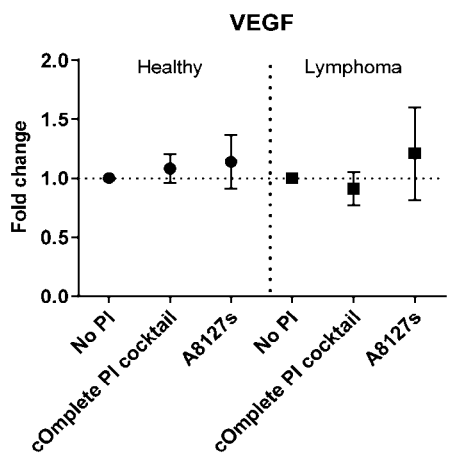
Figure 22Z:
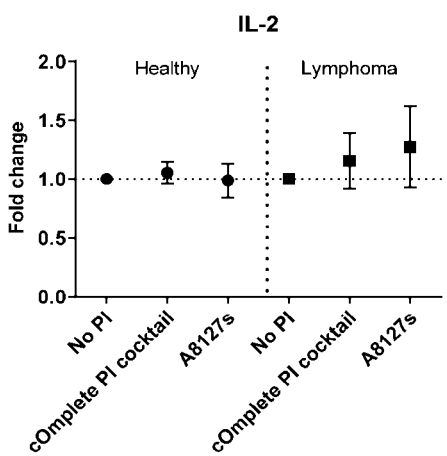
Figure 22A:
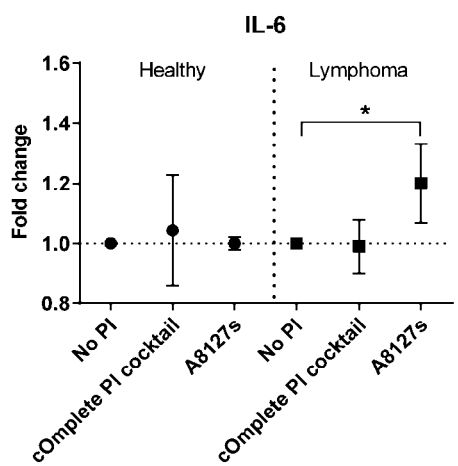
Figure 22B:
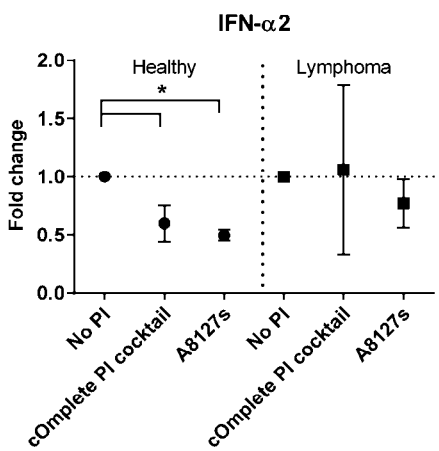
Figure 22C:
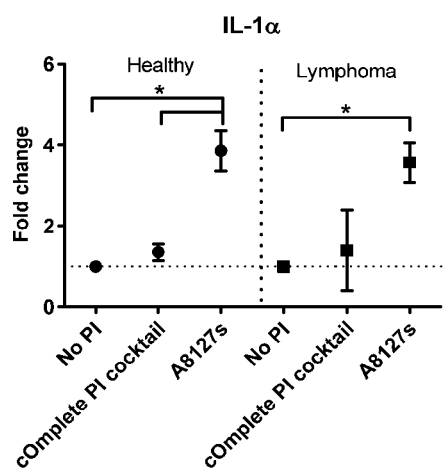
Figure 22D:
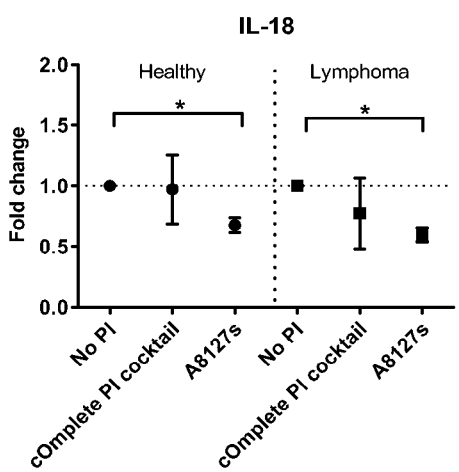
Figure 22E:
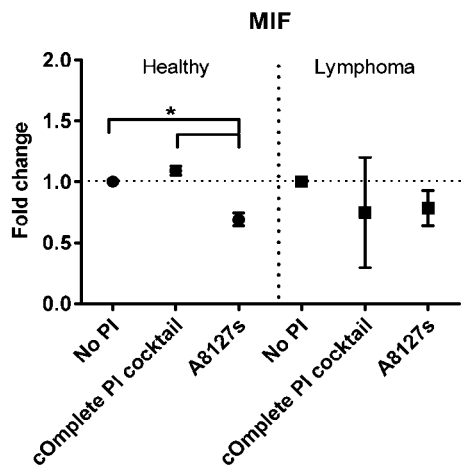
Figure 22F:
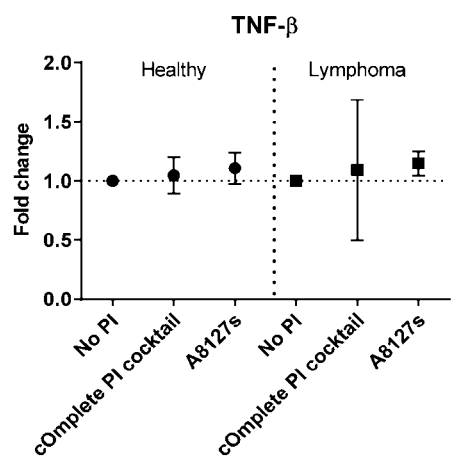
Figure 22G:
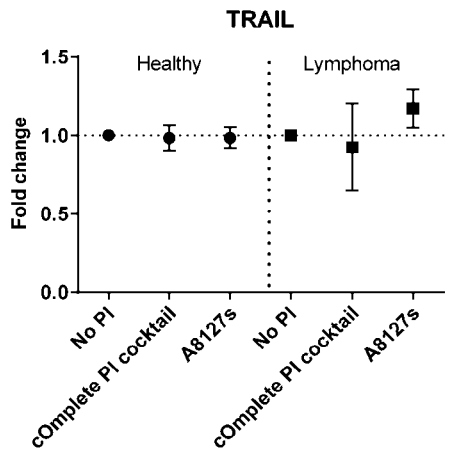
Figure 22H:
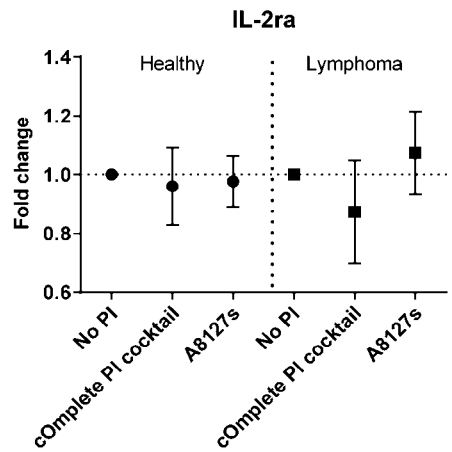
Figure 22I:
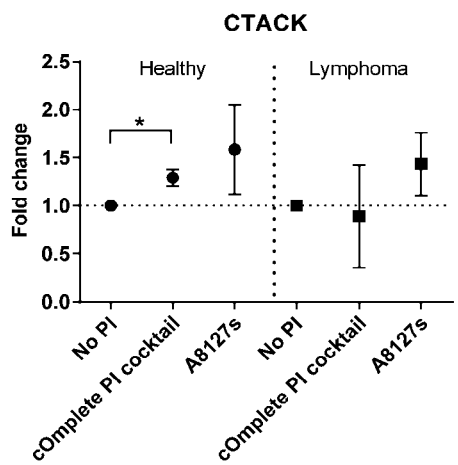
Figure 22J:
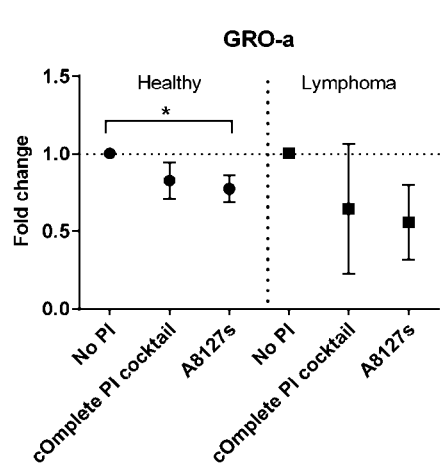
Figure 22K:
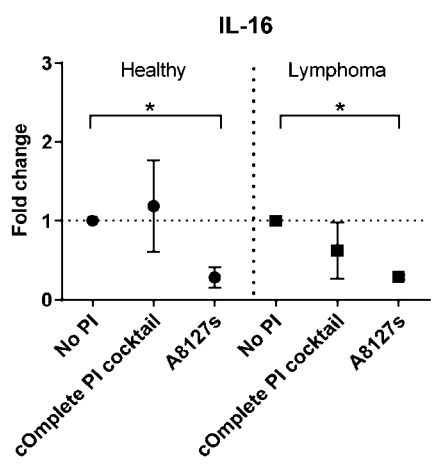
Figure 22L:
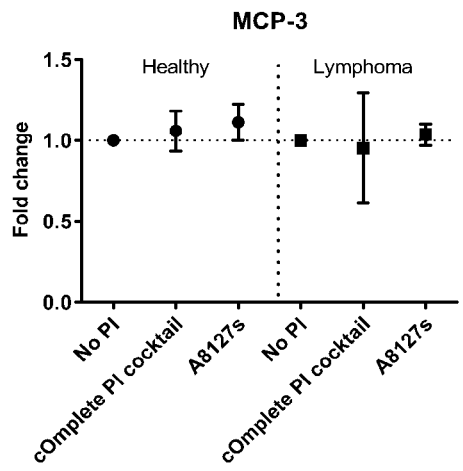
Figure 22M:
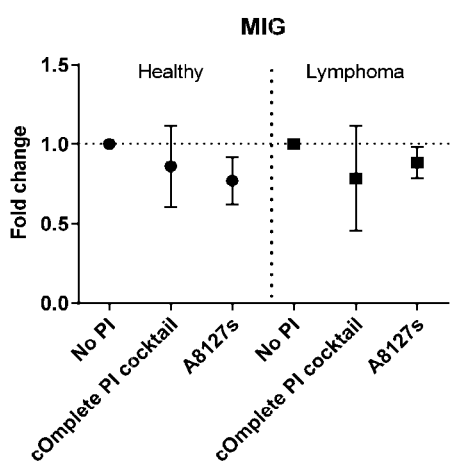
Figure 22N:
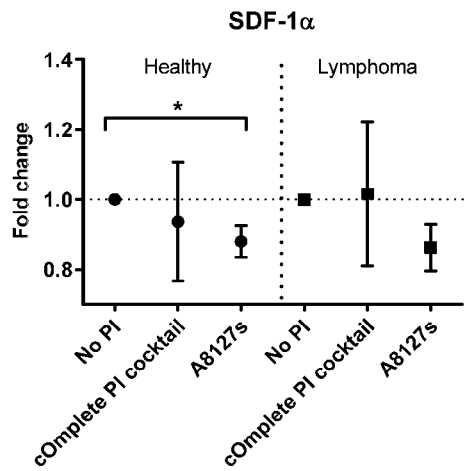
Figure 22O:
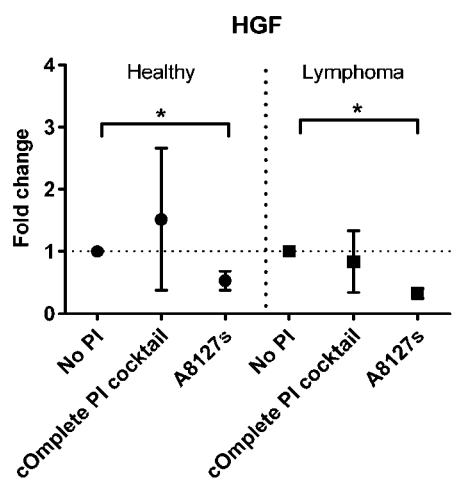
Figure 22P:
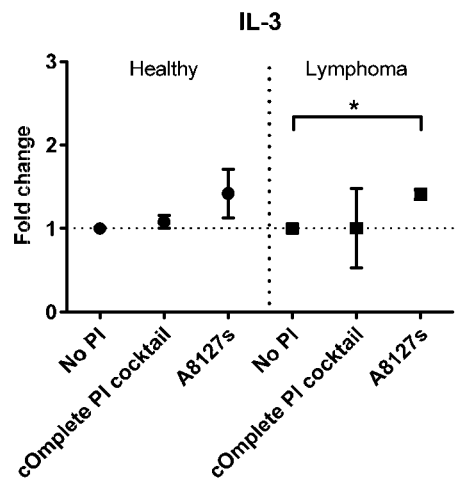
Figure 22Q:
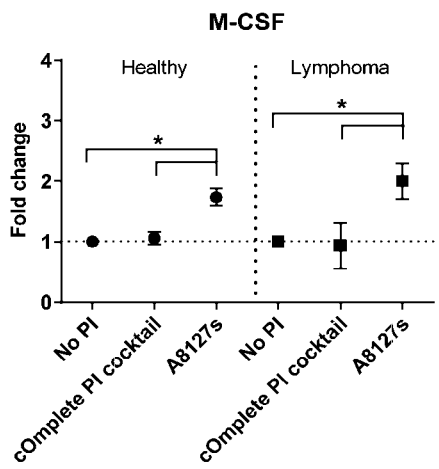
Figure 22R:
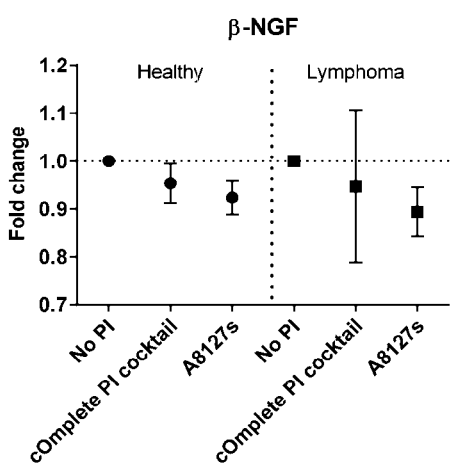
Figure 22S:
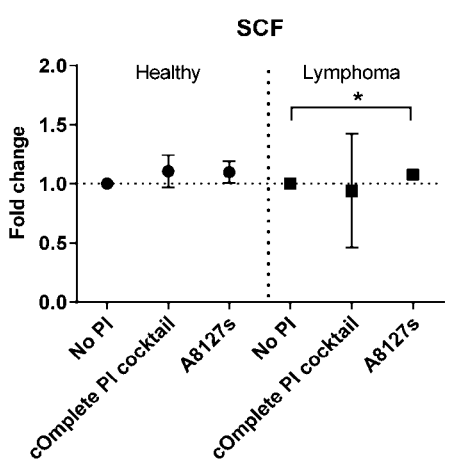
Figure 22T:
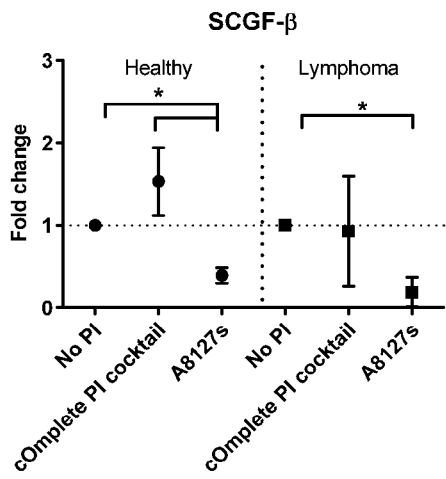
Figure 22U:
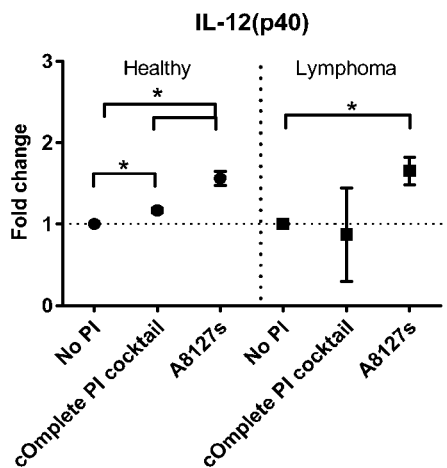
Figure 22V:
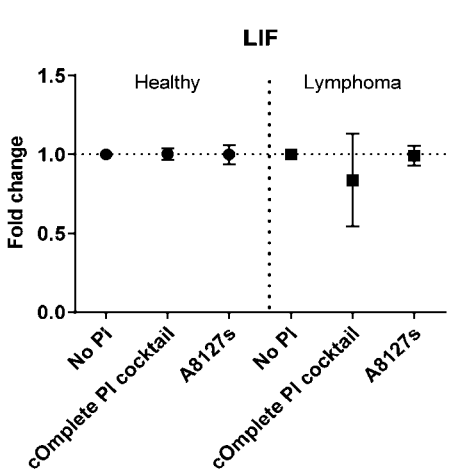
Figure 23A:
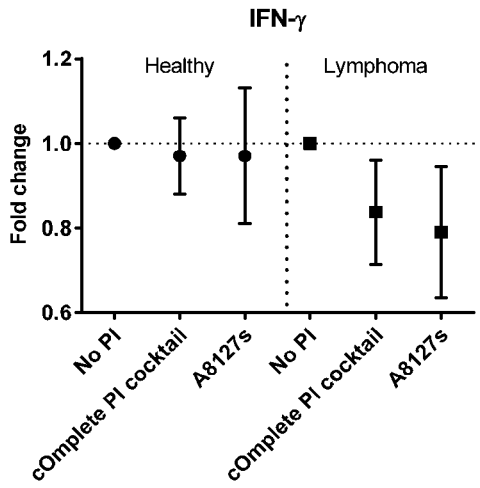
FIG. 23A-23VV is a series of graphs showing the effect of protease inhibitor cocktails on cytokines released from red blood cell membranes obtained isolated red blood cells from healthy individuals compared to individuals having lymphoma.
Figure 23B:
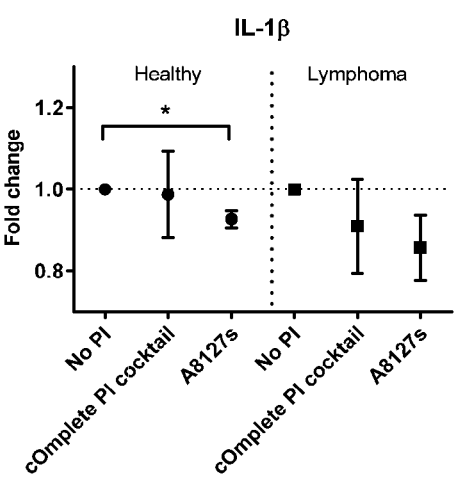
Figure 23C:
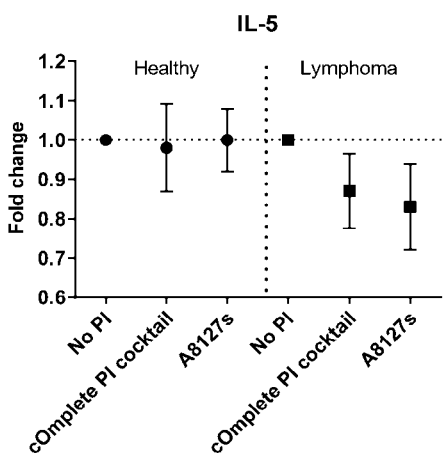
Figure 23D:
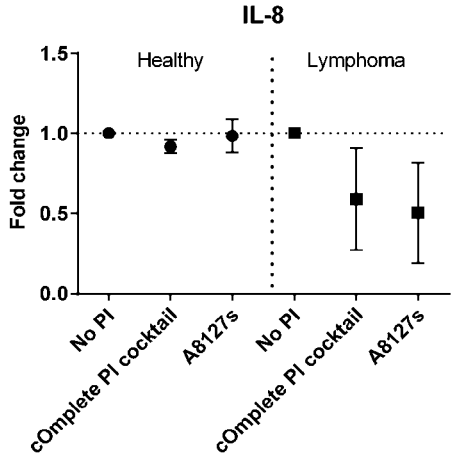
Figure 23E:
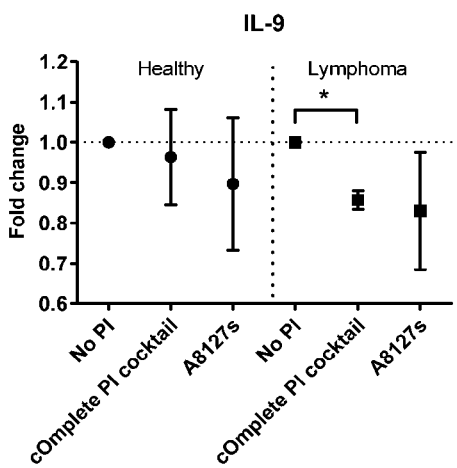
Figure 23F:
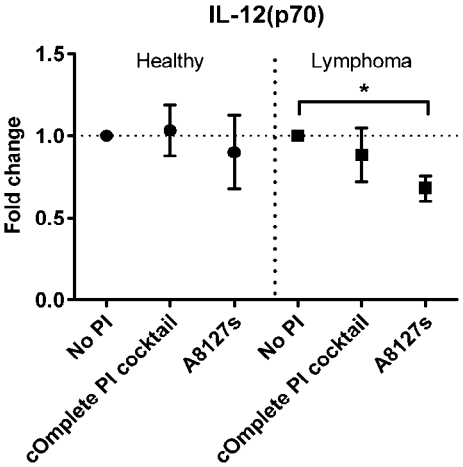
Figure 23G:
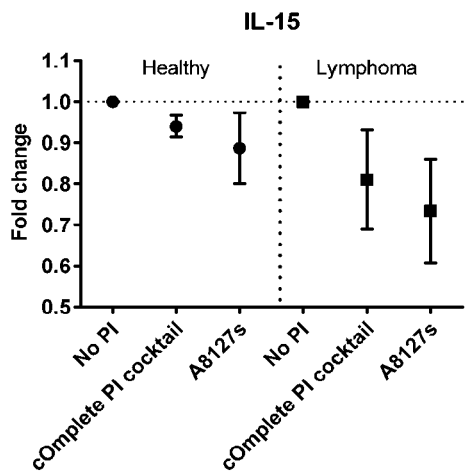
Figure 23H:
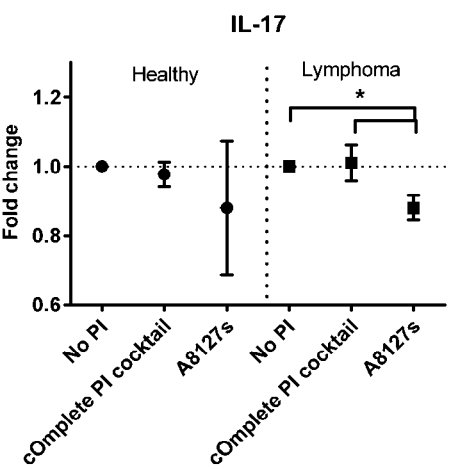
Figure 23I:
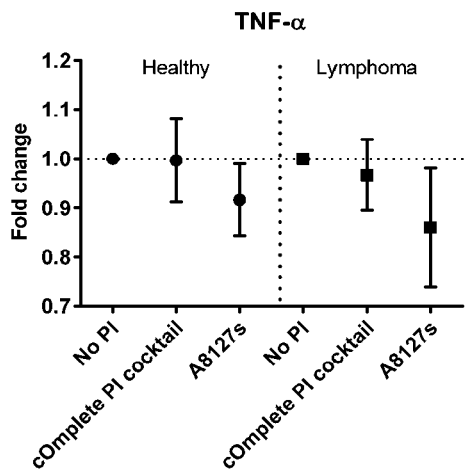
Figure 23J:
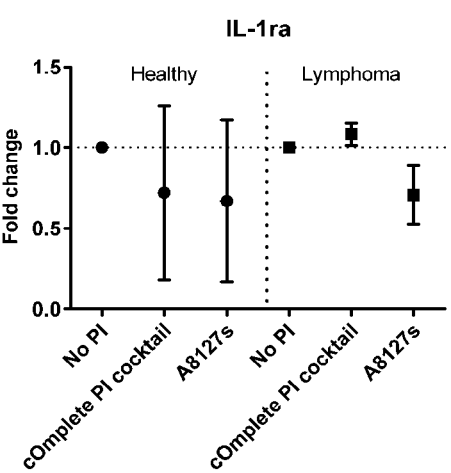
Figure 23K:
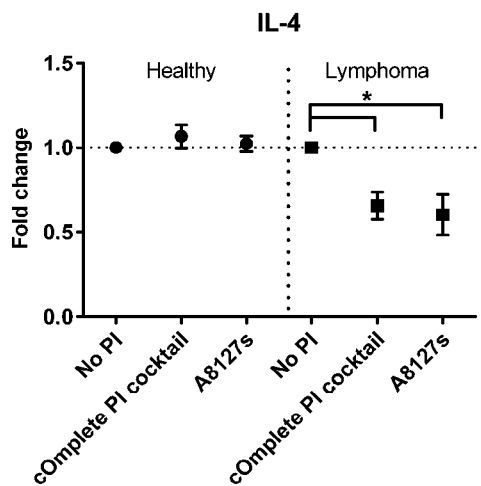
Figure 23L:
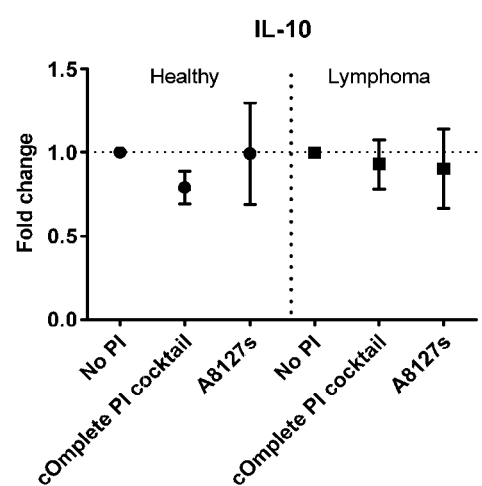
Figure 23M:
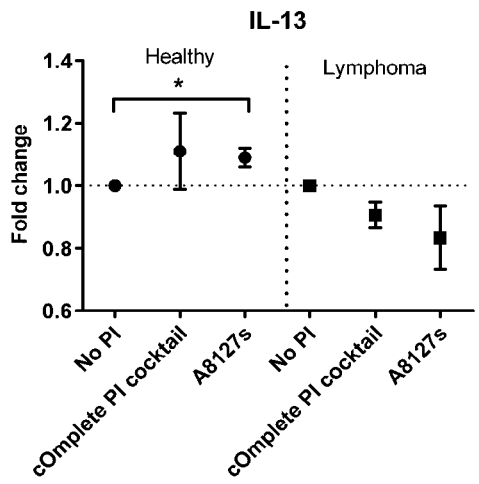
Figure 23N:
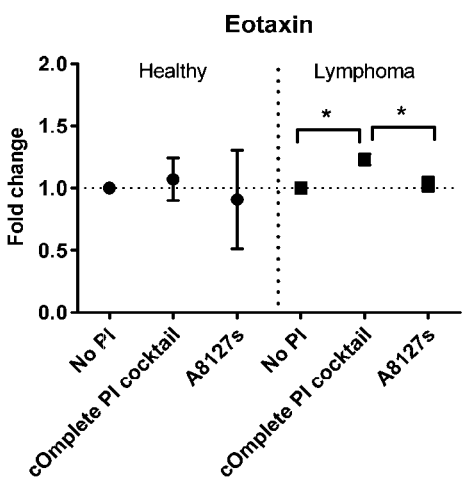
Figure 23O:
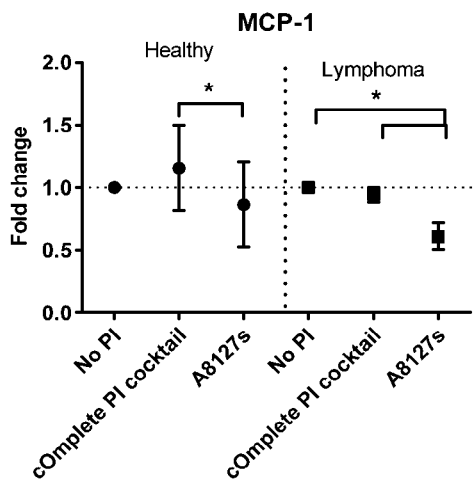
Figure 23P:
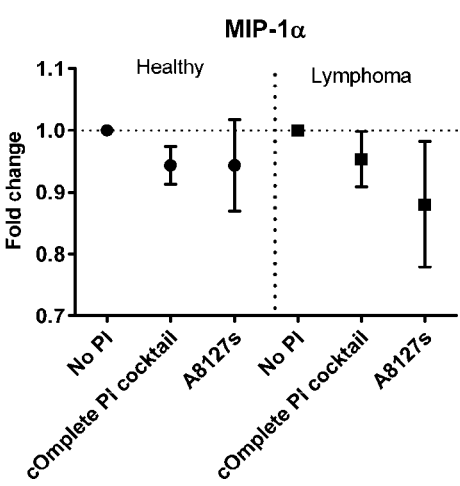
Figure 23Q:
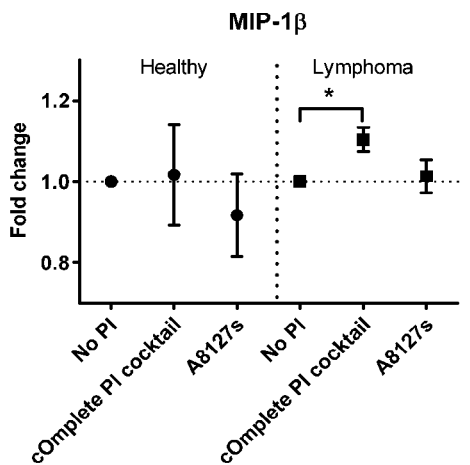
Figure 23R:
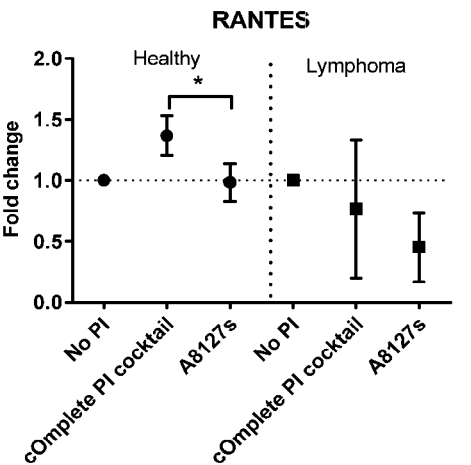
Figure 23S:
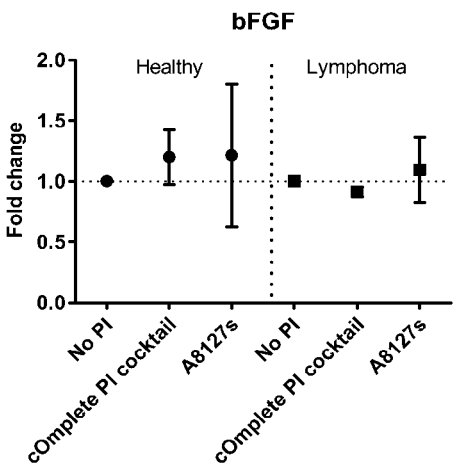
Figure 23T:
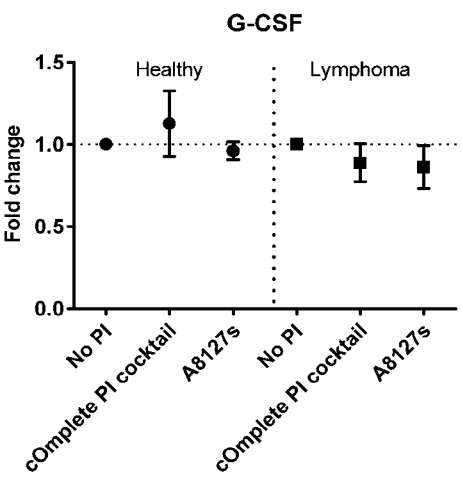
Figure 23U:
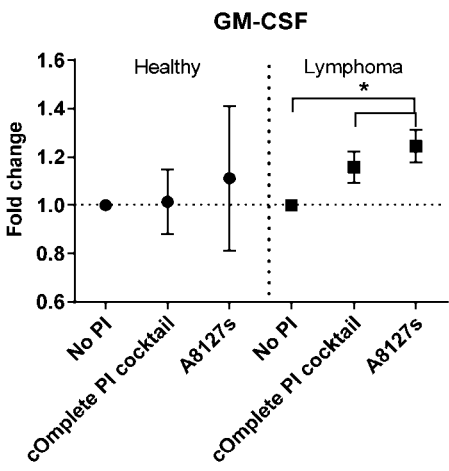
Figure 23V:
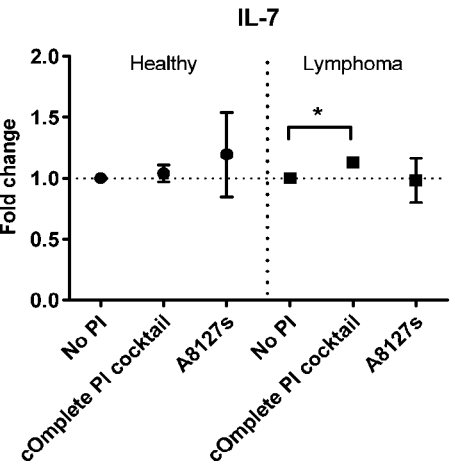
Figure 23W:
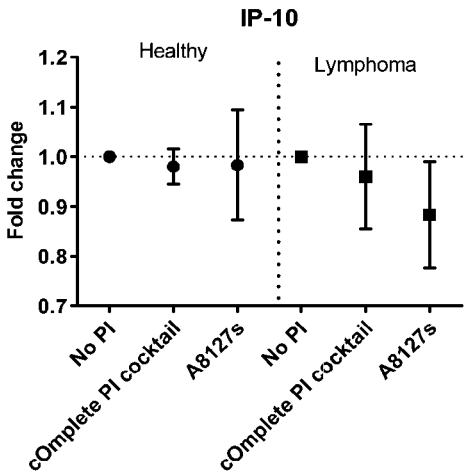
Figure 23X:
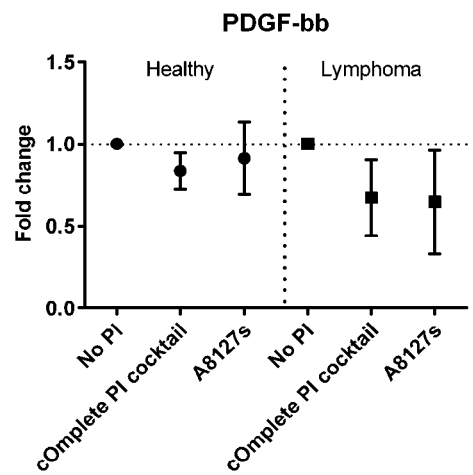
Figure 23Y:
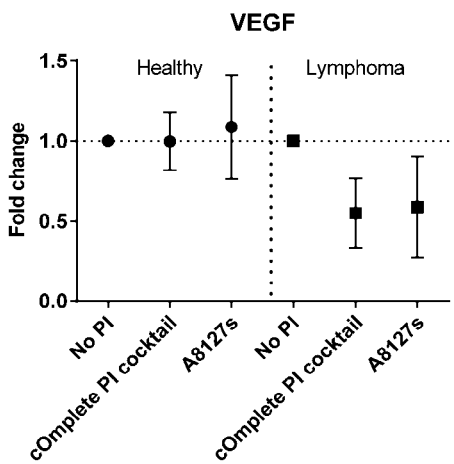
Figure 23Z:
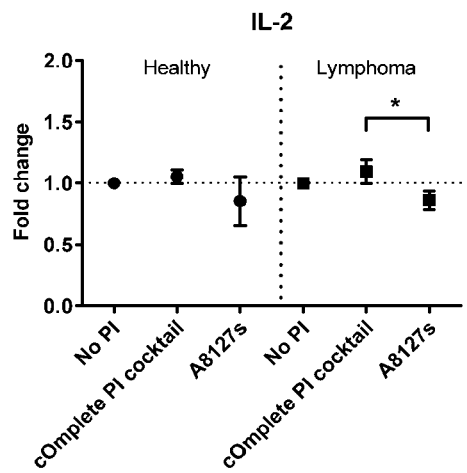
Figure 23A:
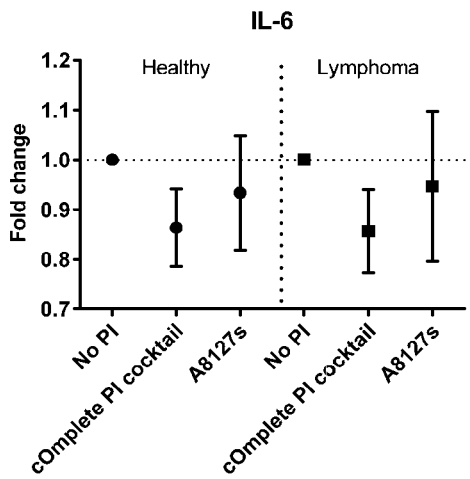
Figure 23B:
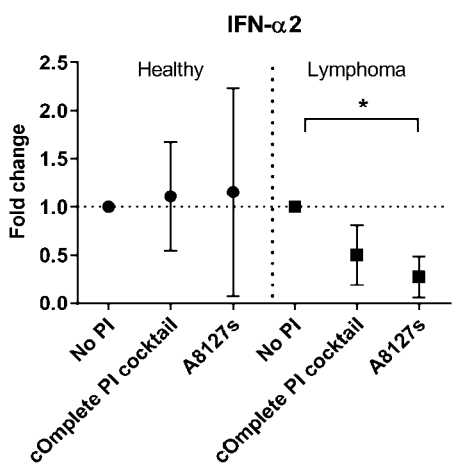
Figure 23C:
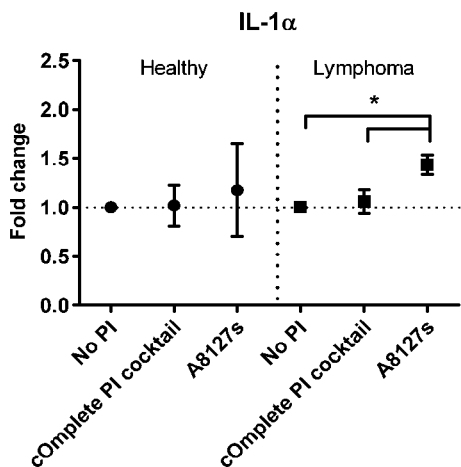
Figure 23D:
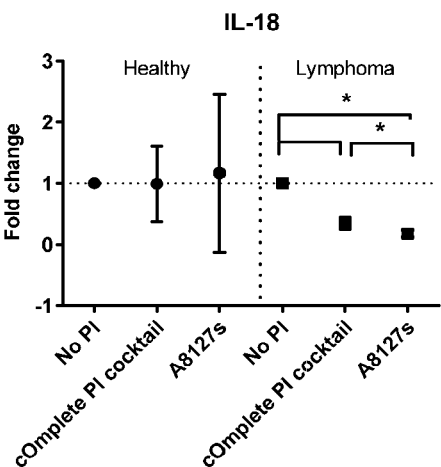
Figure 23E:
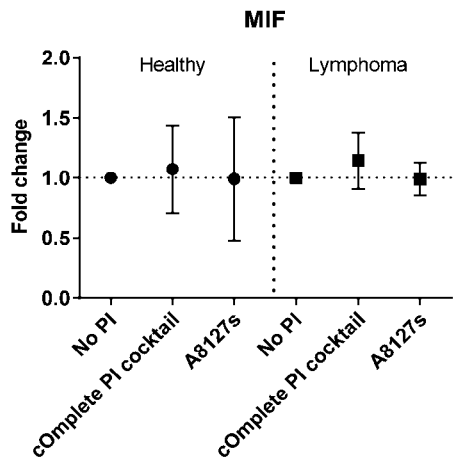
Figure 23F:
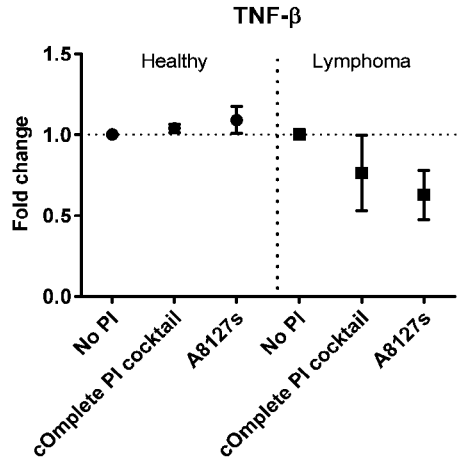
Figure 23G:
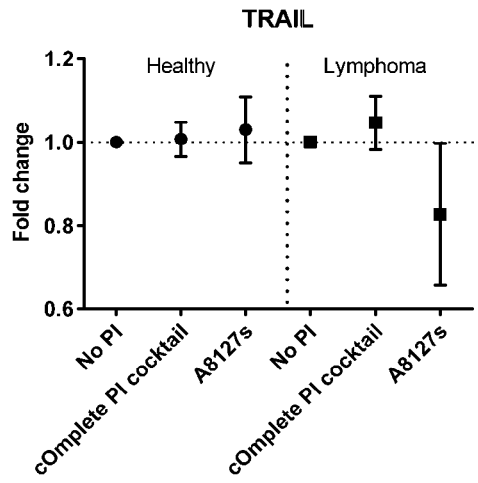
Figure 23H:
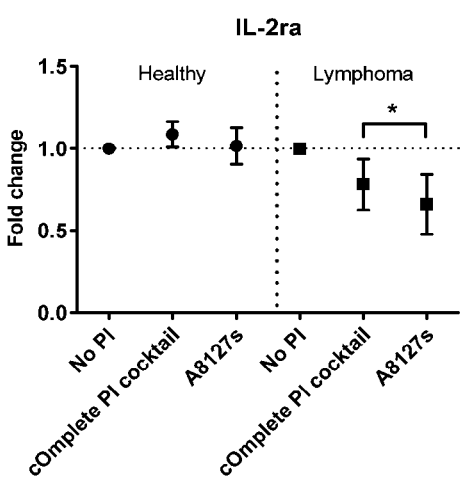
Figure 23I:
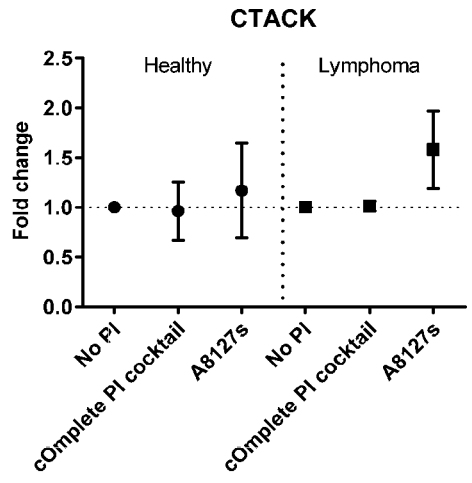
Figure 23J:
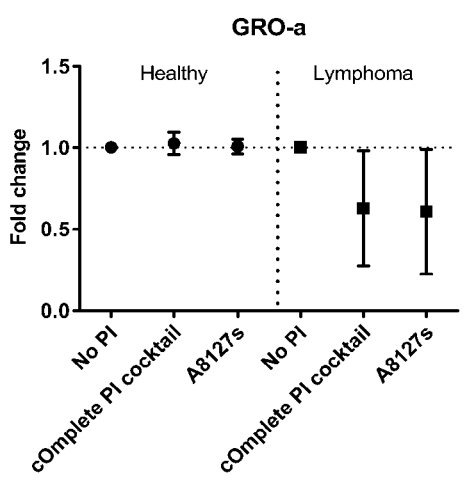
Figure 23K:
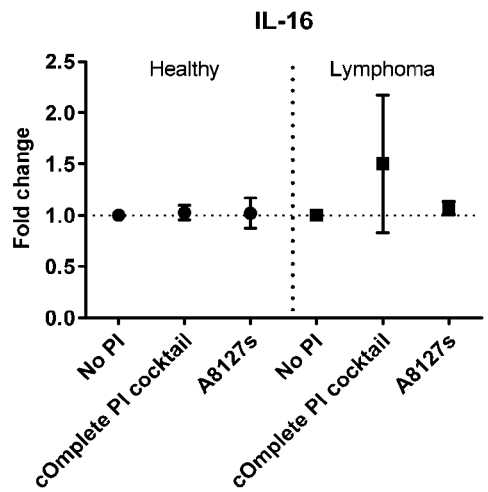
Figure 23L:
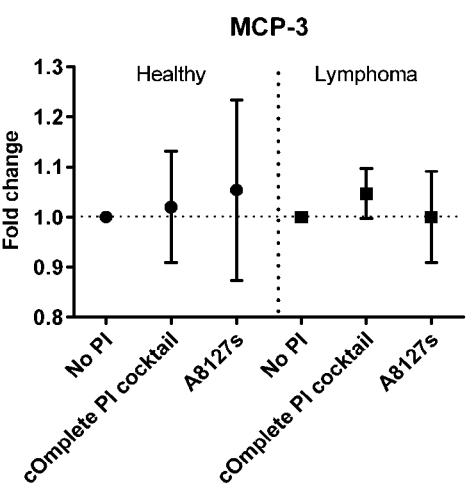
Figure 23M:
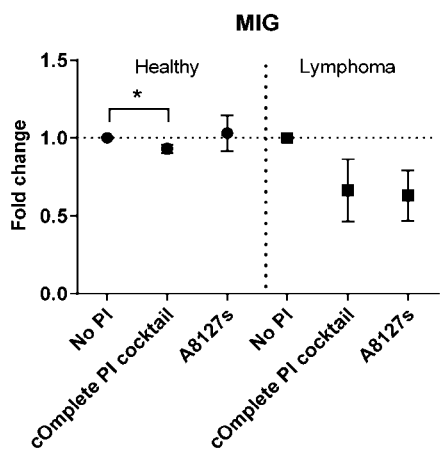
Figure 23N:
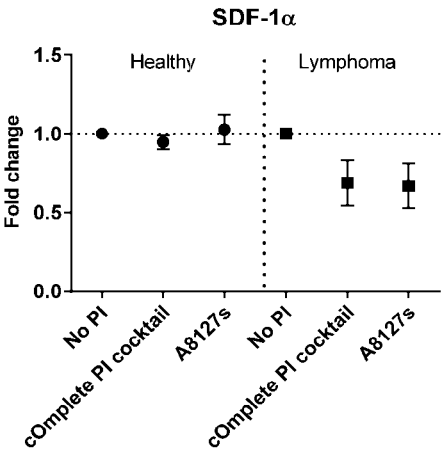
Figure 23O:
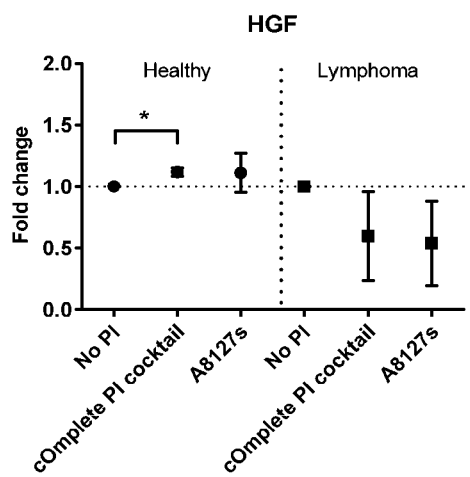
Figure 23P:
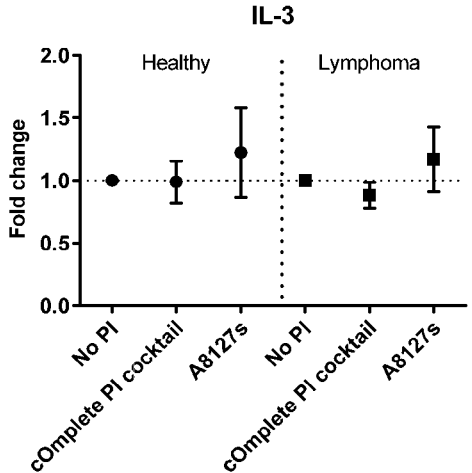
Figure 23Q:
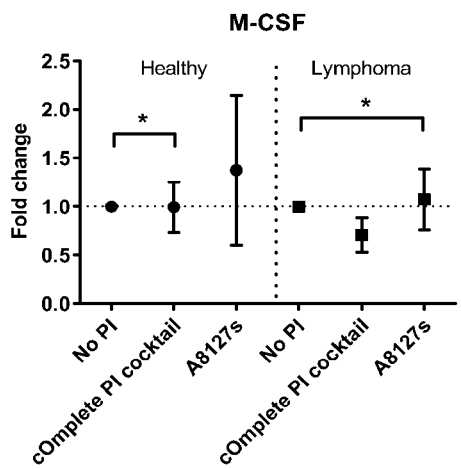
Figure 23R:
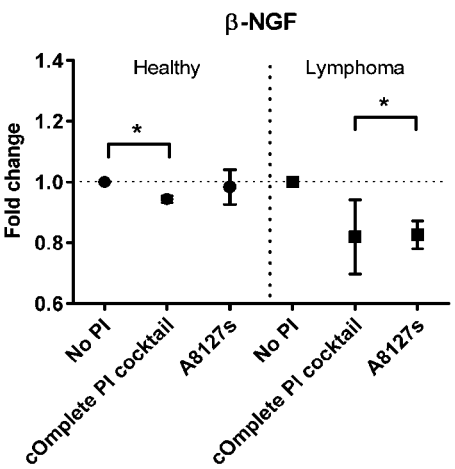
Figure 23S:
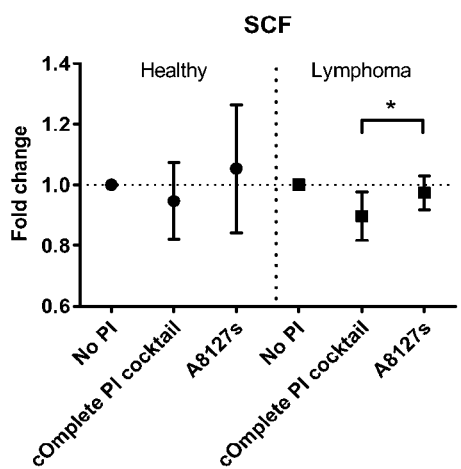
Figure 23T:
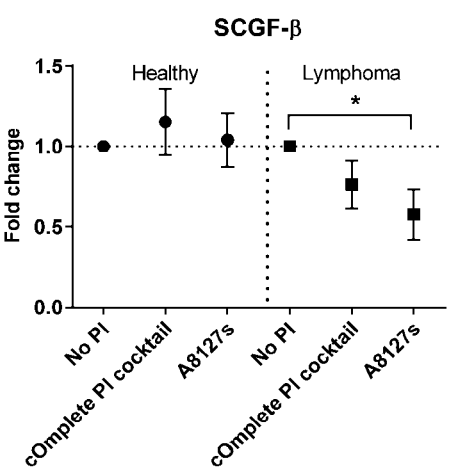
Figure 23U:
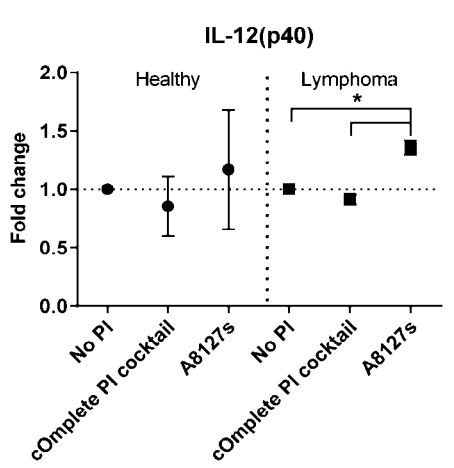
Figure 23V:
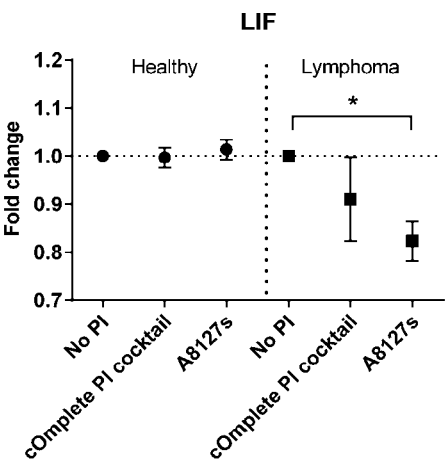

FIG. 22A-22VV shows the change in level of proteins from red blood cell membranes isolated from whole blood lysates, while FIG. 23A-23VV shows the change in the level of proteins from red blood cell membranes obtained from isolated red blood cells in the presence of protease inhibitor cocktails. Red blood cell membrane-conditioned PBS isolated from whole blood lysates or enriched red blood cell lysates, at 1,200 million cells/mL, were incubated at 37° C. for 24 hours with or without protease inhibitors, with red blood cells from healthy participants or participants with lymphoma. Values were significantly different (*) if $p<0.05$. Data are the mean±standard deviation. It may be concluded from the data that the effect of protease inhibitors on the release of cytokines (as has been show in intact red blood cells) is still active in isolated red blood cell membranes. A8127s produced the largest number of cytokine changes in every group except for enriched red blood cell membranes from healthy participants. This was consistent with previous data demonstrating that A8127s resulted in more significant changes in the cytokine profile than a commercial protease inhibitor cocktail (Roche cOmplete).

Notably, the samples isolated from the healthy and lymphoma group differed in how they responded to the protease inhibitor incubation. There were also a number of cytokines that changed significantly when the red blood cell membranes from lymphoma patients were incubated with A8127s. In contrast, no significant change was detected when red blood cell membranes were isolated from healthy participants and treated in the same way. For red blood cell membranes isolated from whole blood, the cytokines IL-8, IL-6, IP-10, IL-3, and SCF behaved in this manner. Similarly, the cytokines IL-12p70, IL-17, IL-4, MCP-1, GM-CSF, IFN-a2, IL-1a, IL-18, M-CSF, SCGF-B, IL-12p40 in red blood cell membranes isolated from enriched red blood cells followed the same pattern. This indicates that red blood cell membranes isolated from enriched red blood cell lysates may be valuable in identifying cytokine profiles that are specific to lymphoma.

The data also indicated that IL-4, IFN-a2, IL-18, SCGF-b, and LIF may be used together as a panel for the differentiation between healthy and lymphoma samples. The cytokines are not only statistically changed in lymphoma samples following incubation with A8127s, but also, the fold change trend (from unincubated control to incubation with A8127s) is different for the lymphoma samples compared to samples from healthy individuals. Table 8 summarizes the number of cytokines that significantly changed in red blood cell membranes from both healthy and lymphoma participants, by protease inhibitor cocktail used.

TABLE 8

Number of statistically significantly (p <0.05) changed cytokines following incubation with each protease inhibitor (PI) cocktail compared to the unincubated control for each sample group.

| Red blood cell membranes (from whole blood) | | | | Red blood cell membranes (from RBC lysates) | | | |
|---|---|---|---|---|---|---|---|
| Healthy | | Lymphoma | | Healthy | | Lymphoma | |
| cOmplete PI cocktail | A8127s | cOmplete PI cocktail | A8127s | cOmplete PI cocktail | A8127s | cOmplete PI cocktail | A8127s |
| 5 | 17 | 3 | 11 | 4 | 2 | 5 | 12 |

Example 11. Effect of Protease Inhibitors on Red Blood Cell Components from Inflammatory Disease Cohorts To further explore whether protease inhibitors have a differential effect on proteins from red blood cell components from individuals that have a range of inflammatory conditions, red blood cells or red blood cell membranes obtained from those having the various inflammatory conditions were incubated with protease inhibitor cocktails and change in protein level assessed.

Whole blood was collected from volunteers by venepuncture directly into EDTA vacutainers ($k_2$EDTA vacutainers, BD Biosciences). The fractions of blood were collected and processed at room temperature within 4 hours of collection. For multiplex analysis (BioPlex analysis) the samples were stored at −80° C. and were subjected to 3 freeze-thaw cycles at −80° C. to ensure complete cellular lysis prior to analysis.

Following collection, whole blood was aliquoted and frozen at −80° C. For the isolation of red blood cell membranes, the frozen aliquots of the whole blood were subjected to 3 freeze thaw cycles to ensure complete cellular lysis. Following this, an aliquot of the lysates (volume equivalent to 120 million red blood cells per 100 μL) was added to PBS at a 1:20 ratio (lysate:PBS). The red blood cell membranes were then isolated by centrifugation out of solution (16,000 g, 20 mins, 4° C.). The upper fraction was then discarded and the resulting membranes were then diluted to 1,200 million cells/mL in PBS and were incubated at 37° C. and 5% $CO_2$ for 24 hours. Some samples were incubated with protease inhibitor cocktails (cOmplete, Roche; A8127s). The A8127s protease inhibitor cocktail is comprised of antipain-dihydrochloride (50 μg/mL); bestatin (40 μg/mL); E-64 (10 μg/mL); leupeptin (5 μg/mL); pepstatin (0.7 μg/mL); phosphoramidon (330 μg/mL); Pefabloc SC (1 mg/mL); EDTA-$Na_2$ (0.5 mg/mL); and aprotinin (2 μg/mL).

After incubation, the resulting conditioned PBS was isolated by centrifugation (16,000 g, 20 minutes, 4° C.). The samples were stored at −80° C., and underwent 3 freeze/thaw cycles before analysis. The conditioned PBS samples were then analyzed on the multiplex cytokine assays. Two multiplex assays were utilised. The first was the 27-plea human cytokine panel that assays for FGF basic, Eotaxin, G-CSF, GM-CSF, IFN-γ, IL-1β, IL-1ra, IL-2, IL-4, IL-5, IL-6, IL-7, IL-8, IL-9, IL-10, IL-12(p70), IL-13, IL-15, IL-17, IP-10, MCP-1, MIP-1α, MIP-1β, PDGF-BB, RANTES, TNF-α, and VEGF, and the second was the 21-plex human cytokine panel that assays for IL-1α, IL-2Ra, IL-3, IL-12, IL-16, IL-18, CTACK, GRO-α, HGF, IFN-α2, LIF, MCP-3, M-CSF, MIF, MIG, β-NGF, SCF, SCGF-β, SDF-1α, TNF-β, TRAIL (Bio-Plex Pro 27-plex and 21-plex, Bio-Rad). The assays were performed according to manufacturer's instructions using an automated magnetic wash station (BioPlex Pro II, Bio-Rad) for the washing steps. The assays were run on the Luminex® 200™ system (Bio-Rad) and fluorescent values were collected. The calibration curve for each cytokine was analysed with 5 parametric logistic curve regression using BioPlex manager software (ver. 5.0, Bio-Rad, USA).

Figure 24A:
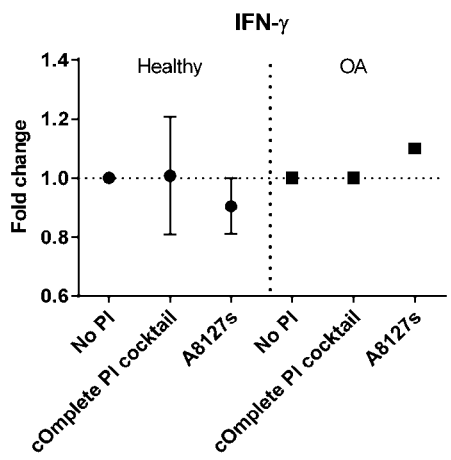
FIG. 24A-24VV is a series of graphs showing the effect of protease inhibitor cocktails on cytokines released from red blood cell membranes from healthy individuals compared to individuals having osteoarthritis.
Figure 24B:
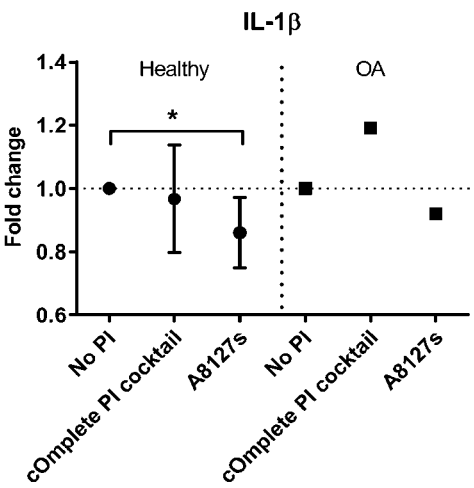
Figure 24C:
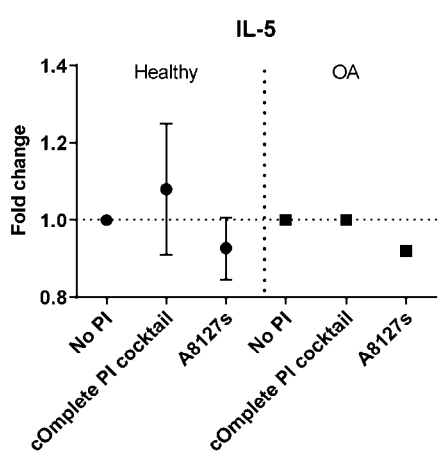
Figure 24D:
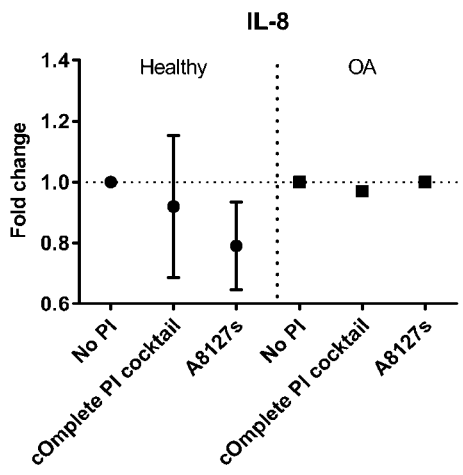
Figure 24E:
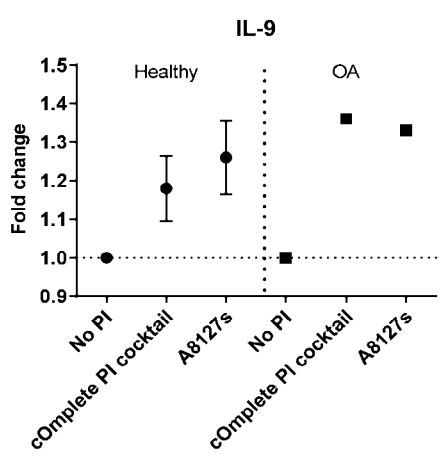
Figure 24F:
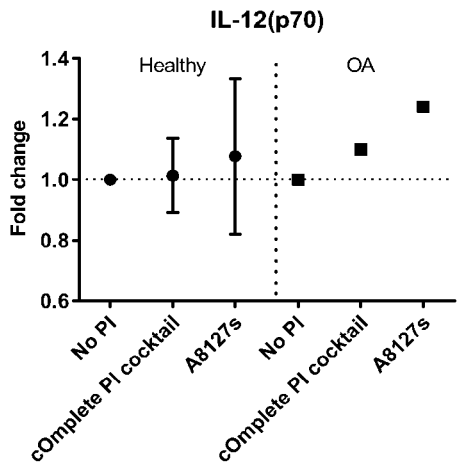
Figure 24G:
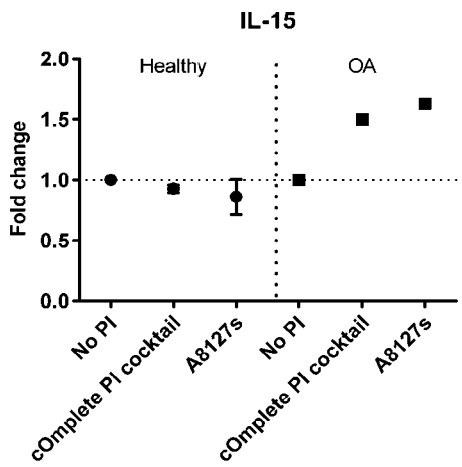
Figure 24H:
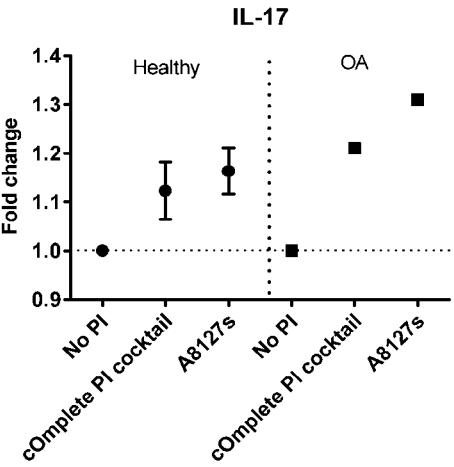
Figure 24I:
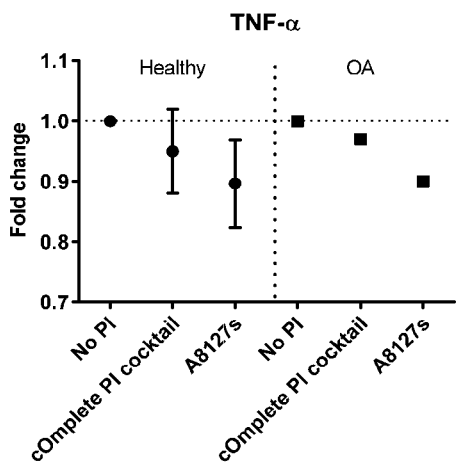
Figure 24J:
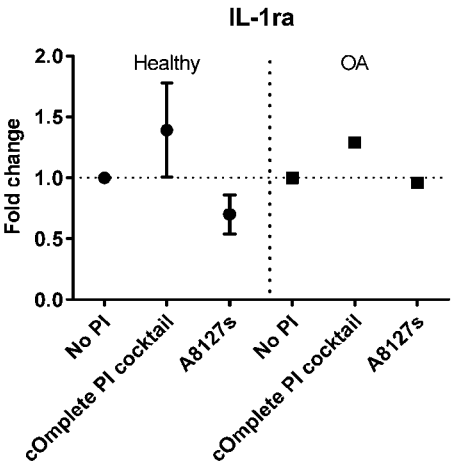
Figure 24K:
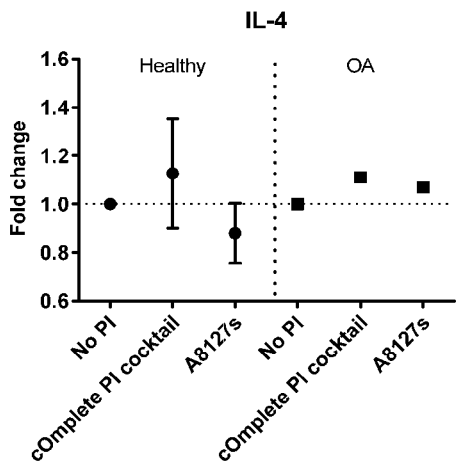
Figure 24L:
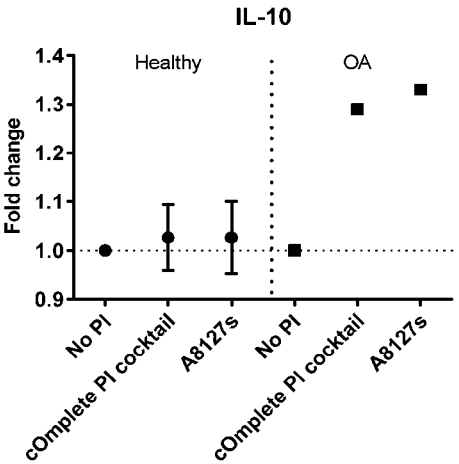
Figure 24M:
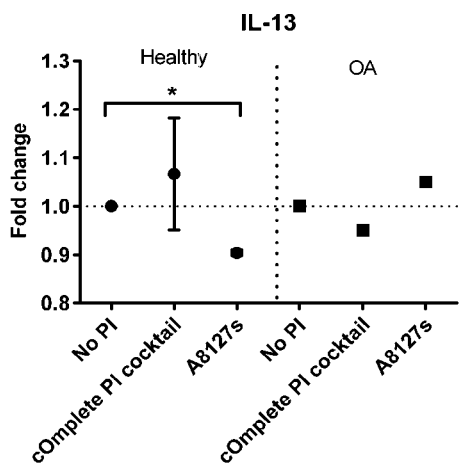
Figure 24N:
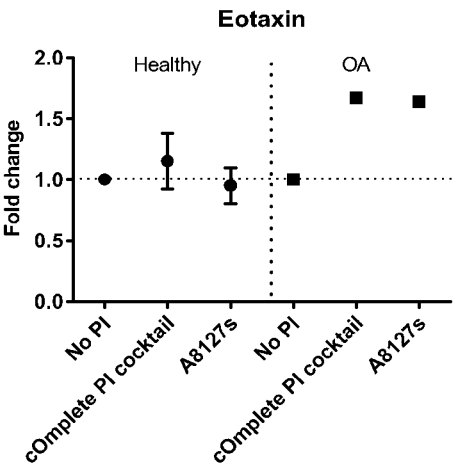
Figure 24O:
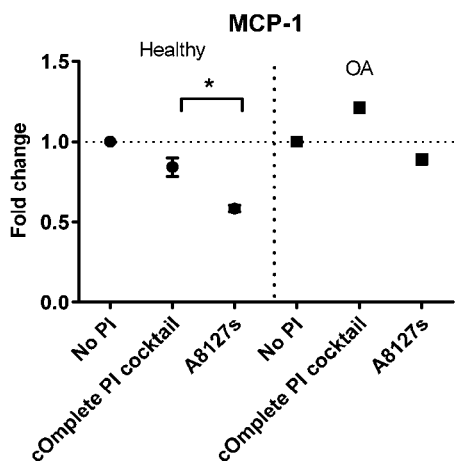
Figure 24P:
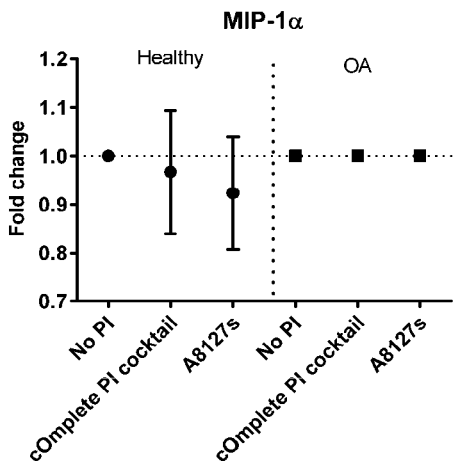
Figure 24Q:
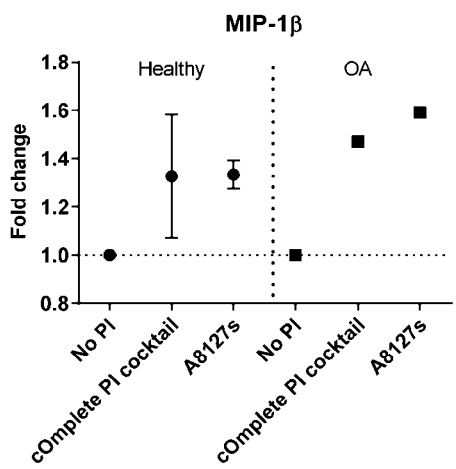
Figure 24R:
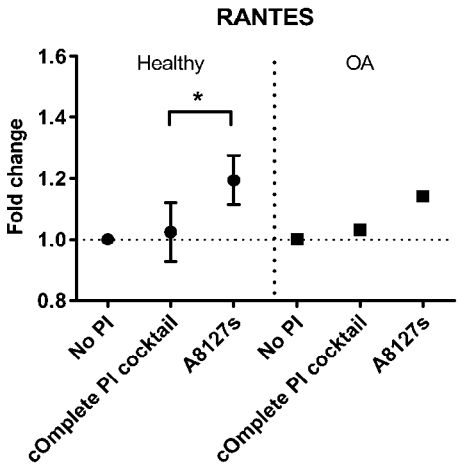
Figure 24S:
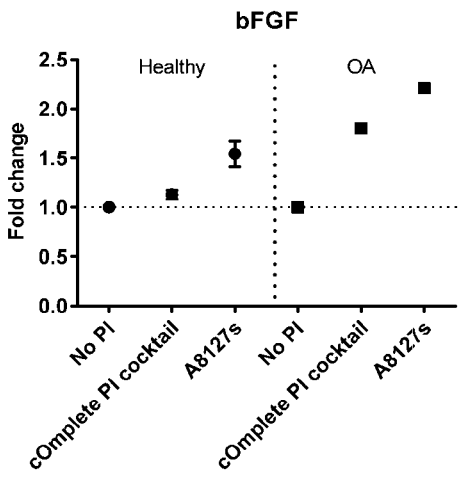
Figure 24T:
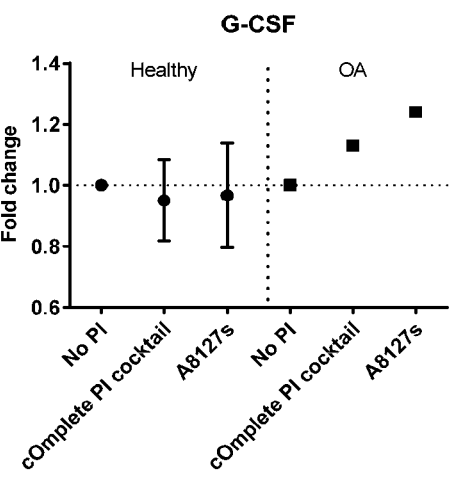
Figure 24U:
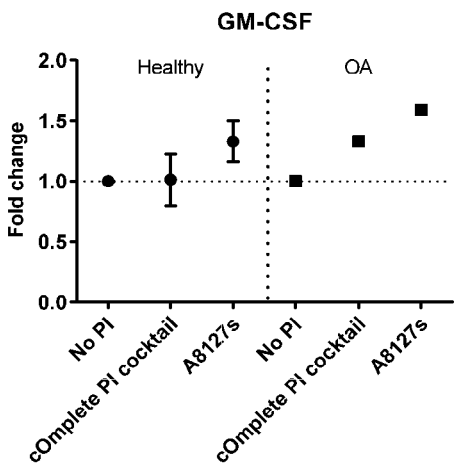
Figure 24V:
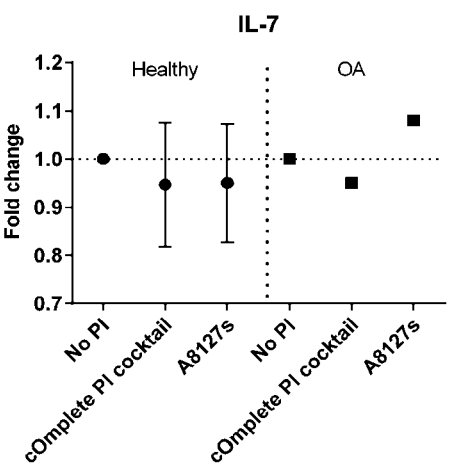
Figure 24W:
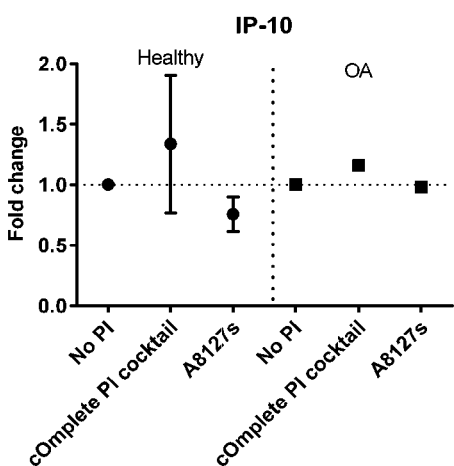
Figure 24X:
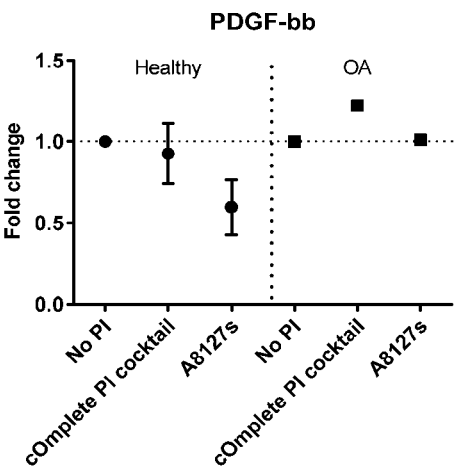
Figure 24Y:
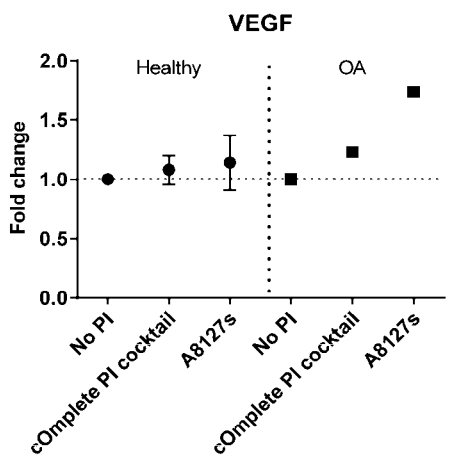
Figure 24Z:
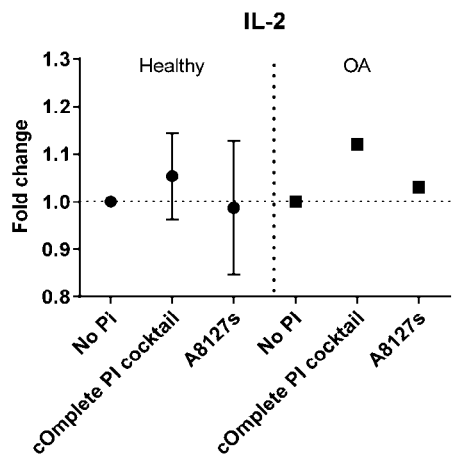
Figure 24A:
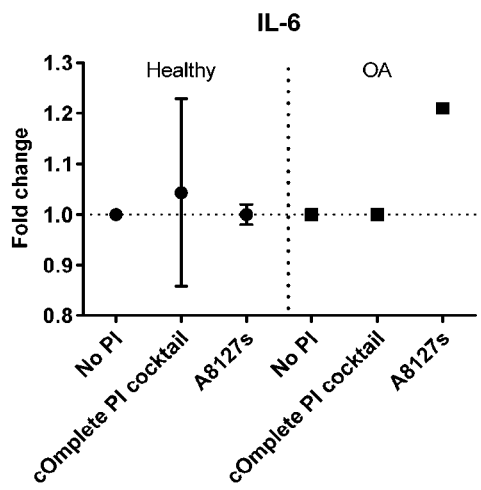
Figure 24B:
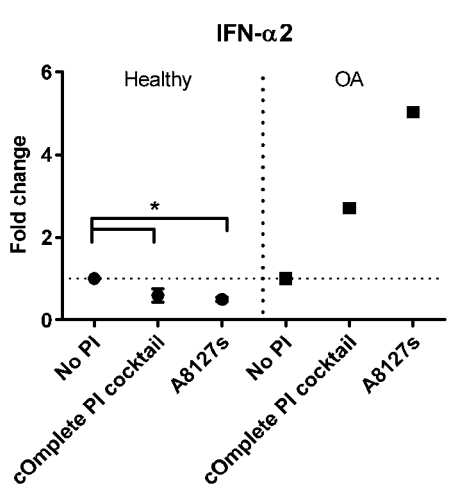
Figure 24C:
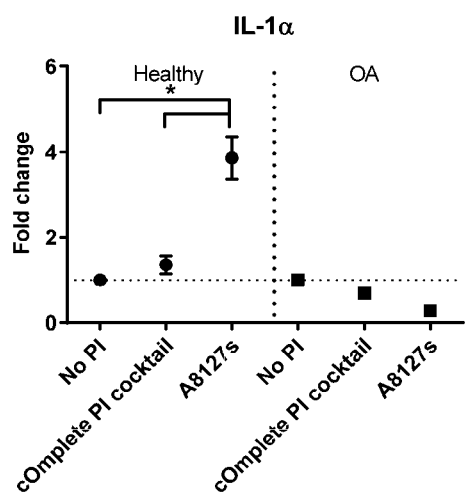
Figure 24D:
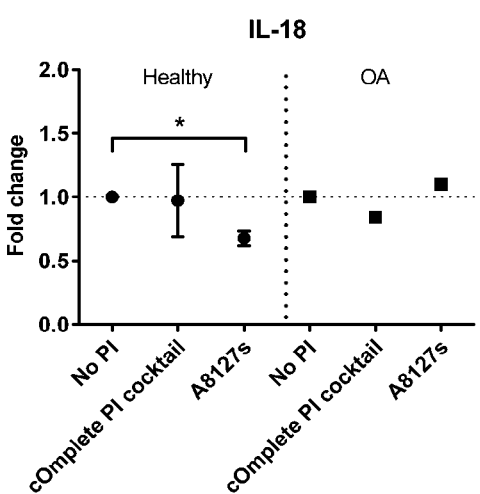
Figure 24E:
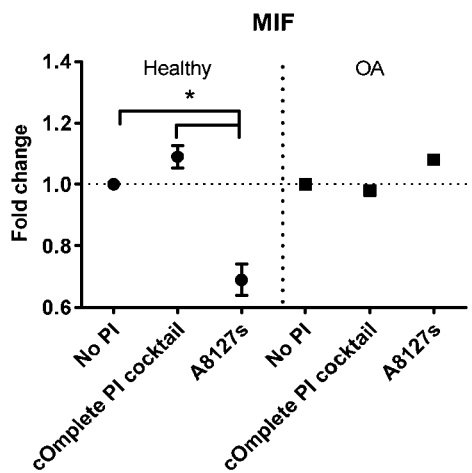
Figure 24F:
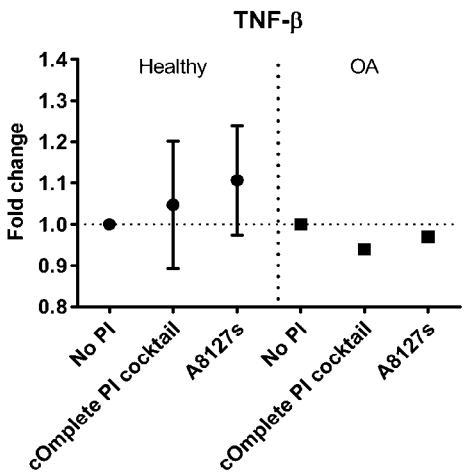
Figure 24G:
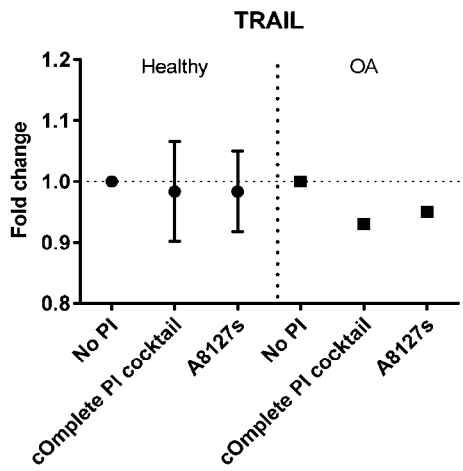
Figure 24H:
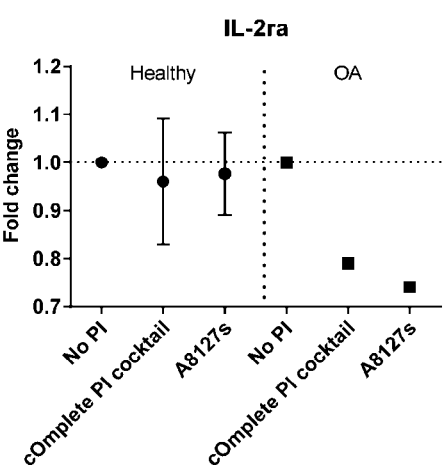
Figure 24I:
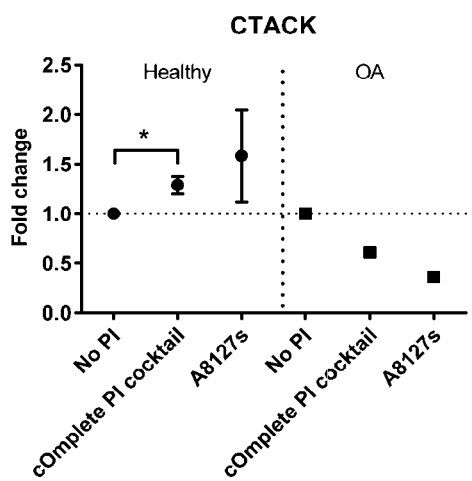
Figure 24J:
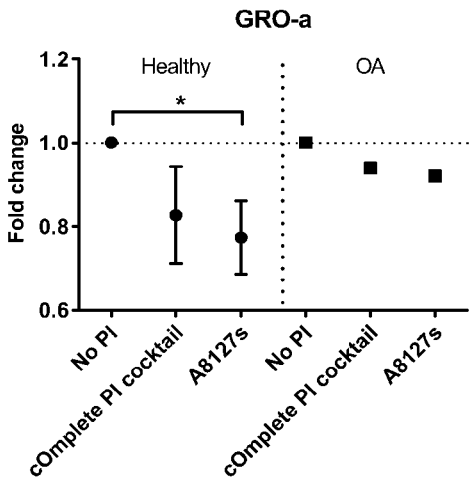
Figure 24K:
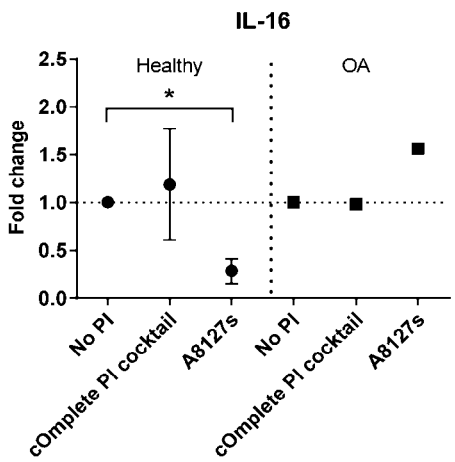
Figure 24L:
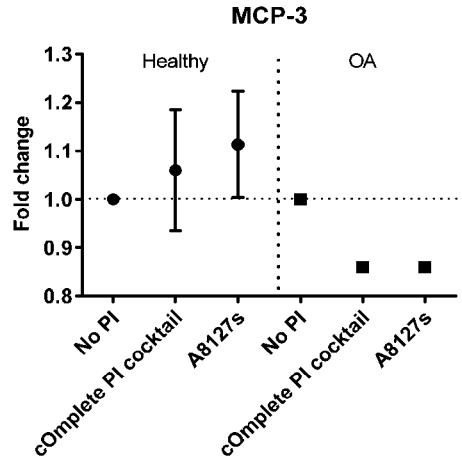
Figure 24M:
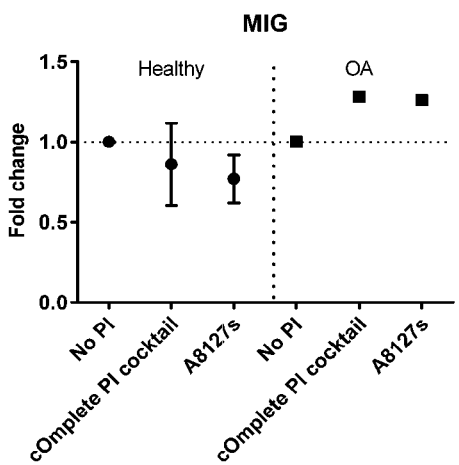
Figure 24N:
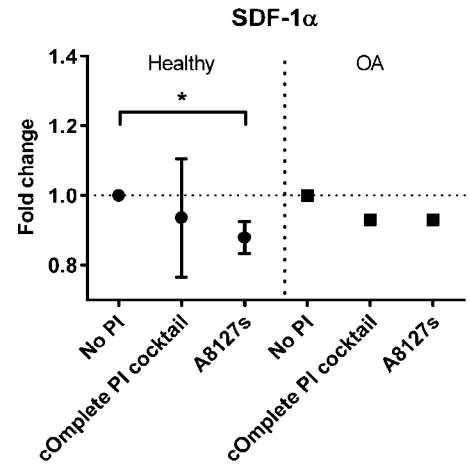
Figure 24O:
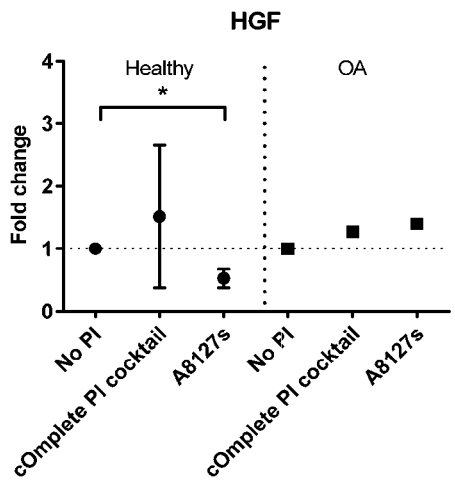
Figure 24P:
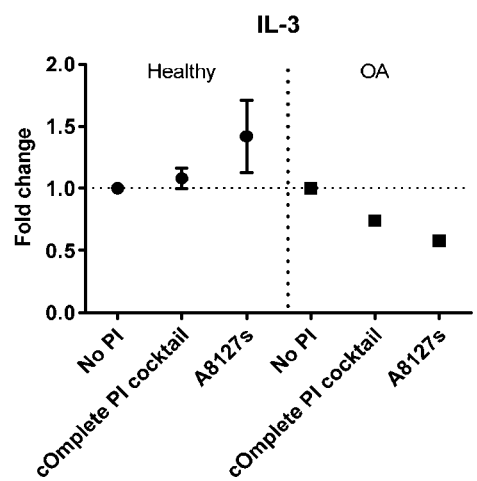
Figure 24Q:
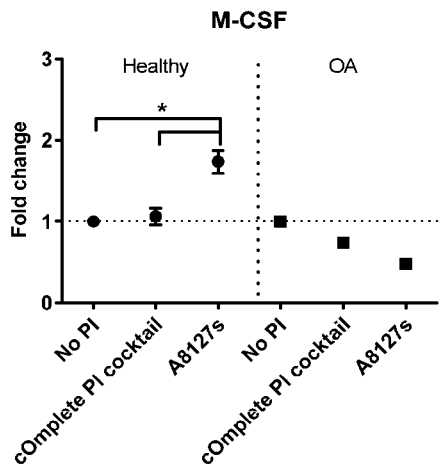
Figure 24R:
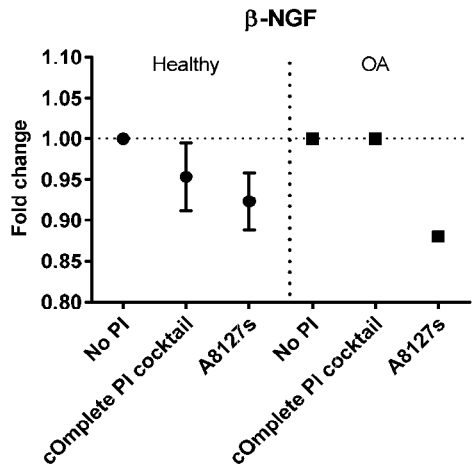
Figure 24S:
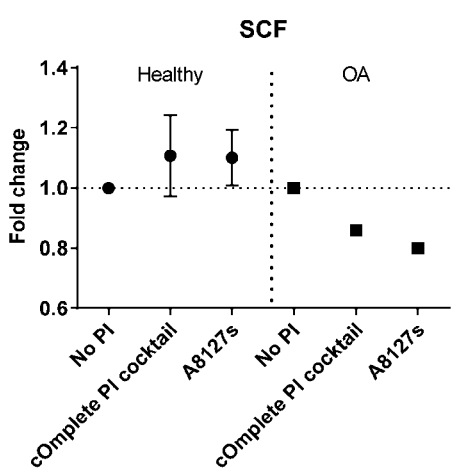
Figure 24T:
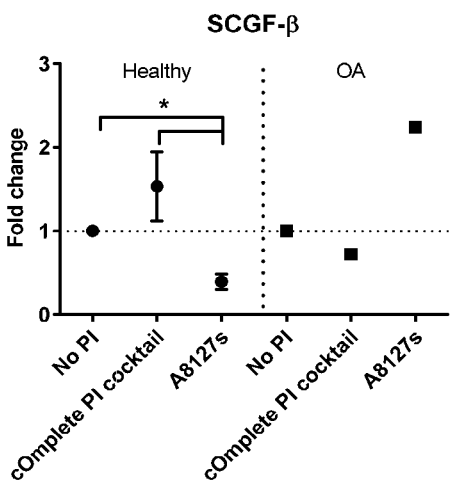
Figure 24U:
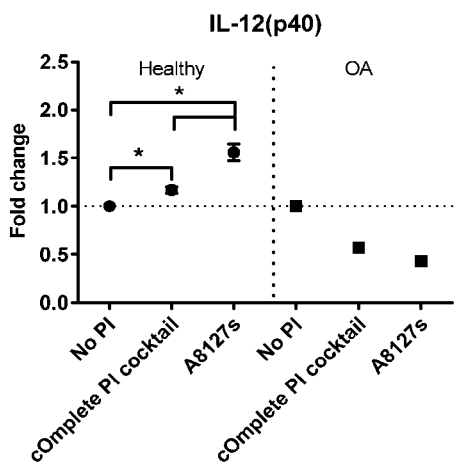
Figure 24V:
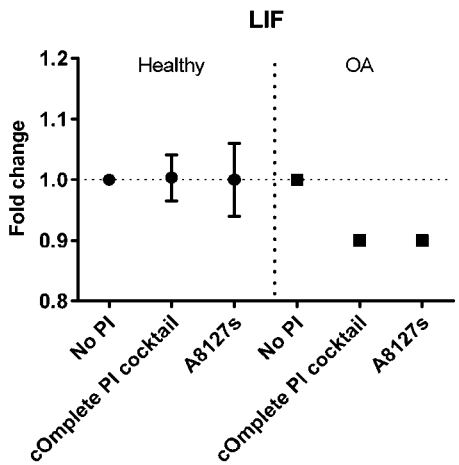
Figure 25A:
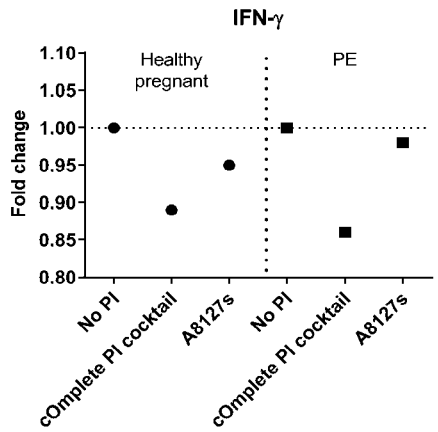
FIG. 25A-25VV is a series of graphs showing the effect of protease inhibitor cocktails on cytokines released from red blood cell membranes from healthy individuals compared to individuals having pre-eclampsia.
Figure 25B:
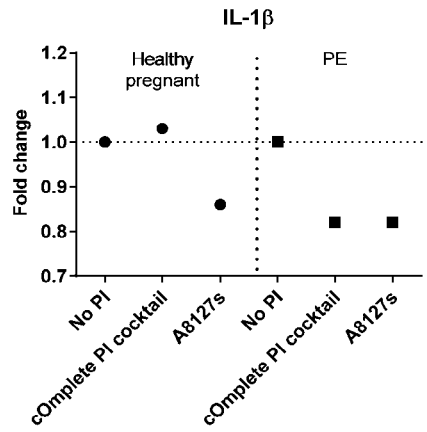
Figure 25C:
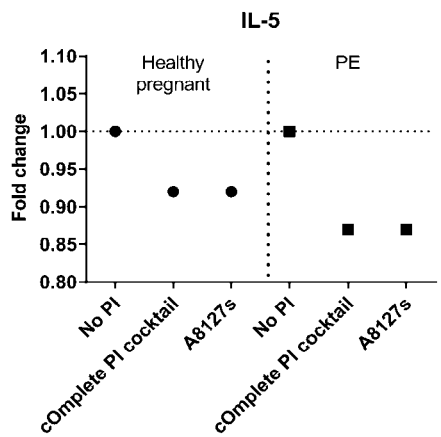
Figure 25D:
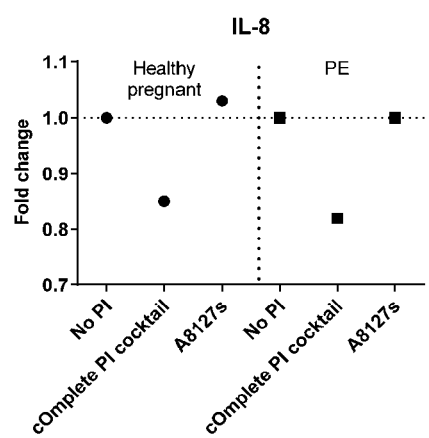
Figure 25E:
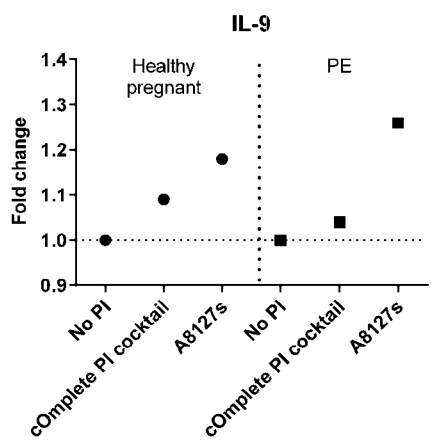
Figure 25F:
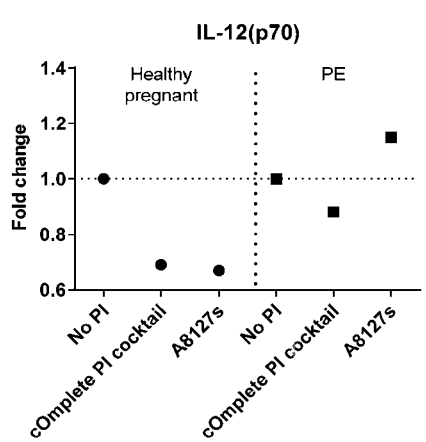
Figure 25G:
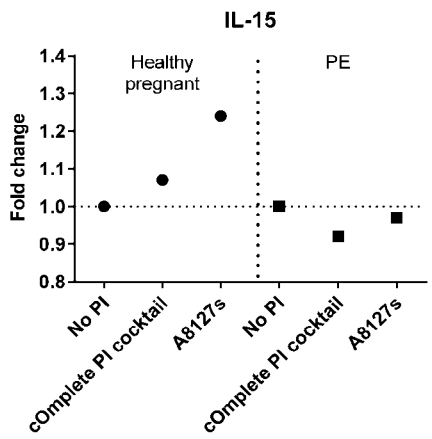
Figure 25H:
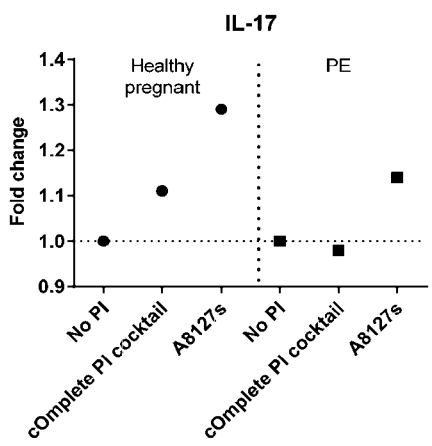
Figure 25I:
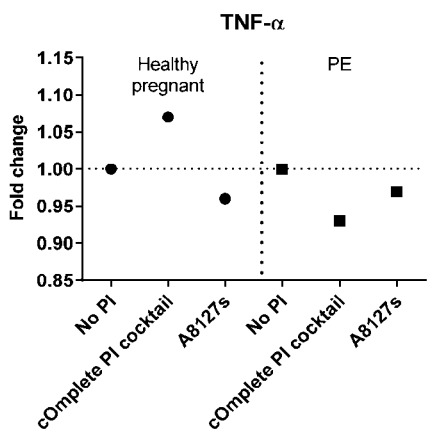
Figure 25J:
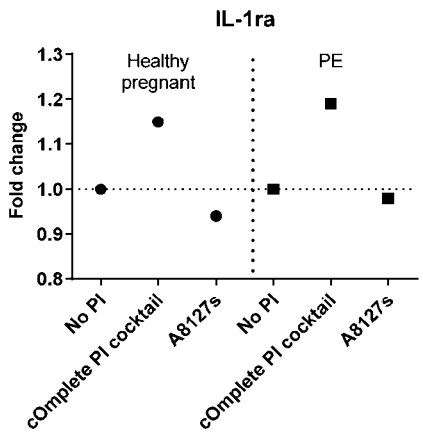
Figure 25K:
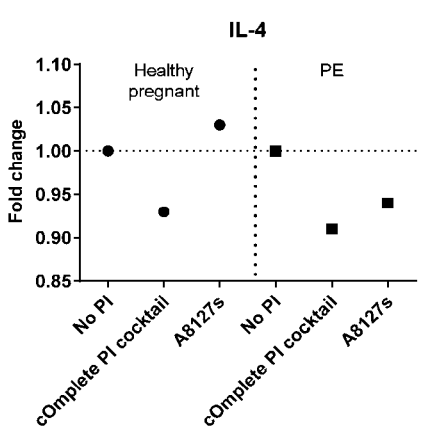
Figure 25L:
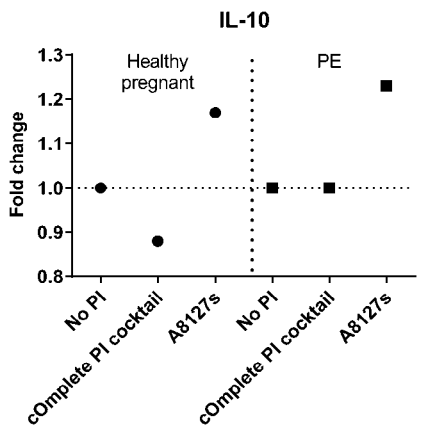
Figure 25M:
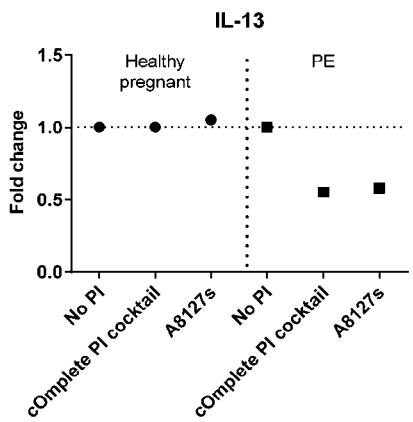
Figure 25N:
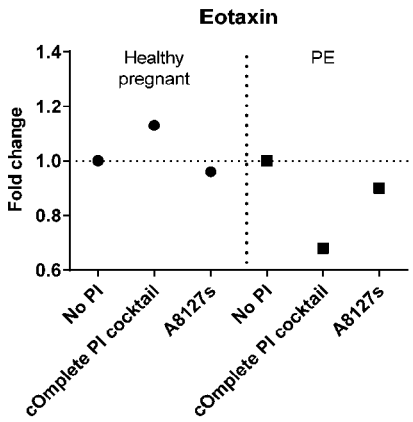
Figure 25O:
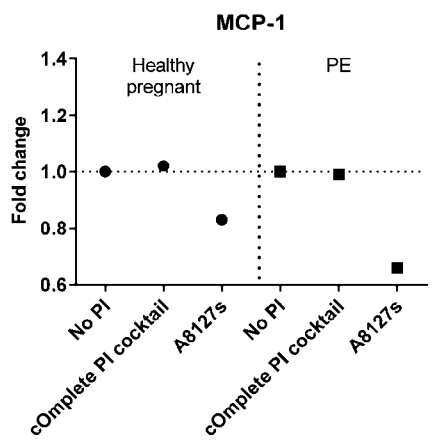
Figure 25P:
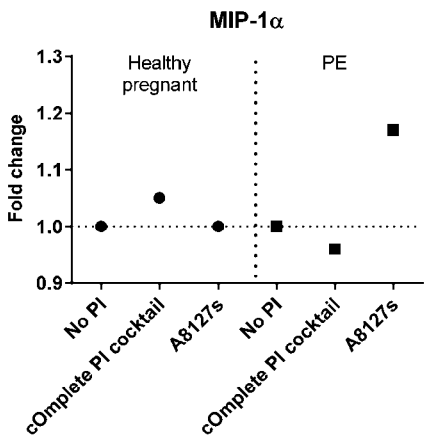
Figure 25Q:
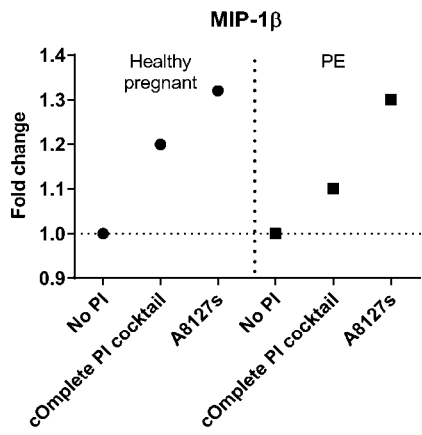
Figure 25R:
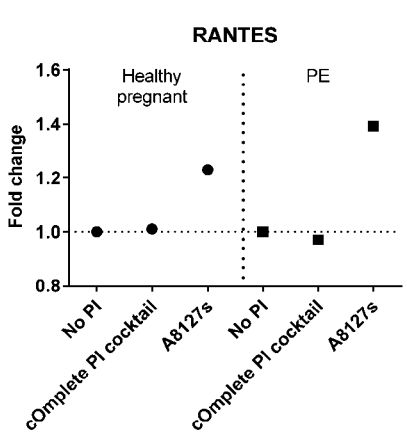
Figure 25S:
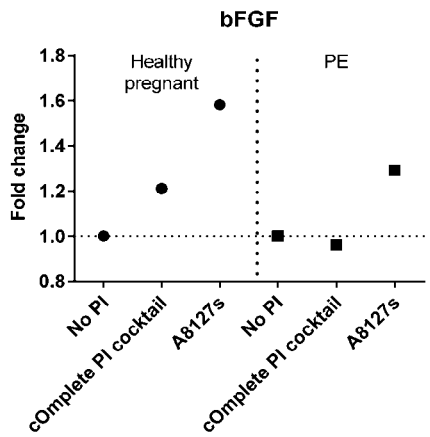
Figure 25T:
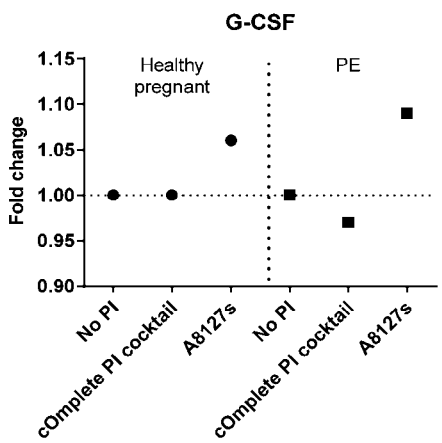
Figure 25U:
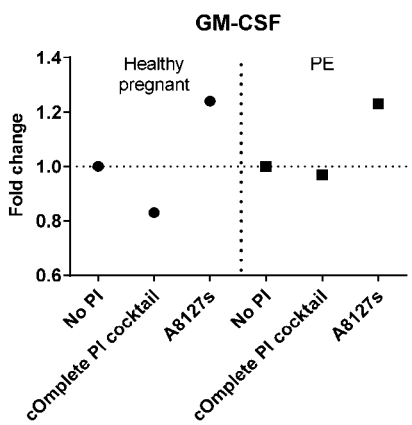
Figure 25V:
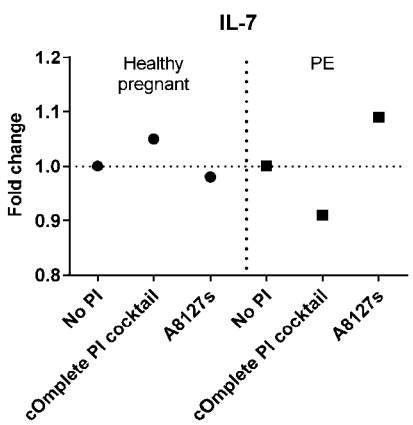
Figure 25W:
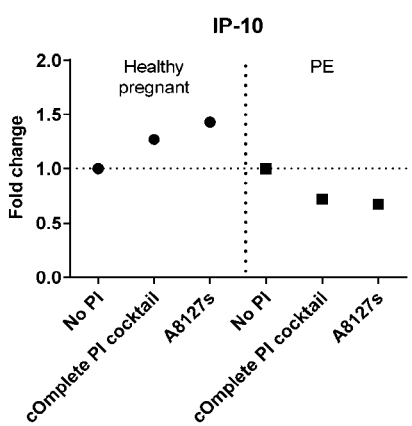
Figure 25X:
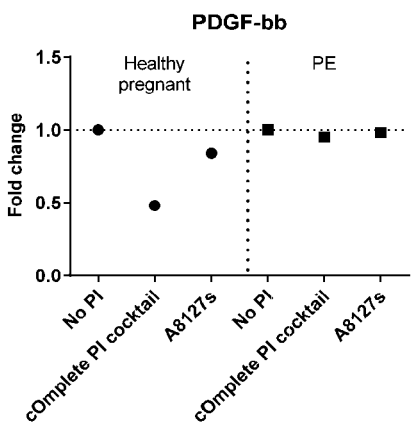
Figure 25Y:
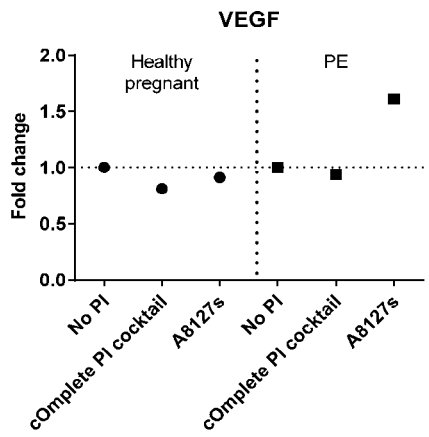
Figure 25Z:
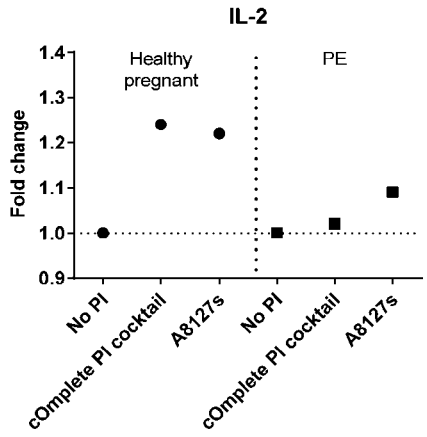
Figure 25A:
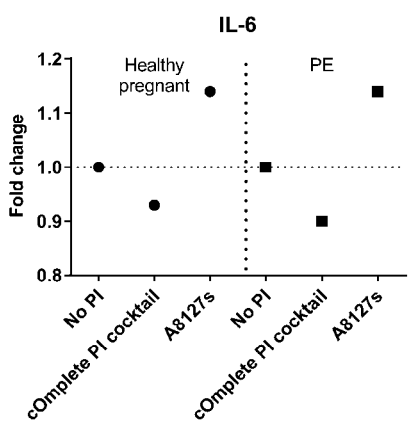
Figure 25B:
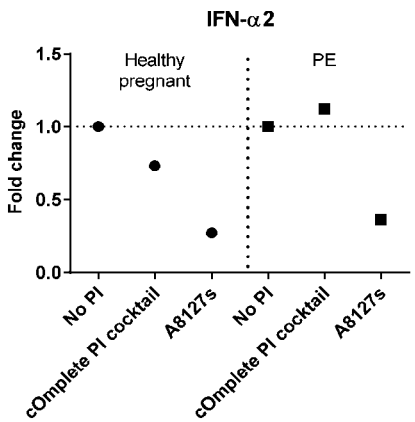
Figure 25C:
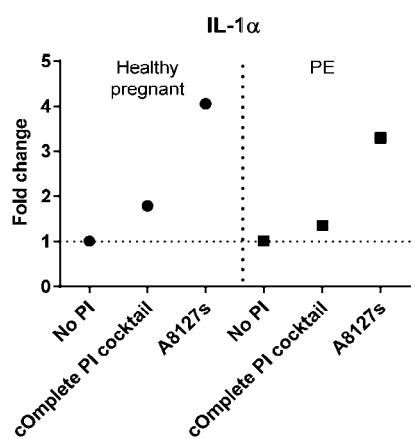
Figure 25D:
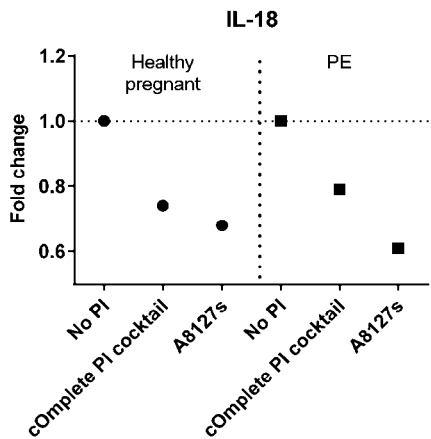
Figure 25E:
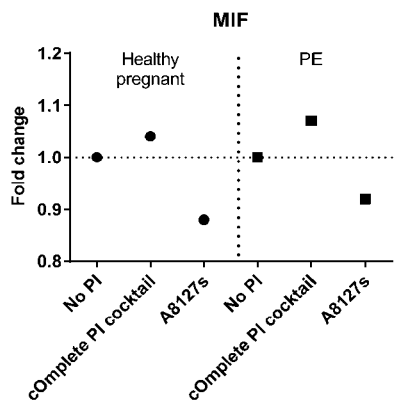
Figure 25F:
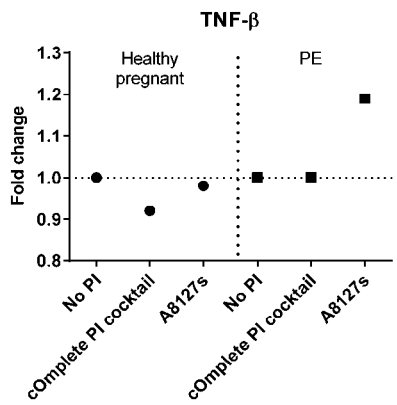
Figure 25G:
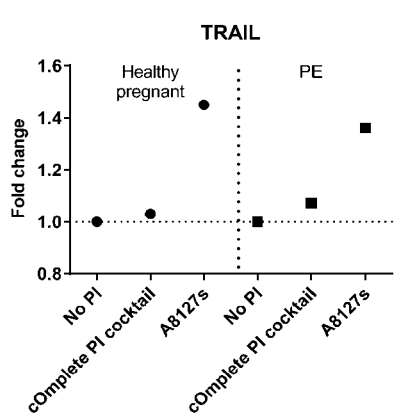
Figure 25H:
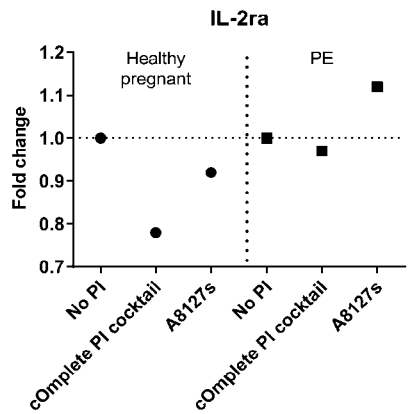
Figure 25I:
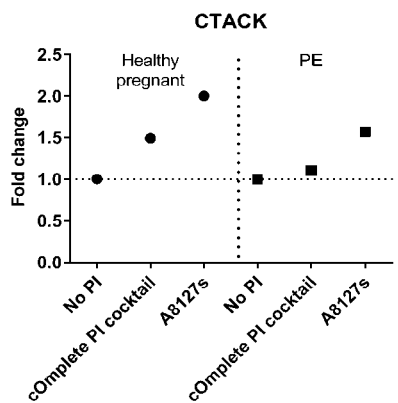
Figure 25J:
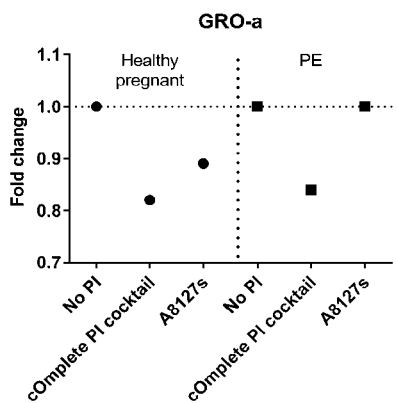
Figure 25K:
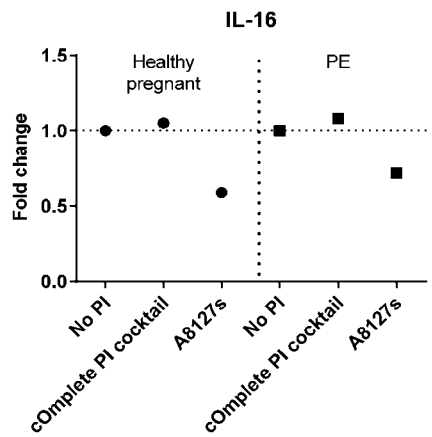
Figure 25L:
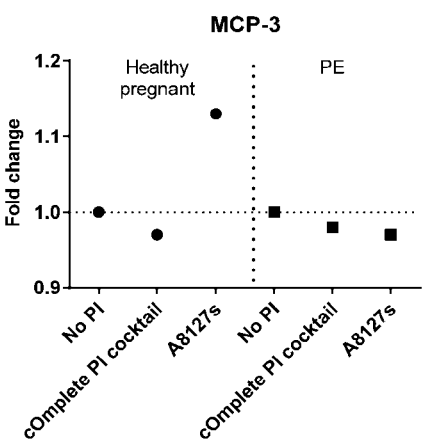
Figure 25M:
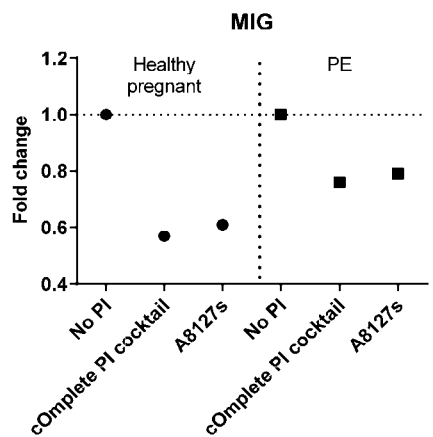
Figure 25N:
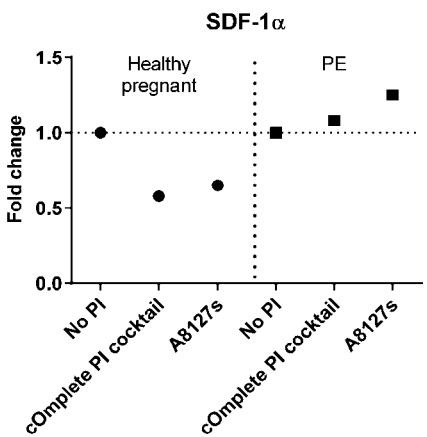
Figure 25O:
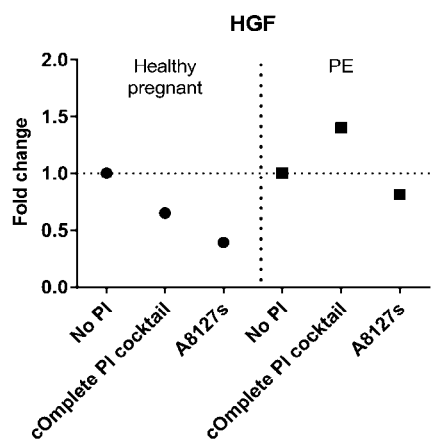
Figure 25P:
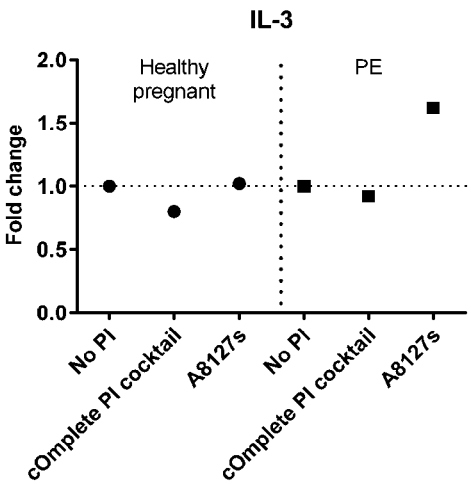
Figure 25Q:
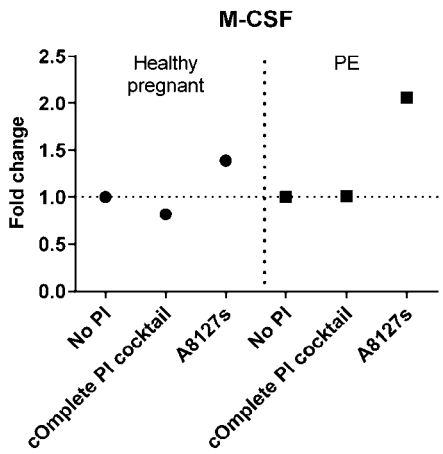
Figure 25R:
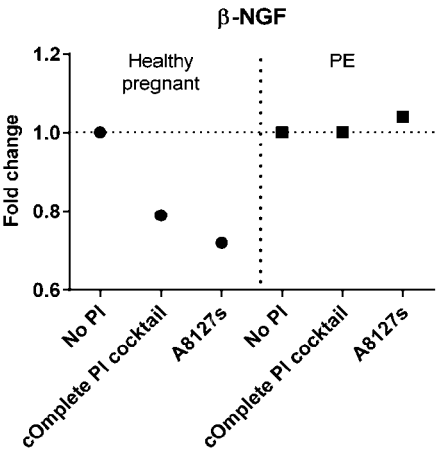
Figure 25S:
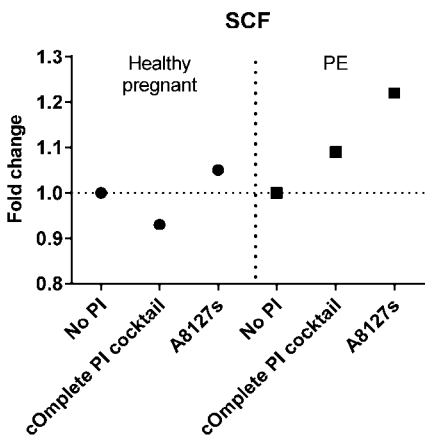
Figure 25T:
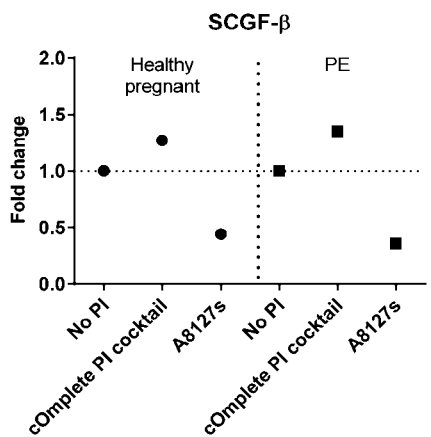
Figure 25U:
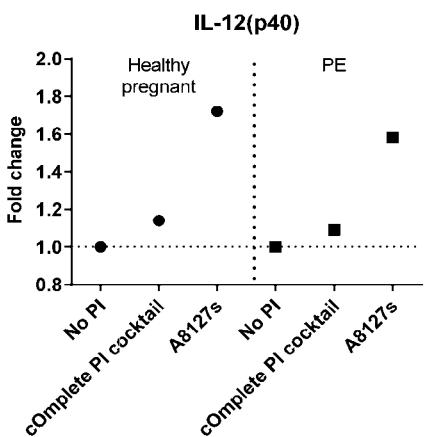
Figure 25V:
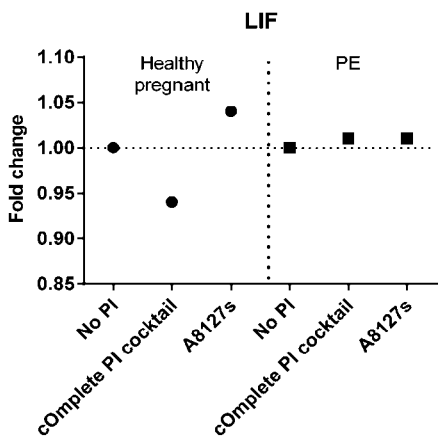
Figure 26A:
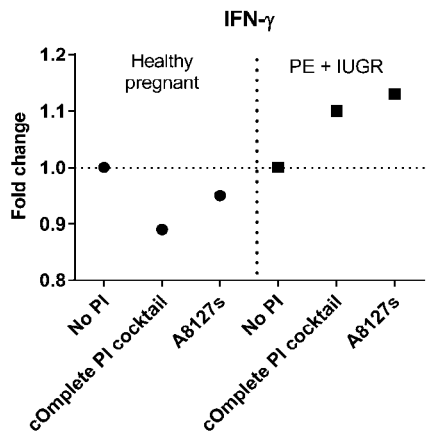
FIG. 26A-26VV is a series of graphs showing the effect of protease inhibitor cocktails on cytokines released from red blood cell membranes from healthy individuals compared to individuals having pre-eclampsia with intrauterine growth restriction.
Figure 26B:
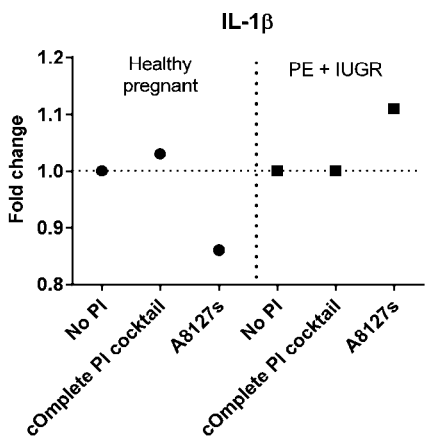
Figure 26C:
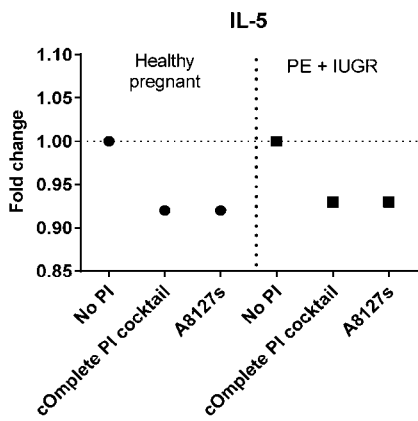
Figure 26D:
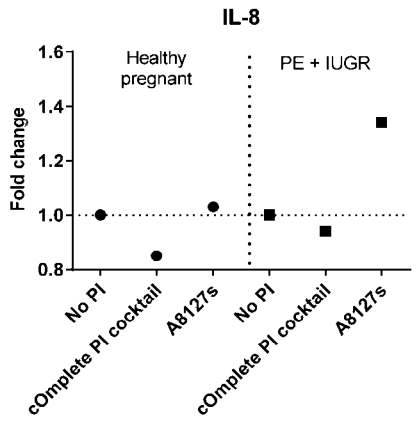
Figure 26E:
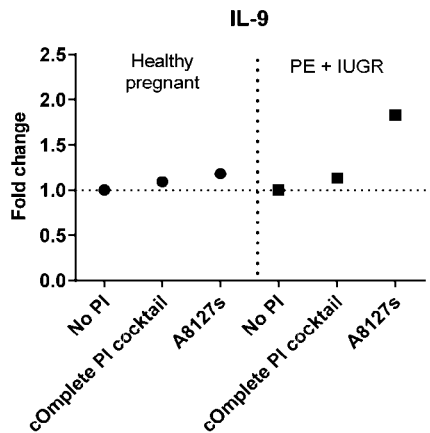
Figure 26F:
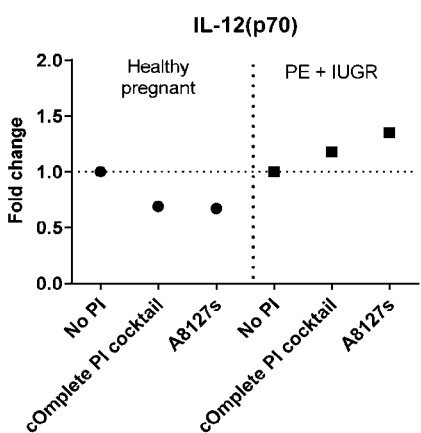
Figure 26G:
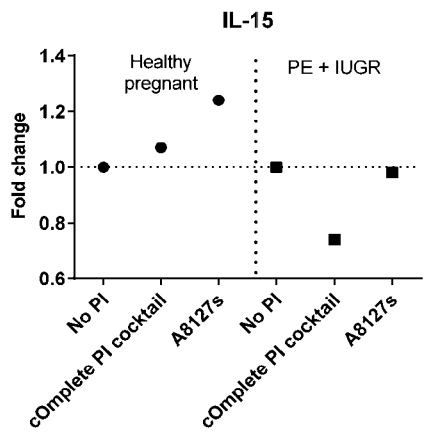
Figure 26H:
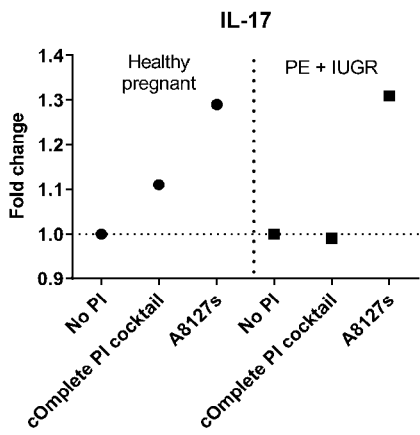
Figure 26I:
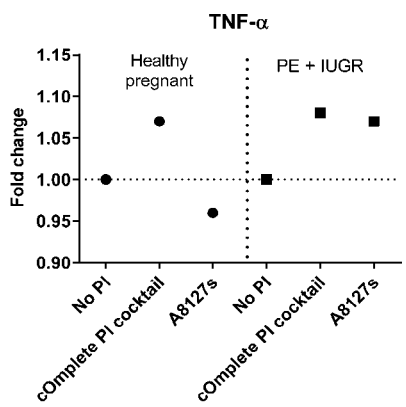
Figure 26J:
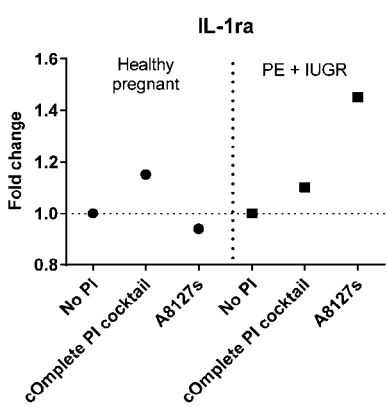
Figure 26K:
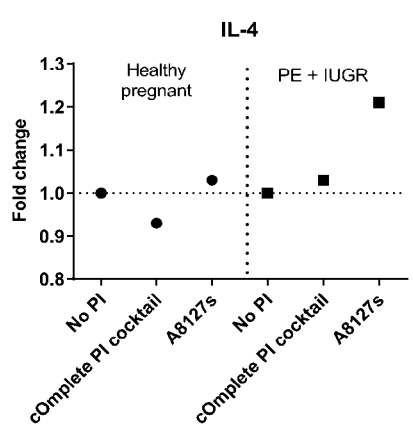
Figure 26L:
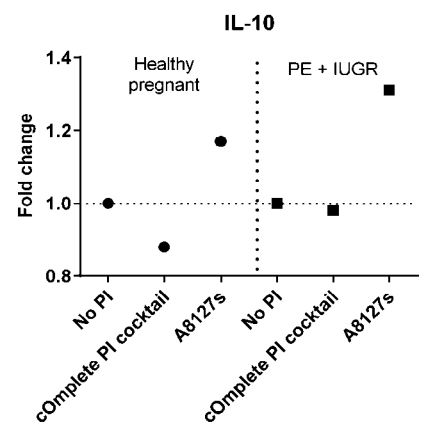
Figure 26M:
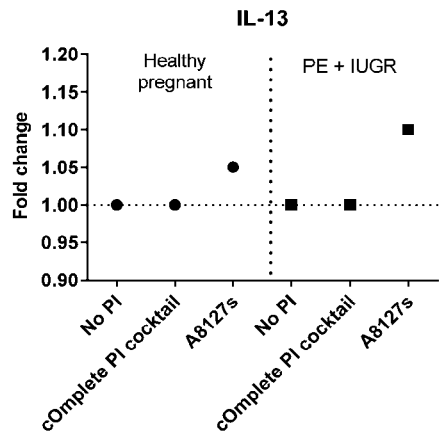
Figure 26N:
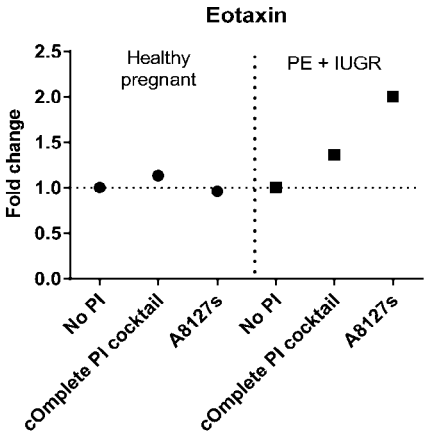
Figure 26O:
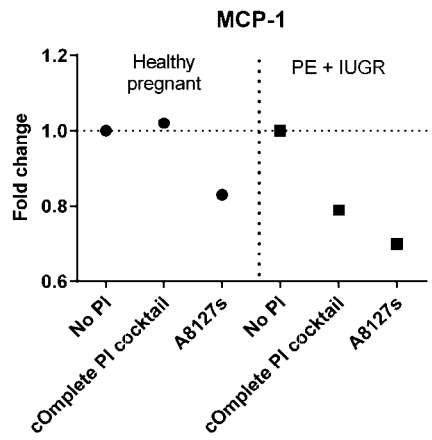
Figure 26P:
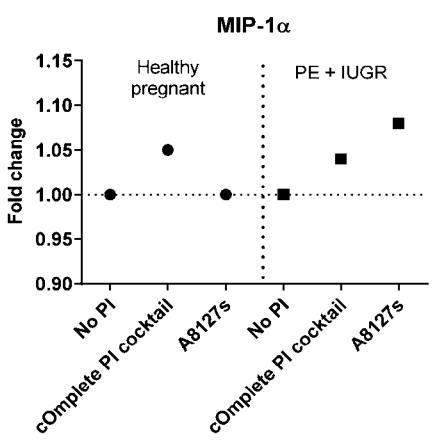
Figure 26Q:
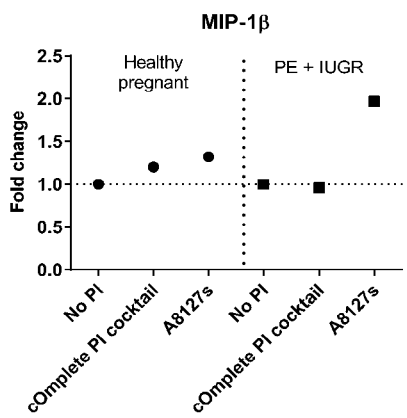
Figure 26R:
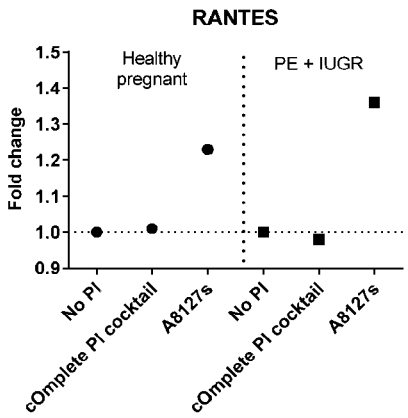
Figure 26S:
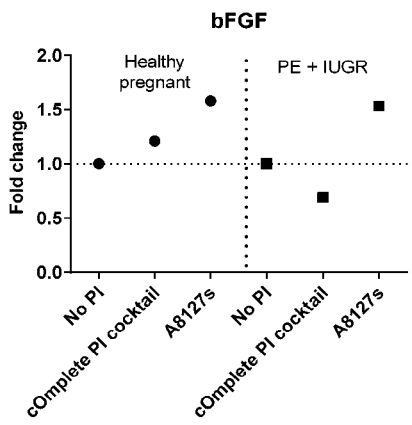
Figure 26T:
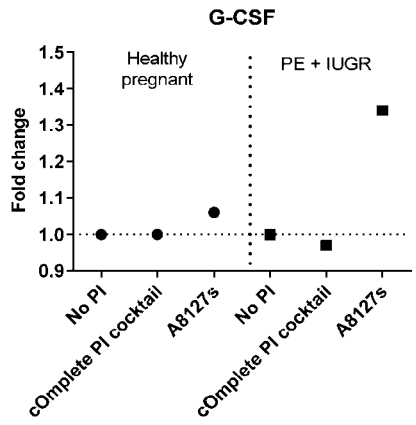
Figure 26U:
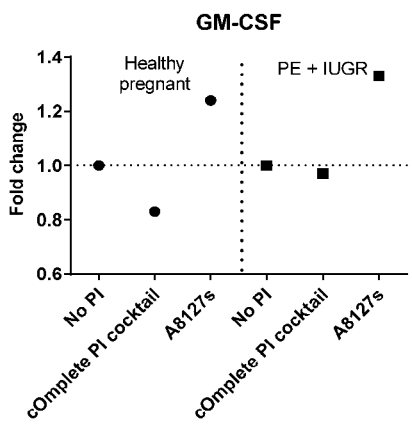
Figure 26V:
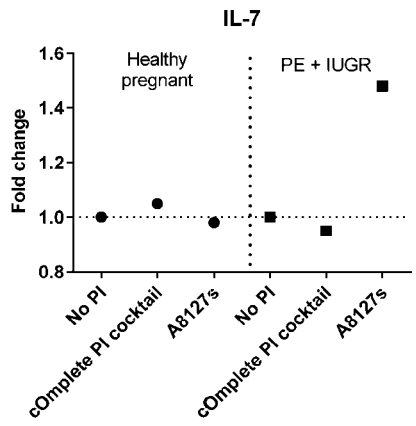
Figure 26W:
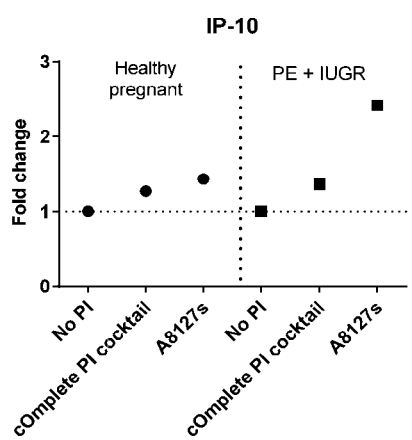
Figure 26X:
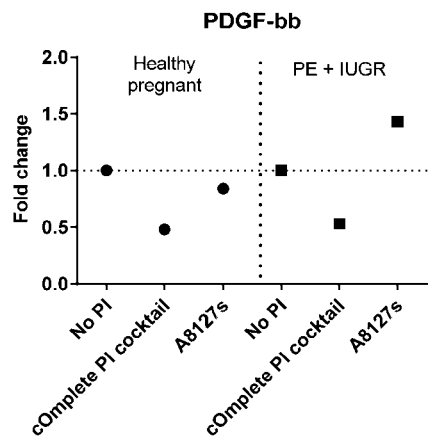
Figure 26Y:
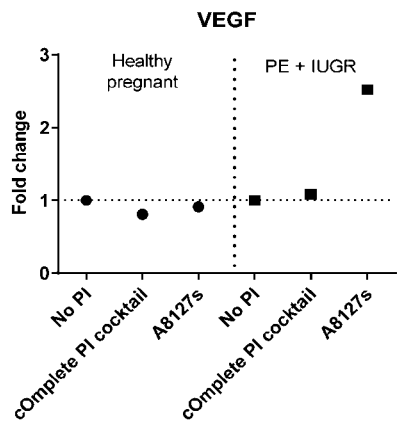
Figure 26Z:
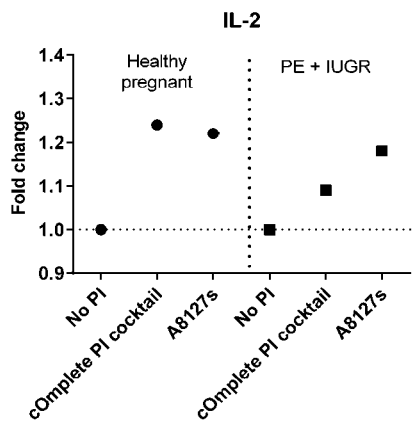
Figure 26A:
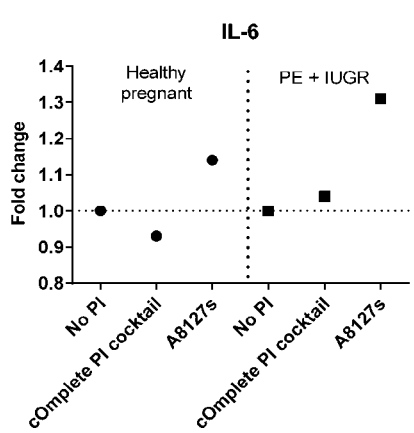
Figure 26B:
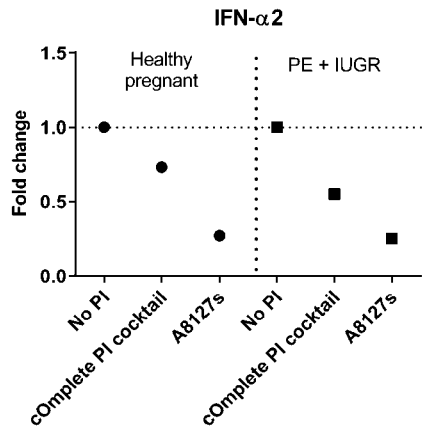
Figure 26C:
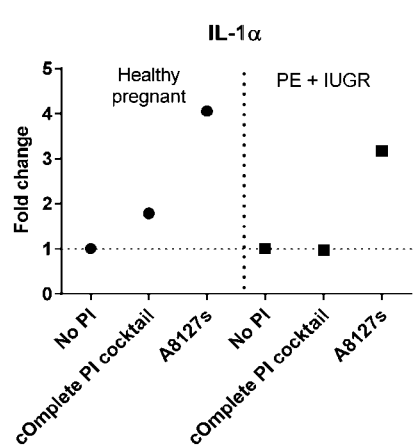
Figure 26D:
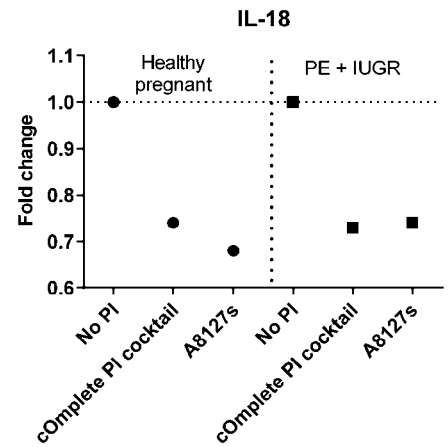
Figure 26E:
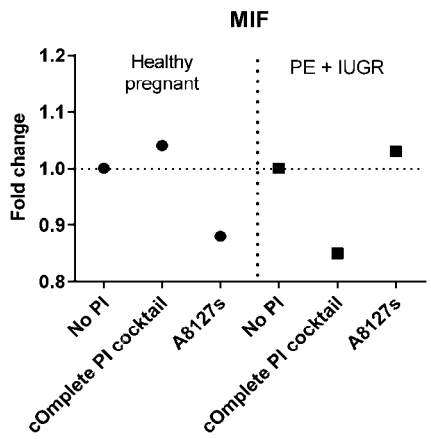
Figure 26F:
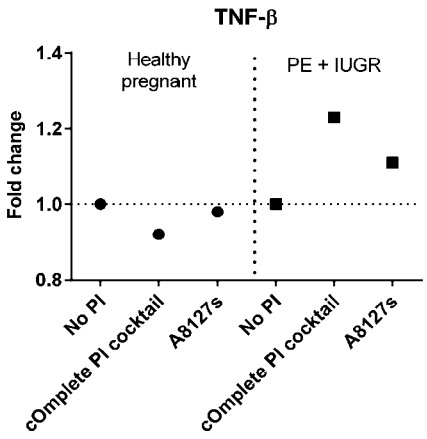
Figure 26G:
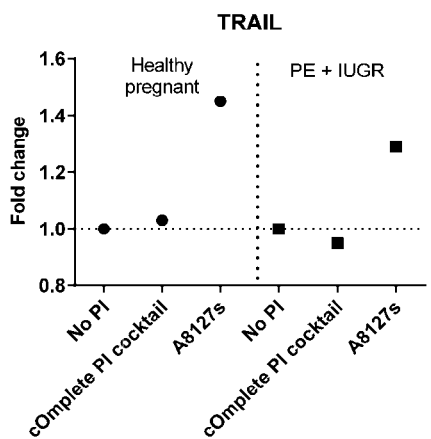
Figure 26H:
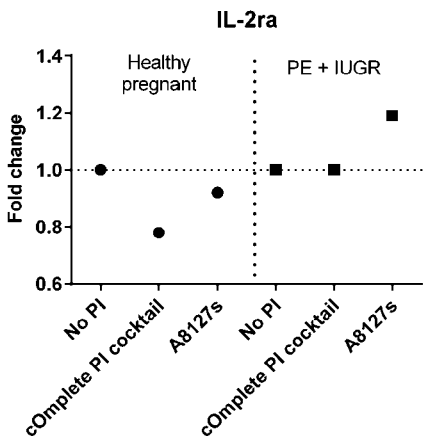
Figure 26I:
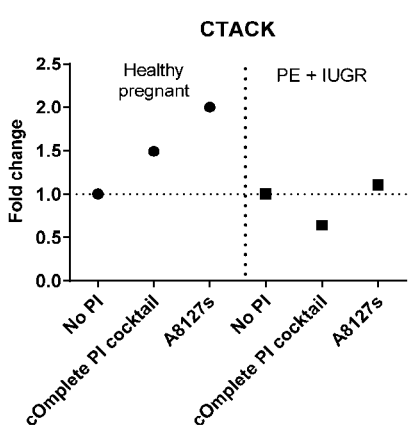
Figure 26J:
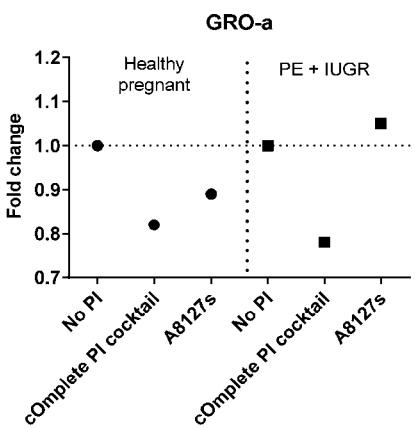
Figure 26K:
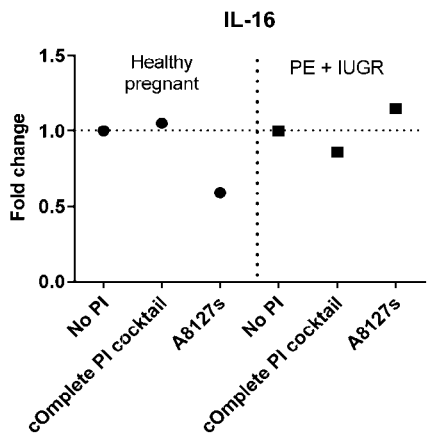
Figure 26L:
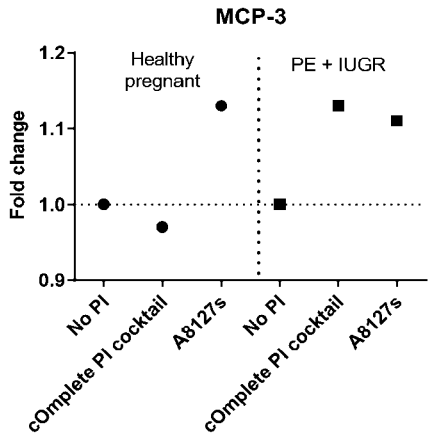
Figure 26M:
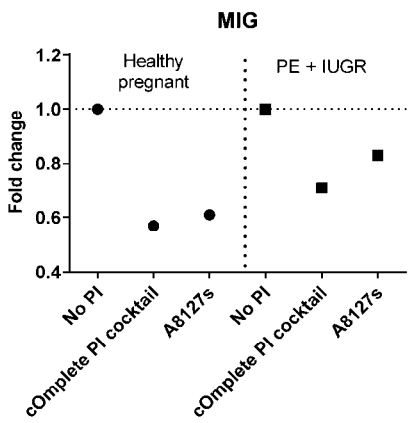
Figure 26N:
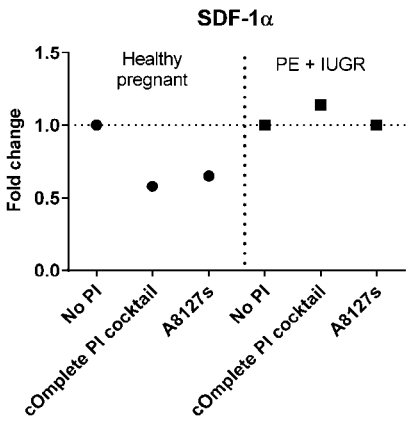
Figure 26O:
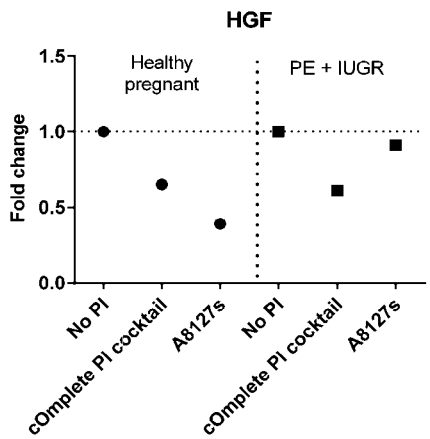
Figure 26P:
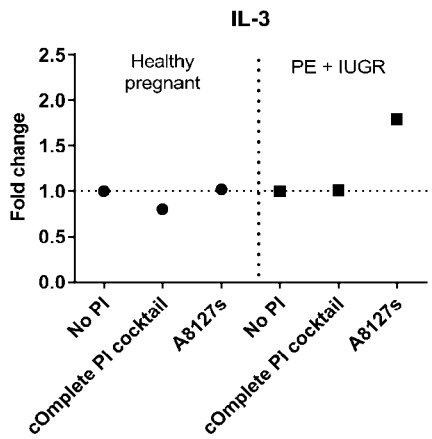
Figure 26Q:
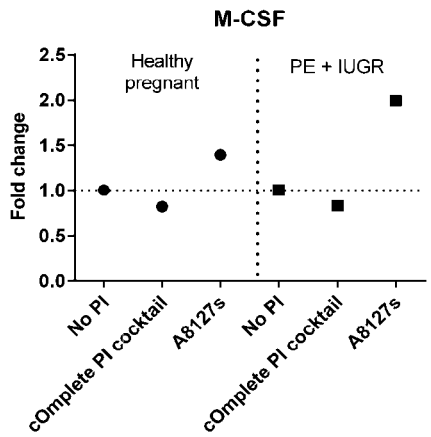
Figure 26R:
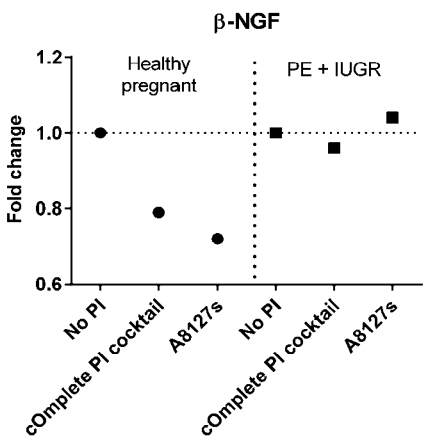
Figure 26S:
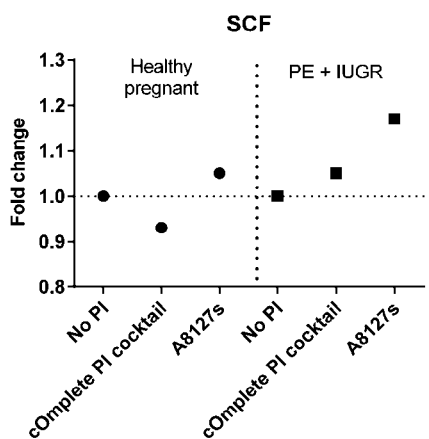
Figure 26T:
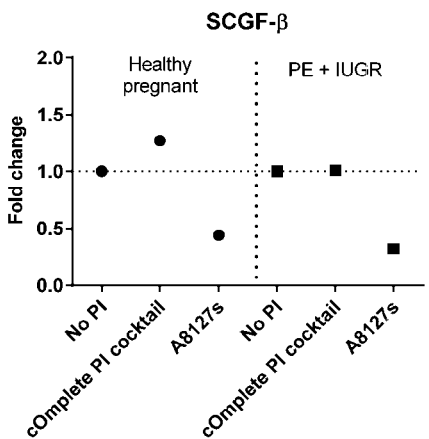
Figure 26U:
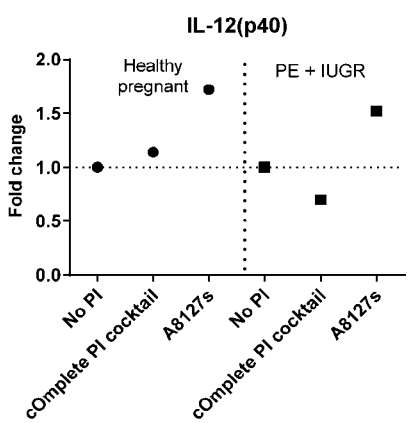
Figure 26V:
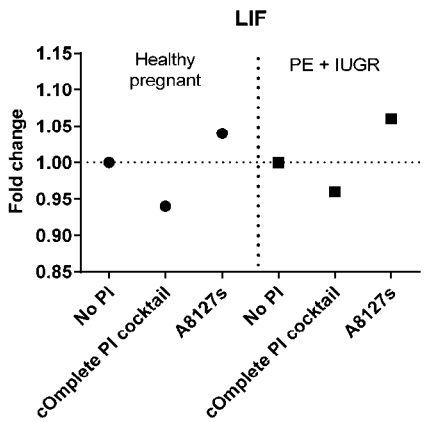
Figure 27A:
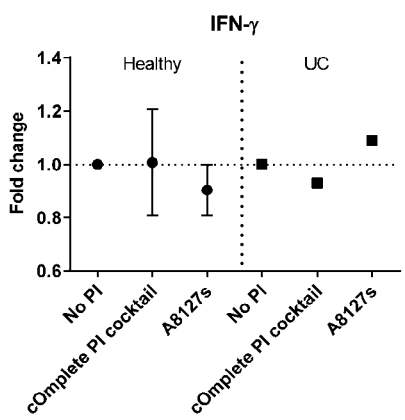
FIG. 27A-27VV is a series of graphs showing the effect of protease inhibitor cocktails on cytokines released from red blood cell membranes from healthy individuals compared to individuals having ulcerative colitis.
Figure 27B:
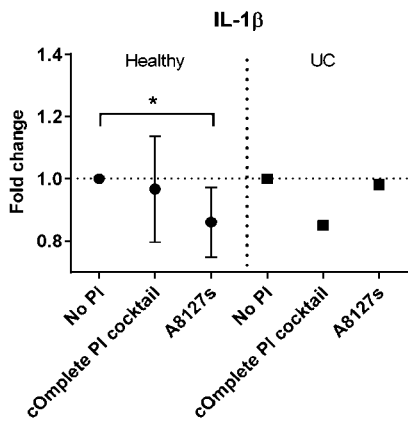
Figure 27C:
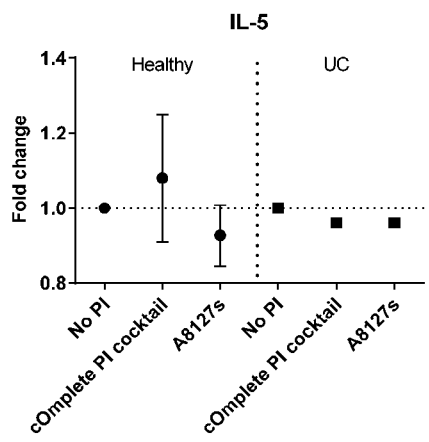
Figure 27D:
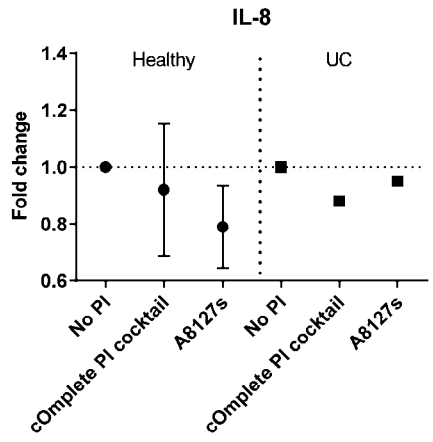
Figure 27E:
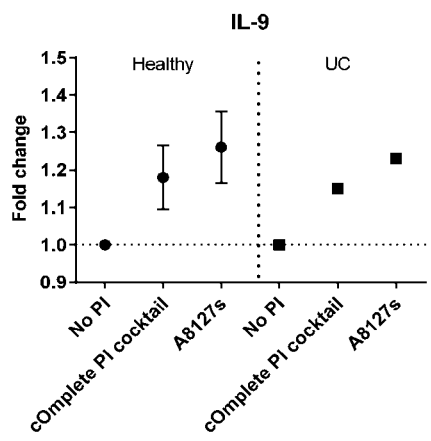
Figure 27F:
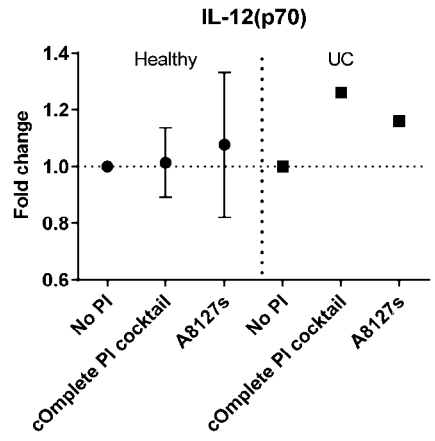
Figure 27G:
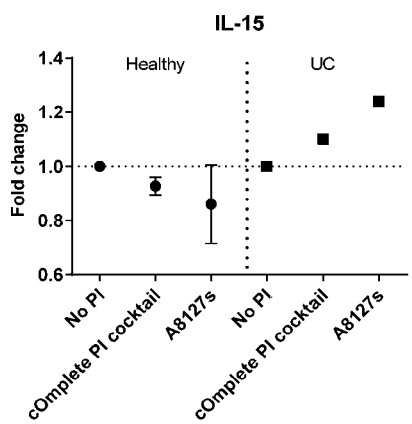
Figure 27H:
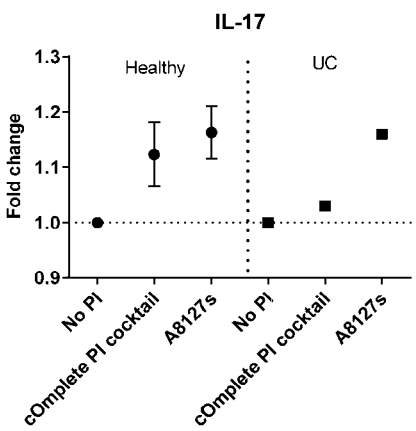
Figure 27I:
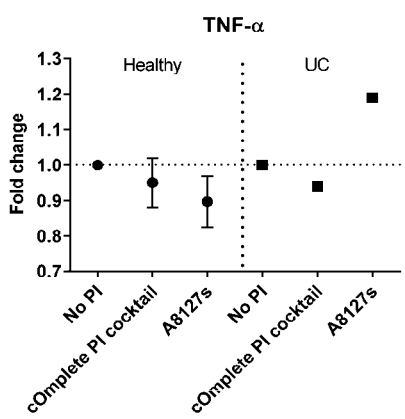
Figure 27J:
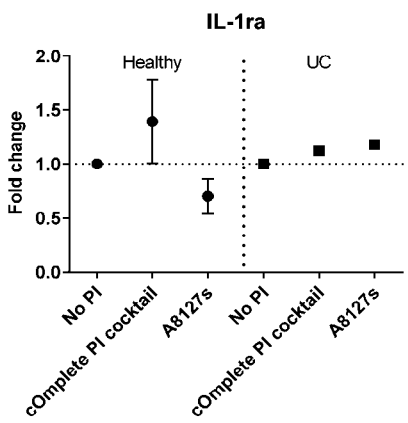
Figure 27K:
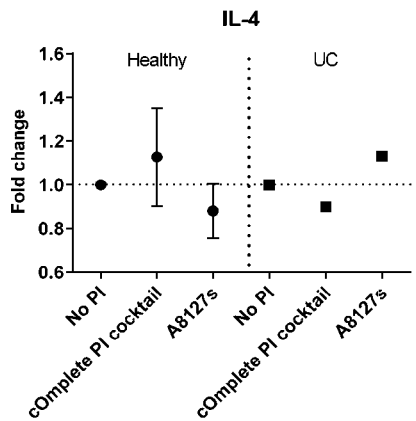
Figure 27L:
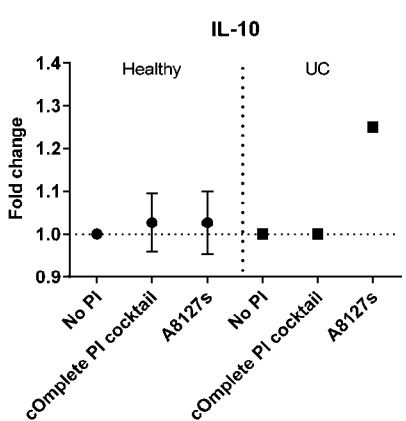
Figure 27M:
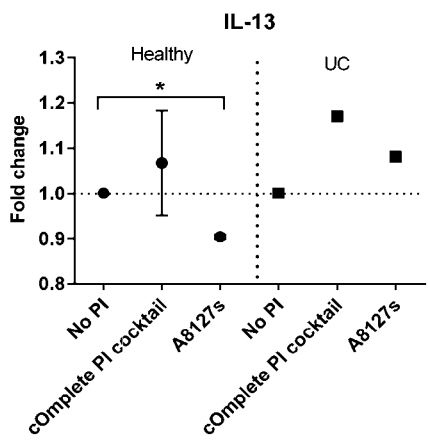
Figure 27N:
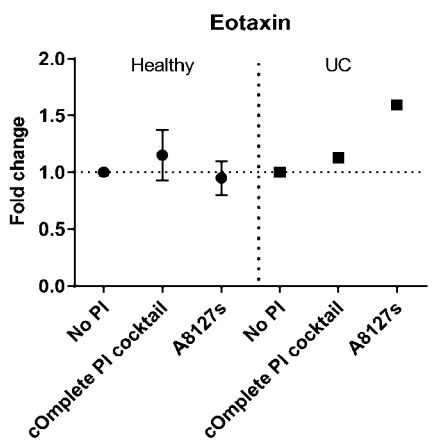
Figure 27O:
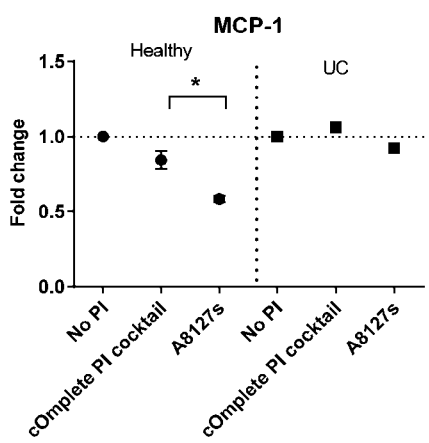
Figure 27P:
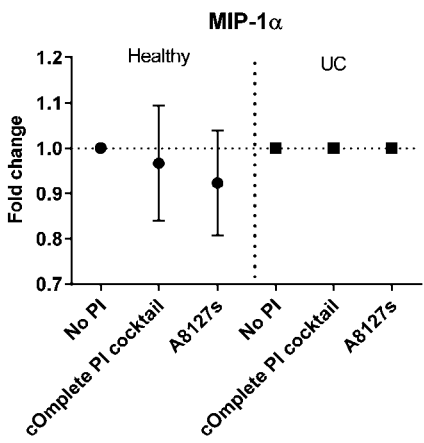
Figure 27Q:
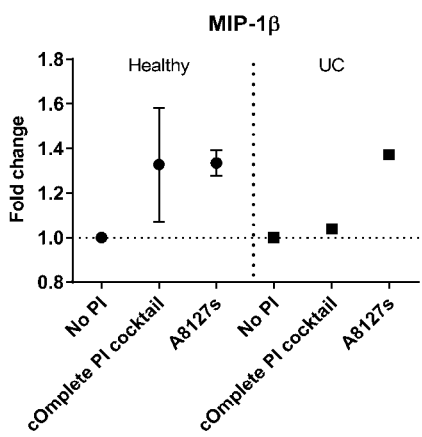
Figure 27R:
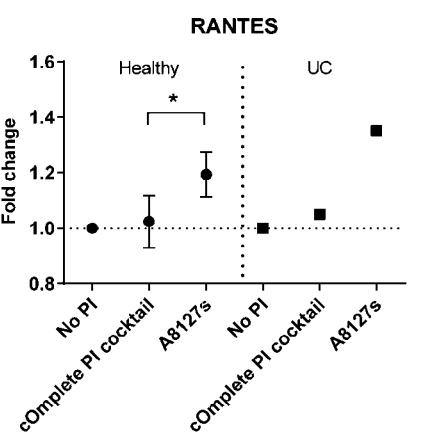
Figure 27S:
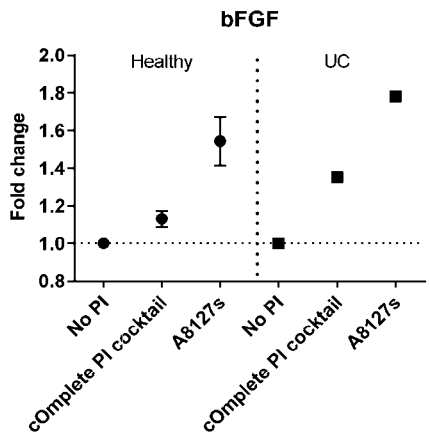
Figure 27T:
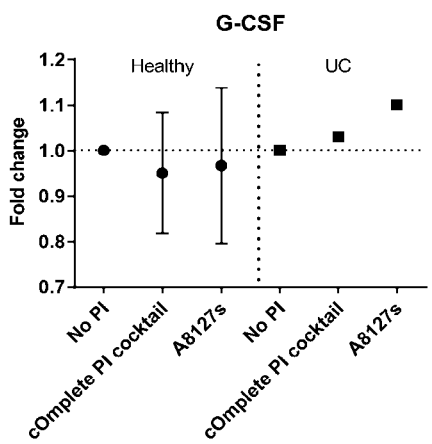
Figure 27U:
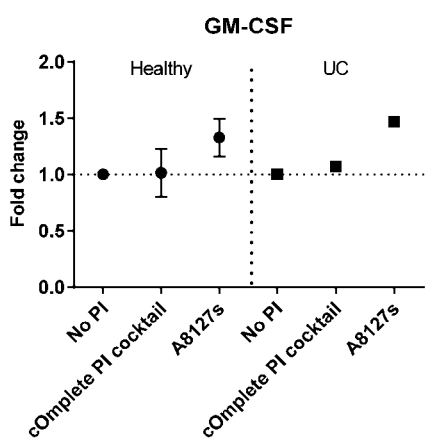
Figure 27V:
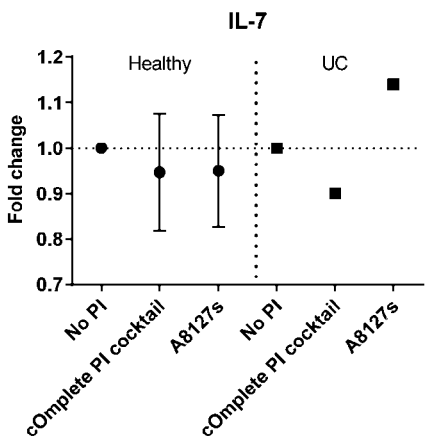
Figure 27W:
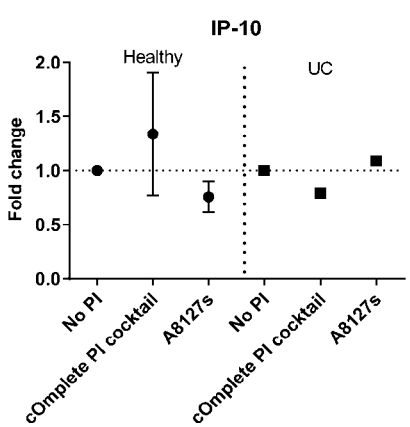
Figure 27X:
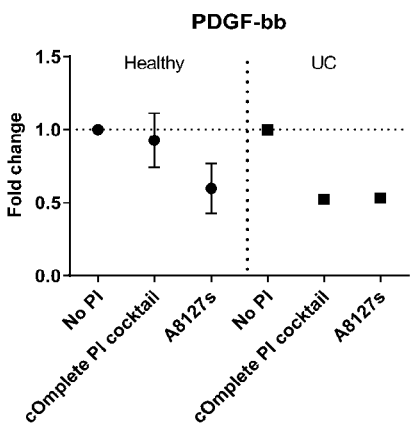
Figure 27Y:
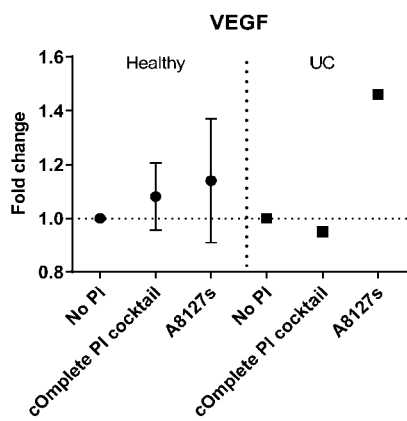
Figure 27Z:
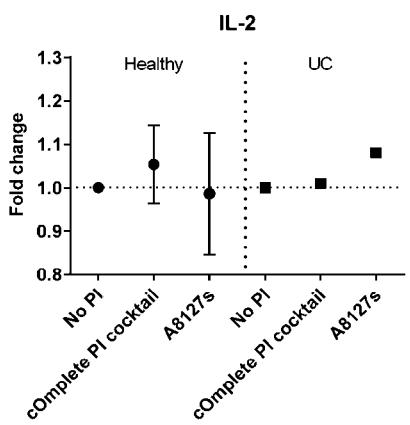
Figure 27A:
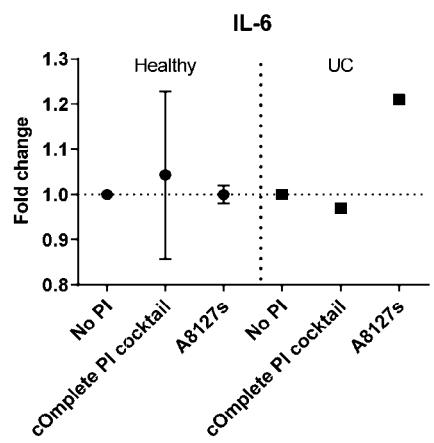
Figure 27B:
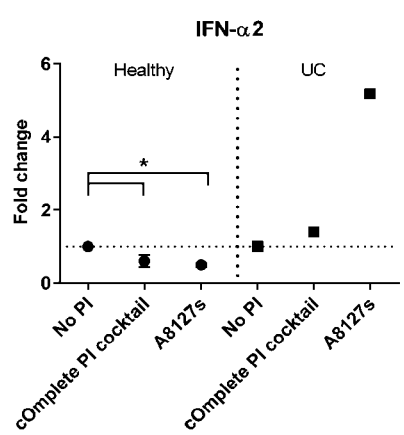
Figure 27C:
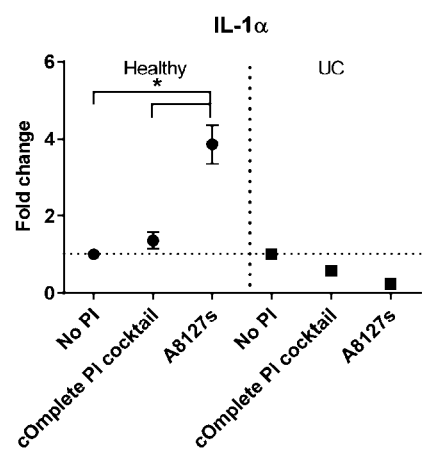
Figure 27D:
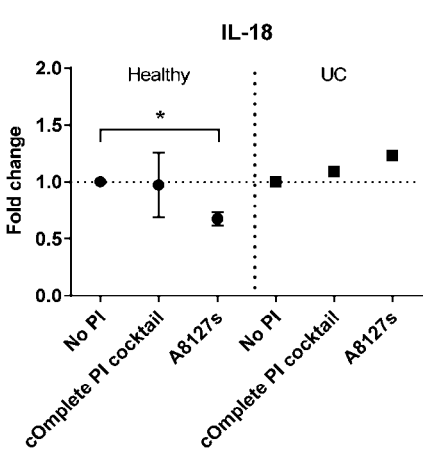
Figure 27E:
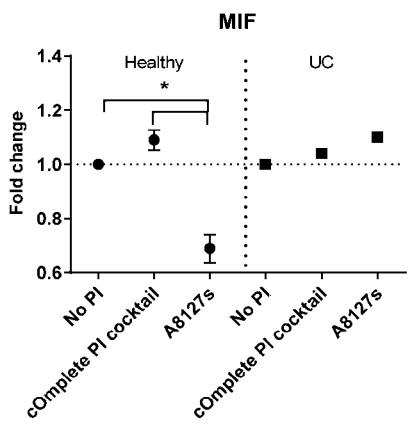
Figure 27F:
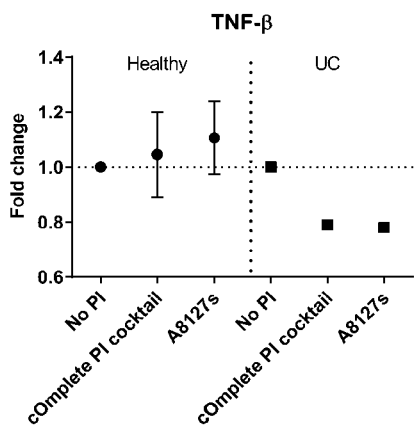
Figure 27G:
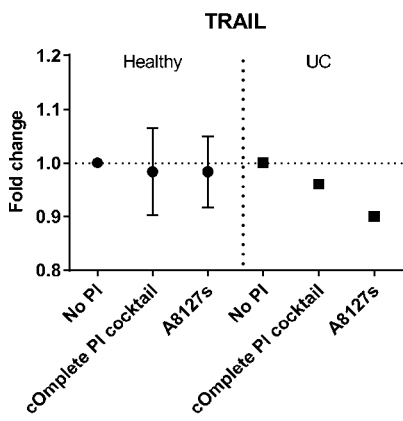
Figure 27H:
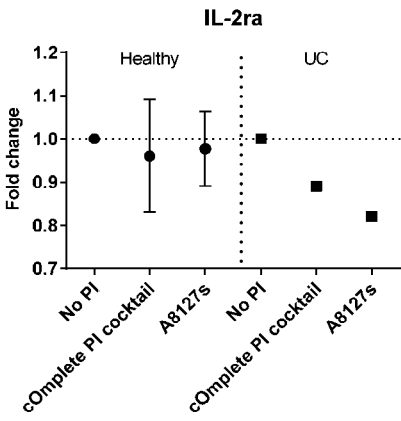
Figure 27I:
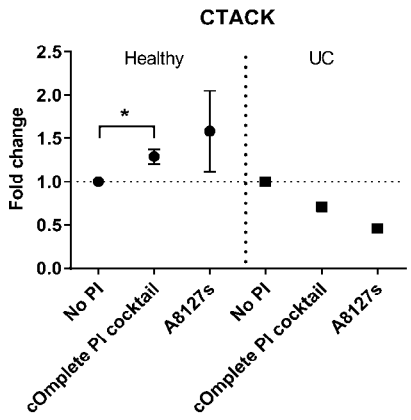
Figure 27J:
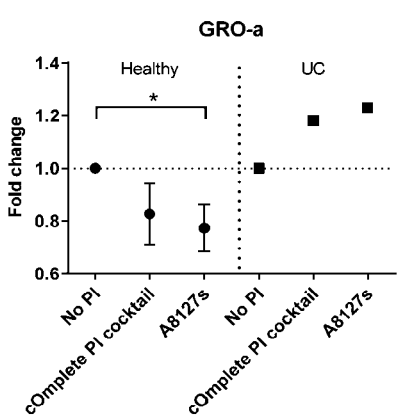
Figure 27K:
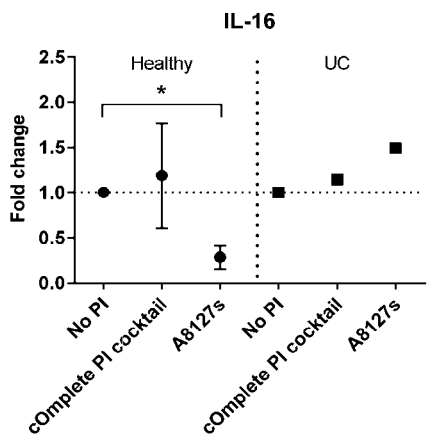
Figure 27L:
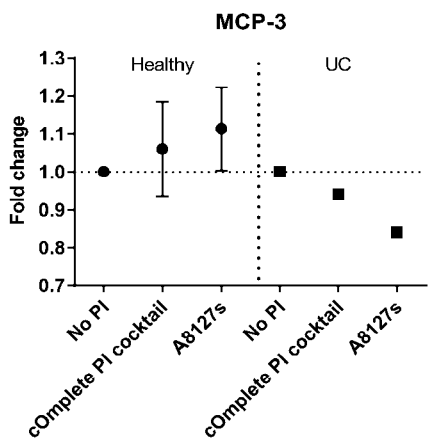
Figure 27M:
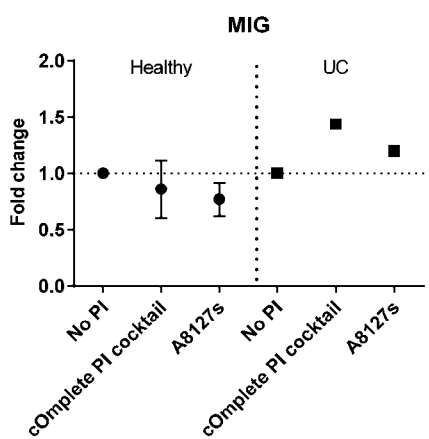
Figure 27N:
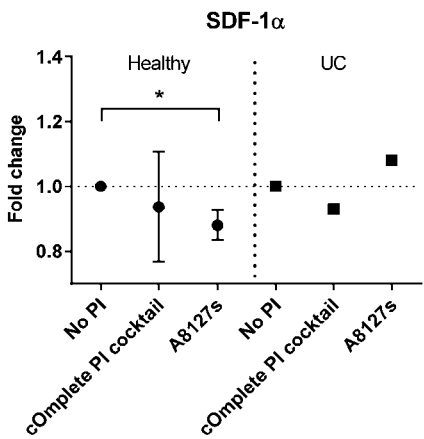
Figure 27O:
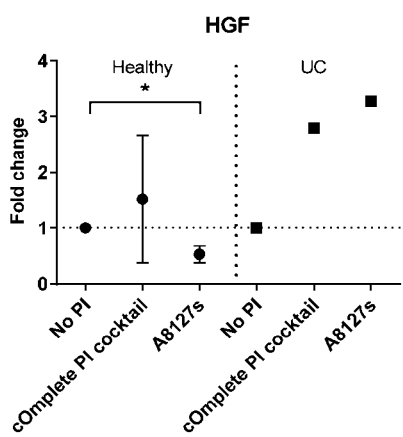
Figure 27P:
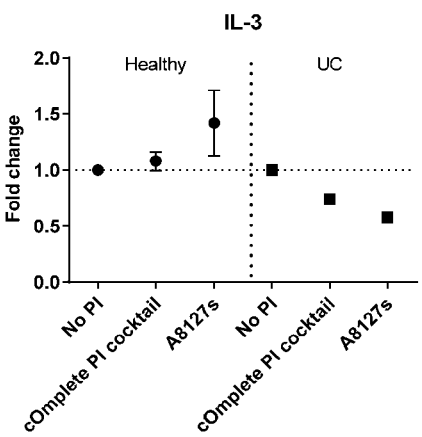
Figure 27Q:
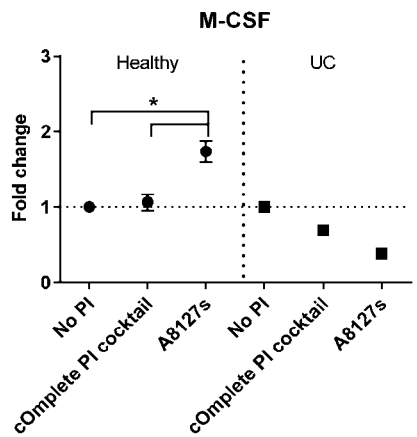
Figure 27R:
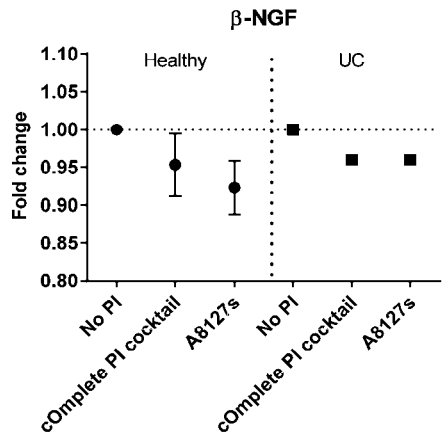
Figure 27S:
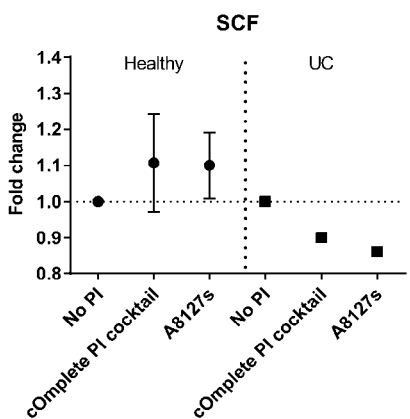
Figure 27T:
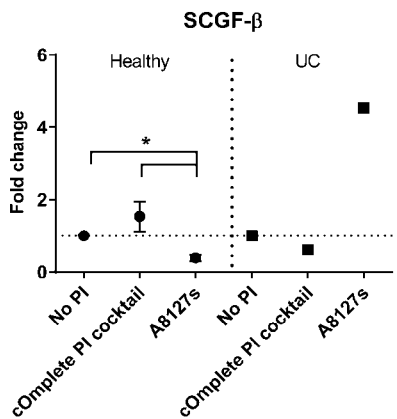
Figure 27U:
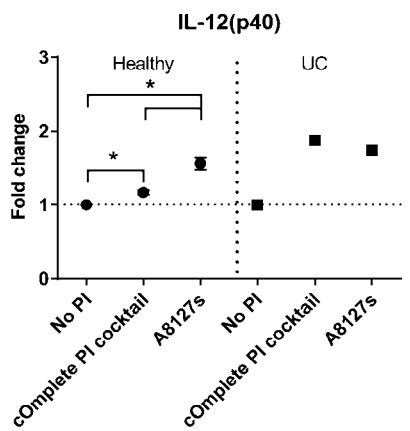
Figure 27V:
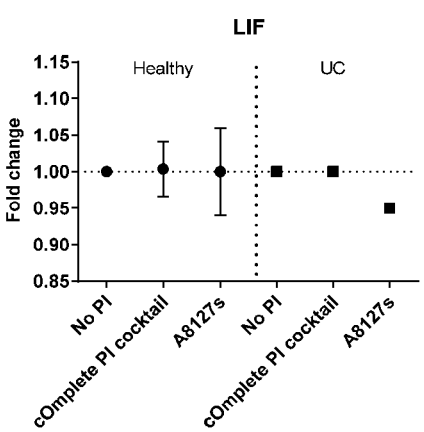
Figure 28A:
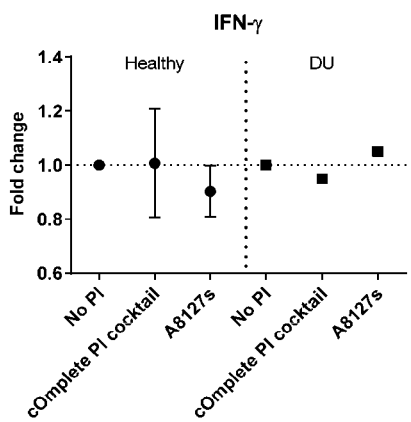
FIG. 28A-28VV is a series of graphs showing the effect of protease inhibitor cocktails on cytokines released from red blood cell membranes from healthy individuals compared to individuals having duodenal ulcer.
Figure 28B:
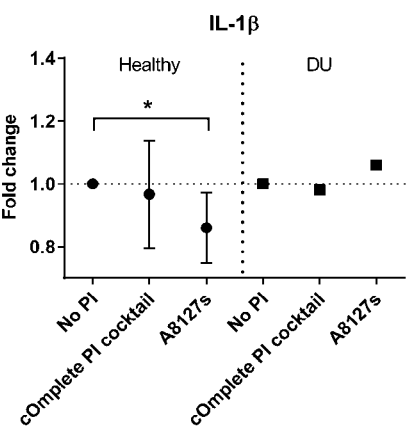
Figure 28C:
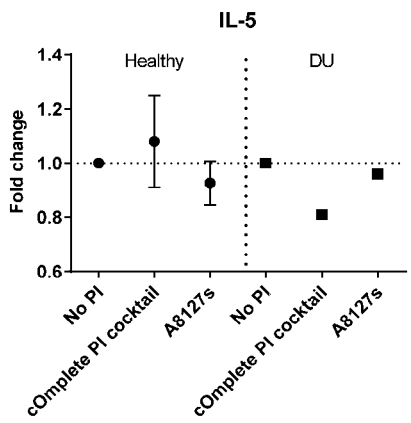
Figure 28D:
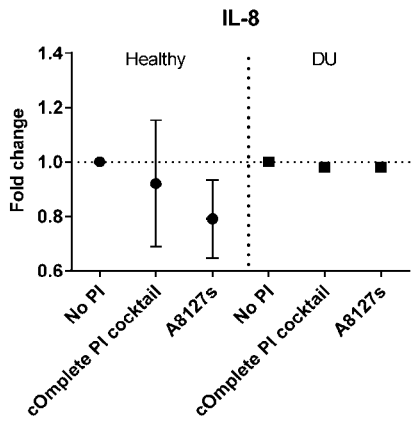
Figure 28E:
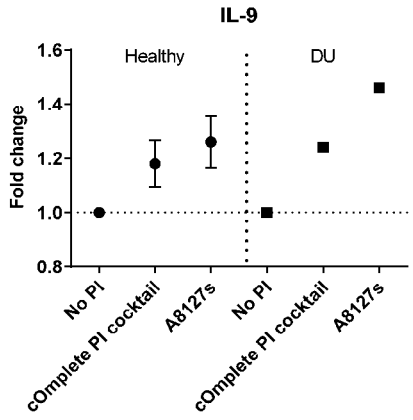
Figure 28F:
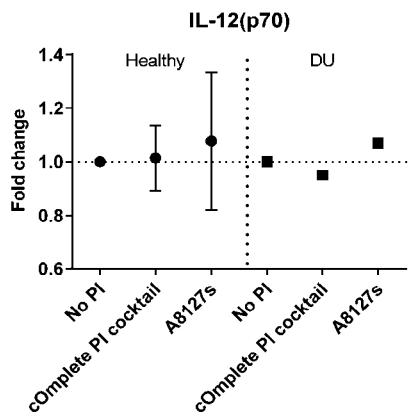
Figure 28G:
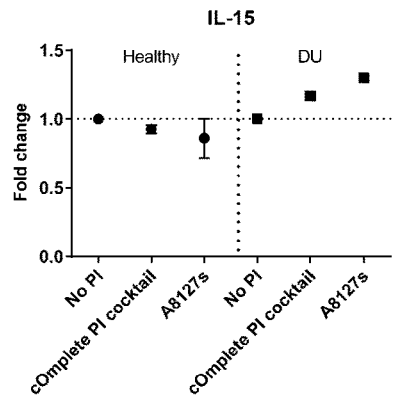
Figure 28H:
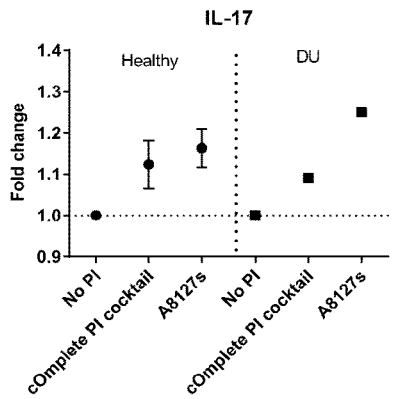
Figure 28I:
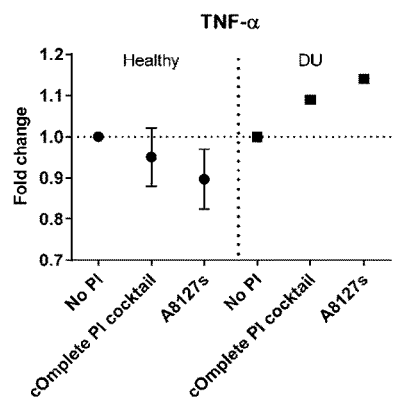
Figure 28J:
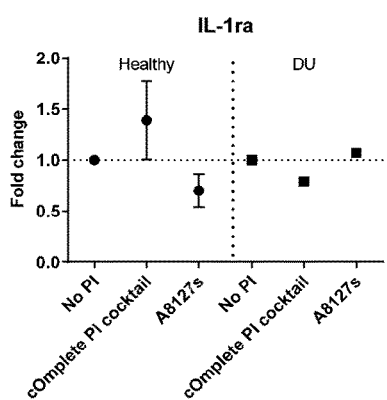
Figure 28K:
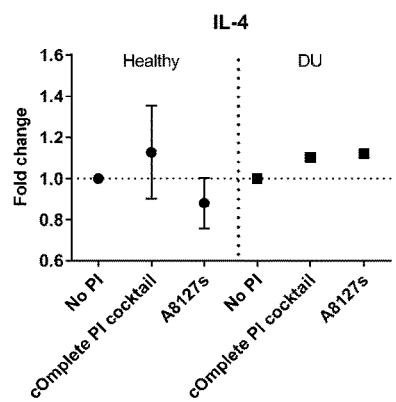
Figure 28L:
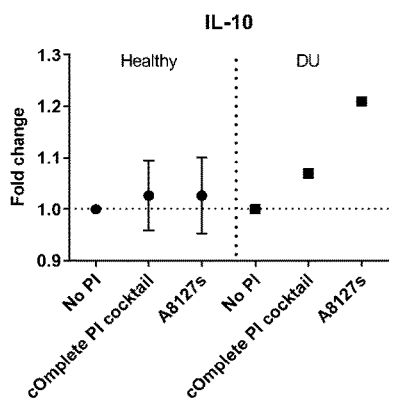
Figure 28M:
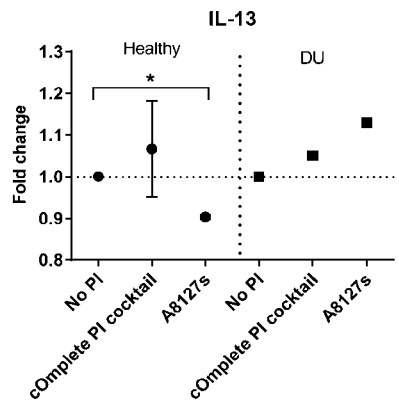
Figure 28N:
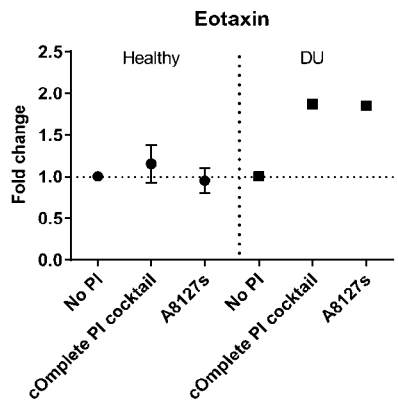
Figure 28O:
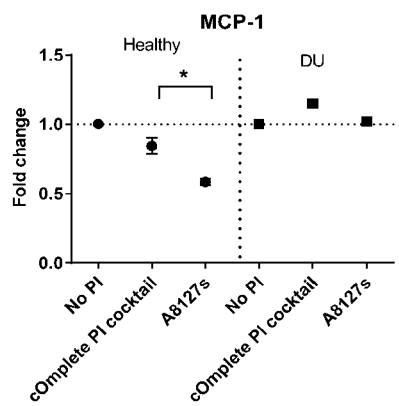
Figure 28P:
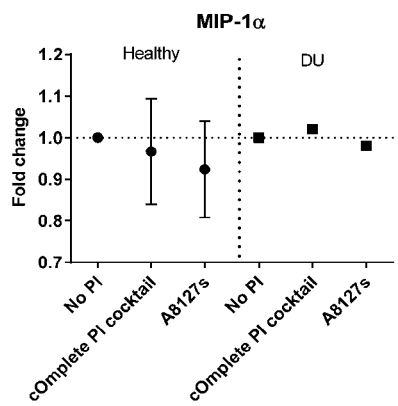
Figure 28Q:
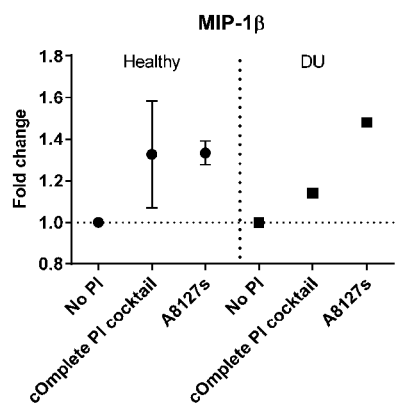
Figure 28R:
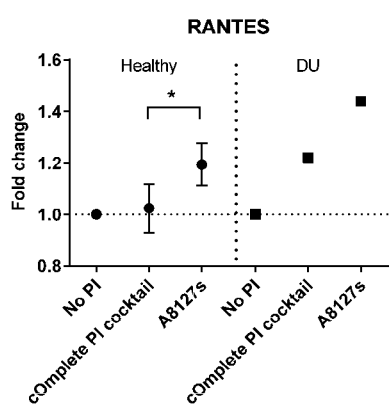
Figure 28S:
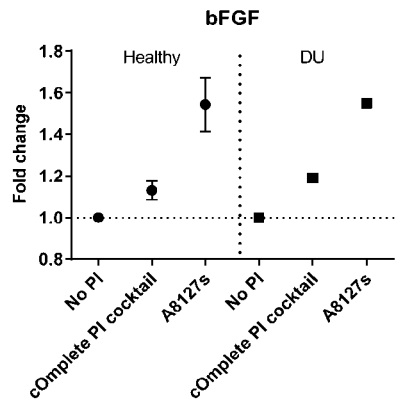
Figure 28T:
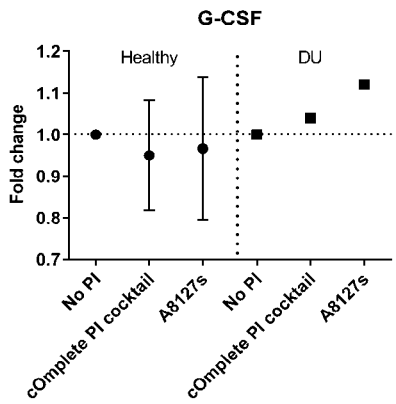
Figure 28U:
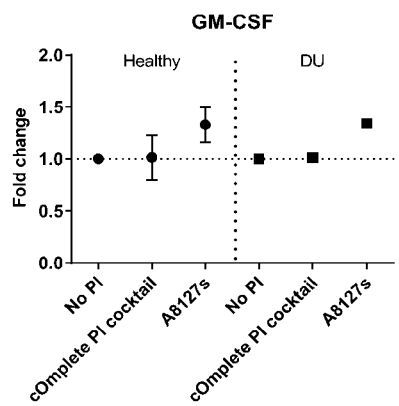
Figure 28V:
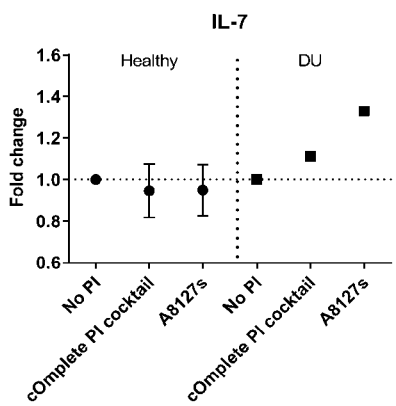
Figure 28W:
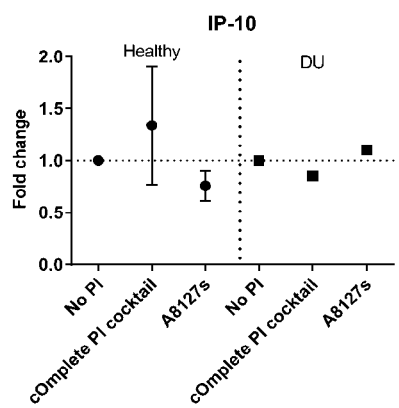
Figure 28X:
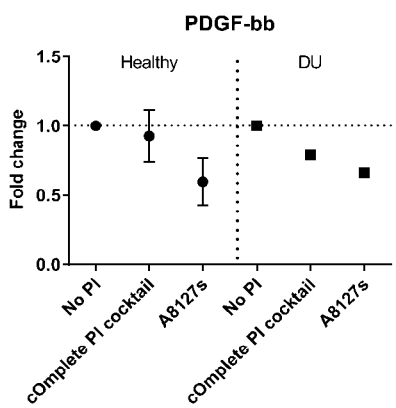
Figure 28Y:
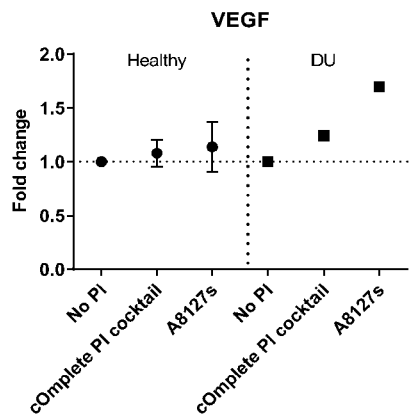
Figure 28Z:
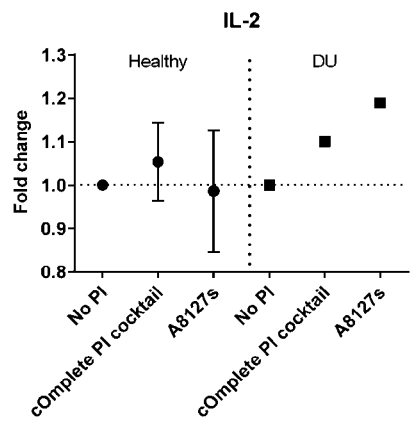
Figure 28A:
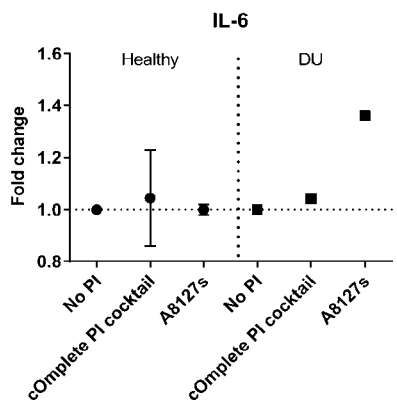
Figure 28B:
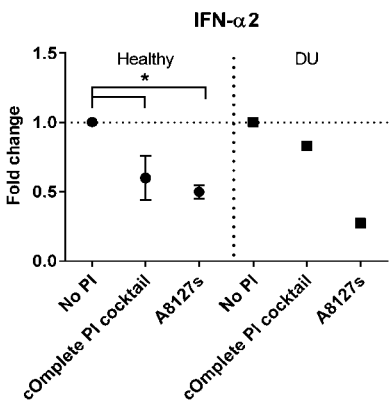
Figure 28C:
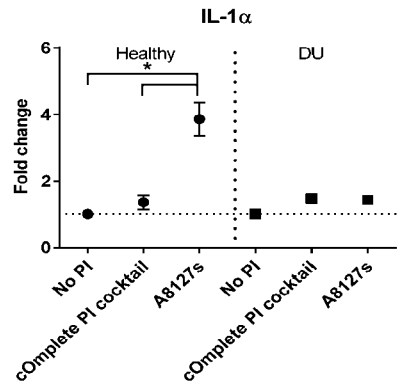
Figure 28D:
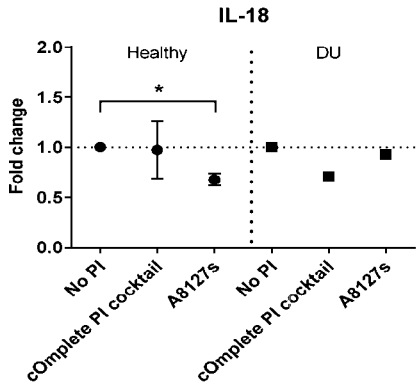
Figure 28E:
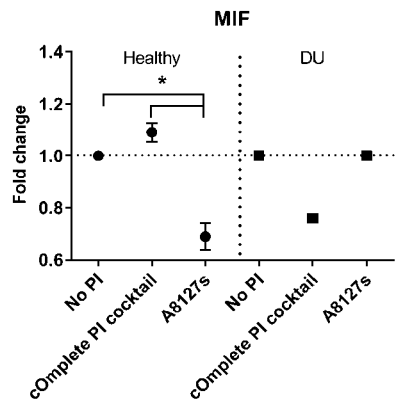
Figure 28F:
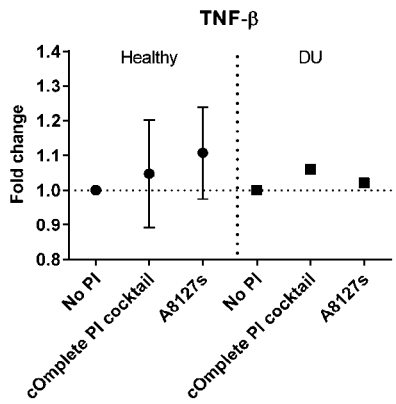
Figure 28G:
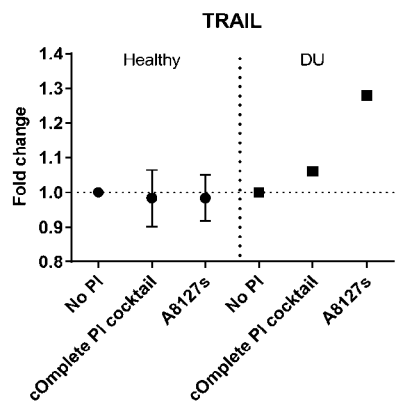
Figure 28H:
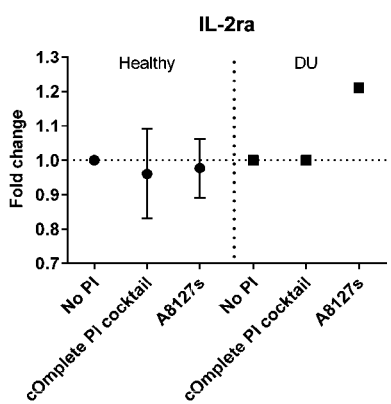
Figure 28I:
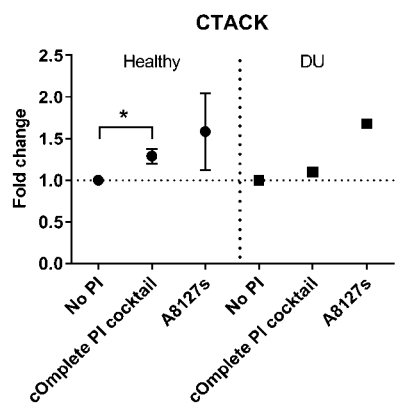
Figure 28J:
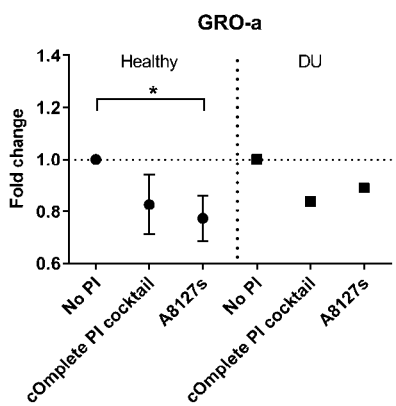
Figure 28K:
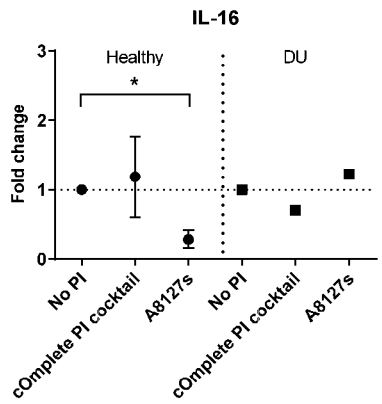
Figure 28L:
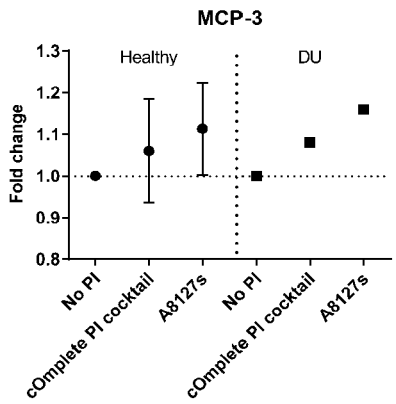
Figure 28M:
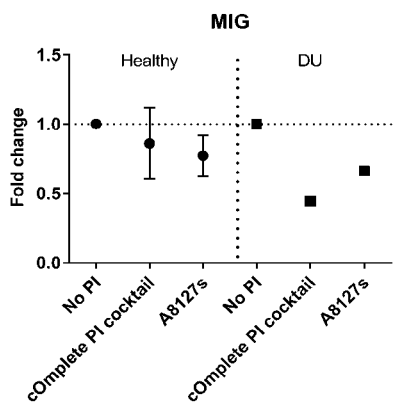
Figure 28N:
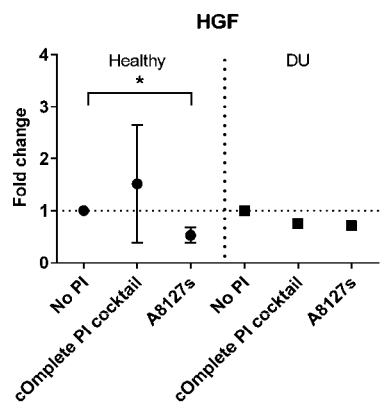
Figure 28O:
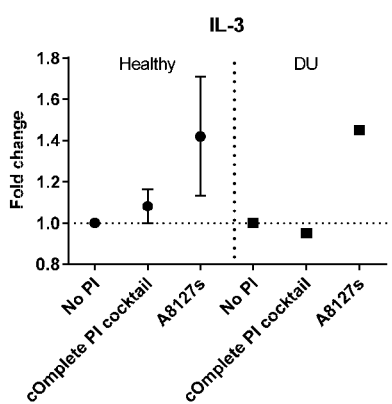
Figure 28P:
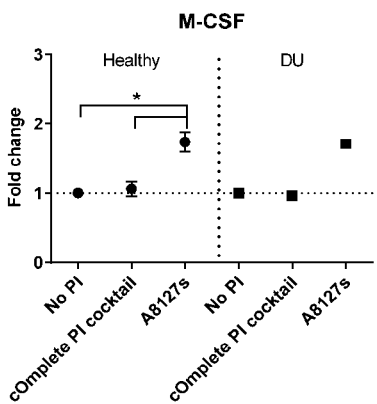
Figure 28Q:
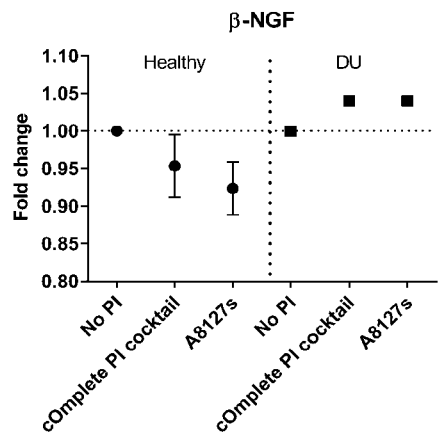
Figure 28R:
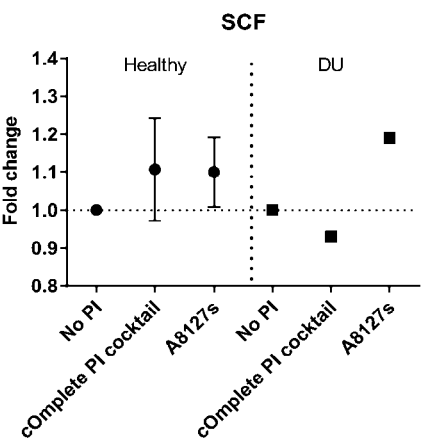
Figure 28S:
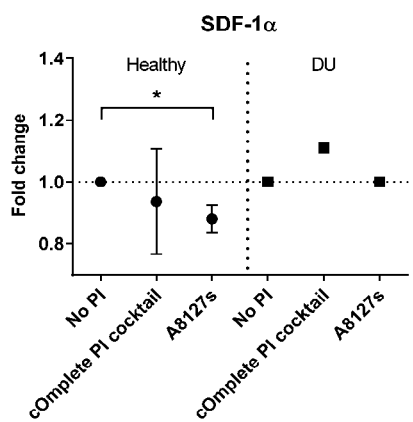
Figure 28T:
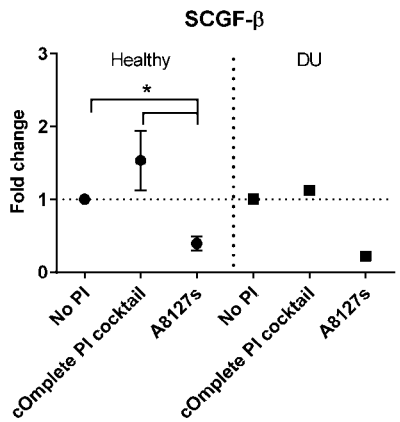
Figure 28U:
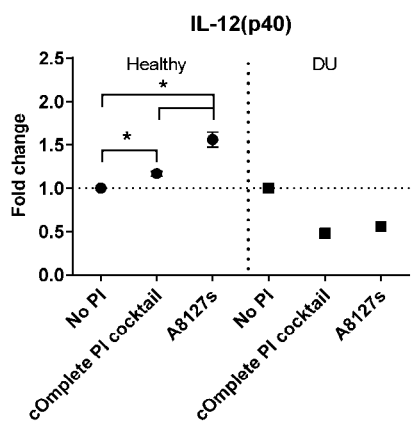
Figure 28V:
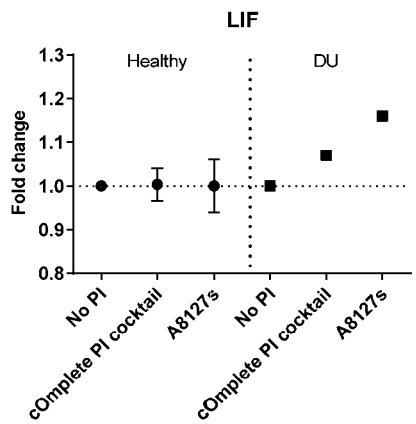
Figure 29A:
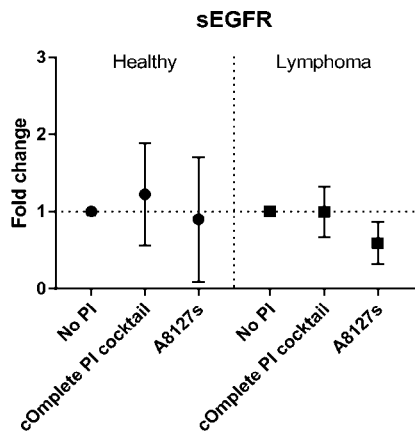
FIG. 29A-29LL is a series of graphs showing the effect of protease inhibitor cocktails on other proteins released from red blood cells from healthy individuals compared to individuals having lymphoma.
Figure 29B:
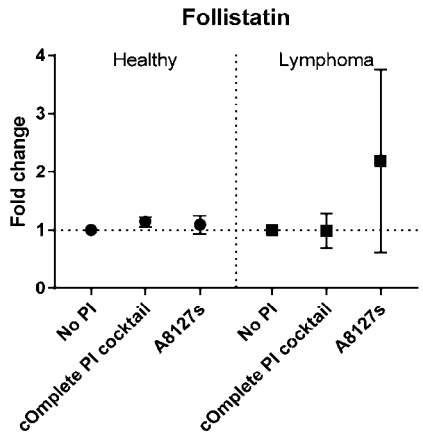
Figure 29C:
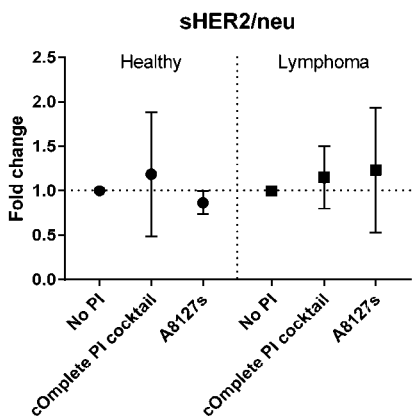
Figure 29D:
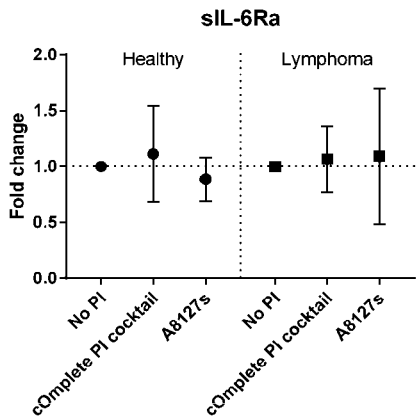
Figure 29E:
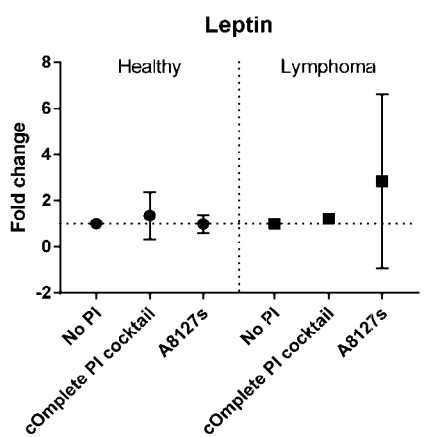
Figure 29F:
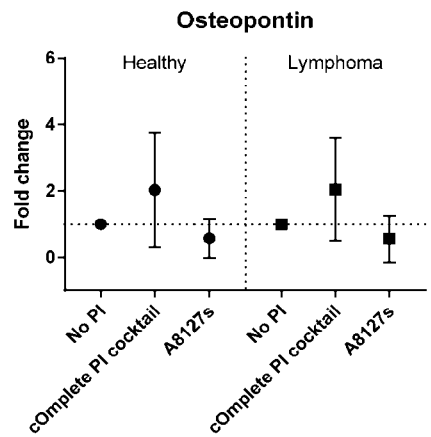
Figure 29G:
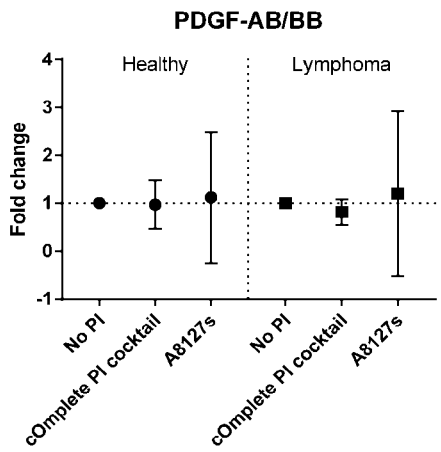
Figure 29H:
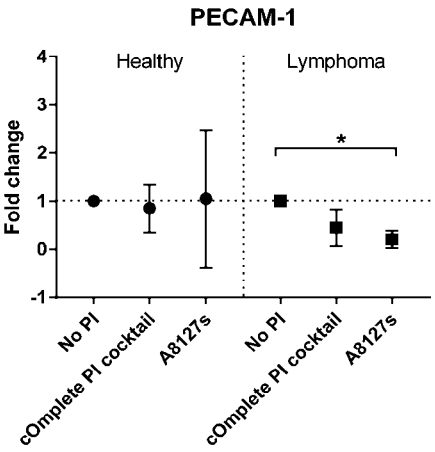
Figure 29I:
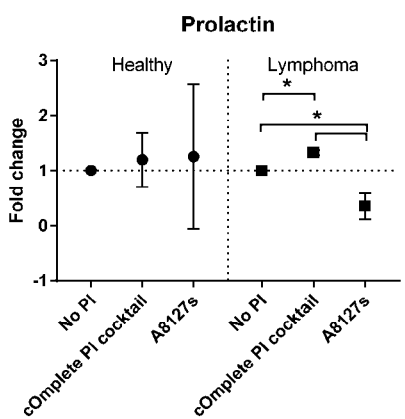
Figure 29J:
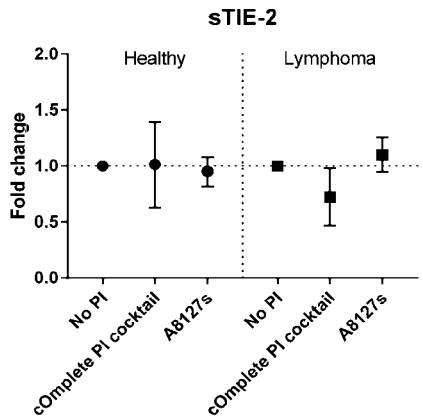
Figure 29K:
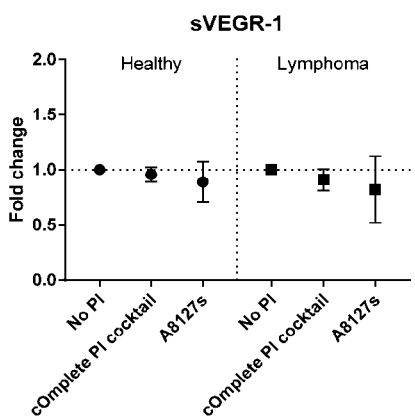
Figure 29L:
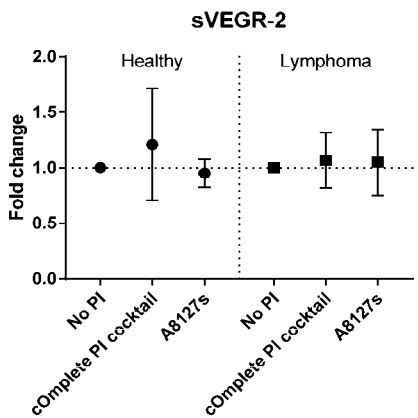
Figure 29M:
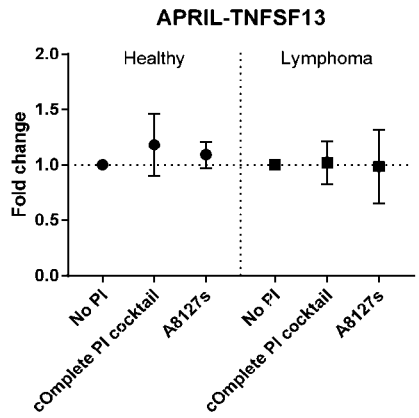
Figure 29N:
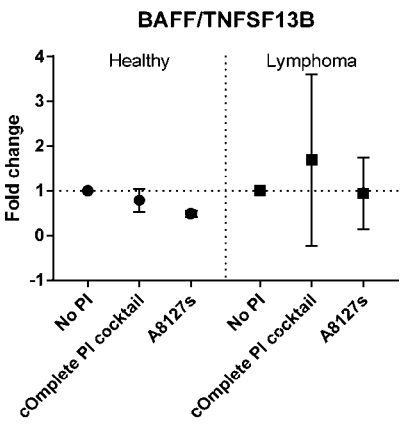
Figure 29O:
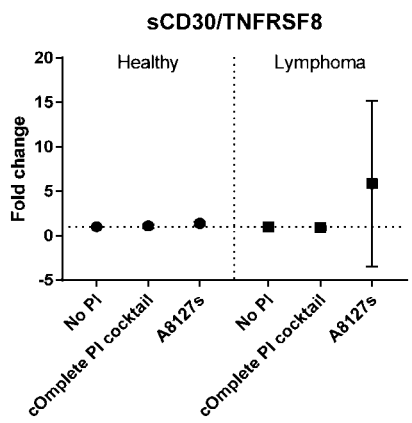
Figure 29P:
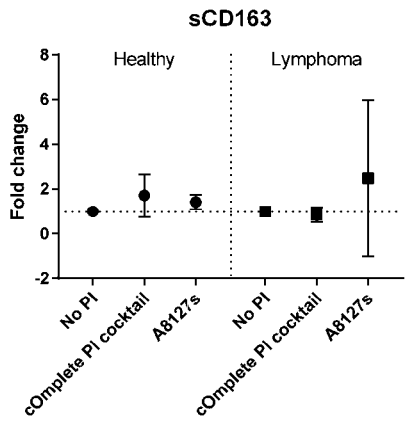
Figure 29Q:
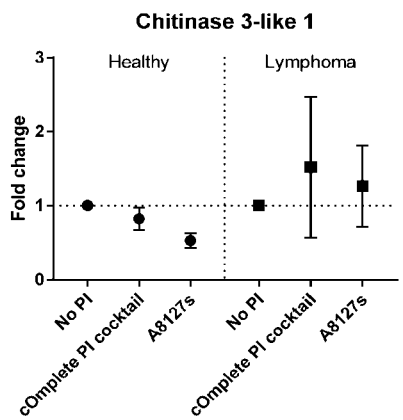
Figure 29R:
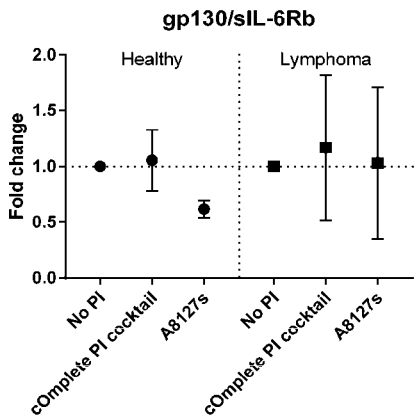
Figure 29S:
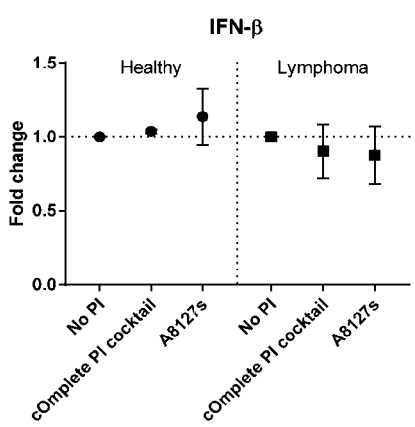
Figure 29T:
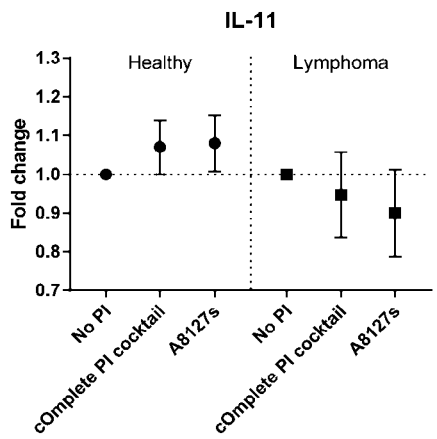
Figure 29U:
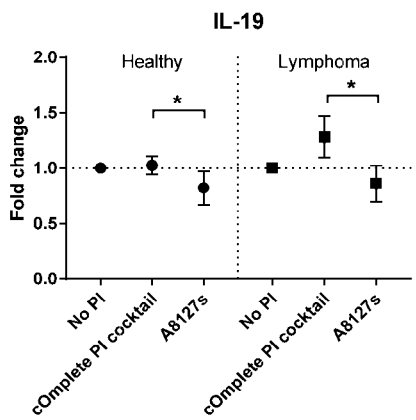
Figure 29V:
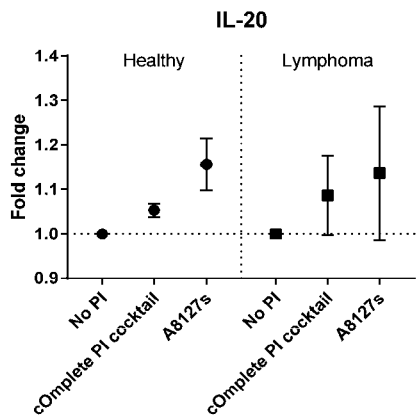
Figure 29W:
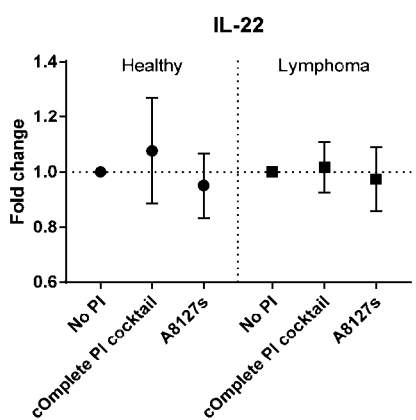
Figure 29X:
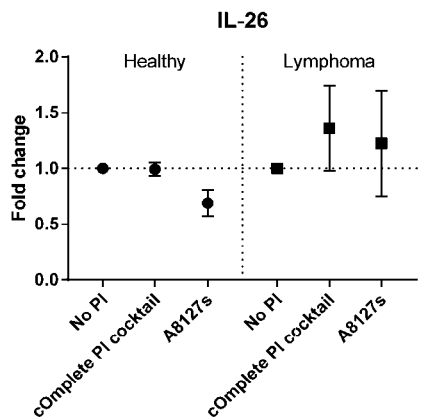
Figure 29Y:
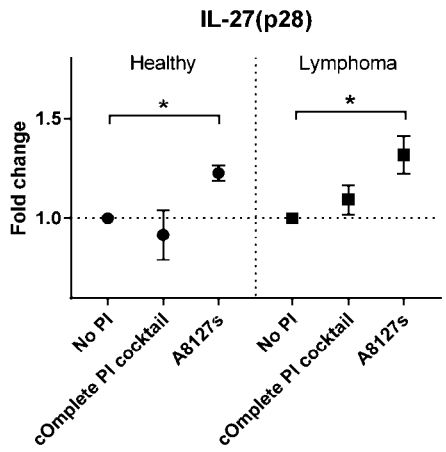
Figure 29Z:
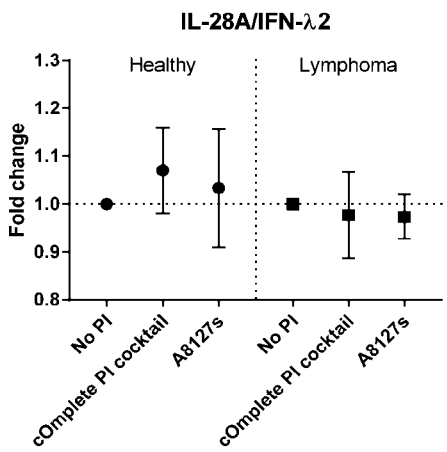
Figure 29A:
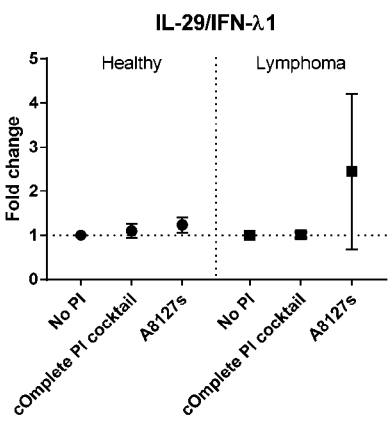
Figure 29B:
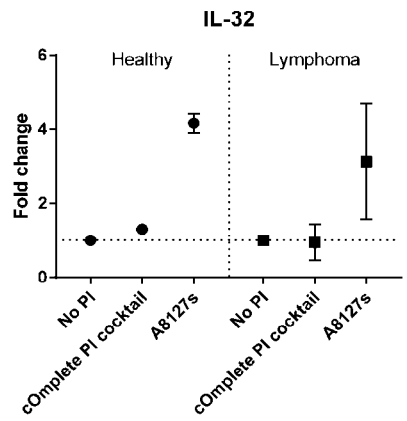
Figure 29C:
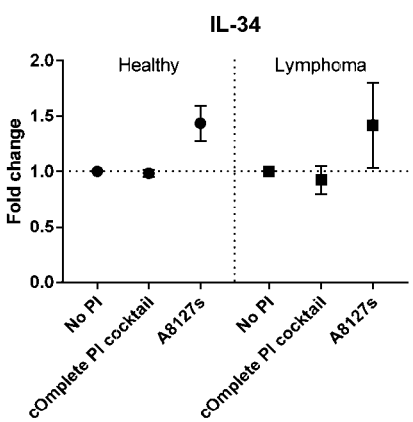
Figure 29D:
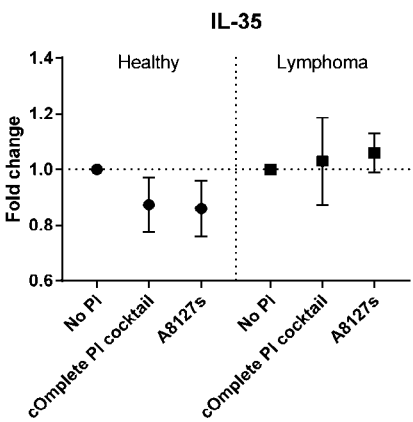
Figure 29E:
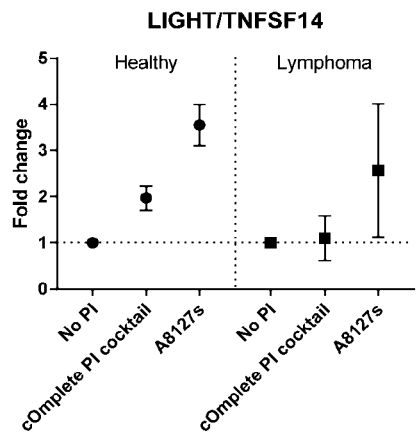
Figure 29F:
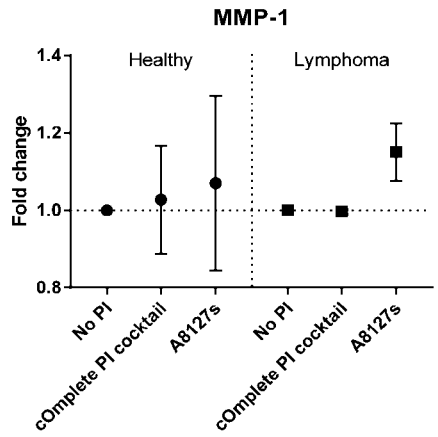
Figure 29G:
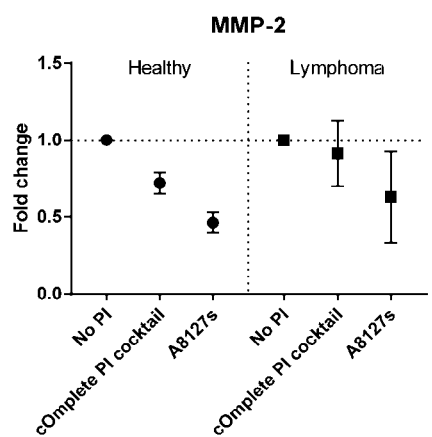
Figure 29H:
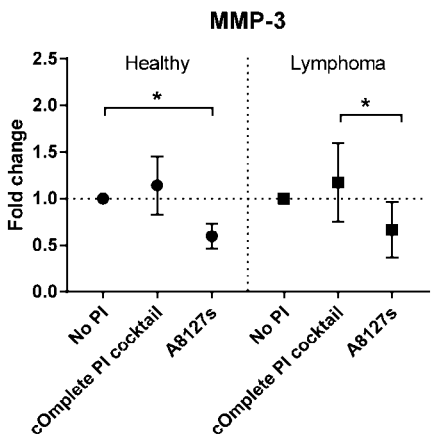
Figure 29I:
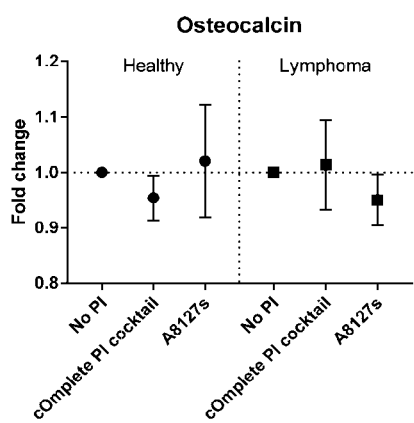
Figure 29J:
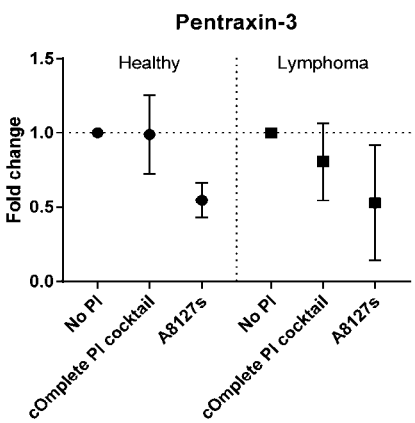
Figure 29K:
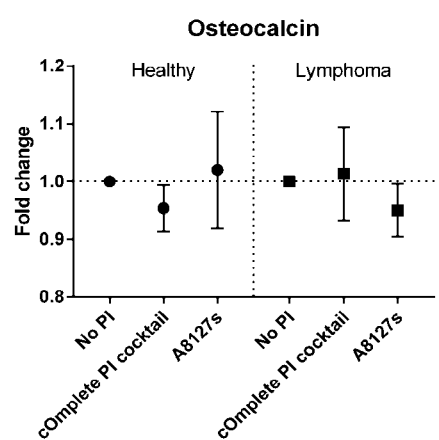
Figure 29L:
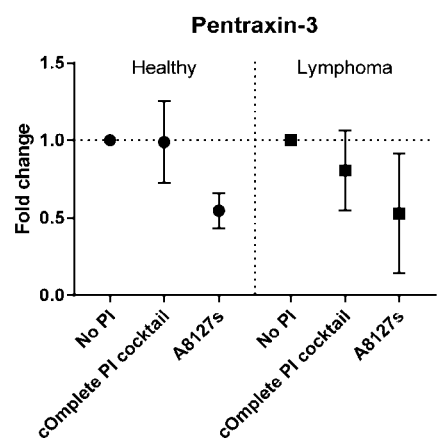

The effect of protease inhibitors on the red blood cell membranes of healthy individuals was compared to that on red blood cell membranes from individuals having osteoarthritis (FIG. 24A-24VV); pre-eclampsia (FIG. 25A-25VV); pre-eclampsia with intrauterine growth restriction (FIG. 26A-26VV); ulcerative colitis (FIG. 27A-27VV); and duodenal ulcer and infection (FIG. 28A-28VV). The fold change of proteins in red blood cell membrane-conditioned PBS (isolated from whole blood lysates) at 1,200 million cells/mL following incubation at 37° C. for 24 hours with protease inhibitors compared to no protease inhibitor of red blood cell membranes from healthy participants or participants with osteoarthritis (OA), pre-eclampsia (PE), pre-eclampsia and intrauterine growth restriction (PE+IUGR), ulcerative colitis (UC), and duodenal ulcer and infection (DU). Values were significantly different (*) if p<0.05. Data are the mean±standard deviation.

The data demonstrated that incubation of red blood cell membranes with protease inhibitors resulted in notable changes in the cytokine profile of the red blood cell membrane-conditioned PBS from healthy and disease participants. The data also demonstrated that A8127s produced larger changes in cytokine levels compared to the control and the cOmplete protease inhibitor cocktail (FIG. 24A-FIG. 28VV).

Samples isolated from the healthy and diseased groups differed in how they responded to protease inhibitor incubation. FIG. 24A-FIG. 28VV identify examples of a number of cytokines that show distinct differences in how A8127s affected cytokine concentration in disease samples compared to healthy samples. For example, IFN-a2 concentration was reduced in red blood cell membranes from the healthy group treated with protease inhibitors, but was substantially increased in the osteoarthritis groups. Likewise, IP-10 increased in the red blood cell membranes from the healthy pregnant cohort with protease inhibitor incubation, but decreased in the pre-eclamptic cohort. Each of the diseases investigated showed a number of cytokines that exhibited a differential response between red blood cell membranes from the healthy and disease cohorts following protease inhibitor incubation. Table 9 summarizes the total number of cytokines for each disease state that showed a significant differential effect.

TABLE 9

Total number of cytokines for each disease state showing a differential concentration change related to protease inhibitor incubation between healthy and disease participant groups

| Disease state | Number of cytokines with differential response to A8127s between healthy and disease |
|---|---|
| Osteoarthritis (OA) | 16 |
| Pre-eclampsia (PE) | 7 |
| Pre-eclampsia (PE + IUGR) | 6 |
| Ulcerative colitis (UC) | 16 |
| Duodenal ulcer and infection (DU) | 5 |

Red blood cell membranes from individuals with various diseases that were incubated with protease inhibitors were assayed for additional proteins involved in disease states. Red blood cell membranes were obtained from healthy individuals, and those having lymphoma, osteoarthritis, and ulcerative colitis. Two multiplex assays were utilised. The first was the 16-plex human cancer biomarker panel 1 that assays for sEGFR, FGF-basic, G-CSF, HGF, sHER-2/neu, sIL-6Ra, Leptin, Osteopontin, PECAM-1, PDGF-AB/BB, Prolactin, SCF, sTIE-2, sVEGFR-1, and sVEGFR-2, and the second was the 37-plex human inflammation cytokine panel that assays for APRIL/TNFSF13, BAFF/TNFSF13B, sCD30/TNFRF8, sCD163, Chitinase-3-like 1, gp130/sIL-6Rβ, IFN-α2, IFN-γ, IL-2, sIL-6Rα, IL-8, IL-10, IL-11, IL-12(p40), IL-12(p70), IL-19, IL-20, IL-22, IL-26, IL-27 (p28), IL-28A/IFN-λ2, IL-29/IFN-λ1, IL-32, IL-34, IL-35, LIGHT/TNFSF14, MMP-1, MMP-2, MMP-3, Osteocalcin, Osteopontin, Pentraxin-3, sTNF-R1, sTNF-R2, TSLP, and TWEAK/TNFSF12 (Bio-Plex cancer biomarker 16-plex panel and inflammation 37-plex panel, Bio-Rad). The assays were performed according to manufacturer's instructions using an automated magnetic wash station (BioPlex Pro II, Bio-Rad) for the washing steps. The assays were run on the Luminex® 200™ system (Bio-Rad) and fluorescent values were collected. The calibration curve for each cytokine was analysed with 5 parametric logistic curve regression using BioPlex manager software (ver. 5.0, Bio-Rad, USA). The fold change of proteins in red blood cell membrane-conditioned PBS (isolated from whole blood lysates) at 1,200 million cells/mL following incubation at 37° C. for 24 hours with protease inhibitors compared to no protease inhibitors from healthy participants or participants with lymphoma, osteoarthritis (OA), and ulcerative colitis (UC). Values were significantly different (*) if p<0.05. Data are the mean±standard deviation.

Figure 30A:
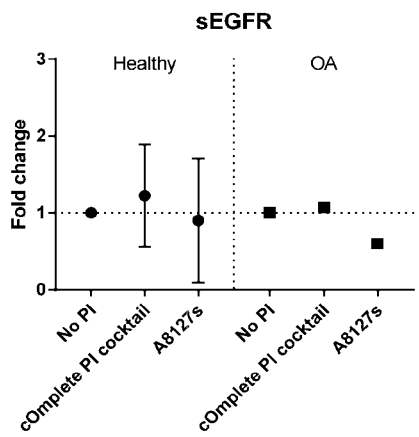
FIG. 30A-30NN is a series of graphs showing the effect of protease inhibitor cocktails on other proteins released from red blood cells from healthy individuals compared to individuals having osteoarthritis.
Figure 30B:
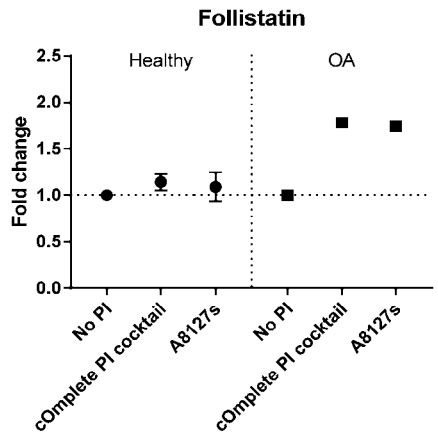
Figure 30C:
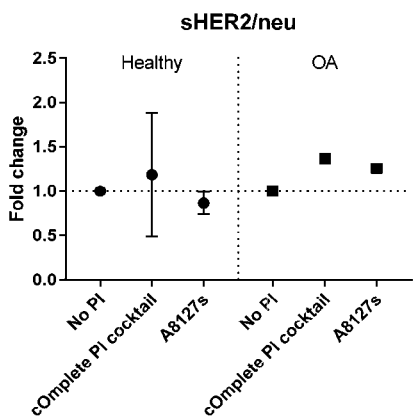
Figure 30D:
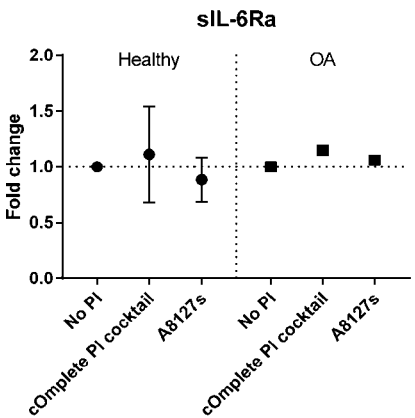
Figure 30E:
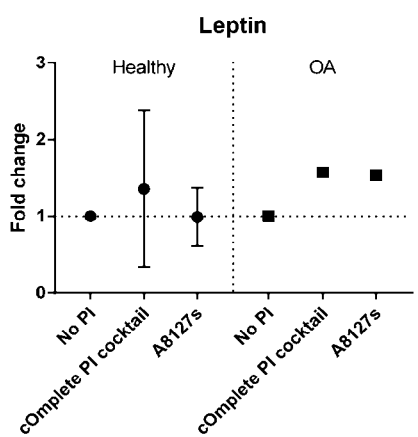
Figure 30F:
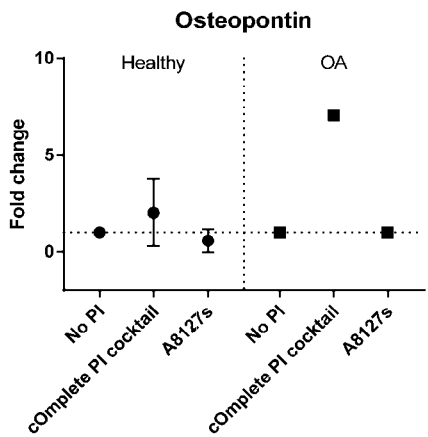
Figure 30G:
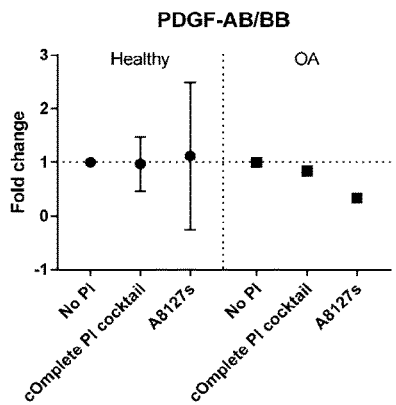
Figure 30H:
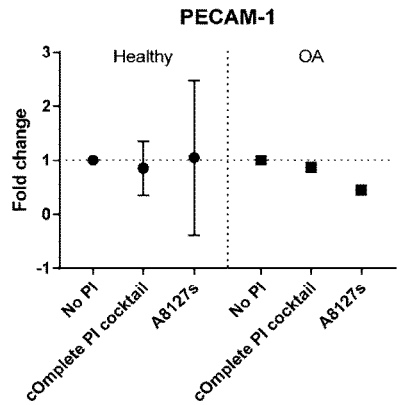
Figure 30I:
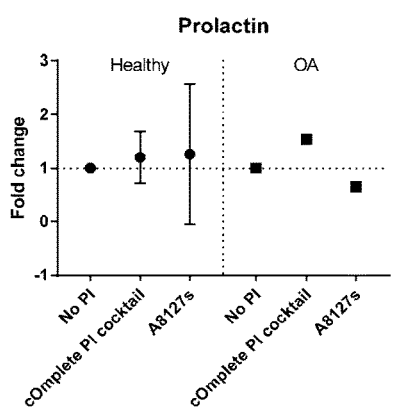
Figure 30J:
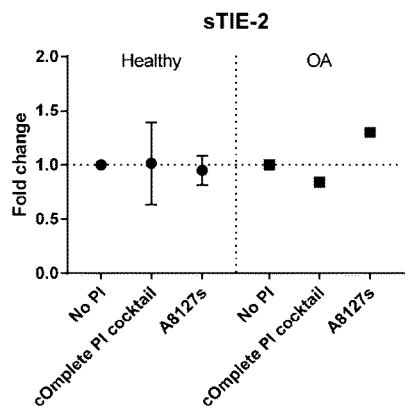
Figure 30K:
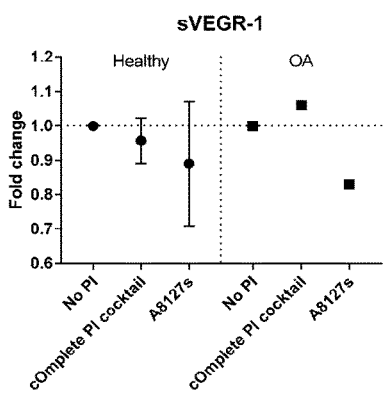
Figure 30L:
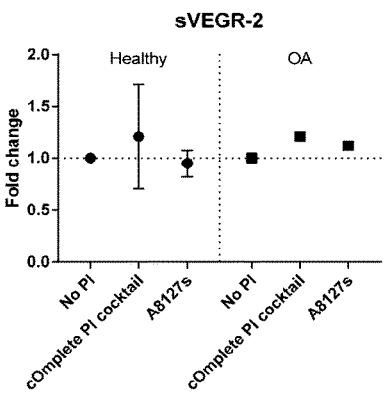
Figure 30M:
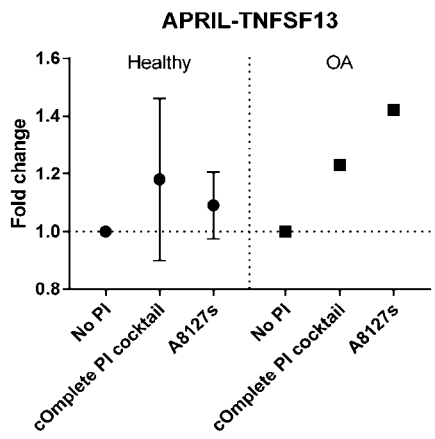
Figure 30N:
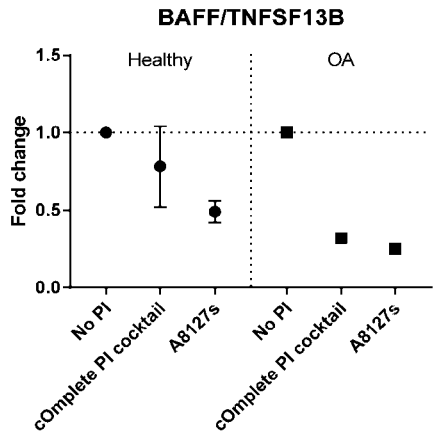
Figure 30O:
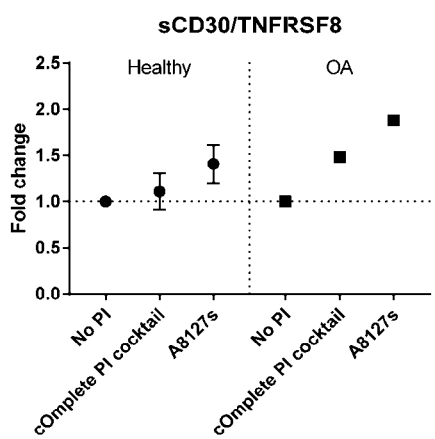
Figure 30P:
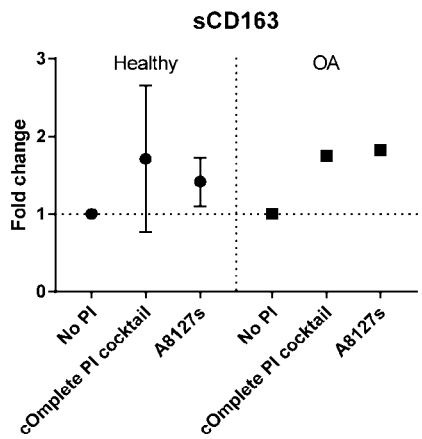
Figure 30Q:
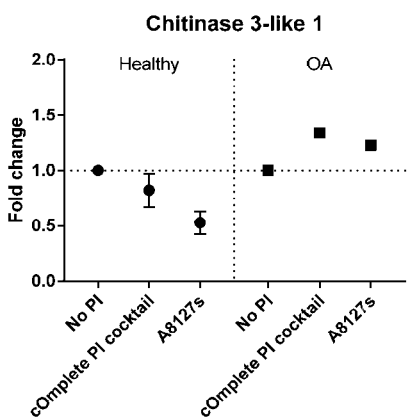
Figure 30R:
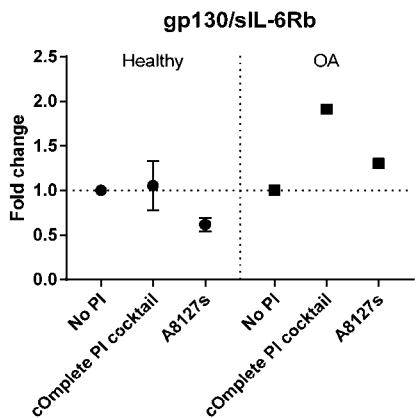
Figure 30S:
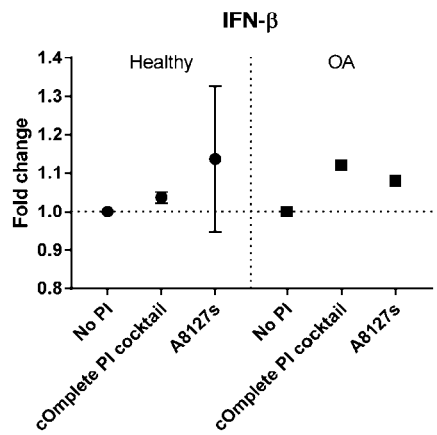
Figure 30T:
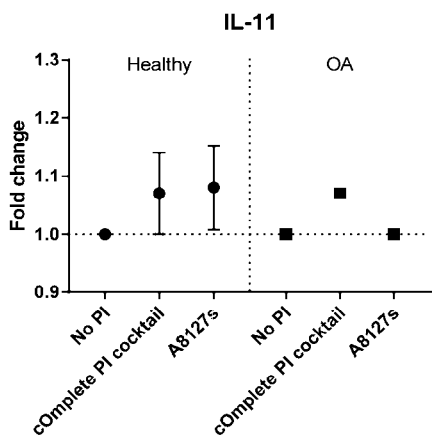
Figure 30U:
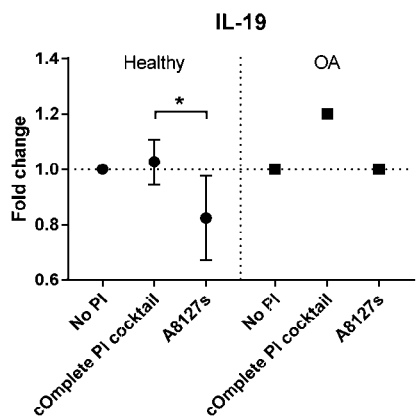
Figure 30V:
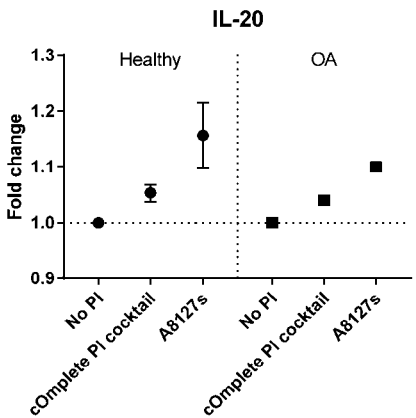
Figure 30W:
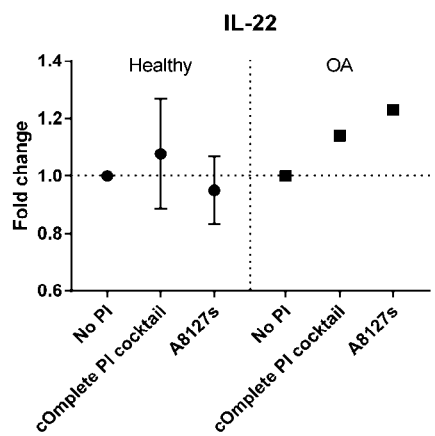
Figure 30X:
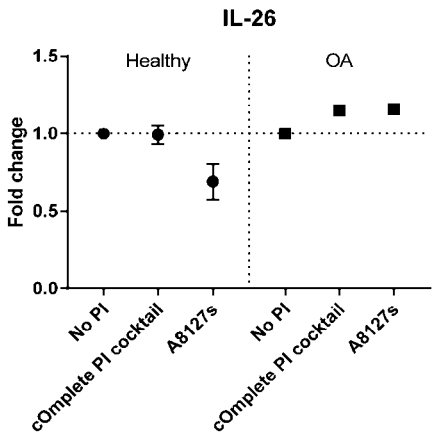
Figure 30Y:
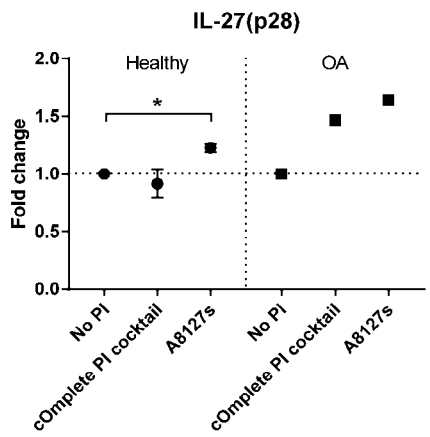
Figure 30Z:
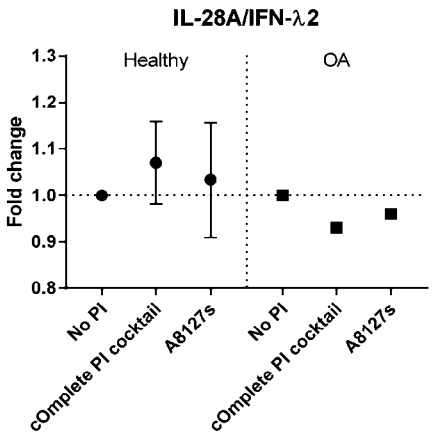
Figure 30A:
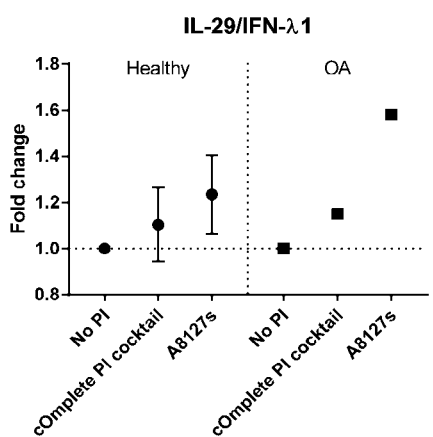
Figure 30B:
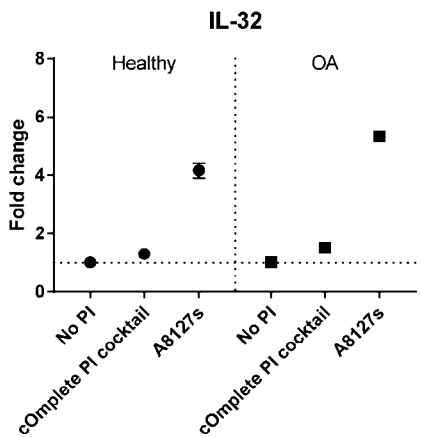
Figure 30C:
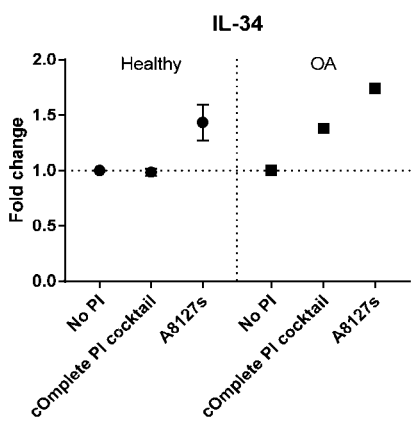
Figure 30D:
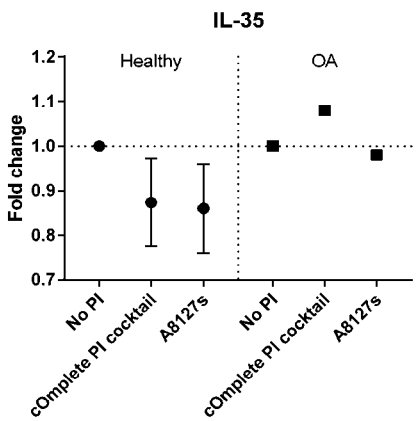
Figure 30E:
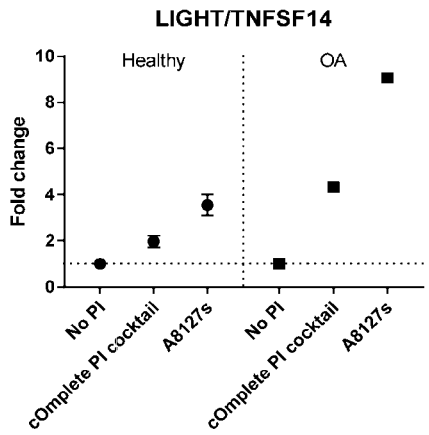
Figure 30F:
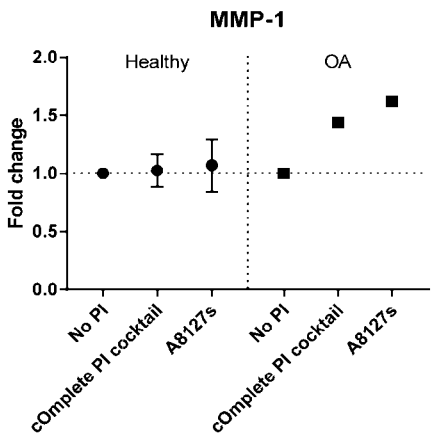
Figure 30G:
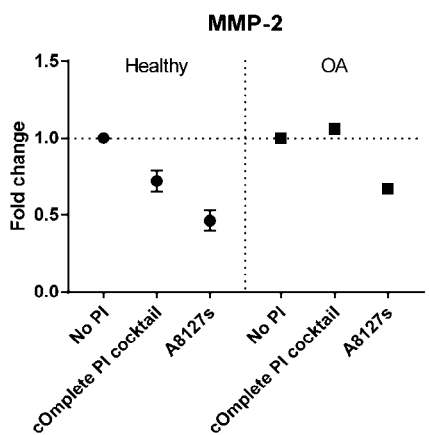
Figure 30H:
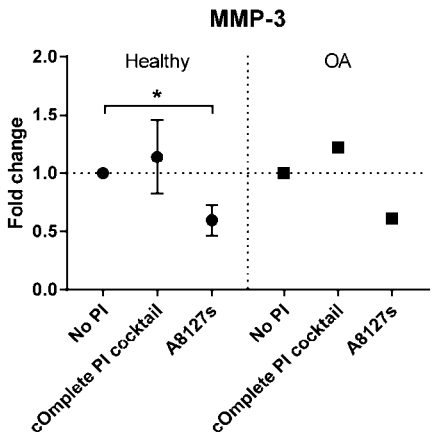
Figure 30I:
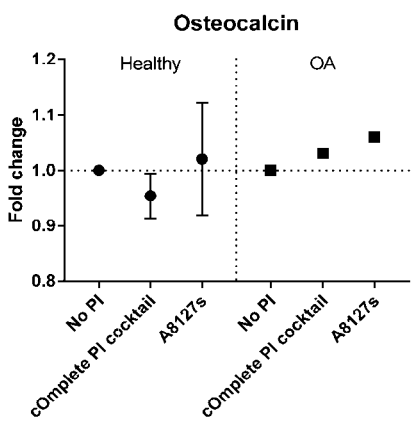
Figure 30J:
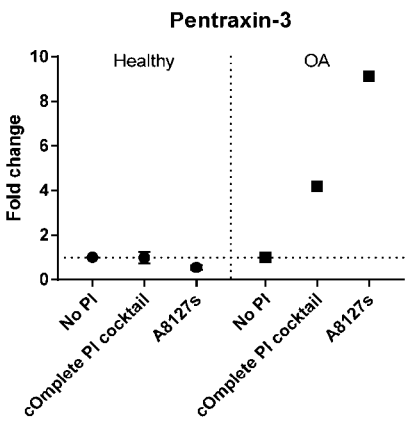
Figure 30K:
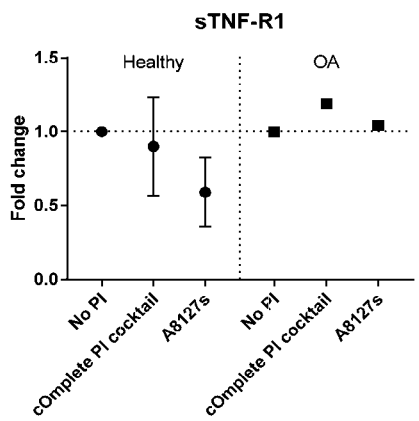
Figure 30L:
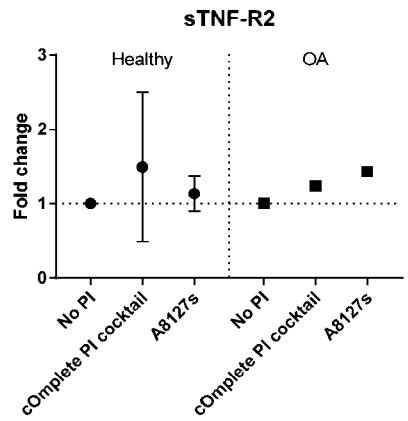
Figure 30M:
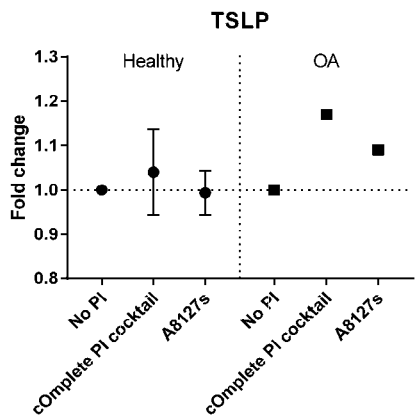
Figure 30N:
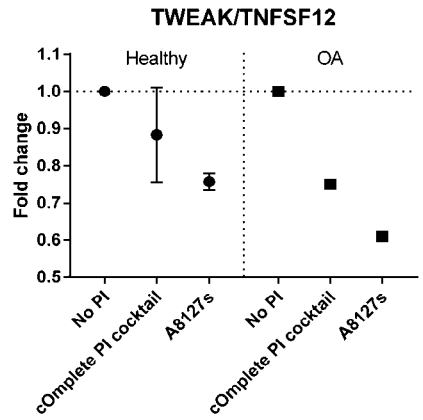
Figure 31A:
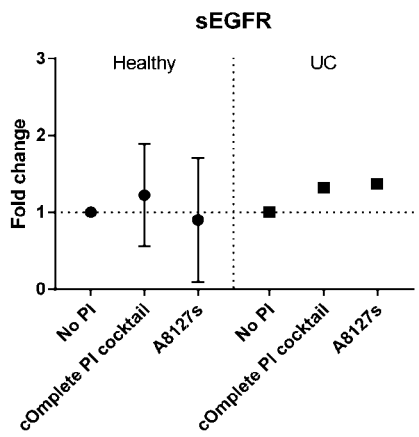
FIG. 31A-31NN is a series of graphs showing the effect of protease inhibitor cocktails on other proteins released from red blood cells from healthy individuals compared to individuals having ulcerative colitis.
Figure 31B:
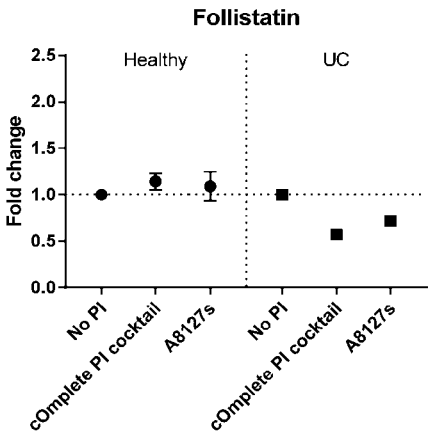
Figure 31C:
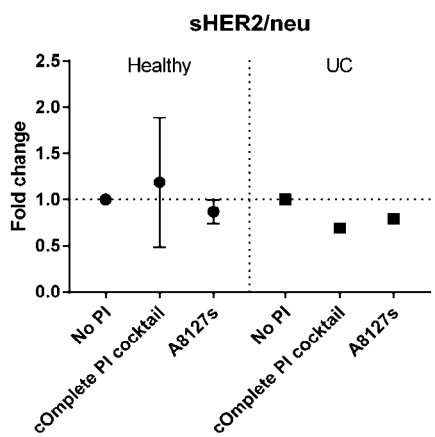
Figure 31D:
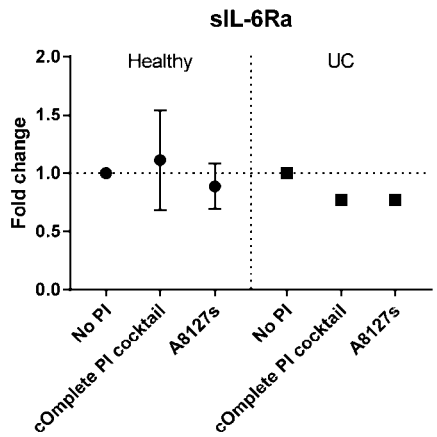
Figure 31E:
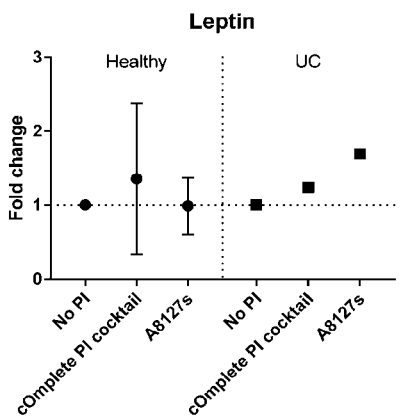
Figure 31F:
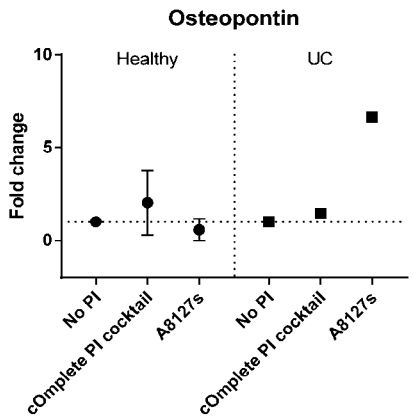
Figure 31G:
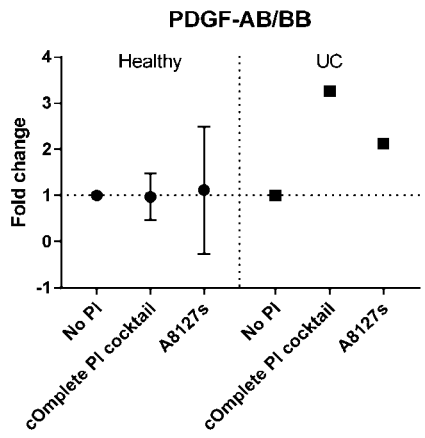
Figure 31H:
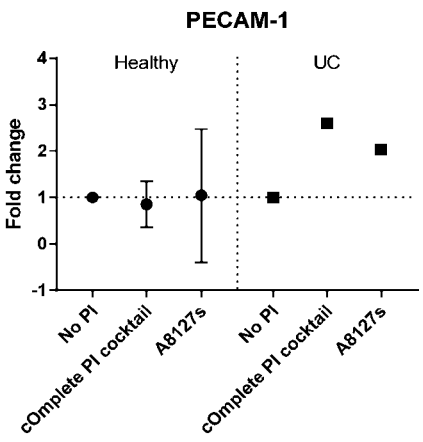
Figure 31I:
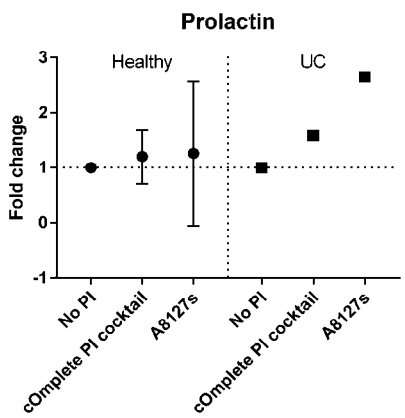
Figure 31J:
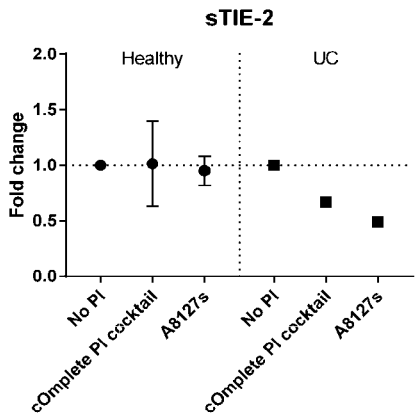
Figure 31K:
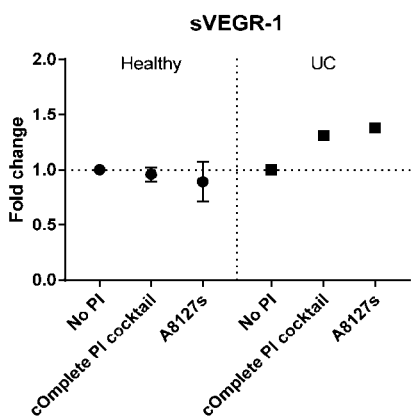
Figure 31L:
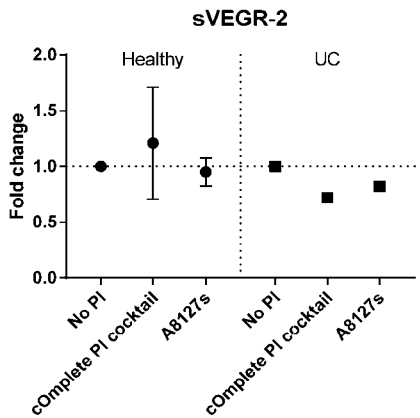
Figure 31M:
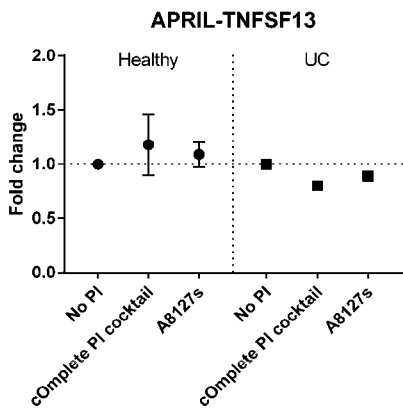
Figure 31N:
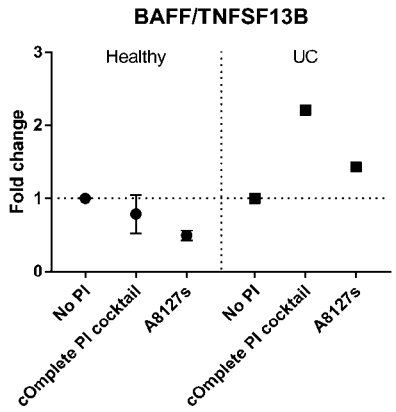
Figure 31O:
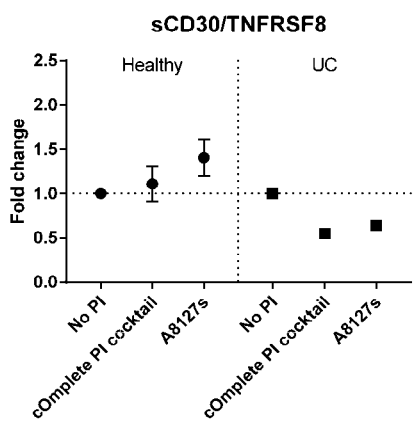
Figure 31P:
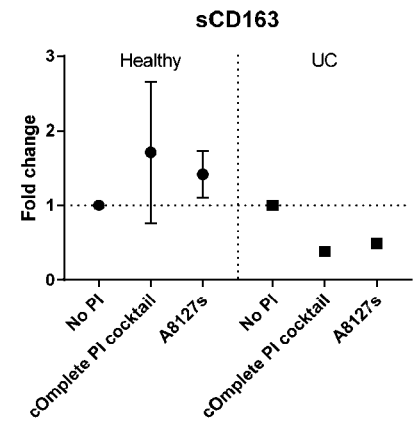
Figure 31Q:
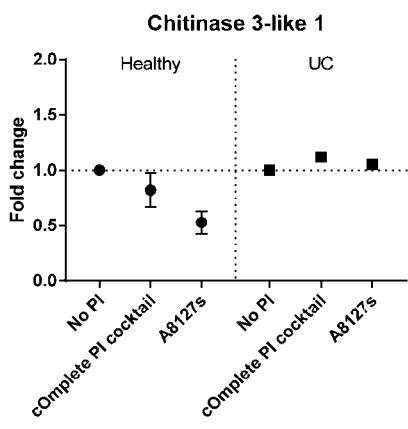
Figure 31R:
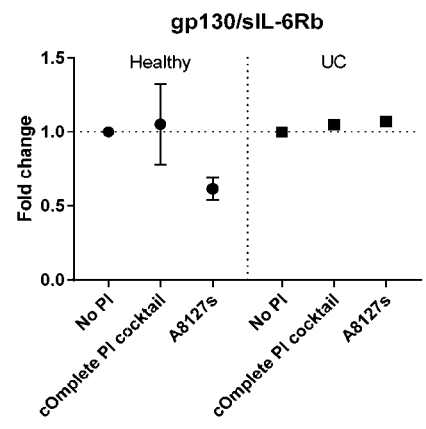
Figure 31S:
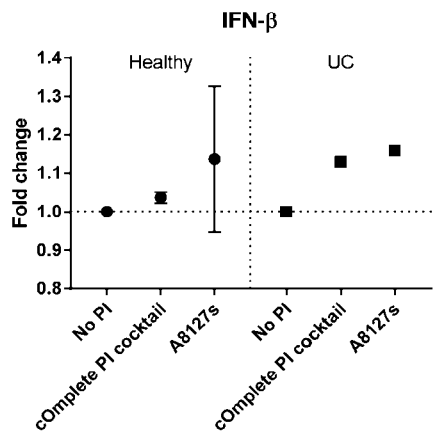
Figure 31T:
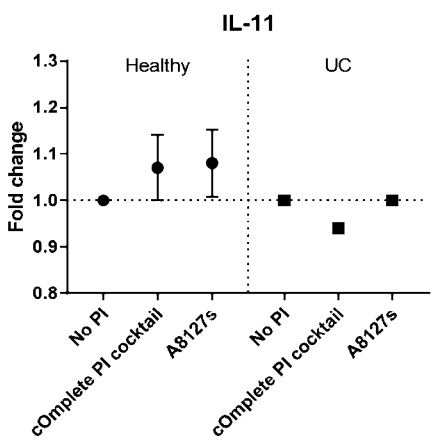
Figure 31U:
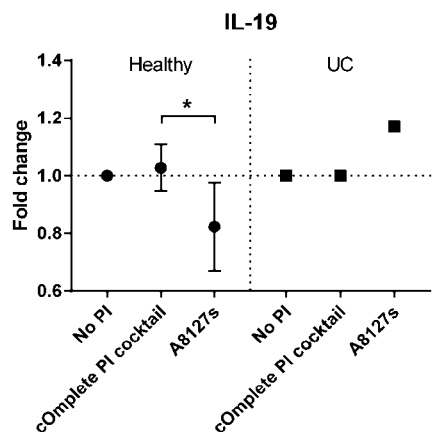
Figure 31V:
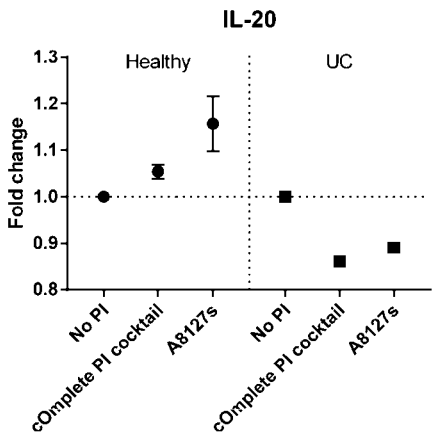
Figure 31W:
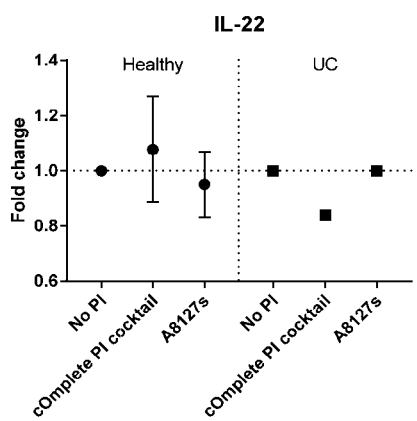
Figure 31X:
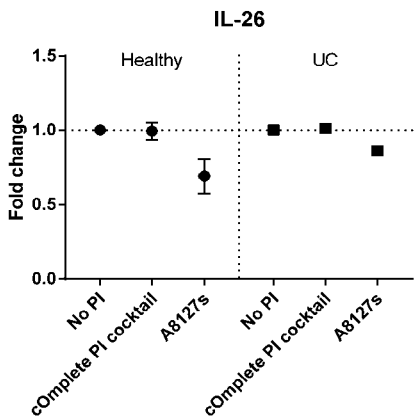
Figure 31Y:
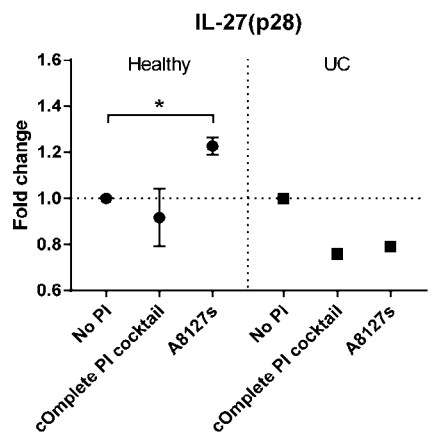
Figure 31Z:
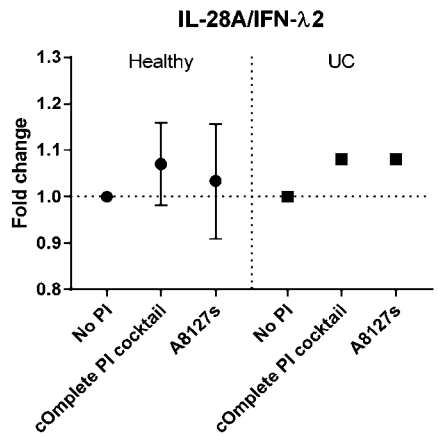
Figure 31A:
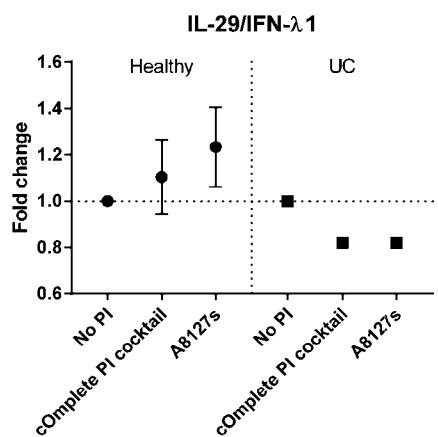
Figure 31B:
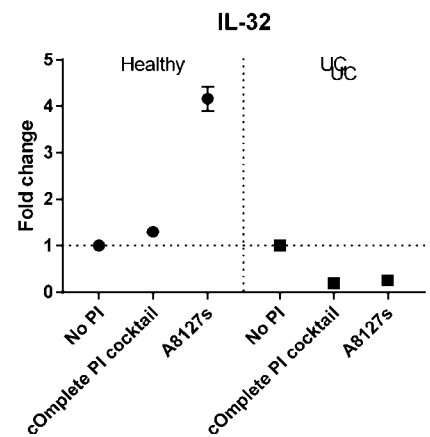
Figure 31C:
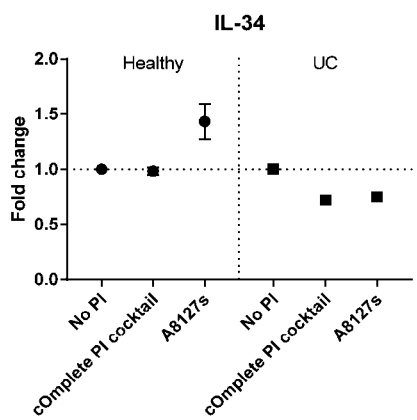
Figure 31D:
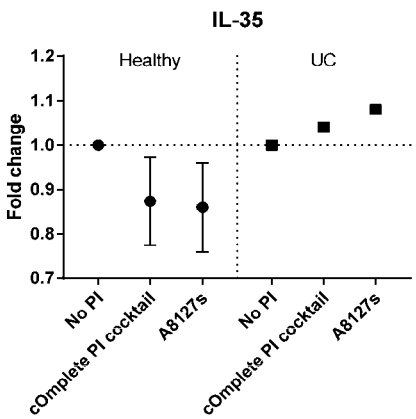
Figure 31E:
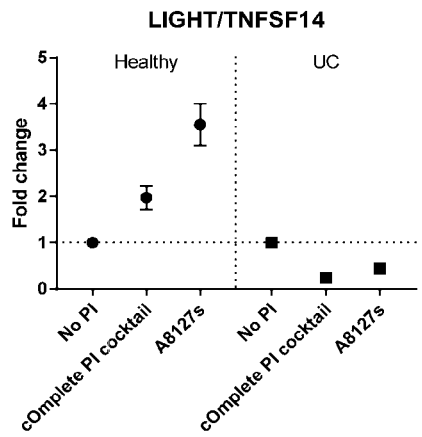
Figure 31F:
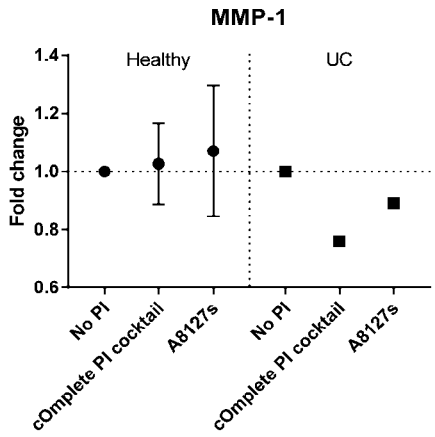
Figure 31G:
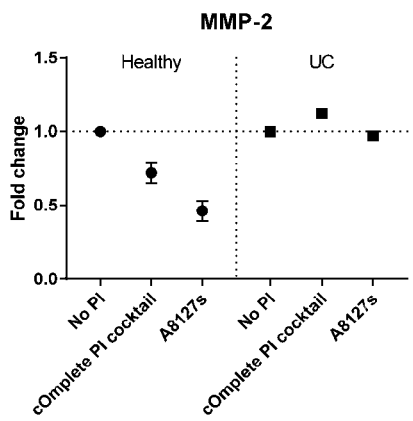
Figure 31H:
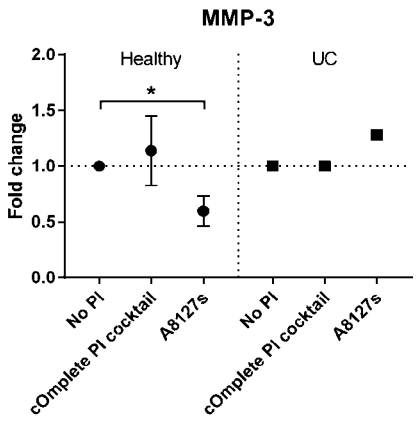
Figure 31I:
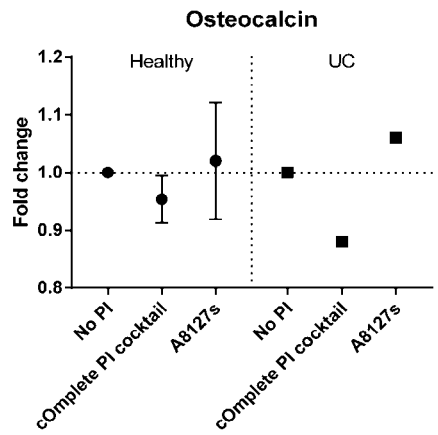
Figure 31J:
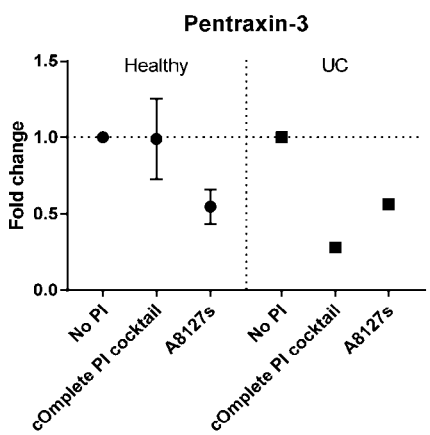
Figure 31K:
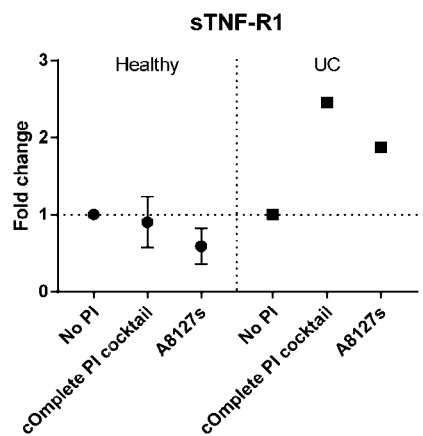
Figure 31L:
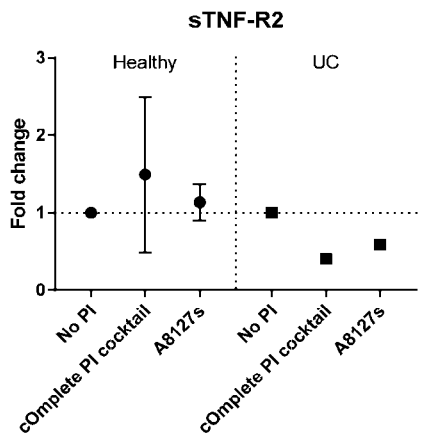
Figure 31M:
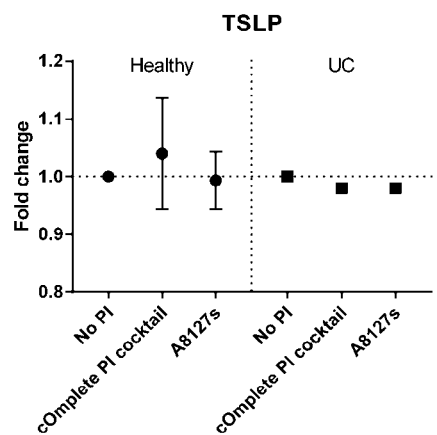
Figure 31N:
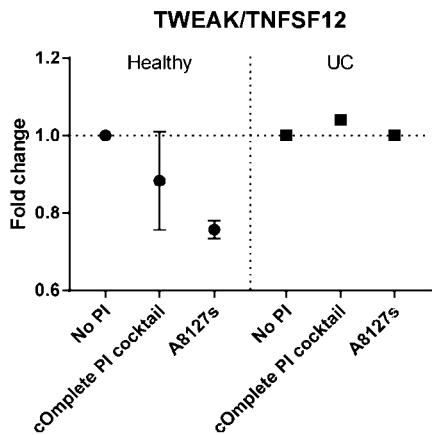
Figure 32:
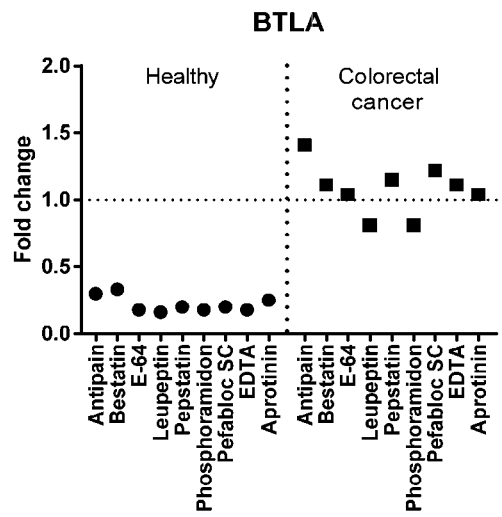
FIG. 32-45 are a series of graphs showing the effect of individual protease inhibitors on proteins released from red blood cells from healthy individuals with colorectal cancer.
Figure 33:
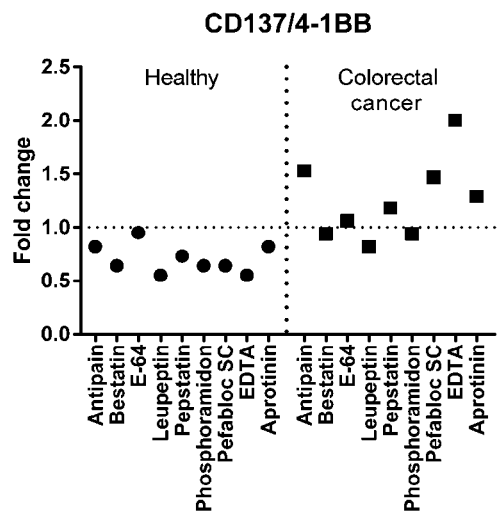
Figure 34:
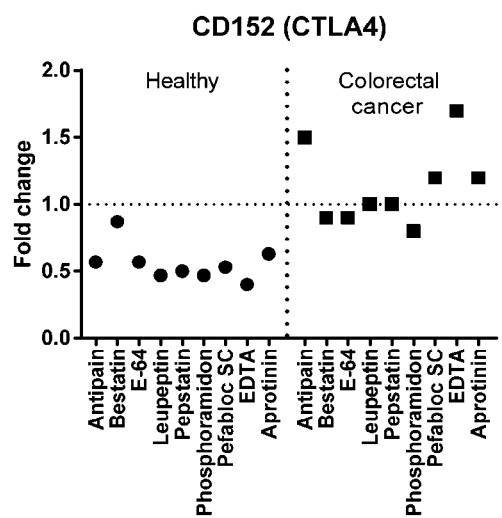
Figure 35:
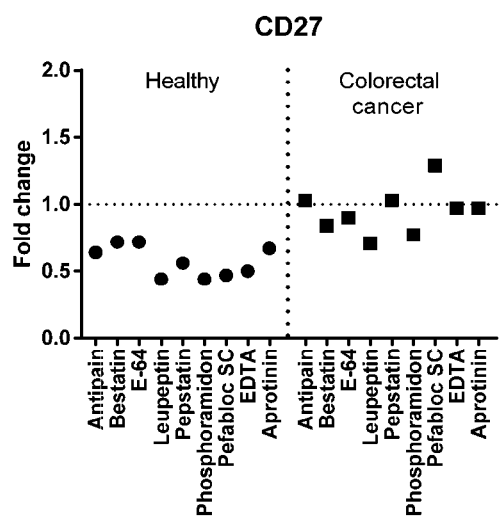
Figure 36:
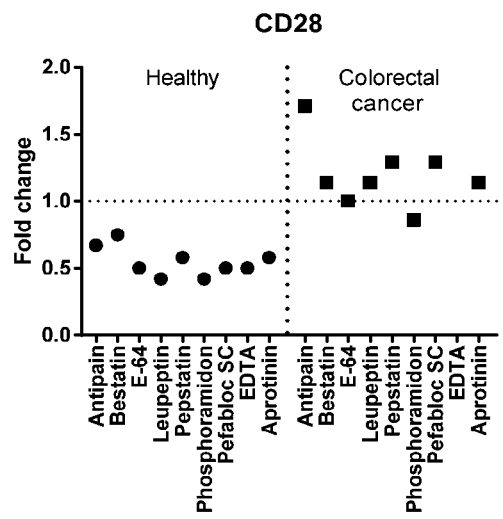
Figure 37:
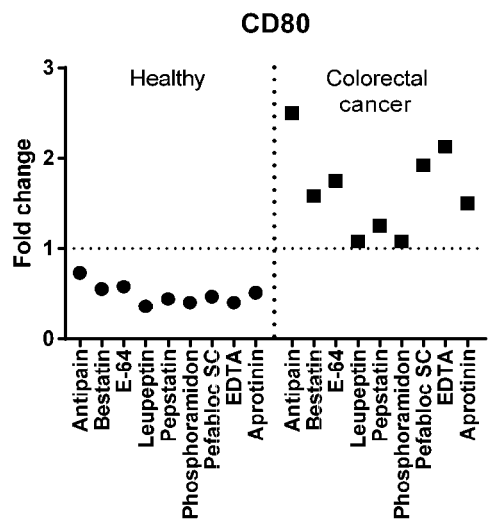
Figure 38:
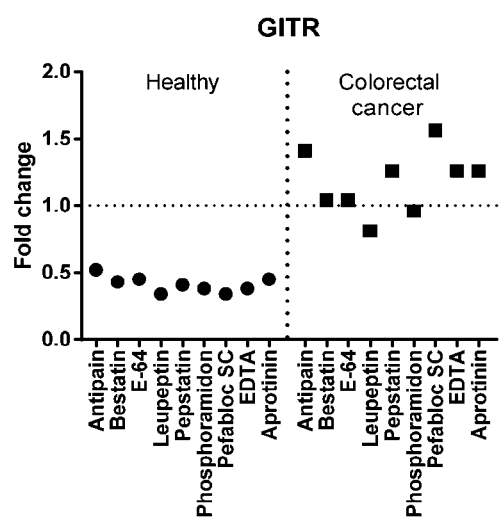
Figure 39:
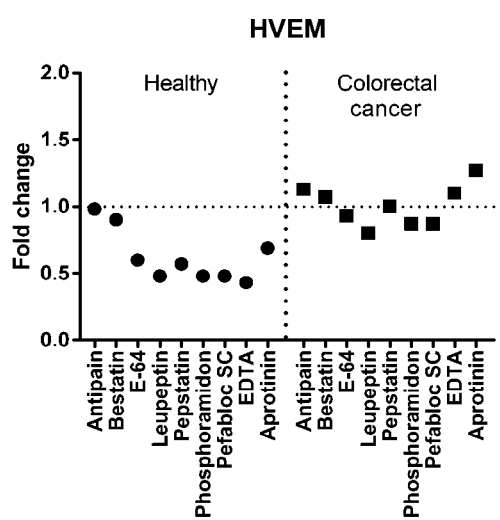
Figure 40:
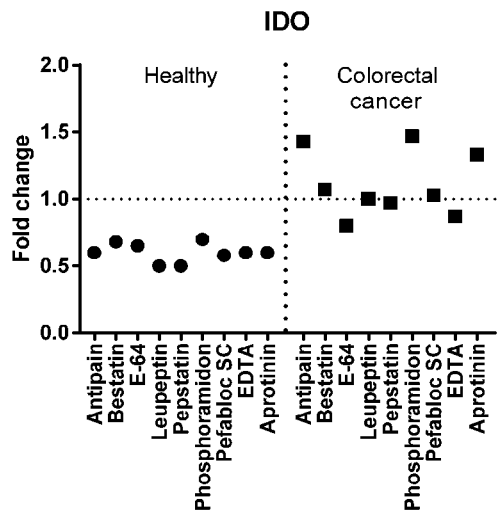
Figure 41:
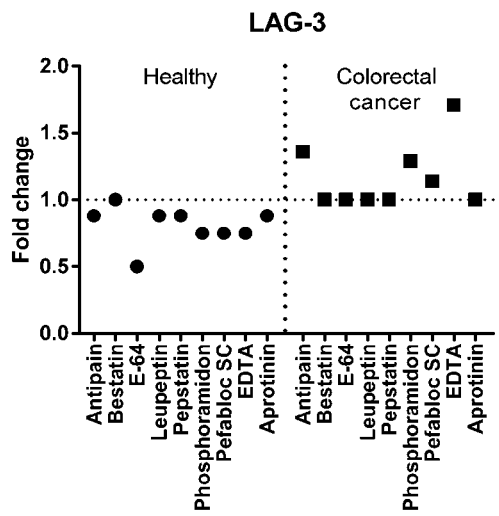
Figure 42:
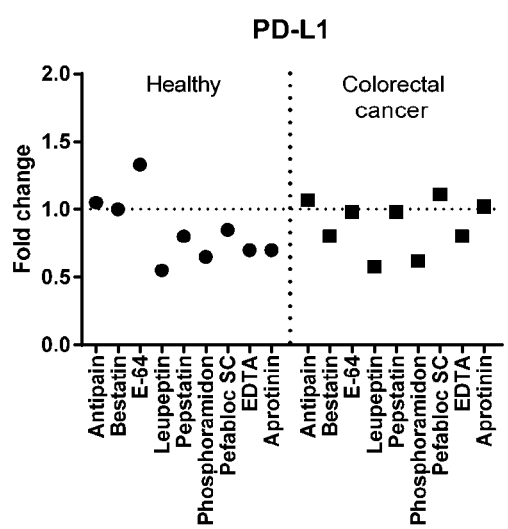
Figure 43:
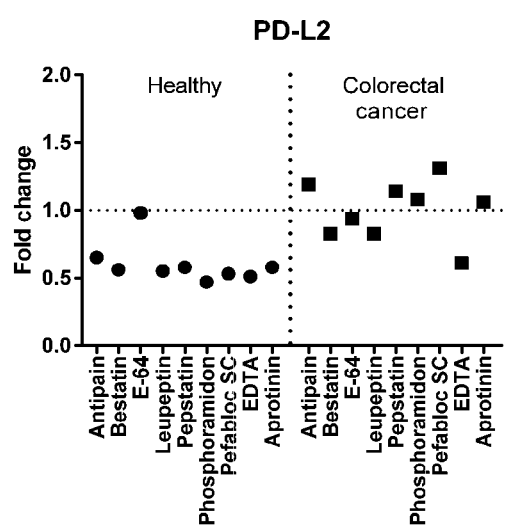
Figure 44:
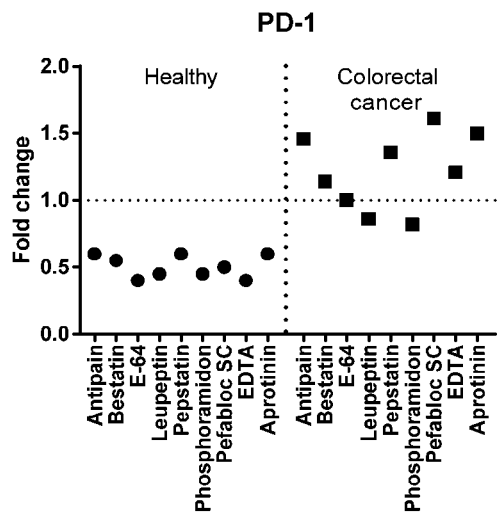
Figure 45:
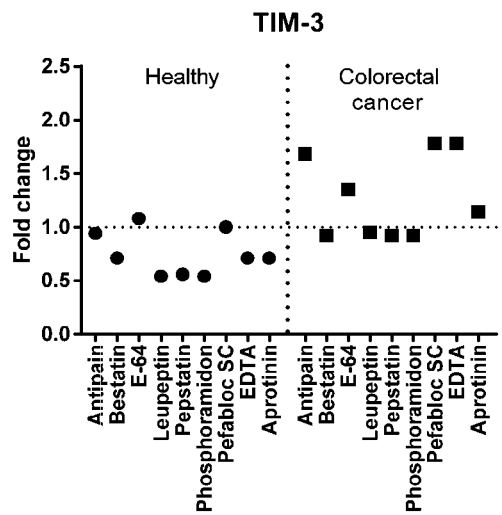
Figure 46:
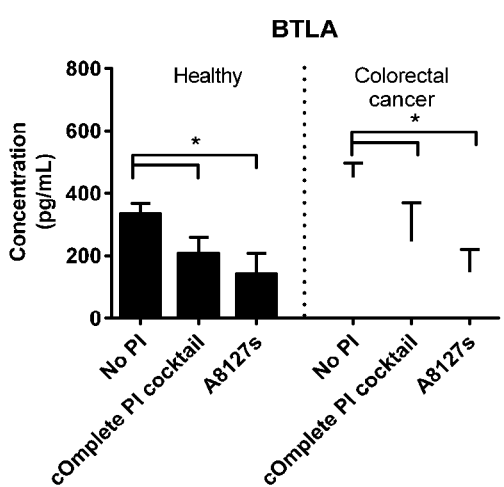
FIG. 46-59 are a series of graphs showing the effect of protease inhibitor cocktails on the concentration of proteins released from red blood cell membranes from healthy individuals compared to proteins released from red blood cell membranes from individuals with colorectal cancer.
Figure 47:
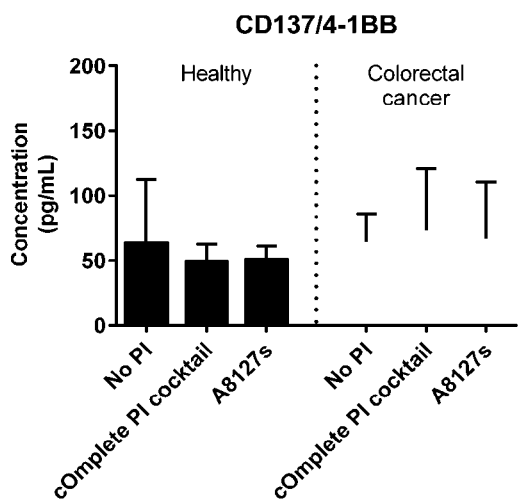
Figure 48:
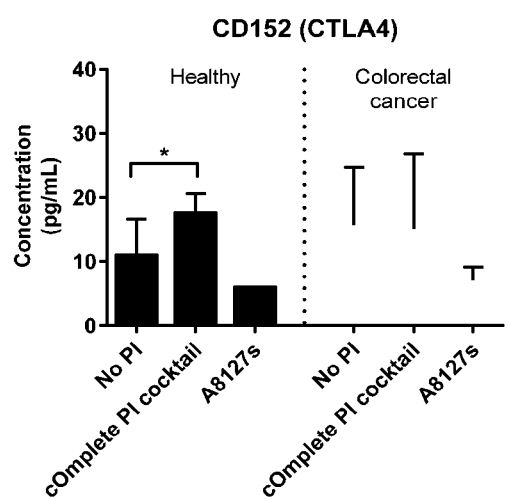
Figure 49:
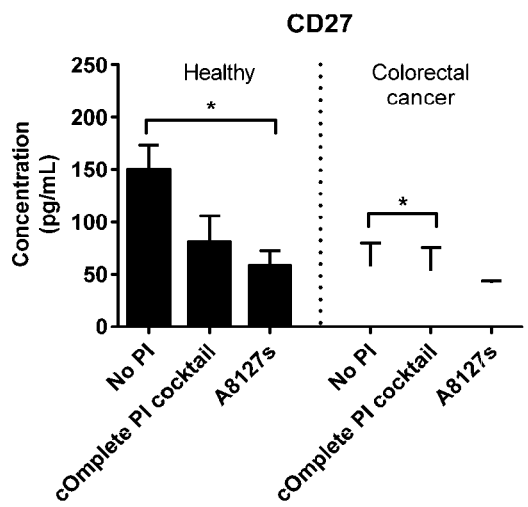
Figure 50:
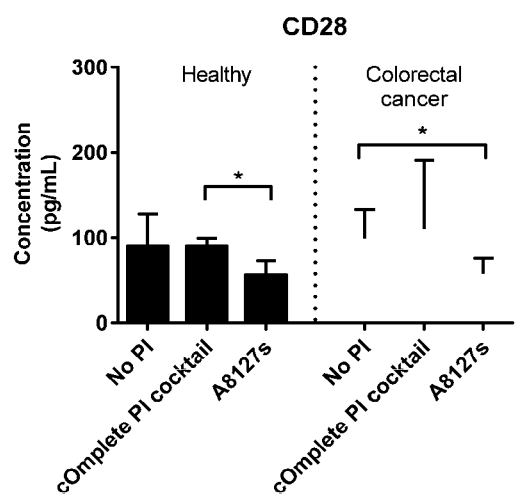
Figure 51:
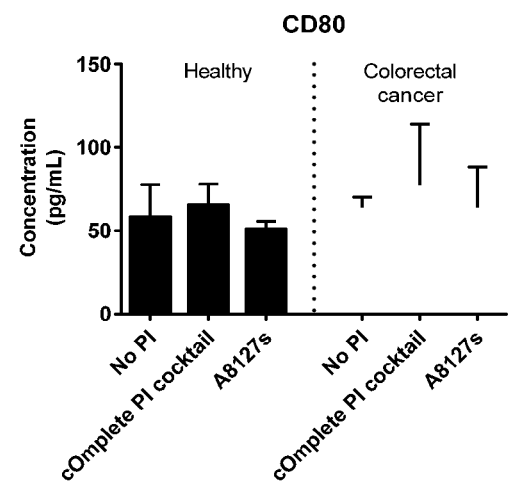
Figure 52:
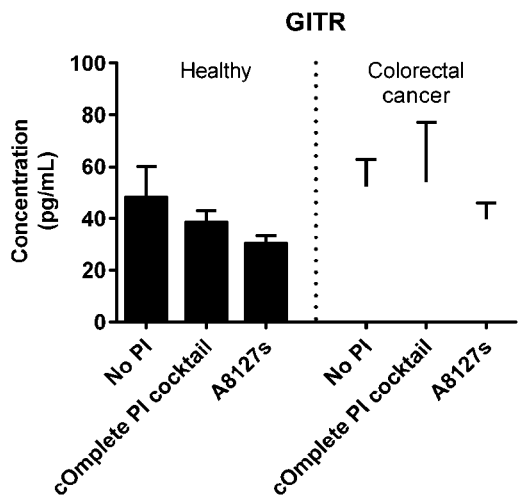
Figure 53:
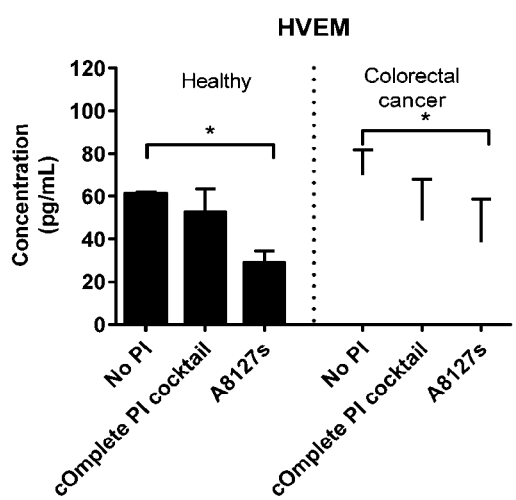
Figure 54:
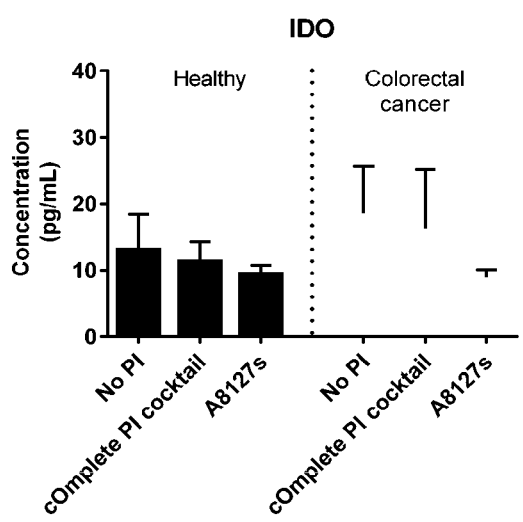
Figure 55:
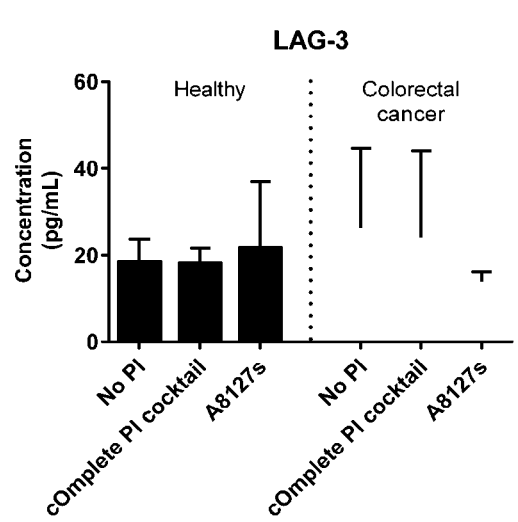
Figure 56:
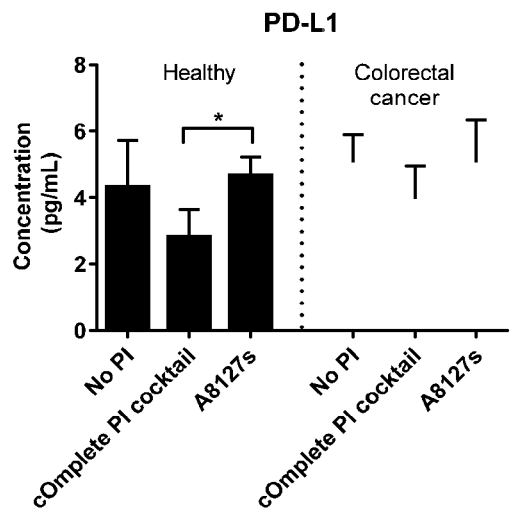
Figure 57:
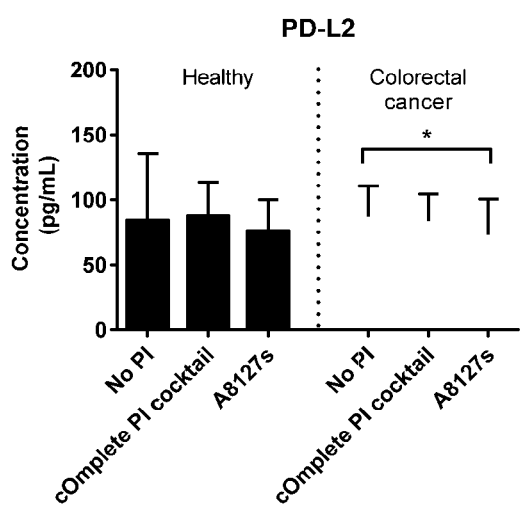
Figure 58:
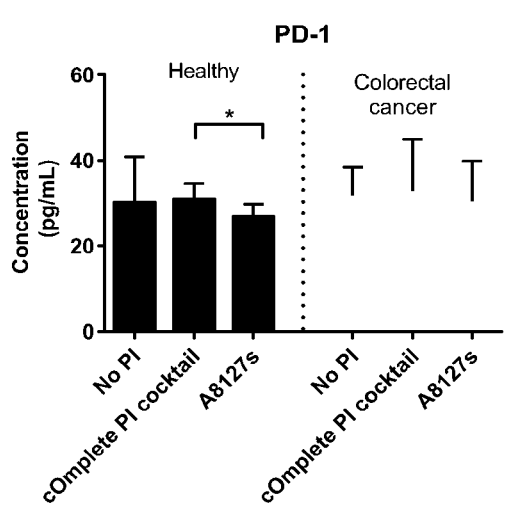
Figure 59:
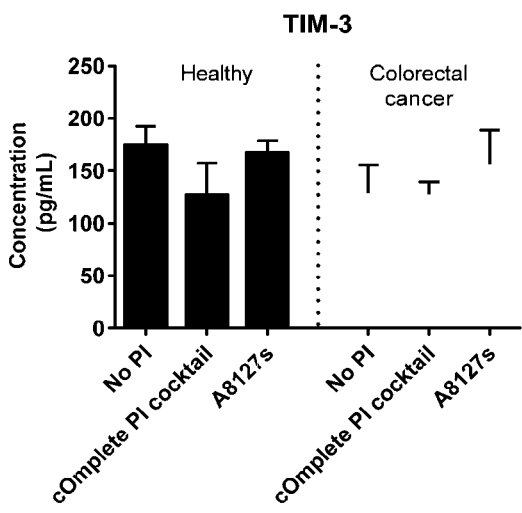
Figure 60:
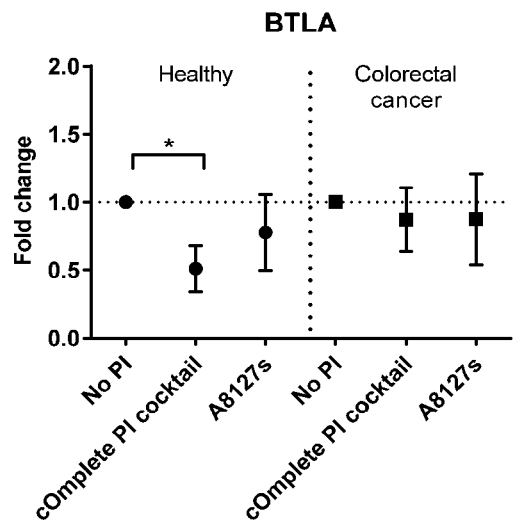
FIG. 60-73 are a series of graphs showing the effect of protease inhibitor cocktails on the fold change of proteins released from red blood cells from healthy individuals compared to proteins released from red blood cells from individuals with colorectal cancer.
Figure 61:
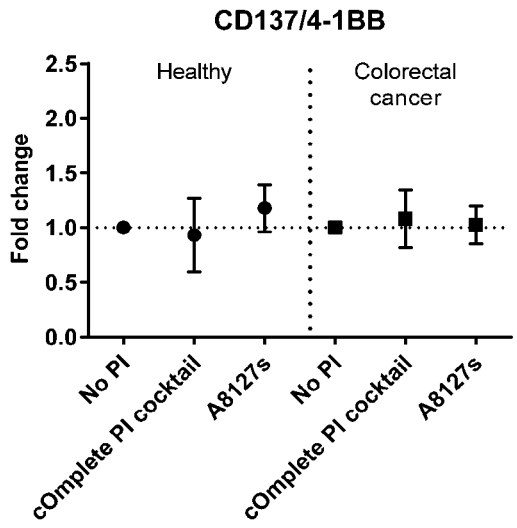
Figure 62:
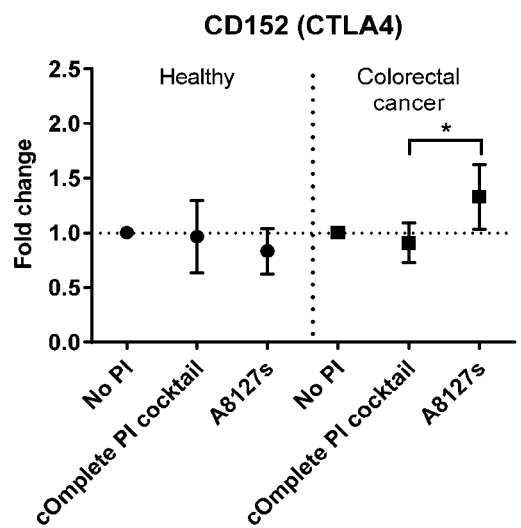
Figure 63:
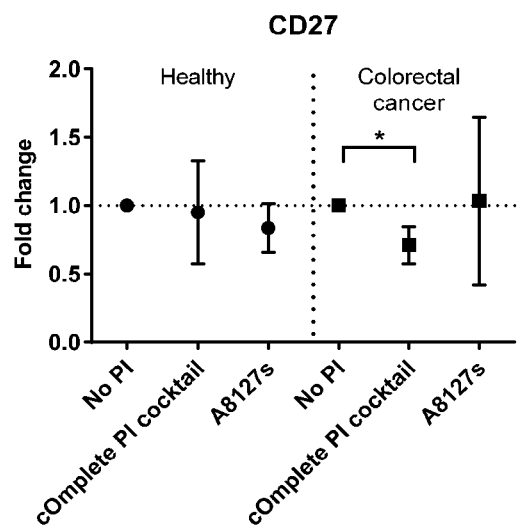
Figure 64:
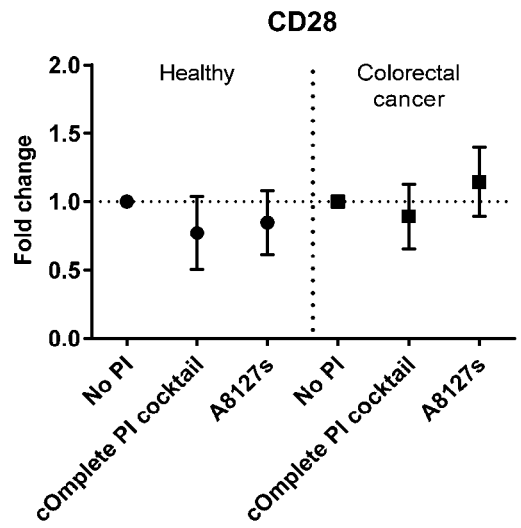
Figure 65:
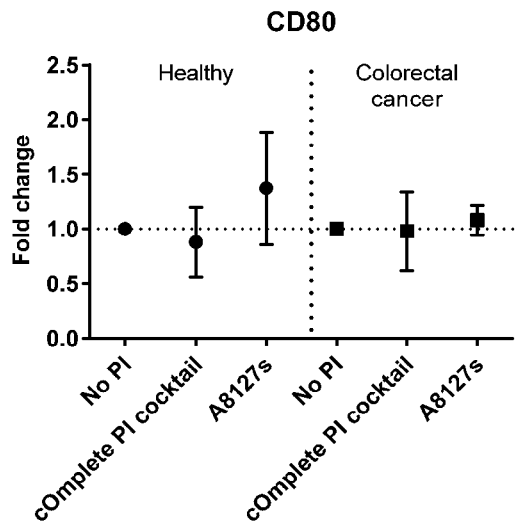
Figure 66:
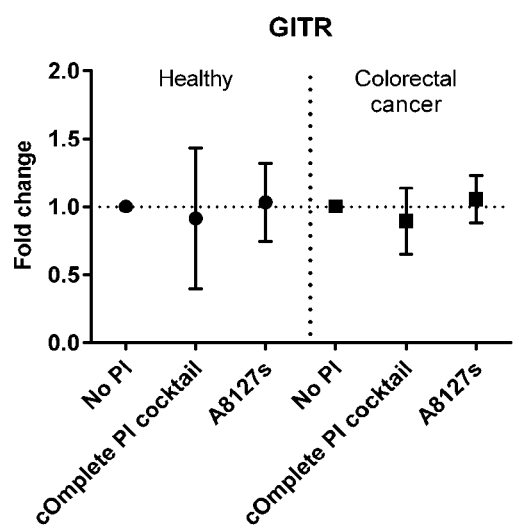
Figure 67:
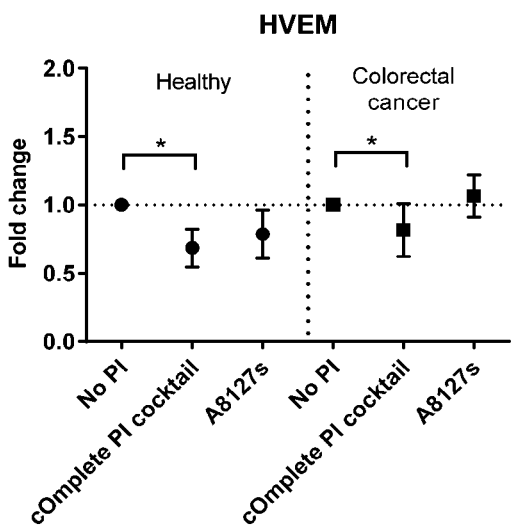
Figure 68:
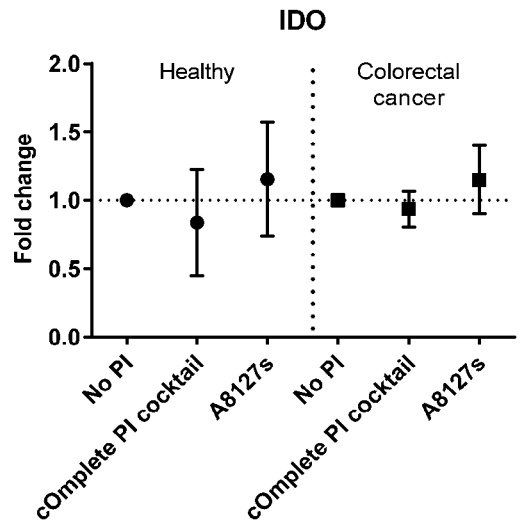
Figure 69:
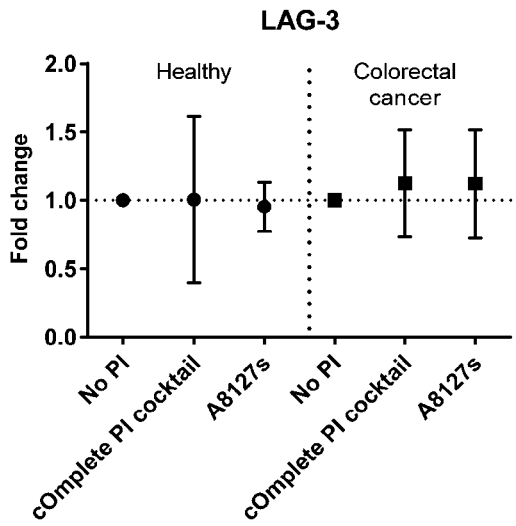
Figure 70:
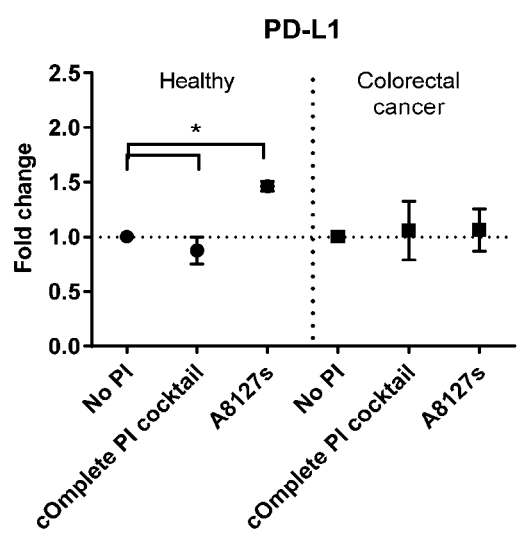
Figure 71:
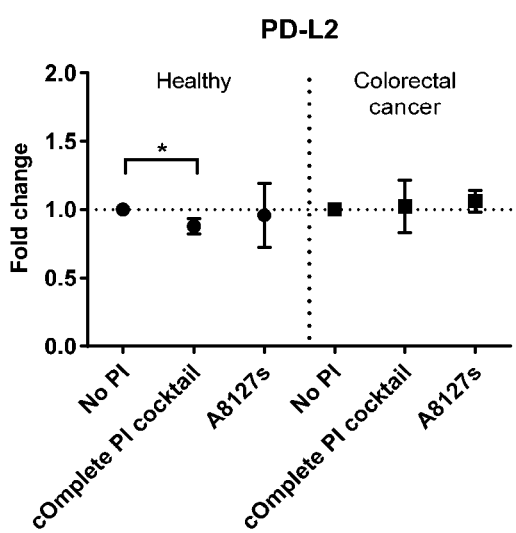
Figure 72:
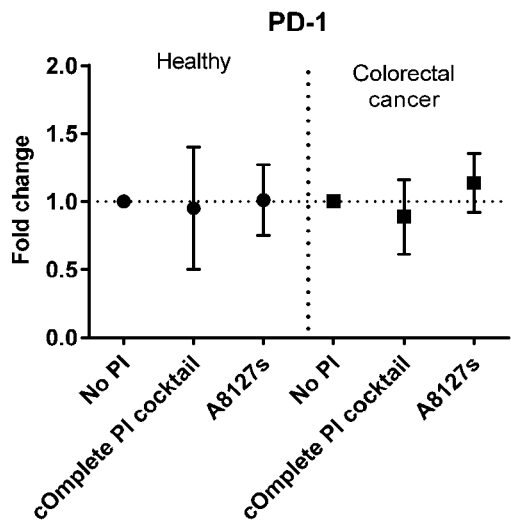
Figure 73:
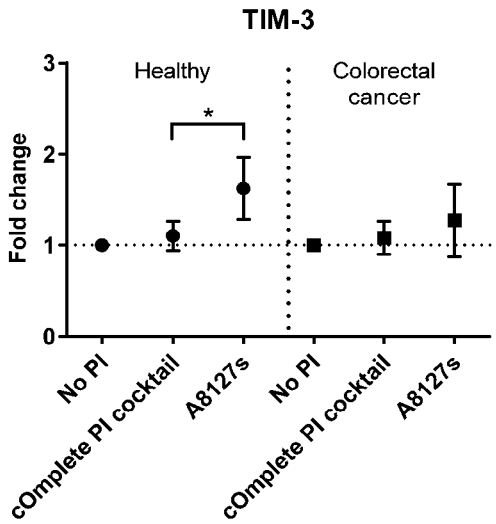
Figure 74:
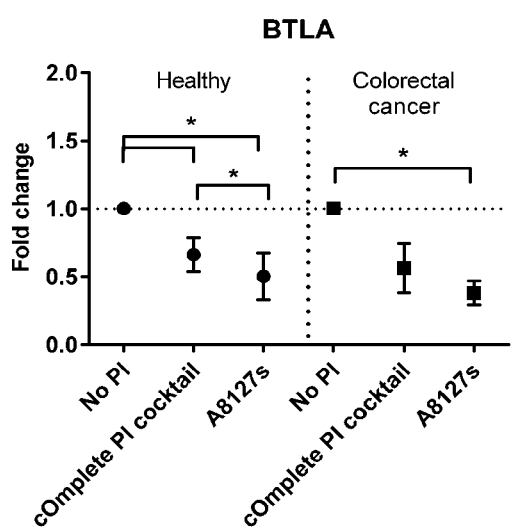
FIG. 74-87 are a series of graphs showing the effect of protease inhibitor cocktails on the fold change of proteins released from red blood cell membranes from healthy individuals compared to proteins released from red blood cell membranes from healthy individuals with colorectal cancer.
Figure 75:
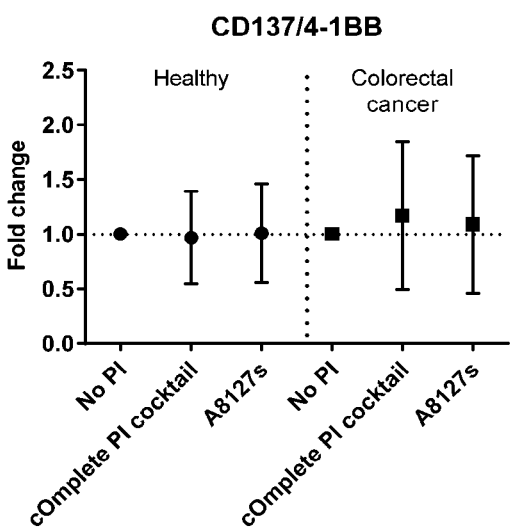
Figure 76:
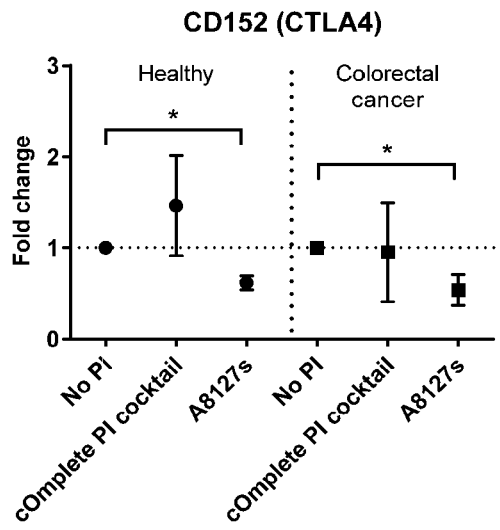
Figure 77:
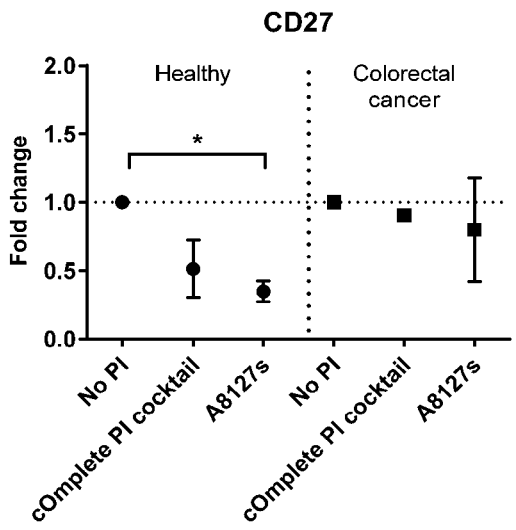
Figure 78:
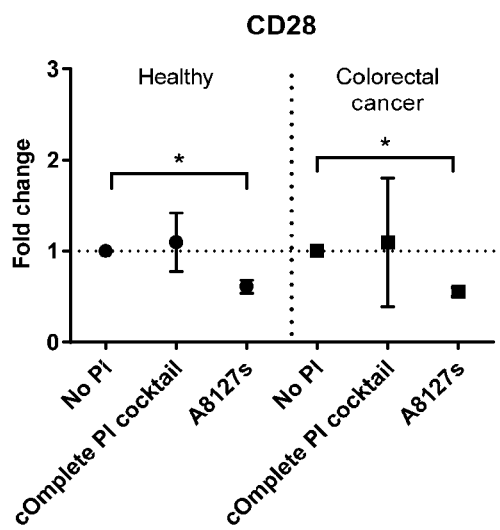
Figure 79:
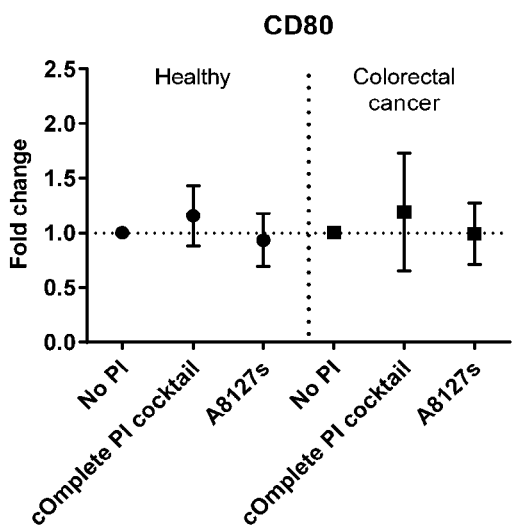
Figure 80:
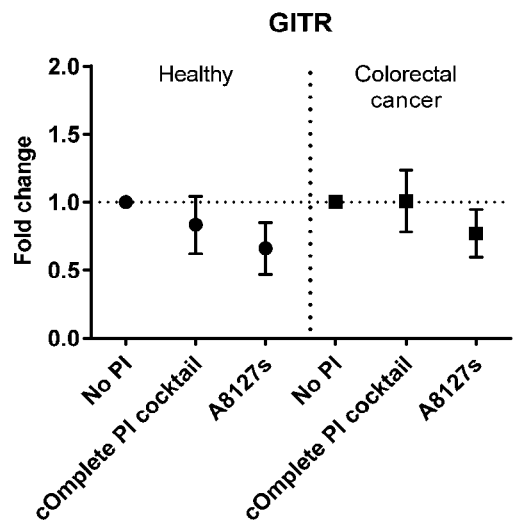
Figure 81:
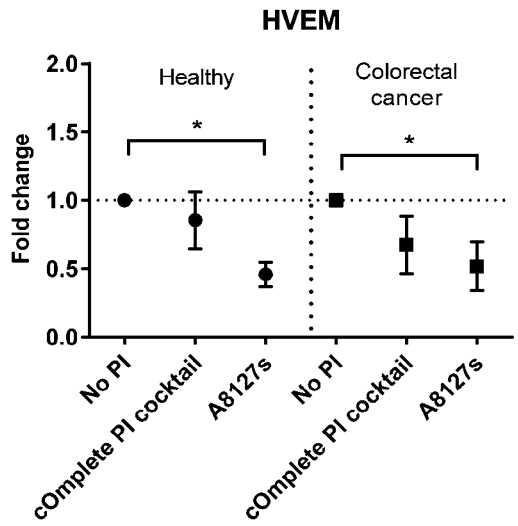
Figure 82:
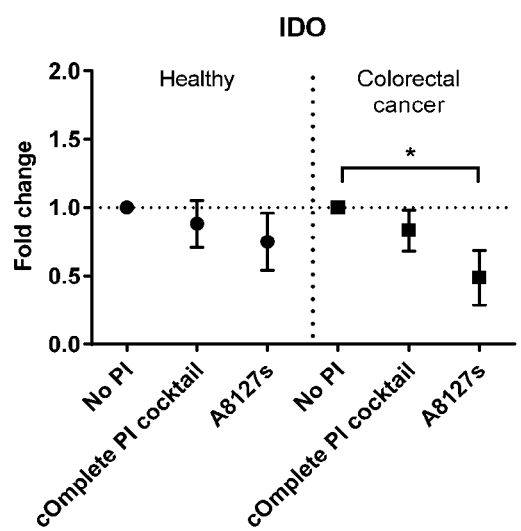
Figure 83:
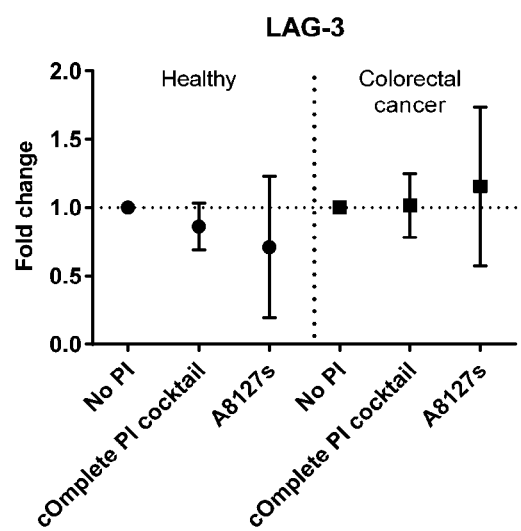
Figure 84:
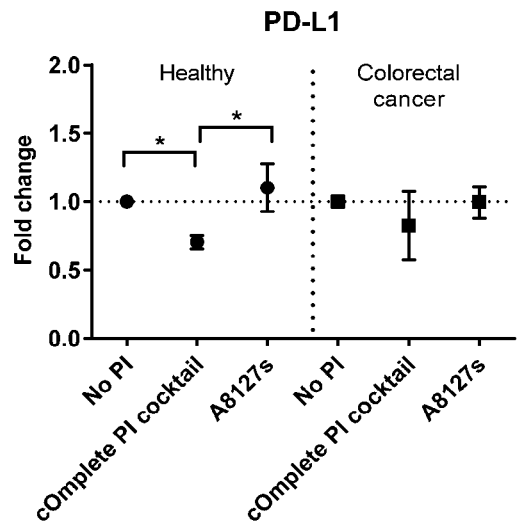
Figure 85:
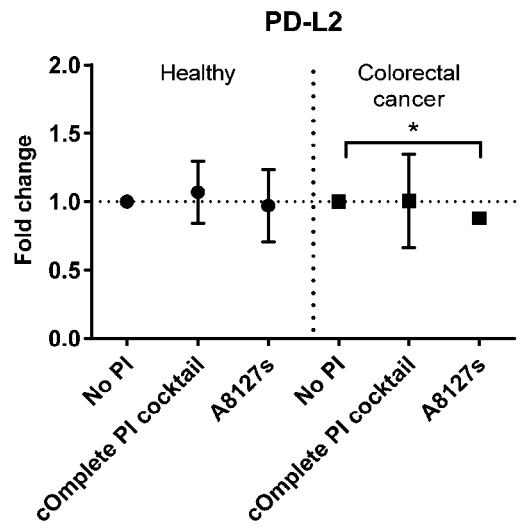
Figure 86:
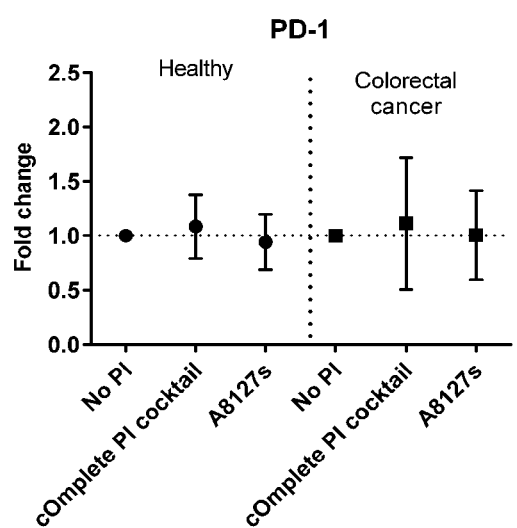
Figure 87:
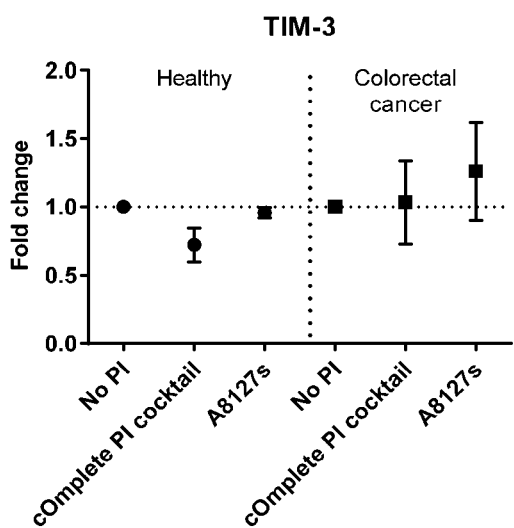

The data demonstrated that protease inhibitors altered the release of several proteins in the healthy participant group (FIG. 29A-FIG. 31NN), and also in the lymphoma (FIG. 29A-FIG. 29LL), osteoarthritis (FIG. 30A-FIG. 30NN), and ulcerative colitis (FIG. 31A-FIG. 31NN) participant groups as well. The effect of protease inhibitors was variable both between proteins and disease groups. For instance, in the lymphoma participant group, a significant decrease was observed for PECAM-1 in red blood cell membranes incubated with A8127s, but no significant change was detected in the healthy group. Similarly, prolactin was significantly decreased following incubation with protease inhibitors but was not significantly changed in the healthy group. Although not statistically significant, a differential trend in fold change following A8127s incubation was observed between the healthy and lymphoma groups for chitinase 3-like 1, IL-26, and IL-35, where the concentration of the respective proteins increased in the healthy group and decreased in the lymphoma group, and vice versa.

Each of the diseases investigated had a number of proteins that exhibited a differential response between healthy and disease cohorts following protease inhibitor incubation. In participants with osteoarthritis, 12 cytokines exhibited a differential response, including pentraxin-3 and chitinase 3-like 1. Similarly, in participants with ulcerative colitis, 26 cytokines a differential response, including IL-20, IL-27 (p28), and BAFF/TNFSF13B. Using the foregoing information, a diagnostic panel may be developed to differentiate between healthy and diseased cohorts.

Example 12. Effect of Protease Inhibitors on Cell Checkpoint Regulator Proteins from Red Blood Cell Components from Cancer Cohorts The concentration and change in concentration of proteins specifically implicated in disease states like carcinogenesis, are investigated in red blood cells and red blood cell membranes in the presence and absence of protease inhibitors. Whole blood is collected from healthy volunteers or volunteers with cancer. Blood is collected from each volunteer by venepuncture directly into EDTA vacutainers ($k_2$EDTA vacutainers, BD Biosciences). The fractions of blood are collected and processed at room temperature within 4 hours of collection. For multiplex analysis (BioPlex analysis) the samples are stored at −80° C. prior to analysis. Following collection, an aliquot of whole blood is frozen at −80° C. The red blood cells are isolated from the remaining whole blood using dextran sedimentation as follows. Whole blood is centrifuged (1500 g, 10 minutes) and the upper plasma layer is discarded. The remaining cell pellet is resuspended in an equal volume of sodium chloride (0.15 M). Dextran (6% w/v in 0.15 M sodium chloride) is then added to this cellular suspension at a 1:4 ratio (dextran:cell suspension). This solution is left at room temperature for 30 minutes for red blood cell sedimentation to the bottom of the tube. The upper white blood cell rich layer is discarded and the lower red blood cell fraction is isolated. The red blood cell fraction is washed once in phosphate buffered saline (PBS, 500 g, 5 minutes) and the remaining red blood cell pellet is counted (Coulter Act Diff, Beckman Coulter). The red blood cells are then diluted to 400 million cells/mL in PBS and incubated at 37° C. and 5% $CO_2$ for 24 hours. Some samples are also treated with individual protease inhibitors in Table 5, a commercial protease inhibitor cocktail (cOmplete, Roche), or A8127s protease inhibitor cocktail during the PBS incubation. The A8127s protease inhibitor cocktail comprises antipain-dihydrochloride (50 µg/mL); bestatin (40 µg/mL); E-64 (10 µg/mL); leupeptin (5 µg/mL); pepstatin (0.7 µg/mL); phosphoramidon (330 µg/mL); Pefabloc SC (1 mg/mL); EDTA-$Na_2$ (0.5 mg/mL); and aprotinin (2 µg/mL).

For the isolation of red blood cell membranes, the frozen aliquots of the whole blood are subjected to 3 freeze thaw cycles to ensure complete cellular lysis. Following this, an aliquot of the lysates (volume equivalent to 120 million red blood cells per 100 µL) was added to PBS at a 1:20 ratio (lysate:PBS). The red blood cell membranes are then isolated by centrifugation out of solution (16,000 g, 20 mins, 4° C.). The upper fraction is then discarded and the resulting membranes were then diluted to 1,200 million cells/mL in PBS and are incubated at 37° C. and 5% $CO_2$ for 24 hours. Some red blood cell membrane samples are treated with the protease inhibitor cocktails (complete, Roche; A8127s).

After incubation, the resulting conditioned PBS is isolated by centrifugation (16,000 g, 20 minutes, 4° C.). The samples are stored at −80° C. The conditioned PBS samples are then analysed on a multiplex assay. A 14-plex human immuno-oncology checkpoint panel that assays CD137 (4-1BB), CD152 (CTLA-4), CD223 (Lag-3), CD27, CD270 (HVEM), CD272 (BTLA), CD279 (PD-1), CD28, CD357 (GITR), CD80 (B7-1), TIM3 (ProcartaPlex 14-plex human immuno-oncology checkpoint panel, Affymetrix eBioscience) is used. The assays are performed according to the manufacturer's instructions using an automated magnetic wash station (BioPlex Pro II, Bio-Rad) for the washing steps. The assays are run on the Luminex® 200™ system (Bio-Rad) and fluorescent values were collected. The calibration curve for each cytokine is analysed with 5 parametric logistic curve regression using BioPlex manager software (ver. 5.0, Bio-Rad, USA).

The concentration is measured of proteins in red blood cell-conditioned PBS at 400 million cells/mL following incubation at 37° C. for 24 hours with individual protease inhibitors, the red blood cells from healthy participants or participants with cancer. The data indicate changes in protein concentration in red blood cells from individuals with cancer compared to those from healthy individuals (FIG. 32-45). In addition, the individual protease inhibitors have varying effects on protein concentration. Such information may be used to customize a protease inhibitor cocktail such that there is a greater magnitude of effect on protein concentration in red blood cell components from individuals with cancer. For example, specific individual protease inhibitors may be added or removed from a protease inhibitor cocktail based on data indicating the effect of the protease inhibitor on protein concentration. A protease inhibitor cocktail may be optimized to emphasize/maximize statistically significant differences between the healthy and cancer profiles.

The concentration is measured of proteins in red blood cell-conditioned PBS at 400 million cells/mL and red blood cell membrane-conditioned PBS at 1,200 million cells/mL following incubation at 37° C. for 24 hours with either no protease inhibitors or protease inhibitor cocktails in red blood cell components from healthy participants or participants with cancer. Values are significantly different (*) if p<0.05. Data are presented as the mean±standard deviation. A range of cancer checkpoint proteins are released from red blood cells and red blood cell membranes (FIG. 46-59). The data further demonstrate that protease inhibitors have an effect on the concentration of a range of cancer checkpoint proteins released from the red blood cells and red blood cell membranes of healthy individuals and those with cancer (FIG. 46-59). Moreover, the observed changes following protease inhibitor incubation is different between red blood cell components isolated from healthy participants and those with colorectal cancer.

The fold change of proteins in red blood cell-conditioned PBS at 400 million cells/mL and red blood cell membrane-conditioned PBS (isolated from whole blood lysates) at 1,200 million cells/mL following incubation at 37° C. for 24 hours with protease inhibitors is compared to no protease inhibitor incubation in red blood cell components from healthy participants or participants with cancer. Values are significantly different (*) if p<0.05. Data are the mean±standard deviation. The data demonstrate that incubation of red blood cells and red blood cell membranes with protease inhibitors results in significant changes to the profile of cancer checkpoint proteins from the red blood cell- and red blood cell membrane-conditioned PBS from both healthy and cancer participant groups (FIG. 60-73 and FIG. 74-87). The samples isolated from the healthy and cancer group differ in how they respond to protease inhibitor incubation. There are a number of checkpoint proteins that change significantly when the red blood cells or red blood cell membranes from cancer patients are incubated with, for instance, the A8127s protease inhibitor cocktail (FIG. 60-73 and FIG. 74-87). In contrast, the protease inhibitors have a different effect on the expression of those same checkpoint proteins in red blood cells and red blood cell membranes from healthy individuals (FIG. 60-73 and FIG. 74-87).

Using the forgoing data, a diagnostic panel may be developed to differentiate between healthy and cancer cohorts.

Example 13. Other Exemplary Non-Limiting Embodiments

Further advantages of the claimed subject matter will become apparent from the following examples describing certain embodiments of the claimed subject matter.
1. A method of producing a protein profile comprising:
   a.) obtaining a blood sample;
   b.) obtaining a red blood cell component from the blood sample;
   c.) measuring the level of one or more proteins from the red blood cell component;
   d.) contacting the red blood cell component with one or more protease inhibitors;
   e.) measuring the level of the one or more proteins from the red blood cell component contacted with the one or more protease inhibitors; and
   f.) determining the change in the level of the one or more proteins from the red blood cell component before and after being contacted with the one or more protease inhibitors,
   wherein the protein profile produced comprises one or more proteins having a change in level before and after the red blood cell component is contacted with the one or more protease inhibitors.

2. A method of producing a protein profile comprising:
   a.) obtaining blood sample or a red blood cell component from a blood sample;
   b.) obtaining a first and second portion from the blood sample or the red blood cell component;
   c.) contacting the second portion from the blood sample or the red blood cell component with one or more protease inhibitors;
   d.) measuring the level of one or more proteins from the first and second portions of the blood sample or the red blood cell component, wherein the first portion has not been contacted with the one or more protease inhibitors; and
   e.) determining the change in the level of the one or more proteins from first portion of the blood sample or the red blood cell component and the second portion of the blood sample or the red blood cell component,
   wherein the protein profile produced comprises one or more proteins having a change in level of the one or more proteins from first portion of the blood sample or the red blood cell component and the second portion of the blood sample or the red blood cell component.

3. The method of example 2, wherein both a blood sample and a red blood cell component are obtained.

4. A method of producing a protein profile comprising:
   a.) obtaining a blood sample that is from a subject not having a disease or disorder;
   b.) obtaining a red blood cell component from the blood sample;
   c.) measuring the level of one or more proteins from the red blood cell component;
   d.) contacting the red blood cell component with one or more protease inhibitors;
   e.) measuring the level of the one or more proteins from the red blood cell component contacted with the one or more protease inhibitors; and
   f.) determining the change in the level of the one or more proteins from the red blood cell component before and after being contacted with the one or more protease inhibitors,
   wherein the protein profile produced comprises the change in the level of the one or more proteins from the red blood cell component before and after being contacted with one or more protease inhibitors.

5. A method of producing a disease protein profile comprising:
   a.) obtaining from a subject having a disease or disorder a first protein profile produced according one or more of examples 1 to 3;
   b.) obtaining from a subject not having the disease or disorder a second protein profile produced according to example 4, wherein the second protein profile is obtained from the same red blood cell component the first protein profile was obtained from; and
   c.) comparing the difference between the change in the level of one or more proteins from the subject having the disease or disorder to the change in the level of the one or more proteins from the subject not having the disease or disorder,
   wherein the disease protein profile produced comprises one or more proteins for which there is a difference between the change in the level of the one or more proteins from the subject having the disease or disorder and the change in the level of the one or more proteins from the subject not having the disease or disorder.

6. The method of one or more of examples 1 to 5, wherein the red blood cell component is obtained from whole blood or isolated red blood cells.
7. The method of example 6, wherein the red blood cell component is red blood cells or red blood cell membranes.
8. The method of one or more of examples 1 to 7, wherein the level of two or more proteins, three or more proteins, four or more proteins, five or more proteins, six or more proteins, seven or more proteins, eight or more proteins, nine or more proteins, or ten or more proteins is measured.
9. The method of example 8, wherein the level of three or more proteins is measured.
10. The method of one or more of examples 1 to 7, wherein the red blood cell component is contacted with one or more protease inhibitors, two or more protease inhibitors, three or more protease inhibitors, four or more protease inhibitors, five or more protease inhibitors, six or more protease inhibitors, seven or more protease inhibitors, eight or more protease inhibitors, nine or more protease inhibitors, or ten or more protease inhibitors.
11. The method of one or more of examples 1 to 7, wherein the red blood component is contacted with a protease inhibitor cocktail comprising at least two protease inhibitors.
12. The method of one or more of examples 1 to 7, wherein the red blood cell component is contacted with the protease inhibitor cocktail A8127s.
13. The method of one or more of examples 1 to 7, wherein the one or more protease inhibitors are selected from the group consisting of serine protease inhibitors, cysteine protease inhibitors, metalloprotease inhibitors, aspartic protease inhibitors, and aminopeptidase inhibitors.
14. The method of one or more of examples 1 to 7, wherein the change in the level of the one or more proteins is determined by a statistical analysis selected from the group consisting of a Student T's test, an ANOVA test, a mixed-effects model, a Mann-Whitney test, a Wilcoxon rank sum, and a Spermans rank correlation.
15. The method of one or more of examples 1 to 7, wherein the change in the level of the one or more proteins is a fold change between 0-fold and 5-fold.
16. The method of one or more of example 5 to 7, wherein the difference between the change in the level of the one or more proteins from the subject having a disease or disorder and the change in the level of the one or more proteins from the subject not having the disease or disorder is determined by a statistical analysis selected from the group consisting of a Student T's test, an ANOVA test, a mixed-effects model, a Mann-Whitney test, a Wilcoxon rank sum, and a Spermans rank correlation.
17. The method of one or more of examples 5 to 7, wherein the difference between the change in the level of the one or more proteins from the subject having a disease or disorder and the change in the level of the one or more proteins from the subject not having the disease or disorder is an increase in the change in the level or a decrease in the change in the level.
18. The method of one or more of examples 1 to 17, wherein the subject is a human or a non-human animal.
19. The method of one or more of examples 1 to 17, wherein the level of the one or more proteins is measured using one or more antibodies.
20. The method of one or more of examples 1 to 17, wherein the one or more proteins are selected from the group consisting of chemokines, cytokines, growth factors, receptors, intracellular signal transmitters, hormones, nuclear transcription factors, neurotransmitters, extracellular matrix components, glycoproteins, inflammatory proteins, and enzymes.
21. The method of one or more of examples 1 to 17, wherein the one or more proteins are selected from the group consisting of the proteins listed in Table 1 or the proteins listed in Table 2.
22. The method of one or more of examples 1 to 17, wherein the disease or disorder is preeclampsia.
23. The method of example 22, wherein the disease protein profile is a preeclampsia protein profile comprising one or more proteins selected from the group consisting of IL-1β, IL-8, TNF-α, IL-1ra, MCP-1, G-CSG, GM-CSF, IL-6, IFNα2, IL-1a, IL-18, MIF, IL-2ra, and HGF.
24. The method of one or more of examples 1 to 17, wherein the disease or disorder is colorectal cancer.
25. The method of example 24, wherein the disease protein profile is a cancer protein profile comprising one or more proteins selected from the group consisting of IL-6, IFN-γ, IL-4, IL-13, MIF, Eotaxin, RANTES, IL-7, IP-10, PDGF, and IL-12p40.
26. A method of monitoring a disease or disorder in a subject comprising:
   a.) obtaining from the subject having a disease or disorder a first blood sample at a first point in time and a second blood sample at a second point in time;
   b.) measuring the level of at least one protein from a disease protein profile produced according to example 5 for the disease or disorder in the first blood sample and second blood sample; and
   c.) determining the difference between the change in the level of the at least one protein in the first blood sample and second blood sample,
   wherein a difference between the change in the level of the at least one protein in the first blood sample and second blood sample indicates a change in the disease or disorder.
27. A method of monitoring the effect of a treatment in a subject comprising:
   a.) obtaining from the subject a first protein profile produced according to one or more of examples 1 to 3 at a first point in time and a second protein profile produced according to one or more of claims 1 to 4 at a second point in time; and
   b.) comparing the change in the level of at least one protein from the first protein profile to the change in the level of the at least one protein from the second protein profile,
   wherein a difference between the change in the level of the at least one protein from the first protein profile and the change in the level of the at least one protein from the second protein profile indicates an effect of the treatment.
28. The method of example 27, wherein the first point in time is before treatment and the second point in time is after treatment.
29. The method of example 27, wherein the first point in time is before treatment and the second point in time is during treatment.
30. The method of example 27, wherein the first point in time and the second point in time are during treatment.
31. The method of example 27, wherein the first point in time is during treatment and the second point in time is after treatment.
32. The method of example 27, wherein the first point in time and the second point in time are after treatment.

33. The method of example 27, wherein the subject has received the same treatment.
34. The method of example 27, wherein the subject has received a different treatment.
35. The method of one or more of examples 27 to 34, wherein the blood sample is a small volume blood sample.
36. The method of example 34, wherein the subject is monitored a number of times selected from the group consisting of one or more times per day, two or more times per day, three or more times per day, four or more times per day, and five or more times per day.
37. The method of example 35, wherein the subject is monitored a number of times selected from the group consisting of one or more times per week, two or more times per week, three or more times per week, four or more times per week, five or more times per week, six or more times per week, and seven or more times per week.
38. The method of example 35, wherein the subject is monitored daily.
39. The method of example 35, wherein the subject is monitored a number of times selected from the group consisting of once a week, once every two weeks, once every three weeks, and once every four weeks.
40. A method of diagnosing a disease or disorder comprising:
    a.) obtaining at least one disease protein profile produced according to claim 3;
    b.) obtaining a blood sample that is from a subject;
    c.) obtaining a red blood cell component from the blood sample;
    d.) contacting at least a first portion of the red blood component with one or more protease inhibitors;
    e.) measuring the level of at least one protein from the disease protein profile in the first portion of the red blood component and the level of the at least one protein in a second portion of the red blood component that has not been contacted with the one or more protease inhibitors;
    f.) determining the change in the level between the at least one protein in the first portion of the red blood component and the at least one protein in a second portion of the red blood component; and
    g.) comparing the change in the level between the at least one protein in the first portion of the red blood cell component and the second portion of the red blood cell component to the change in level of the at least one protein in the disease protein profile,
    wherein a same or similar change in the level of the at least one protein in the first portion of the red blood cell component and the second portion of the red blood cell component compared to the change in level of the at least one protein in the disease protein profile indicates that the subject has the disease or disorder.
41. A method of diagnosing a disease or disorder in a subject comprising:
    a.) obtaining at least one protein profile for the subject produced according to one or more of examples 1 to 3; and
    b.) comparing the change in the level of at least one protein from the at least one protein profile to the change in the level of the at least one protein from a disease protein profile produced according to example 5,
    wherein a same or similar change in level of the at least one protein from the at least one protein profile for the subject to the change in the level of the at least one protein from the disease protein profile indicates that the subject has the disease or disorder.
42. A method of diagnosing a disease or disorder in a subject comprising:
    a.) obtaining at least one protein profile produced according to one or more of examples 1 to 3 for the subject;
    b.) obtaining at least one protein profile produced according to example 4; and
    c.) comparing the change in the level of at least one protein from the at least one protein profile for the subject to the change in the level of the at least one protein from the at least one protein profile produced according to example 4,
    wherein a difference between the change in the level of the at least one protein from the at least one protein profile for the subject and the change in the level of the at least one protein from the at least one protein profile produced according to example 4 indicates that the subject has the disease or disorder.
43. A kit for producing a protein profile of a blood sample comprising:
    a.) at least one reagent to obtain a red blood cell component;
    b.) one or more protease inhibitors; and
    c.) at least one reagent to measure the level of one or more proteins from the red blood cell component.
44. The method of example 43, wherein the kit further comprises at least one reagent to obtain a blood sample from a subject.
45. The method of example 43, wherein the reagent to measure the level of one or more proteins is one or more antibodies.
46. The method of example 45, wherein the reagent to detect the measure the level of one or more proteins is an enzyme-linked immunosorbent assay (ELISA) apparatus.
47. The method of example 43, wherein the one or more protease inhibitors comprise a protease inhibitor cocktail.
48. The method of example 47, wherein the protease inhibitor cocktail is A8127s.
49. A method of producing a protein profile comprising:
    a.) obtaining a blood sample from a subject having a disease or disorder;
    b.) leukodepleting at least a portion of the blood sample to produce a red blood cell-enriched sample;
    c.) contacting the red blood cell-enriched sample with one or more protease inhibitors; and
    d.) detecting the presence of one or more proteins in the red blood cell-enriched sample,
    wherein the protein profile produced comprises one or more proteins detected in the red blood cell-enriched sample.
50. A method of producing a protein profile comprising:
    a.) obtaining a blood sample from a subject having a disease or disorder;
    b.) leukodepleting at least a portion of the blood sample to produce a red blood cell-enriched sample;
    c.) isolating red blood cells and plasma in the red blood cell-enriched sample;
    d.) contacting the red blood cells with one or more protease inhibitors;
    e.) measuring the level of one or more proteins in the red blood cells and the level of the one or more proteins in the plasma; and
    e.) calculating a protein ratio comprising the level of the one or more proteins in the red blood cells to the level of the one or more proteins in the plasma, wherein the protein profile produced comprises one or more proteins that have a protein ratio of at least 2:1.
51. The method of example 49, wherein the one or more proteins have a protein ratio selected from the group consisting of at least 3:1, at least 4:1, at least 5:1, at least 10:1, at least 15:1, and at least 20:1.
52. A method of producing a protein profile comprising:
   a.) obtaining a blood sample from a subject having a disease or disorder;
   b.) leukodepleting at least a portion of the blood sample to produce a red blood cell-enriched sample;
   c.) incubating the red blood cells in the red blood cell-enriched sample in a medium containing one or more protease inhibitors; and
   d.) detecting one or more proteins in the medium, wherein the protein profile produced comprises one or more proteins detected in the medium.
53. The method of example 48 or example 51, wherein the method further comprises measuring the level of the one or more proteins detected in the red blood cell-enriched sample.
54. The method of one or more of examples 48 to 52, wherein the presence of two or more proteins, three or more proteins, four or more proteins, five or more proteins, six or more proteins, seven or more proteins, eight or more proteins, nine or more proteins, or ten or more proteins is detected or the level of two or more proteins, three or more proteins, four or more proteins, five or more proteins, six or more proteins, seven or more proteins, eight or more proteins, nine or more proteins, or ten or more proteins, eleven or more proteins, twelve or more proteins, thirteen or more proteins, fourteen or more proteins, or fifteen or more proteins is measured.
55. The method of example 53, wherein the presence of three or more proteins is detected or the level of three or more proteins is measured.
56. The method of one or more of examples 48 to 54, wherein the red blood cell-enriched sample is contacted with two or more protease inhibitors, three or more protease inhibitors, four or more protease inhibitors, five or more protease inhibitors, six or more protease inhibitors, seven or more protease inhibitors, eight or more protease inhibitors, nine or more protease inhibitors, or ten or more protease inhibitors.
57. The method of example 55, wherein the red blood cell-enriched sample is contacted with three or more protease inhibitors.
58. The method of example 55, wherein the red blood cell-enriched sample is contacted with three or more protease inhibitors and wherein the presence of two or more proteins is detected or the level of two or more proteins is measured.
59. The method of example 55, wherein the red blood cells are contacted with two or more protease inhibitors and wherein the presence of three or more proteins is detected or the level of three or more proteins is measured.
60. The method of one or more of examples 48 to 58, wherein the one or more protease inhibitors are selected from the group consisting of serine protease inhibitors, cysteine protease inhibitors, metalloprotease inhibitors, and aspartic protease inhibitors.
61. The method of one or more of examples 48 to 59, wherein the subject is a human or a non-human animal.
62. The method of one or more of examples 48 to 60, wherein the presence of one or more proteins is detected or the level of one or more proteins is measured using one or more antibodies.
63. The method of one or more of examples 48 to 60, wherein the one or more proteins are selected from the group consisting of chemokines, cytokines, growth factors, receptors, intracellular signal transmitters, hormones, nuclear transcription factors, neurotransmitters, and extracellular matrix components, and enzymes.
64. The method of one or more of examples 48 to 60, wherein the one or more proteins are selected from the group consisting of the proteins listed in Table 1 or the proteins listed in Table 2.
65. The method of one or more of examples 48 to 60, wherein the blood sample is leukodepleted by one or more methods selected from the group consisting of flow cytometry, magnetic bead separation, centrifugation, cellulose column, and dextran sedimentation.
66. The method of example 64, wherein the blood sample is leukodepleted by dextran sedimentation.
67. A method of monitoring a disease or disorder in a subject comprising:
   a.) obtaining at least one protein profile produced according to one or more of examples 48 to 60 from the subject at a first point in time and a second point in time; and
   b.) comparing the at least one protein profile of the subject at the first point in time to the at least one protein profile of the subject at the second point in time,
   wherein a difference in the presence or level of one or more proteins in the at least one protein profile of the subject at the first point in time compared to the at least one protein profile of the subject at the second point in time indicates a change in the disease or disorder.
68. A method of monitoring treatment in a subject comprising:
   a.) obtaining at least one protein profile produced according to one or more of examples 48 to 60 from a subject before treatment and after treatment; and
   b.) comparing the at least one protein profile of the subject before treatment to the at least one protein profile of the subject after treatment,
   wherein a difference in the presence or level of one or more proteins in the at least one protein profile of the subject before treatment compared to the at least one protein profile of the subject after treatment indicates an effect of the treatment on the subject.
69. The method of example 67, wherein the at least one protein profile of a subject who has received no treatment is compared to the at least one protein profile of the subject after receiving treatment.
70. The method of example 67, wherein the at least one protein profile of a subject after treatment at one point in time is compared to the at least one protein profile of the subject after treatment at a different point in time.
71. The method of example 69, wherein the subject has received the same treatment.
72. The method of example 69, wherein the subject has received a different treatment.
73. The method of one or more of examples 66 to 71, wherein the blood sample is a small volume blood sample.
74. The method of one or more of examples 66 to 72, wherein the subject is monitored a number of times selected from the group consisting of one or more times per day, two or more times per day, three or more times per day, four or more times per day, and five or more times per day.
75. The method of one or more of examples 66 to 72, wherein the subject is monitored a number of times selected from the group consisting of one or more times per week, two or more times per week, three or more times per week, four or more times per week, five or more times per week, six or more times per week, and seven or more times per week.

76. The method of one or more of examples 66 to 72, wherein the subject is monitored daily.

77. The method of one or more of examples 66 to 72, wherein the subject is monitored a number of times selected from the group consisting of once a week, once every two weeks, once every three weeks, and once every four weeks.

78. A method of producing a disease or disorder protein profile comprising:
   a.) obtaining a blood sample from one or more subjects having a disease or disorder;
   b.) leukodepleting at least a portion of the blood sample to produce a red blood cell-enriched sample;
   c.) contacting a first portion of the red blood cell-enriched sample with one or more protease inhibitors;
   d.) measuring the level of one or more proteins in the first portion of the red blood cell-enriched sample and the level of the one or more proteins in a second portion of the red blood cell-enriched sample that has not been contacted with the one or more protease inhibitors; and
   e.) comparing the level of the one or more proteins in the first portion of the red blood cell-enriched sample to the level of the one or more proteins in the second portion of the red blood cell-enriched sample,
   wherein the disease protein profile produced comprises one or more proteins that have different level in the first portion of the red blood cell-enriched sample compared to the level of the one or more proteins in the second portion of the red blood cell-enriched sample.

79. The method of example 77, wherein the level of the difference in the level of the one or more proteins in the first portion of the red blood cell-enriched sample compared to the level of the one or more proteins in the second portion of the red blood cell-enriched sample is determined by a statistical analysis selected from the group consisting of a Student T's test, an ANOVA test, a mixed-effects model, a Mann-Whitney test, a Wilcoxon rank sum, and a Spermans rank correlation.

80. The method of example 77 or example 78, wherein the level of two or more proteins, three or more proteins, four or more proteins, five or more proteins, six or more proteins, seven or more proteins, eight or more proteins, nine or more proteins, or ten or more proteins is measured.

81. The method of example 79, wherein the level of three or more proteins is measured.

82. The method of example 80, wherein the disease or disorder is preeclampsia.

83. The method of example 81, wherein the disease protein profile is a preeclampsia protein profile comprising one or more proteins selected from the group consisting of IL-1β, IL-8, TNF-α, IL-1ra, MCP-1, G-CSG, GM-CSF, IL-6, IFNα2, IL-1a, IL-18, MIF, IL-2ra, and HGF.

84. The method of example 80, wherein the disease or disorder is cancer.

85. The method of example 83, wherein the disease protein profile is a cancer protein profile comprising one or more proteins selected from the group consisting of IL-6, IFN-γ, IL-4, IL-13, MIF, Eotaxin, RANTES, IL-7, IP-10, PDGF, and IL-12p40.

86. A method of diagnosing a disease or disorder comprising:
   a.) obtaining a blood sample from a subject;
   b.) leukodepleting at least a portion of the blood sample to produce a red blood cell-enriched sample;
   c.) contacting at least a first portion of the red blood cell-enriched sample with one or more protease inhibitors;
   d.) measuring the level of one or more proteins in the first portion of the red blood cell-enriched sample and the level of the one or more proteins in a second portion of the red blood cell-enriched sample that has not been contacted with the one or more protease inhibitors; and
   e.) comparing the level of the one or more proteins in the first portion of the red blood cell-enriched sample to the level of the one or more proteins in the second portion of the red blood cell-enriched sample,
   wherein a difference in the level of one or more proteins in the first portion of the red blood cell-enriched sample compared to the level of the one or more proteins in the second portion of the red blood cell-enriched sample indicates the subject has the disease or disorder.

87. The method of example 85, wherein no difference in the level of the one or more proteins indicates the subject does not have the disease or disorder.

88. A method of determining whether a subject has a disease or disorder comprising:
   a.) obtaining a blood sample from the subject;
   b.) leukodepleting at least a portion of the blood sample to produce a red blood cell-enriched sample;
   c.) contacting at least a first portion of the red blood cell-enriched sample with one or more protease inhibitors;
   c.) measuring the level of one or more proteins in the first portion of the red blood cell-enriched sample and the level of the one or more proteins in a second portion of the red blood cell-enriched sample that has not been contacted with the one or more protease inhibitors; and
   d.) comparing the level of the one or more proteins in the first portion of the red blood cell-enriched sample to the level of the one or more proteins in the second portion of the red blood cell-enriched sample,
   wherein no difference in the level of the one or more proteins in the first portion of the red blood cell-enriched sample compared to the level of the one or more proteins in the second portion of the red blood cell-enriched sample indicates that the subject does not have the disease or disorder.

89. A method of diagnosing a disease or disorder in a subject comprising:
   a.) obtaining at least one protein profile from the subject produced according to one or more of examples 48 to 60; and
   b.) comparing the at least one protein profile to at least one disease protein profile,
   wherein the presence or level of one or more proteins in the at least one protein profile that is similar to the presence or level of the one or more proteins in the at least one disease protein profile indicates the subject has the disease or disorder.

90. The method of example 88, wherein the at least one disease protein profile obtained is produced according to one or more of examples 30 to 33.

91. A method of diagnosing a disease or disorder in a subject comprising:
   a.) obtaining at least one protein profile from the subject produced according to one or more of examples 48 to 60;
   b.) obtaining at least one protein profile from one or more subjects not having the disease or disorder; and c.) comparing the at least one protein profile obtained from the subject to the at least one protein profile obtained from one or more subjects not having the disease or disorder, wherein a difference in the presence or level of the one or more proteins in the at least one protein profile obtained from the subject compared to the presence or level of the one or more proteins in the at least one protein profile obtained from one or more subjects not having the disease or disorder indicates that the subject has the disease or disorder.

92. A kit for producing a protein profile of a blood sample comprising:
    a.) at least one reagent to leukodeplete a blood sample and produce a red blood cell-enriched sample;
    b.) one or more protease inhibitors; and
    c.) at least one reagent to detect the presence or measure the level of one or more proteins in the red blood cell-enriched sample.
93. The method of example 91, wherein the kit further comprises at least one reagent to obtain a blood sample from a subject.
94. The method of example 91, wherein the reagent to detect the presence or measure the level of one or more proteins is one or more antibodies.
95. The method of example 93, wherein the reagent to detect the presence or measure the level of one or more proteins is an enzyme-linked immunosorbent assay (ELISA) apparatus.

What is claimed:
1. A method of producing a protein profile comprising:
A)
   a) obtaining a red blood cell component from a blood sample;
   b) obtaining a first and second portion from the red blood cell component;
   c) contacting the second portion from the red blood cell component with one or more protease inhibitors;
   d) measuring the level of one or more proteins from the first portion of the red blood cell component and from the contacted second portion of the red blood cell component, wherein the one or more proteins are selected from the group consisting of chemokines, cytokines, growth factors, receptors, intracellular signal transmitters, hormones, nuclear transcription factors, neurotransmitters, extracellular matrix components, glycoproteins, inflammatory proteins, and enzymes; and
   e) determining the difference in the measured level of the one or more proteins from the first portion of the red blood cell component and the contacted second portion of the red blood cell component,
wherein the protein profile produced comprises the one or more proteins having a difference in the measured level of said one or more proteins from first portion of the red blood cell component and the contacted second portion of the red blood cell component; or
B)
   a) obtaining a red blood cell component from a blood sample;
   b) measuring the level of one or more proteins from the red blood cell component, wherein the one or more proteins are selected from the group consisting of chemokines, cytokines, growth factors, receptors, intracellular signal transmitters, hormones, nuclear transcription factors, neurotransmitters, extracellular matrix components, glycoproteins, inflammatory proteins, and enzymes;
   c) contacting the red blood cell component with one or more protease inhibitors;
   d) measuring the level of the one or more proteins from the contacted red blood cell component; and
   e) determining the difference in the measured level of the one or more proteins from the red blood cell component and the contacted red blood cell component;
wherein the protein profile produced comprises the one or more proteins having a difference in the measured level of said one or more proteins from the red blood cell component and the contacted red blood cell component.

2. The method of claim 1, wherein the protein profile produced is according to step A).
3. The method of claim 2, wherein the red blood cell component comprises red blood cells or red blood cell membranes.
4. The method of claim 2, wherein:
   a) the first portion of the red blood cell component is in a first medium, wherein the measured level of one or more proteins is one or more proteins released into the first medium; and
   b) the second portion of the red blood cell component is in a second medium, wherein the measured level of one or more proteins is one or more proteins released into the second medium.
5. The method of claim 2, wherein the obtained blood sample is whole blood or isolated red blood cells.
6. The method of claim 5, wherein the red blood cell component is contacted with one or more protease inhibitors, two or more protease inhibitors, three or more protease inhibitors, four or more protease inhibitors, five or more protease inhibitors, six or more protease inhibitors, seven or more protease inhibitors, eight or more protease inhibitors, nine or more protease inhibitors, or ten or more protease inhibitors.
7. The method of claim 5, wherein the red blood cell component is contacted with a protease inhibitor cocktail comprising at least two protease inhibitors.
8. The method of claim 5, wherein the red blood cell component is contacted with a protease inhibitor cocktail comprising at least two protease inhibitors of the protease inhibitor cocktail A8127s, wherein the protease inhibitor cocktail A8127s comprises antipain-dihydrochloride, bestatin, E-64 (N—(N-L-3-trans-carbonyl)-L-leucyl)-agmatine), leupeptin, pepstatin, phosphoramidon, pefabloc SC, EDTA-Na2, and aprotinin.
9. The method of claim 5, wherein the measured level of said one or more proteins is two or more proteins, three or more proteins, four or more proteins, five or more proteins, six or more proteins, seven or more proteins, eight or more proteins, nine or more proteins, or ten or more proteins.
10. The method of claim 2, wherein the one or more protease inhibitors are selected from the group consisting of serine protease inhibitors, cysteine protease inhibitors, metalloprotease inhibitors, aspartic protease inhibitors, and aminopeptidase inhibitors.
11. The method of claim 2, wherein the one or more proteins are selected from the group consisting of basic fibroblast growth factor (basic FGF), cutaneous T cell-attracting chemokine (CTACK (CCL27)); CCL11 (Eotaxin 1); granulocyte-colony stimulating factor (G-CSF or GCSF)); granulocyte-macrophage colony-stimulating factor (GM-CSF or CSF2); hepatocyte growth factor (HGF); interferon alpha subtype α2 (IFN-α2); interferon gamma (IFN-γ); interleukin 10 (IL-10); interleukin 12 p35 and p40 heterodimer (IL-12, IL-12p70); interleukin 13 (IL-13); interleukin 12 p40 subunit (IL-12 p40); interleukin 15 (IL-15); interleukin 16 (IL-16); interleukin 17 A (IL-17A); interleukin 18 (IL-18); interleukin 1 alpha (IL-1α); interleukin 1 beta (IL-1β); interleukin 2 (IL-2); interleukin 2 receptor alpha chain (IL-2rα); interleukin 3 (IL-3); interleukin 5 (IL-5); interleukin 6 (IL-6); interleukin 7 (IL-7); interleukin 9 (IL-9); interferon gamma-induced protein 10 (IP-10, CXCL 10); leukaemia inhibitory factor (LIF); macrophage colony-stimulating factor (M-CSF or CSF1); monokine induced by IFN-γ (MIG); Chemokine (C—X—C motif) ligand 9 (CXCL9); macrophage inflammatory protein-1 alpha (MIP-1α or CCL3); macrophage inflammatory protein-1 alpha (MIP-1β or CCL4); platelet-derived growth factor B chain homodimer (PDGF-BB); stromal cell-derived factor 1 (SDF-1α or CXCL12); tumour necrosis factor alpha (TNF-α or cachexin); tumour necrosis factor-beta (TNF-β or lymphotoxin); TNF-related apoptosis-inducing ligand (TRAIL); vascular endothelial growth factor (VEGF); interleukin 8 (IL-8); monocyte chemoattractant protein-1 (MCP-1 or CCL2); maintenance of genome stability protein A (MGSA); prostaglandin E2 (PGE-2); regulated on activation, normal T cell expressed and secreted (RANTES or CCL5); macrophage migration inhibitory factor (MIF or MMIF); Growth-regulated oncogene α (GRO-α or CXCL1); C-reactive protein (CRP); D-dopachrome tautomerase (DDT or MIF-2); insulin like growth factor 1 (IGF-1); epidermal growth factor receptor (sEGFR); receptor tyrosine-protein kinase erbB-2 (sHER-2/neu or CD340); interleukin-6 receptor (sIL-6Ra); Leptin; Osteopontin; platelet endothelial cell adhesion molecule precursor (PECAM-1 or CD31); platelet-derived growth factor AB/platelet derived growth factor BB (PDGF-AB/BB); prolactin; tyrosine kinase with Ig and EGF homology domains-1 (sTIE-1); tyrosine kinase with Ig and EGF homology domains-2 (sTIE-2); vascular endothelial growth factor receptor-1 (sVEGFR-1); vascular endothelial growth factor receptor-2 (sVEGFR-2); A proliferation-inducing ligand/tumor necrosis factor ligand superfamily member 13 (APRIL/TNFSF13); B-cell activating factor/tumor necrosis factor ligand superfamily member 13B (BAFF/TNFSF13B); TNF receptor superfamily member 8 (TNFRSFS (CD30); cluster of differentiation 163 (sCD163); Chitinase-3-like 1 (CH13L1); glycoprotein 130/interleukin-6 receptor beta (gp130/sIL-6Rβ); interleukin-11 (IL-11); interleukin-19 (IL-19); interleukin-20 (IL-20); interleukin-22 (IL-22); interleukin-26 (IL-26); interleukin-27(p28) (IL-27(p28)); interleukin-28/interferon gamma 2 (IL-28A/IFN-γ2); interleukin-29/interferon gamma 1 (IL-29/IFN-γ1); interleukin-32 (IL-32); interleukin-34 (IL-34); interleukin-35 (IL-35); tumor necrosis factor superfamily member 14/homologous to lymphotoxin, exhibits inducible expression and competes with HSV glycoprotein D for binding to herpesvirus entry mediator, a receptor expressed on T lymphocytes (TNFSF14/LIGHT); matrix metalloproteinase-1 (MMP-1); matrix metalloproteinase-2 (MMP-2); matrix metalloproteinase-3 (MMP-3); Osteocalcin; Pentraxin-3; tumor necrosis factor receptor 1 (sTNF-R1); tumor necrosis factor receptor 2 (sTNF-R2); thymic stromal lymphopoietin (TSLP); TNF-related weak inducer of apoptosis/tumor necrosis factor superfamily member 12 (TWEAK/TNFSF12); 4-1BB (CD137); cytotoxic T-lymphocyte associated protein 4 (CTLA-4 or CD152); lymphocyte-activation gene 3 (Lag-3 or CD223); CD27; herpesvirus entry mediator/tumor necrosis factor superfamily member 14 (HVEM/TNFRSF14 (CD270)); B- and T-lymphocyte associated (BTLA (CD272)); programmed cell death protein 1 (PD-1 (CD279)); CD28; glucocorticoid-induced TNFR family related gene/tumor necrosis factor superfamily member 18 (GITR/TNFRSF1 8 (CD357)); B7-1 (CD80); and T-cell immunoglobulin domain and mucin domain 3 (TIM3).

12. The method of claim 1, wherein the protein profile produced is according to step B).

13. The method of claim 12, wherein the red blood cell component comprises red blood cells or red blood cell membranes.

14. The method of claim 12, wherein:
    a) the first portion of the red blood cell component is in a first medium, wherein the measured level of one or more proteins is one or more proteins released into the first medium; and
    b) the second portion of the red blood cell component is in a second medium, wherein the measured level of one or more proteins is one or more proteins released into the second medium.

15. The method of claim 12, wherein the obtained blood sample is whole blood or isolated red blood cells.

16. The method of claim 15, wherein the red blood cell component is contacted with one or more protease inhibitors, two or more protease inhibitors, three or more protease inhibitors, four or more protease inhibitors, five or more protease inhibitors, six or more protease inhibitors, seven or more protease inhibitors, eight or more protease inhibitors, nine or more protease inhibitors, or ten or more protease inhibitors.

17. The method of claim 15, wherein the red blood cell component is contacted with a protease inhibitor cocktail comprising at least two protease inhibitors.

18. The method of claim 15, wherein the red blood cell component is contacted with a protease inhibitor cocktail comprising at least two protease inhibitors of the protease inhibitor cocktail A8127s, wherein the protease inhibitor cocktail A8127s comprises antipain-dihydrochloride, bestatin, E-64 (N—(N-L-3-trans-carbonyl)-L-leucyl)-agmatine), leupeptin, pepstatin, phosphoramidon, pefabloc SC, EDTA-Na2, and aprotinin.

19. The method of claim 15, wherein the measured level of said one or more proteins is two or more proteins, three or more proteins, four or more proteins, five or more proteins, six or more proteins, seven or more proteins, eight or more proteins, nine or more proteins, or ten or more proteins.

20. The method of claim 12, wherein the one or more protease inhibitors are selected from the group consisting of serine protease inhibitors, cysteine protease inhibitors, metalloprotease inhibitors, aspartic protease inhibitors, and aminopeptidase inhibitors.

21. The method of claim 12, wherein the one or more proteins are selected from the group consisting of basic fibroblast growth factor (basic FGF), cutaneous T cell-attracting chemokine (CTACK (CCL27)); CCL11 (Eotaxin 1); granulocyte-colony stimulating factor (G-CSF or GCSF)); granulocyte-macrophage colony-stimulating factor (GM-CSF or CSF2); hepatocyte growth factor (HGF); interferon alpha subtype α2 (IFN-α2); interferon gamma (IFN-γ); interleukin 10 (IL-10); interleukin 12 p35 and p40 heterodimer (IL-12, IL-12p70); interleukin 13 (IL-13); interleukin 12 p40 subunit (IL-12 p40); interleukin 15 (IL-15); interleukin 16 (IL-16); interleukin 17 A (IL-17A); interleukin 18 (IL-18); interleukin 1 alpha (IL-1α); interleukin 1 beta (IL-1β); interleukin 2 (IL-2); interleukin 2 receptor alpha chain (IL-2rα); interleukin 3 (IL-3); interleukin 5 (IL-5); interleukin 6 (IL-6); interleukin 7 (IL-7); interleukin 9 (IL-9); interferon gamma-induced protein 10 (IP-10, CXCL10); leukaemia inhibitory factor (LIF); macrophage colony-stimulating factor (M-CSF or CSF1); monokine induced by IFN-γ (MIG); Chemokine (C—X—C motif) ligand 9 (CXCL9); macrophage inflammatory protein-1 alpha (MIP-1α or CCL3); macrophage inflammatory protein-1 alpha (MIP-1β or CCL4); platelet-derived growth factor B chain homodimer (PDGF-BB); stromal cell-derived factor 1 (SDF-1α or CXCL 12); tumour necrosis factor alpha (TNF-α or cachexin); tumour necrosis factor-beta (TNF-β or lymphotoxin); TNF-related apoptosis-inducing ligand (TRAIL); vascular endothelial growth factor (VEGF); interleukin 8 (IL-8); monocyte chemoattractant protein-1 (MCP-1 or CCL2); maintenance of genome stability protein A (MGSA); prostaglandin E2 (PGE-2); regulated on activation, normal T cell expressed and secreted (RANTES or CCL5); macrophage migration inhibitory factor (MIF or MMIF); Growth-regulated oncogene α (GRO-α or CXCL1); C-reactive protein (CRP); D-dopachrome tautomerase (DDT or MIF-2); insulin like growth factor 1 (IGF-1); epidermal growth factor receptor (sEGFR); receptor tyrosine-protein kinase erbB-2 (sHER-2/neu or CD340); interleukin-6 receptor (sIL-6Ra); Leptin; Osteopontin; platelet endothelial cell adhesion molecule precursor (PECAM-1 or CD31); platelet-derived growth factor AB/platelet derived growth factor BB (PDGF-AB/BB); prolactin; tyrosine kinase with Ig and EGF homology domains-1 (sTIE-1); tyrosine kinase with Ig and EGF homology domains-2 (sTIE-2); vascular endothelial growth factor receptor-1 (sVEGFR-1); vascular endothelial growth factor receptor-2 (sVEGFR-2); A proliferation-inducing ligand/tumor necrosis factor ligand superfamily member 13 (APRIL/TNFSF13); B-cell activating factor/tumor necrosis factor ligand superfamily member 13B (BAFF/TNFSF13B); TNF receptor superfamily member 8 (TNFRSFS (CD30); cluster of differentiation 163 (sCD163); Chitinase-3-like 1 (CH13L1); glycoprotein 130/interleukin-6 receptor beta (gp130/sIL-6Rβ); interleukin-11 (IL-11); interleukin-19 (IL-19); interleukin-20 (IL-20); interleukin-22 (IL-22); interleukin-26 (IL-26); interleukin-27(p28) (IL-27(p28)); interleukin-28/interferon gamma 2 (IL-28A/IFN-γ2); interleukin-29/interferon gamma 1 (IL-29/IFN-γ1); interleukin-32 (IL-32); interleukin-34 (IL-34); interleukin-35 (IL-35); tumor necrosis factor superfamily member 14/homologous to lymphotoxin, exhibits inducible expression and competes with HSV glycoprotein D for binding to herpesvirus entry mediator, a receptor expressed on T lymphocytes (TNFSF14/LIGHT); matrix metalloproteinase-1 (MMP-1); matrix metalloproteinase-2 (MMP-2); matrix metalloproteinase-3 (MMP-3); Osteocalcin; Pentraxin-3; tumor necrosis factor receptor 1 (sTNF-R1); tumor necrosis factor receptor 2 (sTNF-R2); thymic stromal lymphopoietin (TSLP); TNF-related weak inducer of apoptosis/tumor necrosis factor superfamily member 12 (TWEAK/TNFSF12); 4-1BB (CD137); cytotoxic T-lymphocyte associated protein 4 (CTLA-4 or CD152); lymphocyte-activation gene 3 (Lag-3 or CD223); CD27; herpesvirus entry mediator/tumor necrosis factor superfamily member 14 (HVEM/TNFRSF14 (CD270)); B- and T-lymphocyte associated (BTLA (CD272)); programmed cell death protein 1 (PD-1 (CD279)); CD28; glucocorticoid-induced TNFR family related gene/tumor necrosis factor superfamily member 18 (GITR/TNFRSF1 8 (CD357)); B7-1 (CD80); and T-cell immunoglobulin domain and mucin domain 3 (TIM3).

\* \* \* \* \*